United States Patent
Wang et al.

(10) Patent No.: US 9,012,462 B2
(45) Date of Patent: Apr. 21, 2015

(54) PHOSPHOROUS DERIVATIVES AS KINASE INHIBITORS

(75) Inventors: Yihan Wang, Newton, MA (US);
Wei-Sheng Huang, Acton, MA (US);
Shuangying Liu, Wellesley, MA (US);
William C. Shakespeare, Southborough, MA (US); R. Mathew Thomas, Sharon, MA (US); Jiwei Qi, West Roxbury, MA (US); Feng Li, Winchester, MA (US); Xiaotian Zhu, Newton, MA (US); Anna Kohlman, Winchester, MA (US); David C. Dalgarno, Brookline, MA (US); Jan Antoinette C. Romero, Somerville, MA (US); Dong Zou, Concord, MA (US)

(73) Assignee: Ariad Pharmaceuticals, Inc., Cambridge, MA (US)

( * ) Notice: Subject to any disclaimer, the term of this patent is extended or adjusted under 35 U.S.C. 154(b) by 752 days.

(21) Appl. No.: 12/736,910

(22) PCT Filed: May 21, 2009
(Under 37 CFR 1.47)

(86) PCT No.: PCT/US2009/044918
§ 371 (c)(1),
(2), (4) Date: Jan. 17, 2012

(87) PCT Pub. No.: WO2009/143389
PCT Pub. Date: Nov. 26, 2009

(65) Prior Publication Data
US 2012/0202776 A1  Aug. 9, 2012

Related U.S. Application Data

(60) Provisional application No. 61/128,317, filed on May 21, 2008, provisional application No. 61/137,490, filed on Jul. 31, 2008, provisional application No. 61/188,796, filed on Aug. 13, 2008, provisional application No. 61/192,938, filed on Sep. 23, 2008, provisional application No. 61/192,964, filed on Sep. 23, 2008.

(51) Int. Cl.
| | |
|---|---|
| *A61K 31/506* | (2006.01) |
| *C07F 9/30* | (2006.01) |
| *C07D 239/48* | (2006.01) |
| *C07F 9/6509* | (2006.01) |
| *C07F 9/6512* | (2006.01) |
| *C07F 9/6521* | (2006.01) |
| *C07F 9/6558* | (2006.01) |
| *C07F 9/6561* | (2006.01) |
| *C07F 9/6568* | (2006.01) |
| *C07F 9/6571* | (2006.01) |

(52) U.S. Cl.
CPC ........ *C07D 239/48* (2013.01); *C07F 9/650941* (2013.01); *C07F 9/65122* (2013.01); *C07F 9/65127* (2013.01); *C07F 9/65217* (2013.01); *C07F 9/65218* (2013.01); *C07F 9/65583* (2013.01); *C07F 9/65586* (2013.01); *C07F 9/6561* (2013.01); *C07F 9/65616* (2013.01); *C07F 9/65685* (2013.01); *C07F 9/657172* (2013.01)

(58) Field of Classification Search
USPC ................ 514/258.1, 275; 544/243, 280, 323
See application file for complete search history.

(56) References Cited

U.S. PATENT DOCUMENTS

| | | | |
|---|---|---|---|
| 4,966,622 | A | 10/1990 | Rempfler et al. |
| 5,521,184 | A | 5/1996 | Zimmermann |
| 5,612,340 | A | 3/1997 | Zimmermann |
| 6,008,234 | A | 12/1999 | Kochanny et al. |
| 6,015,455 | A | 1/2000 | Yano et al. |
| 6,030,977 | A | 2/2000 | Stock et al. |
| 6,048,390 | A | 4/2000 | Yano et al. |
| 6,107,301 | A | 8/2000 | Aldrich et al. |
| 6,432,963 | B1 | 8/2002 | Hisamichi et al. |
| 6,573,044 | B1 | 6/2003 | Gray et al. |
| 6,770,652 | B2 | 8/2004 | Gangjee |
| 6,878,697 | B2 | 4/2005 | Metcalf et al. |
| 6,949,644 | B2 | 9/2005 | Ding et al. |

(Continued)

FOREIGN PATENT DOCUMENTS

| | | |
|---|---|---|
| CA | 2598893 | 4/2008 |
| EP | 0242081 | 10/1987 |

(Continued)

OTHER PUBLICATIONS

Definition of "moiety", http://goldbook.iupac.org/M03968.html, accessed Sep. 16, 2013.*

(Continued)

*Primary Examiner* — Rebecca Anderson
*Assistant Examiner* — Karen Cheng
(74) *Attorney, Agent, or Firm* — David L. Berstein

(57) ABSTRACT

The invention features compounds of the general formula (I) in which the variable groups are as defined herein, and to their preparation and use.

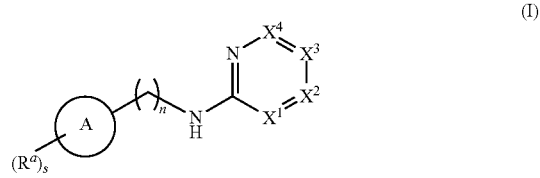

(I)

72 Claims, No Drawings

(56) References Cited

U.S. PATENT DOCUMENTS

| | | |
|---|---|---|
| 7,151,096 B2 | 12/2006 | Ren et al. |
| 7,169,817 B2 | 1/2007 | Pan et al. |
| 7,176,312 B2 | 2/2007 | Ding et al. |
| 7,189,729 B2 | 3/2007 | Chopiuk et al. |
| 7,253,166 B2 | 8/2007 | Ding et al. |
| 7,256,206 B2 | 8/2007 | Pan et al. |
| 7,338,957 B2 | 3/2008 | Ding et al. |
| 7,371,750 B2 | 5/2008 | Sim et al. |
| 7,423,031 B2 | 9/2008 | Wan et al. |
| 7,423,038 B2 | 9/2008 | Ren et al. |
| 7,449,582 B2 | 11/2008 | Ding et al. |
| 7,514,446 B2 | 4/2009 | Davis-Ward et al. |
| 7,521,457 B2 | 4/2009 | Stadtmueller et al. |
| 7,569,561 B2 | 8/2009 | Stadtmueller et al. |
| 7,569,593 B2 | 8/2009 | Gray et al. |
| 7,589,101 B2 | 9/2009 | Okram et al. |
| 7,605,131 B2 | 10/2009 | Mano et al. |
| 7,642,255 B2 | 1/2010 | Sim et al. |
| 7,671,063 B2 | 3/2010 | Baenteli et al. |
| 7,713,958 B2 | 5/2010 | Wan et al. |
| 7,728,120 B2 | 6/2010 | Mano et al. |
| 7,745,437 B2 | 6/2010 | Ren et al. |
| 7,868,018 B2 | 1/2011 | Xie et al. |
| 7,893,074 B2 | 2/2011 | Garcia-Echeverria et al. |
| 7,939,519 B2 | 5/2011 | Pan et al. |
| 7,943,629 B2 | 5/2011 | Luecking et al. |
| 7,964,592 B2 | 6/2011 | Garcia-Echeverria et al. |
| 7,964,710 B2 | 6/2011 | Mano et al. |
| 7,968,557 B2 | 6/2011 | Choi et al. |
| 8,039,479 B2 | 10/2011 | Michellys et al. |
| 8,071,609 B2 | 12/2011 | Wang et al. |
| 8,101,608 B2 | 1/2012 | Wan et al. |
| 8,197,818 B2 | 6/2012 | Mano et al. |
| 8,383,793 B2 | 2/2013 | Morris et al. |
| 8,450,335 B2 | 5/2013 | Singh et al. |
| 2003/0171583 A1 | 9/2003 | Ding et al. |
| 2003/0186324 A1 | 10/2003 | Liao et al. |
| 2003/0191312 A1 | 10/2003 | Ding et al. |
| 2004/0048857 A1 | 3/2004 | Pan et al. |
| 2004/0121316 A1 | 6/2004 | Birkus et al. |
| 2004/0235841 A1 | 11/2004 | Ren et al. |
| 2004/0248952 A1 | 12/2004 | Pan et al. |
| 2005/0014753 A1 | 1/2005 | Ding et al. |
| 2005/0038049 A1 | 2/2005 | Ding et al. |
| 2005/0113398 A1 | 5/2005 | Argade et al. |
| 2005/0124637 A1 | 6/2005 | Cheng et al. |
| 2005/0136396 A1 | 6/2005 | McDermott |
| 2005/0136397 A1 | 6/2005 | McDermott |
| 2005/0136398 A1 | 6/2005 | McDermott |
| 2005/0153955 A1 | 7/2005 | Wan et al. |
| 2005/0159391 A1 | 7/2005 | Ding et al. |
| 2005/0159446 A1 | 7/2005 | Chew et al. |
| 2005/0171105 A1 | 8/2005 | Chopiuk et al. |
| 2005/0187230 A1 | 8/2005 | Ding et al. |
| 2005/0192301 A1 | 9/2005 | Li |
| 2005/0197320 A1 | 9/2005 | Chen et al. |
| 2005/0203114 A1 | 9/2005 | Armistead et al. |
| 2005/0209197 A1 | 9/2005 | Arimilli et al. |
| 2005/0209224 A1 | 9/2005 | Singh et al. |
| 2005/0209285 A1 | 9/2005 | Gray et al. |
| 2005/0222177 A1 | 10/2005 | Sim et al. |
| 2005/0234049 A1 | 10/2005 | Singh et al. |
| 2005/0239054 A1 | 10/2005 | Arimilli et al. |
| 2005/0261295 A1 | 11/2005 | Stadtmueller |
| 2005/0267304 A1 | 12/2005 | Cox et al. |
| 2006/0009642 A1 | 1/2006 | Ding et al. |
| 2006/0035891 A1 | 2/2006 | Li et al. |
| 2006/0079543 A1 | 4/2006 | Sum et al. |
| 2006/0115815 A1 | 6/2006 | Birkus et al. |
| 2006/0128692 A1 | 6/2006 | Chen et al. |
| 2006/0148800 A1 | 7/2006 | Stadtmueller |
| 2006/0167249 A1 | 7/2006 | Argade et al. |
| 2006/0211709 A1 | 9/2006 | Buhr et al. |
| 2006/0247241 A1 | 11/2006 | Garcia-Echeverria et al. |
| 2006/0247262 A1 | 11/2006 | Baenteli et al. |
| 2007/0010489 A1 | 1/2007 | Arimilli et al. |
| 2007/0010668 A1 | 1/2007 | Davis-Ward et al. |
| 2007/0032514 A1 | 2/2007 | Zahn et al. |
| 2007/0066660 A1 | 3/2007 | Stahle et al. |
| 2007/0167439 A1 | 7/2007 | Singh et al. |
| 2007/0179140 A1 | 8/2007 | Argade et al. |
| 2007/0190523 A1 | 8/2007 | Birkus et al. |
| 2007/0191380 A1 | 8/2007 | Ding et al. |
| 2007/0203161 A1 | 8/2007 | Argade et al. |
| 2007/0207999 A1 | 9/2007 | Stadtmueller |
| 2007/0208164 A1 | 9/2007 | Olszewski et al. |
| 2007/0225286 A1 | 9/2007 | Ren et al. |
| 2007/0259904 A1 | 11/2007 | Noronha et al. |
| 2007/0299060 A1 | 12/2007 | Li et al. |
| 2008/0009484 A1 | 1/2008 | Argade et al. |
| 2008/0009494 A1 | 1/2008 | Li et al. |
| 2008/0021020 A1 | 1/2008 | Argade et al. |
| 2008/0027045 A1 | 1/2008 | Argade et al. |
| 2008/0051412 A1 | 2/2008 | Argade et al. |
| 2008/0058358 A1 | 3/2008 | Luecking et al. |
| 2008/0090776 A1 | 4/2008 | Mano et al. |
| 2008/0108616 A1 | 5/2008 | Ding et al. |
| 2008/0113986 A1 | 5/2008 | Ren et al. |
| 2008/0132504 A1 | 6/2008 | Garcia-Echeverria et al. |
| 2008/0167330 A1 | 7/2008 | Luecking et al. |
| 2008/0176866 A1 | 7/2008 | Jautelat et al. |
| 2008/0188483 A1 | 8/2008 | Ren et al. |
| 2008/0194605 A1 | 8/2008 | Heinrich et al. |
| 2008/0221098 A1 | 9/2008 | Sim et al. |
| 2008/0221192 A1 | 9/2008 | Wan et al. |
| 2008/0227783 A1 | 9/2008 | Wan et al. |
| 2008/0227786 A1 | 9/2008 | Ferlita et al. |
| 2008/0255112 A1 | 10/2008 | Zhang et al. |
| 2008/0269170 A1 | 10/2008 | Bosch et al. |
| 2008/0280946 A1 | 11/2008 | Nazare et al. |
| 2008/0287432 A1 | 11/2008 | Okram et al. |
| 2008/0300246 A1 | 12/2008 | Xie et al. |
| 2008/0300267 A1 | 12/2008 | Okram et al. |
| 2008/0312438 A1 | 12/2008 | Singh et al. |
| 2009/0036423 A1 | 2/2009 | Pan et al. |
| 2009/0069327 A1 | 3/2009 | Ding et al. |
| 2009/0099193 A1 | 4/2009 | Mano et al. |
| 2009/0105250 A1 | 4/2009 | Sim et al. |
| 2009/0118273 A1 | 5/2009 | Nagle et al. |
| 2009/0137555 A1 | 5/2009 | Wan et al. |
| 2009/0137804 A1 | 5/2009 | Ding et al. |
| 2009/0156596 A1 | 6/2009 | Wang et al. |
| 2009/0181991 A1 | 7/2009 | Zhang et al. |
| 2009/0221555 A1 | 9/2009 | Ahmed et al. |
| 2009/0258910 A1 | 10/2009 | Gray et al. |
| 2009/0286789 A1 | 11/2009 | Hood et al. |
| 2009/0312321 A1 | 12/2009 | Ren et al. |
| 2009/0318687 A1 | 12/2009 | Singh et al. |
| 2010/0016296 A1 | 1/2010 | Singh et al. |
| 2010/0081679 A1 | 4/2010 | Greul et al. |
| 2010/0093668 A1 | 4/2010 | Babin et al. |
| 2010/0240673 A1 | 9/2010 | Mano et al. |
| 2010/0249092 A1 | 9/2010 | Singh et al. |
| 2010/0249126 A1 | 9/2010 | Burger et al. |
| 2010/0298295 A1 | 11/2010 | Marsilje et al. |
| 2010/0324062 A1 | 12/2010 | Nagle et al. |
| 2011/0021524 A1 | 1/2011 | Adrian et al. |
| 2011/0046108 A1 | 2/2011 | Kettle et al. |
| 2011/0053932 A1 | 3/2011 | Sim et al. |
| 2011/0092491 A1 | 4/2011 | Cheng et al. |
| 2011/0098280 A1 | 4/2011 | Garcia-Echeverria et al. |
| 2011/0105472 A1 | 5/2011 | Greul et al. |
| 2011/0144107 A1 | 6/2011 | Chatterjee et al. |
| 2011/0207736 A1 | 8/2011 | Gray et al. |
| 2011/0212077 A1 | 9/2011 | Noronha et al. |
| 2011/0230478 A1 | 9/2011 | Greul et al. |
| 2011/0230494 A1 | 9/2011 | Singh et al. |
| 2011/0230545 A1 | 9/2011 | Mano et al. |
| 2011/0288091 A1 | 11/2011 | Gray et al. |
| 2011/0312908 A1 | 12/2011 | Gray et al. |
| 2012/0040961 A1 | 2/2012 | Gray et al. |
| 2012/0094999 A1 | 4/2012 | Gray et al. |
| 2012/0108572 A1 | 5/2012 | Wagner et al. |
| 2012/0122902 A1 | 5/2012 | Chen et al. |

(56) References Cited

U.S. PATENT DOCUMENTS

| | | |
|---|---|---|
| 2012/0252818 A1 | 10/2012 | Chiosis et al. |
| 2013/0225527 A1 | 8/2013 | Wang et al. |
| 2013/0225528 A1 | 8/2013 | Wang et al. |
| 2014/0024620 A1 | 1/2014 | Dalgarno et al. |
| 2014/0066406 A1 | 3/2014 | Wang et al. |

FOREIGN PATENT DOCUMENTS

| | | |
|---|---|---|
| EP | 0382375 | 8/1990 |
| EP | 0468684 | 1/1992 |
| EP | 0472053 | 2/1992 |
| EP | 0542420 | 5/1993 |
| EP | 0564409 | 10/1993 |
| EP | 0372729 | 1/1995 |
| EP | 0763576 | 3/1997 |
| EP | 1054004 | 11/2000 |
| EP | 1132387 | 9/2001 |
| EP | 2123654 | 11/2009 |
| EP | 2 172 461 A1 | 4/2010 |
| FR | 2 911 138 A1 | 7/2008 |
| GB | 1129797 | 10/1968 |
| JP | 11-60573 | 3/1999 |
| WO | WO 95/09847 | 4/1995 |
| WO | WO 96/28427 | 9/1996 |
| WO | WO 97/10887 | 3/1997 |
| WO | WO 97/19065 | 5/1997 |
| WO | WO 97/20822 | 6/1997 |
| WO | WO 98/11094 | 3/1998 |
| WO | WO 98/15547 | 4/1998 |
| WO | WO 99/03854 | 1/1999 |
| WO | WO 99/63821 | 12/1999 |
| WO | WO 00/15645 | 3/2000 |
| WO | WO 00/27825 | 5/2000 |
| WO | WO 00/31068 | 6/2000 |
| WO | WO 00/33844 | 6/2000 |
| WO | WO 00/46203 | 8/2000 |
| WO | WO 00/67900 | 11/2000 |
| WO | WO 00/78731 | 12/2000 |
| WO | WO 01/09134 | 2/2001 |
| WO | WO 01/47507 | 7/2001 |
| WO | WO 01/64200 | 9/2001 |
| WO | WO 01/64654 | 9/2001 |
| WO | WO 01/64656 | 9/2001 |
| WO | WO 01/72744 | 10/2001 |
| WO | WO 01/85699 | 11/2001 |
| WO | WO 01/85700 | 11/2001 |
| WO | WO 02/00024 | 1/2002 |
| WO | WO 02/04429 | 1/2002 |
| WO | WO 02/22597 | 3/2002 |
| WO | WO 02/46318 | 6/2002 |
| WO | WO 02/059110 A1 | 8/2002 |
| WO | WO 02/083653 | 10/2002 |
| WO | WO 02/102800 | 12/2002 |
| WO | WO 03/000186 | 1/2003 |
| WO | WO 03/030909 | 4/2003 |
| WO | WO 03/037891 | 5/2003 |
| WO | WO 03/057165 | 7/2003 |
| WO | WO 03/066601 | 8/2003 |
| WO | WO 03/078404 | 9/2003 |
| WO | WO 03/094920 | 11/2003 |
| WO | WO 2004/011443 | 2/2004 |
| WO | WO 2004/014382 | 2/2004 |
| WO | WO 2004/018435 | 3/2004 |
| WO | WO 2004/041789 | 5/2004 |
| WO | WO 2004/046118 | 6/2004 |
| WO | WO 2004/074244 | 9/2004 |
| WO | WO 2004/074261 | 9/2004 |
| WO | WO 2004/074262 | 9/2004 |
| WO | WO 2004/080980 | 9/2004 |
| WO | WO 2004/085385 | 10/2004 |
| WO | WO 2004/085409 | 10/2004 |
| WO | WO 2004/096818 | 11/2004 |
| WO | WO 2005/013996 | 2/2005 |
| WO | WO 2005/016528 | 2/2005 |
| WO | WO 2005/016893 | 2/2005 |
| WO | WO 2005/016894 | 2/2005 |
| WO | WO 2005/026130 | 3/2005 |
| WO | WO 2005/026158 | 3/2005 |
| WO | WO 2005/061458 | 7/2005 |
| WO | WO 2005/070890 | 8/2005 |
| WO | WO 2006/021454 | 3/2006 |
| WO | WO 2006/038594 | 4/2006 |
| WO | WO 2006/068826 | 6/2006 |
| WO | WO 2006/074057 | 7/2006 |
| WO | WO 2006/078846 | 7/2006 |
| WO | WO 2006/084015 | 8/2006 |
| WO | WO 2006/101977 | 9/2006 |
| WO | WO 2006/123165 | 11/2006 |
| WO | WO 2006/124874 | 11/2006 |
| WO | WO 2006/128129 | 11/2006 |
| WO | WO 2006/128172 | 11/2006 |
| WO | WO 2006/129100 | 12/2006 |
| WO | WO 2006/133426 | 12/2006 |
| WO | WO 2007/015923 | 2/2007 |
| WO | WO 2007/021937 A2 | 2/2007 |
| WO | WO 2007/042299 | 4/2007 |
| WO | WO 2007/043835 | 4/2007 |
| WO | WO 2007/048064 | 4/2007 |
| WO | WO 2007/053452 | 5/2007 |
| WO | WO 2007/056151 | 5/2007 |
| WO | WO 2007/067506 | 6/2007 |
| WO | WO 2007/071455 | 6/2007 |
| WO | WO 2007/085833 | 8/2007 |
| WO | WO 2007/089768 | 8/2007 |
| WO | WO 2007/113254 | 10/2007 |
| WO | WO 2007/113256 | 10/2007 |
| WO | WO 2007/120339 | 10/2007 |
| WO | WO 2007/125351 | 11/2007 |
| WO | WO 2007/130468 | 11/2007 |
| WO | WO 2008/005538 | 1/2008 |
| WO | WO 2008/009458 | 1/2008 |
| WO | WO 2008/009963 | 1/2008 |
| WO | WO 2008/039359 A2 | 4/2008 |
| WO | WO 2008/045978 | 4/2008 |
| WO | WO 2008/049123 | 4/2008 |
| WO | WO 2008/051493 | 5/2008 |
| WO | WO 2008/057280 | 5/2008 |
| WO | WO 2008/073687 | 6/2008 |
| WO | WO 2008/079719 | 7/2008 |
| WO | WO 2008/079907 | 7/2008 |
| WO | WO 2008/080964 | 7/2008 |
| WO | WO 2008/080965 | 7/2008 |
| WO | WO 2008/092049 | 7/2008 |
| WO | WO 2008/099073 A1 | 8/2008 |
| WO | WO 2008/092199 | 9/2008 |
| WO | WO 2008/115738 | 9/2008 |
| WO | WO 2008/115742 | 9/2008 |
| WO | WO 2008/118822 | 10/2008 |
| WO | WO 2008/121670 | 10/2008 |
| WO | WO 2008/151183 | 12/2008 |
| WO | WO 2009/012421 | 1/2009 |
| WO | WO 2009/020990 | 2/2009 |
| WO | WO 2009/032668 | 3/2009 |
| WO | WO 2009/032694 | 3/2009 |
| WO | WO 2009/032703 | 3/2009 |
| WO | WO 2009/051822 | 4/2009 |
| WO | WO 2009/071535 | 6/2009 |
| WO | WO 2009/080638 | 7/2009 |
| WO | WO 2009/082697 | 7/2009 |
| WO | WO 2009/082701 | 7/2009 |
| WO | WO 2009/087225 | 7/2009 |
| WO | WO 2009/102446 | 8/2009 |
| WO | WO 2009/109605 | 9/2009 |
| WO | WO 2009/112490 | 9/2009 |
| WO | WO 2009/126514 | 10/2009 |
| WO | WO 2009/126515 | 10/2009 |
| WO | WO 2009/127642 | 10/2009 |
| WO | WO 2009/127822 | 10/2009 |
| WO | WO 2009/131687 | 10/2009 |
| WO | WO 2009/143018 | 11/2009 |
| WO | WO 2009/158571 | 12/2009 |
| WO | WO 2010/008739 | 1/2010 |
| WO | WO 2010/028236 | 3/2010 |

(56) References Cited

FOREIGN PATENT DOCUMENTS

| | | |
|---|---|---|
| WO | WO 2010/048149 | 4/2010 |
| WO | WO 2010/051781 | 5/2010 |
| WO | WO 2010/056311 | 5/2010 |
| WO | WO 2010/062571 | 6/2010 |
| WO | WO 2010/068292 | 6/2010 |
| WO | WO 2010/093928 | 8/2010 |
| WO | WO 2010/098866 | 9/2010 |
| WO | WO 2010/106097 | 9/2010 |
| WO | WO 2010/111406 | 9/2010 |
| WO | WO 2010/112210 | 10/2010 |
| WO | WO 2010/123870 | 10/2010 |
| WO | WO 2010/129053 | 11/2010 |
| WO | WO 2010/136559 | 12/2010 |
| WO | WO 2010/142766 | 12/2010 |
| WO | WO 2010/146132 | 12/2010 |
| WO | WO 2011/002807 | 1/2011 |
| WO | WO 2011/002808 | 1/2011 |
| WO | WO 2011/022440 | 2/2011 |
| WO | WO 2011/031896 | 3/2011 |
| WO | WO 2011/034907 | 3/2011 |
| WO | WO 2011/036566 | 3/2011 |
| WO | WO 2011/053518 | 5/2011 |
| WO | WO 2011/079231 | 6/2011 |
| WO | WO 2011/082285 | 7/2011 |
| WO | WO 2011/090760 | 7/2011 |
| WO | WO 2011/103196 | 8/2011 |
| WO | WO 2011/140338 | 11/2011 |
| WO | WO 2011/143495 | 11/2011 |
| WO | WO 2011/162515 | 12/2011 |
| WO | WO 2012/021444 | 2/2012 |
| WO | WO 2012/022045 | 2/2012 |
| WO | WO 2012/051587 | 4/2012 |
| WO | WO 2012/061299 | 5/2012 |
| WO | WO 2012/061303 | 5/2012 |
| WO | WO 2012/064706 | 5/2012 |
| WO | WO 2012/151561 | 11/2012 |
| WO | WO 2013/014448 | 1/2013 |
| WO | WO 2013/042006 | 3/2013 |
| WO | WO 2013/169401 | 11/2013 |

OTHER PUBLICATIONS

Giurginca, 2001, Polymer Degradation and Stability, vol. 73, p. 477-480.*
Bruning, 2000, Science, vol. 289, p. 2122-2125.*
Michael et al, 2000, Molecular Cell, vol. 6, p. 87-97.*
Kitamura et al, 2003, Annu Rev Physiol, vol. 65, p. 313-332.*
Abbot, "On the Offensive", Nature, (2002), pp. 470-474, vol. 416.
Carmi et al., "Novel Irreversible Epidermal Growth Factor Receptor . . . Chemical Modulation of the Cysteine-Trap Portion", J. Med. Chem., (2010), pps. 2038-2050, vol. 53.
Database Caplus on STN. Accession No. 1969:28936. Pesticidal Pyrimidinyl Phosphates. Abstract #28936d, Chem Imperial Industries, (1969), p. 324.
Dubinina et al, "Novel 5,7-disubstituted 6-amino- . . . with antiproliferative activity", European Journal of Medicinal Chemistry, 2006, pp. 727-737, vol. 41.
Eck et al., "Structural and Mechanistic Underpinnings of the . . . of EGFR Mutations in Non-small Cell Lung Cancer", Biochimica et Biophysica Acta, (2010), pp. 559-566.
Fletcher, "Approval Heralds New Generation of Kinase Inhibitors?", Nature Biotechnology, (2001), pp. 599-600, vol. 19.
Grande et al., "Targeting Oncogenic ALK: A Promising Strategy for Cancer Treatment", Molecular Cancer Therapeutics, (2011), pp. 569-579 + 1529, vol. 10.
Gundla et al., "Discovery of Novel Small-Molecule Inhibitors . . . Receptor-2: Combined Ligand and Target-Based Approach", J. Med. Chem., (2008), pp. 3367-3377, vol. 51.
Katayama et al., "Therapeutic Strategies to Overcome Crizotinib Resistance in Non-small Cell Lung Cancers . . . Oncogene EML4-ALK", PNAS, (2011), pp. 7535-7540, vol. 108 (18).
Klutchko et al., "Tyrosine Kinase Inhibitors. 19. 6-Alkynamides . . . of the erbB Family of Tyrosine Kinase Receptors", J. Med. Chem., (2006), pp. 1475-1485, vol. 49.
Kwak et al., "Irreversible Inhibitors of the EGF Receptor May Circumvent Acquired Resistance to Gefitinib", PNAS, (2005), pp. 7665-7670, vol. 102, No. 21.
Liao, "Molecular Recognition . . . and Selective Kinase Inhibitors", Jrnl of Medicinal Chemistry, 2007, pp. 409-424, vol. 50.
McCormick, "New-age Drug Meets Resistance", Nature, (2001), pp. 281-282, vol. 412.
Michalczyk et al., "Structural Insights Into How Irreversible Inhibitors Can Overcome Drug Resistance in EGFR", Bioorganic & Medicinal Chem, (2008), pp. 3482-3488, vol. 16.
Mishani et al., "High-Affinity Epidermal Growth Factor Receptor (EGFR) . . . Agent Candidates of EGFR Overexpessing Tumors", J. Med. Chem., (2005), pp. 5337-5348, vol. 48.
Ogiso et al., "Crystal Structure of the Complex of Human Epidermal Growth Factor and Receptor Extracellular Domains", Cell., (2002), pp. 775-787, vol. 110.
Pao et al., "Rational, Biologically Based Treatment of EGFR-mutant Non-small-cell Lung Cancer", Nature, (2010), pp. 760-774, vol. 10.
Porter et al, "Discovery of 4-azaindoles as novel inhibitors of c-Met kinase", Bioorganic & Medicinal Chemistry Letters, 2009, pp. 2780-2784, vol. 19.
Schindler et al, "Structual Mechanism for STI=571 Inhibition of Abelson Tyrosine Kinase", Science, (2000), pp. 1938-1942, vol. 289.
Simone, "Oncology; Introduction", Cecil Textbook of Medicine, 20th Edition, (1996), pp. 1004-1010, vol. 1.
Smaill et al., "Tyrosine Kinase Inhibitors. 18. 6-Substituted . . . of the Epidermal Growth Factor Receptor", J. Med. Chem., (2001), pp. 429-440, vol. 44.
Sos et al., "Chemogenomic Profiling Provides Insights . . . in Tumor Cells Expessing the T790M EGFR Resistance Mutation", Cancer Research, (2010), pp. 868-874, vol. 70.
Traxler, "Review: Onocolgic, Endocrine, Metabolic Protein Tyrosine Kinase Inhibitors in Cancer Treatment", Exp.Opin. Ther. Patents, (1997), pp. 571-588, vol. 7(6).
Wakeling et al., "ZD1839 (Iressa): An Orally Active Inhibitor Epidermal . . . with Potential for Cancer Therapy", Cancer Research, (2002), pp. 5749-5754.
Wissner et al., "Synthesis and Structure-Activity Relationships of . . . Human Epidermal Growth Factor Receptor-2 (HER-2)", J. Med. Chem., (2003), pp. 49-63, vol. 46.
Wu et al., "Design and Synthesis of . . . Side Chain Chirality and Michael Acceptor Group for Maximal Potency", J. Med. Chem., (2010), pp. 7316-7326, vol. 53.
Yun et al., "The T790M Mutation in EGFR Kinase Causes Drug Resistance by Increasing the Affinity for ATP", PNAS, (2008), pp. 2070-2075, vol. 105, No. 6.
Zhou et al., "Novel Mutant-Selective EGFR Kinase Inhibitors Against EGFR T790M", Nature, (2009), pp. 1070-1074, vol. 462.
Zhou et al., "Novel Mutant-Selective EGFR Kinase Inhibitors Against EGFR T790M", Supplementary Information, Nature, (2009), pp. 1070-1074, vol. 462.
Zimmerman et al, "Potent and selective inhibitors of the ABL-kinase: phenylamino-pyrimidine (PAP) derivatives", Biorg. Med. Chem. Letters, (1997), pp. 187-192, vol. 7(2).
EP Search Report dated May 31, 2005 for EP Appl. 02742236.9.
EP Search Report dated Jul. 10, 2012 for EP Appl. 09832253.0.
EP Search Report dated Oct. 5, 2012 for EP Appl. 09826414.6.
Int'l Search Report dated Jan. 7, 2003 for PCT/US2002/19631.
Int'l Search Report dated Mar. 11, 2010 for PCT/US2009/06057.
Int'l Search Report dated Feb. 24, 2010 for PCT/US2009/06520.
Int'l Search Report dated Mar. 1, 2012 for PCT/US2011/56457.
Int'l Search Report dated Aug. 7, 2012 for PCT/US2012/36683.
Int'l Search Report dated Jun. 12, 2013 for PCT/US2013/032713.
Dalgarno et al., "Structural Basis of Src Tyrosine Kinase Inhibition . . . Trisubstituted Purine-based Compounds", Chem. Biol. Drug Des., (2006), pp. 46-57, vol. 67.
Wang et al., "Bone-Targeted 2,6,9-Trisubstituted Purines: Novel . . . Treatment of Bone Diseases", Bioorganic & Medicinal Chemistry Letters, (2003), pp. 3067-3070, vol. 13.
EA Search Report dated Jul. 1, 2011 for EA application 201071339.

(56) References Cited

OTHER PUBLICATIONS

EP Supplemental Search Report dated Aug. 13, 2012 for EP application 09751617.3.
International Search Report for PCT/US09/44918 dated Aug. 24, 2009.
McDermott et al., "Identification of Genotype-Correlated Sensitivity to Selective Kinase Inhibitors . . . Tumor Cell Line Profiling", PNAS, (2007), pp. 19936-19941, vol. 104(50).
McDermott et al., "Genomic Alterations of Anaplastic Lymphoma Kinase . . . to Anaplastic Lymphoma Kinase Inhibitors", Cancer Research, (2008), pp. 3389-3395, vol. 68(9).
McDermott et al., "Acquired Resistance of Non-small Cell Lung Cancer Cells . . . Epidermal Growth Factor Receptor Dependency", Cancer Research, (2010), pp. 1625-1634, vol. 70(4).
EA Search Report dated Sep. 4, 2013 for EA Appl. 201390550.
Office Action from the European Patent Office for European Application No. 09 751 617.3, dated Apr. 14, 2014 (7 pages).
Response filed in the European Patent Office for European Application No. 09 751 617.3, dated Aug. 13, 2014 (141 pages).
Bennett and Plum (eds.), "Part XVI. Oncology" in *Cecil Textbook of Medicine*. 20$^{th}$ Ed., vol. 1. W.B. Saunders Co., 1996: pp. 1004-1010.
Brüning et al., "Role of Brain Insulin Receptor in Control of Body Weight and Reproduction" *Science*, 289:2122-2125 (2000).
Chiarle et al., "The anaplastic lymphoma kinase in the pathogenesis of cancer" *Nat. Rev. Cancer*, 8:11-23 (2008).
Dermer, "Another Anniversary for the War on Cancer" *Bio/Technology*, 12:320 (1994).
Doebele et al., "New strategies to overcome limitations of reversible EGFR tyrosine kinase inhibitor therapy in non-small cell lung cancer" *Lung Cancer*, 69:1-12 (2010).
Extended European Search Report issued Feb. 27, 2014, in European Patent Appiication No. 11833524.9 by ARIAD Pharmaceuticals (9 pages).
Fabbro et al., "Protein kinases as targets for anticancer agents: from inhibitors to useful drugs" *Pharmacology & Therapeutics*, 93:79-98 (2002).
Ferrara, "VEGF as a therapeutic target in cancer" *Oncology*, 69(suppl 3):11-16 (2005).
Freshney, *Culture of Animal Cells*, Alan R. Liss, Inc., 1983: pp. 1-6.
Galkin et al. "Identification of NVP-TAE684, a Potent, Selective, and Efficacious Inhibitor of NPM-ALK" *PNAS*, 104(1):270-275 (2007).
Gautschi et al. "Aurora Kinases as Anticancer Drug Targets" *Clin. Cancer Res.*, 14(6):1639-1648 (2008).
Golub et al., "Molecular Classification of Cancer: Class Discovery and Class Prediction by Gene Expression Monitoring" *Science*, 286:531-537 (1999).

Haluska et al., "In vitro and in vivo Antitumor Effects of the Dual Insulin-Like Growth Factor-I/Insulin Receptor Inhibitor, BMS-554417" *Cancer Res.*, 66(1):362-371 (2006).
Kitamura et al., "Insulin receptor knockout mice" *Annu. Rev. Physiol.*, 65:313-332 (2003).
Kulkarni et al., "Tissue-Specific Knockout of the Insulin Receptor in Pancreatic β Cells Creates an Insulin Secretory Defect Similar to that in Type 2 Diabetes" *Cell*, 96(3):329-339 (1999).
Li et al., "Development of Anaplastic Lymphoma Kinase (ALK) Small-Molecule Inhibitors for Cancer Therapy" *Med. Res. Rev.*, 28(3):372-412 (2008).
Mass, "The HER Receptor Family: A Rich Target for Therapeutic Development" *Int. J. Radiation Oncology Biol. Phys.*, 58:932-940 (2004).
Michael et al., "Loss of Insulin Signaling in Hepatocytes Leads to Severe Insulin Resistance and Progressive Hepatic Dysfunction" *Molecular Cell*, 6:87-97 (2000).
Mountzios et al., "Aurora kinases as targets for cancer therapy" *Cancer Treatment Reviews*, 34:175-182 (2008).
National Cancer Institute, "Cancer Prevention Overview (PDQ®)" [online]. http://www.cancer.gov/cancertopics/pdq/prevention/overview/patient, modified on May 25, 2012, downloaded on Nov. 14, 2012 (1 page).
National Cancer Institute, U.S. Dept. of Health and Human Services, "Fact Sheet. Targeted Cancer Therapies" Jun. 21, 2010 [online]. http/www.cancer.gov/cancertopics/factsheet/therapy/targeted. downloaded on Jan. 12, 2011 (7 pages).
Okamoto et al., "Transgenic rescue of insulin receptor-deficient mice" *J. Clin. Invest.*, 114:214-223 (2004).
Palmer et al., "Anaplastic lymphoma kinase: signaling in development and disease" *Biochem J.*, 420:345-361 (2009).
Pyne et al., "Sphingosine Kinase Inhibitors and Cancer: Seeking the Golden Sword of Hercules" *Cancer Res.*, 71(21):1-7 (2011).
Qiu et al., "Signaling network of the Btk family kinases" *Oncogene*, 19:5651-5661 (2000).
Remon et al., "Beyond EGFR TKI in *EGFR*-mutant Non-Small Cell Lung Cancer patients: Main challenges still to be overcome" *Cancer Treatment Reviews*, 40:723-729 (2014).
Tartari et al., "Characterization of Some Molecular Mechanisms Governing Autoactivation of the Catalytic Domain of the Anaplastic Lymphoma Kinase" *J. Biol. Chem.*, 283(7):3743-3750 (2008).
Voskoglou-Nomikos et al., "Clinical Predictive Value of the In Vitro Cell Line, Human Xenograft, and Mouse Allograft Preclinical Cancer Models" *Clin. Cancer Res.*, 9:4227-4239 (2003).

\* cited by examiner

PHOSPHOROUS DERIVATIVES AS KINASE INHIBITORS

CROSS-REFERENCE TO RELATED APPLICATIONS

The present application claims benefit under 35 U.S.C. §371 of International Application No. PCT/US2009/044918 (published PCT application No. WO 2009/143389), filed May 21 2009, which claims priority to 35 U.S.C. §119(e) to U.S. Provisional Patent Application No. 61/128,317, filed May 21, 2008, U.S. Provisional Patent Application No. 61/137,490, filed Jul. 31, 2008, U.S. Provisional Patent Application No. 61/188,796, filed Aug. 13, 2008, U.S. Provisional Patent Application No. 61/192,938, filed Sep. 23, 2008 and U.S. Provisional Application No. 61/192,964, filed Sep. 23, 2008, the entire contents of each of the above-referenced applications are hereby incorporated by reference.

BACKGROUND OF THE INVENTION

The protein kinases represent a large family of proteins which play a central role in the regulation of a wide variety of cellular processes and maintain control over cellular function. A partial, non limiting, list of such kinases includes ALK, abl, Akt, bcr-abl, Blk, Brk, c-kit, c-met, c-src, CDK1, CDK2, CDK3, CDK4, CDK5, CDK6, CDK7, CDK8, CDK9, CDK10, bRaf, cRafl, CSK, EGFR, ErbB2, ErbB3, ErbB4, Erk, Pak, fes, FGFR1, FGFR2, FGFR3, FGFR4, FGFR5, Fgr, flt-1, flt-3, Fps, Frk, Fyn, Hck, IGF-1R, INS-R, Jak1, Jak2, Jak3, KDR, Lck, Lyn, FAK, MEK, p38, PDGFR, PIK, PKC, PYK2, ros, tie, tie2, Pim-1, Pl3k, TRK and Zap70. Abnormal protein kinase activity has been related to several disorders, ranging from non-life threatening diseases such as psoriasis to extremely serious diseases such as cancers.

In view of this large number of protein kinases and the multitude of protein kinase-related diseases, there is an ever-existing need to provide new classes of compounds with increased selectivity that are useful as protein kinase inhibitors and therefore useful in the treatment of protein tyrosine-kinase related diseases.

The invention concerns a new family of phosphorous compounds and their use in treating cancers and other diseases.

DESCRIPTION OF THE INVENTION

1. General Description of Compounds of the Invention

Compounds of the invention can have a broad range of useful biological and pharmacological activities, permitting their use in pharmaceutical compositions and methods for treating cancer (including lymphoma, solid tumors and leukemia among other cancers), including, also among others, advanced cases and cases which are resistant or refractory to one or more other treatments.

Included are compounds of Formula I, and tautomers and pharmaceutically acceptable salts and solvate thereof:

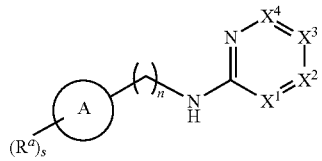

Formula I wherein
$X^1$ is $NR^{b1}$ or $CR^b$;
$X^2$ is $NR^{c1}$ or $CR^c$;
$X^3$ is $NR^{d1}$ or $CR^d$;
$X^4$ is $NR^{e1}$ or $CR^e$;
Ring A is an aryl, a 5- or a 6-membered heteroaryl ring which contains 1 to 4 heteroatoms selected from N, O and $S(O)_r$;
at each occurrence $R^a$, $R^b$, $R^c$, $R^d$ and $R^e$ are independently selected from the group consisting of halo, —CN, —NO$_2$, —R$^1$, —OR$^2$, —O—NR$^1$R$^2$, —NR$^1$R$^2$, —NR$^1$—NR$^1$R$^2$, —NR$^1$—OR$^2$, —C(O)YR$^2$, —OC(O)YR$^2$, —NR$^1$C(O)YR$^2$, —SC(O)YR$^2$, —NR$^1$C(=S)YR$^2$, —OC(=S)YR$^2$, —C(=S)YR$^2$, —YC(=NR$^1$)YR$^2$, —YC(=N—OR$^1$)YR$^2$, —YC(=N—NR$^1$R$^2$)YR$^2$, —YP(=O)(YR$^3$)(YR$^3$), —Si(R$^{3a}$)$_3$,
—NR$^1$SO$_2$R$^2$, —S(O)$_r$R$^2$, —SO$_2$NR$^1$R$^2$ and —NR$^1$SO$_2$NR$^1$R$^2$, and $R^{b1}$, $R^{c1}$, $R^{d1}$ and $R^{e1}$ are absent; wherein each Y is independently a bond, —O—, —S— or —NR$^1$—; or alternatively two adjacent substituents selected from $R^b$, $R^{b1}$, $R^c$, $R^{c1}$, $R^d$, $R^{d1}$, $R^e$ and $R^{e1}$; or two adjacent $R^a$ moieties, can form with the atoms to which they are attached a 5-, 6- or 7-membered saturated, partially saturated or unsaturated ring, which contains 0-4 heteroatoms selected from N, O and $S(O)_r$ and which is substituted with one to four $R^f$ moieties wherein;

each $R^f$ moiety is independently selected from the group consisting of halo, =O, =S, —CN, —NO$_2$, —R$^1$, —OR$^2$, —O—NR$^1$R$^2$, —NR$^1$R$^2$, —NR$^1$—NR$^1$R$^2$, —NR$^1$—OR$^2$, —C(O)YR$^2$, —OC(O)YR$^2$, —NR$^1$C(O)YR$^2$, —SC(O)YR$^2$, —NR$^1$C(=S)YR$^2$, —OC(=S)YR$^2$, —C(=S)YR$^2$, —YC(=NR$^1$)YR$^2$, —YC(=N—OR$^1$)YR$^2$, —YC(=N—NR$^1$R$^2$)YR$^2$, —YP(=O)(YR$^3$)(YR$^3$), —Si(R$^{3a}$)$_3$, —NR$^1$SO$_2$R$^2$, —S(O)$_r$R$^2$, —SO$_2$NR$^1$R$^2$ and —NR$^1$SO$_2$NR$^1$R$^2$; or alternatively two adjacent $R^f$ moieties can form with the atoms to which they are attached a 5-, 6- or 7-membered saturated, partially saturated or unsaturated ring, optionally substituted; and which contains 0-4 heteroatoms selected from N, O and $S(O)_r$; at least one of $R^a$, $R^b$, $R^c$, $R^d$, $R^e$, $R^f$, $R^{b1}$, $R^{c1}$, $R^{d1}$ and $R^{e1}$, when present, is or contains —P(=O)(R$^3$)$_2$ or a ring system containing the moiety —P(=O)(R$^3$)— as a ring member.

r is 0, 1 or 2;
s is 1, 2, 3, 4 or 5
n is 0 or 1;
each occurrence of Y is independently a bond, —O—, —S— or —NR$^1$—;
each occurrence of $R^1$ and $R^2$ is independently selected from H, alkyl, alkenyl, alkynyl, cycloalkyl, cycloalkenyl, cycloalkynyl, aryl, heteroalkyl, heterocyclic and heteroaryl;
each occurrence of $R^3$ is independently selected from alkyl, alkenyl, alkynyl, cycloalkyl, cycloalkenyl, cycloalkynyl, aryl, heteroalkyl, heterocyclic and heteroaryl, or two adjacent $R^3$ moieties combine to form a ring system including a phosphorous atom;

each occurrence of $R^{3a}$ is independently selected from alkyl, alkenyl, alkynyl, cycloalkyl, cycloalkenyl, cycloalkynyl, aryl, heteroalkyl, heterocyclic, and heteroaryl;

alternatively, each $NR^1R^2$ moiety may be a 5-, 6- or 7-membered saturated, partially saturated or unsaturated ring, which can be optionally substituted and which contains 0-2 additional heteroatoms selected from N, O and $S(O)_r$; and each of the foregoing alkyl, alkenyl, alkynyl, cycloalkyl, cycloalkenyl, cycloalkynyl, aryl, heteroaryl and heterocyclic moiety is optionally substituted.

The foregoing definitions are further elaborated upon and exemplified below and apply to all subsequent occurrences except to the extent otherwise specified.

2. Featured Classes of Compounds and their Use, Generally

One class of compounds which is of special interest for use in the invention are compounds of Formula I, as described above in Part 1, in which $X^2$ is $CR^c$, $X^3$ is $CR^d$ and $X^4$ is CRC. This class is illustrated by compounds of Formula IA:

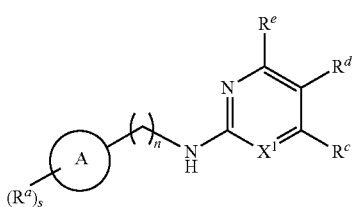

wherein $X^1$ is N or $CR^b$; and Ring A, $R^a$, $R^b$, $R^c$, $R^d$, $R^e$, n, and s are as defined in Formula I.

One class of interest includes compounds in which Ring A is a phenyl.

Another class of interest includes compounds in which Ring A is a 5- or 6-membered heteroaryl.

Another class of compounds which is of special interest for use in the invention are compounds of Formula Ia, as described above, in which $X^1$ is $CR^b$.

This class is illustrated by compounds of Formula IB:

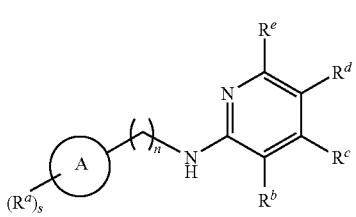

A subclass of interest include compound of Formula IB in which n is 0.

Another subclass of interest includes compounds of Formula IB in which n is 1.

Another subclass of interest includes compounds of Formula IB in which Ring A is phenyl.

Of special interest is another class of compounds of Formula IA as described above in Part 1 in which $X^1$ is N. This class is illustrated by compounds of Formula IC:

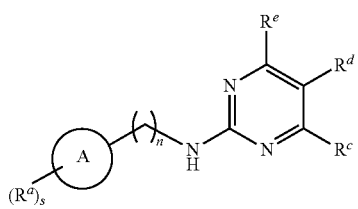

A subclass of interest include compound of Formula IC in which n is 0.

Another subclass of interest includes compounds of Formula IC in which n is 1.

Another subclass of interest includes compounds of Formula IC in which Ring A is phenyl.

In Formulas IB and IC, s, $R^a$, $R^b$, $R^c$, $R^d$ and $R^e$ are as defined above in Formula I. In a particular embodiment of the previous classes and subclasses, one of $R^a$ is or contains a $—P(=O)(R^3)_2$ group. Examples of $R^a$ containing a $—P(=O)(R^3)_2$ group include, without limitation, $—(CH_2)_m—P(=O)(R^3)_2$, $—(CH_2)_m—NR^1—P(=O)(R^3)_2$, $—(CH_2)_m—O—P(=O)(R^3)_2$, $—(CH_2)_m—NR^1—(CH_2)_m—P(=O)(R^3)_2$, $—(CH_2)_m—NR^1C(O)O—(CH_2)_m—P(=O)(R^3)_2$, $—(CH_2)_m—C(O)—(CH_2)_m—P(=O)(R^3)_2$, $—(CH_2)_m—C(O)NR^1—(CH_2)_m—P(=O)(R^3)_2$ in which m is 0, 1, 2, 3 or 4.

Illustrative examples of this class are the following compounds of Formula IA:

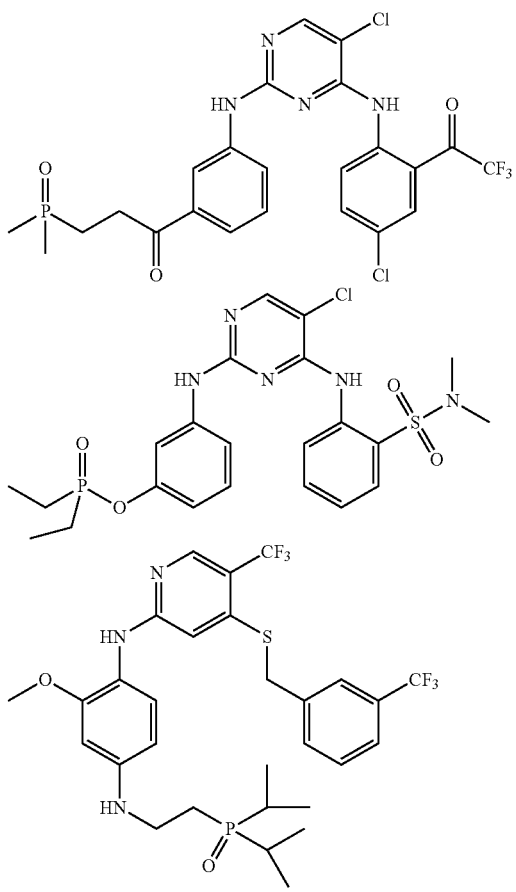

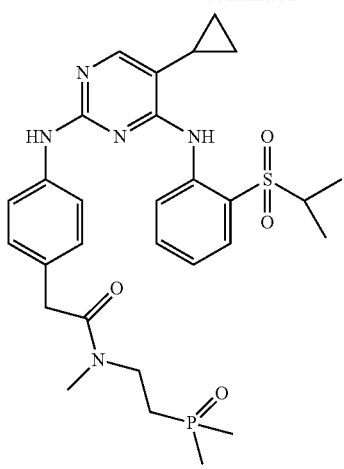

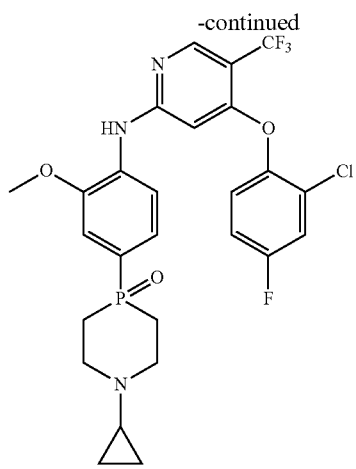

In certain embodiments, $R^a$ contains a —P(=O)($R^3$)$_2$ substituent as part of a cyclic structure. For example, two $R^3$ groups can combine to form a ring system including a phosphorous atom, wherein the ring system is a 5-, 6- or 7-membered saturated ring, optionally substituted; and which can optionally contain one heteroatom selected from N, O and S(O)$_r$. In certain embodiments, $R^a$ is or contains a group described by one of the following formulas:

In other cases, $R^a$ is a ring system containing the moiety —P(=O)($R^3$)— as a ring member, such as a 5-, 6- or 7-membered saturated ring, optionally substituted; which contains a phosphorous atom and can optionally contains 1 heteroatom selected from N, O and S(O)$_r$. In certain embodiments, $R^a$ is or contains a group described by one of the following formulas:

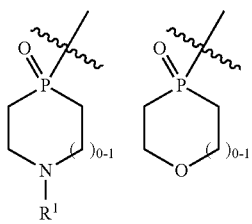

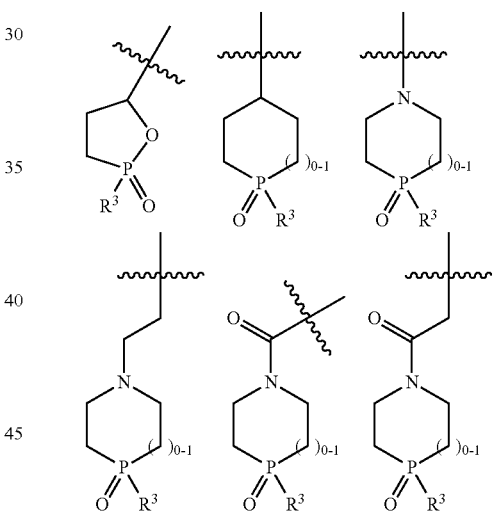

Illustrative examples of this class are compounds of Formula Ia include:

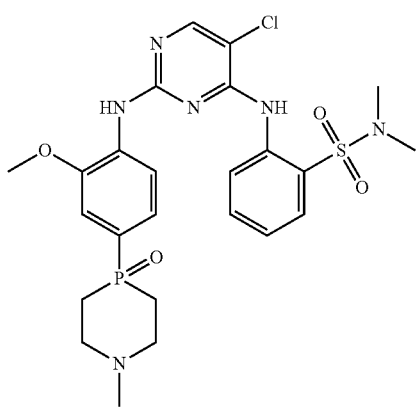

Illustrative examples of this class are compounds of Formula IA include:

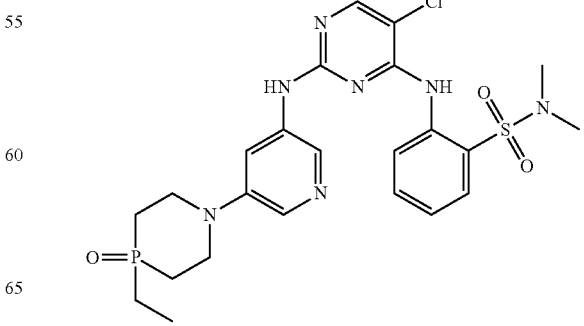

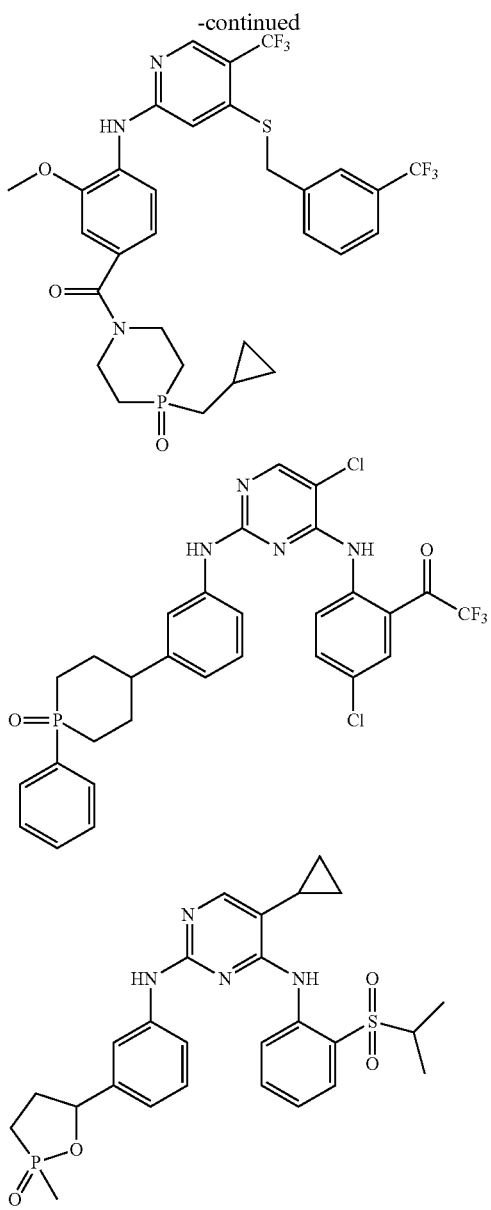

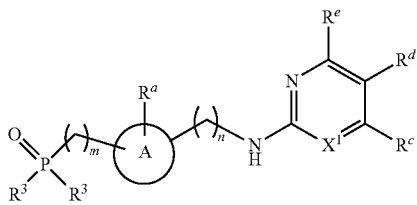

in which variables $R^3$, $R^a$, Ring A, n, $X^1$, $R^c$, $R^d$, and $R^e$ are as defined above in Formula I and m is 0, 1, 2, 3 or 4.

In one subclass of interest are compounds of Formula II or IIA in which m is 0. In another subclass m is 1.

In another subclass of interest are compounds of Formula II or Formula IIA in which X is N.

In another subclass of interest are compounds of Formula II or Formula IIA in which X is $CR^b$.

In another subclass of interest are compounds of the above classes and subclasses in which n is 0. In another subclass n is 1.

One class of compounds of special interest are compounds of Formula IIA in which Ring A is a phenyl.

Non limiting examples of this embodiment include the following compounds of Formula IIA:

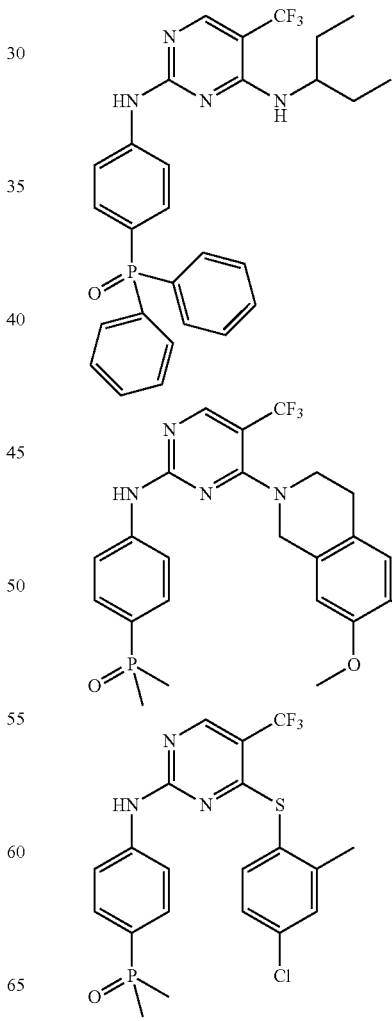

In one subclass of interest, one of $R^a$ is —$(CH_2)_m$—$P(=O)(R^3)_2$. This class is illustrated by compounds of Formula II.

Formula II

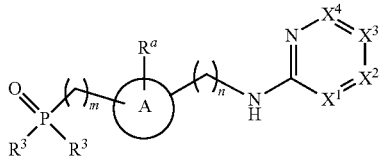

in which variables $R^3$, $R^a$, n, Ring A, $X^1$, $X^2$, $X^3$ and $X^4$ are as defined above in Formula I and m is 0, 1, 2, 3 or 4.

One class of compounds which is of special interest for use in the invention are compounds of Formula II, as described above, in which $X^2$ is $CR^c$, $X^3$ is $CR^d$ and $X^4$ is $CR^e$. This class is illustrated by compounds of Formula IIA:

-continued

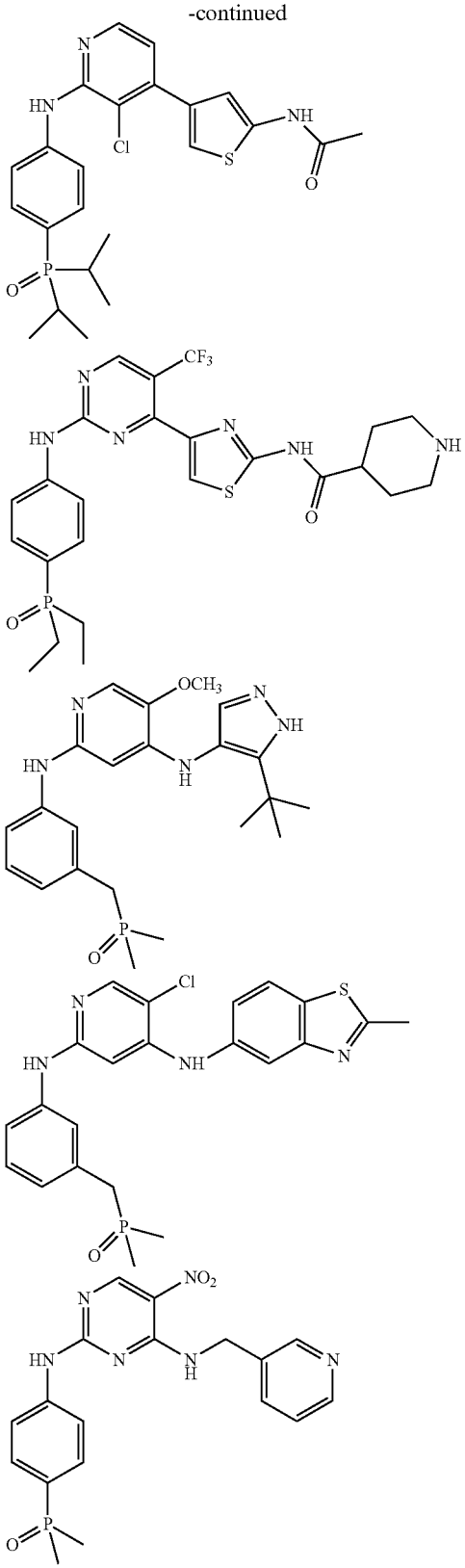

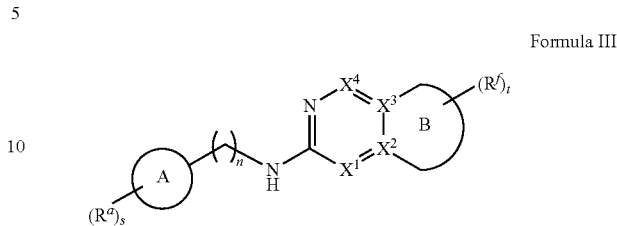

$R^f$; and which contains 0-4 heteroatoms selected from N, O and $S(O)_r$. This class is illustrated by compounds of Formula III:

Formula III in which variables $R^a$, $R^f$, Ring A, n, s, $X^1$, $X^2$, $X^3$ and $X^4$ are as described in Formula I; and t is 1, 2, 3 or 4.

One class of compounds which is of special interest for use in the invention are compounds of Formula III, as described above, in which $X^2$ is $CR^C$, $X^3$ is $CR^d$ and $X^4$ is $CR^e$ and $R^c$ and $R^d$ moieties form with the atoms to which they are attached a 5-, 6- or 7-membered saturated, partially saturated or unsaturated Ring B. This class is illustrated by compounds of Formula IIIA:

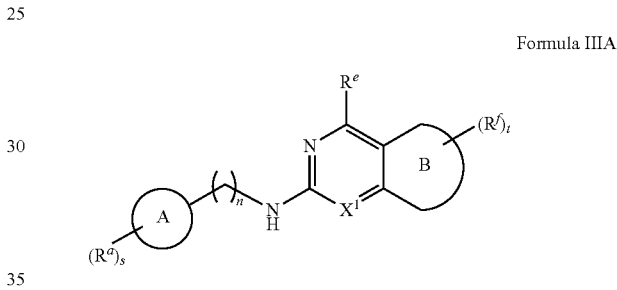

Formula IIIA in which variables $R^a$, $X^1$, Ring A, n, s, t, $X^1$, $R^e$ and $R^f$ are as described in Formula III.

In one particular embodiment, one $R^a$ is or contains —P(=O)($R^3$)$_2$ or a ring system containing the moiety —P(=O)($R^3$)— as a ring member (i.e. $(CH_2)_m P(=O)$ (alkyl)$_2$, in which m is 0, 1, 2, 3 or 4 and other examples of phosphorous containing substituents, including cyclic ones as listed above). In another particular embodiment, $R^f$ is or contains —P(=O)($R^3$)$_2$ or a ring system containing the moiety —P(=O)($R^3$)— as a ring member (i.e. $(CH_2)_m P(=O)$ (alkyl)$_2$, in which m is 0, 1, 2, 3 or 4 and other examples of phosphorous containing substituents, including cyclic ones as listed above).

One class of compounds of special interest are compounds of Formula III or IIIA in which Ring A is a phenyl.

Illustrative examples of this class are the following compounds of Formula IIIA:

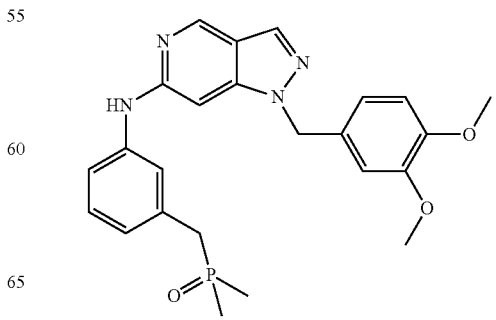

In one embodiment, two adjacent substituents selected from $R^{c1}$, $R^{d1}$, $R^c$ and $R^d$, form with the atoms to which they are attached a 5-, 6- or 7-membered saturated, partially saturated or unsaturated Ring B, which is substituted with 1 to 4

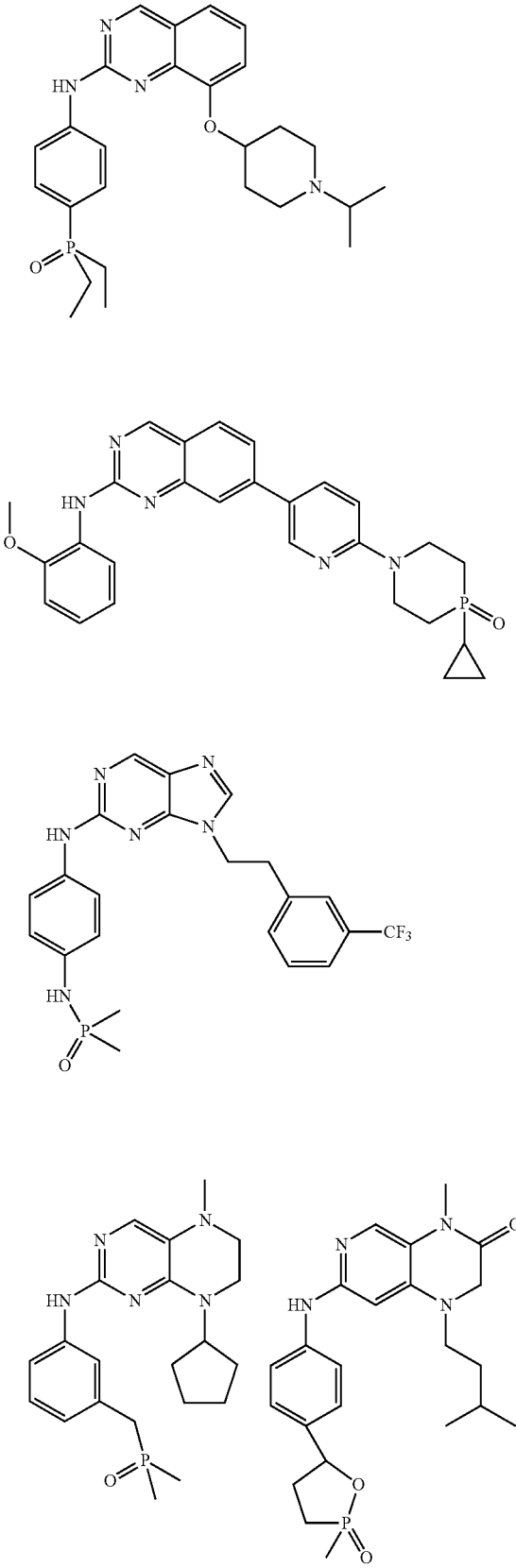
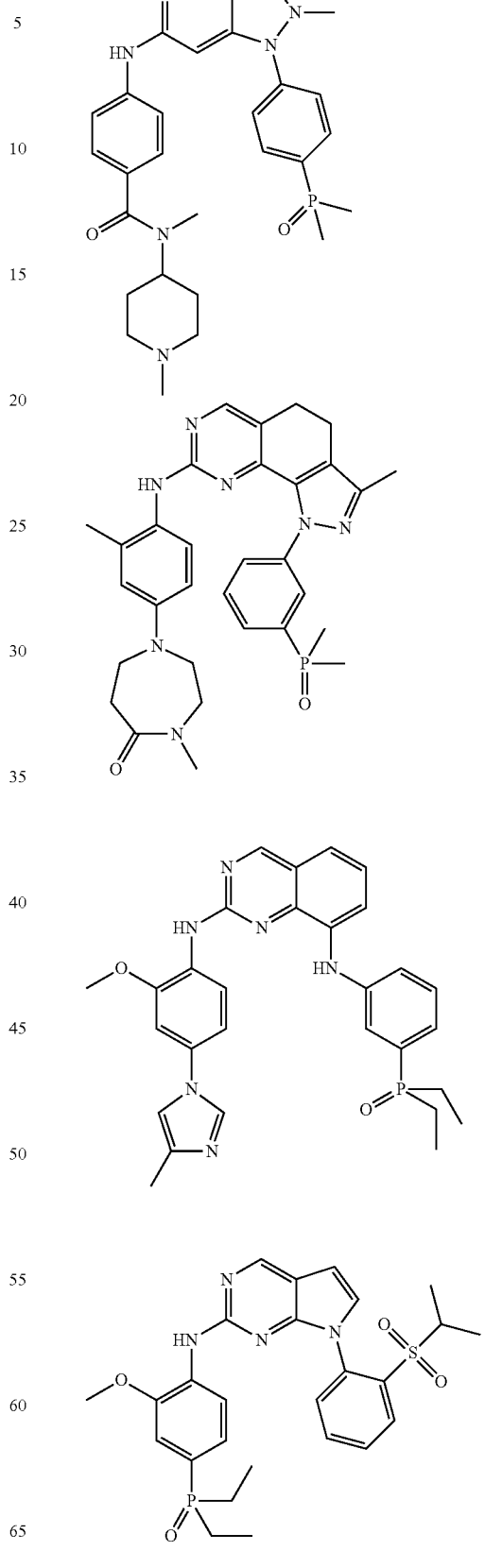

Other Illustrative examples of this class are the following compounds of Formula III:

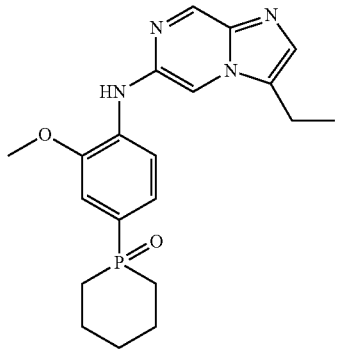

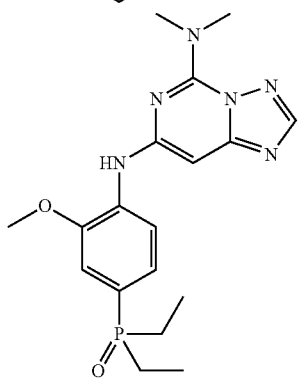

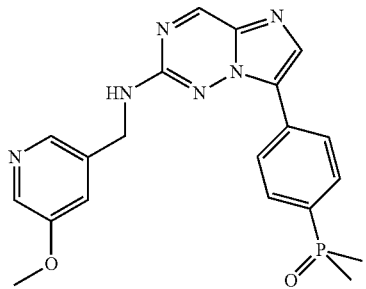

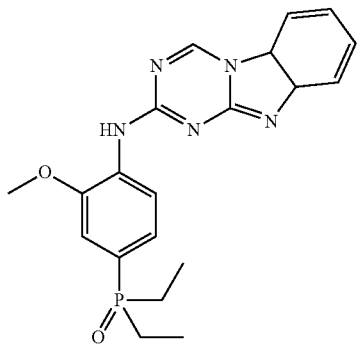

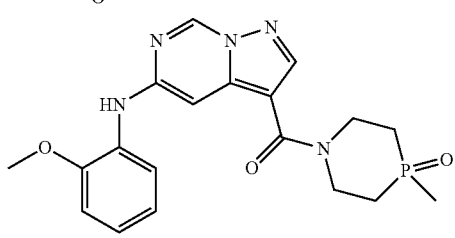

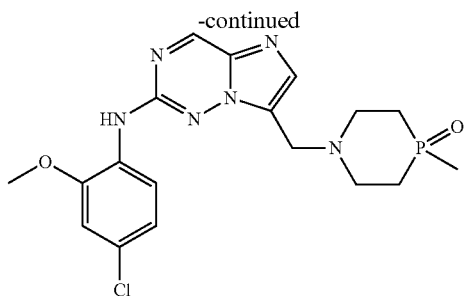

In another embodiment, two adjacent substituents selected from $R^{d1}$, $R^{e1}$, $R^d$ and $R^e$ form with the atoms to which they are attached a 5-, 6- or 7-membered saturated, partially saturated or unsaturated Ring C, which is substituted with 1 to 4 $R^f$; and which contains 0-4 heteroatoms selected from N, O and $S(O)_r$. This class is illustrated by compounds of Formula IV:

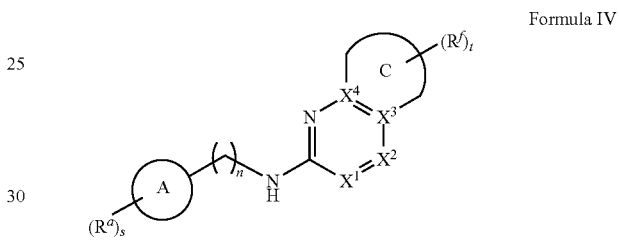

Formula IV in which Ring A, $R^a$, $R^f$, s, n, $X^1$, $X^2$, $X^3$ and $X^4$ are as defined in Formula I; and t is 1, 2, 3 or 4.

Illustrative examples of this class are the following compounds of Formula IV:

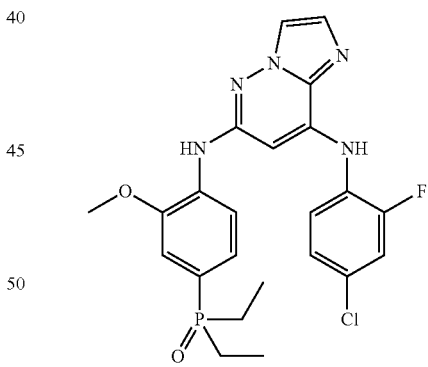

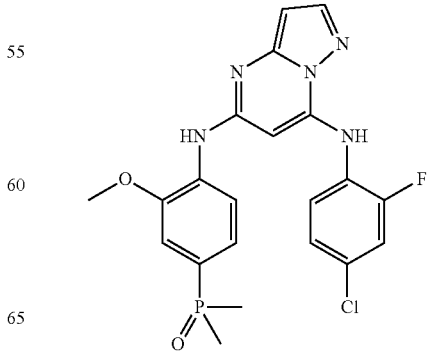

-continued

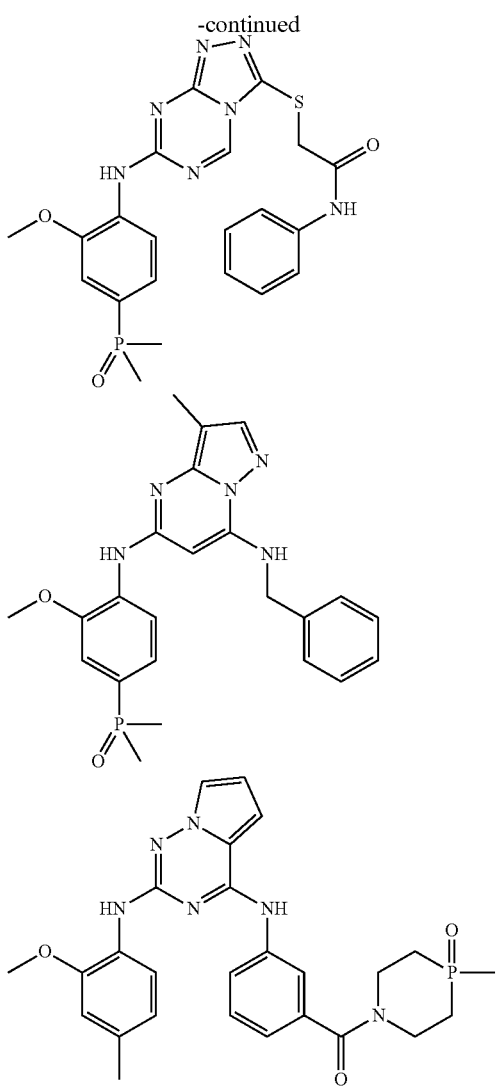

One class of compounds which is of special interest for use in the invention are compounds of Formula IV, as described above, in which $X^1$ is $CR^b$, $X^2$ is $CR^c$, $X^3$ is $CR^d$ and $X^4$ is $CR^e$ and $R^d$ and $R^e$ moieties form with the atoms to which they are attached a 5-, 6- or 7-membered saturated, partially saturated or unsaturated Ring C. This class is illustrated by compounds of Formula IVA:

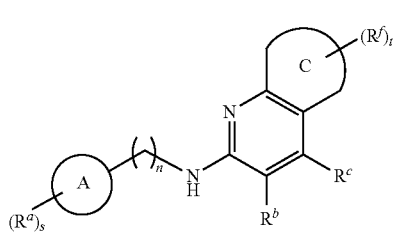

Formula IVA in which Ring A, Ring C, $R^a$, s, n, $R^b$, $R^c$, $R^f$ and t are as defined above in Formula IV.

In one particular aspect of this embodiment, one $R^a$ is or contains —P(=O)($R^3$)$_2$ or a ring system containing the moiety —P(=O)($R^3$)— as a ring member.

In another aspect of this embodiment, one of $R^f$ is or contains —P(=O)($R^3$)$_2$ or a ring system containing the moiety —P(=O)($R^3$)— as a ring member.

In another aspect of this embodiment, $R^c$ is or contains —P(=O)($R^3$)$_2$ or a ring system containing the moiety —P(=O)($R^3$)— as a ring member.

One class of compounds of special interest are compounds of Formula IV or IVA in which Ring A is a phenyl.

Illustrative examples of this class are the following compounds of Formula IVA:

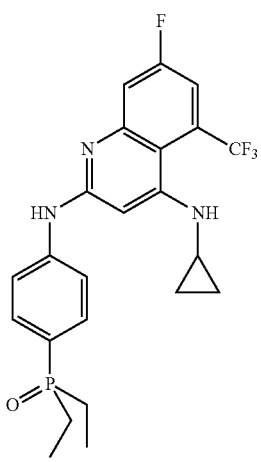

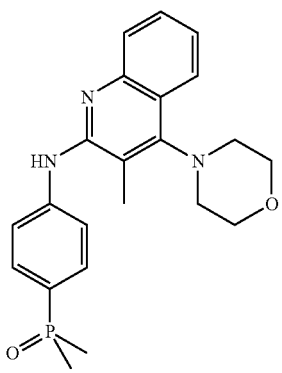

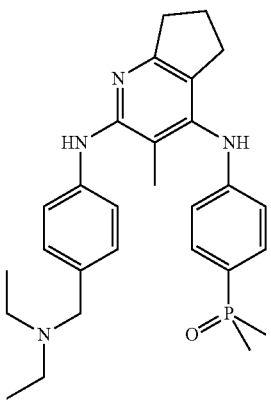

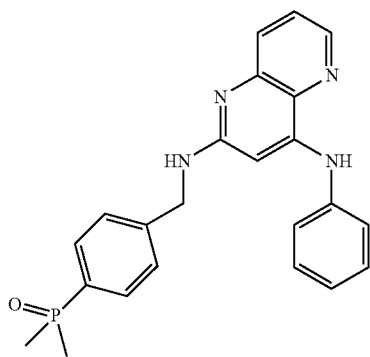
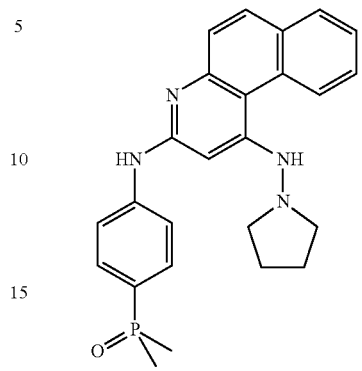
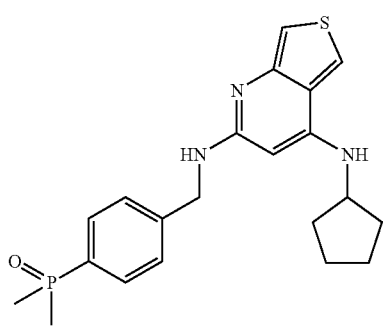
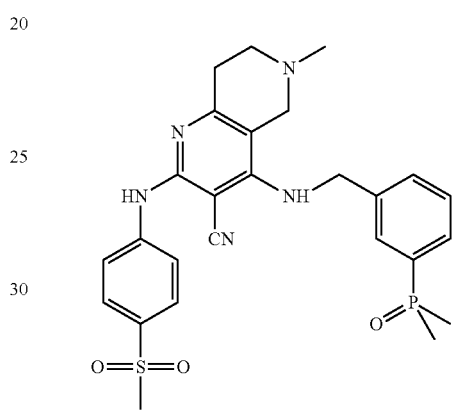
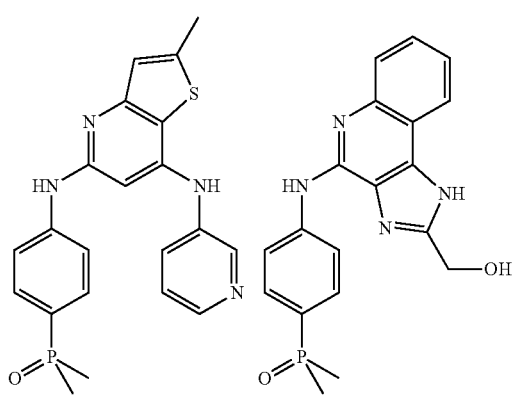
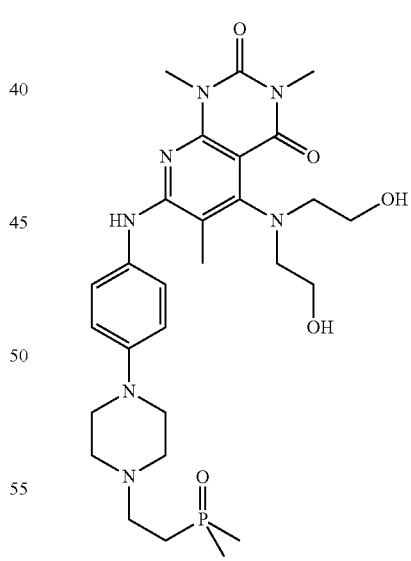
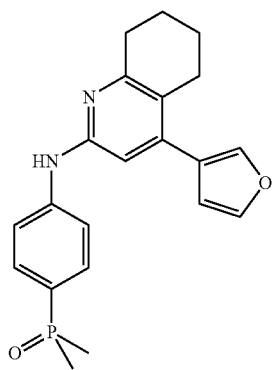
In another embodiment, two adjacent substituents selected from $R^b$, $R^c$, $R^{b1}$ and $R^{c1}$ form with the atoms to which they are attached a 5-, 6- or 7-membered saturated, partially saturated or unsaturated Ring D, which is substituted with 1 to 4 $R^f$ groups; and which contains 0-4 heteroatoms selected from N, O and $S(O)_r$. This class is illustrated by compounds of Formula V:

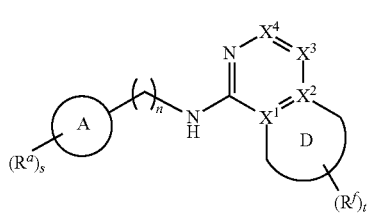

Formula V in which R$^a$, s, n, X$^1$, X$^2$, X$^3$, X$^4$ and R$^f$ are as defined above in Formula I; and t is 1, 2, 3 or 4.

Illustrative examples of this class are the following compounds of Formula V:

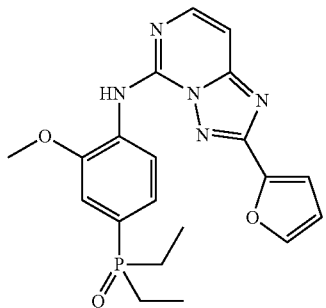

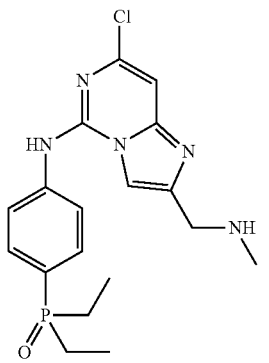

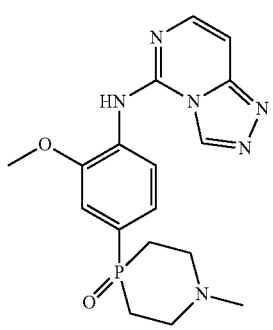

One class of compounds which is of special interest for use in the invention are compounds of Formula V, as described above, in which X$^1$ is CR$^b$, X$^2$ is CR$^c$, X$^3$ is CR$^d$ and X$^4$ is CR$^e$ and R$^b$ and R$^c$ form with the atoms to which they are attached a 5-, 6- or 7-membered saturated, partially saturated or unsaturated Ring D. This class is illustrated by compounds of Formula VA:

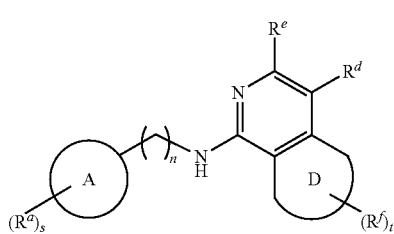

Formula VA in which R$^a$, s, n, t, Ring A, Ring D, R$^d$, R$^e$ and R$^f$ are as defined above in Formula V.

In one particular aspect of this embodiment, one R$^a$ is or contains —P(=O)(R$^3$)$_2$ or a ring system containing the moiety —P(=O)(R$^3$)— as a ring member.

In another aspect of this embodiment, one of R$^f$ is or contains —P(=O)(R$^3$)$_2$ or a ring system containing the moiety —P(=O)(R$^3$)— as a ring member.

One class of compounds of special interest are compounds of Formula V or VA in which Ring A is a phenyl.

Illustrative examples of this class are the following compounds of Formula VA:

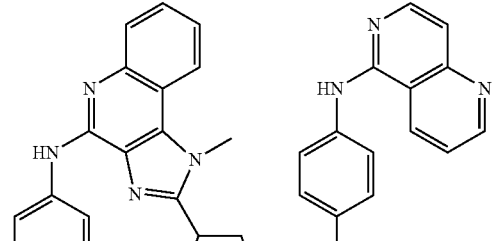

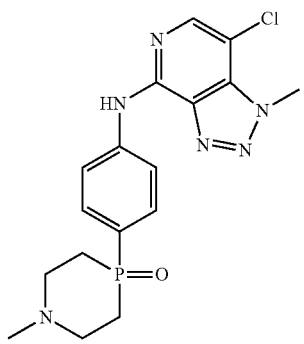

-continued

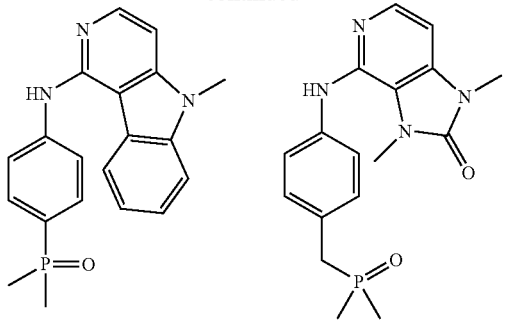

The invention also features compounds of Formula VI:

Formula VI

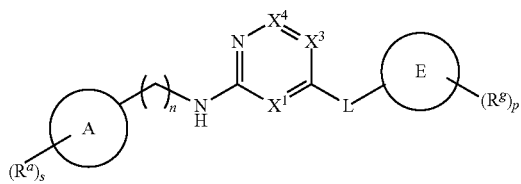

wherein
$X^1$ is $NR^{b1}$ or $CR^b$;
$X^3$ is $NR^{d1}$ or $CR^d$;
$X^4$ is $NR^{e1}$ or $CR^e$;
Ring A is an aryl, a 5- or a 6-membered heteroaryl ring which contains 1 to 4 heteroatoms selected from N, O and $S(O)_r$;
Ring E represents an aryl, a carbocyclyl or a 5-, 6- or 7-membered heterocyclic or heteroaryl ring comprising carbon atoms and 1-4 heteroatoms independently selected from O, N and $S(O)_r$; Ring E is optionally fused with a 5-, 6- or 7-membered saturated, partially saturated or unsaturated ring and Ring E is substituted on carbon or on the heteroatom(s) with 1-7 $R^g$ groups.
L is a bond, $O(CH_2)_y$, $NR^4(CH_2)_y$, $S(O)_r(CH_2)_y$, $(CH_2)_y$, $(CH_2)_ySO_2NR^4$, $(CH_2)_yNR^4SO_2$, $(CH_2)_yCH=CH$, $(CH_2)_yC\equiv C$, $(CH_2)_y$

, $(CH_2)_yC(O)NR^4$, $(CH_2)_yNR^4C(O)$; y is 0, 1, 2, 3 or 4; p is 1, 2, 3, 4, 5, 6 or 7; r is 0, 1 or 2, $R^4$ is H or alkyl; and the linker L can be included in either direction.
at each occurrence $R^a$, $R^b$, $R^d$ and $R^e$ are independently selected from the group consisting of halo, —CN, —$NO_2$, —$R^1$, —$OR^2$, —O—$NR^1R^2$, —$NR^1R^2$, —$NR^1$—$NR^1R^2$, —$NR^1$—$OR^2$, —C(O)$YR^2$, —OC(O)$YR^2$, —$NR^1$C(O)$YR^2$, —SC(O)$YR^2$, —$NR^1$C(=S)$YR^2$, —OC(=S)$YR^2$, —C(=S)$YR^2$, —YC(=$NR^1$)$YR^2$, —YC(=N—$OR^1$)$YR^2$, —YC(=N—$NR^1R^2$)$YR^2$, —YP(=O)($YR^3$)($YR^3$), —Si($R^{3a}$)$_3$, —$NR^1SO_2R^2$, —S(O)$_rR^2$, —$SO_2NR^1R^2$ and —$NR^1SO_2NR^1R^2$, and $R^{b1}$, $R^{d1}$ and $R^{e1}$ are absent; wherein each Y is independently a bond, —O—, —S— or —$NR^1$—; or
alternatively two adjacent substituents selected from $R^b$, $R^{b1}$, $R^d$, $R^{d1}$, $R^e$ and $R^{e1}$; or two adjacent $R^a$ moieties, can form with the atoms to which they are attached a 5-, 6- or 7-membered saturated, partially saturated or unsaturated ring, which contains 0-4 heteroatoms selected from N, O and $S(O)_r$ and which is substituted with one to four $R^f$ moieties wherein;
each $R^f$ moiety is independently selected from the group consisting of halo, =O, =S, —CN, —$NO_2$, —$R^1$, —$OR^2$, —O—$NR^1R^2$, —$NR^1R^2$, —$NR^1$—$NR^1R^2$, —$NR^1$—$OR^2$, —C(O)$YR^2$, —OC(O)$YR^2$, —$NR^1$C(O)$YR^2$, —SC(O)$YR^2$, —$NR^1$C(=S)$YR^2$, —OC(=S)$YR^2$, —C(=S)$YR^2$, —YC(=$NR^1$)$YR^2$, —YC(=N—$OR^1$)$YR^2$, —YC(=N—$NR^1R^2$)$YR^2$, —YP(=O)($YR^3$)($YR^3$), —Si($R^{3a}$)$_3$, —$NR^1SO_2R^2$, —S(O)$_rR^2$, —$SO_2NR^1R^2$ and —$NR^1SO_2NR^1R^2$; or alternatively two adjacent $R^f$ moieties can form with the atoms to which they are attached a 5-, 6- or 7-membered saturated, partially saturated or unsaturated ring, optionally substituted; and which contains 0-4 heteroatoms selected from N, O and $S(O)_r$;
each $R^g$ moiety is independently selected from the group consisting of halo, =O, =S, —CN, —$NO_2$, —$R^1$, —$OR^2$, —O—$NR^1R^2$, —$NR^1R^2$, —$NR^1$—$NR^1R^2$, —$NR^1$—$OR^2$, —C(O)$YR^2$, —OC(O)$YR^2$, —$NR^1$C(O)$YR^2$, —SC(O)$YR^2$, —$NR^1$C(=S)$YR^2$, —OC(=S)$YR^2$, —C(=S)$YR^2$, —YC(=$NR^1$)$YR^2$, —YC(=N—$OR^1$)$YR^2$, —YC(=N—$NR^1R^2$)$YR^2$, —YP(=O)($YR^3$)($YR^3$), —Si($R^{3a}$)$_3$, —$NR^1SO_2R^2$, —S(O)$_rR^2$, —$SO_2NR^1R^2$ and —$NR^1SO_2NR^1R^2$; wherein each Y is independently a bond, —O—, —S— or —$NR^1$—;
and at least one of $R^a$, $R^b$, $R^d$, $R^e$ or $R^g$, when present, is or contains —P(=O)($R^3$)$_2$ or a ring system containing the moiety —P(=O)($R^3$)— as a ring member;
r is 0, 1 or 2;
s is 1, 2, 3, 4 or 5
n is 0 or 1;
p is 1, 2, 3 or 4;
each occurrence of Y is independently a bond, —O—, —S— or —$NR^1$—;
each occurrence of $R^1$ and $R^2$ is independently selected from H, alkyl, alkenyl, alkynyl, cycloalkyl, cycloalkenyl, cycloalkynyl, aryl, heteroalkyl, heterocyclic and heteroaryl;
each occurrence of $R^3$ is independently selected from alkyl, alkenyl, alkynyl, cycloalkyl, cycloalkenyl, cycloalkynyl, aryl, heteroalkyl, heterocyclic and heteroaryl, or two adjacent $R^3$ moieties combine to form a ring system including a phosphorous atom;
each occurrence of $R^{3a}$ is independently selected from alkyl, alkenyl, alkynyl, cycloalkyl, cycloalkenyl, cycloalkynyl, aryl, heteroalkyl, heterocyclic, and heteroaryl;
alternatively, each $NR^1R^2$ moiety may be a 5-, 6- or 7-membered saturated, partially saturated or unsaturated ring, which can be optionally substituted and which contains 0-2 additional heteroatoms selected from N, O and $S(O)_r$; and
each of the foregoing alkyl, alkenyl, alkynyl, cycloalkyl, cycloalkenyl, cycloalkynyl, aryl, heteroaryl and heterocyclic moiety is optionally substituted.

In one embodiment are compounds of Formula VI in which one of $R^a$ is or contains —P(=O)($R^3$)$_2$.

In another embodiment are compounds of Formula VI in which one of $R^g$ is or contains —P(=O)($R^3$)$_2$.

In one embodiment are compounds of formula VI in which L is a bond. Non-limiting examples of this class include the following compounds:

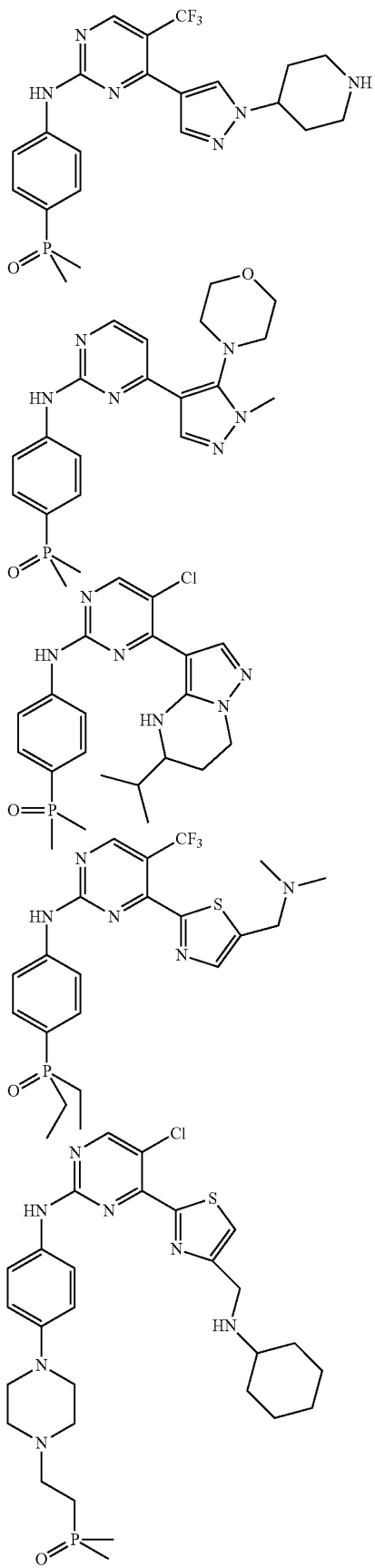
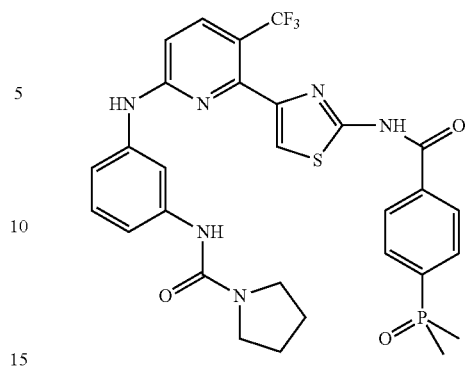
In another embodiment are compounds of formula VI in which L is $NR^4(CH_2)_y$. In a particular aspect, L is $NR^4$. In another particular aspect, L is $NR^4(CH_2)_{1-3}$. Non-limiting examples of L linker are $NHCH_2CH_2$, $NHCH_2$, NH and $NCH_3$. Non limiting examples of this class include the following compounds:
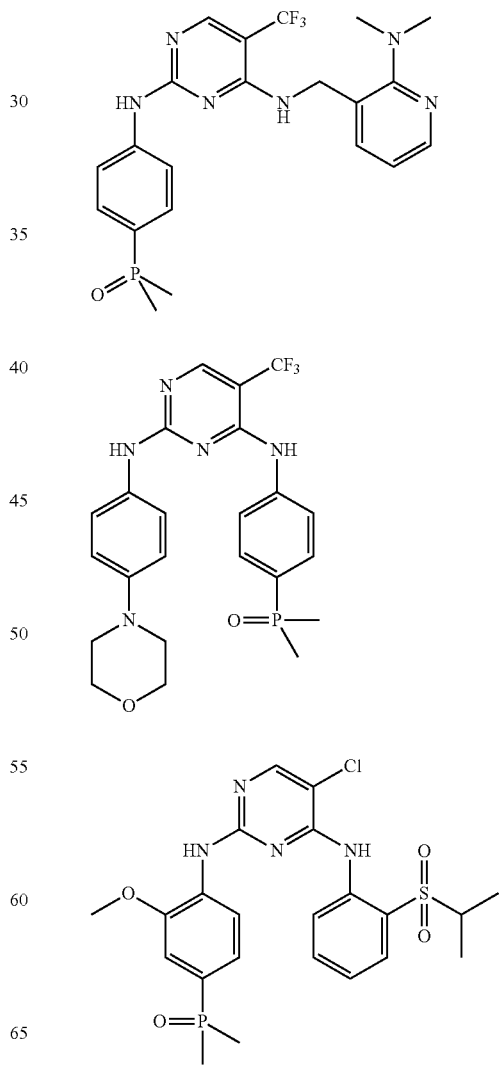

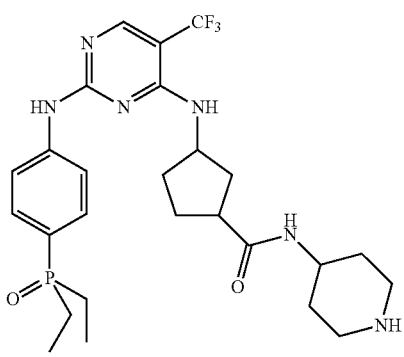
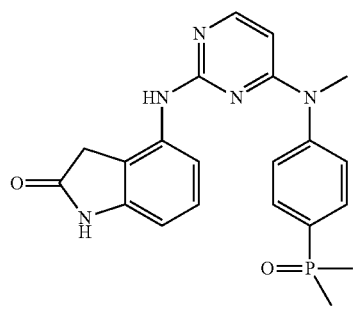
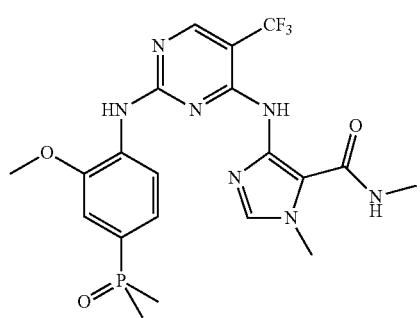
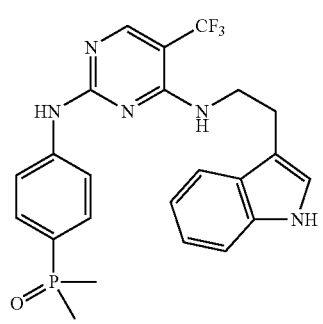
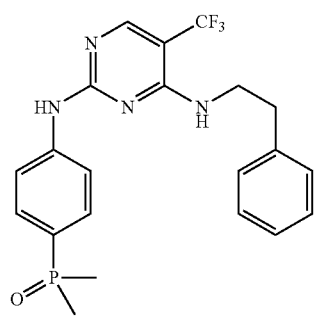
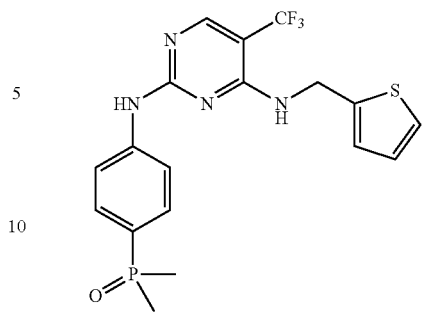
In another embodiment are compounds of formula VI in which L is O(CH$_2$)$_y$. Non limiting examples of this class include the following compounds:
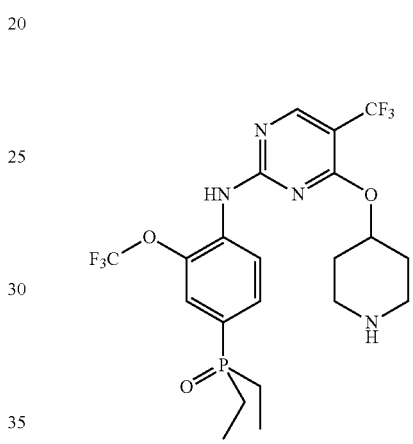
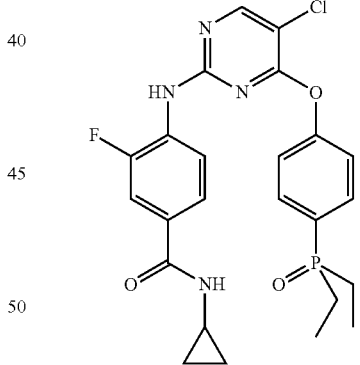
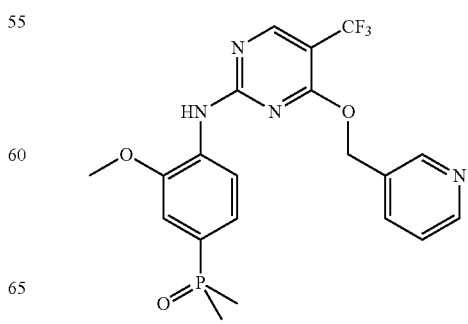

-continued

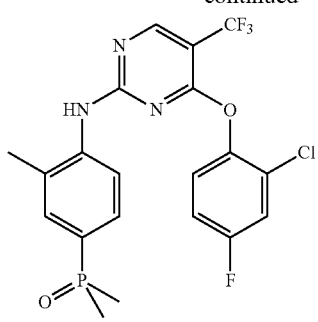

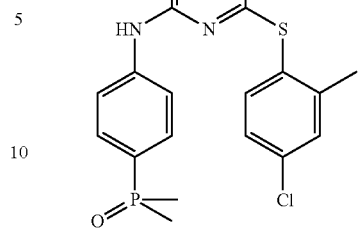

In another embodiment are compounds of Formula VI in which L is $(CH_2)_y C(O)NR^4$ or $(CH_2)_y NR^4 C(O)$. Non limiting examples of this class include the following compounds:

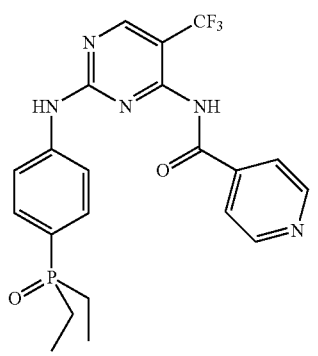

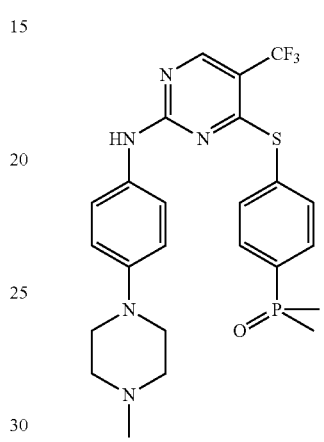

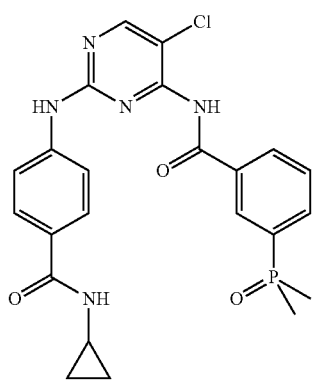

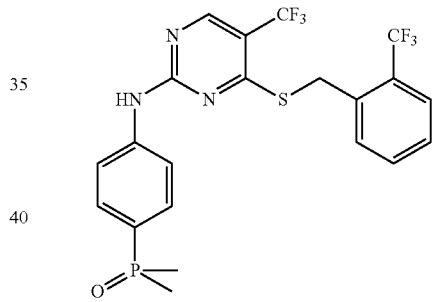

In still another embodiment are compounds of Formula VI in which Ring E is an aryl, substituted with 1 to 5 $R^g$ groups. Non-limiting examples of this class are compounds of the following types:

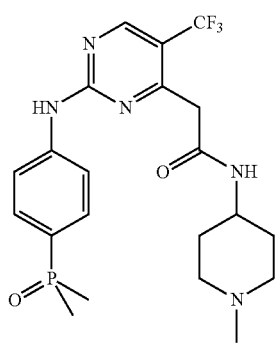

In another embodiment are compounds of formula VI in which L is $S(CH_2)_y$. Non limiting examples of this class include the following compounds:

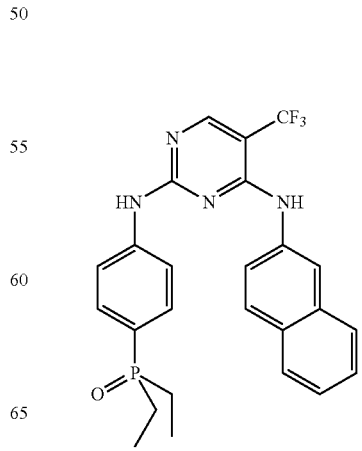

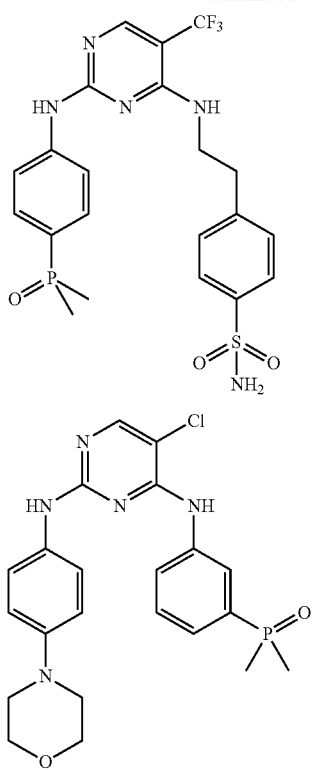

In another embodiment are compounds of Formula VI in which Ring E is a 5-, 6- or 7-membered heterocyclyl ring comprising carbon atoms and 1-3 heteroatoms independently selected from O, N and S(O)$_r$, and Ring E is substituted on carbon or on the heteroatom(s) with 1-7 R$^g$ groups. It is understood that the total number of substituents R$^g$ does not exceed the normal available valencies. Non-limiting examples of this class are compounds of formula VI in which Ring E is of the following types:

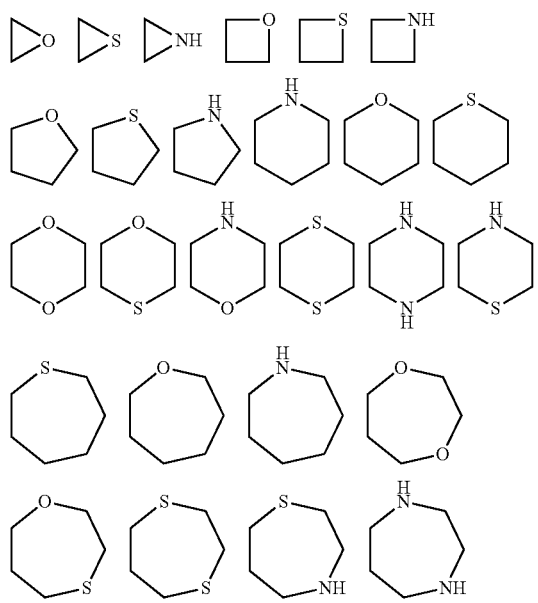

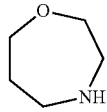

Non-limiting illustrative examples are compounds of the following formulae:

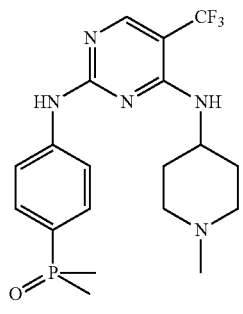

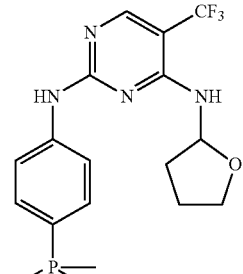

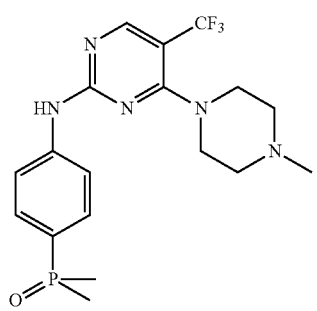

In another embodiment are compounds of Formula VI in which Ring E is a carbocyclyl ring and Ring E is substituted with 1-7 R$^g$ groups. Non-limiting examples of this class are compounds of the following types:

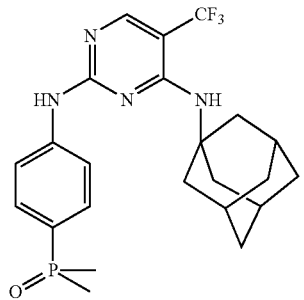

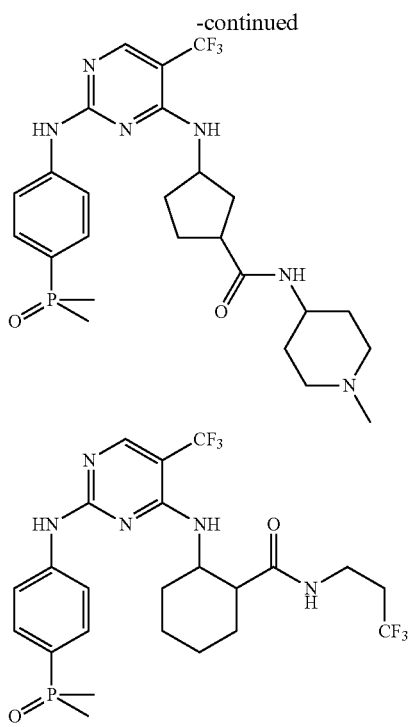

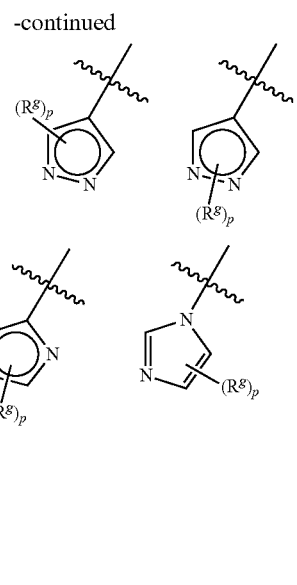

In another aspect of the previous embodiment, Ring E is a 5-, 6- or 7-membered heteroaryl ring comprising carbon atoms and 1-3 heteroatoms independently selected from O, N and $S(O)_r$. For example, Ring E can be a 5-membered ring heteroaryl comprising carbon atoms and 1-3 Nitrogen atoms. Non-limiting examples of this class are compounds in which Ring E is of the following types:

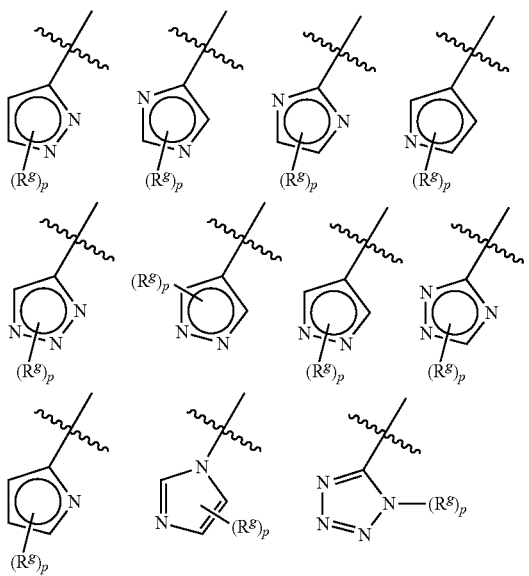

In certain embodiments, Ring E has the following formulae:

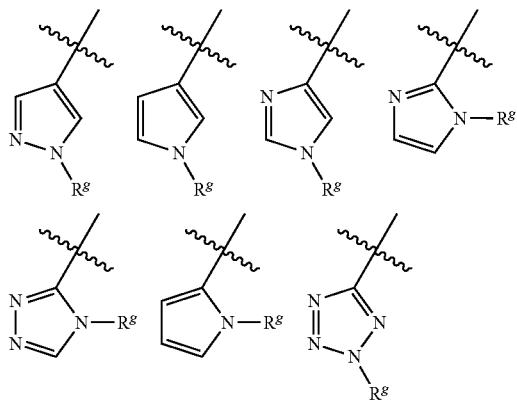

Of additional interest is a class of compounds as described above in which $R^g$ is selected from the group consisting of —$R^1$ and —C(O)$YR^2$. In another subclass of interest, are compounds of the above embodiment in which $R^g$ is an aryl, heteroaryl, substituted alkyl or heterocyclyl. Non limiting examples of substituted alkyl are —$(CH_2)_zC(=O)NR^1R^2$, —$(CH_2)_zNHC(=O)R^2$, —$(CH_2)_zNR^1R^2$, —$(CH_2)_zC(=O)$ $OR^1$, —$(CH_2)_z$heterocyclyl, —$(CH_2)_z$ aryl, —$(CH_2)_z$heteroaryl in which z is 1, 2, 3 or 4 and alkyl include straight (i.e. unbranched or acyclic), branched and cyclic alkyl groups and alkyl, aryl, heteroaryl, heterocyclyl groups are optionally substituted.

Illustrative examples of such Ring E groups including substituent $R^g$ include, without limitation:

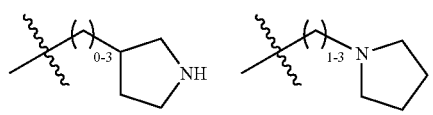

-continued

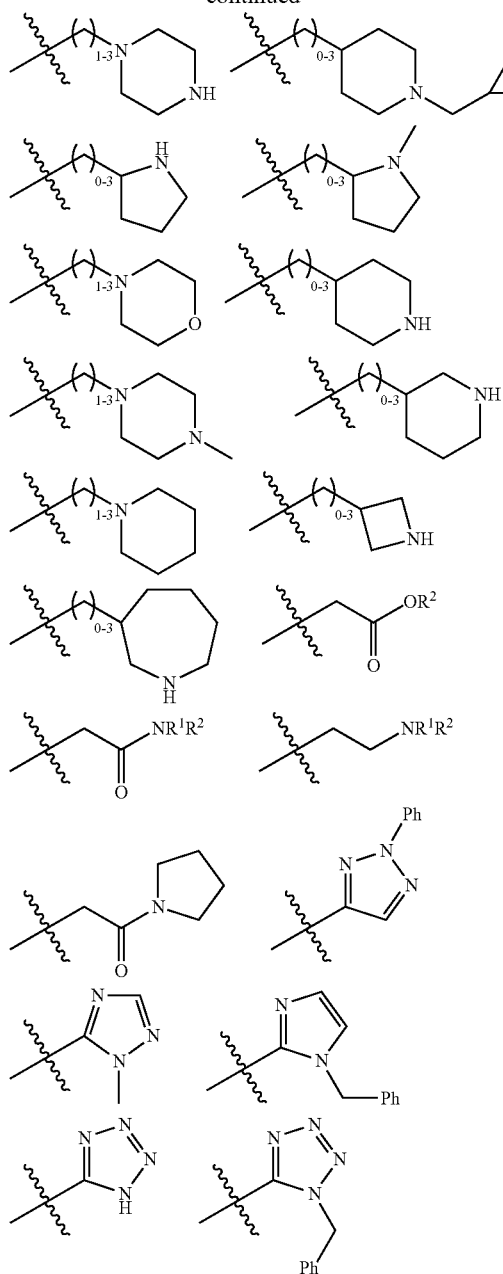

Non-limiting Illustrative examples of this class are compounds of the following formulae:

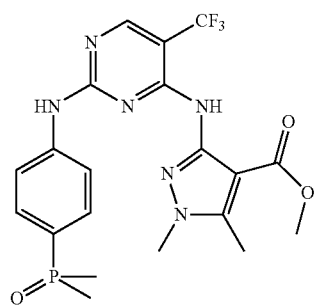

-continued

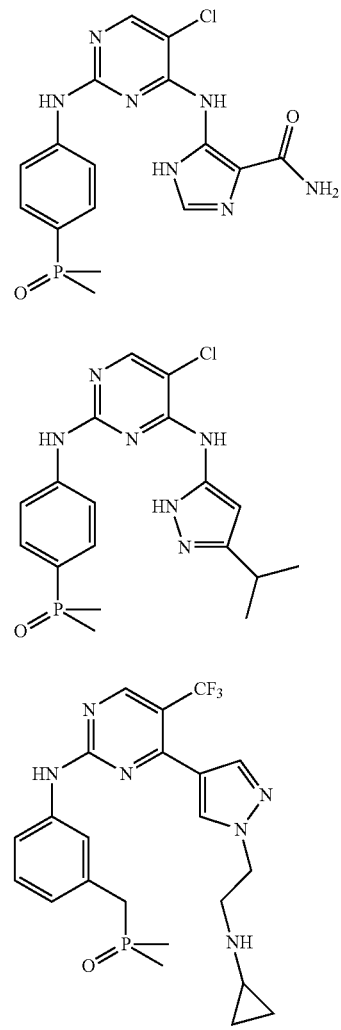

In another embodiment, Ring E is a 5-membered ring heteroaryl comprising carbon atoms and 1-3 Nitrogen atoms and the heteroaryl ring is linked to the core moiety via a nitrogen atom. In one preferred aspect of this embodiment L is a bond or $(CH_2)_y$.

Of additional interest is a class of compounds as described above in which $R^g$ is selected from the group consisting of —$R^1$, —$OR^2$, —$P(=O)(R^3)_2$, —$NR^1R^2$, —$C(O)YR^2$, —$NR^1C(O)YR^2$, —$NR^1SO_2R^2$, —$S(O)_rR^2$, —$SO_2NR^1R^2$ and —$NR^1SO_2NR^1R^2$. In another subclass of interest, are compounds of the above embodiment in which $R^g$ is an aryl, heteroaryl, substituted alkyl or heterocyclyl. Non limiting examples of $R^g$ are —$(CH_2)_yC(=O)NR^1R^2$, —$(CH_2)_yNHC(=O)R^2$, —$(CH_2)_yNR^1R^2$, —$(CH_2)_y$heterocyclyl, —$(CH_2)_y$aryl, —$(CH_2)_y$heteroaryl, NH-aryl, NH-heteroaryl and NH-heterocyclyl; in which y is 0, 1, 2, 3 or 4 and alkyl include straight (i.e. unbranched or acyclic), branched and cyclic alkyl groups and alkyl, aryl, heteroaryl, heterocyclyl groups are optionally substituted.

Illustrative non limiting examples of such compounds include compounds of Formula VI in which Ring E is a triazole of the following formulae:

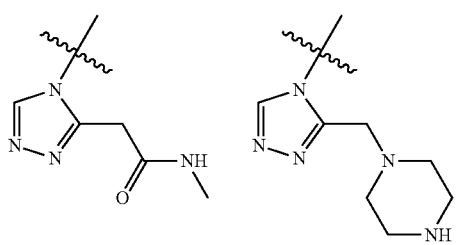
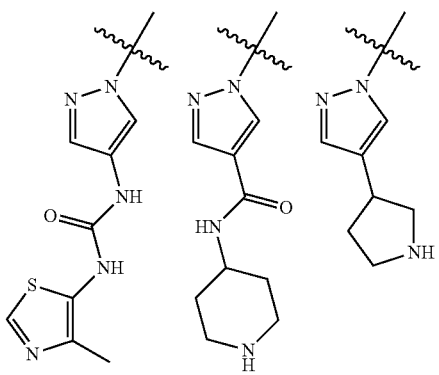
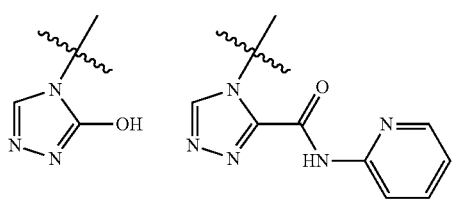
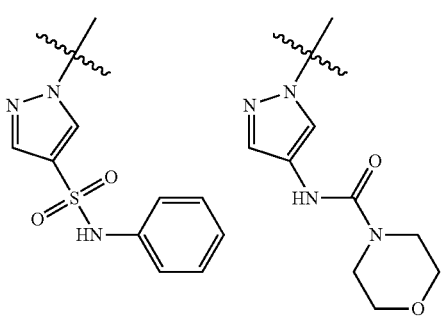
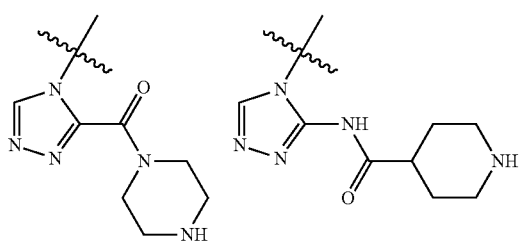
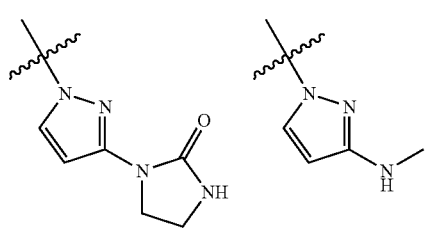
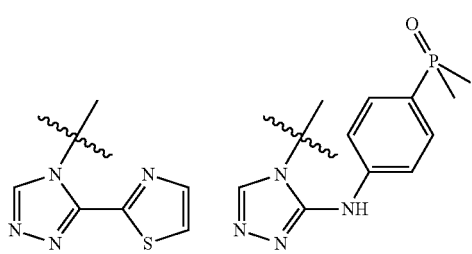
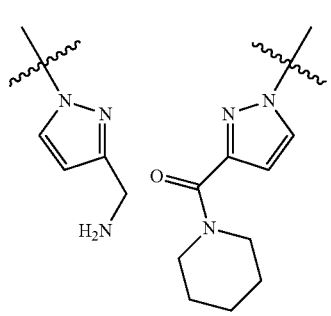
In another embodiment, Ring E is a pyrazole of the following formulae:
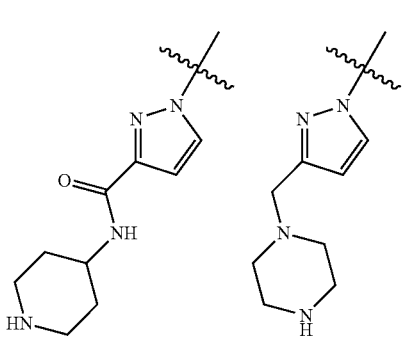

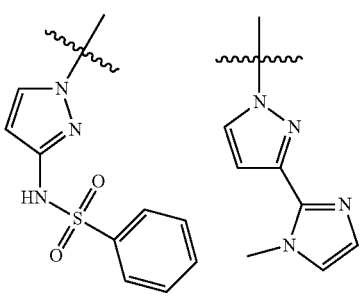

In another aspect of the previous embodiment, Ring E is a tetrazole of the following formulae:

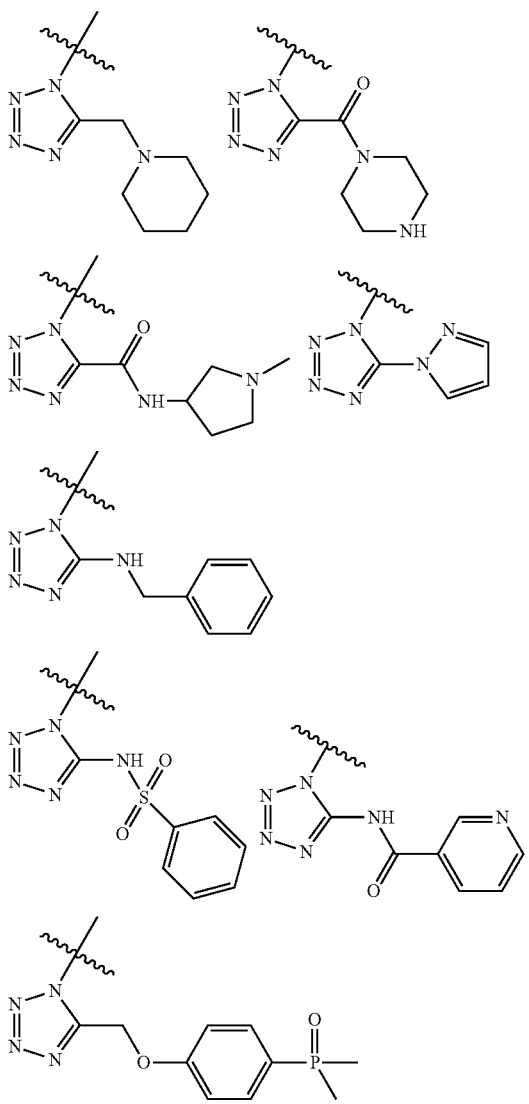

In another embodiment, Ring E is a 5-membered ring heteroaryl comprising carbon atoms and 1-3 heteroatoms selected from N and O. Non limiting examples are compounds of formula VI in which Ring E is of the following type:

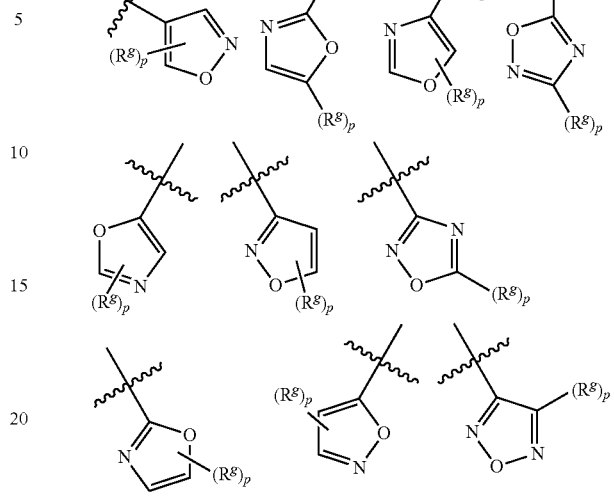

in which p is defined previously and the total number of substituents $R^g$ does not exceed the normal available valencies.

In certain particular embodiments, Ring E has the following formulae:

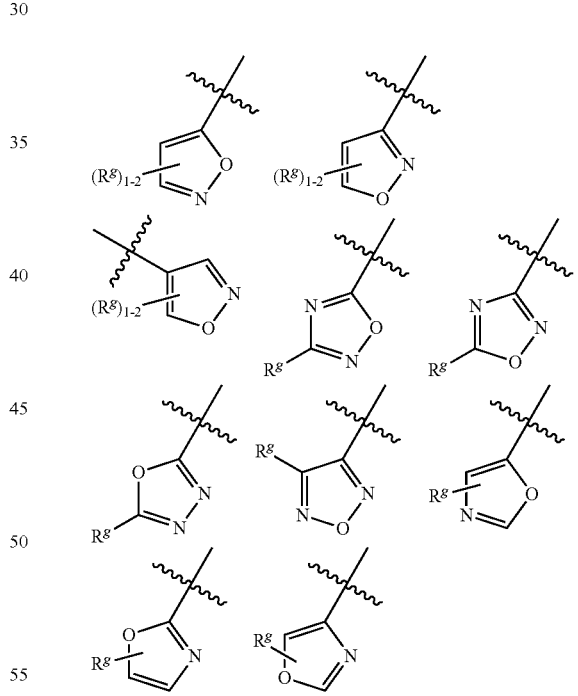

in which Ring E is substituted with one or two $R^g$ substituents.

Of additional interest is a class of compounds as described above in which $R^g$ is selected from the group consisting of —$R^1$, —P(=O)($R^3$)$_2$, —O$R^2$, —N$R^1R^2$, —C(O)Y$R^2$, —N$R^1$C(O)Y$R^2$, —N$R^1$SO$_2R^2$, —S(O)$_rR^2$, —SO$_2$N$R^1R^2$ and —N$R^1$SO$_2$N$R^1R^2$. In another subclass of interest, are compounds of the above embodiment in which $R^g$ is NHC(O)$R^1$, NHC(O)N$R^1R^2$, C(O)NH$R^1$, C(O)N$R^1R^2$, N$R^1R^2$, an aryl, heteroaryl, substituted alkyl or heterocyclyl. Non limiting examples of $R^g$ are —$(CH_2)_yC(=O)NR^1R^2$, —$(CH_2)_yNHC(=O)R^2$, —$(CH_2)_yNR^1R^2$, —$(CH_2)_yOR^2$, —$(CH_2)_y$heterocyclyl, —$(CH_2)_y$aryl, —$(CH_2)_y$heteroaryl, NH-aryl, NH-heteroaryl and NH-heterocyclyl, —$(CH_2)_mP(=O)(alkyl)_2$; in which y and m are independently selected from 0, 1, 2, 3 and 4 and alkyl include straight (i.e. unbranched or acyclic), branched and cyclic alkyl groups and alkyl, aryl, heteroaryl, heterocyclyl groups are optionally substituted.

Non-limiting examples of this class include compounds of formula VI in which Ring E is:

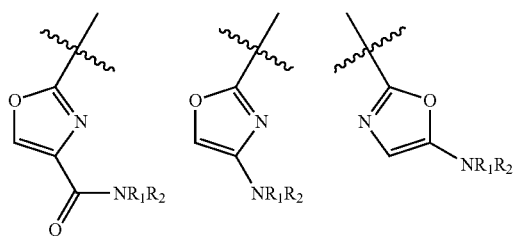
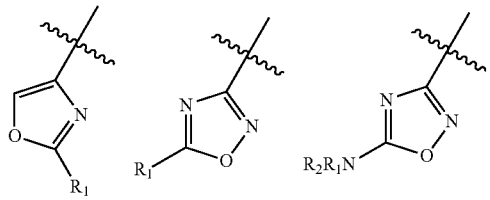
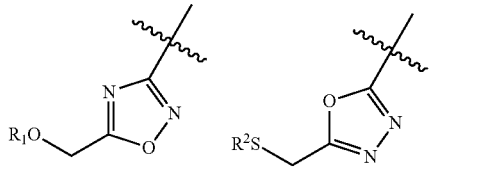
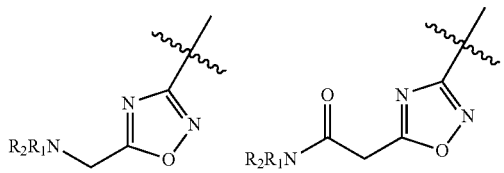
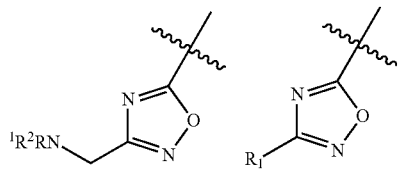
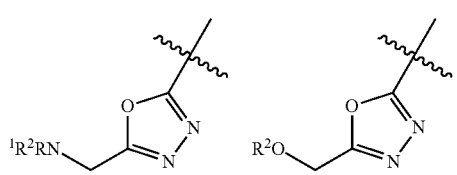
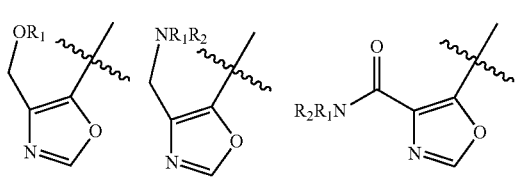
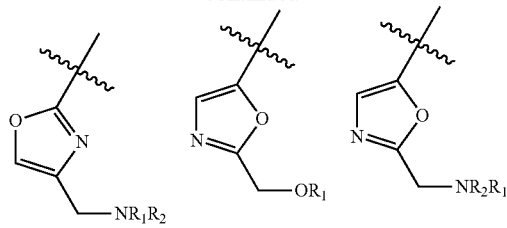
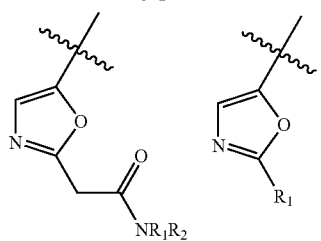

Specific, non-limiting illustrative examples of this class include compounds of formula VI in which substituted Ring E is of the following formulae:

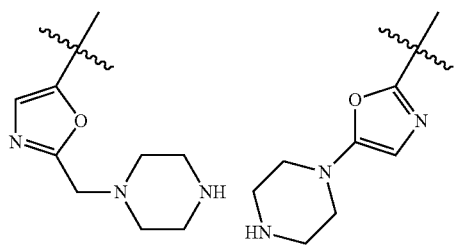
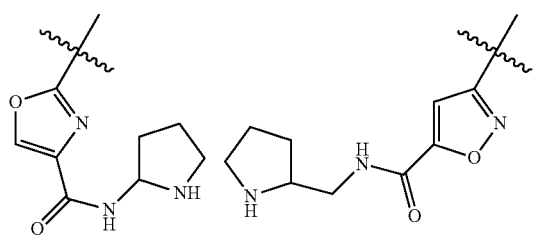
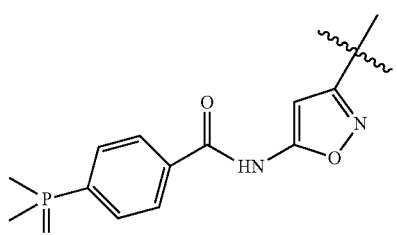
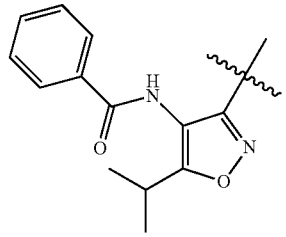

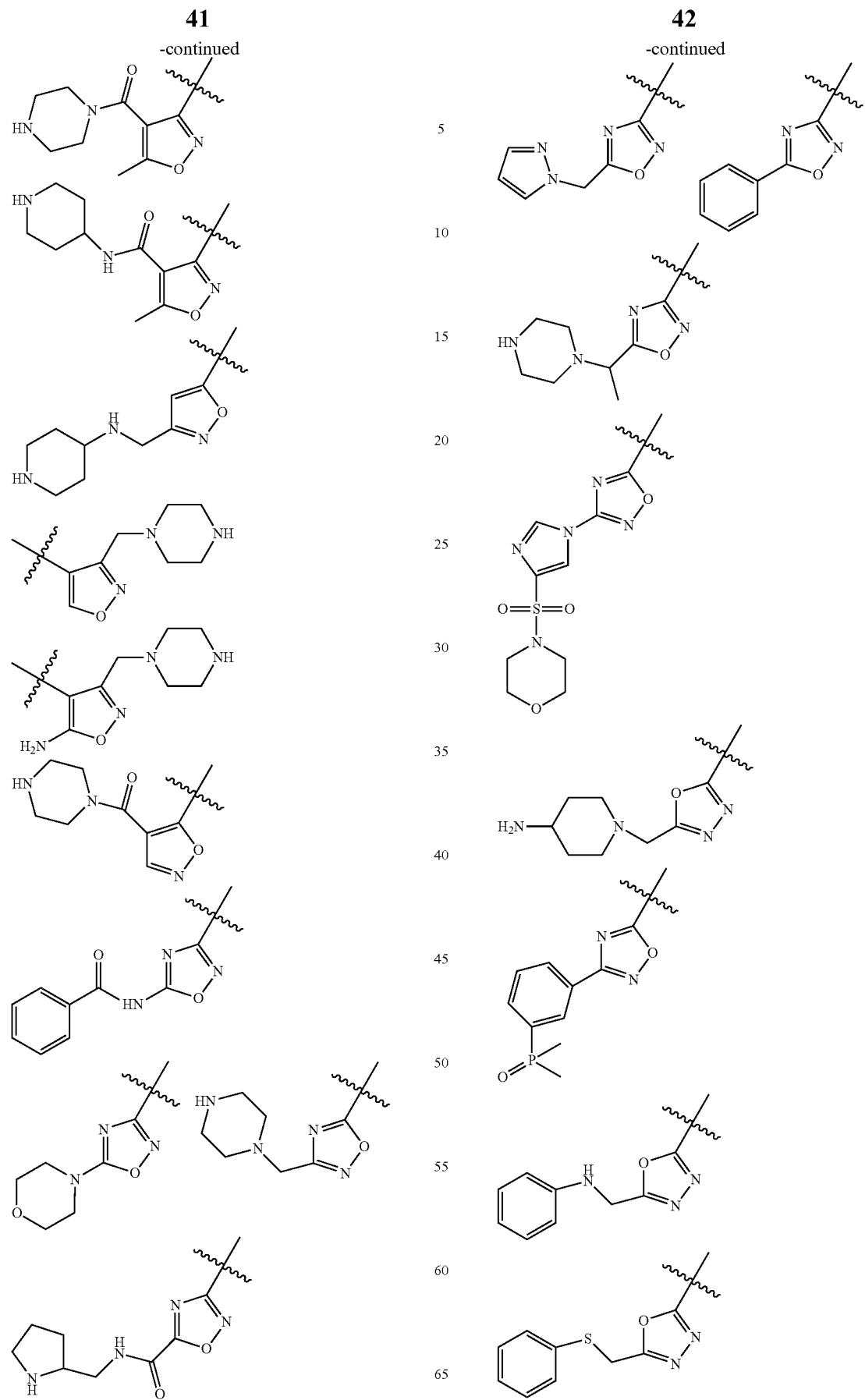

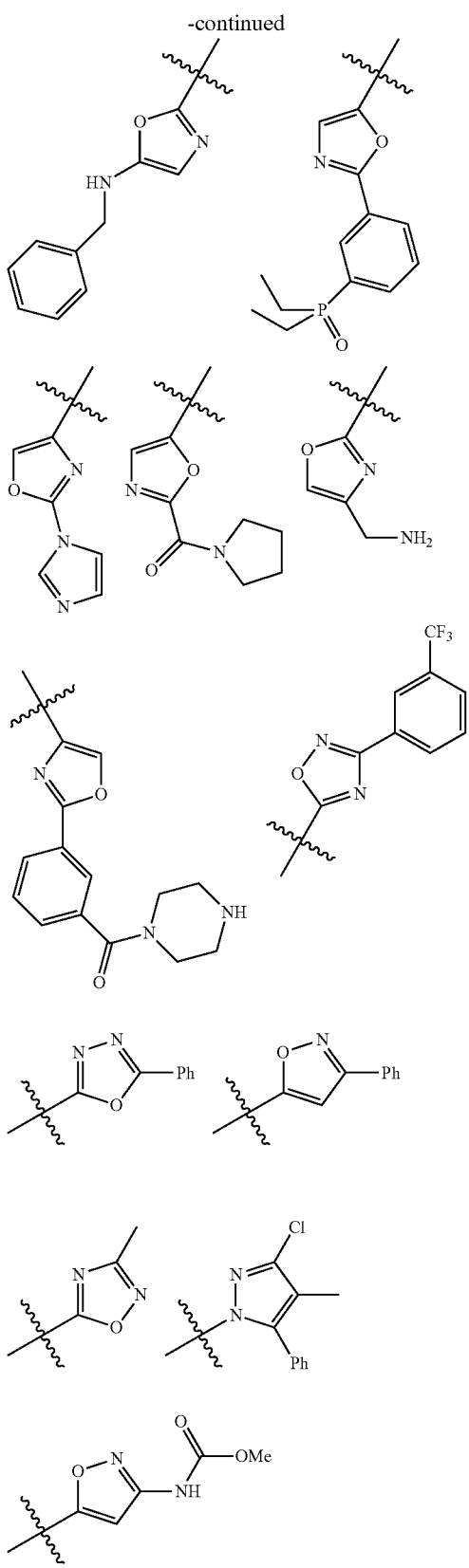

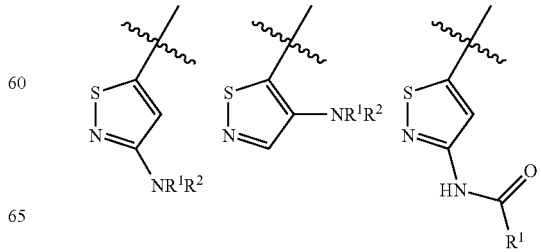

in which p is defined previously and the total number of substituents $R^g$ does not exceed the normal available valencies.

Of particular interest is a class of compounds as described above in which $R^g$ is selected from the group consisting of —$R^1$, —P(=O)($R^3$)$_2$, —$OR^2$, —$NR^1R^2$, —C(O)$YR^2$, —$NR^1$C(O)$YR^2$, —$NR^1SO_2R^2$, —S(O)$_rR^2$, —$SO_2NR^1R^2$ and —$NR^1SO_2NR^1R^2$. In another subclass of interest, are compounds of the above embodiment in which $R^g$ is NHC(O)$R^1$, C(O)$NHR^1$, C(O)$NR^1R^2$, NHC(O)$NHR^1$, $NR^1R^2$, an aryl, heteroaryl, substituted alkyl or heterocyclyl. Non limiting examples of $R^g$ are —(CH$_2$)$_y$C(=O)$NR^1R^2$, —(CH$_2$)$_y$NHC(=O)$R^2$, —(CH$_2$)$_y$$NR^1R^2$, —(CH$_2$)$_y$$OR^2$, —$SO_2NR^1R^2$, —(CH$_2$)$_y$$SR^2$, —(CH$_2$)$_y$heterocyclyl, —(CH$_2$)$_y$aryl, —(CH$_2$)$_y$heteroaryl, —NH-aryl, —NH-heteroaryl, NH-heterocyclyl and —(CH$_2$)$_m$P(=O)(alkyl)$_2$; in which y and m are independently selected from 0, 1, 2, 3 and 4 and alkyl include straight (i.e. unbranched or acyclic), branched and cyclic alkyl groups and alkyl, aryl, heteroaryl, heterocyclyl groups are optionally substituted.

Non-limiting examples of this class include compounds of formula VI in which Ring E is:

In another specific embodiment, Ring E is a 5-membered heteroaryl comprising carbon atoms and 1-3 heteroatoms selected from N and S.

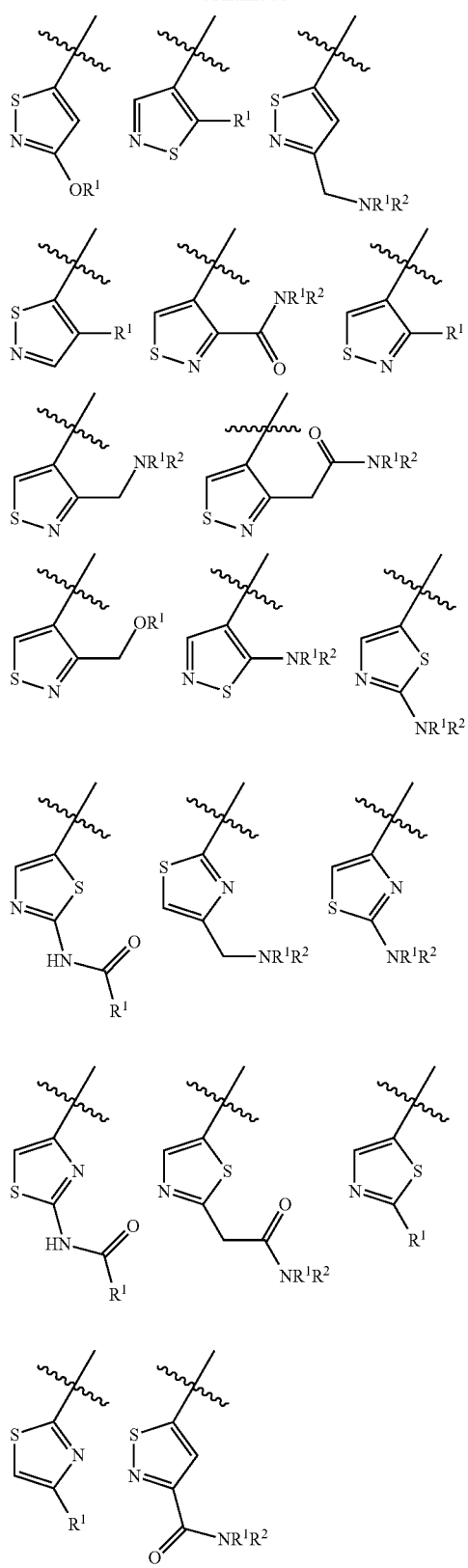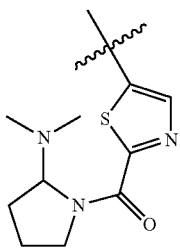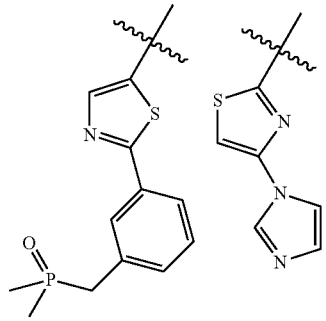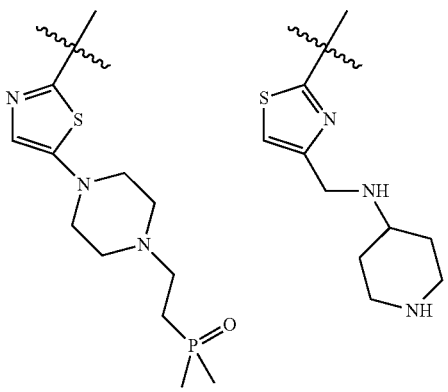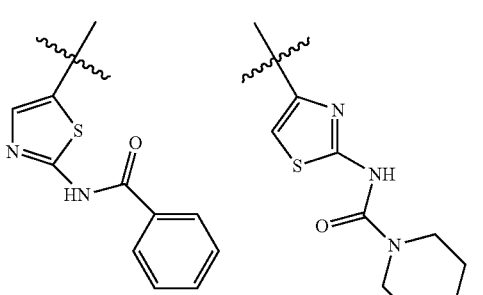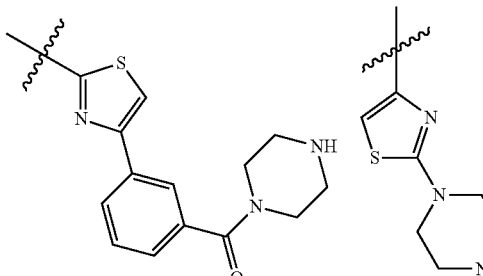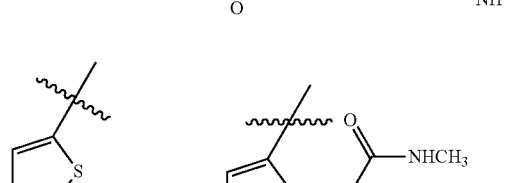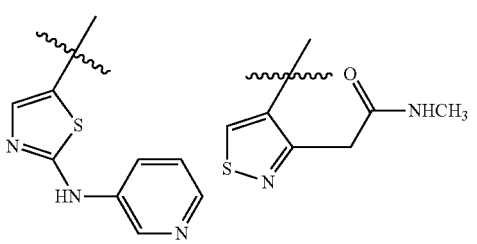
Specific, non-limiting illustrative examples of this class include compounds of formula VI in which substituted Ring E is of the following formulae:

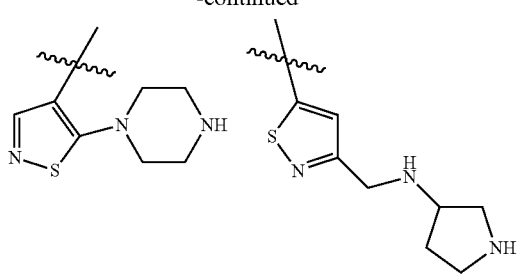

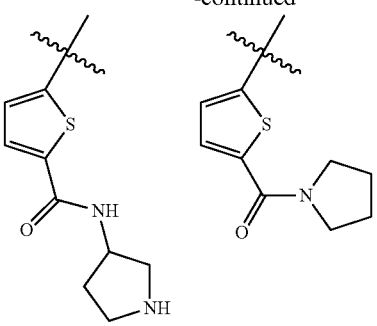

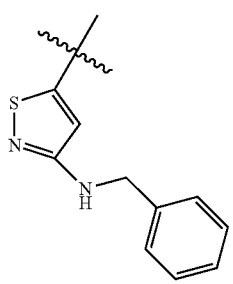 [SMILES: *c1cc(NCc2ccccc2)ns1]

Other non-limiting examples include compounds of formula VI in which Ring E is furan or thiofuran:

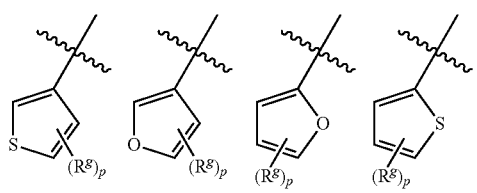

in which p is defined previously and the total number of substituents R$^g$ does not exceed the normal available valencies.

Specific, non-limiting illustrative examples of this class include compounds of formula VI in which substituted Ring E is of the following formulae:

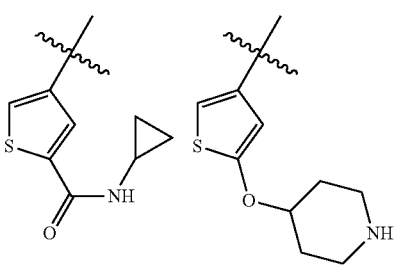

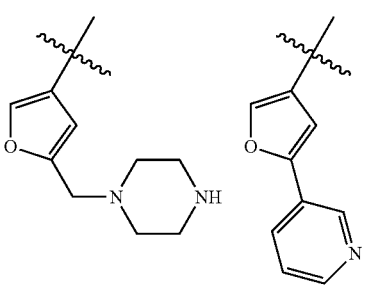

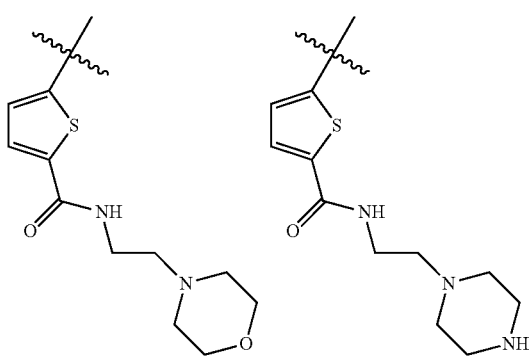

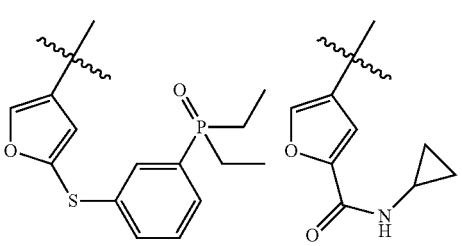

In another embodiment, Ring E is a 6-membered heteroaryl ring. For example, Ring E can be a pyrimidine of the following types:

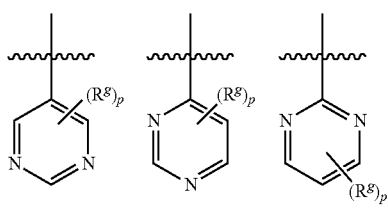

in which p is as previously described and the total number of substituents $R^g$ does not exceed the normal available valencies.

Of particular interest is a class of compounds as described above in which $R^g$ is selected from the group consisting of —$R^1$, —P(=O)($R^3$)$_2$, —O$R^2$, —N$R^1R^2$, —C(O)Y$R^2$, —N$R^1$C(O)Y$R^2$, —N$R^1$SO$_2R^2$, —S(O)$_rR^2$, —SO$_2$N$R^1R^2$ and —N$R^1$SO$_2$N$R^1R^2$. In another subclass of interest, are compounds of the above embodiment in which $R^g$ is NHC(O)$R^1$, NHC(O)NH$R^1$, C(O)NH$R^1$, C(O)N$R^1R^2$, N$R^1R^2$, an aryl, heteroaryl, substituted alkyl or heterocyclyl. Non limiting examples of $R^a$ are —OCH$_2$CH$_2$N$R^1R^2$, —OCH$_2$C(O)N$R^1R^2$, —N$R^1$C(O)N$R^1R^2$, —(CH$_2$)$_y$C(=O)N$R^1R^2$, —(CH$_2$)$_y$NHC(=O)$R^2$, —(CH$_2$)$_y$N$R^1R^2$, —(CH$_2$)$_y$O$R^2$, —SO$_2$N$R^1R^2$, —(CH$_2$)$_y$S$R^2$, —(CH$_2$)$_y$heterocyclyl, —(CH$_2$)$_y$aryl, —(CH$_2$)$_y$heteroaryl, NH-aryl, NH-heteroaryl, NH-heterocyclyl and —(CH$_2$)$_m$P(=O)(alkyl)$_2$; in which y and m are independently selected from 0, 1, 2, 3 and 4 and alkyl include straight (i.e. unbranched or acyclic), branched and cyclic alkyl groups and alkyl, aryl, heteroaryl, heterocyclyl groups are optionally substituted.

Non-limiting examples of this class are compounds of formula VI in which Ring E is:

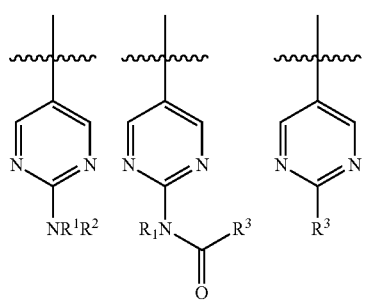

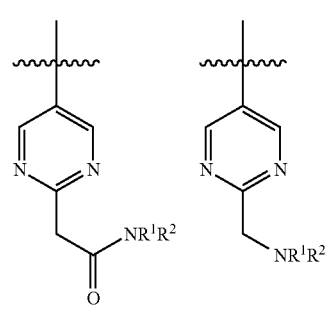

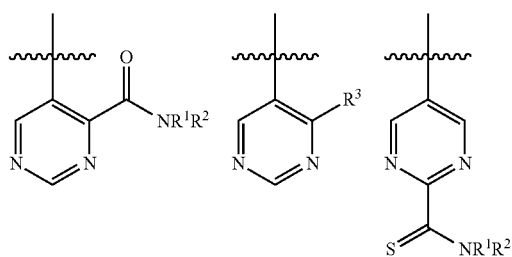

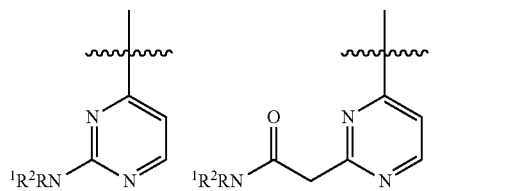

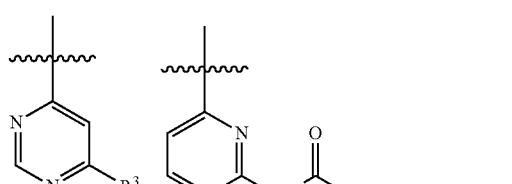

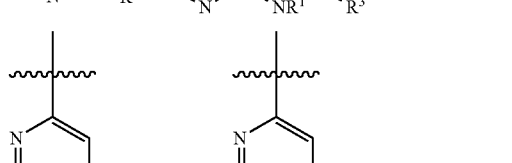

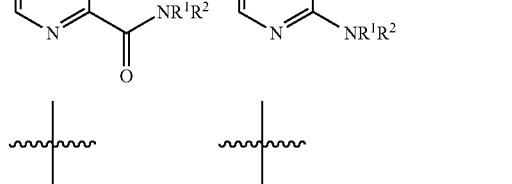

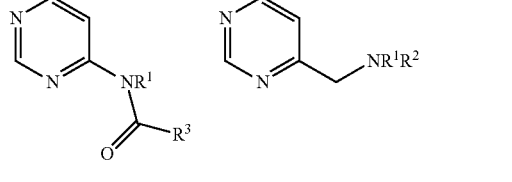

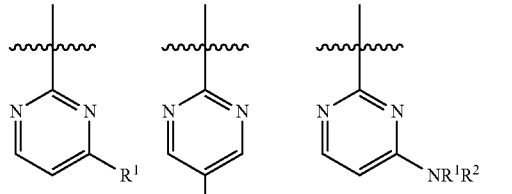

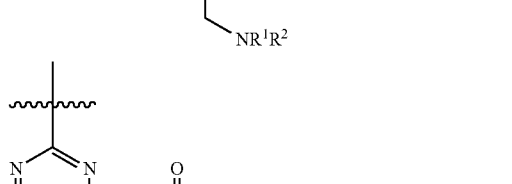

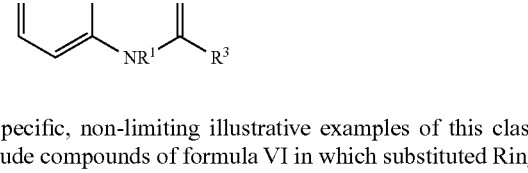

Specific, non-limiting illustrative examples of this class include compounds of formula VI in which substituted Ring E is of the following formulae:

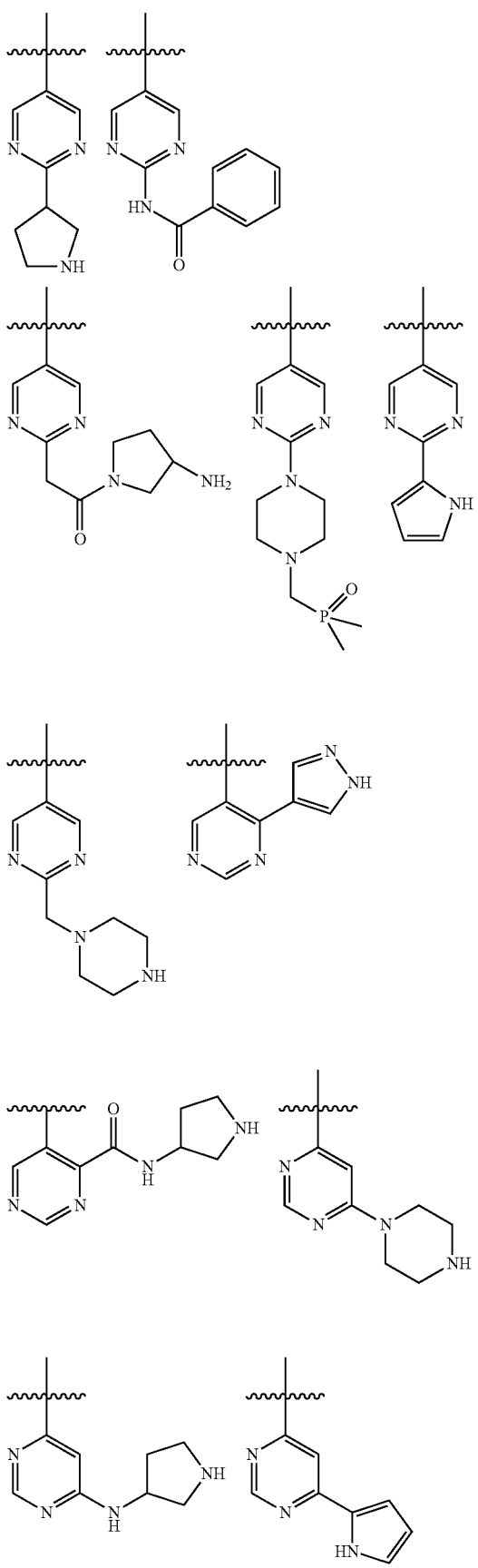
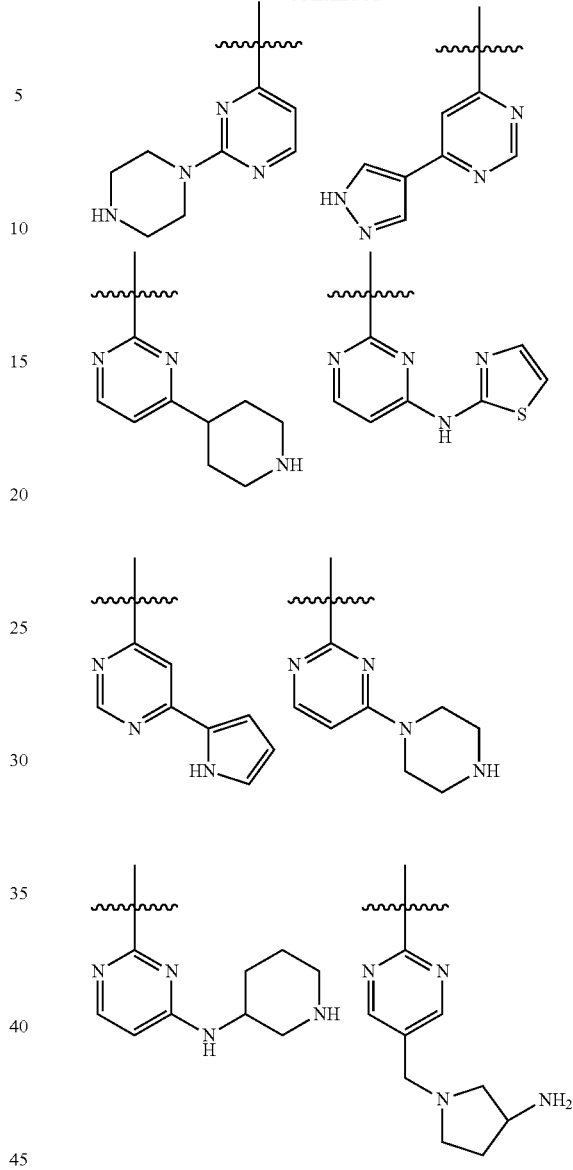

In another embodiment, Ring E is a pyridine substituted with 1-4 $R^g$. Of particular interest is a class of compounds as described above in which $R^g$ is selected from the group consisting of —$R^1$, —P(=O)($R^3$)$_2$, —$OR^2$, —$NR^1R^2$, —$NR^1C(O)R^2$, —$NR^1SO_2R^2$. In another subclass of interest, are compounds of the above embodiment in which $R^g$ is NHC(O)$R^2$, $NR^1R^4$, an aryl, heteroaryl, substituted alkyl or heterocyclyl. Non limiting examples of $R^g$ are —(CH$_2$)$_y$C(=O)NR$^1$R$^2$, —(CH$_2$)$_y$C(=O)aryl, —(CH$_2$)$_y$C(=O)heteroaryl, —(CH$_2$)$_y$C(=O)heterocyclyl, —(CH$_2$)$_y$NHC(=O)R$^2$, —(CH$_2$)$_y$NR$^1$R$^2$, —(CH$_2$)$_y$OR$^2$, —(CH$_2$)$_y$SR$^2$, —(CH$_2$)$_y$heterocyclyl, —(CH$_2$)$_y$aryl, —(CH$_2$)$_y$heteroaryl, —NH-aryl, NH-heteroaryl, NH-heterocyclyl and —(CH$_2$)$_m$P(=O)(alkyl)$_2$, in which y and m are independently selected from 0, 1, 2, 3 and 4; and alkyl include straight (i.e. unbranched or acyclic), branched and cyclic alkyl groups and alkyl, aryl, heteroaryl, heterocyclyl groups are optionally substituted.

Non-limiting examples of this class are compounds of formula VI in which Ring E is:

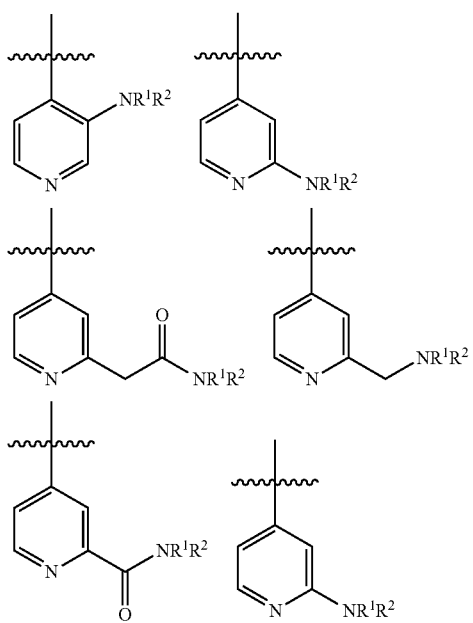
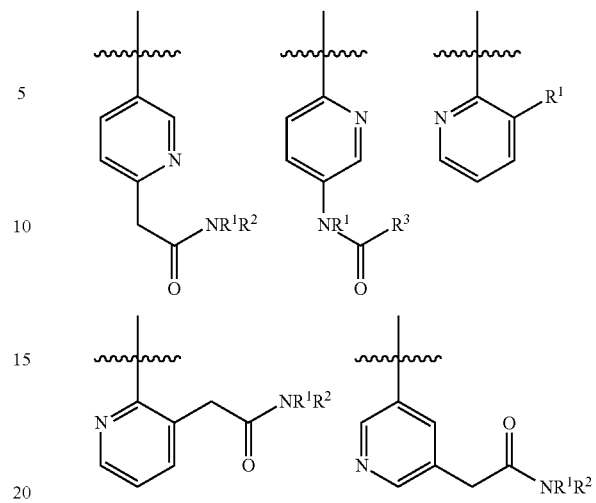
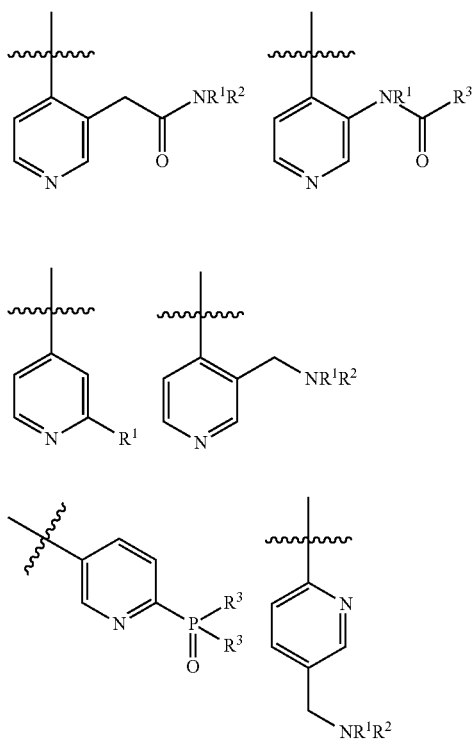
Specific, non-limiting illustrative examples of this class include compounds of formula VI in which substituted Ring E is of the following formulae:
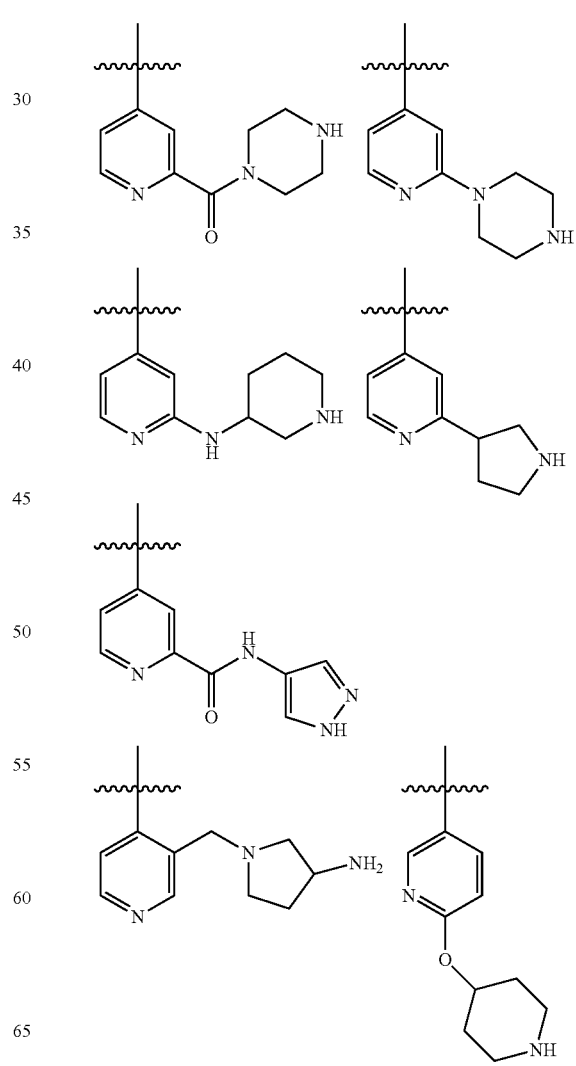

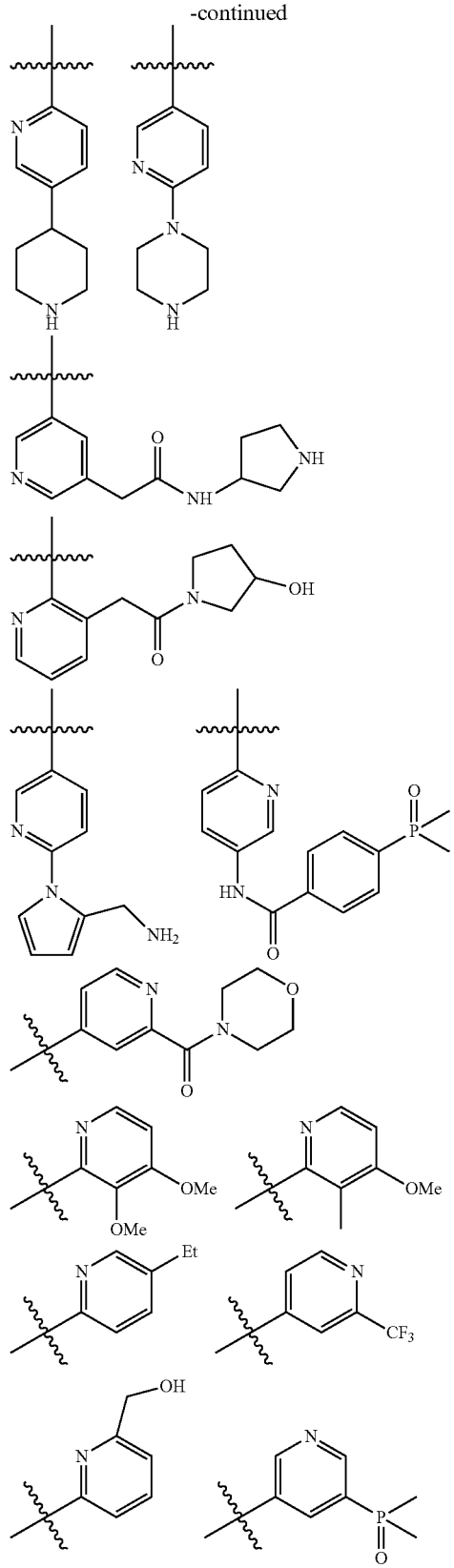
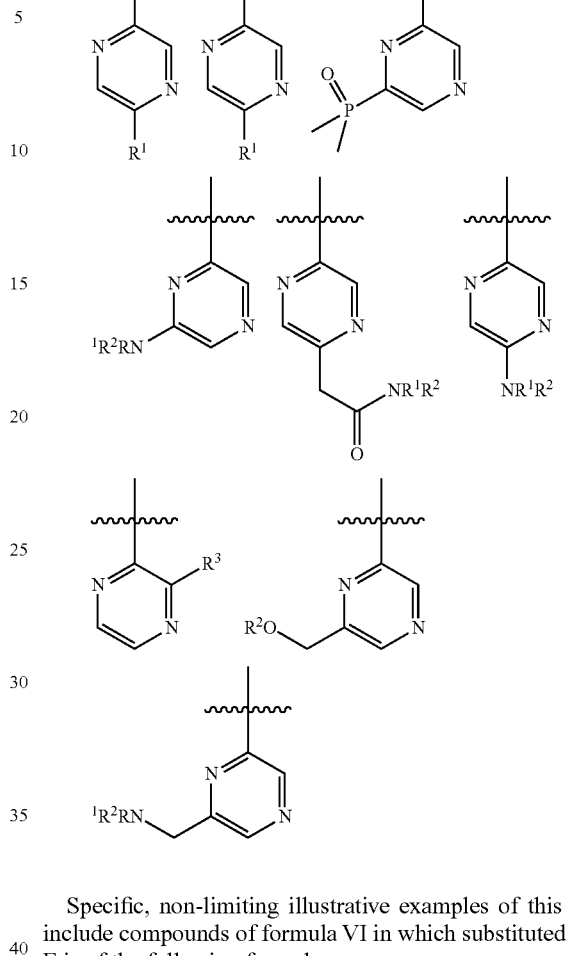
Specific, non-limiting illustrative examples of this class include compounds of formula VI in which substituted Ring E is of the following formulae:
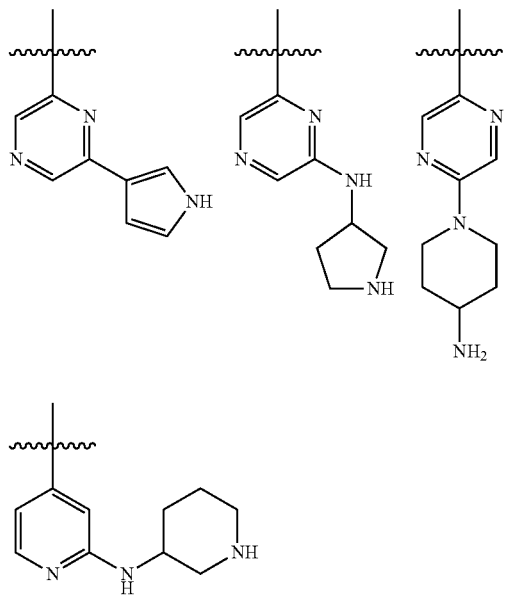
In another embodiment, Ring E is a pyrazine substituted with 1-3 $R^g$ groups. Non-limiting examples of this class of compounds in which Ring E is:

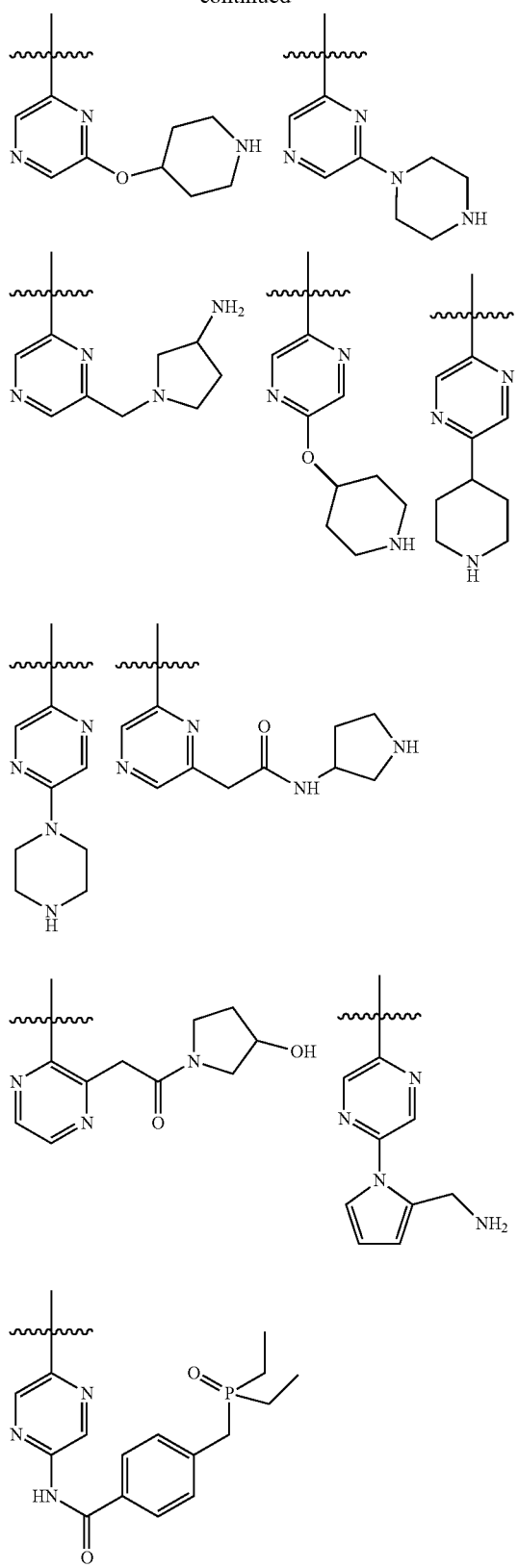

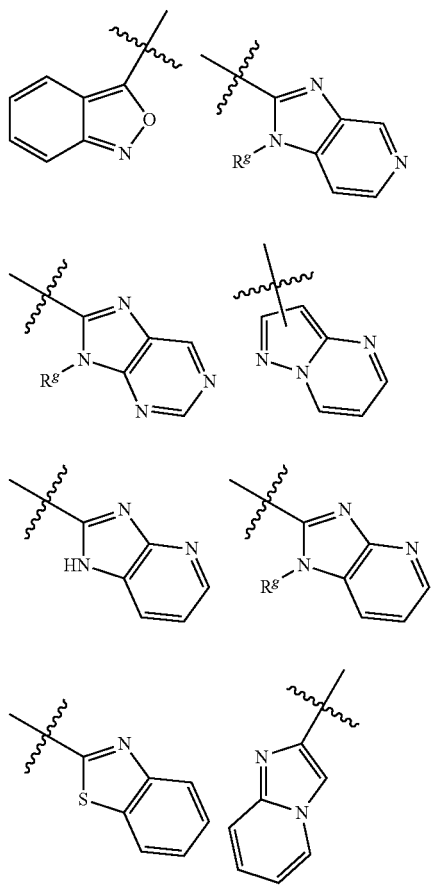

in which p is defined previously and the number of substituents $R^g$ does not exceed the maximum available valencies, which in the triazine case p is 0, 1 or 2.

In one embodiment, Ring E is an aryl, a carbocyclyl or a 5-, 6- or 7-membered heterocyclic or heteroaryl ring which is fused with a 5- or 6- or 7-membered saturated, partially saturated or unsaturated ring, and Ring E is optionally substituted with 1-5 $R^g$ groups.

In certain embodiments, Ring E is a 5,6- or 5,5-bicyclic fused system. Non-limiting examples include compounds of formula VI in which Ring E has the following formulae:

In another embodiment, Ring E is a triazine substituted with 1 to 2 $R^g$ groups. Examples include compounds in which Ring E has the following formulae:

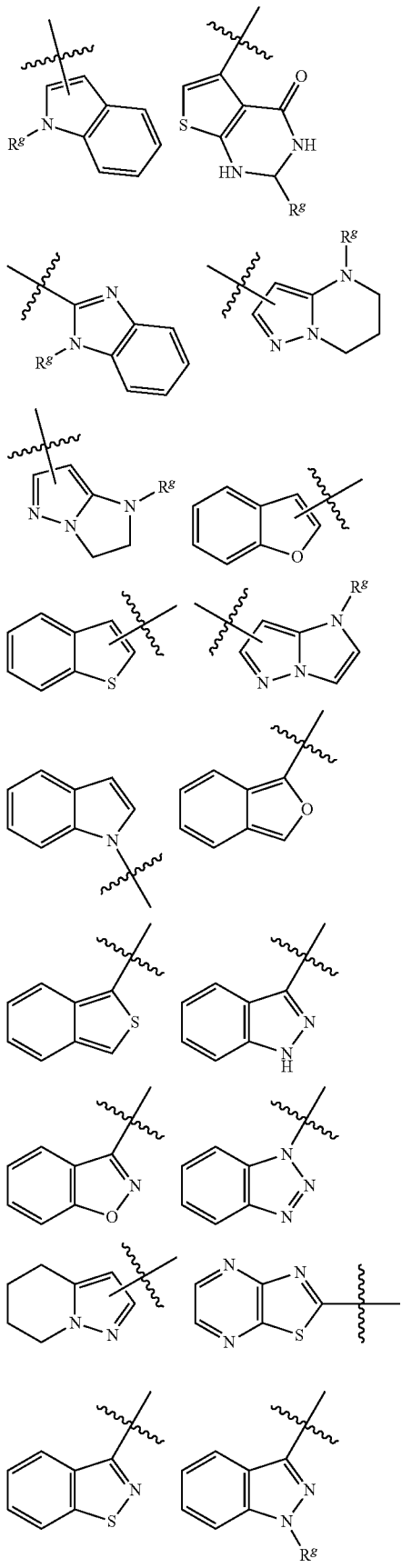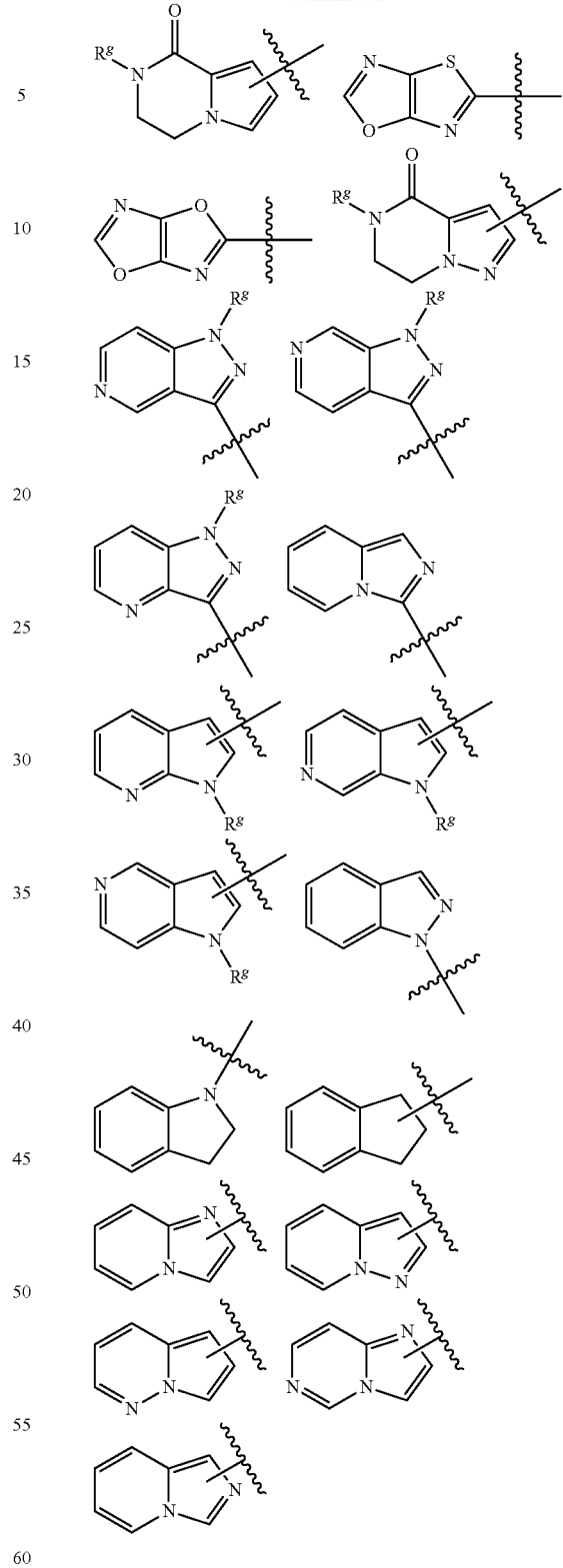
and the depicted fused ring systems can be substituted with additional R$^g$ groups.
In some other embodiments of interest, Ring E is a 6,6- or 6,5-bicyclic fused system. Non limiting examples of this class include compounds of formula VI in which Ring E has the following formulae:

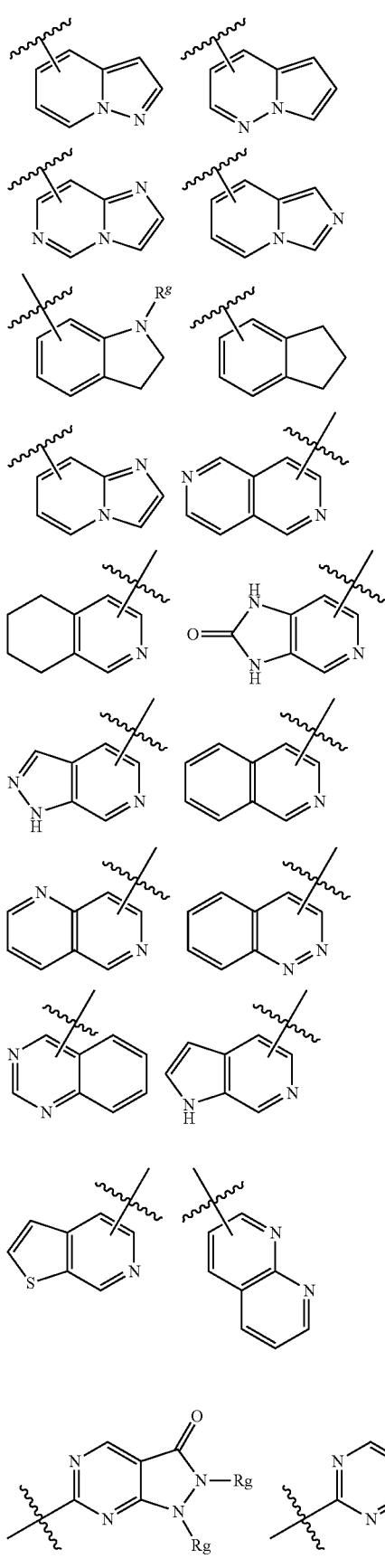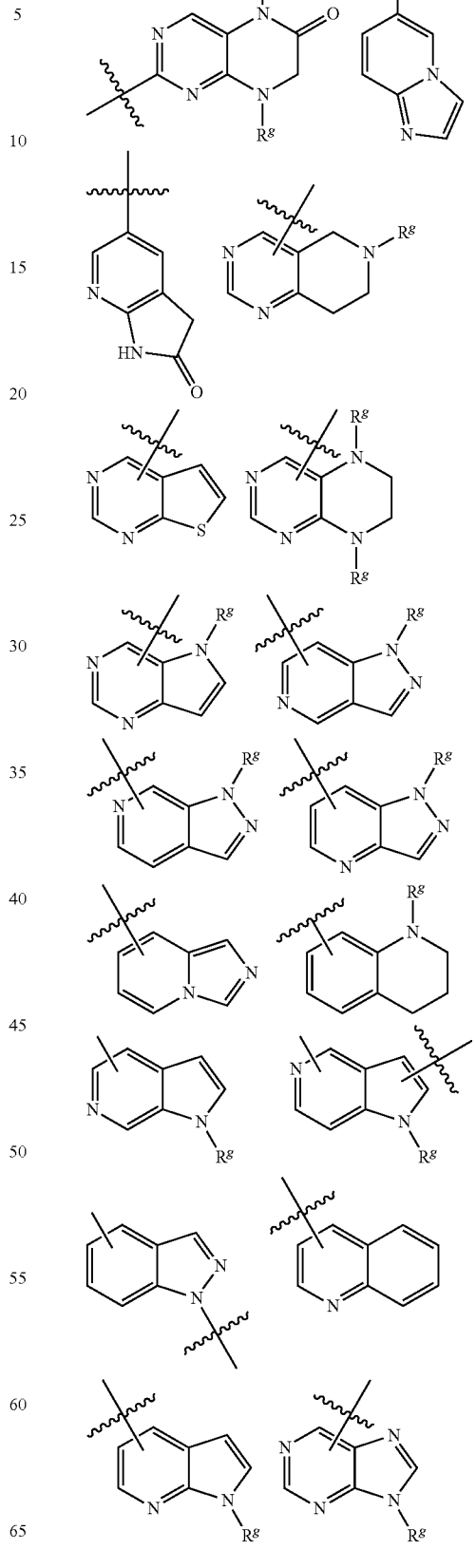

and the depicted fused ring systems can be substituted with additional R^g groups.
Specific, non-limiting illustrative examples of this class include compounds of formula VI in which substituted Ring E is of the following formulae:
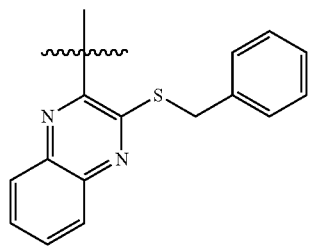
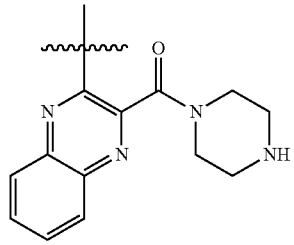
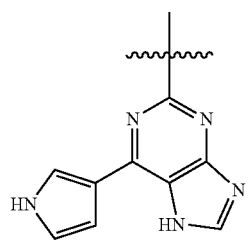
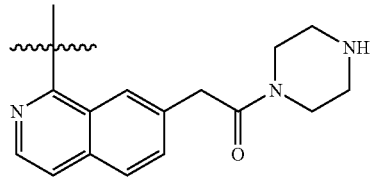
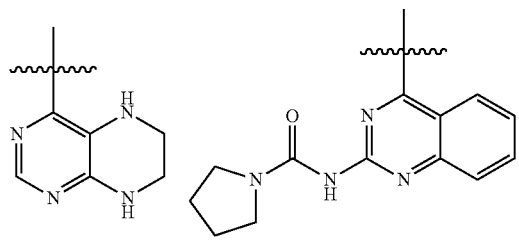
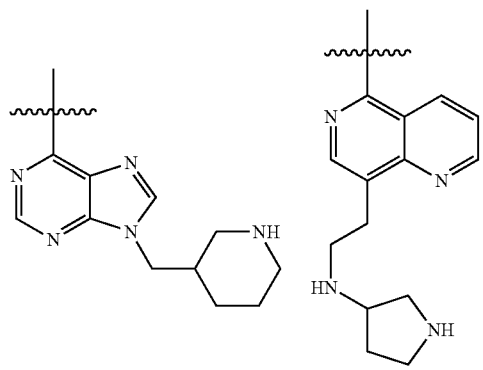
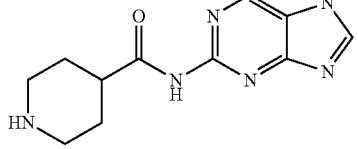
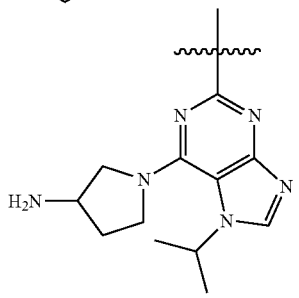
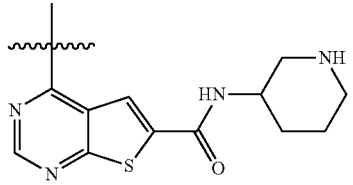
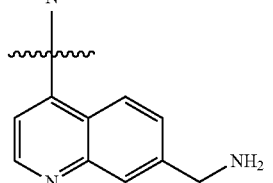
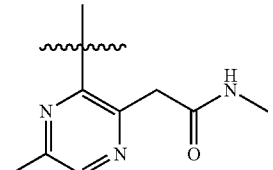
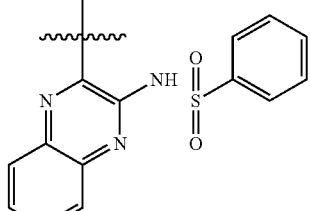
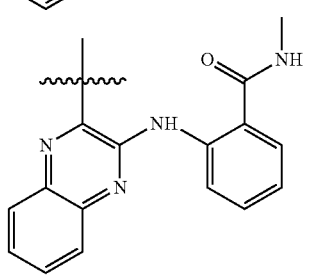
In some other embodiments of interest, Ring E is an aryl fused with a 5-, 6- or 7-membered saturated, partially saturated or unsaturated ring, and Ring E is substituted with 1-5 R^g groups. Non limiting examples of this class include compounds of formula VI in which Ring E has the following formulae:
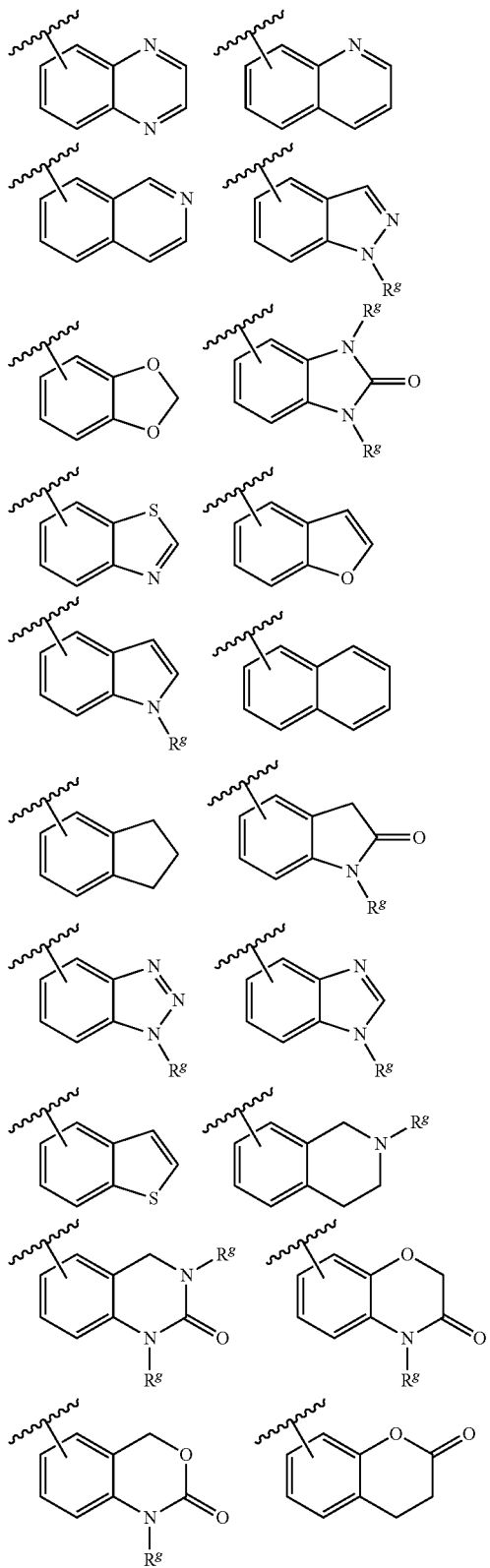
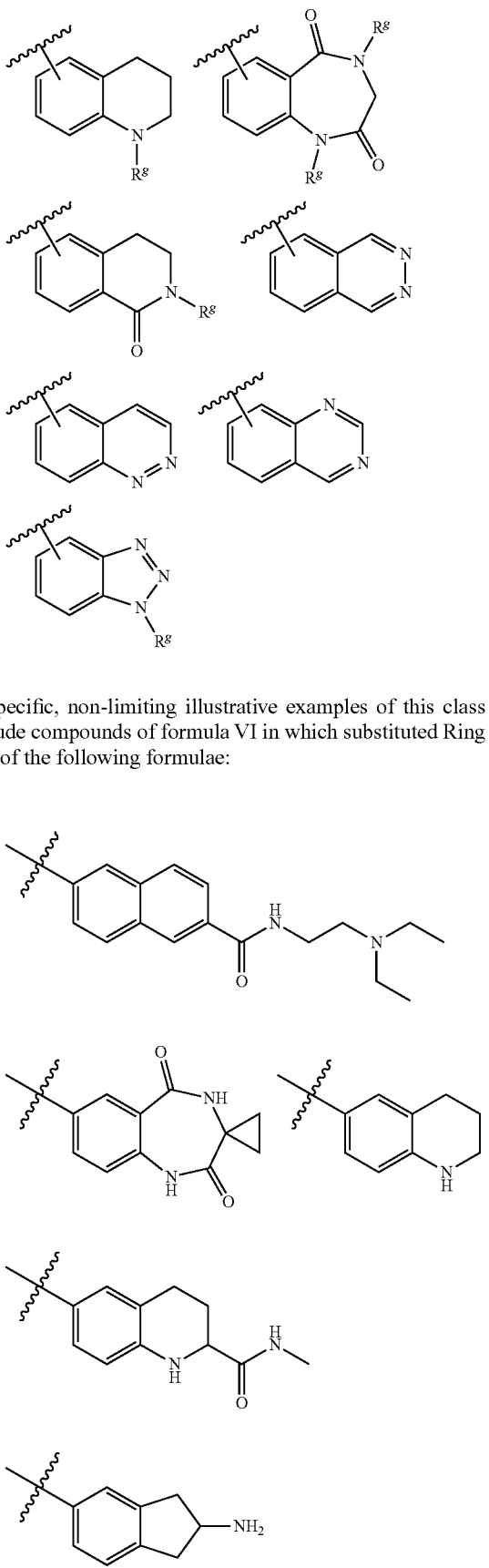
Specific, non-limiting illustrative examples of this class include compounds of formula VI in which substituted Ring E is of the following formulae:

-continued

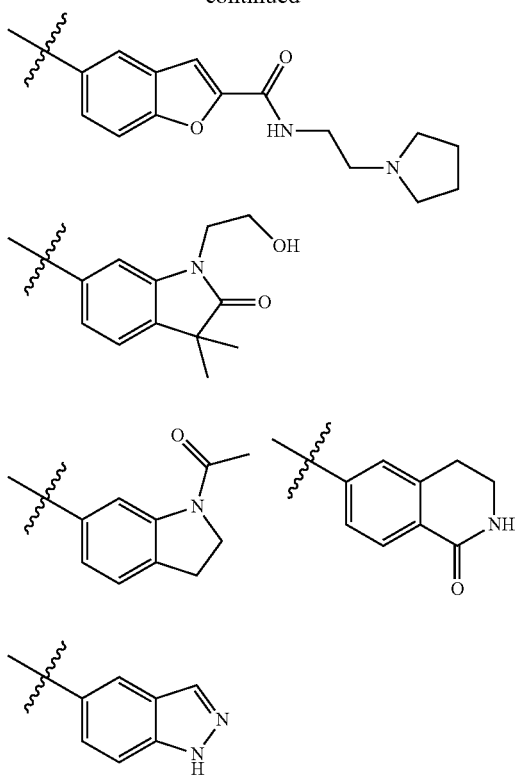

In embodiments of the compounds of formula VI, Ring A is a 6-membered ring heteroaryl. Examples of this class are compounds of the above classes and subclasses in which Ring A is a pyridine, pyrazine, pyridazine, pyrimidine or triazine.

In still other embodiments, Ring A is a 5-membered ring heteroaryl. Examples of this class are compounds of the above classes and subclasses in which Ring A is imidazole, pyrazole, tetrazole, oxazole, thiazole, isoxazole, pyrrole, and the like.

Of particular interest is a class of compounds as described above in which $R^a$ is selected from the group consisting of halo, —P═O($R^3$)$_2$, —$R^1$, —O$R^2$, —N$R^1R^2$, —N$R^1$C(O)$R^2$, —N$R^1$C(O)N$R^2$, —C(O)N$R^1R^2$, C(O)O$R^1$, —SO$_2$N$R^1R^2$, —SO$_2R^1$, SO$_2R^2$. In another subclass of interest, are compounds of the above embodiment in which $R^a$ is —P(═O)(alkyl)$_2$, alkyl, alkynyl, halo, aryl, heteroaryl, heterocyclyl, O-alkyl (i.e: OMe and the like), —CN, —C(O)NH-alkyl, —C(O)NH-aryl, C(O)NH-heterocyclyl, OH, —N$R^1R^2$, NHS(O)$_2$-alkyl, NHS(O)$_2$-aryl. Non limiting examples of $R^a$ are is —(CH$_2$)$_m$P(═O)(Me)$_2$, —(CH$_2$)$_m$ P(═O)(Et)$_2$, F, Cl, CF$_3$, OCF$_3$, —(CH$_2$)$_y$C(═O)N$R^1R^2$, —(CH$_2$)$_y$C(═O)aryl, —SO$_2$N$R^1R^2$, NHSO$_2R^1$, lower alkyl, —(CH$_2$)$_y$C(═O)heteroaryl, —(CH$_2$)$_y$C(═O)heterocyclyl, —(CH$_2$)$_y$NHC(═O)$R^2$, —(CH$_2$)$_y$N$R^1R^2$, —(CH$_2$)$_y$O$R^2$, —(CH$_2$)$_y$S$R^2$, —(CH$_2$)$_y$heterocyclyl, —(CH$_2$)$_y$aryl, —(CH$_2$)$_y$heteroaryl, NH-aryl, NH-heteroaryl, NH-heterocyclyl, in which y and m are independently selected from 0, 1, 2, 3 and 4; and alkyl include straight (i.e. unbranched or acyclic), branched and cyclic alkyl groups and alkyl, aryl, heteroaryl, heterocyclyl groups are optionally substituted.

The invention also features compounds of Formula VIa:

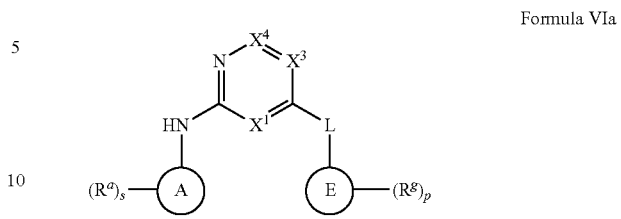

Formula VIa wherein
$X^1$ is NR$^{b1}$ or CR$^b$;
$X^3$ is NR$^{d1}$ or CR$^d$;
$X^4$ is NR$^{e1}$ or CR$^e$;
Ring A and Ring E are each an independently selected aryl or heteroaryl ring, the heteroaryl ring being a 5- or 6-membered ring containing 1 to 4 heteroatoms selected from N, O and S(O)$_r$;
each occurrence of $R^a$, $R^b$, $R^d$, $R^e$, and $R^g$ is independently selected from the group consisting of halo, —CN, —NO$_2$, —$R^1$, —O$R^2$, —O—N$R^1R^2$, —N$R^1R^2$, —N$R^1$—N$R^1R^2$, —N$R^1$—O$R^2$, —C(O)Y$R^2$, —OC(O)Y$R^2$, —N$R^1$C(O)Y$R^2$, —SC(O)Y$R^2$, —N$R^1$C(═S)Y$R^2$, —OC(═S)Y$R^2$, —C(═S)Y$R^2$, —YC(═N$R^1$)Y$R^2$, —YC(═N—O$R^1$)Y$R^2$, —YC(═N—N$R^1R^2$)Y$R^2$, —YP(═O)(Y$R^3$)(Y$R^3$), —Si($R^{3a}$)$_3$, —N$R^1$SO$_2R^2$, —S(O)$_rR^2$, —SO$_2$N$R^1R^2$ and —N$R^1$SO$_2$N$R^1R^2$; or alternatively, each $R^a$ and $R^g$ may also be or include an independently selected moiety, —P(═O)($R^3$)$_2$ or a ring system containing the moiety —P(═O)($R^3$)— as a ring member;
$R^{b1}$, $R^{d1}$ and $R^{e1}$ are absent;
or alternatively two adjacent substituents selected from $R^d$, $R^{d1}$, $R^e$, and $R^{e1}$ or two adjacent $R^a$ moieties, can form, with the atoms to which they are attached, a fused, 5-, 6- or 7-membered saturated, partially saturated or unsaturated ring, which contains 0-4 heteroatoms selected from N, O and S(O)$_r$ and which may bear up to four substituents suitable for heterocycles (see infra), a variety of which are illustrated in exemplary compounds disclosed herein; at least one of $R^a$ and $R^g$ is or contains a moiety, —P(═O)($R^3$)$_2$ or a ring system containing the moiety —P(═O)($R^3$)— as a ring member;
L is O or NH;
r is 0, 1 or 2;
s is 1, 2, 3, 4 or 5;
p is 1, 2, 3 or 4;
each occurrence of Y is independently a bond, —O—, —S— or —N$R^1$—;
each occurrence of $R^1$ and $R^2$ is independently H or an alkyl, alkenyl, alkynyl, cycloalkyl, cycloalkenyl, cycloalkynyl, aryl, heteroalkyl, heterocyclic or heteroaryl moiety;
each occurrence of $R^3$ is independently an alkyl, alkenyl, alkynyl, cycloalkyl, cycloalkenyl, cycloalkynyl, aryl, heteroalkyl, heterocyclic or heteroaryl moiety, or two adjacent $R^3$ moieties combine to form a ring system including a phosphorous atom;
each occurrence of $R^{3a}$ is independently selected from alkyl, alkenyl, alkynyl, cycloalkyl, cycloalkenyl, cycloalkynyl, aryl, heteroalkyl, heterocyclic, and heteroaryl;
alternatively, each N$R^1R^2$ moiety may be a 5-, 6- or 7-membered saturated, partially saturated or unsaturated ring, which can be optionally substituted and which contains 0-2 additional heteroatoms selected from N, O and S(O)$_r$; and
each of the foregoing alkyl, alkenyl, alkynyl, cycloalkyl, cycloalkenyl, cycloalkynyl, aryl, heteroaryl and heterocyclic moieties is optionally substituted.

In certain embodiments of the compounds of Formula VIA are further defined as follows (1) $X^1$ is N; (2) $X^3$ is N and $X^4$ is $CR^e$; (3) $X^3$ is $CR^d$ and $X^4$ is $CR^e$; (4) $X^1$ is $CR^b$; (5) $X^3$ is N and $X^4$ is $CR^e$; or (6) $X^3$ is $CR^d$ and $X^4$ is $CR^e$.

In certain specific embodiments of the compounds of Formula VIA, when $X^3$ is $CR^d$, $R^d$ is selected from Cl, F, C1-C4 alkyl, trihaloalkyl, cycloalkyl, C2-C4 alkenyl, and alkynyl. In such embodiments, Cl, F, Me and cyclopropyl are of particular interest.

In another embodiment of the compounds of Formula VIA, $X^3$ is $CR^d$ and $X^4$ is $CR^e$ wherein $R^d$ and $R^e$, together with the atoms to which they are attached, form a fused, 5-, 6- or 7-membered saturated, partially saturated or unsaturated ring, which contains 0-4 heteroatoms selected from N, O and $S(O)_r$ and which may bear up to four substituents.

Compounds of Formula VIA of particular interest, generally and including the individual embodiments described above, include those in which s is 1, 2, 3 or 4, and each of the substituents $R^a$ is independently selected from halo, —$R^1$, —$OR^2$, —$NR^1R^2$ and —$P(=O)(R^3)_2$, wherein each $R^1$ and $R^2$ moiety may be further substituted or unsubstituted. In certain embodiments, the compounds include at least one substituent $R^a$ that is —$OR^2$ and $R^2$ is selected from C1-C6 alkyl, C2-C6, and C2-C6 alkynyl. In such cases, as illustrated in compounds shown herein, MeO—, EtO— and iPrO— are often chosen as an W moiety.

Compounds of Formula VIA, generally and including the individual embodiments described thus far, also include compounds having at least one substituent $R^a$ which is a 4-, 5-, 6- or 7-membered heterocyclic or 5- or 6-membered heteroaryl moiety, linked to Ring A either directly or by an ether bond, and which may be further substituted with 1-3 substituents independently selected from halo, —CN, —$NO_2$, —$R^1$, —$OR^2$, —O—$NR^1R^2$, —$NR^1R^2$, —$NR^1$— $NR^1R^2$, —$NR^1$—$OR^2$, —$C(O)YR^2$, —$OC(O)YR^2$, —$NR^1C(O)YR^2$, —$SC(O)YR^2$, —$NR^1C(=S)YR^2$, —$OC(=S)YR^2$, —$C(=S)YR^2$, —$YC(=NR^1)YR^2$, —$YC(=N-OR^1)YR^2$, —$YC(=N-NR^1R^2)YR^2$, —$YP(=O)(YR^3)(YR^3)$, —$Si(R^{3a})_3$, —$NR^1SO_2R^2$, —$S(O)_rR^2$, —$SO_2NR^1R^2$ and —$NR^1SO_2NR^1R^2$; wherein each Y is independently a bond, —O—, —S— or —$NR^1$—.

For example, compounds of Formula VIA include those having a heterocyclic or heteroaryl substituent $R^a$ is selected from the following:

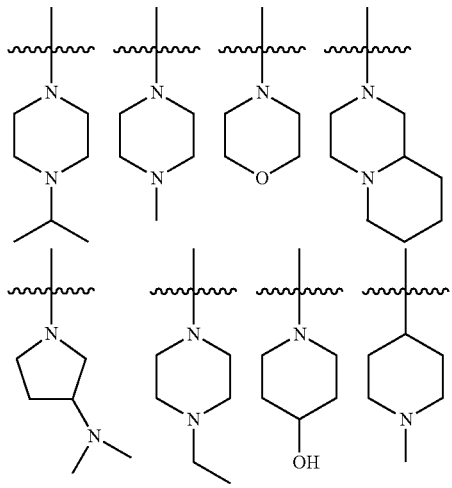

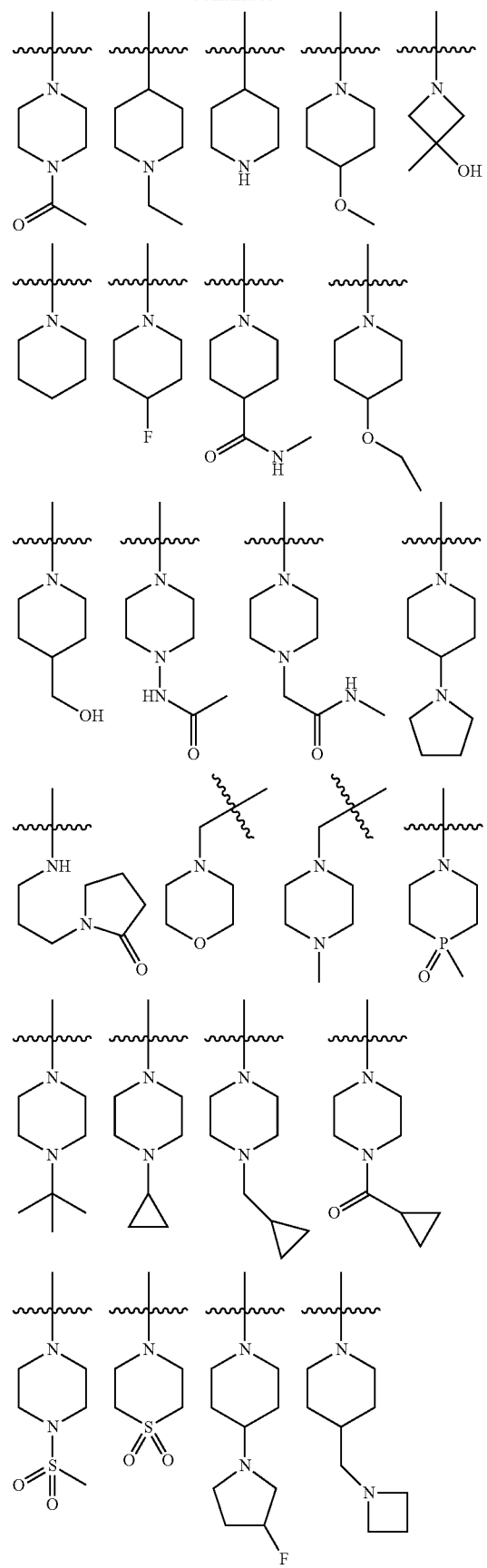

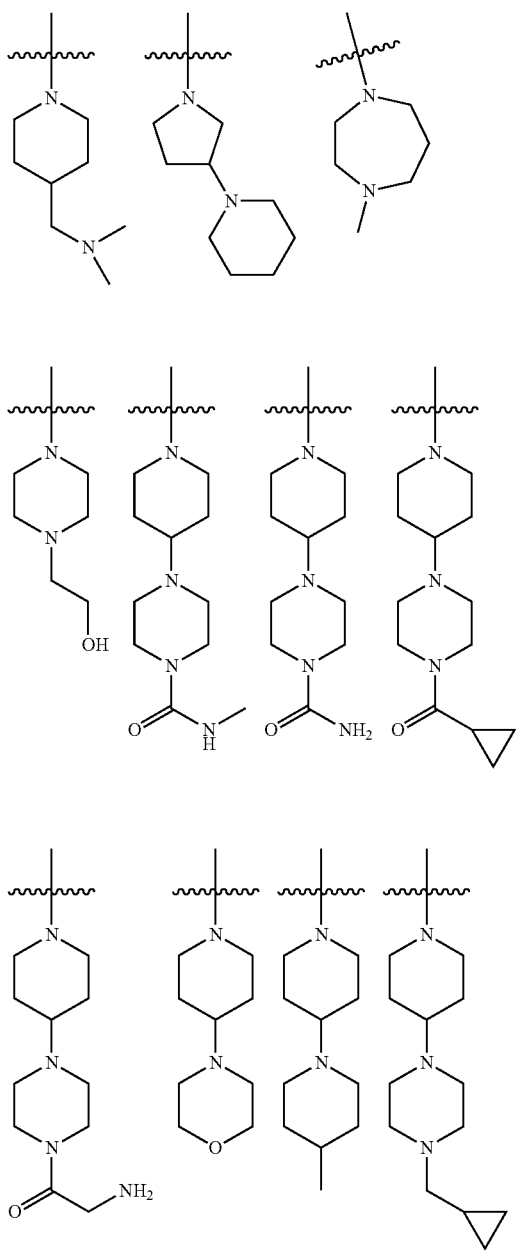

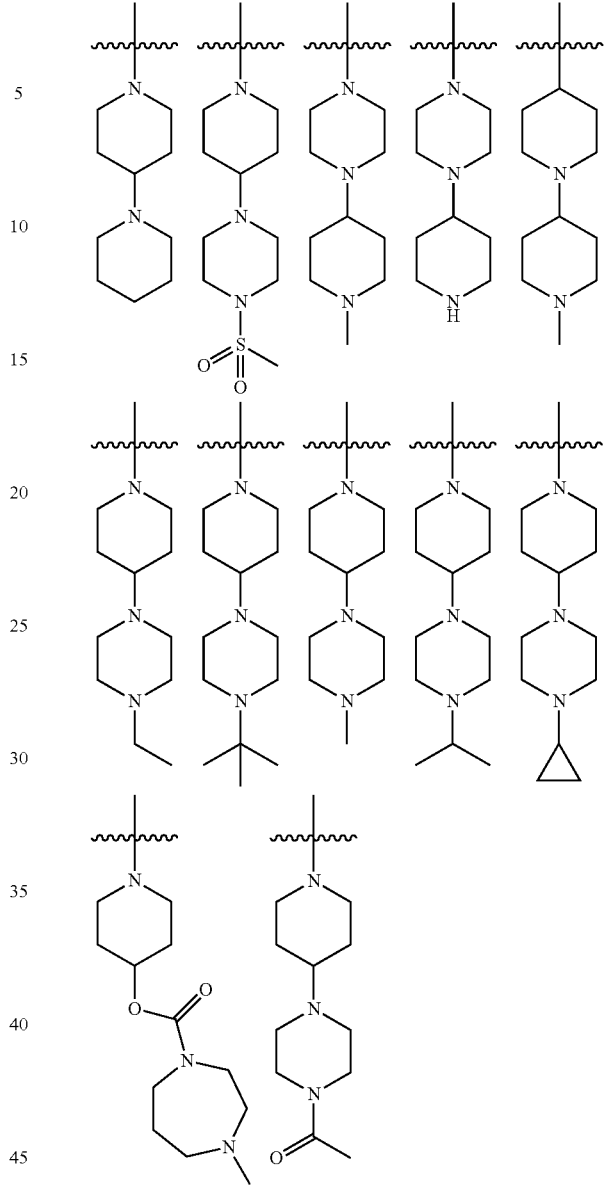

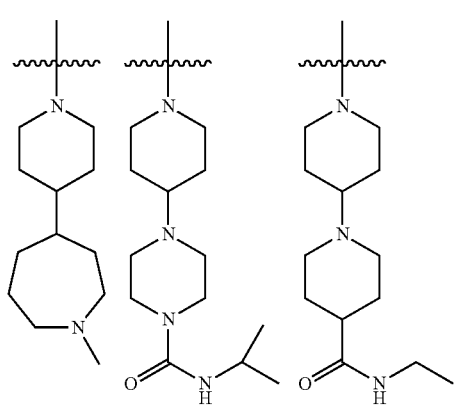

Compounds of Formula VIA, generally and, again, including the individual embodiments described thus far, also include compounds of Formula VIA in which at least one substituent $R^a$ is or bears a moiety, —P(=O)($R^3$)$_2$, in which $R^3$ is a C1-C4 alkyl.

Compounds of Formula VIA, generally and, again, including the embodiments described thus far, also include embodiments of Formula VIA in which L is NH, Ring E is aryl, and each $R^g$ is independently selected from halo, —$R^1$, —$OR^2$, —S(O)$_r R^2$ and —P(=O)($R^3$)$_2$. In certain embodiments, Ring E contains at least one such $R^g$ moiety in the ortho position relative to the ring atom attached to L. In other embodiments, that $R^g$ moiety is in the meta position relative to the ring atom attached to L, and in still other embodiments, that $R^g$ moiety is in the para position relative to the ring atom attached to L.

Embodiment of the compounds of formulas VI and VIA, generally and, again, including the individual embodiments described thus far, also include those compounds in which the group —P(=O)(R³)₂ is selected from —P(=O)(CH₃)₂ and —P(=O)(CH₂CH₃)₂.

In another embodiment of compounds of Formula I, two adjacent R$^a$ form a 5-, 6- or 7-membered saturated, partially saturated or unsaturated Ring F which is substituted with 1-4 R$^f$ groups. This class of compounds is represented by compounds of formula VII:

Formula VII

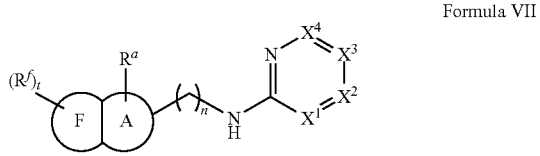

in which Ring A, R$^a$, R$^f$, n, X$^1$, X$^2$, X$^3$ and X$^4$ are as defined in Formula I; t is 1, 2, 3 or 4; and Ring F is an aryl, a carbocyclyl, a 5- or 6- or 7-membered heteroaryl or heterocyclyl ring substituted with 1-4 R$^f$ groups.

One class of compounds which is of special interest for use in the invention are compounds of Formula VII are those in which X$^2$ is CR$^C$, X$^3$ is CR$^d$ and X$^4$ is CR$^e$. This class is illustrated by compounds of formula VIIA:

Formula VIIA

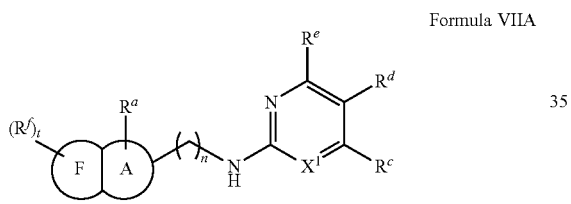

in which Ring A, Ring F, R$^a$, R$^f$, t, n, X$^1$, R$^c$, R$^d$ and R$^e$ are as defined previously in Formula VII.

One class of compounds of further interest are compounds of Formula VIIA in which Ring A is a phenyl. This is represented by compounds of Formula VIIB:

Formula VIIB

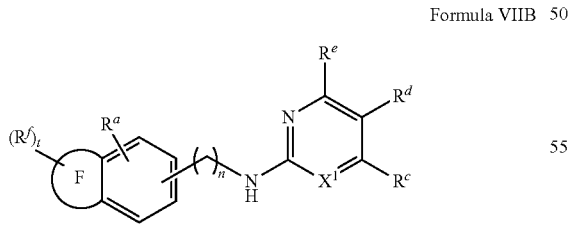

in which Ring F, R$^a$, R$^f$, t, n, X$^1$, R$^c$, R$^d$ and R$^e$ are as described in Formula VII.

In Formulas VII, VIIA, and VIIB, Ring A and Ring F together form a fused ring system. Fused ring systems that can be utilized in compounds of formulas VII, VIIA, and VIIB include, without limitation, those depicted for Ring E of Formula VI (see below) and the following fused ring systems:

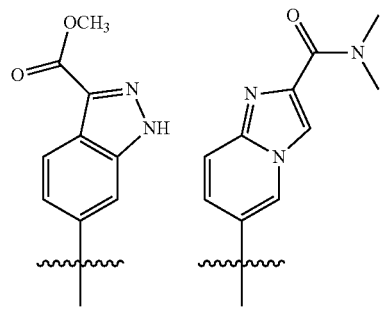

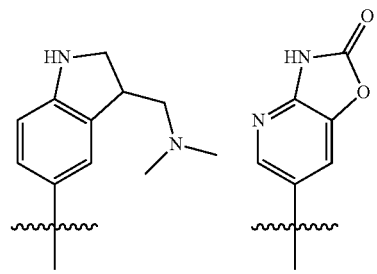

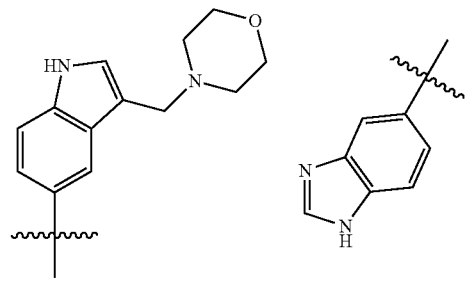

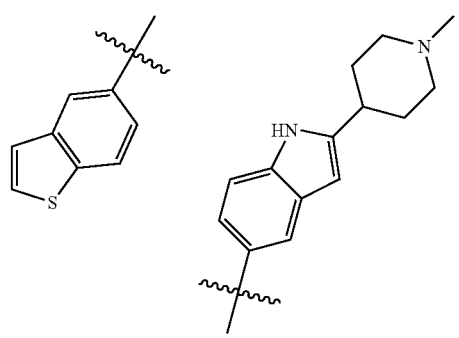

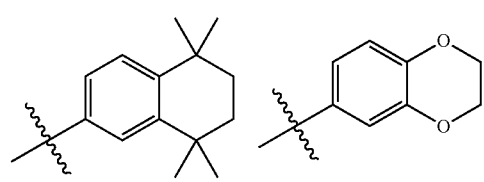

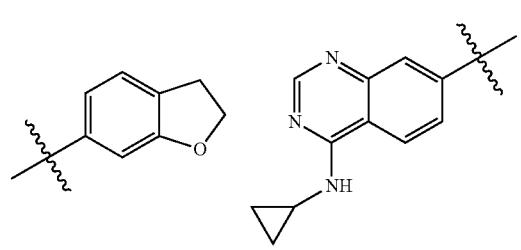

-continued

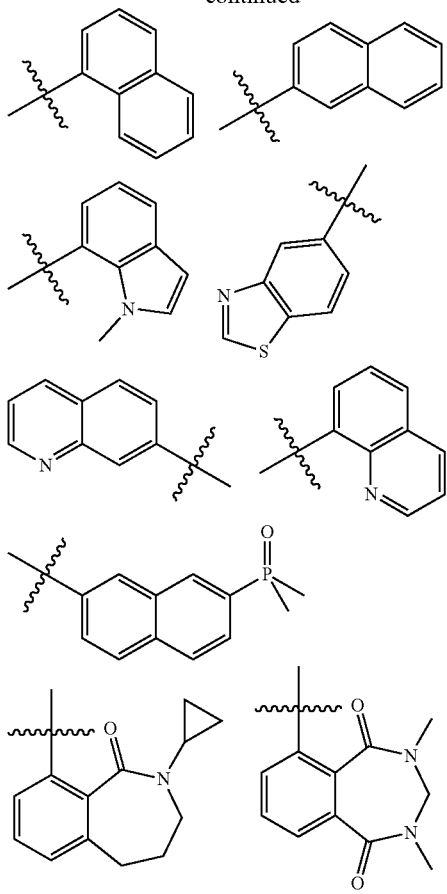

The fused ring systems are optionally substituted with additional $R^a$ or $R^f$ groups. Of special interest are compounds of formula VII or VIIA or VIIB in which $R^f$ is or contains —P(=O)($R^3$)$_2$. Examples of $R^f$ containing —P(=O)($R^3$)$_2$ include, without limitation, —(CH$_2$)$_m$—P(=O)($R^3$)$_2$, —(CH$_2$)$_m$—NR$^1$—P(=O)($R^3$)$_2$, —(CH$_2$)$_m$—O—P(=O)($R^3$)$_2$, —(CH$_2$)$_m$—NR$^1$—(CH$_2$)$_m$—P(=O)($R^3$)$_2$, —(CH$_2$)$_m$—NR$^1$C(O)O—(CH$_2$)$_m$—P(=O)($R^3$)$_2$, and —(CH$_2$)$_m$—C(O)NR$^1$—(CH$_2$)$_m$—P(=O)($R^3$)$_2$, in which m is 0, 1, 2, 3 or 4 and ring systems containing the moiety —P(=O)($R^3$)— as a ring member.

Of other special interest are compounds of Formula VII or VIIA or VIIB in which $R^e$ is or contains —P(=O)($R^3$)$_2$.

In one embodiment of any of the above classes and subclasses of compounds, Ring A is a phenyl group substituted with 1-5 $R^a$ moieties. In certain embodiments of any of the above classes and subclasses of compounds, Ring A is a 6-membered ring heteroaryl (e.g., a pyridine, pyrazine, pyridazine, pyrimidine or triazine ring). In still other embodiments of any of the above classes and subclasses of compounds, Ring A is a 5-membered ring heteroaryl (e.g., an imidazole, pyrazole, tetrazole, oxazole, thiazole, isoxazole, or pyrrole ring).

In another embodiment of any of the above classes and subclasses of compounds, $R^a$ is selected from halo, —P=O($R^3$)$_2$, —$R^1$, —O$R^2$, —NR$^1$R$^2$, —NR$^1$C(O)R$^2$, —NR$^1$C(O)NR$^2$, —C(O)NR$^1$R$^2$, —C(O)OR$^1$, —SO$_2$NR$^1$R$^2$, —SO$_2$R$^1$, and —NR$^1$SO$_2$R$^2$.

Another subclass of interest are compounds of the above embodiment in which $R^a$ is —P(=O)(alkyl)$_2$, alkyl, alkynyl, halo, aryl, heteroaryl, heterocyclyl, —O-alkyl (i.e: OMe and the like), —CN, —C(O)NH-alkyl, —C(O)NH-aryl, —C(O)NH-heterocyclyl, —OH, —NR$^1$R$^2$, NHS(O)$_2$-alkyl, —NHS(O)$_2$-aryl. Non limiting examples of $R^a$ include —(CH$_2$)$_m$P(=O)(Me)$_2$, —(CH$_2$)$_m$—P(=O)(Et)$_2$, —F, —Cl, —CF$_3$, —OCF$_3$, —(CH$_2$)$_y$C(=O)NR$^1$R$^2$, —(CH$_2$)$_y$C(=O)aryl, —SO$_2$NR$^1$R$^2$, —NHSO$_2$R$^1$, lower alkyl, —(CH$_2$)$_y$C(=O)heteroaryl, —(CH$_2$)$_y$C(=O)heterocyclyl, —(CH$_2$)$_y$NHC(=O)R$^2$, —(CH$_2$)$_y$NR$^1$R$^2$, —(CH$_2$)$_y$OR$^2$, —(CH$_2$)$_y$SR$^2$, —(CH$_2$)$_y$heterocyclyl, —(CH$_2$)$_y$aryl, —(CH$_2$)$_y$heteroaryl, —NH-aryl, —NH-heteroaryl, —NH-heterocyclyl, wherein y and m are independently selected from 0, 1, 2, 3 and 4.

In still another embodiment of any of the above classes and subclasses of compounds, $R^a$ is selected from —P(=O)(alkyl)$_2$, —(CH$_2$)$_{1-2}$P(=O)(alkyl)$_2$, —O-lower alkyl (i.e OMe and the like), lower alkyl (i.e: methyl, ethyl, cyclopropyl and the like), halo, —CF$_3$, —OCF$_3$, —CN, —NH(alkyl), alkenyl, and alkynyl (i.e: acetylene).

Illustrative examples of Phenyl moieties substituted with $R^a$ include, without limitation, the following moieties:

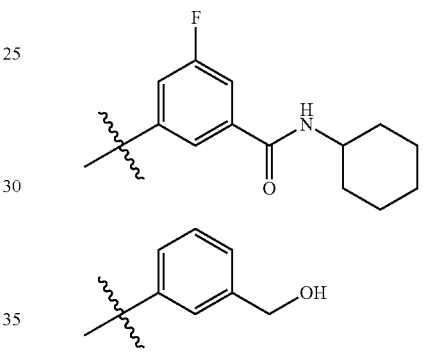

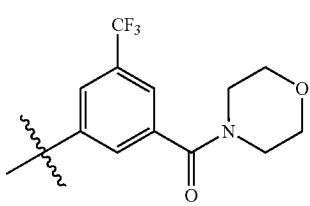

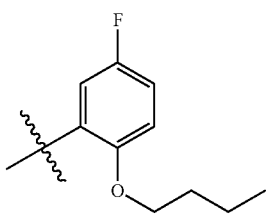

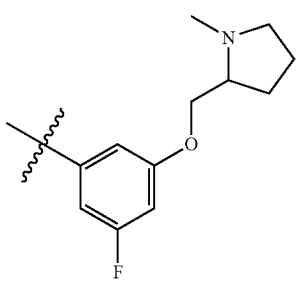

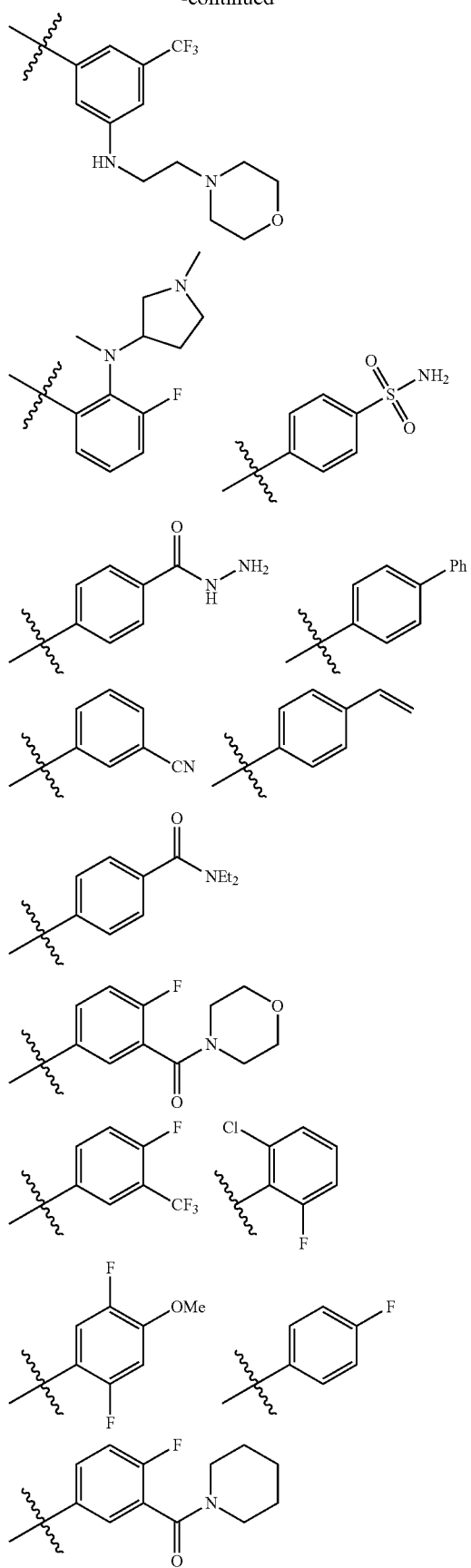
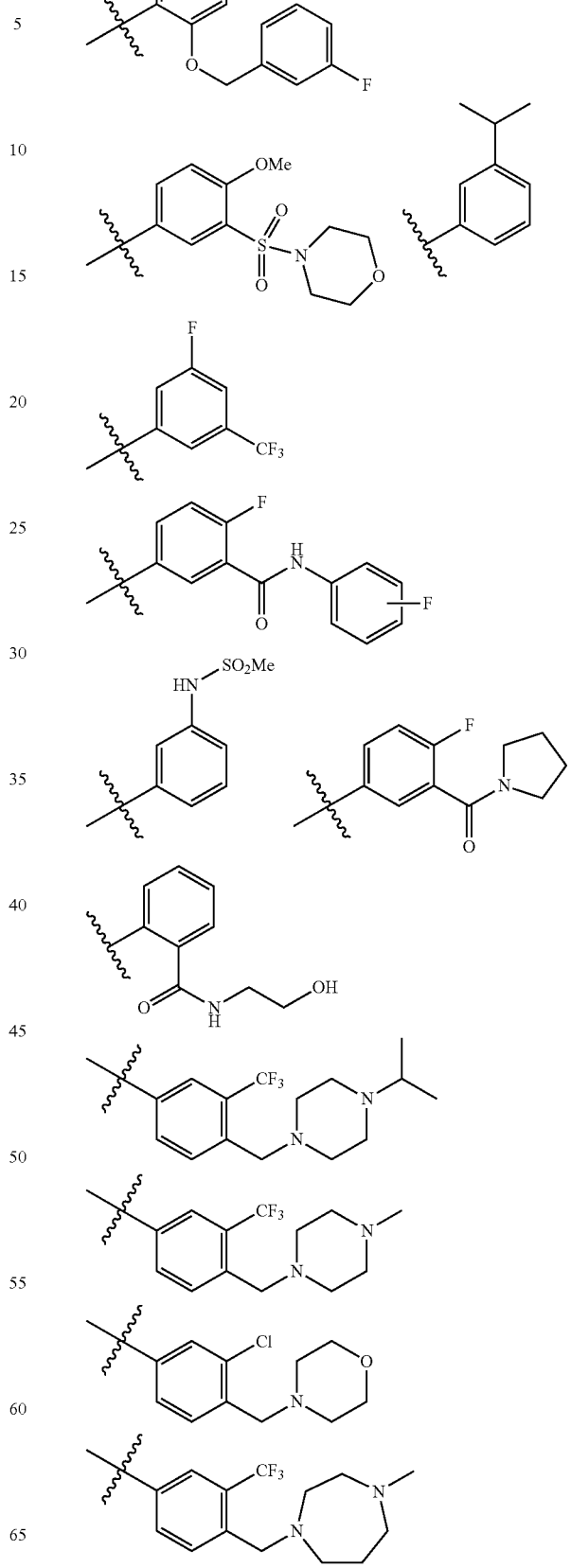

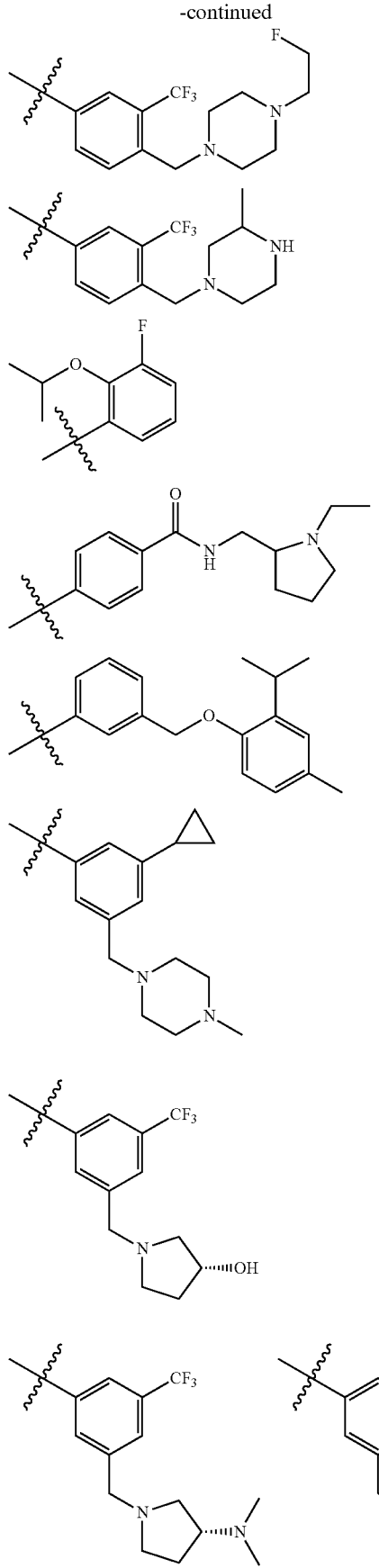
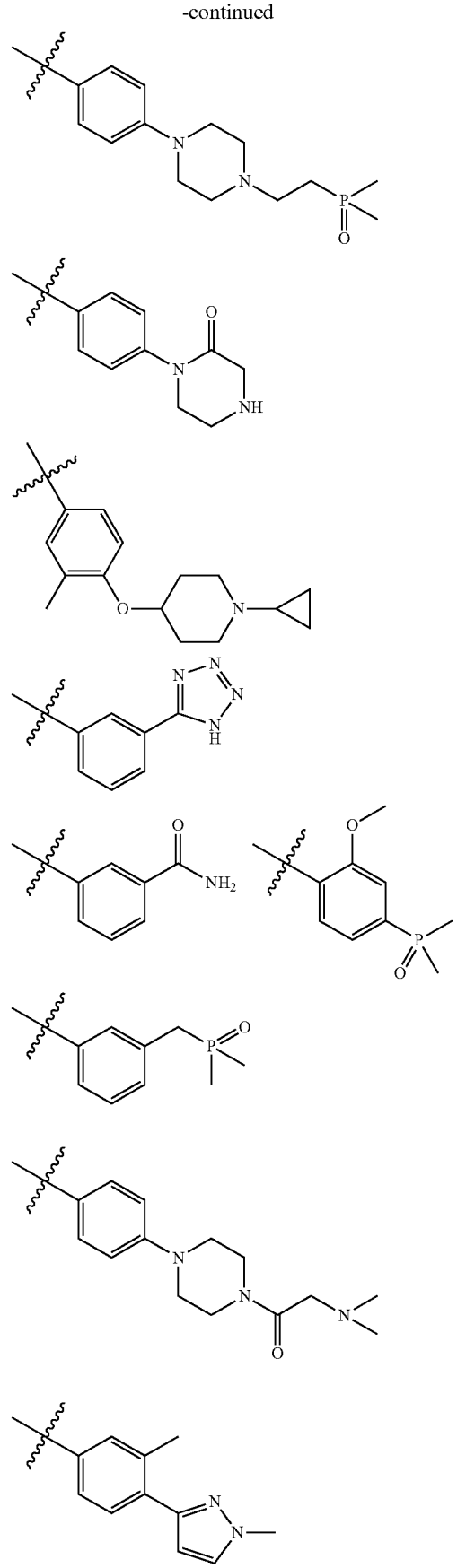

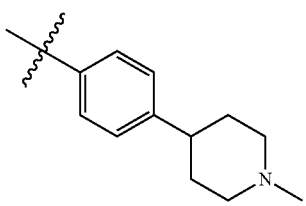
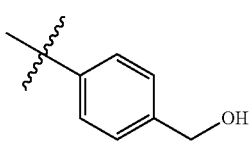
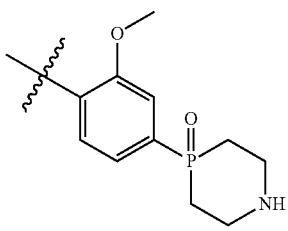
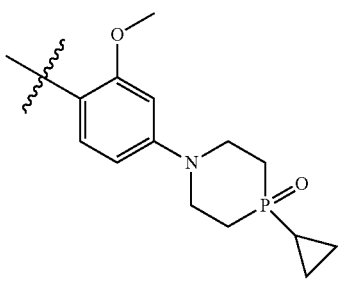
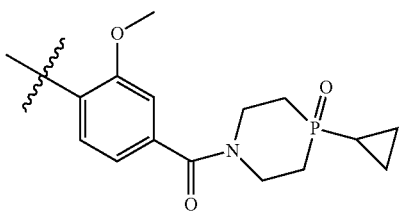

In any of the above classes and subclasses of compounds, R$^a$ is selected from —(CH$_2$)$_m$—P(=O)(R$^3$)$_2$, —(CH$_2$)$_m$—NR$^1$—P(=O)(R$^3$)$_2$, —(CH$_2$)$_m$—O—P(=O)(R$^3$)$_2$, —(CH$_2$)$_m$—NR$^1$—(CH$_2$)$_m$—P(=O)(R$^3$)$_2$, —(CH$_2$)$_m$—NR$^1$C(O)O—(CH$_2$)$_m$—P(=O)(R$^3$)$_2$, and —(CH$_2$)$_m$—C(O)NR$^1$—(CH$_2$)$_m$—P(=O)(R$^3$)$_2$, in which m is 0, 1, 2, 3 or 4. Alternatively, R$^a$ is a moiety of one of the following formulas:

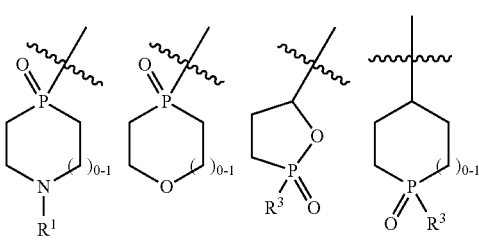

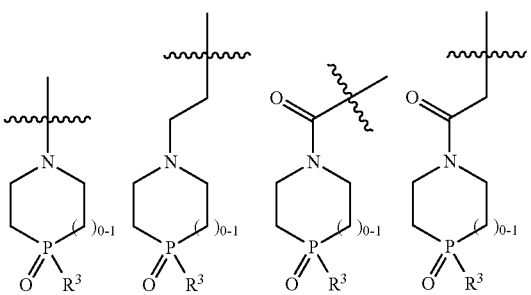

For these classes and other classes and subclasses of the invention, compounds of interest include among others compounds in which one of R$^a$ is or contains —P(=O)(R$^3$)$_2$. Examples of R$^a$ containing —P(=O)(R$^3$)$_2$ include, without limitation, —(CH$_2$), —P(=O)(R$^3$)$_2$, —(CH$_2$)$_m$—NR$^1$—P(=O)(R$^3$)$_2$, —(CH$_2$)$_m$—O—P(=O)(R$^3$)$_2$, —(CH$_2$)$_m$—NR$^1$—(CH$_2$)$_m$—P(=O)(R$^3$)$_2$, —(CH$_2$)$_m$—NR$^1$C(O)O—(CH$_2$)$_m$—P(=O)(R$^3$)$_2$, —(CH$_2$)$_m$—C(O)NR$^1$—(CH$_2$)$_m$—P(=O)(R$^3$)$_2$ in which m is 0, 1, 2, 3 or 4 and cyclic structures containing —P(=O) as depicted above. Of particular current interest are compounds of Formula Ia or VIa in which Ring A is phenyl, X$^1$ is N, n is 0, s is 2, p is 1, R$^e$ is H and R$^d$ is halo (i.e. F, Cl), lower alkyl (i.e. methyl, ethyl, isopropyl and the like), cyano, nitro, alkoxy (i.e. methoxy and the like) or CF$_3$; one of R$^a$ is or contains —P(=O)(R$^3$)$_2$ and the other R$^a$ is selected from lower alkyl, halo, cyano and alkoxy (i.e. methoxy); and R$^9$ is S(O)$_2$alkyl.

Of other special interest for use in the invention are compounds of formula IIIA in which Ring A is phenyl. Illustrative, non-limiting examples of this subclass are compounds of the formulae:

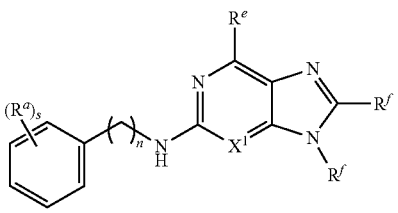

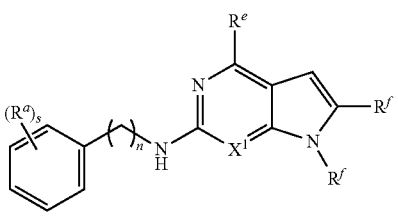

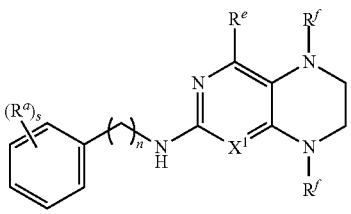

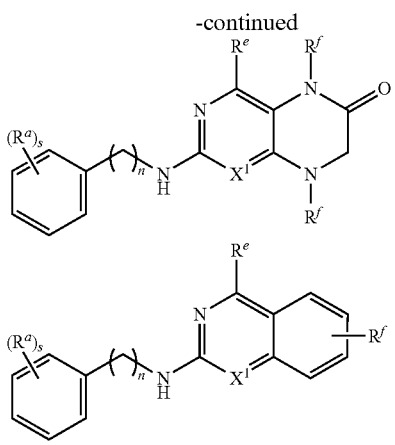

Of special interest for use in the invention are compounds of formula IIIA in which one of $R^a$ is or contains —P(=O) $(R^3)_2$ (i.e CH$_2$P(=O)Me$_2$, —P(=O)Me$_2$, —P(=O)Et$_2$, —OP(=O)Me$_2$, —NHP(=O)Me$_2$, —NHCH$_2$P(=O)Et$_2$ and the like). Of particular current interest are compounds of this subclass in which $X^1$ is N, n is 0, $R^e$ is H and $R^f$ is selected from alkyl, H, aryl, heteroaryl, heterocyclyl, halo (i.e, F, Cl), NHR$^1$, OR$_2$, CF$_3$, SO$_2$-lower alkyl (i.e. SO$_2$-iPr and the like), —SO$_2$NR$^1$R$^2$ and C(O)NR$^1$R$^2$.

Other compounds of interest include among others, compounds of formula IIIA in which $R^f$ is —(CH$_2$)$_m$P(=O)(alkyl)$_2$ (i.e —CH$_2$P(=O)Me$_2$, —P(=O)Me$_2$, —P(=O)Et$_2$, etc.). Of particular current interest are compounds of this subclass in which $X^1$ is N, n is 0, $R^a$ is methoxy, and $R^e$ is H.

Other compounds of interest include among others, compounds of the previous classes and subclasses in which $R^d$ is selected from H, halo (i.e Chloro, Fluoro, Bromo), —CF$_3$, optionally substituted lower alkyl group (i.e Methyl, Ethyl, Isopropyl, Cyclopropyl and the like), —CN, optionally substituted acetylene, —NO$_2$, —O-alkyl, —S-alkyl, —C(=O)alkyl, —NH-alkyl and —C(=O)N(alkyl)$_2$. Of further interest are compounds of this class in which $R^d$ is halo or CF$^3$.

Other compounds of interest include among others, compounds of the Formula I and IA and of all previous classes and subclasses in which $R^e$ is selected from halo, —CN, —NO$_2$, —R$^1$, —OR$^2$, —O—NR$^1$R$^2$, —C(O)YR$^2$, —OC(O)YR$^2$, —SC(O)YR$^2$, —NR$^1$C(=S)YR$^2$, —OC(=S)YR$^2$, —C(=S)YR$^2$, —YC(=NR$^1$)YR$^2$, —YC(=N—OR$^1$)YR$^2$, —YC(=N—NR$^1$R$^2$)YR$^2$. Of further interest are compounds of this class in which $R^e$ is H, CN, NO$_2$, lower alkyl or halo, wherein R$^1$, R$^2$, and Y are as defined in Formula I. Of further interest, $R^e$ is selected from H, lower alkyl and halo.

Compounds of the invention of particular interest include those with on or more of the following characteristics:
 a molecular weight of less than 1000, preferably less than 750 and more preferably less than 600 mass units (not including the weight of any solvating or co-crystallizing species, of any counter-ion in the case of a salt); or
 inhibitory activity against a wild type or mutant (especially a clinically relevant mutant) kinase, especially a kinase such as ALK, Met, Jak2, bRaf, EGFR, Tie-2, FLT3 or another kinase of interest with an IC$_{50}$ value of 1 μM or less (as determined using any scientifically acceptable kinase inhibition assay), preferably with an IC$_{50}$ of 500 nM or better, and optimally with an IC$_{50}$ value of 250 nM or better; or
 inhibitory activity against a given kinase with an IC$_{50}$ value at least 100-fold lower than their IC$_{50}$ values for other kinases of interest; or
 inhibitory activity for ALK, Met, Jak2 or B-Raf with a 1 μM or better IC$_{50}$ value against each; or
 a cytotoxic or growth inhibitory effect on cancer cell lines maintained in vitro, or in animal studies using a scientifically acceptable cancer cell xenograft model, (especially preferred are compounds of the invention which inhibit proliferation of Ba/F3 NMP-ALK, Ba/F3 EML4-ALK, Karpas 299 and/or SU-DHL-1 cells with a potency at least as great as the potency of known ALK inhibitors such as NVP-TAE684 and PF2341066 among others, preferably with a potency at least twice that of known ALK inhibitors, and more preferably with a potency at least 10 times that of known ALK inhibitors as determined by comparative studies.

Also provided is a composition comprising at least one compound of the invention or a salt, hydrate or other solvate thereof, and at least one pharmaceutically acceptable excipient or additive. Such compositions can be administered to a subject in need thereof to inhibit the growth, development and/or metastasis of cancers, including solid tumors (e.g., prostate cancer, colon cancer, pancreatic and ovarian cancers, breast cancer, non small cell lung cancer (NSCLS), neural tumors such as glioblastomas and neuroblastomas; esophageal carcinomas, soft tissue cancers such as rhabdomyosarcomas; among others); various forms of lymphoma such as a non-Hodgkin's lymphoma (NHL) known as anaplastic large-cell lymphoma (ALCL), various forms of leukemia; and including cancers which are resistant to other treatment, including those which are resistant to treatment with another kinase inhibitor, and generally for the treatment and prophylaxis of diseases or undesirable conditions mediated by one or more kinases which are inhibited by a compound of the invention.

The invention features a method for treating cancer. The method includes administering (as a monotherapy or in combination with one or more other anti-cancer agents, one or more agents for ameliorating side effects, radiation, etc) a therapeutically effective amount of a compound of the invention to a human or animal in need of it in order to inhibit, slow or reverse the growth, development or spread of cancer, including solid tumors or other forms of cancer such as leukemias, in the recipient. Such administration constitutes a method for the treatment or prophylaxis of diseases mediated by one or more kinases inhibited by one of the disclosed compounds or a pharmaceutically acceptable derivative thereof. "Administration" of a compound of the invention encompasses the delivery to a recipient of a compound of the sort described herein, or a prodrug or other pharmaceutically acceptable derivative thereof, using any suitable formulation or route of administration, as discussed herein. Typically the compound is administered one or more times per month, often one or more times per week, e.g. daily, every other day, 5 days/week, etc. Oral and intravenous administrations are of particular current interest.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite (MW>300) thereof which is pharmacologically active as a kinase inhibitor. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the invention.

Particularly favored derivatives and prodrugs of a parent compound are those derivatives and prodrugs that increase the bioavailability of the compound when administered to a mammal (e.g., by permitting enhanced absorption into the blood following oral administration) or which enhance delivery to a biological compartment of interest (e.g., the brain or lymphatic system) relative to the parent compound. Preferred prodrugs include derivatives of a compound of the invention with enhanced aqueous solubility or active transport through the gut membrane, relative to the parent compound.

One important aspect of the invention is a method for treating cancer in a subject in need thereof, which comprises administering to the subject a treatment effective amount of a composition containing a compound of the invention. Treatment may be provided in combination with one or more other cancer therapies, include surgery, radiotherapy (e.g., gamma-radiation, neutron beam radiotherapy, electron beam radiotherapy, proton therapy, brachytherapy, and systemic radioactive isotopes, etc.), endocrine therapy, biologic response modifiers (e.g., interferons, interleukins, and tumor necrosis factor (TNF) to name a few), hyperthermia, cryotherapy, agents to attenuate any adverse effects (e.g., antiemetics), and other cancer chemotherapeutic drugs. The other agent(s) may be administered using a formulation, route of administration and dosing schedule the same or different from that used with the compound of the invention.

Such other drugs include but not limited to one or more of the following: an anti-cancer alkylating or intercalating agent (e.g., mechlorethamine, chlorambucil, Cyclophosphamide, Melphalan, and Ifosfamide); antimetabolite (e.g., Methotrexate); purine antagonist or pyrimidine antagonist (e.g., 6-Mercaptopurine, 5-Fluorouracil, Cytarabile, and Gemcitabine); spindle poison (e.g., Vinblastine, Vincristine, Vinorelbine and Paclitaxel); podophyllotoxin (e.g., Etoposide, Irinotecan, Topotecan); antibiotic (e.g., Doxorubicin, Bleomycin and Mitomycin); nitrosourea (e.g., Carmustine, Lomustine); inorganic ion (e.g., Cisplatin, Carboplatin, Oxaliplatin or oxiplatin); enzyme (e.g., Asparaginase); hormone (e.g., Tamoxifen, Leuprolide, Flutamide and Megestrol); mTOR inhibitor (e.g., Sirolimus (rapamycin), Temsirolimus (CCI779), Everolimus (RAD001), AP23573 or other compounds disclosed in U.S. Pat. No. 7,091,213); proteasome inhibitor (such as Velcade, another proteasome inhibitor (see e.g., WO 02/096933) or another NF-kB inhibitor, including, e.g., an IkK inhibitor); other kinase inhibitors (e.g., an inhibitor of Src, BRC/Abl, kdr, flt3, aurora-2, glycogen synthase kinase 3 ("GSK-3"), EGF-R kinase (e.g., Iressa, Tarceva, etc.), VEGF-R kinase, PDGF-R kinase, etc); an antibody, soluble receptor or other receptor antagonist against a receptor or hormone implicated in a cancer (including receptors such as EGFR, ErbB2, VEGFR, PDGFR, and IGF-R; and agents such as Herceptin, Avastin, Erbitux, etc.); etc. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference. Examples of other therapeutic agents are noted elsewhere herein and include among others, Zyloprim, alemtuzmab, altretamine, amifostine, nastrozole, antibodies against prostate-specific membrane antigen (such as MLN-591, MLN591RL and MLN2704), arsenic trioxide, bexarotene, bleomycin, busulfan, capecitabine, Gliadel Wafer, celecoxib, chlorambucil, cisplatin-epinephrine gel, cladribine, cytarabine liposomal, daunorubicin liposomal, daunorubicin, daunomycin, dexrazoxane, docetaxel, doxorubicin, Elliott's B Solution, epirubicin, estramustine, etoposide phosphate, etoposide, exemestane, fludarabine, 5-FU, fulvestrant, gemcitabine, gemtuzumab-ozogamicin, goserelin acetate, hydroxyurea, idarubicin, idarubicin, Idamycin, ifosfamide, imatinib mesylate, irinotecan (or other topoisomerase inhibitor, including antibodies such as MLN576 (XR11576)), letrozole, leucovorin, leucovorin levamisole, liposomal daunorubicin, melphalan, L-PAM, mesna, methotrexate, methoxsalen, mitomycin C, mitoxantrone, MLN518 or MLN608 (or other inhibitors of the flt-3 receptor tyrosine kinase, PDFG-R or c-kit), itoxantrone, paclitaxel, Pegademase, pentostatin, porfimer sodium, Rituximab (RITUXAN®), talc, tamoxifen, temozolamide, teniposide, VM-26, topotecan, toremifene, 2C4 (or other antibody which interferes with HER2-mediated signaling), tretinoin, ATRA, valrubicin, vinorelbine, or pamidronate, zoledronate or another bisphosphonate.

The invention further comprises the preparation of a compound of any of Formulae I, Ia, II, IIa, III, IIIc, IV, IVa, V, Va, VI, VIa VII, VIIa and VIIb or of any other of compounds of the invention using a method described herein.

The invention also comprises the use of a compound of the invention, or a pharmaceutically acceptable derivative thereof, in the manufacture of a medicament for the treatment either acutely or chronically of cancer (including lymphoma and solid tumors, primary or metastatic, including cancers such as noted elsewhere herein and including cancers which are resistant or refractory to one or more other therapies). Compounds of the invention can be useful in the manufacture of an anti-cancer medicaments. Compounds of the invention can also be useful in the manufacture of a medicament to attenuate or prevent disorders through inhibition of one or more kinases such as ALK, jak2, b-raf, met, Tie-2, EGFR, FLT3, FAK, Pim-1, Pl3k, etc.

The invention further encompasses a composition comprising a compound of the invention, including a compound of any of the described classes or subclasses, including those of any of the formulas noted above, among others, preferably in a therapeutically-effective amount, in association with a least one pharmaceutically acceptable carrier, adjuvant or diluent.

Compounds of the invention can also be useful as standards and reagents for characterizing various kinases, especially but not limited to ALK, Met, Jak2, b-Raf, Tie-2, EGFR, FLT3 among others as well as for studying the role of such kinases in biological and pathological phenomena; for studying intracellular signal transduction pathways mediated by such kinases, for the comparative evaluation of new kinase inhibitors; and for studying various cancers in cell lines and animal models.

3. Definitions

In reading this document, the following information and definitions apply unless otherwise indicated.

The term "alkyl" is intended to include linear (i.e., unbranched or acyclic), branched, cyclic, or polycyclic non aromatic hydrocarbon groups, which are optionally substituted with one or more functional groups. Unless otherwise specified, "alkyl" groups contain one to eight, and preferably one to six carbon atoms. $C_{1-6}$ alkyl is intended to include $C_1$, $C_2$, $C_3$, $C_4$, $C_5$, and $C_6$ alkyl groups. Lower alkyl refers to alkyl groups containing 1 to 6 carbon atoms. Examples of alkyl include, but are not limited to, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, etc. Alkyl may be substituted or unsubstituted. Illustrative substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl, phenethyl, substituted phenethyl, etc.

The term "alkoxy" represents a subset of alkyl in which an alkyl group as defined above with the indicated number of carbons attached through an oxygen bridge. For example, "alkoxy" refers to groups —O-alkyl, wherein the alkyl group contains 1 to 8 carbons atoms of a linear, branched, cyclic configuration. Examples of "alkoxy" include, but are not limited to, methoxy, ethoxy, n-propoxy, i-propoxy, t-butoxy, n-butoxy, s-pentoxy and the like.

"Haloalkyl" is intended to include both branched and linear chain saturated hydrocarbon having one or more carbon substituted with a Halogen. Examples of haloalkyl, include, but are not limited to, trifluoromethyl, trichloromethyl, pentafluoroethyl and the like.

The term "alkenyl" is intended to include hydrocarbon chains of linear, branched, or cyclic configuration having one or more unsaturated Carbon-carbon bonds that may occur in any stable point along the chain or cycle. Unless otherwise specified, "alkenyl" refers to groups usually having two to eight, often two to six carbon atoms. For example, "alkenyl" may refer to prop-2-enyl, but-2-enyl, but-3-enyl, 2-methyl-prop-2-enyl, hex-2-enyl, hex-5-enyl, 2,3-dimethylbut-2-enyl, and the like. Furthermore, alkenyl groups may be substituted or unsubstituted.

The term "alkynyl" is intended to include hydrocarbon chains of either linear or branched configuration, having one or more carbon-carbon triple bond that may occur in any stable point along the chain. Unless otherwise specified, "alkynyl" groups refer refers to groups having two to eight, preferably two to six carbons. Examples of "alkynyl" include, but are not limited to prop-2-ynyl, but-2-ynyl, but-3-ynyl, pent-2-ynyl, 3-methylpent-4-ynyl, hex-2-ynyl, hex-5-ynyl, etc. Furthermore, alkynyl groups may be substituted or unsubstituted.

Cycloalkyl is a subset of alkyl and includes any stable cyclic or polycyclic hydrocarbon groups of from 3 to 13 carbon atoms, any of which is saturated. Examples of such cycloalkyl include, but are not limited to cyclopropyl, norbornyl, [2.2.2]bicyclooctane, [4.4.0]bicyclodecane, and the like, which, as in the case of other alkyl moieties, may optionally be substituted. The term "cycloalkyl" may be used interchangeably with the term "carbocycle".

Cycloalkenyl is a subset of alkenyl and includes any stable cyclic or polycyclic hydrocarbon groups of from 3 to 13 carbon atoms, preferably from 5 to 8 carbon atoms, which contains one or more unsaturated carbon-carbon double bonds that may occur in any point along the cycle. Examples of such cycloalkenyl include, but are not limited to cyclopentenyl, cyclohexenyl and the like.

Cycloalkynyl is a subset of alkynyl and includes any stable cyclic or polycyclic hydrocarbon groups of from 5 to 13 carbon atoms, which contains one or more unsaturated carbon-carbon triple bonds that may occur in any point along the cycle. As in the case of other alkenyl and alkynyl moieties, cycloalkenyl and cycloalkynyl may optionally be substituted.

The term "heteroalkyl" is meant a branched or unbranched alkyl, alkenyl, or alkynyl group having from 1 to 7 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Examples of heteroalkyls include, without limitation, polyethers, such as methoxymethyl and ethoxyethyl.

"Heterocycle", "heterocyclyl", or "heterocyclic" as used herein refers to non-aromatic ring systems having five to fourteen ring atoms in which one or more ring carbons, preferably one to four, are each replaced by a heteroatom such as N, O, or S. Heterocyclic groups may be substituted or unsubstituted and may include one, two, or three fused or unfused ring systems. Non-limiting examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. A heterocylic group can include two or more of the ring systems listed above. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "aryl" used alone or as part of a larger moiety as in "aralkyl", "aralkoxy", or "aryloxyalkyl", refers to aromatic ring groups having six to fourteen ring atoms, such as phenyl, 1-naphthyl, 2-naphthyl, 1-anthracyl and 2-anthracyl. An "aryl" ring may contain one or more substituents. The term "aryl" may be used interchangeably with the term "aryl ring". "Aryl" also includes fused polycyclic aromatic ring systems in which an aromatic ring is fused to one or more rings. Non-limiting examples of useful aryl ring groups include phenyl, hydroxyphenyl, halophenyl, alkoxyphenyl, dialkoxyphenyl, trialkoxyphenyl, alkylenedioxyphenyl, naphthyl, phenanthryl, anthryl, phenanthro and the like, as well as 1-naphthyl, 2-naphthyl, 1-anthracyl and 2-anthracyl. Also included within the scope of the term "aryl", as it is used herein, is a group in which an aromatic ring is fused to one or more non-aromatic rings, such as in a indanyl, phenanthridinyl, or tetrahydronaphthyl, where the radical or point of attachment is on the aromatic ring.

The term "heteroaryl" as used herein refers to stable heterocyclic, and polyheterocyclic aromatic moieties having 5-14 ring atoms. Heteroaryl groups may be substituted or unsubstituted and may comprise one or more rings. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like (see e.g. Katritzky, Handbook of Heterocyclic Chemistry). Further specific examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisoxazolyl. Heteroaryl groups further include a group in which a heteroaromatic ring is fused to one or more aromatic or nonaromatic rings where the radical or point of attachment is on the heteroaromatic ring. Examples include tetrahydroquinoline, tetrahydroisoquinoline, and pyrido[3,4-d]pyrimidinyl, imidazo[1,2-a]pyrimidyl, imidazo[1,2-a]pyrazinyl, imidazo[1,2-a]pyridinyl, imidazo[1,2-c]pyrimidyl, pyrazolo[1,5-a][1,3,5]triazinyl, pyrazolo[1,5-c]pyrimidyl, imidazo[1,2-b]pyridazinyl, imidazo[1,5-a]pyrimidyl, pyrazolo[1,5-b][1,2,4]triazine, quinolyl, isoquinolyl, quinoxalyl, imidazotriazinyl, pyrrolo[2,3-d]pyrimidyl, triazolopyrimidyl, pyridopyrazinyl. The term "heteroaryl" also refers to rings that are optionally substituted. The term "heteroaryl" may be used interchangeably with the term "heteroaryl ring" or the term "heteroaromatic".

An aryl group (including the aryl portion of an aralkyl, aralkoxy, or aryloxyalkyl moiety and the like) or heteroaryl group (including the heteroaryl portion of a heteroaralkyl or heteroarylalkoxy moiety and the like) may contain one or more substituents. Examples of suitable substituents on the unsaturated carbon atom of an aryl or heteroaryl group include halogen (F, Cl, Br or I), alkyl, alkenyl, alkynyl, heteroalkyl, —CN, —OR$^2$, —S(O)$_r$R$^2$, (wherein r is an integer of 0, 1 or 2), —SO$_2$NR$^1$R$^2$, —NR$^1$R$^2$, —O—NR$^1$R$^2$, —NR$^1$R$^2$, —(CO)YR$^2$, —O(CO)YR$^2$, —NR$^1$(CO)YR$^2$, —S(CO)YR$^2$, —NR$^1$C(=S)YR$^2$, —OC(=S)YR$^2$, —C(=S)YR$^2$, wherein each occurrence of Y is independently —O—, —S—, —NR$^1$, or a chemical bond; —(CO)YR$^2$ thus encompasses —C(=O)R$^2$, —C(=O)OR$^2$, and —C(=O)NR$^1$R$^2$. Additional substituents include —YC(=NR$^1$)YR$^2$, —YC(=N—OR$^1$)YR$^2$, —YC(=N—NR$^1$R$^2$)YR$^2$, —COCOR$^2$, —COMCOR$^2$ (where M is a 1-6 carbon alkyl group), —YP(=O)(YR$^3$)(YR$^3$) (including among others —P(=O)(R$^3$)$_2$), —Si(R$^{3a}$)$_3$, —NO$_2$, —NR$^1$SO$_2$R$^2$ and —NR$^1$SO$_2$NR$^1$R$^2$. To illustrate further, substituents in which Y is —NR$^1$ thus include among others, —NR$^1$C(=O)R$^2$, —NR$^1$C(=O)NR$^1$R$^2$, —NR$^1$C(=O)OR$^2$, and —NR$^1$C(=NH)NR$^1$R$^2$. R$^3$ substituent is selected from alkyl, alkenyl, alkynyl, cycloalkyl, cycloalkenyl, cycloalkynyl, aryl, heteroaryl, heterocyclyl; R$^1$ and R$^2$ substituents at each occurrence are independently selected from hydrogen, alkyl, alkenyl, alkynyl, cycloalkyl, cycloalkenyl, cycloalkynyl, aryl, heteroaryl, heterocyclyl, and R$^1$, R$^2$ and R$^3$ substituents may themselves be substituted or unsubstituted. Examples of substituents allowed on R$^1$, R$^2$ and R$^3$ include, among others amino, alkylamino, dialkylamino, aminocarbonyl, halogen, alkyl, aryl, heteroalkyl, heteroaryl, carbocycle, heterocycle, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, haloalkoxy groups. Additional illustrative examples include protected OH (such as acyloxy), phenyl, substituted phenyl, —O-phenyl, —O— (substituted) phenyl, -benzyl, substituted benzyl, —O-phenethyl (i.e., —OCH$_2$CH$_2$C$_6$H$_5$), —O— (substituted)phenethyl. Non-limiting illustrations of a substituted R$^1$, R$^2$ or R$^3$ moiety include haloalkyl and trihaloalkyl, alkoxyalkyl, halophenyl, -M-heteroaryl, -M-heterocycle, -M-aryl, -M-OR$^2$, -M-SR$^2$, -M-NR$^1$R$^2$, -M-OC(O)NR$^1$R$^2$, M-C(=NR$^2$)NR$^1$R$^2$, -M-C(=NR$^1$)OR$^2$, -M-P(=O)(R$^3$)$_2$, Si(R$^{3a}$)$_3$, -M-NR$^1$C(O)R$^2$, -M-NR$^1$C(O)OR$^2$, -M-C(O)R$^2$, -M-C(=S)R$^2$, -M-C(=S)NR$^1$R$^2$, -M-C(O)NR$^1$R$^2$, -M-C(O)NR$^2$, -M-NR$^1$R$^2$, -M-NR$^2$C(NR$^1$)NR$^1$R$^2$, -M-NR$^1$C(S)NR$^1$R$^2$, -M-S(O)$_2$R$^1$, -M-C(O)R$^1$, -M-OC(O)R$^1$, -MC(O)SR$^2$, -M-S(O)$_2$NR$^1$R$^2$, —C(O)-M-C(O)R$^2$, -MCO$_2$R$^2$, -MC(=O)NR$^1$R$^2$, -M-C(=NH)NR$^1$R$^2$, and -M-OC(=NH)NR$^1$R$^2$ (wherein M is a 1-6 carbon alkyl group).

Some more specific examples include but are not limited to chloromethyl, trichloromethyl, trifluoromethyl, methoxyethyl, alkoxyphenyl, halophenyl, —CH$_2$-aryl, —CH$_2$-heterocycle, —CH$_2$C(O)NH$_2$, —C(O)CH$_2$N(CH$_3$)$_2$, —CH$_2$CH$_2$OH, —CH$_2$OC(O)NH$_2$, —CH$_2$CH$_2$NH$_2$, —CH$_2$CH$_2$CH$_2$NEt$_2$, —CH$_2$OCH$_3$, —C(O)NH$_2$, —CH$_2$CH$_2$-heterocycle, —C(=S)CH$_3$, —C(=S)NH$_2$, —C(=NH)NH$_2$, —C(=NH)OEt, —C(O)NH-cyclopropyl, C(O)NHCH$_2$CH$_2$-heterocycle, —C(O)NHCH$_2$CH$_2$OCH$_3$, —C(O)CH$_2$CH$_2$NHCH$_3$, —CH$_2$CH$_2$F, —C(O)CH$_2$-heterocycle, —CH$_2$C(O)NHCH$_3$, —CH$_2$CH$_2$P(=O)(CH$_3$)$_2$, Si(CH$_3$)$_3$ and the like.

When a ring system (e.g., cycloalkyl, heterocyclyl, aryl, or heteroaryl) is substituted with a number of substituents varying within an expressly defined range, it is understood that the total number of substituents does not exceed the normal available valencies under the existing conditions. Thus, for example, a phenyl ring substituted with "n" substituents (where "n" ranges from 1 to 5) can have 1 to 5 substituents, whereas it is understood that a pyridinyl ring substituted with "n" substituents has a number of substituents ranging from 1 to 4. The maximum number of substituents that a group in the compounds of the invention may have can be easily determined.

An alkyl, alkenyl, alkynyl, alkoxy, haloalkyl, heteroalkyl, cycloalkyl, cycloalkenyl, cycloalkynyl or non-aromatic heterocyclic group may thus also contain one or more substituents. Examples of suitable substituents on such groups include, but are not limited to those listed above for the carbon atoms of an aryl or heteroaryl group and in addition include the following substituents for a saturated carbon atom: =O, =S, =NH, =NNR$^2$R$^3$, =NNHC(O)R$^2$, =NNHCO$_2$R$^2$, or =NNHSO$_2$R$^2$, wherein R$^2$ and R$^3$ at each occurrence are independently hydrogen, alkyl, alkenyl, alkenyl, alkynyl, cycloalkyl, cycloalkenyl, cycloalkynyl, heteroalkyl, aryl, heteroaryl, heterocyclyl.

Illustrative examples of substituents on an aliphatic, heteroaliphatic or heterocyclic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, —CN, carboxy, alkoxycarbonyl, alkylcarbonyl, —OH, haloalkoxy, or haloalkyl groups.

Illustrative substituents on a nitrogen, e.g., in an heteroaryl or non-aromatic heterocyclic ring include R$^1$, —NR$^1$R$^2$, —C(=O)R$^2$, —C(=O)OR$^2$, —C(=O)SR$^2$, —C(=O)NR$^1$R$^2$, —C(=NR$^2$)NR$^1$R$^2$, —C(=NR$^2$)OR$^2$, —C(=NR$^1$)R$^3$, —COCOR$^2$, —COMCOR$^2$, —CN, —SO$_2$R$^2$, S(O)R$^2$, —P(=O)(YR$^3$)(YR$^3$), —NR$^1$SO$_2$R$^2$ and —NR$^1$SO$_2$NR$^1$R$^2$, wherein each occurrence of R$^3$ is alkyl, alkenyl, alkynyl, cycloalkkyl, cycloalkenyl, cycloalkynyl, aryl, heteroaryl and heterocyclyl; each occurrence of $R^1$ and $R^2$ is independently hydrogen, alkyl, alkenyl, alkynyl, cycloalkkyl, cycloalkenyl, cycloalkynyl, aryl, heteroaryl and heterocyclyl.

When a ring system (e.g., cycloalkyl, heterocyclyl, aryl, or heteroaryl) is substituted with a number of substituents varying within an expressly defined range, it is understood that the total number of substituents does not exceed the normal available valencies under the existing conditions. Thus, for example, a phenyl ring substituted with "m" substituents (where "m" ranges from 0 to 5) can have 0 to 5 substituents, whereas it is understood that a pyridinyl ring substituted with "m" substituents has a number of substituents ranging from 0 to 4. The maximum number of substituents that a group in the compounds of the invention may have can be easily determined.

Certain compounds of the invention may exist in tautomeric forms, and the invention includes all such tautomeric forms of those compounds unless otherwise specified.

Unless otherwise stated, structures depicted herein are also meant to include all stereochemical forms of the structure; i.e., the R and S configurations for each asymmetric center. Thus, single stereochemical isomers as well as enantiomeric and diastereomeric mixtures of the present compounds are within the scope of the invention. Thus, the invention encompasses each diasteriomer or enantiomer substantially free of other isomers (>90%, and preferably >95%, free from other stereoisomers on a molar basis) as well as a mixture of such isomers.

Particular optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound.

Optically active compounds of the invention can be obtained by using active starting materials. These isomers may be in the form of a free acid, a free base, an ester or a salt.

Compounds of the invention can exist in radiolabelled form, i.e., said compounds may contain one or more atoms containing an atomic mass or mass number different from the atomic mass or mass number ordinarily found in nature. Radioisotopes of hydrogen, carbon, phosphorous, fluorine and chlorine include $^3H$, $^{14}C$, $^{32}P$, $^{35}S$, $^{18}F$ and $^{36}Cl$, respectively. Compounds of the invention which contain those radioisotopes and/or other radioisotopes of other atoms are within the scope of the invention. Tritiated, i.e., $^3H$, and carbon-14, i.e., $^{14}C$, radioisotopes are particularly preferred for their ease of preparation and detectability.

Radiolabelled compounds of the invention can generally be prepared by methods well known to those skilled in the art. Conveniently, such radiolabelled compounds can be prepared by carrying out the procedures disclosed herein except substituting a readily available radiolabelled reagent for a non-radiolabelled reagent.

4. Synthetic Overview

The practitioner has a well-established literature of heterocyclic and other relevant chemical transformations, recovery and purification technologies to draw upon, in combination with the information contained in the examples which follow, for guidance on synthetic strategies, protecting groups, and other materials and methods useful for the synthesis, recovery and characterization of compounds of the invention, including compounds containing the various choices for the $R^a$, $R^b$, $R^c$, $R^d$, $R^e$, $R^{b1}$, $R^{c1}$, $R^{d1}$, $R^{e1}$, $R^f$, $R^g$, and Rings A, B, C, D, E and F.

Various synthetic approaches may be used to produce the compounds described herein, including those approaches depicted schematically below. The practitioner will appreciate that protecting groups may be used in these approaches. "Protecting groups", are moieties that are used to temporarily block chemical reaction at a potentially reactive site (e.g., an amine, hydroxy, thiol, aldehyde, etc.) so that a reaction can be carried out selectively at another site in a multifunctional compound. In preferred embodiments, a protecting group reacts selectively in good yield to give a protected substrate that is suitable for the planned reactions; the protecting group should be selectively removable in good yield by readily available, preferably nontoxic reagents that do not unduly attack the other functional groups present; the protecting group preferably forms an readily separable derivative (more preferably without the generation of new stereogenic centers); and the protecting group preferably has a minimum of additional functionality to avoid the complication of further sites of reaction. A wide variety of protecting groups and strategies, reagents and conditions for deploying and removing them are known in the art. See, e.g., "Protective Groups in Organic Synthesis" Third Ed. Greene, T. W. and Wuts, P. G., Eds., John Wiley & Sons, New York: 1999. For additional background information on protecting group methodologies (materials, methods and strategies for protection and deprotection) and other synthetic chemistry transformations useful in producing the compounds described herein, see in R. Larock, Comprehensive organic Transformations, VCH Publishers (1989); T. W. Greene and P. G. M. Wuts, Protective Groups in Organic Synthesis, 3rd. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995). The entire contents of these references are hereby incorporated by reference.

Also, one may chose reagents enriched for a desired isotope, e.g. deuterium in place of hydrogen, to create compounds of the invention containing such isotope(s). Compounds containing deuterium in place of hydrogen in one or more locations, or containing various isotopes of C, N, P and O, are encompassed by the invention and may be used, for instance, for studying metabolism and/or tissue distribution of the compounds or to alter the rate or path of metabolism or other aspects of biological functioning.

Compounds of the invention can be synthesized using the methods described below, together with synthetic methods known in the art of synthetic organic chemistry, or by a variation thereon as appreciated by those skilled in the art. Preferred methods include, but are not limited to those described below. The reactions are preformed in a solvent appropriate to the reagents and materials employed and suitable for the transformation being effected. It will be understood by those skilled in the art of organic synthesis that the functionality present on the molecule should be consistent the transformations proposed. This will sometimes required some judgment to modify the order of the synthetic steps or to select one particular process scheme over another in order to obtain a desired compound of the invention.

A compound of the invention could be prepared as outlined from Scheme 1 to Scheme 57a and via standard methods known to those skilled in the art. For certain compounds of the invention, microwave-assisted synthesis may be carried out using conventional procedures and the conditions noted in the examples which follow. Reactions may be carried out using commercially available microwave reactors such as the Biotage Initiator 2.0™ (Biotage AB, Kungsgatan 76, SE-753 18 Uppsala, Sweden or 1725 Discovery Drive Charlottesville, Va. 22911) or the CEM Discover™ System (CEM Corporation, Matthews, N.C.) which were used in the examples below.

A compound of Formula Ia or VIA in which n is 0 and X is N can be prepared in a 2 steps synthesis as shown in Scheme 1. A [Ring A] moiety can first be incorporated to the central pyrimidine moiety by reacting [Ring A]-NH$_2$ with 2,4-dichloro-5-(trifluoromethyl)pyrimidine in the presence of a base such as di-isopropylethyl amine at high temperature generating intermediate 1. The [Ring E]-L-moiety can then be incorporated onto intermediate 1 using various conditions depending on the nature of the L linker. The variables in the intermediate [Ring E]-[L]- and [Ring A] are as defined previously, Rings A and E being substituted with permitted R$^a$ and R$^g$ groups respectively.

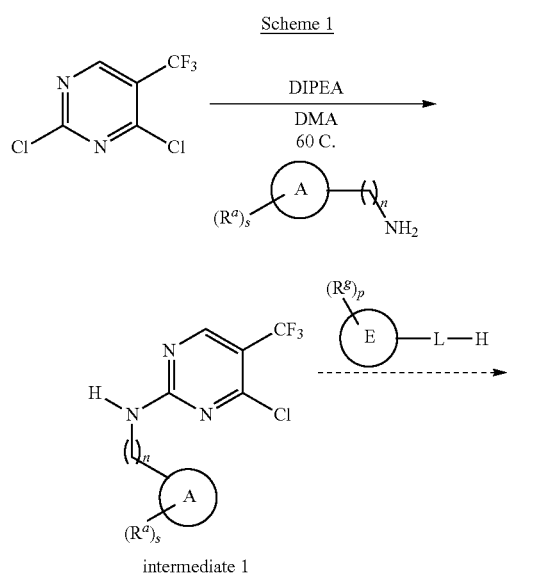

intermediate 1

An approach to the preparation of an intermediate 1 is illustrated below in Scheme IA in which Ring A is a phenyl:

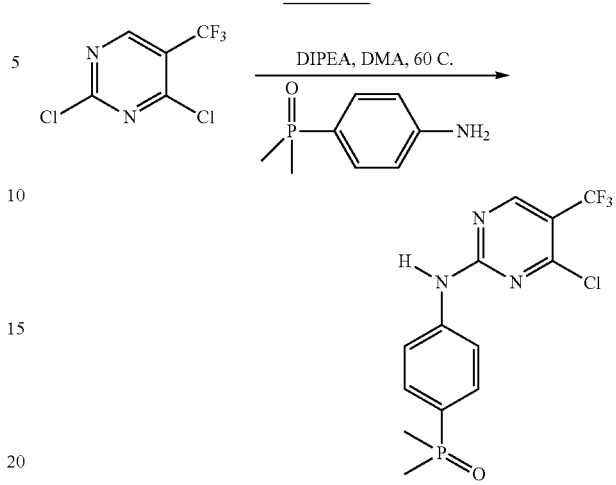

A compound of Formula VIA in which L is O can be prepared using microwave chemistry, by reacting an intermediate 1 with [Ring E]-OH in a solvent such as dimethylformamide and high temperatures as shown in Scheme 2.

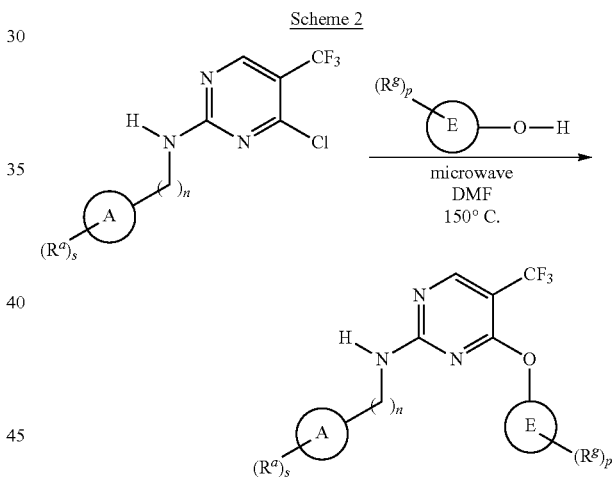

An approach to the preparation of a compound of Formula VIA in which L is O, is illustrated below in Scheme 2A in which Ring A and Ring E are phenyls:

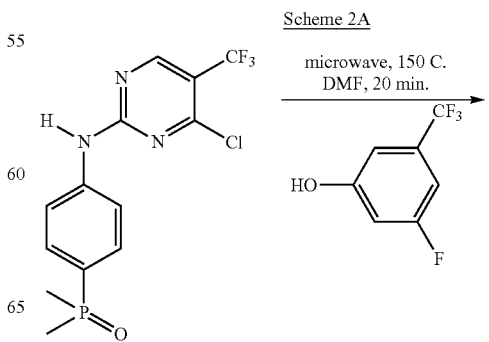

-continued

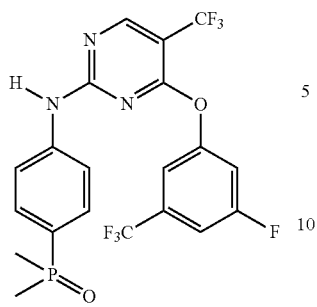

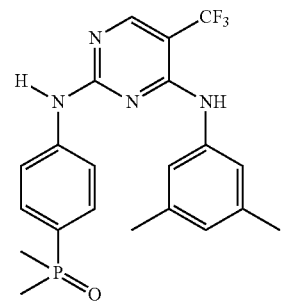

A compound of Formula VIA in which L is NH can be prepared using microwave chemistry, by reaction an intermediate 1 with [Ring E]-NH$_2$, in a polar solvent such as Ethanol, and using high temperatures, as shown in Scheme 3. A base (i.e. di-isopropylethyl amine, triethylamine or the like) or an acid may be added to facilitate the displacement reaction.

Scheme 3

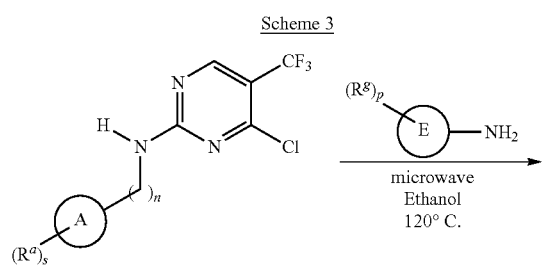

An approach to the preparation of a few compounds of Formula VIA in which L is NH, is illustrated below in Scheme 3A and 3B in which E is a phenyl or adamantanamine:

Scheme 3A

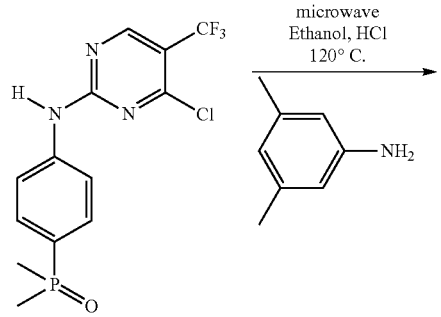

Scheme 3B

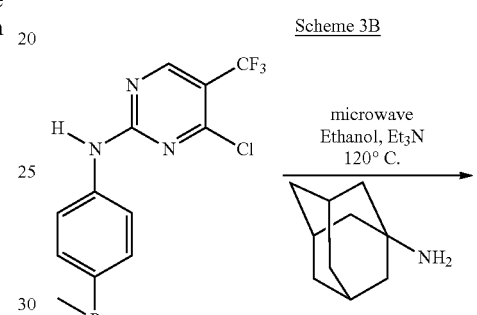

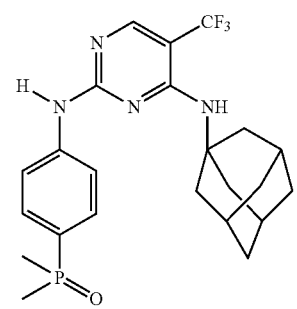

A compound of Formula VIA in which L is NH(CH$_2$)$_{1-4}$ can be prepared using microwave chemistry, by reaction an intermediate 1 with [Ring E]-(CH$_2$)$_{1-4}$NH$_2$, in the presence of a base such as triethylamine, in a polar solvent such as Ethanol, and using high temperatures, as shown in Scheme 4:

Scheme 4

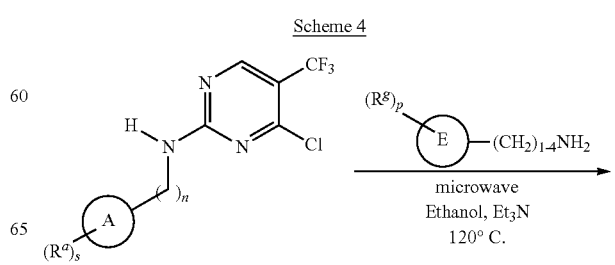

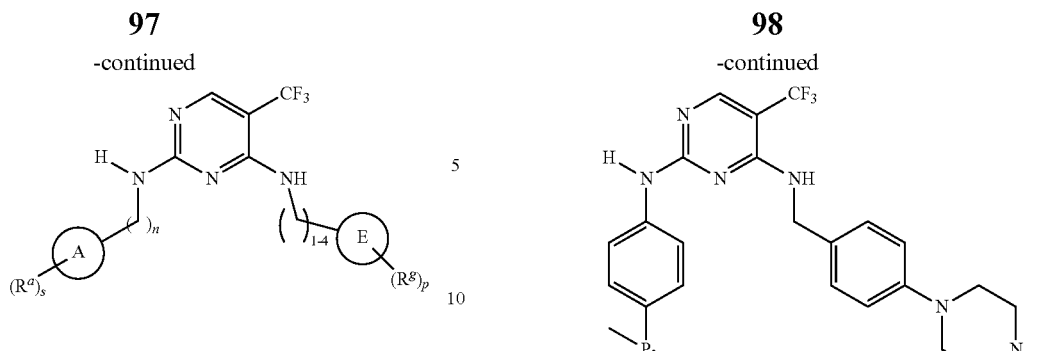

An approach to the preparation of a few compounds of Formula VIA in which L is $NH(CH_2)_{1-4}$, is illustrated below in Schemes 4A and 4B. Scheme 4A illustrates the synthesis of a compound of Formula VIa in which E is a phenyl and L is $NHCH_2$ and Scheme 4B illustrates the synthesis of a compound of Formula VIA in which E is 3-1H-indole and L is $NH(CH_2)_2$:

A compound of Formula VIA in which L is $SH(CH_2)y$ can be prepared using microwave chemistry, by reaction an intermediate 1 with [Ring E]-$(CH_2)_y$SH, in the presence of a base such as Cesium carbonate, and in a solvent such as dimethylformamide at high temperatures, as shown in Scheme 5. The variable y is defined above.

Scheme 4A

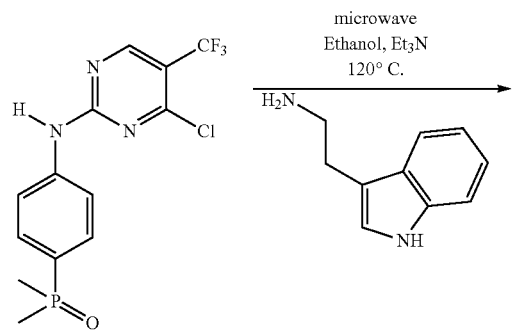

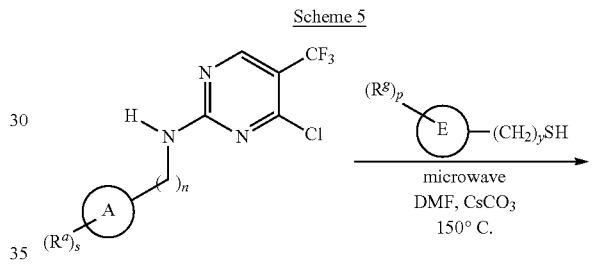

Scheme 5

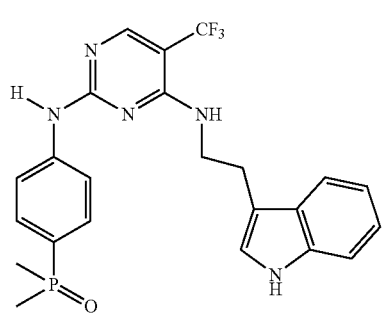

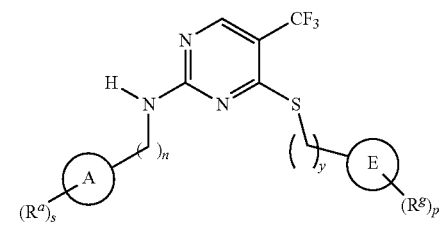

An approach to the preparation of a compound of Formula VIa in which L is $S(CH_2)_y$, is illustrated below in Scheme 5A:

Scheme 4B

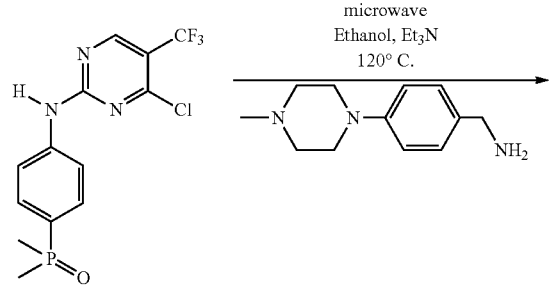

Scheme 5A

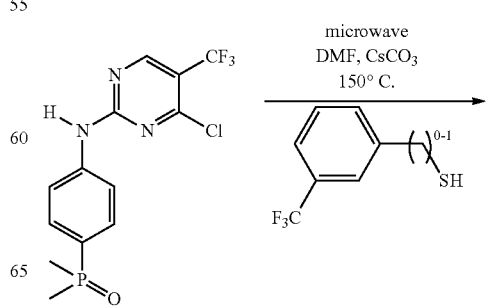

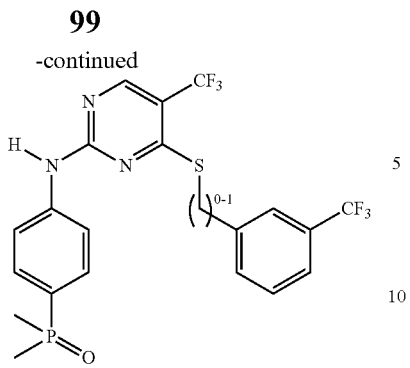

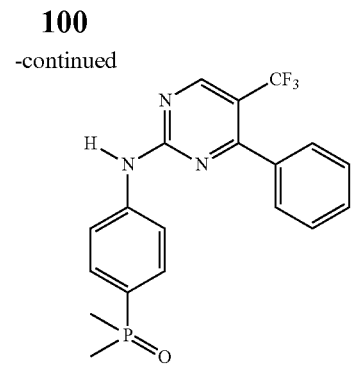

A compound of Formula VIA in which L is bond and [Ring E] is an aryl or heteroaryl, can be prepared using Suzuki coupling conditions. Scheme 6 illustrates the Suzuki coupling reaction.

A compound of Formula VIA in which L is bond and [Ring E] is a N-linked heterocyclyl, can be prepared using microwave chemistry, by reaction an intermediate 1 with the heterocyclyl, in the presence of a base such as triethylamine, in a polar solvent such as Ethanol, and using high temperatures, as shown in Scheme 7:

Scheme 6

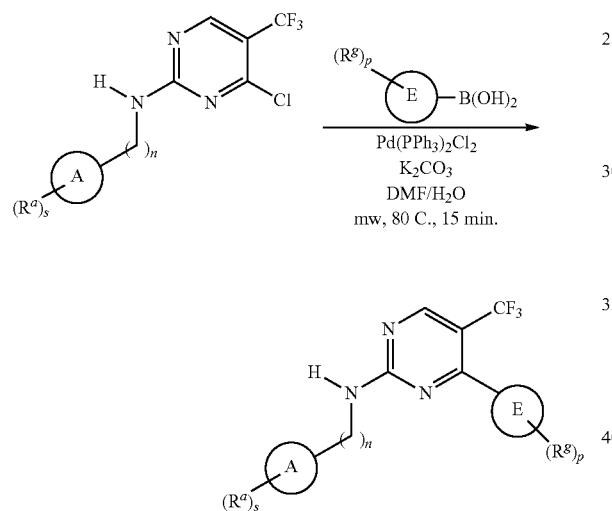

In a non limiting example, Scheme 6A illustrates the preparation of a compound of Formula VIA in which L is a bond and [Ring E] is a phenyl.

Scheme 7

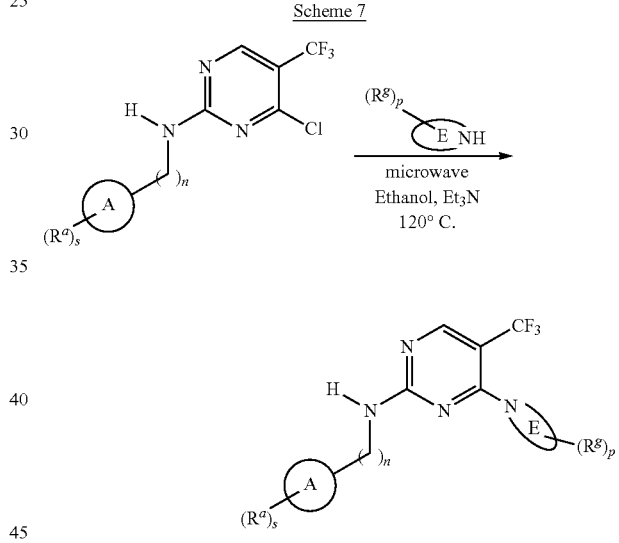

In a non limiting example, Scheme 7A illustrates the preparation of a compound of Formula VIA in which L is a bond and [Ring E] is N-phenyl-piperazine.

Scheme 6A

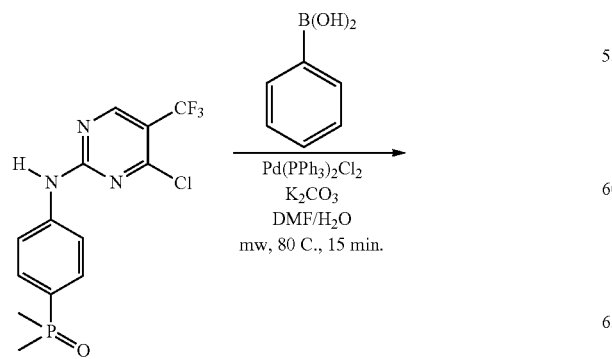

Scheme 7A

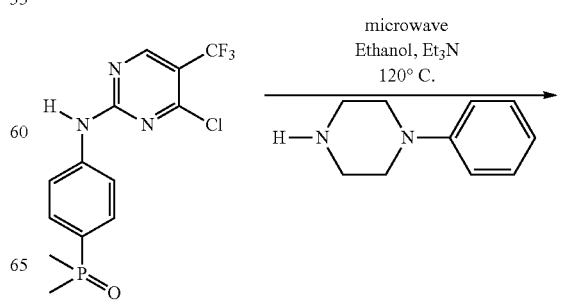

-continued

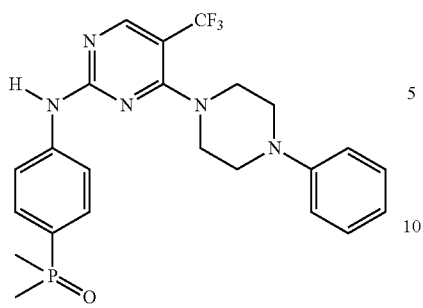

An alternative reaction sequence can be used for the preparation of compounds of Formula VIa in which L is NH. [Ring E]-NH moiety can be first incorporated to the central pyrimidine moiety prior to the incorporation of [Ring A]-NH moiety. Scheme 8 illustrates the reaction of 2,4,5-trichloropyrimidine with a [Ring-E]-NH$_2$ moiety in the presence of a base (i.e. potassium carbonate or sodium hydride or the like) in a solvent such as dimethylformamide or Ethanol in order to generate intermediate 2. The reaction can be perform at room temperature or may require higher temperature.

Scheme 8

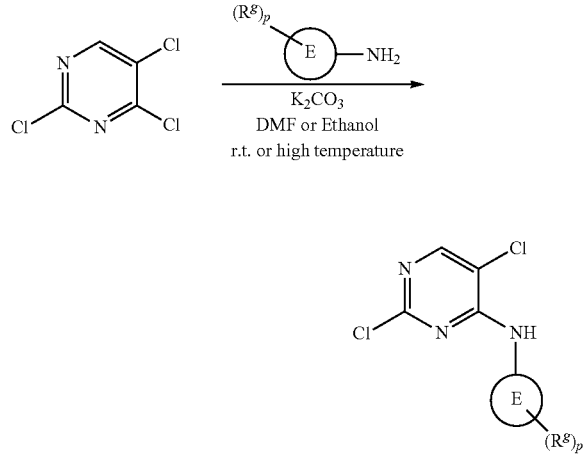

Intermediate 2.

Another example of this reaction is shown below in Scheme 9 in which intermediate 3 is prepared by reacting 2,4-dichloro-5-(trifluoromethyl)pyrimidine with a [Ring E]-NH$_2$ moiety in the presence of sodium hydride in dimethylformamide at lower temperatures.

Scheme 9

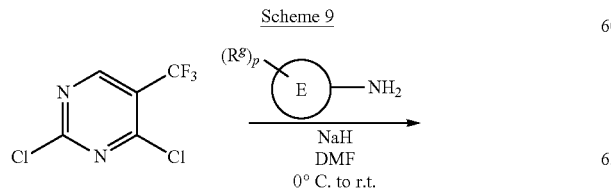

-continued

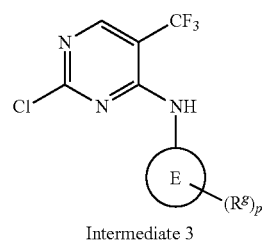

Intermediate 3

Intermediate 2 or 3 can then be reacted with a [Ring-A]-(CH$_2$)$_n$NH$_2$ moiety using regular displacement conditions as shown below in Scheme 10.

Scheme 10

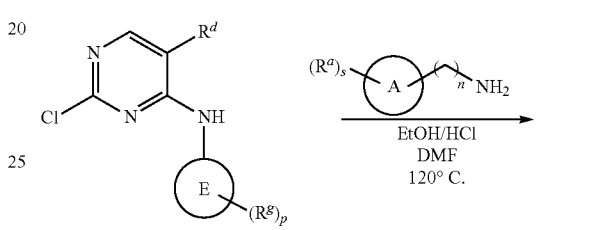

R$^d$ is Cl: Intermediate 2
R$^d$ is CF$_3$: Intermediate 3

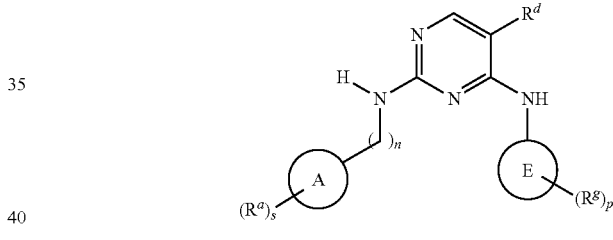

In a non limiting example, Schemes 10A and 10B illustrate the preparation of compounds of Formula VIA in which L is NH and Ring A and Ring E are substituted phenyl:

Scheme 10A

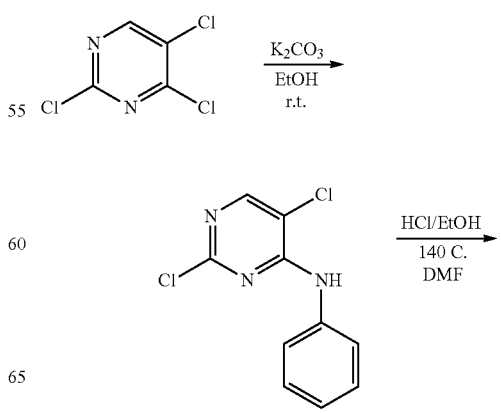

103
-continued

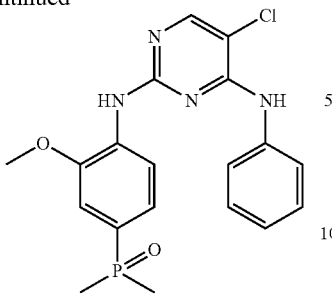

Scheme 10B

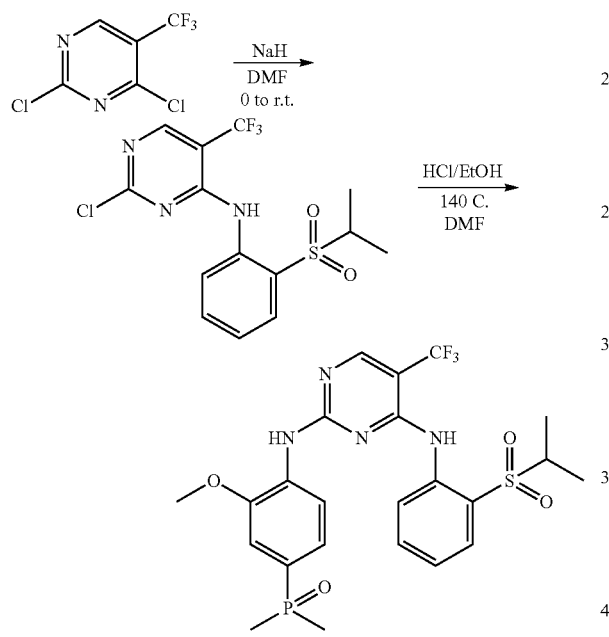

The synthetic guidance provided in Schemes 1 through 10 is applicable to a variety of Ring A and Ring E of the invention and allows the preparation of all compounds of the invention.

Scheme 11 illustrates the preparation of a compound of Formula IA and VIA in which n is 0, L is NH and $X^1$ is CH.

In Scheme 11, [Ring E]-NH moiety is incorporated onto the pyridine central scaffold by reacting 2-chloro-4-iodo-5-(trifluoromethyl)pyridine with [Ring E]-NH$_2$ using Palladium coupling reaction conditions. [Ring A]-NH moiety is then incorporated by displacement chemistry as previously described in the above Schemes. Microwaves and heat can also be used to accelerate or drive the displacement reaction to completion.

Scheme 11

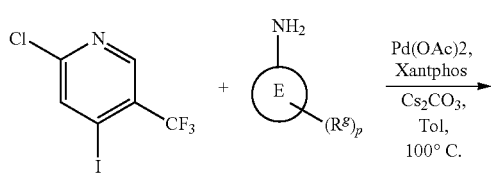

104
-continued

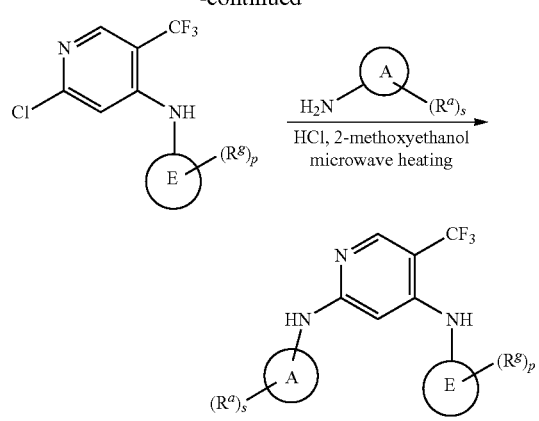

In a non limiting example, Scheme 11A illustrates the preparation of compounds of Formula VIA in which L is NH, $X^1$ is CH, and Ring A and Ring E are substituted phenyl.

Scheme 11A

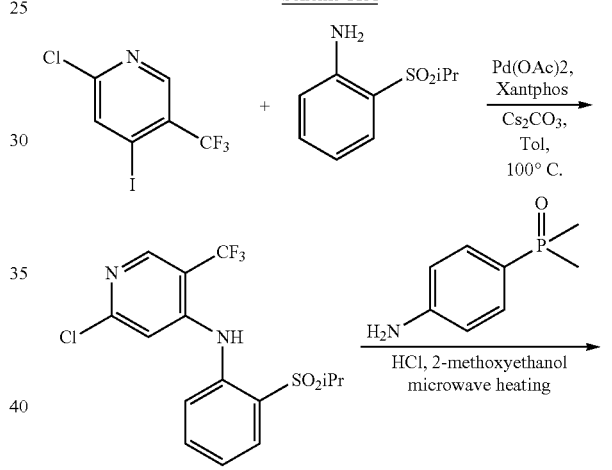

Scheme 12 illustrates the synthesis of a compound of Formula IVA in which $X^1$ is CH and $R^d$ and $R^e$ form a phenyl ring.

Scheme 12

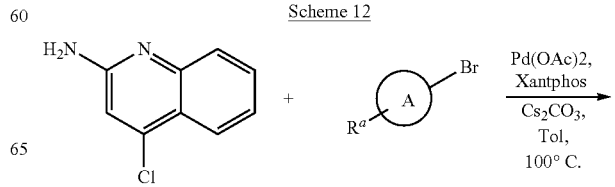

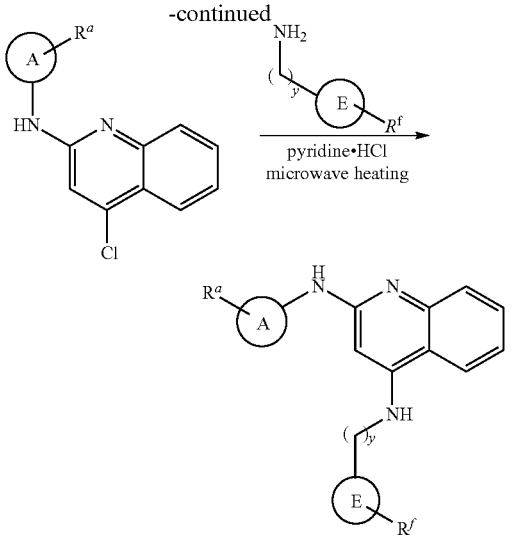

In a non limiting example, Scheme 12A illustrates the preparation of compounds of Formula IVA in which $X^1$ is CH and $R^d$ and $R^e$ form a phenyl ring, Ring A and Ring E are substituted phenyl.

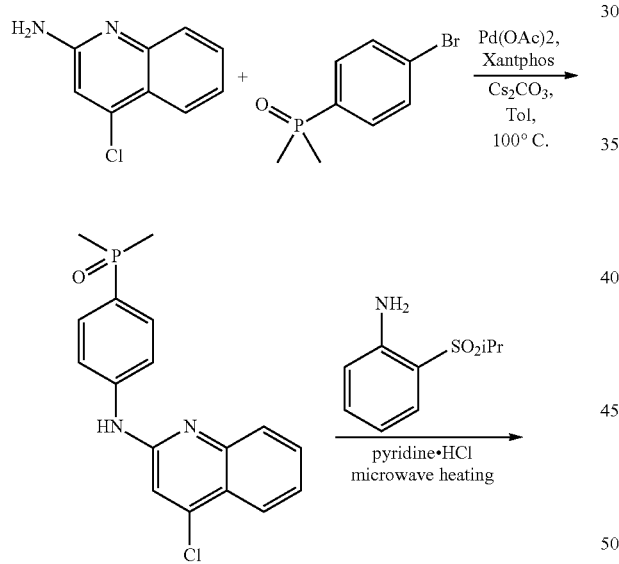

Scheme 13 illustrates the synthesis of a compound of Formula IIIA in which $X^1$ is CH and $R^b$ and $R^c$ form a phenyl ring which is further substituted with a phenyl ring.

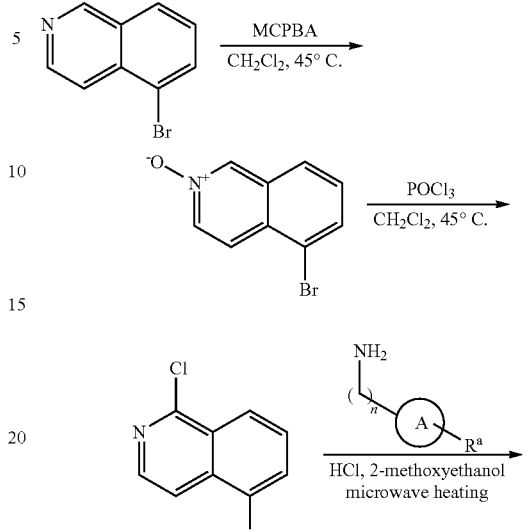

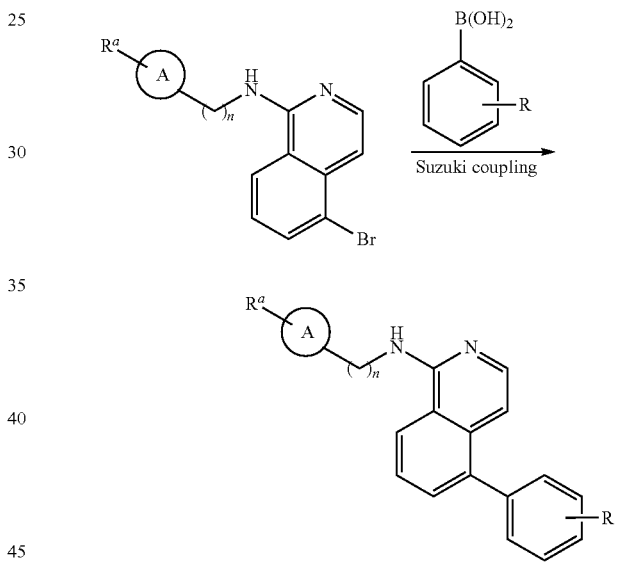

In a non limiting example, Scheme 13A illustrates the preparation of compounds of Formula VA in which $X^1$ is CH and $R^b$ and $R^c$ form a phenyl ring, Ring A is substituted phenyl and $R^f$ is a substituted phenyl.

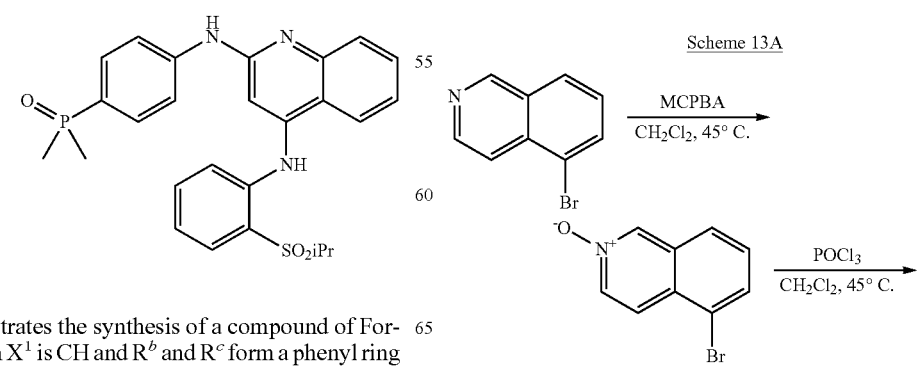

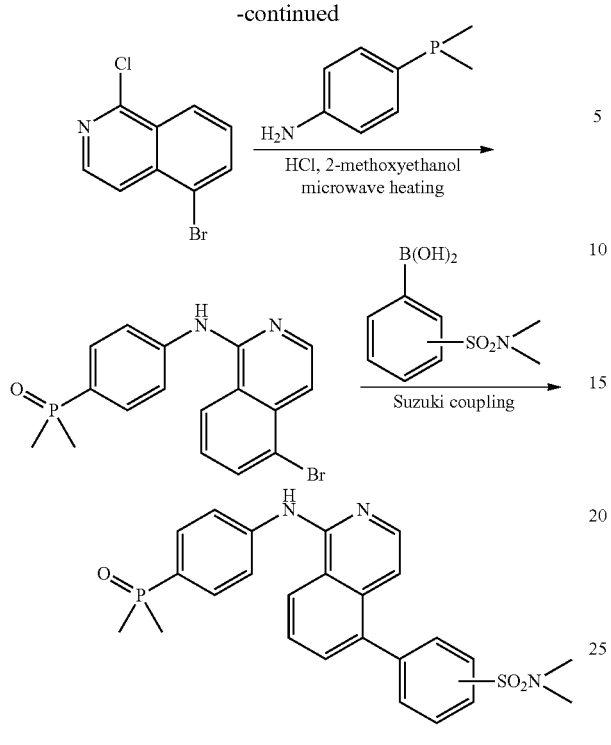

Scheme 14 illustrates the synthesis of a compound of Formula IIIA in which $X^1$ is N and $R^c$ and $R^d$ form a pyrrole.

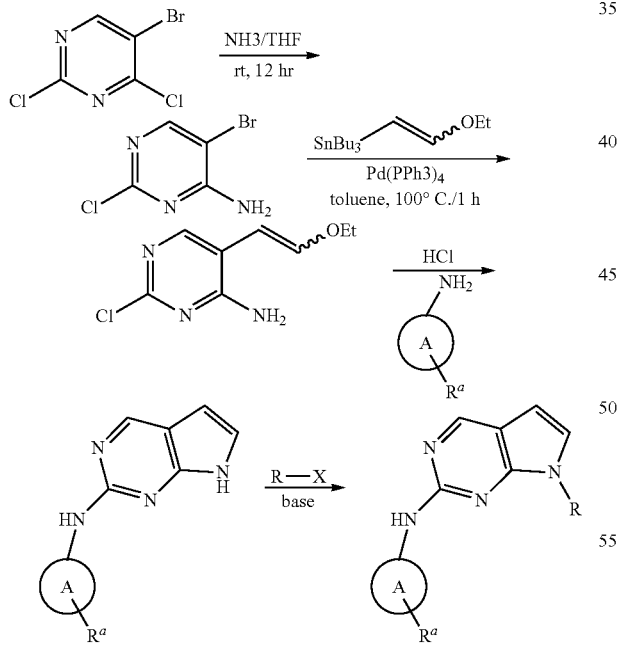

in which Ring A and $R^a$ are as defined in part 1 and in R—X, R is alkyl, heteroaryl, aryl, aryl alkyl, heteroaryl alkyl, heterocyclyl and other groups selected from the $R^f$ list of substituents; and X is a halide or other leaving groups.

Another example of preparation of a compound of Formula IIIA is illustrated below in Scheme 15 in which substituent R depicted in scheme 14 is a phenyl.

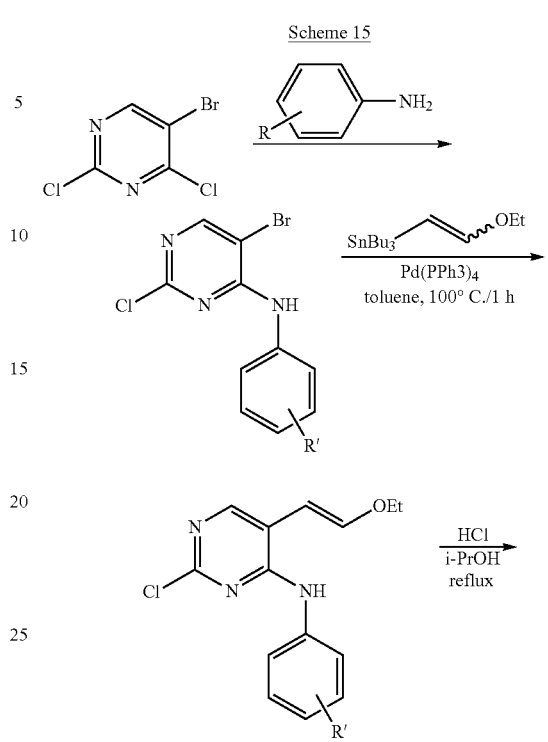

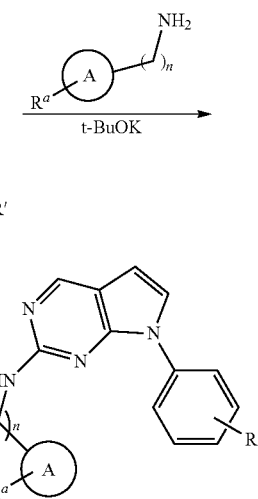

in which R' is a substituent selected from $R^f$ list and Ring A and $R^a$ are defined in part 1.

In a non limiting example, Scheme 15A illustrates the preparation of compounds of Formula IIIA in which $X^1$ is N, $R^c$ and $R^d$ form a pyrrole, Ring A is a substituted phenyl and $R^f$ is a substituted phenyl:

Scheme 15A

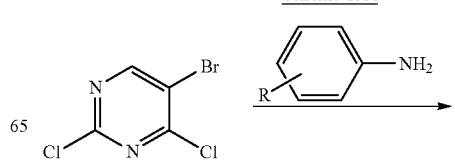

-continued

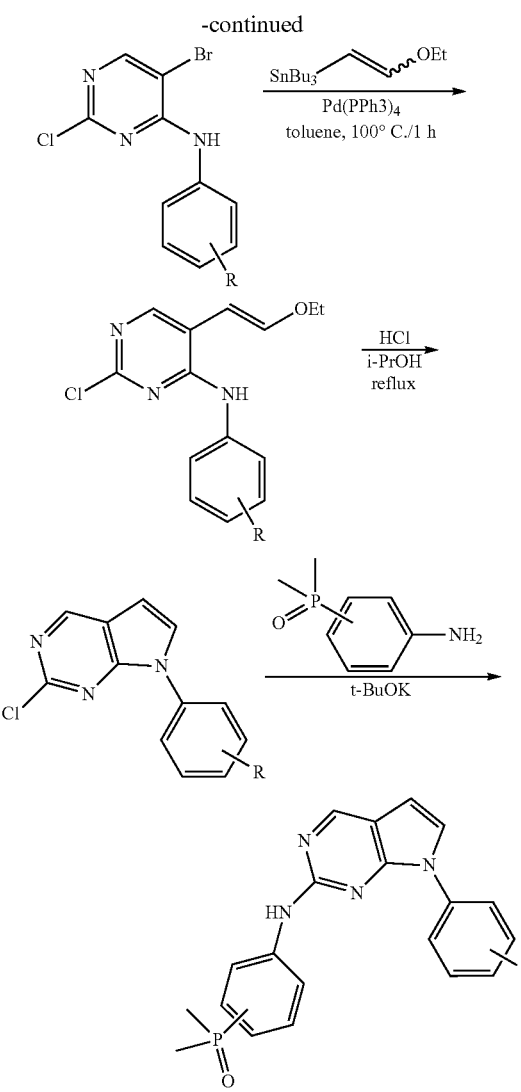

In a non limiting example, Scheme 16 illustrates the preparation of compounds of Formula IIIA in which $X^1$ is N and $R^c$ and $R^d$ form an imidazole ring which is substituted with a phenyl.

Scheme 16

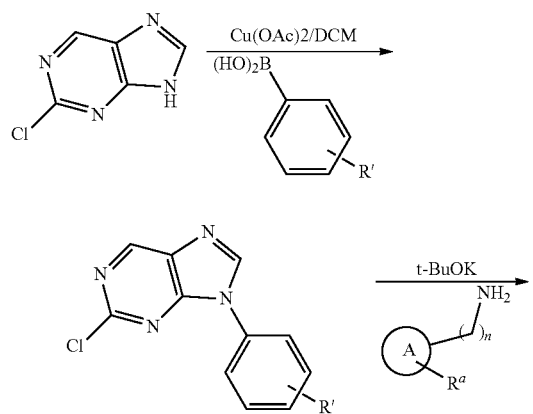

-continued

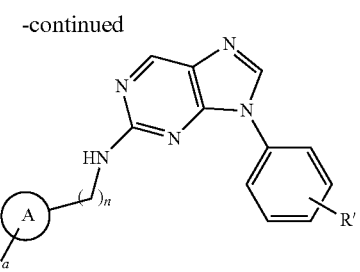

in which R' is a substituent selected from $R^f$ list and Ring A and $R^a$ are defined in part 1.

For the compounds of the invention, one of $R^a$, $R^b$, $R^{b1}$, $R^c$, $R^{c1}$, $R^d$, $R^{d1}$, $R^e$, $R^{e1}$, $R^f$ or $R^g$ when present, is or contains —P(=O)(R$^3$)$_2$.

Schemes 17 to 24 illustrate the preparation of phosphorous containing substituents and phosphorous containing moieties of current interest.

Scheme 17 illustrates the preparation of a [Ring A]-NH$_2$ moiety in which Ring A is a pyridine substituted with —P(=O)(R$^3$)$_2$.

Scheme 17

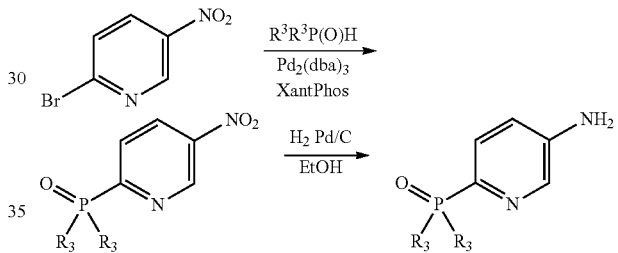

in which $R^3$ is defined in part 1. A similar synthetic route could be used to introduce a —P(=O)(R$^3$)$_2$ substituent onto a phenyl or heteroaryl ring whether the ring is Ring A or Ring E. This synthetic scheme also illustrates the preparation of a [Ring E]-L moiety in which L is NH and Ring E is aryl or heteroaryl. This scheme can be used for the synthesis of compounds of the invention of Formulae I to VI.

Of other interest are compounds in which $R^a$ substituent is phosphorous containing substituent. Scheme 18 illustrates the synthesis of an intermediate [Ring A]-NH$_2$ in which Ring A is a phenyl substituted with —P(=O)(CH$_3$)$_2$.

Scheme 18

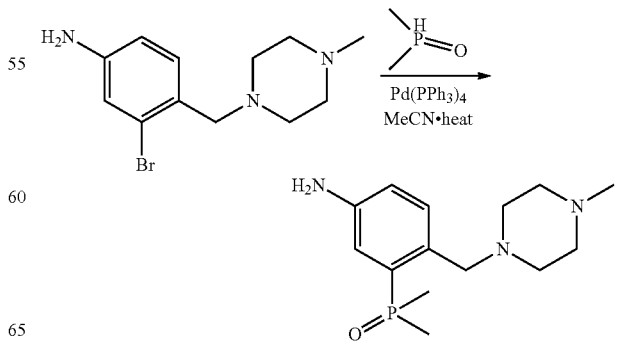

Scheme 19 illustrates the preparation of a [Ring A]-NH$_2$ intermediate in which Ring A is a phenyl substituted with (CH$_2$)$_m$—P(=O)(R$^3$)$_2$ and m is 1. This scheme is useful for the synthesis of compounds of Formulae II and IIA.

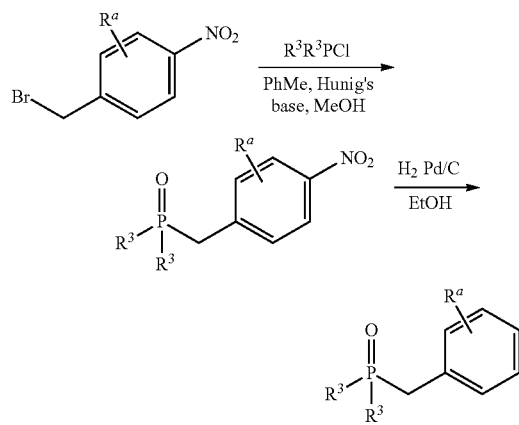

Scheme 20 illustrates the preparation of a [Ring A]-NH$_2$ moiety in which Ring A is a bicyclic structure such as naphthalene substituted with R$^f$ being —P(=O)(R$^3$)$_2$.

This scheme could also be used to prepare a [Ring E]-L moiety in which Ring E is naphthalene, L is NH and R$^g$ is —P(=O)(R$^3$)$_2$. This scheme can also be used for the synthesis of compounds of the invention of Formulae VIIA.

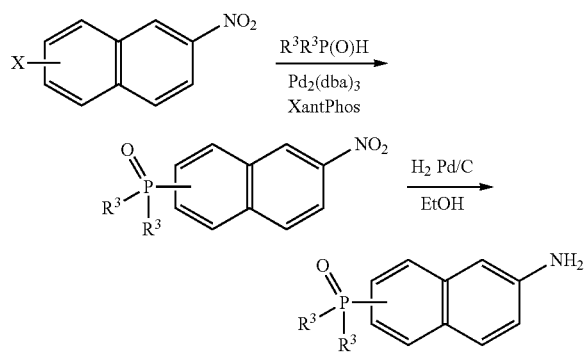

Scheme 21 illustrates the synthesis of [Ring A]-(CH$_2$)$_n$—NH$_2$ intermediate in which Ring A is phenyl substituted with —P(=O)(R$^3$)$_2$ and n is 1.

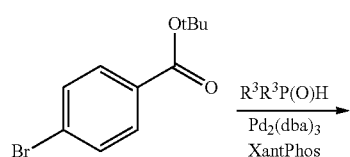

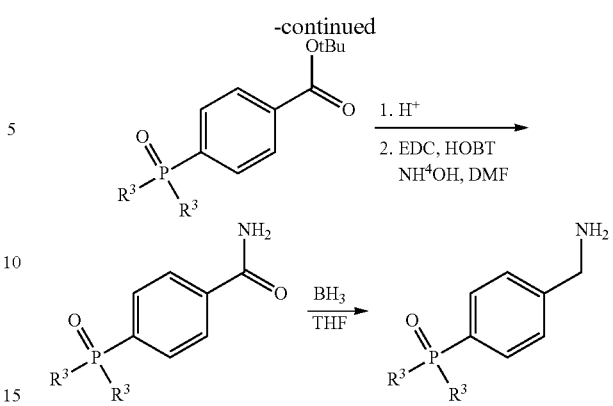

Scheme 21 can also be used for the synthesis of a [Ring E]-L moiety in which L is CH$_2$NH and Ring E is a phenyl substituted with —P(=O)(R$^3$)$_2$ In some embodiment, a R$^a$, R$^f$ or R$^g$ containing —P(=O)(R$^3$)$_2$ substituent can be of cyclic structure.

Schemes 22 to 23 illustrate the synthesis of cyclic structures of interest containing —P(=O)(R$^3$)$_2$.

Scheme 22 illustrates the preparation of cyclic substituent R$^a$ (or R$^f$ or R$^g$) containing —P(=O)(R$^3$)$_2$

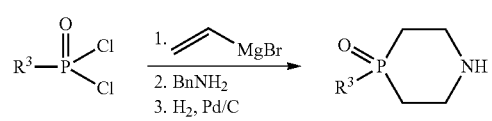

Schemes 22A and 22B illustrate the incorporation of this cyclic substituent onto a Ring A or Ring E.

Scheme 22A illustrates the synthesis of a [Ring A]-NH$_2$ moiety in which Ring A is a phenyl substituted with a methoxy group and with a —P(=O)(R$^3$)$_2$ containing cyclic substituent. This scheme could also be used for the synthesis of a [Ring E]-L moiety in which L is NH and Ring E is a phenyl substituted with a methoxy group and with a —P(=O)(R$^3$)$_2$ containing cyclic substituent.

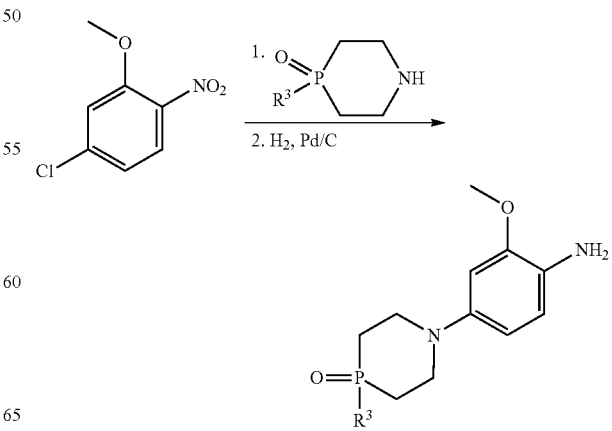

Scheme 22B

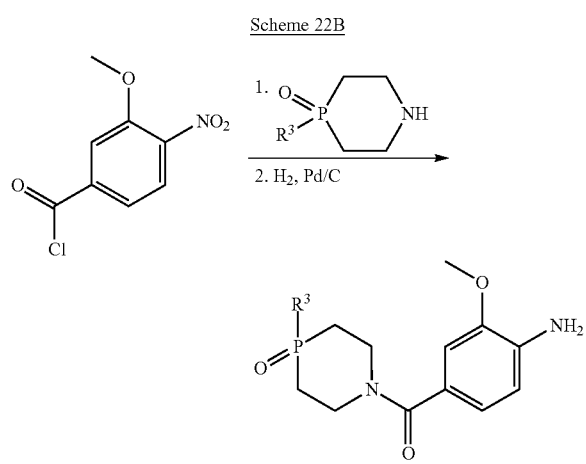

Scheme 23 illustrates the synthesis of a [Ring A]-NH$_2$ intermediate in which Ring A is phenyl substituted by methoxy and a —P(=O)(R$_3$)$_2$ group in which the two R$^3$ groups form with the phosphorous atom to which they are attached 6-membered saturated ring.

Scheme 23

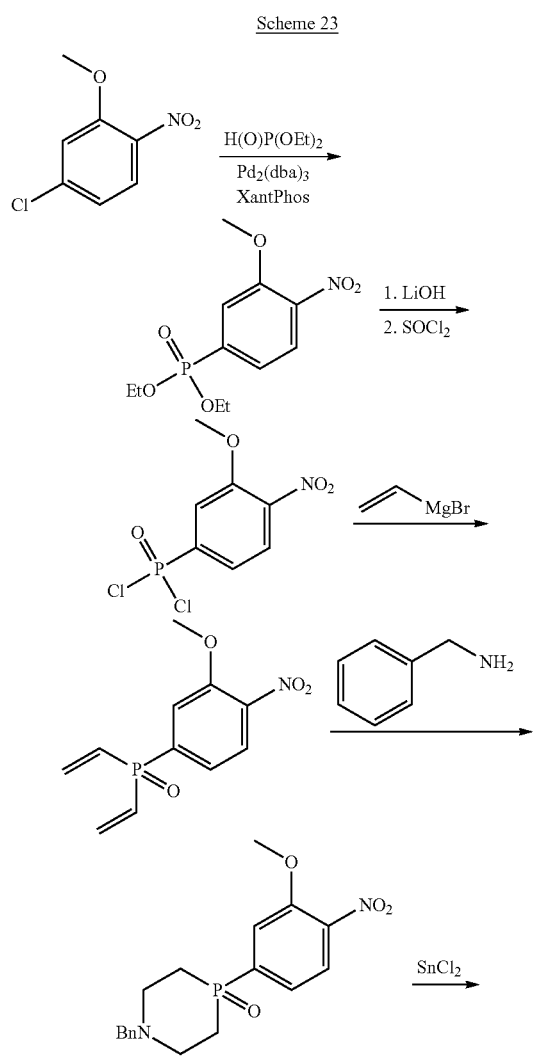

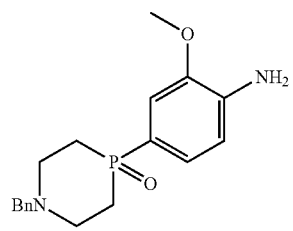

Scheme 24 illustrates the synthesis of a piperazine substituent which is further substituted with —CH$_2$P(=O)(CH$_3$)$_2$. This scheme can be used for the synthesis of [Ring A]-NH$_2$ intermediate in which Ring A is a phenyl substituted with a phosphorous containing piperazine group. It could also be used for the synthesis of a compound of any of the Formulae of the invention in which one of the substituents (R$^a$, R$^b$, R$^c$, R$^d$, R$^e$, R$^f$ or R$^g$) is NR$^1$R$^2$ and NR$^1$R$^2$ form a piperazine ring substituted with —CH$_2$P(=O)(CH$_3$)$_2$.

Scheme 24

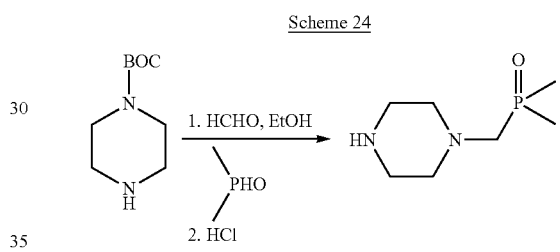

A compound of Formula IB or VI can be prepared in a 2 steps synthesis as shown in Scheme 1. A [Ring A] moiety can first be incorporated to the central pyrimidine moiety by reacting [Ring A]-NH$_2$ with a substituted or unsubstituted 4,6-dichloropyrimidine in the presence of a base such as di-isopropylethyl amine at high temperature generating intermediate 1a. The [Ring E]-L-moiety can then be incorporated onto intermediate 1a using various conditions depending on the nature of the L linker. The variables in the intermediate [Ring E]-[L]- and [Ring A] are as defined previously, Rings A and E being substituted with permitted R$^a$ and R$^g$ groups respectively.

Scheme 25

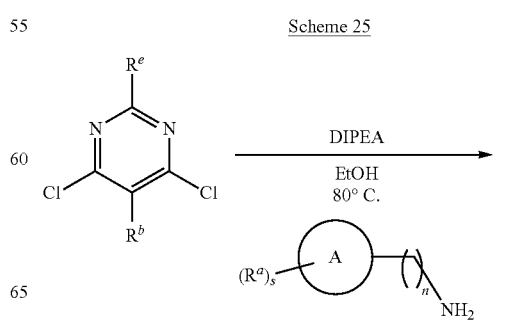

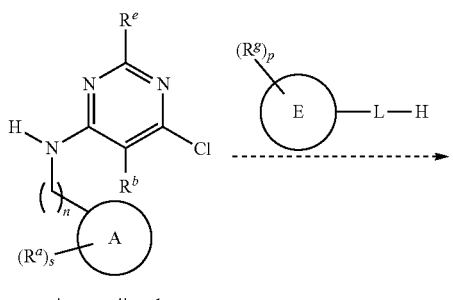

intermediate 1

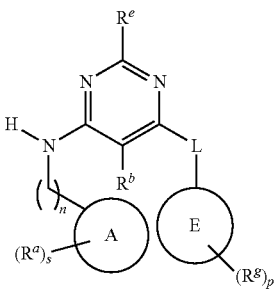

An approach to the preparation of an intermediate 1a is illustrated below in Scheme 1A in which Ring A is a phenyl:

Scheme 25A

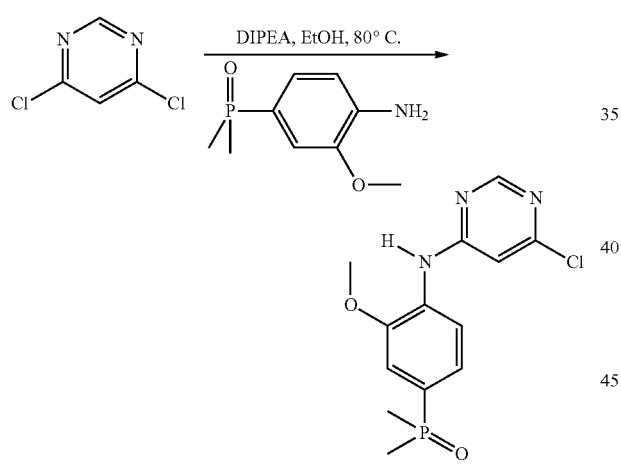

A compound of Formula IB or VII in which L is NH can be prepared using microwave chemistry, by reacting an intermediate 1a with [Ring E]-$NH_2$ in a solvent such as n-Butanol under acidic conditions as shown in Scheme 26.

Scheme 26

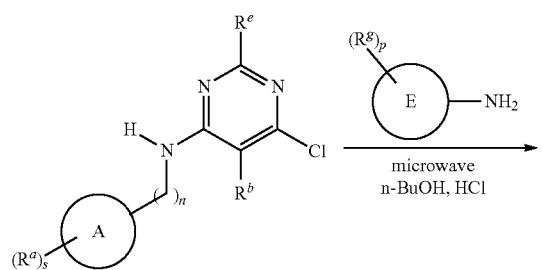

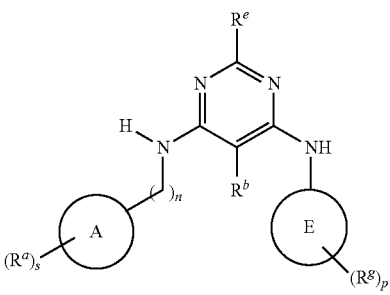

An approach to the preparation of a compound of Formula VI in which L is NH, is illustrated below in Scheme 26A in which Ring A and Ring E are phenyls:

Scheme 26A

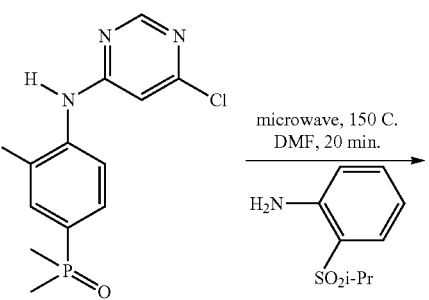

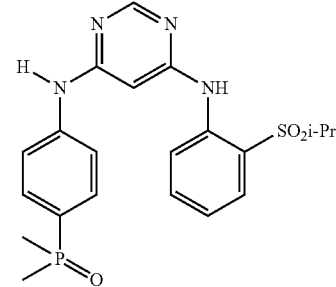

A compound of Formula IB or VII in which L is bond and [Ring E] is a N-linked heterocyclyl, can be prepared by reacting an intermediate 1a with the heterocyclyl, in the presence of a base such as di-isopropyldiethylamine, in a polar solvent such as iso-propanol, and using high temperatures, as shown in Scheme 27:

Scheme 27

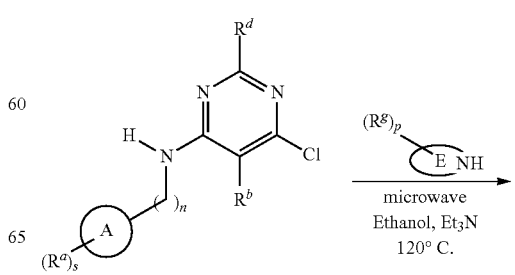

-continued

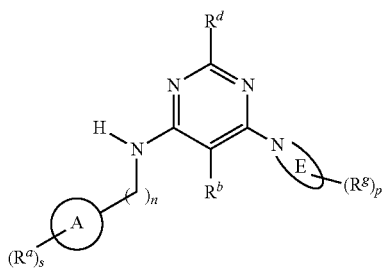

In a non limiting example, Scheme 27A illustrates the preparation of a compound of Formula VII or IB in which $R^c$ is [L]-[Ring E] in which L is a bond and [Ring E] is N-phenyl-piperazine.

Scheme 27A

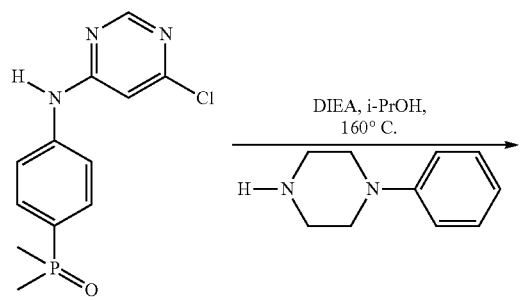

A compound of Formula IB or VII in which $R^c$ is [L]-[Ring E] with L being O can be prepared by reacting 4,6-dichloro-pyrimidine with an optionally substituted phenol; in the presence of sodium hydride in a solvent such as dimethylformamide as shown in Scheme 28. A [Ring A] moiety can then be incorporated to the central pyrimidine moiety by reacting [Ring A]-(CH$_2$)$_n$NH$_2$ in the presence of a base (i.e. di-isopropylethyl amine, triethylamine or the like) or an acid in order to facilitate the displacement reaction.

Scheme 28

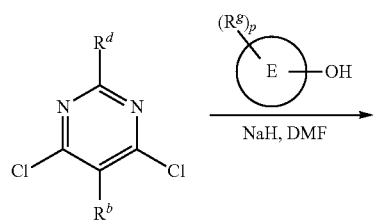

-continued

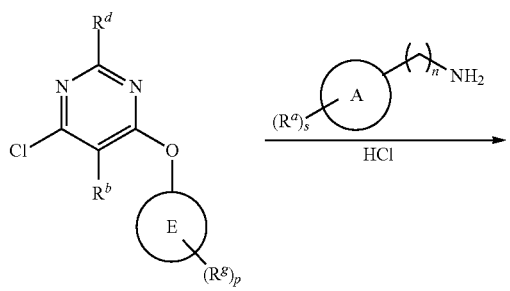

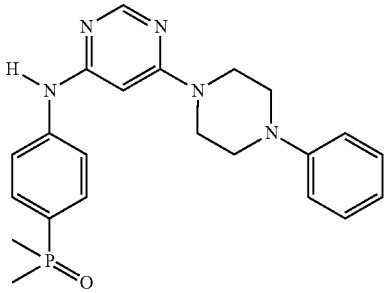

An approach to the preparation of a few compounds of Formula IB or VII in which L is NH, is illustrated below in Scheme 28A in which Ring A and Ring E are phenyls:

Scheme 28A

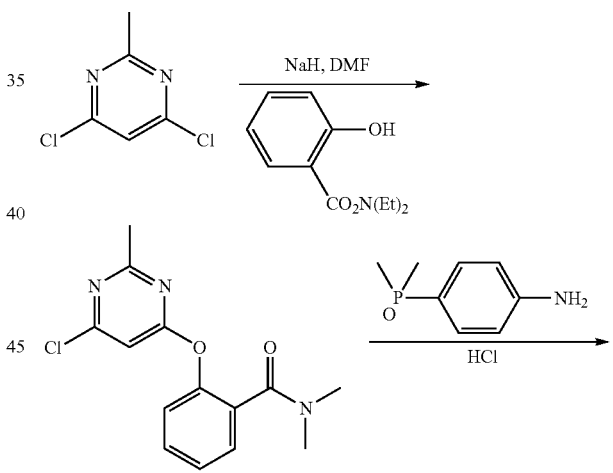

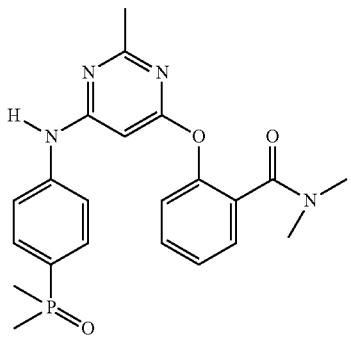

A compound of Formula IB or VII in which L is NH(CH$_2$)$_{1-4}$ can be prepared using microwave chemistry, by reaction an intermediate 1a with [Ring E]-(CH$_2$)$_{1-4}$NH$_2$, in the presence of a base such as triethylamine, in a polar solvent such as Ethanol, and using high temperatures, as shown in Scheme 29:

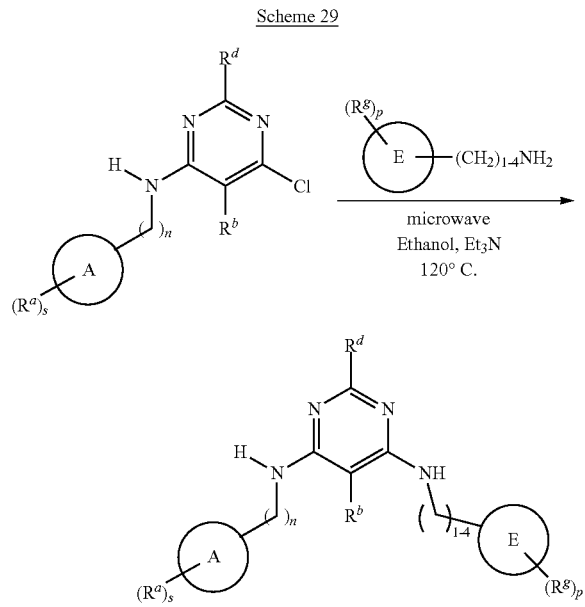

An approach to the preparation of a few compounds of Formula VII in which L is $NH(CH_2)_{1-4}$, is illustrated below in Schemes 29A and 29B. Scheme 29A illustrates the synthesis of a compound of Formula VII in which Ring E is a phenyl and L is $NHCH_2$ and Scheme 29B illustrates the synthesis of a compound of Formula VII in which Ring E is 3-1H-indole and L is $NH(CH_2)_2$:

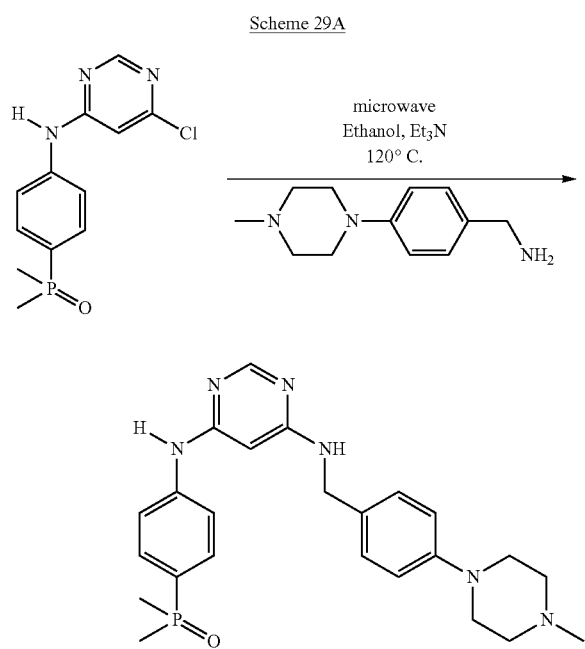

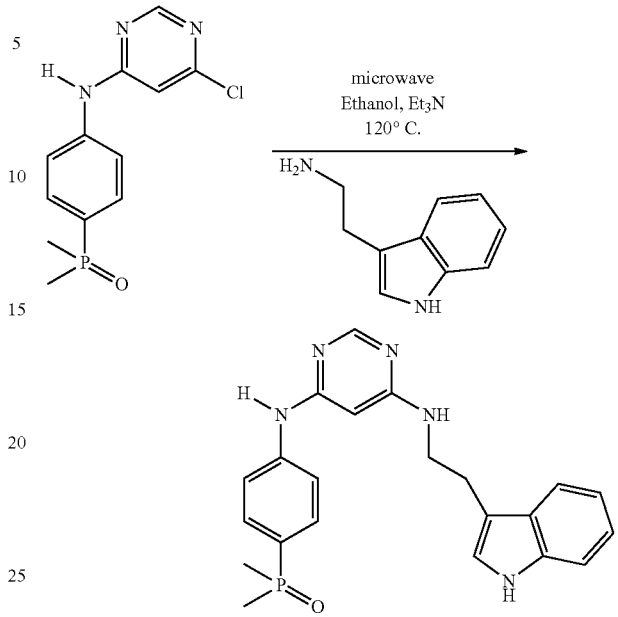

A compound of Formula IB and VII in which L is $SH(CH_2)y$ can be prepared using microwave chemistry, by reaction an intermediate 1a with [Ring E]-$(CH_2)_y$SH, in the presence of a base such as Cesium carbonate, and in a solvent such as dimethylformamide at high temperatures, as shown in Scheme 30. The variable y is defined above.

An approach to the preparation of a compound of Formula VII in which $X^3$ is CH, $X^2$ is N, L is $S(CH_2)_y$, and Rings A and E are substituted phenyls, is illustrated below in Scheme 30A:

Scheme 30A

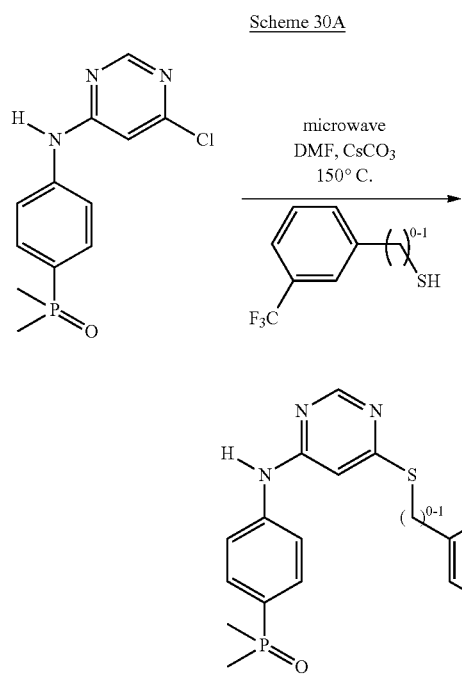

A compound of Formula IB or VII in which L is bond and [Ring E] is an aryl or heteroaryl, can be prepared using Suzuki coupling conditions. Scheme 31 illustrates the Suzuki coupling reaction.

Scheme 31

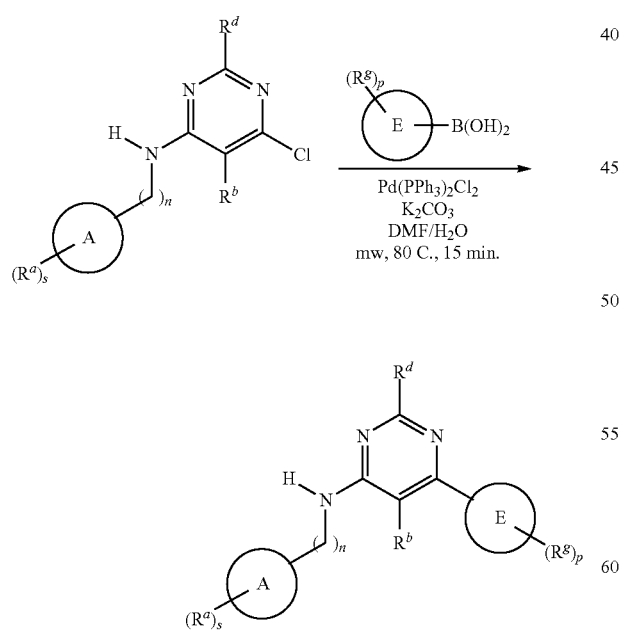

In a non limiting example, Scheme 31A illustrates the preparation of a compound of Formula VII in which $X^3$ is CH, $X^2$ is N, L is a bond and [Ring E] and [Ring A] are phenyl.

Scheme 31A

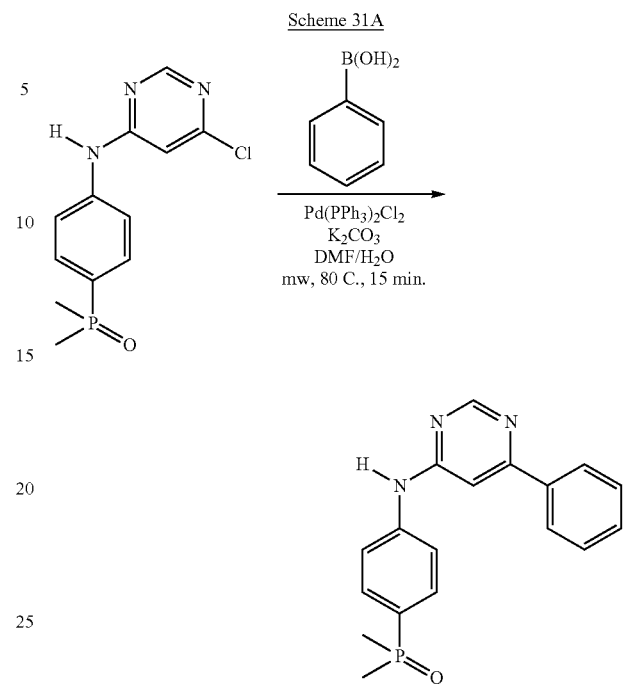

A compound of Formula IC or VI in which $R^c$ is [L]-[Ring E] with L being O, can be prepared in a 2 steps synthesis as shown in Scheme 32. A [Ring E]-L-moiety can first be incorporated to the central pyridazine moiety by reacting [Ring E]-OH with a substituted or unsubstituted 3,5-dichloropyridazine in the presence of a base such as sodium hydride generating intermediate 2a. The [Ring A]-$(CH_2)_n$$NH_2$ moiety can then be reacted with intermediate 2a in the presence of a base (i.e. di-isopropylethyl amine, triethylamine or the like) or an acid in order to facilitate the displacement reaction.

Scheme 32

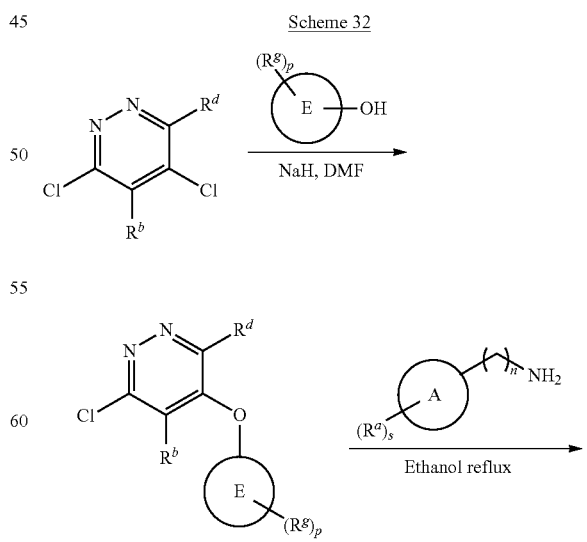

Intermediate 2a

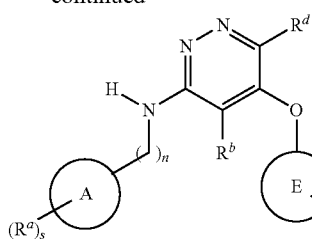

In a non limiting example, Scheme 32A illustrates the preparation of a compound of Formula VII in which L is O, $X^3$ is N, $X^2$ is CH and [Ring E] and [Ring A] are substituted phenyl.

Scheme 32A

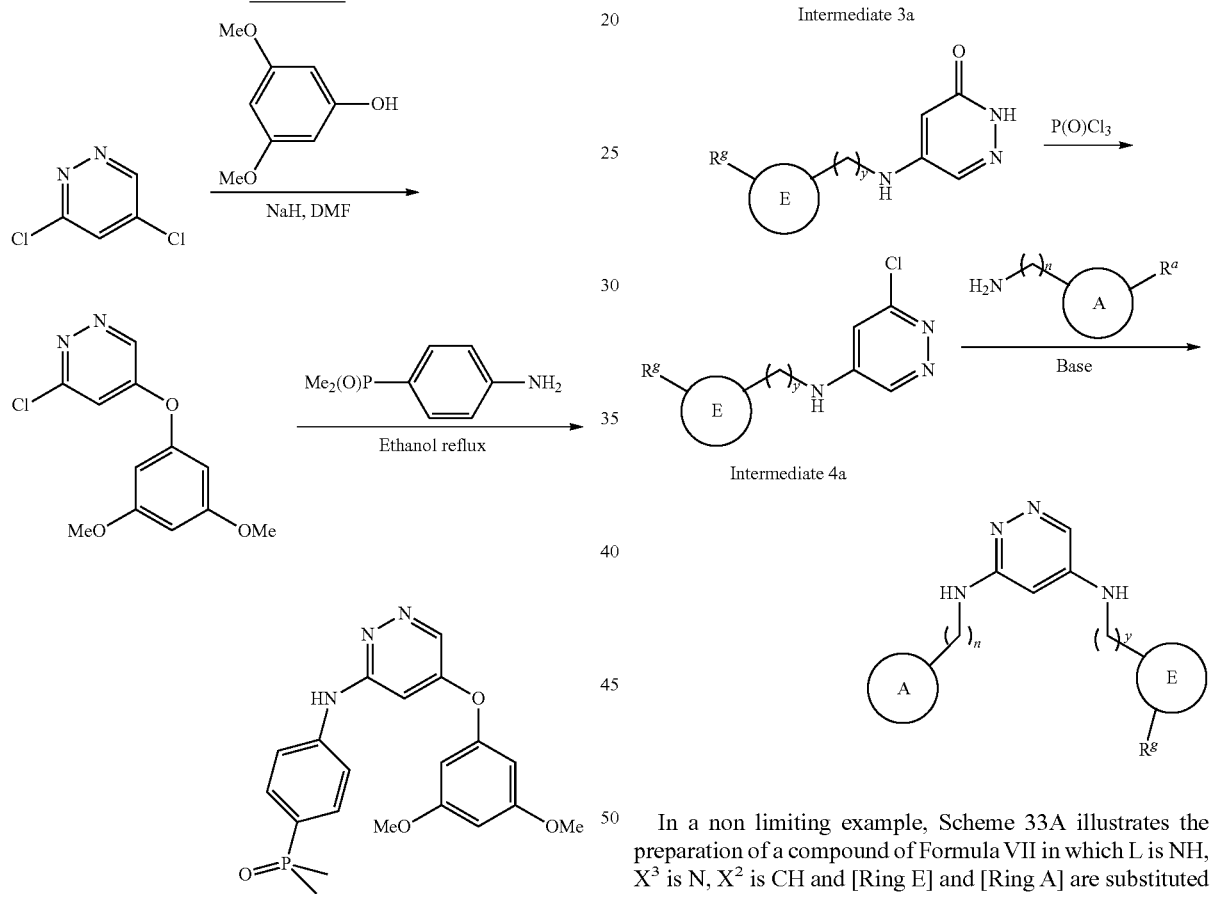

A compound of Formula IC in which $R^c$ is [L]-[Ring E] with L being $NH(CH_2)_y$, can be prepared in 4 steps as shown in Scheme 33. A [Ring E]$CH_2)_y$—$NH_2$ moiety can first be incorporated to the central pyridazine moiety by reacting [Ring E]-$(CH_2)_y$—$NH_2$ with 4,5-dichloropyridazin-3(2H)-one in the presence of triethylamine in a solvent such as Ethanol generating intermediate 3a. Intermediate 3a is then hydrogenated and reduced with phosphoric trichloride generating intermediate 4a. The [Ring A]-$(CH_2)_n NH_2$ moiety can then be reacted with intermediate 4a in the presence of a base (i.e. di-isopropylethyl amine, triethylamine or the like) or an acid in order to facilitate the displacement reaction.

Scheme 33

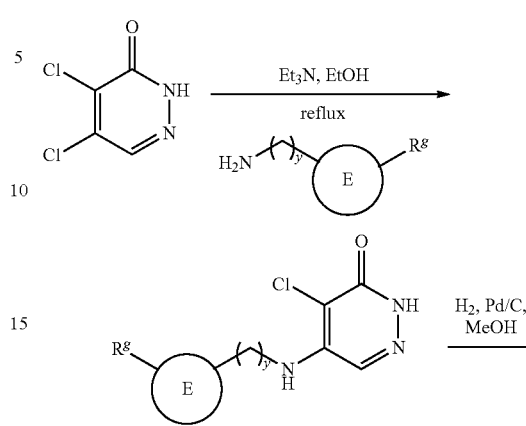

In a non limiting example, Scheme 33A illustrates the preparation of a compound of Formula VII in which L is NH, $X^3$ is N, $X^2$ is CH and [Ring E] and [Ring A] are substituted phenyl.

Scheme 33A

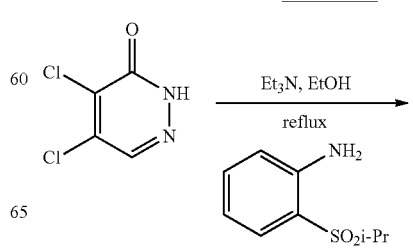

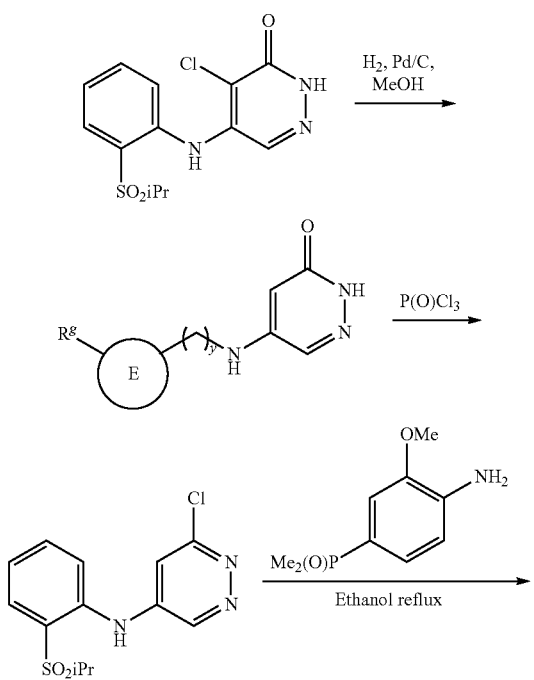

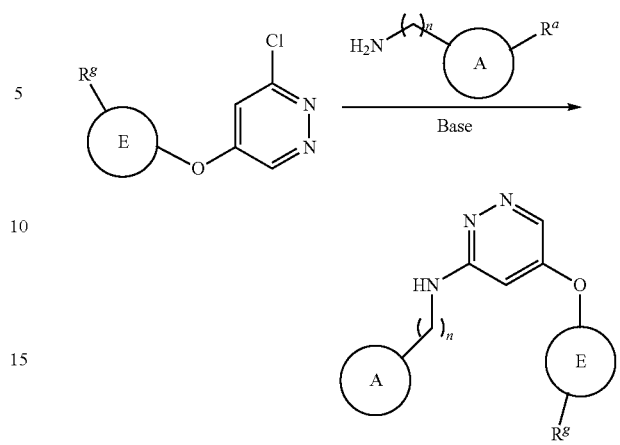

In a similar way, a compound of Formula IC in which $R^c$ is a N-linked heterocyclyl can be prepared by reacting a heterocyclyl such as a substituted piperidine with 4,5-dichloropyridazin-3(2H)-one followed by the same sequence of steps as described in Scheme 9. This synthesis is illustrated in Scheme 35:

Scheme 35

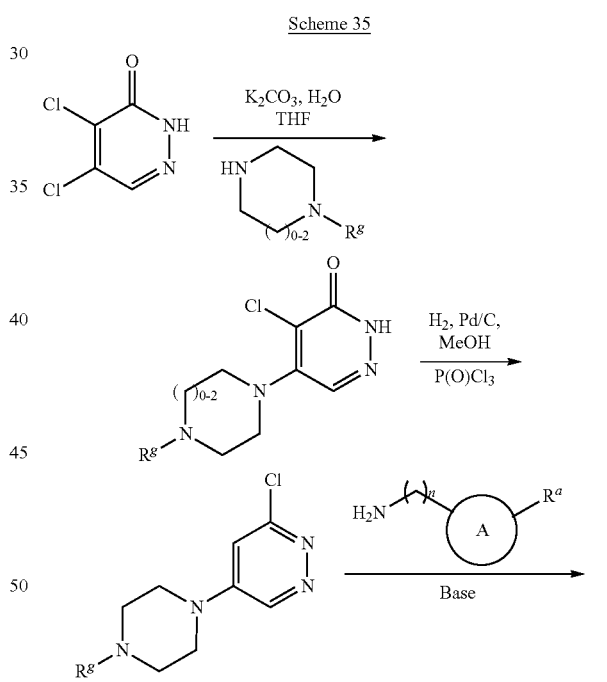

In a similar way, a compound of Formula IC or VI in which $R^c$ is [L]-[Ring E] with L being O, can be prepared by reacting [Ring E]-OH with 4,5-dichloropyridazin-3(2H)-one in the presence of potassium carbonate; followed by the same sequence of steps as described in Scheme 33. This alternative synthesis is illustrated in Scheme 34:

Scheme 34

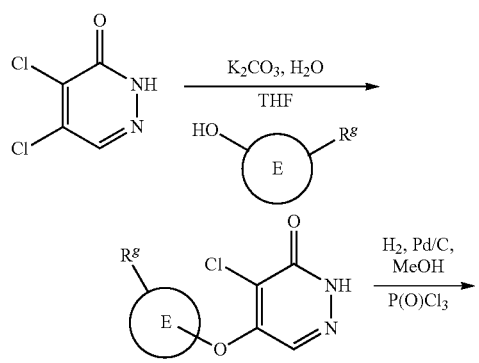

Scheme 36 illustrates the synthesis of a compound of Formula IIIA in which $R^e$ and $R^b$ are H and $R^c$ and $R^d$ form an imidazole substituted with a phenyl group.

Scheme 36

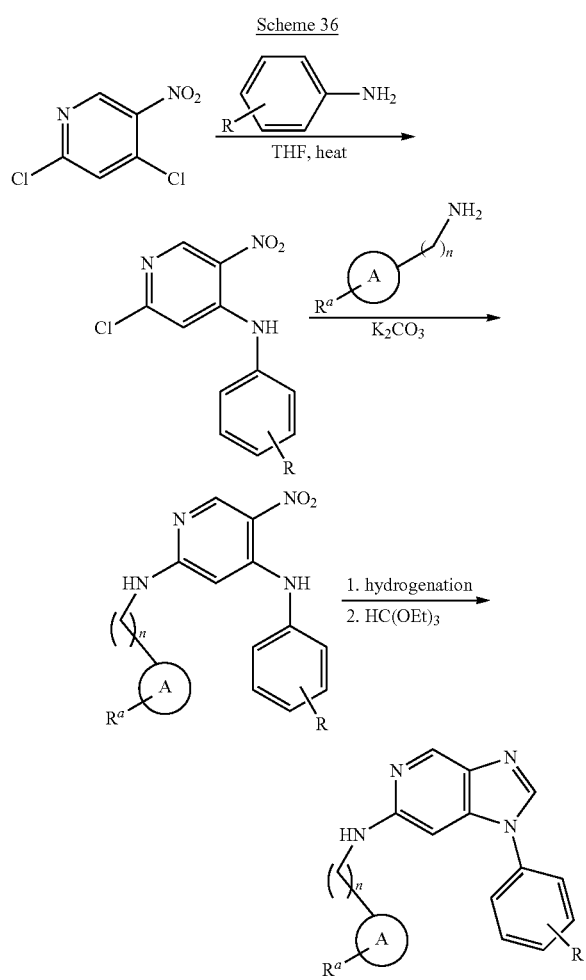

in which R is a substituent selected from $R^f$ and Ring A, Ra and n are defined above.

In a non limiting example, Scheme 36A illustrates the preparation of compounds of Formula IIIA in which $R^c$ and $R^d$ form an imidazole, Ring A is a substituted phenyl and $R^f$ is a substituted phenyl:

Scheme 36A

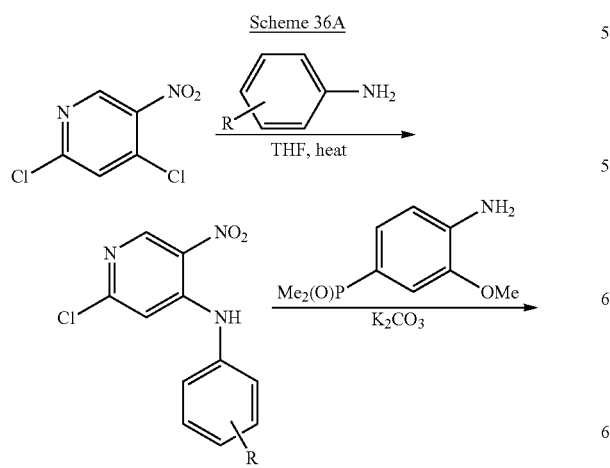

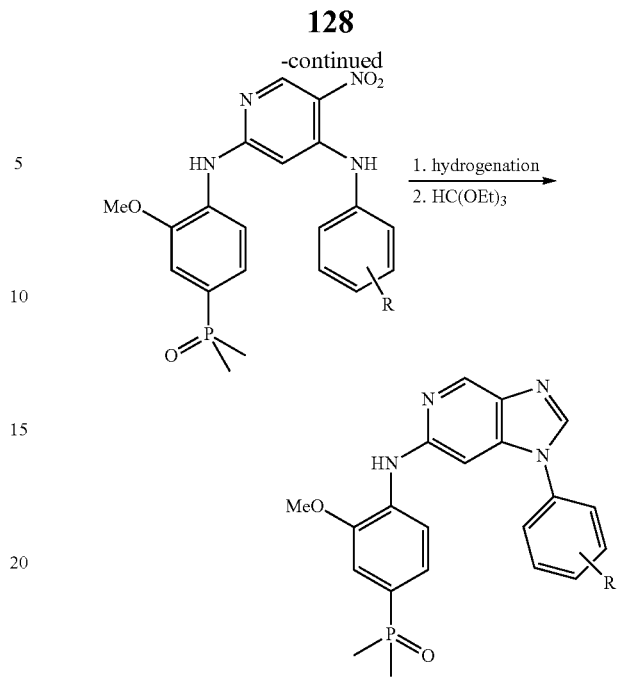

A compound of Formula I, IB, IIB or VIA in which n is 0 can be prepared in a 2 steps synthesis as shown in Scheme 37. A [Ring A] moiety can first be incorporated to the central triazine moiety by reacting [Ring A]-Br with 5-chloro-6-substituted-1,2,4-triazin-3-amine under Buchwald Hartwig cross coupling conditions to generate intermediate 1 (I-1). The [Ring E]-L-moiety can then be incorporated onto I-1 using various conditions depending on the nature of the L linker. The variables in the intermediate [Ring E]-[L]- and [Ring A] are as defined previously, Rings A and E being substituted with permitted $R^a$ and $R^g$ groups respectively.

Scheme 37

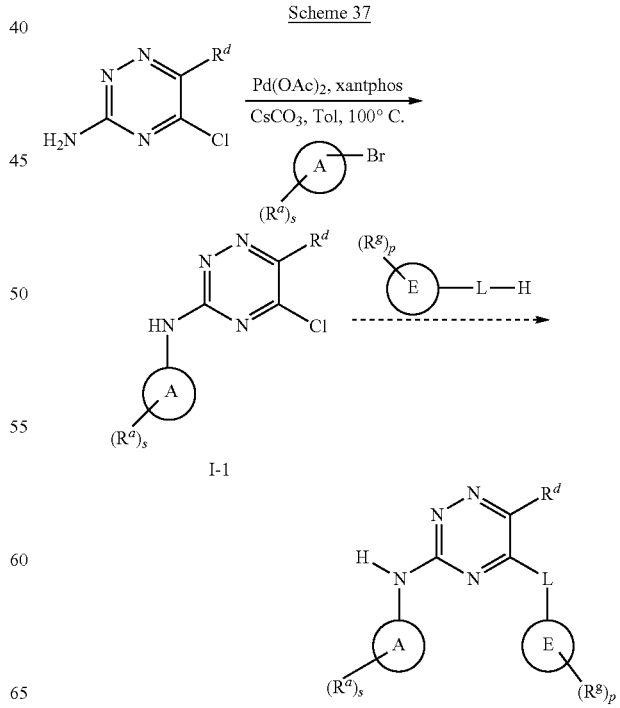

An approach to the preparation of an intermediate 1c is illustrated below in Scheme 37A in which Ring A is a phenyl:

Scheme 37A

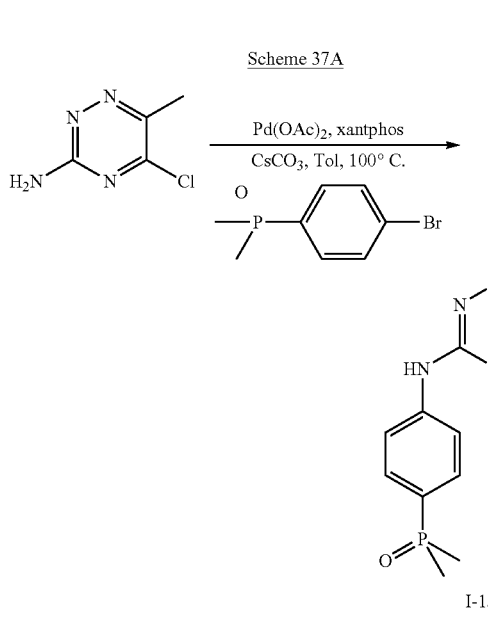

I-1a

Intermediate I-1a is then reacted with a substituted aniline, as illustrated in Scheme 37B, to generate compound of Formula VIA in which L is NH, Ring A and Ring E are phenyl, n is 0, and $R^d$ is methyl.

Scheme 37B

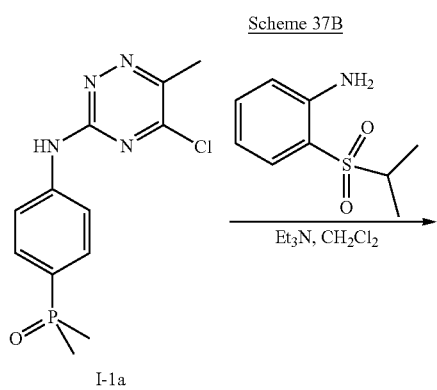

Intermediate I-1a can also be reacted with a substituted phenol or thiophenol, as illustrated in Scheme 37C, to generate compound of Formula VIA in which L is O or S, Ring A and Ring E are phenyl, n is 0, and $R^d$ is methyl.

Scheme 37C

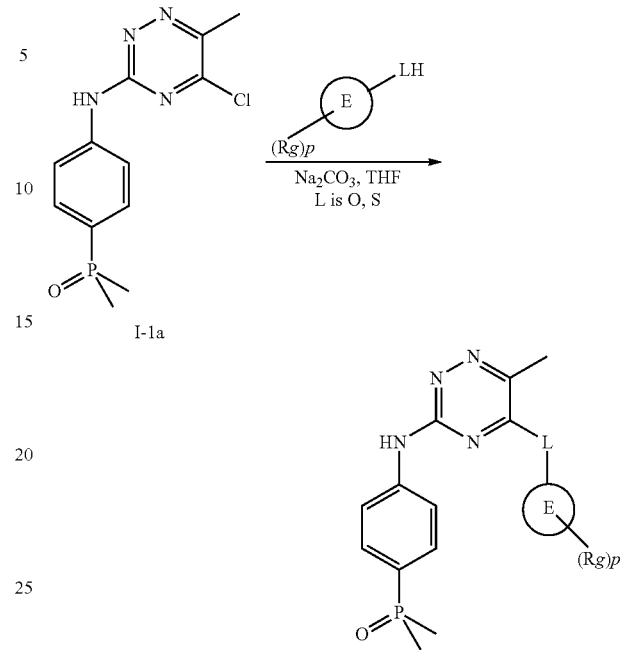

An alternative synthesis to compounds of Formula I, IB, IIB or VIA is illustrated in Scheme 38. [Ring E]-LH moiety, in which L is O, S or NH, can be first incorporated to the central triazine moiety prior to the incorporation of [Ring A]-NH moiety. Schemes 38 and 39 illustrates the reaction of 3,5-dichloro-6-substituted-1,2,4-triazine with a [Ring-E]-LH moiety in the presence of a base (for example triethyamine, potassium carbonate, sodium carbonate or sodium hydride or the like) in a suitable solvent such as for example dimethylformamide, methylene chloride or tetrahydrofuran in order to generate intermediate I-2 and I-3. The reaction can be performed at room temperature or may require higher temperature. Intermediates I-2 and I-3 are then reacted with a [Ring A]-NH$_2$ moiety under acidic conditions (i.e Camphor sulfonic acid) in the presence of a suitable solvent such as for example tetrahydrofuran at high temperature. This sequence of reactions is described in PCT application WO 2006/015985.

Scheme 38

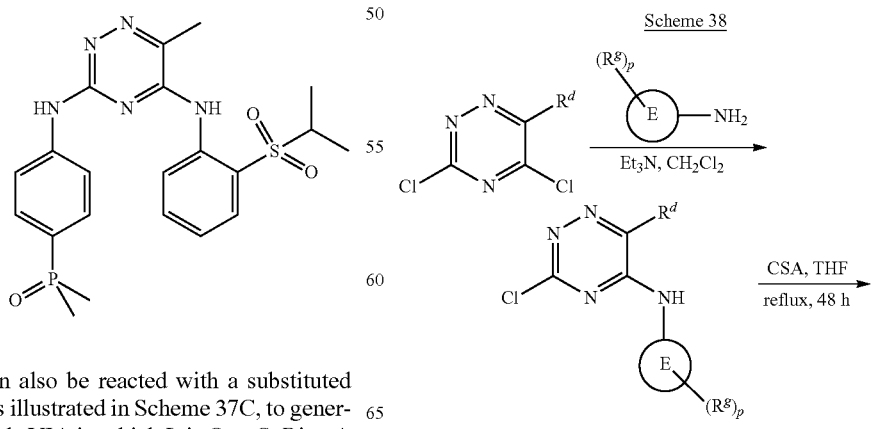

I-2

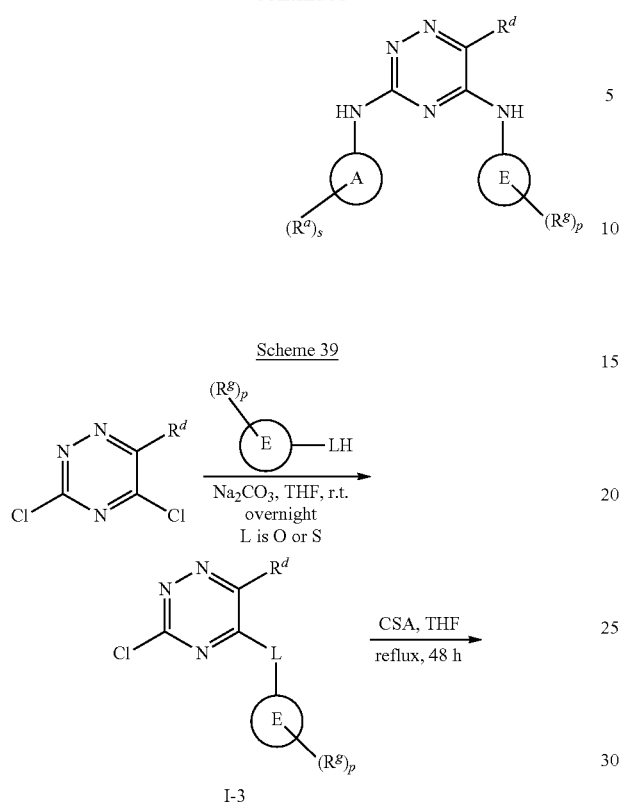

Scheme 39

I-3

When $R^d$ is chloro, 3,5,6-trichloro-1,2,4-triazine, can be prepared according to methods described in PCT patent application WO 2004/074266, by reacting 1,2,4-triazine-3,5 (2H, 4H)dione with bromine in a presence of a suitable solvent, such as for example water, to generate an intermediate of Formula I-4a. Synthesis of 3,5,6-trichloro-1,2,4-triazine is illustrated in Scheme 40. Intermediate I-4a is then reacted with POCl$_3$ and PCl$_5$ in the presence of a base such as for example N,N-diethylaniline.

Scheme 40

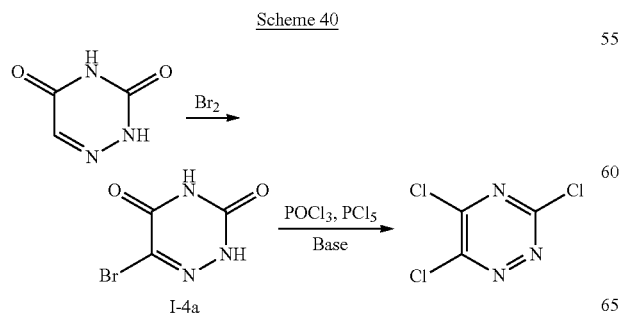

I-4a

When $R^d$ is Methyl, 3,5-dichloro-6-methyl-1,2,4-triazine can be prepared according to methods described in PCT patent application WO 2005/054199.

When $R^d$ is H; 3,5-dichloro-1,2,4-triazine can be prepared according to methods described in Journal of Organic Chemistry, 23, 1522-4; 1958 in which 1,2,4-triazine-3,5(2H, 4H)dione is reacted with POCl$_3$. The synthesis of 3,5-dichloro-1,2,4-triazine is illustrated in Scheme 41.

Scheme 41

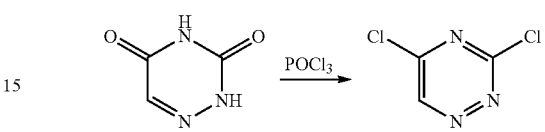

A compound of Formula I, IA, IC, IIC or VIB can be prepared in a 2 steps synthesis as shown in Scheme 42. A [Ring A]-(CH$_2$)$_n$NH— moiety can first be incorporated to the central triazine moiety by reacting [Ring A]-(CH$_2$)$_n$NH$_2$ with 2,4-dichloro-6-substituted-1,3,5-triazine in the presence of a base as for example di-isopropylethylamine in a suitable solvent. The [Ring E]-L-moiety can then be incorporated onto 1-6 using various conditions depending on the nature of the L linker. The variables in the intermediate [Ring E]-[L]- and [Ring A] are as defined previously, Rings A and E being substituted with permitted $R^a$ and $R^g$ groups respectively.

Scheme 42

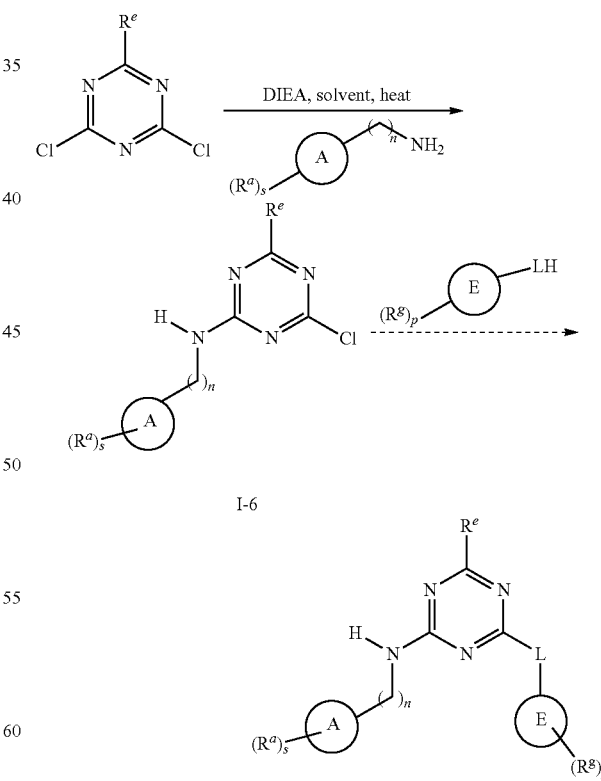

When $R^e$ is methyl, 2,4-dichloro-6-methyl-1,3,5-triazine can be prepared according to methods described in Bioorganic Medicinal Chemistry letters 16(21), 5664-5667, 2006. 2,4,6-trichloro-1,3,5-triazine is reacted with methyl magnesium bromide to generate 2,4-dichloro-6-methyl-1,3,5-triazine as illustrated in Scheme 42A.

Scheme 42A

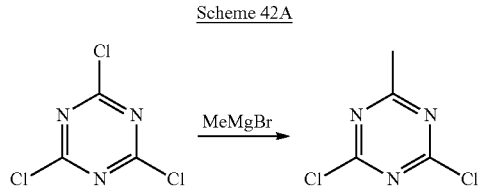

In a non limiting example, an intermediate of formula I-6 in which $R^e$ is H, n is 0 and Ring A is phenyl is illustrated in Scheme 42B:

Scheme 42B

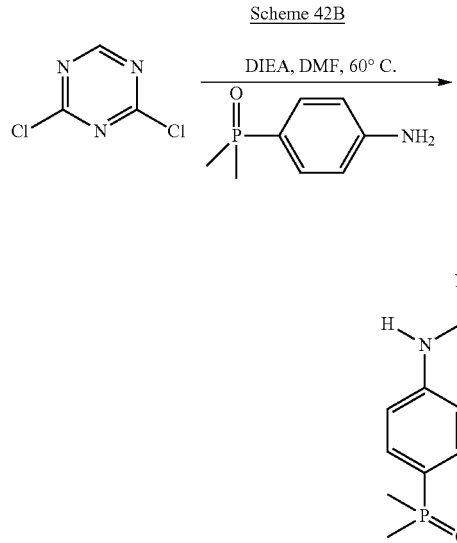

A compound of Formula VIB in which L is O can be prepared using microwave chemistry, by reacting an intermediate I-6 with [Ring E]-OH in a solvent such as dimethylformamide and high temperatures as shown in Scheme 43.

Scheme 43

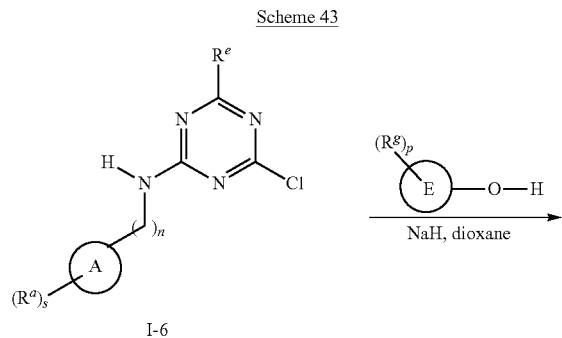

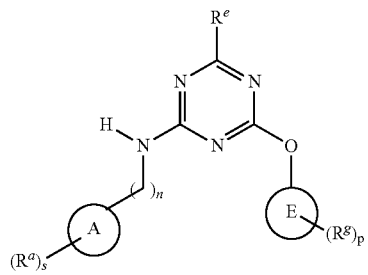

An approach to the preparation of a compound of Formula VIB in which L is O, is illustrated below in Scheme 43A in which Ring A and Ring E are phenyls:

Scheme 43A

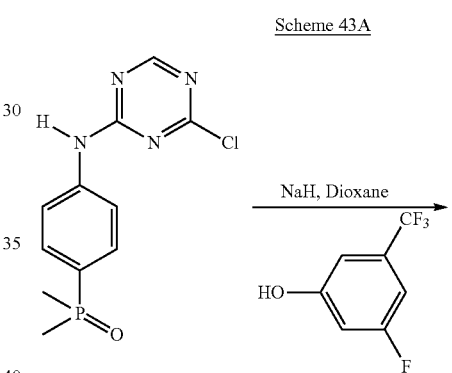

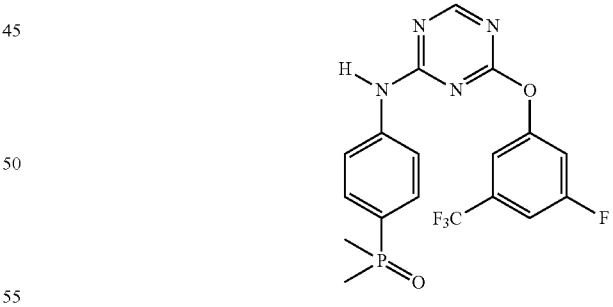

A compound of Formula VIB in which L is NH can be prepared using microwave chemistry, by reaction an intermediate I-6 with [Ring E]-NH$_2$, in a polar solvent such as Ethanol, and using high temperatures, as shown in Scheme 44. A base (i.e. di-isopropylethyl amine, triethylamine, or the like) or an acid may be added to facilitate the displacement reaction. A similar displacement reaction is described in PCT patent application WO 2005/047279.

Scheme 44

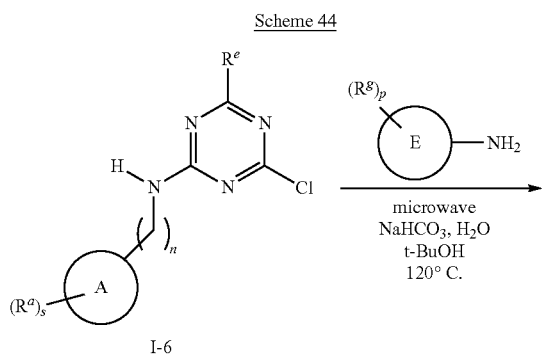

I-6

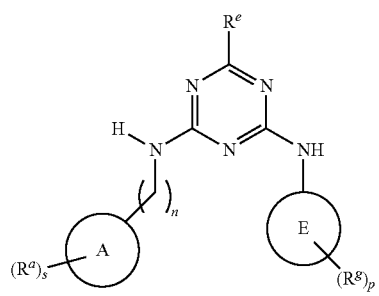

An approach to the preparation of a few compounds of Formula VIB in which L is NH, is illustrated below in Scheme 44A and 44B in which Ring E is a phenyl or adamantane respectively:

Scheme 44A

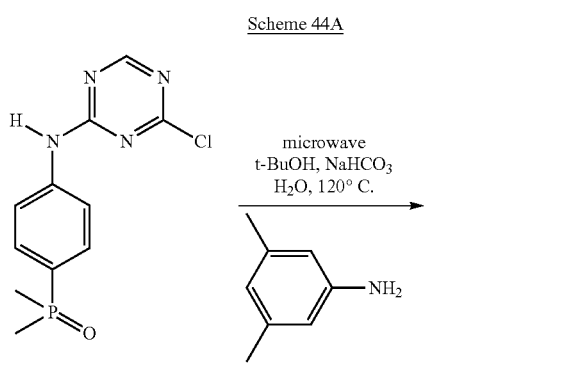

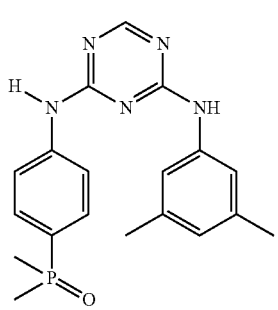

Scheme 44B

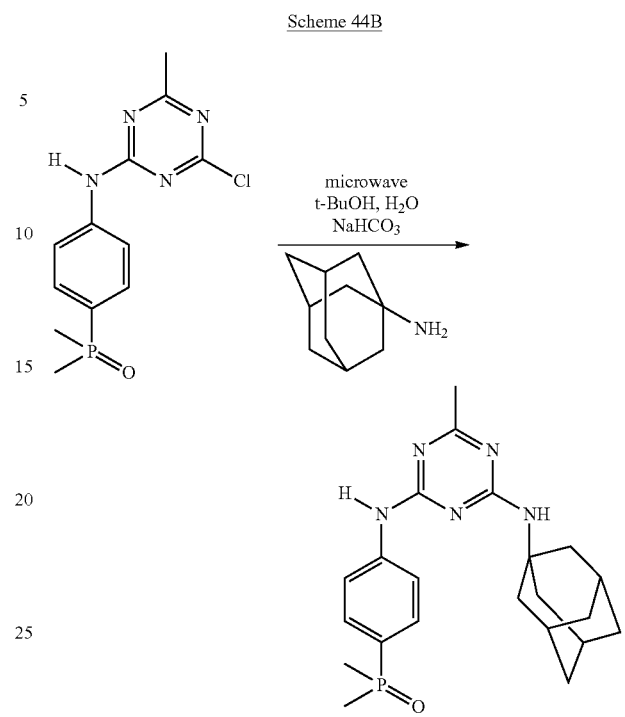

A compound of Formula VIB in which L is $NH(CH_2)_{1-4}$ can be prepared using microwave chemistry, by reaction an intermediate I-6 with [Ring E]-$(CH_2)_{1-4}NH_2$, in the presence of a base such as triethylamine, in a polar solvent such as Ethanol, and using high temperatures, as shown in Scheme 45:

Scheme 45

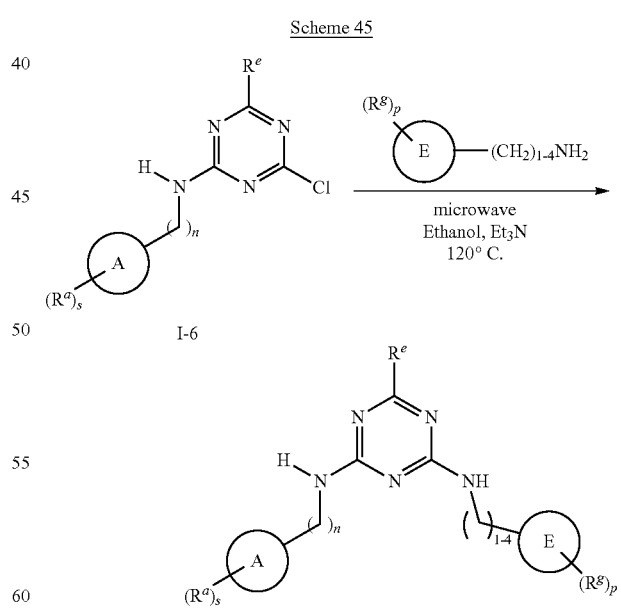

An approach to the preparation of a few compounds of Formula VIB in which L is $NH(CH_2)_{1-4}$, is illustrated below in Schemes 45A and 45B. Scheme 45A illustrates the synthesis of a compound of Formula VIB in which $R^e$ is Cl, Ring E is a phenyl and L is $NHCH_2$ and Scheme 45B illustrates the synthesis of a compound of Formula VIB in which $R^e$ is Cl, Ring E is 3-1H-indole and L is $NH(CH_2)_2$:

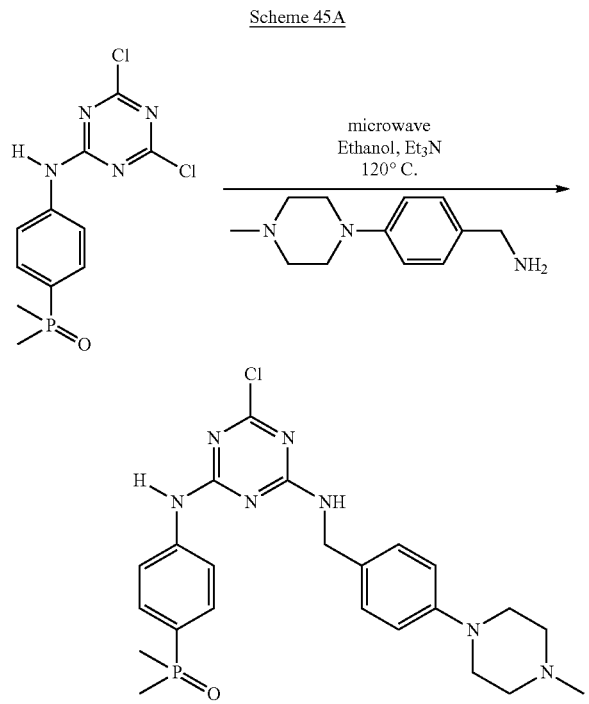

A compound of Formula VIB in which L is $SH(CH_2)_y$, can be prepared using microwave chemistry, by reaction an intermediate I-6 with [Ring E]-$(CH_2)_y$SH, in the presence of a base such as Cesium carbonate, and in a solvent such as dimethylformamide at high temperatures, as shown in Scheme 46. The variable y is defined above.

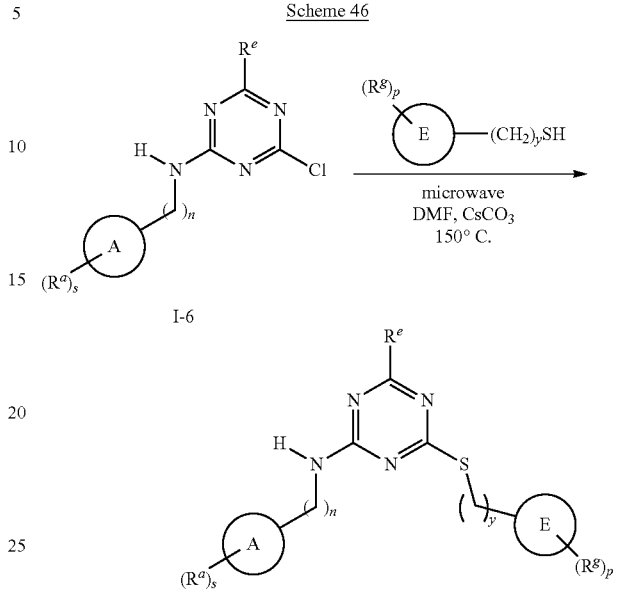

An approach to the preparation of a compound of Formula VIB in which L is $S(CH_2)_y$, is illustrated below in Scheme 46A:

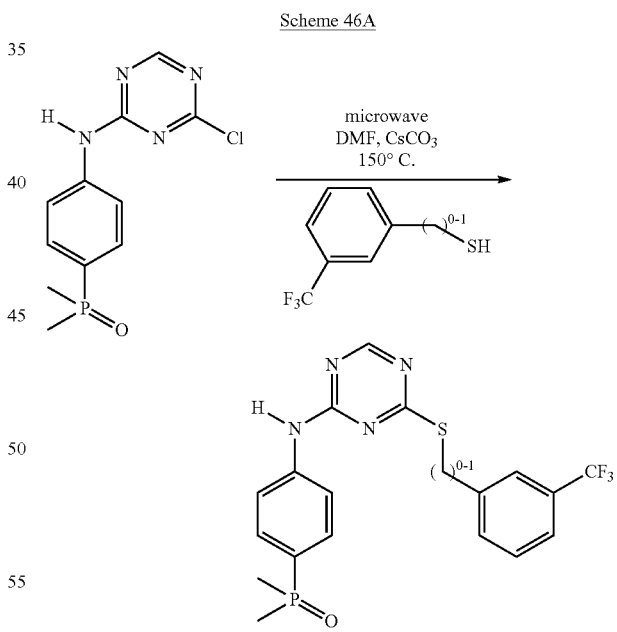

A compound of Formula VIB in which L is bond and [Ring E] is an aryl or heteroaryl, can be prepared using Suzuki coupling conditions. Scheme 11 illustrates the Suzuki coupling reaction. The displacement of one of the chlorine by and aryl Grignard or and aryl boronic acid is described in PCT patent application WO 01/25220 and Helv. Chim. Acta, 33, 1365 (1950). The displacement of one of the chlorines by a heteroaryl ring is described in WO 01/25220, J. Het. Chem., 11, 417 (1974); and Tetrahedron 31, 1879 (1975). These reactions can be facilitated by using Microwave chemistry. Microwave assisted Suzuki coupling reaction is also described in Journal of Medicinal Chemistry, 2007, 50(17), 3497.

Scheme 47

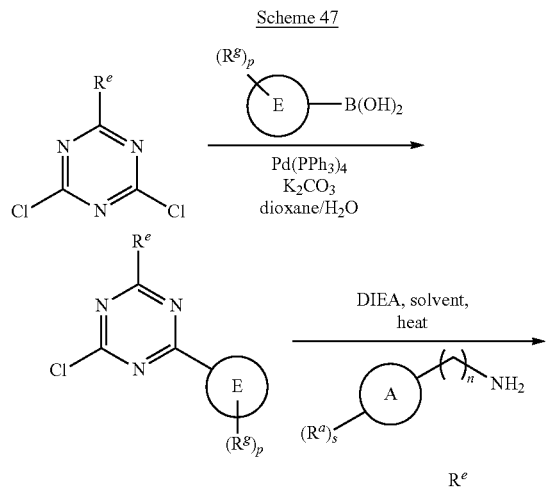

When $R^e$ is chloro, the Suzuki reaction is also described in PCT patent application WO 2002/22605.

In a non limiting example, Scheme 47A illustrates the preparation of a compound of Formula VIB in which L is a bond and [Ring E] is a substituted phenyl.

Scheme 47A

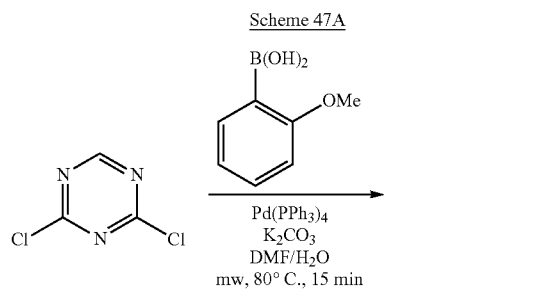

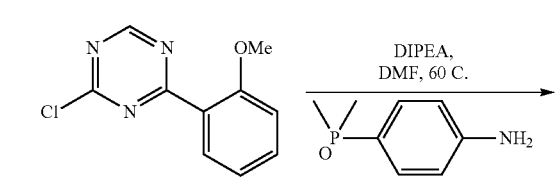

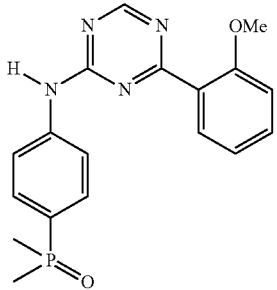

A compound of Formula I, IB or VIA in which L is a bond and Ring E is an aryl or heteroaryl ring, can also be prepared in a similar way using Suzuki coupling conditions. A similar sequence of reaction is described in PCT patent application WO 2005/054199 and is illustrated below in Scheme 48:

Scheme 48

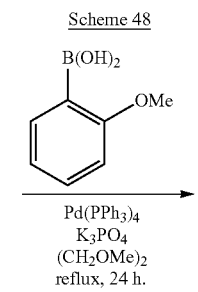

A compound of Formula VIA in which L is bond and [Ring E] is a N-linked heterocyclyl, can be prepared using microwave chemistry, by reaction an intermediate I-6 with the heterocyclyl, in the presence of a base such as triethylamine, in a polar solvent such as Ethanol, and using high temperatures, as shown in Scheme 49. A similar displacement is described in PCT patent application WO 2005/059668.

Scheme 49

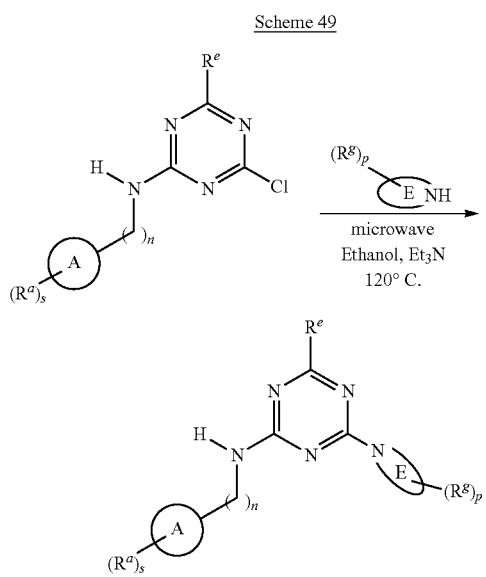

In a non limiting example, Scheme 49A illustrates the preparation of a compound of Formula VIA in which L is a bond, $R^e$ is Cl and [Ring E] is N-phenyl-piperazine.

Scheme 49A

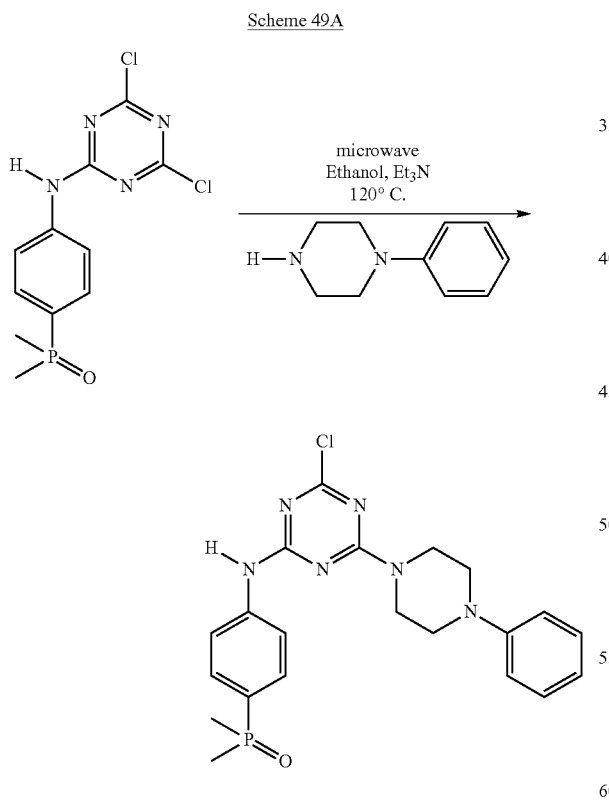

Scheme 50 illustrates the preparation of a compound of Formula IVA in which $R^c$ is L-[Ring E]; L is NH, $X^3$ is N, $X^4$ is C and Ring C is a triazole. A similar sequence of reaction is described in Bioorganic & Medicinal Chemistry Letters, 16(5), 1353-1357; 2006. Microwave chemistry can also be used to accelerate the displacement reaction.

Scheme 50

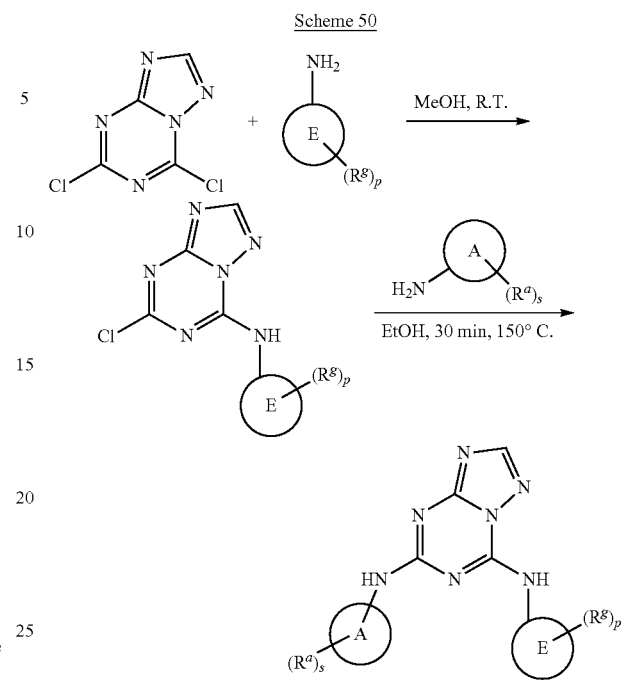

In a non limiting example, Scheme 50A illustrates the preparation of compounds of Formula IVA in which L is NH, $X^3$ is N, $X^4$ is C, Ring C is a triazole, and Ring A and Ring E are substituted phenyl.

Scheme 50A

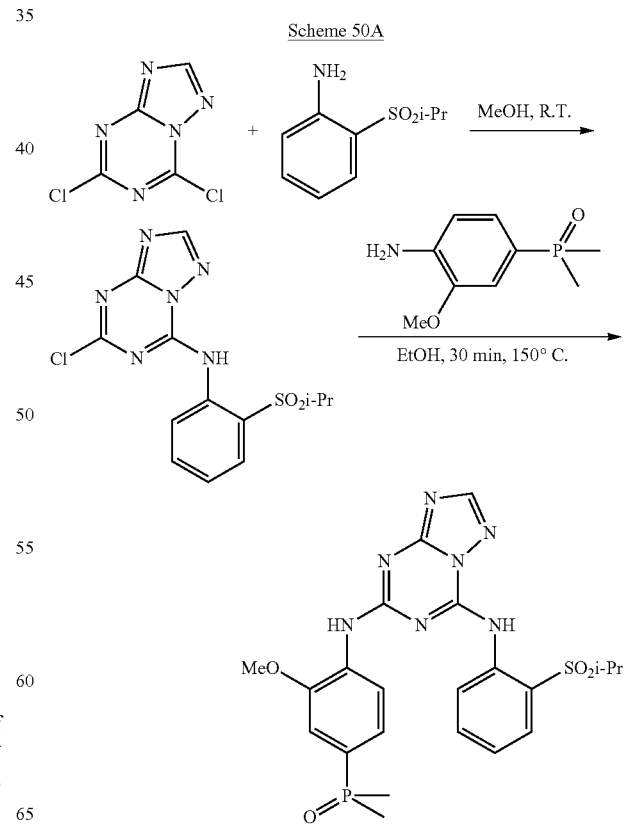

An alternative route to compounds of Formula IVA in which Ring C is a triazole is illustrated in Scheme 51. A compound of Formula I-15 can be reacted with an aryl halide (such as aryl bromide) or heteroaryl halide in the presence of a base, such as for example Cesium carbonate, and in the presence of a palladium acetate and a phosphorous ligand (i.e. xanphos); which generates intermediate I-15a. Intermediate I-15a is then subjected to m-CPBA and the oxidized sulfur is displaced with a Ring A-$NH_2$ moiety. The synthesis of intermediate I-15 is described in Journal of heterocyclic chemistry, 37(6), 1587-1590, 2000.

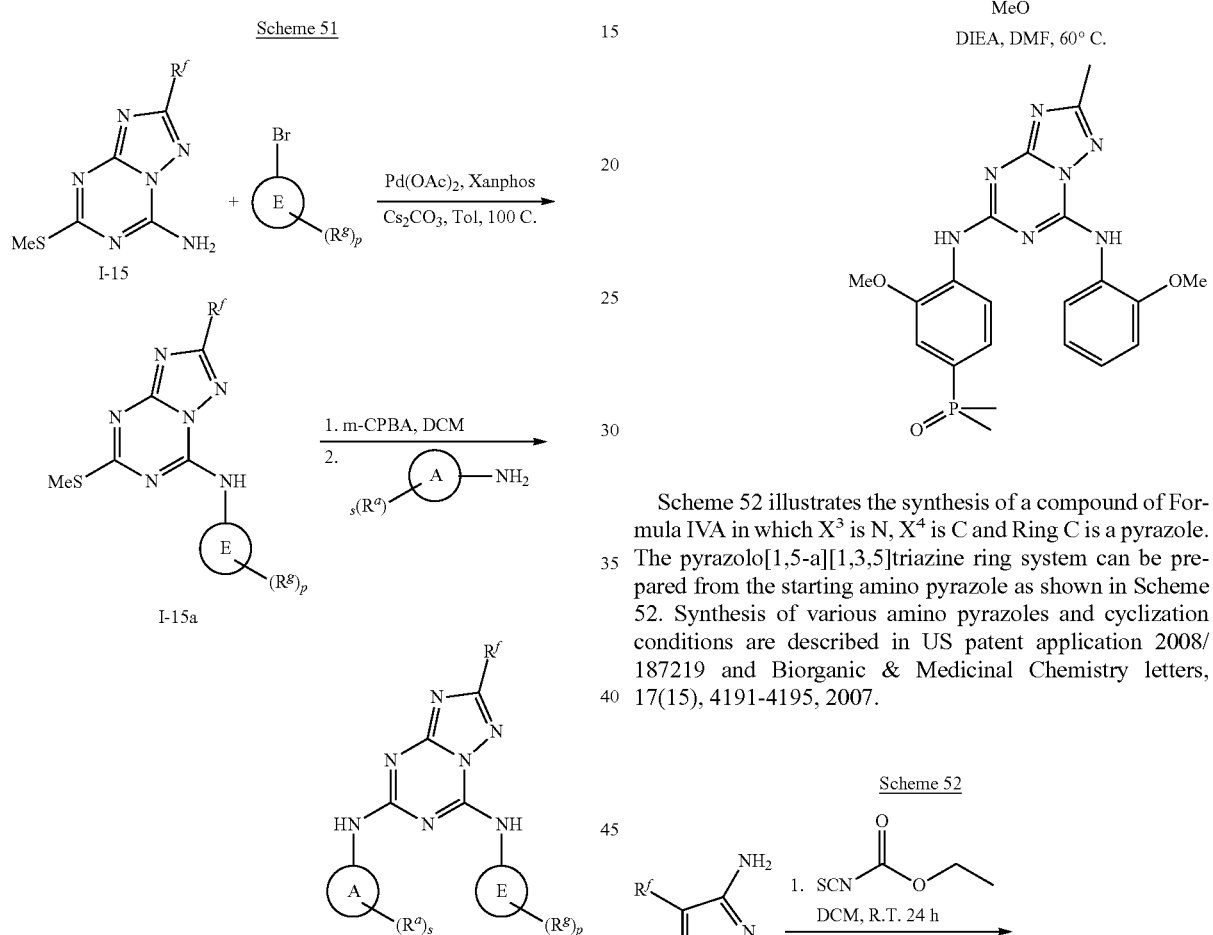

In a non limiting example, Scheme 51A illustrates the preparation of compounds of Formula IVA in which $R^c$ is L-[Ring E], and L is NH, $X^3$ is N, $X^4$ is C, Ring C is a triazole, $R^f$ is Me and Ring A and Ring E are substituted phenyl.

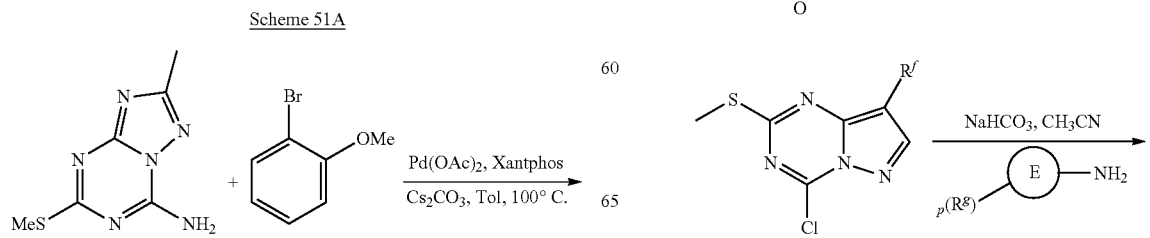

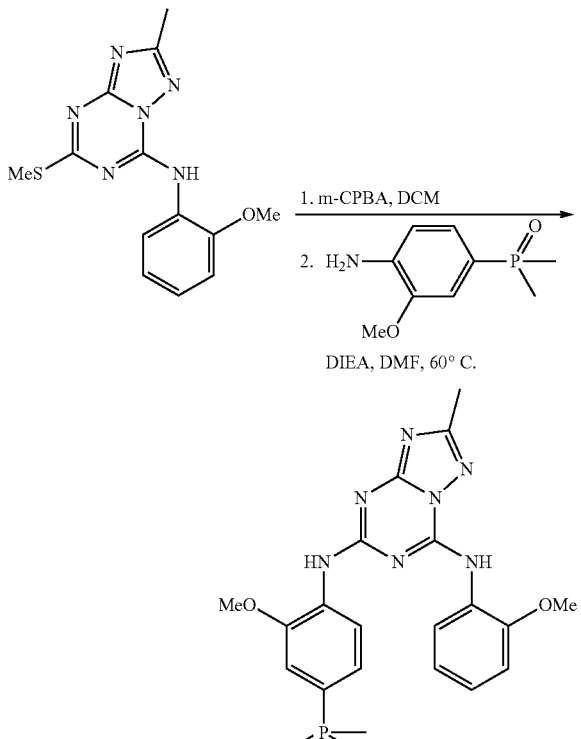

Scheme 52 illustrates the synthesis of a compound of Formula IVA in which $X^3$ is N, $X^4$ is C and Ring C is a pyrazole. The pyrazolo[1,5-a][1,3,5]triazine ring system can be prepared from the starting amino pyrazole as shown in Scheme 52. Synthesis of various amino pyrazoles and cyclization conditions are described in US patent application 2008/187219 and Biorganic & Medicinal Chemistry letters, 17(15), 4191-4195, 2007.

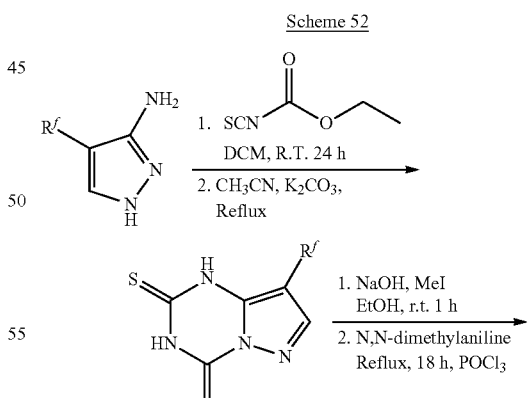

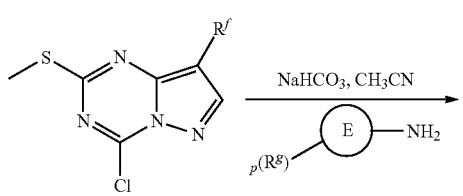

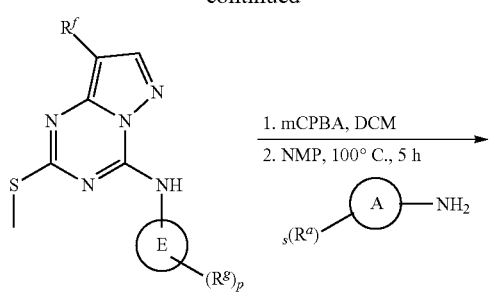

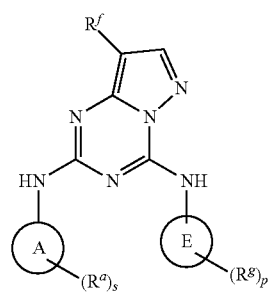

In a non limiting example, Scheme 52A illustrates the preparation of compounds of Formula IVA in which $X^3$ is N, $X^4$ is C, Ring C is a pyrazole, Ring A and Ring E are substituted phenyl.

Scheme 52A

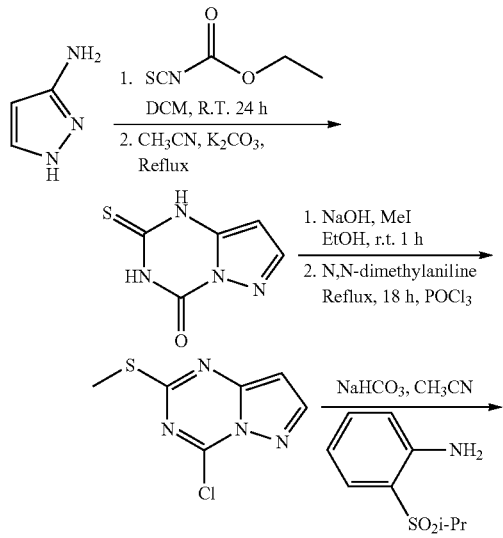

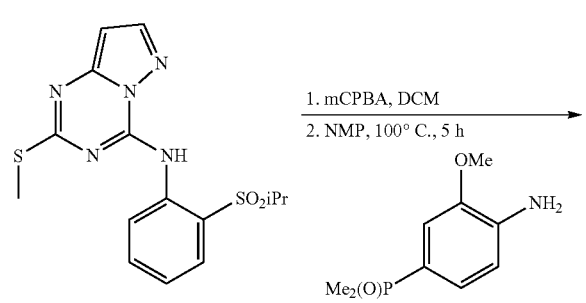

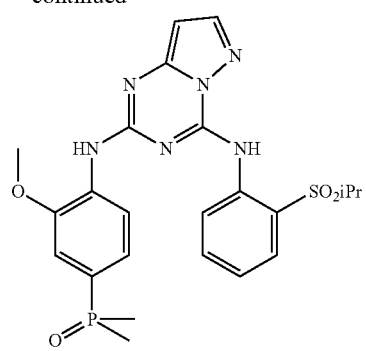

Scheme 53 illustrates the synthesis of a compound of Formula IVA in which $X^4$ is N and $X^3$ is C, $R^c$ is L-[Ring E], L is NH and [Ring C] is a pyrrole. This synthesis is described in PCT application WO 2008/057994.

Scheme 53

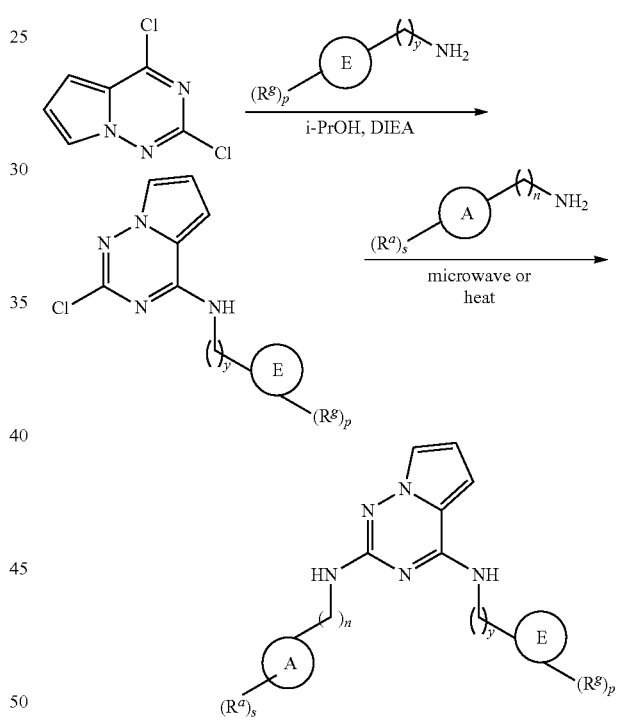

In a non limiting example, Scheme 53A illustrates the preparation of compounds of Formula IVA in which $X^4$ is N and $X^3$ is C, $R^c$ is L-[Ring E], L is NH and [Ring C] is a pyrrole; and Ring A and Ring E are substituted phenyl.

Scheme 53A

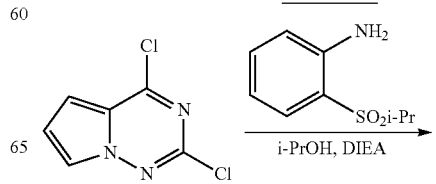

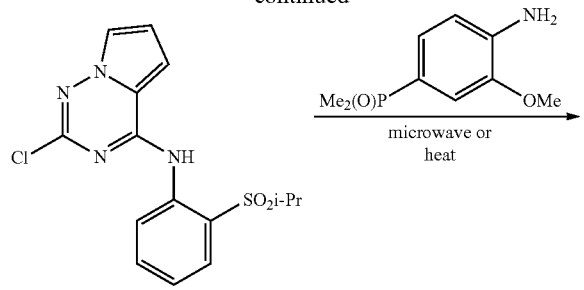

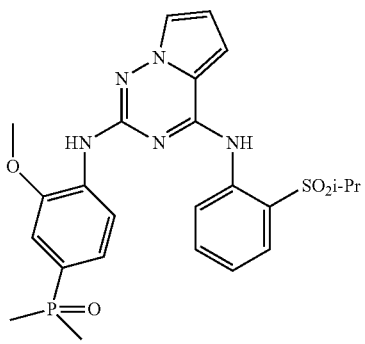

Scheme 54 illustrates the synthesis of a compound of Formula IIIA in which Ring B is a pyrrole. 3,6-Dichloro-N-substituted-1,2-4-triazin-5-amine is reacted with a substituted alkyne under Sonogashira conditions to generate 3-chloro-5-substituted-pyrrolo[2,3-e][1,2,4]triazine. A similar synthetic route using Sonogashira reaction is described in Tetrahedron Letters, 48(29), 5069-5072; 2007.

Scheme 54

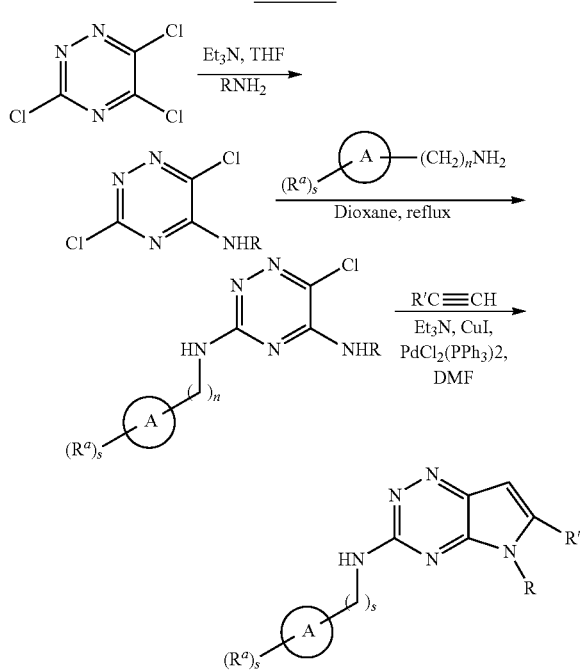

in which Ring A and $R^a$, n and s are as defined in part 1 and R and R' are alkyl, heteroaryl, aryl, aryl alkyl, heteroaryl alkyl, heterocyclyl and other groups selected from the $R^f$ list of substituents. Examples of R' are methyl, ethyl, methyl dialkylamino, phenyl and the like. Examples of R are substituted phenyl, substituted benzyl, substituted pyridine and the like.

In a non limiting example, Scheme 54A illustrates the preparation of compounds of Formula IIIA in which Ring B is a pyrrole; R' is a methyl group, R is a substituted phenyl and Ring A is a substituted phenyl.

Scheme 54A

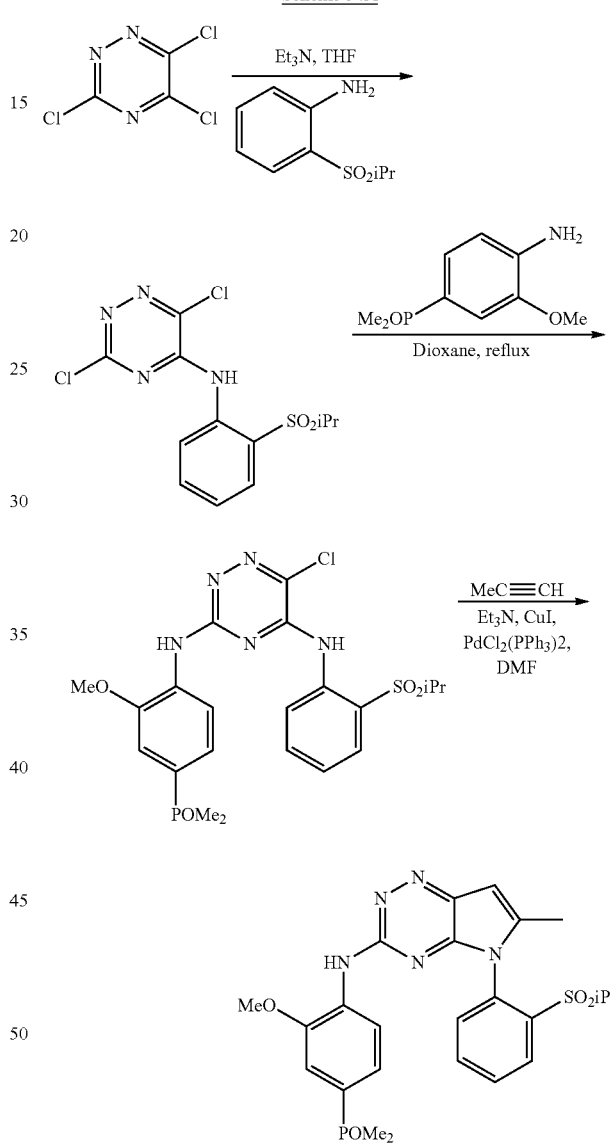

Another example of preparation of a compound of Formula IIIA is illustrated below in Scheme 55 in which Ring B is an imidazole. An intermediate I-19 can be reacted with an amine to generate intermediate I-19a and the cyclization occurs in the presence of SOCl$_2$ and trimethoxymethane and generates intermediate I-19b. The cyclization step is described in Liebigs Annalen der Chemie, 7, 631-40, 1990. The methyl thioether in intermediate I-19b can then be oxidized with m-CPBA and displaced with a [Ring A]-(CH$_2$)$_n$NH$_2$ moiety as previously described in Scheme 52.

Scheme 55

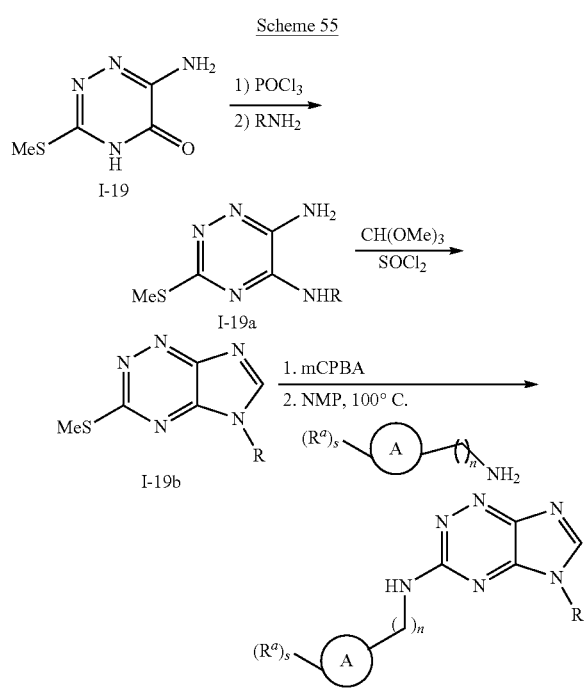

in which R is alkyl, heteroaryl, aryl, aryl alkyl, heteroaryl alkyl, heterocyclyl and other groups selected from the $R^f$ list of substituents. Examples of R are methyl, ethyl, methyl dialkylamino, phenyl and the like. Examples of R are substituted phenyl, substituted benzyl, substituted pyridine and the like. Ring A and $R^a$ are defined in part 1.

In a non limiting example, Scheme 55A illustrates the preparation of compounds of Formula IIIA in which Ring B is an imidazole, Ring A is a substituted phenyl and R is a substituted phenyl:

Scheme 55A

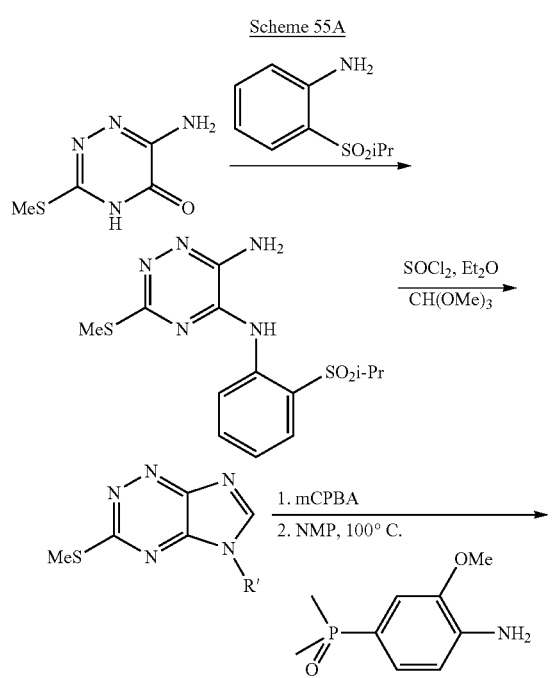

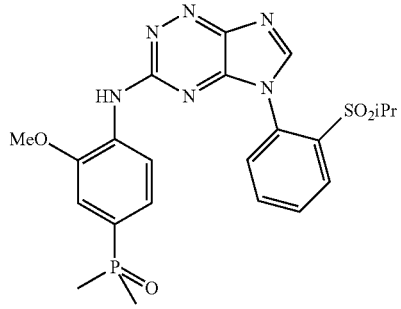

Another example of preparation of a compound of Formula IIIA is illustrated below in Scheme 56 in which Ring B is a pyrazole. An intermediate I-20 can be reacted with hydrazinecarbothioamide and the cyclization occurs in the presence of potassium carbonate which generates intermediate I-20a. The cyclization step is described in Journal of Heterocyclic Chemistry, 21(3), 923-6, 1984. Intermediate I-20a is then reacted with a [Ring]A-(CH$_2$)$_n$NH$_2$ moiety. A similar displacement is described in Journal fuer Praktische Chemie (Leipzig), 326(6), 994-8, 1984.

Scheme 56

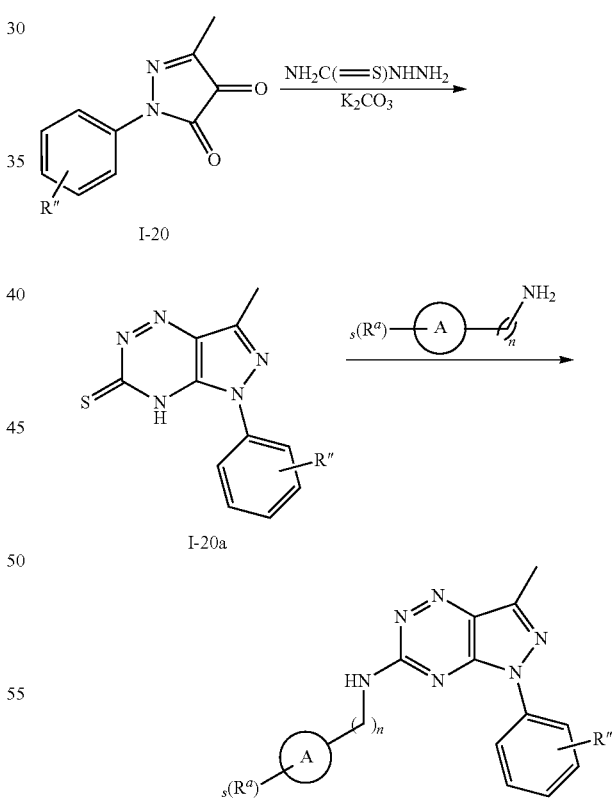

in which R" is a substituent selected from $R^f$ list and Ring A and $R^a$ are defined in part 1.

In a non limiting example, Scheme 56A illustrates the preparation of compounds of Formula IIIA in which Ring B is a pyrazole, Ring A is a substituted phenyl and R" is a methoxy group.

Scheme 56A

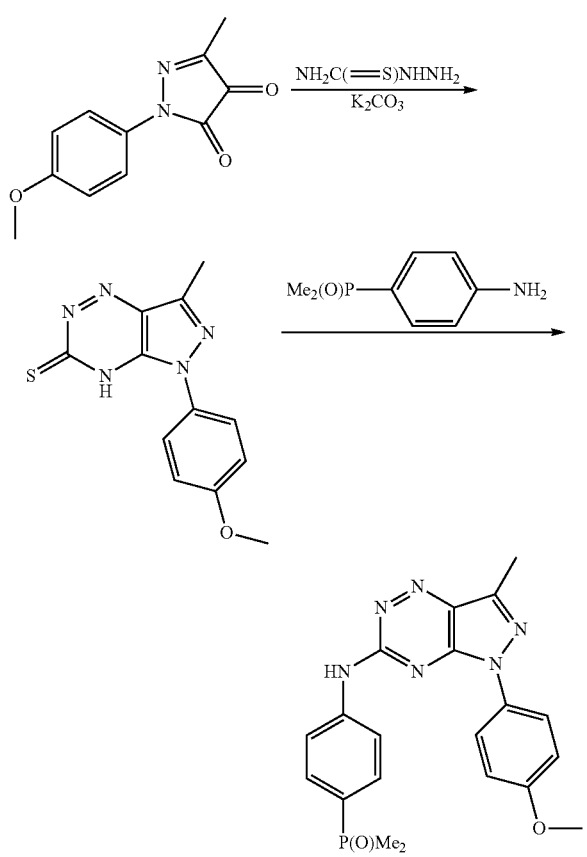

Another example of preparation of a compound of Formula IIIA is illustrated below in Scheme 57 in which Ring B is a phenyl. A substituted 2-nitroaniline can undergo cyclization in the presence of Raney Nickel as described in Bioorganic & Medicinal Chemistry Letters, 17(21), 5818, 2007. When 2-nitroaniline is substituted with a bromide or halide, a Suzuki coupling reaction can be used to introduce an aryl or heteroaryl onto the fused phenyl ring B. The Ring A-NH$_2$ moiety can be introduced using Buchwald-Hartwig cross-coupling reaction.

Scheme 57

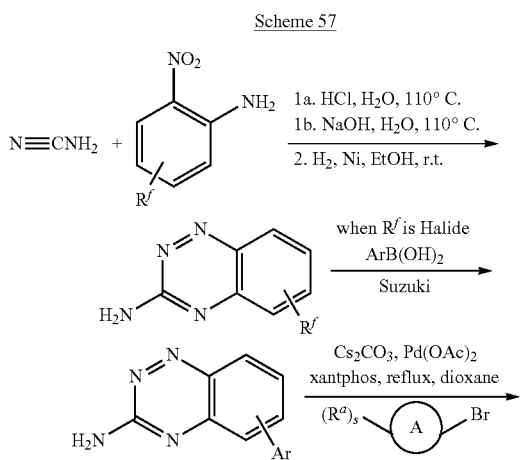

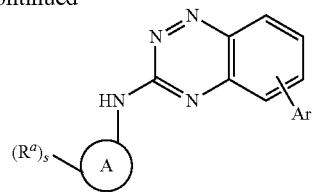

In a non limiting example, Scheme 57A illustrates the preparation of compounds of Formula IIIA in which Ring B and Ring A are substituted phenyl:

Scheme 57A

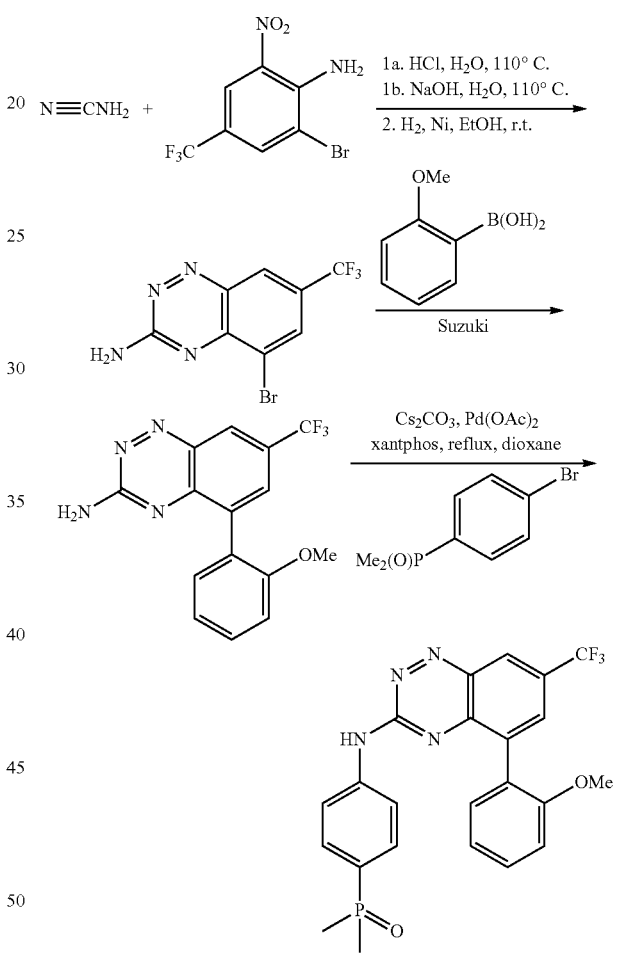

With synthetic approaches such as the foregoing, combined with the examples which follow, additional information provided herein and conventional methods and materials, the practitioner should be able to prepare the full range of compounds disclosed herein.

5. Uses, Formulations, Administration

Pharmaceutical Uses; Indications

The invention features compounds having biological properties which make them of interest for treating or modulating disease in which kinases may be involved, symptoms of such disease, or the effect of other physiological events mediated by kinases. For instance, a number of compounds of the invention have been shown to inhibit tyrosine kinase activity of ALK, fak and c-met, among other tyrosine kinases which are believed to mediate the growth, development and/or metastasis of cancer. A number of compounds of the invention have also been found to possess potent in vitro activity against cancer cell lines, including among others karpas 299 cells. Such compounds are thus of interest for the treatment of cancers, including solid tumors as well as lymphomas and including cancers which are resistant to other therapies.

Such cancers include, among others, cancers of the breast, non small cell lung cancer (NSCLS), neural tumors such as glioblastomas and neuroblastomas; esophaegeal carcinomas, soft tissue cancers such as rhabdomyosarcomas, among others); various forms of lymphoma such as a non-Hodgkin's lymphoma (NHL) known as anaplastic large-cell lymphoma (ALCL), various forms of leukemia; and including cancers which are ALK or c-met mediated.

Anaplastic Lymphoma Kinase (ALK) is a cell membrane-spannning receptor tyrosine kinase, which belong to the insulin receptor subfamily. ALK receptor tyrosine kinase (RTK) was initially identified due to its involvement in the human non-Hodgkin lymphoma subtype known as anaplastic large-cell lymphoma (ALCL). ALK normally has a restricted distribution in mammalian cells, being found at significant levels only in nervous system during embryonic development, suggesting a possible role for ALK in brain development (Duyster, J. Et al., *Oncogene*, 2001, 20, 5623-5637).

In addition to its role in normal development, expression of the full-length normal ALK has also been detected in cell lines derived from a variety of tumors such as neuroblastomas, neuroectodermal tumors (Lamant L. Et al., *Am. J. Pathol.*, 2000, 156, 1711-1721; Osajima-Hakomori Y., et al., *Am. J. Pathol.* 2005, 167, 213-222) and glioblastoma (Powers C. et al., *J. Biol. Chem.* 2002, 277, 14153-14158; Grzelinski M. et al., *Int. J. Cancer*, 2005, 117, 942-951; Mentlein, R. Et al., *J. Neurochem.*, 2002, 83, 747-753) as well as breast cancer and melanoma lines (Dirk W G. Et al., *Int. J. Cancer*, 2002, 100, 49-56).

In common with other RTKs, translocations affect the ALK gene, resulting in expression of oncogenic fusion kinases—the most common of which is NPM-ALK. For example, approximately sixty percent of anaplastic large cell lymphomas (ALCL) are associated with a chromosome mutation that generates a fusion protein consisting of nucleophosmin (NMP) and the intracellular domain of ALK. (Armitage, J. O. et al., Cancer: principle and practice of oncology, 6$^{th}$ Edition, 2001, 2256-2316; kutok, J. L. & Aster J. C., *J. Clin. Oncol.*, 2002, 20, 3691-3702; Wan, W. et al., *Blood*, 2006, 107, 1617-1623. This mutant protein, NMP-ALK, possesses a constitutively active tyrosine kinase domain that is responsible for its oncogenic property through activation of downstream effectors (Falini, B and al., *Blood*, 1999, 94, 3509-3515; Morris, S. W. et al., *Brit. J. Haematol.*, 2001, 113, 275-295). Experimental data have demonstrated that the aberrant expression of constitutively active ALK is directly implicated in the pathogenesis of ALCL and that inhibition of ALK can markedly impair the growth of ALK positive lymphoma cells (Kuefer, Mu et al., *Blood*, 1997, 90, 2901-2910; Bai, R. Y. et al., *Exp. Hematol.*, 2001, 29, 1082-1090; Slupianek, A. et al., *Cancer Res.*, 2001, 61, 2194-2199; Turturro, F. et al., *Clin. Cancer. Res.*, 2002, 8, 240-245). The constitutively activated chimeric ALK has also been demonstrated in about 60% of inflammatory myofibroblastic tumors (IMTs), a slow growing sarcoma that mainly affects children and young adults (Lawrence, B. et al., *Am. J. Pathol.*, 2000, 157, 377-384). Furthermore, recent reports have also described the occurrence of a variant ALK fusion, TPM4-ALK, in cases of squamous cell carcinoma (SCC) of the esophagus (Jazzi fr., et al., *World J. Gastroenterol.*, 2006, 12, 7104-7112; Du X., et al., *J. Mol. Med.*, 2007, 85, 863-875; Aklilu M., *Semin. Radiat. Oncol.*, 2007, 17, 62-69). Thus, ALK is one of the few examples of an RTK implicated in oncogenesis in both non-hematopoietic and hematopoietic malignancies. More recently it has been shown that a small inversion within chromosome 2p results in the formation of a fusion gene comprising portions of the echinoderm microtubule-associated protein-like 4 (EML4) gene and the anaplastic lymphoma kinase (ALK) gene in non-small-cell lung cancer (NSCLC) cells (Soda M., et al., Nature, 2007, 448, 561-567).

We therefore envision that an ALK inhibitor would either permit durable cures when used as a single therapeutic agent or combined with current chemotherapy for ALCL, IMT, proliferative disorders, glioblastoma and other possible solid tumors cited herein, or, as a single therapeutic agent, could be used in a maintenance role to prevent recurrence in patients in need of such a treatment.

Pharmaceutical Methods

The invention features methods for treating a subject having or at risk of contracting cancer by administering to the subject a therapeutically effective amount of a compound of the invention.

A "therapeutically effective amount" is that amount effective for detectable killing or inhibition of the growth or spread of cancer cells; the size or number of tumors; or other measure of the level, stage, progression or severity of the cancer. The exact amount required will vary from subject to subject, depending on the species, age, and general condition of the subject, the severity of the disease, the particular anticancer agent, its mode of administration, combination treatment with other therapies, and the like.

The compound, or a composition containing the compound, may be administered using any amount and any route of administration effective for killing or inhibiting the growth of tumors or other forms of cancer.

The anticancer compounds of the invention are preferably formulated in dosage unit form for ease of administration and uniformity of dosage. The expression "dosage unit form" as used herein refers to a physically discrete unit of anticancer agent appropriate for the patient to be treated. As is normally the case, the total daily usage of the compounds and compositions of the invention will be decided by the attending physician using routine reliance upon sound medical judgment. The specific therapeutically effective dose level for any particular patient or organism will depend upon a variety of factors including the disorder being treated; the severity of the disorder; the potency of the specific compound employed; the specific composition employed; the age, body weight, general health, sex and diet of the patient; the route and schedule of administration; the rate of metabolism and/or excretion of the compound; the duration of the treatment; drugs used in combination or coincident with administration of the compound of the invention; and like factors well known in the medical arts.

Furthermore, after formulation with an appropriate pharmaceutically acceptable carrier in a desired dosage, the compositions of the invention can be administered to humans and other animals orally, rectally, parenterally, intracisternally, intravaginally, intraperitoneally, topically (as by transdermal patch, powders, ointments, or drops), sublingually, bucally, as an oral or nasal spray, or the like.

The effective systemic dose of the compound will typically be in the range of 0.01 to 500 mg of compound per kg of patient body weight, preferably 0.1 to 125 mg/kg, and in some cases 1 to 25 mg/kg, administered in single or multiple doses.

Generally, the compound may be administered to patients in need of such treatment in a daily dose range of about 50 to about 2000 mg per patient. Administration may be once or multiple times daily, weekly (or at some other multiple-day interval) or on an intermittent schedule. For example, the compound may be administered one or more times per day on a weekly basis (e.g. every Monday) indefinitely or for a period of weeks, e.g. 4-10 weeks. Alternatively, it may be administered daily for a period of days (e.g. 2-10 days) followed by a period of days (e.g. 1-30 days) without administration of the compound, with that cycle repeated indefinitely or for a given number of repetitions, e.g. 4-10 cycles. As an example, a compound of the invention may be administered daily for 5 days, then discontinued for 9 days, then administered daily for another 5 day period, then discontinued for 9 days, and so on, repeating the cycle indefinitely, or for a total of 4-10 times.

The amount of compound which will be effective in the treatment or prevention of a particular disorder or condition will depend in part on well known factors affecting drug dosage. In addition, in vitro or in vivo assays may optionally be employed to help identify optimal dosage ranges. A rough guide to effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

When administered for the treatment or inhibition of a particular disease state or disorder, the effective dosage of the compound of the invention may vary depending upon the particular compound utilized, the mode of administration, the condition, and severity thereof, of the condition being treated, as well as the various physical factors related to the individual being treated. In many cases, satisfactory results may be obtained when the compound is administered in a daily dosage of from about 0.01 mg/kg-500 mg/kg, preferably between 0.1 and 125 mg/kg, and more preferably between 1 and 25 mg/kg. The projected daily dosages are expected to vary with route of administration. Thus, parenteral dosing will often be at levels of roughly 10% to 20% of oral dosing levels.

When the compound of the invention is used as part of a combination regimen, dosages of each of the components of the combination are administered during a desired treatment period. The components of the combination may administered at the same time; either as a unitary dosage form containing both components, or as separate dosage units; the components of the combination can also be administered at different times during a treatment period, or one may be administered as a pretreatment for the other.

Regarding the Compounds

Compounds of present invention can exist in free form for treatment, or where appropriate, as a pharmaceutically acceptable salt, ester, or prodrug. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, phosphonates and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the isolation and purification of compounds of the invention, or separately by reacting the free base or free acid of a compound of the invention with a suitable base or acid, respectively. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers preferably to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates. Obviously, esters can be formed with a hydroxyl or carboxylic acid group of the compound of the invention.

Furthermore, the term "pharmaceutically acceptable prodrugs" as used herein refers to those prodrugs of compounds of the invention. The term "prodrug" refers to compounds that are transformed in vivo to yield the parent compound of the above formula, for example by hydrolysis in blood. See, e.g., T. Higuchi and V. Stella, Pro-drugs as Novel Delivery Systems, Vol. 14 of the A.C.S. Symposium Series, and Edward B. Roche, ed., Bioreversible Carriers in Drug Design, American Pharmaceutical Association and Pergamon Press, 1987, both of which are incorporated herein by reference.

Pharmaceutical Compositions

The invention also features pharmaceutical compositions including a compound of the invention, or a prodrug, pharmaceutically acceptable salt or other pharmaceutically acceptable ester thereof, and one or more pharmaceutically acceptable carriers or excipients. The pharmaceutical compositions optionally further comprise one or more additional therapeutic agents. In certain instances a compound of the invention may be administered to a subject undergoing one or more other therapeutic interventions (e.g. Gleevec or other kinase inhibitors, interferon, bone marrow transplant, farnesyl transferase inhibitors, bisphosphonates, thalidomide, cancer vaccines, hormonal therapy, antibodies, radiation, etc).

For example, the compound of the invention can be used as one component of a combination therapy in which one or more additional therapeutic agents (e.g., an anticancer agent), the agents being either formulated together or separately, is administered to the subject.

The pharmaceutical compositions of the invention include a pharmaceutically acceptable carrier or excipient. Pharmaceutically acceptable carriers and excipient that can be used in the pharmaceutical compositions of the invention include, without limitation, solvents, diluents, or other vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Some examples of materials which can serve as pharmaceutically acceptable carriers or excipients include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition.

Compounds of the invention may be administered by any suitable route, preferably in the form of a pharmaceutical composition adapted to such a route, and in a dose effective for the treatment intended. Compounds of the invention may, for example, be administered orally, mucosally, topically, rectally, pulmonarily such as by inhalation spray, or parentally including intravascularly, intravenously, intraperitoneally, subcutaneously, intramuscularly, intrasternally and infusion techniques, in dosage unit formulations containing conventional pharmaceutically acceptable carriers, adjuvants, and vehicles.

For oral administration, the pharmaceutical composition may be in the form of for example, a tablet, capsule, suspension or liquid. The pharmaceutical composition is preferably made in the form of a dosage unit containing a particular amount of the active ingredient. Each unit dosage may contain an amount of active ingredient from about 1 to 2000 mg, preferably from about 1 to 500 mg, more commonly from about 5 to 200 mg. The amount of a compound of the invention to be administered will typically be in the range of 0.01 to 500 mg of compound per kg body weight, preferably between 0.1 and 125 mg/kg body weight and in some cases between 1 and 25 mg/kg body weight. As mentioned previously, the daily dose can be given in one administration or may be divided between 2, 3, 4 or more administrations.

In the case of skin conditions, it may be preferable to apply a topical preparation of compounds of the invention to the affected area two to four times a day. Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

Compounds of the invention can also be administered by a transdermal device. Preferably transdermal administration will be accomplished using a patch either of the reservoir and porous membrane type or of a solid matrix variety. In either case, the active agent is delivered—continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of the invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required.

Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients.

The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers.

Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Combination Therapy

Compounds of the invention can be administered as part of a treatment regimen in which the compound is the sole active pharmaceutical agent, or used in combination with one or more other therapeutic agents as part of a combination therapy. When administered as one component of a combination therapy, the therapeutic agents being administered can be formulated as separate compositions that are administered at the same time or sequentially at different times (e.g., within 72 hours, 48 hours, or 24 hours of one another), or the therapeutic agents can be formulated together in a single pharmaceutical composition and administered simultaneously.

Thus, the administration of compounds of the invention may be in conjunction with additional therapies known to those skilled in the art in the prevention or treatment of cancer, such as radiation therapy or cytostatic agents, cytotoxic agents, other anti-cancer agents and other drugs to ameliorate symptoms of the cancer or side effects of any of the drugs.

If formulated as a fixed dose, such combination products employ compounds of the invention within the accepted dosage ranges. Compounds of the invention may also be administered sequentially with other anticancer or cytotoxic agents when a combination formulation is inappropriate. The invention is not limited in the sequence of administration; compounds of the invention may be administered prior to, simultaneously with, or after administration of the other anticancer or cytotoxic agent.

Currently, standard treatment of primary tumors consists of surgical excision, when appropriate, followed by either radiation or chemotherapy, and typically administered intravenously (IV). The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of cancer by combination drug chemotherapy. And there are several major categories of such antineoplastic agents, namely, antibiotic-type agents, alkylating agents, antimetabolite agents, hormonal agents, immunological agents, interferon-type agents and a category of miscellaneous agents.

A first family of antineoplastic agents which may be used in combination with compounds of the invention includes antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, CibaGeigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl) fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC788, thioguanine, tiazofurin, Erbamont TIF, trimetrexate, tyrosine kinase inhibitors, Taiho UFT and uricytin.

A second family of antineoplastic agents which may be used in combination with compounds of the invention consists of alkylating-type antineoplastic agents. Suitable alkylating-type antineoplastic agents may be selected from but not limited to the group consisting of Shionogi 254-S, aldophosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D 384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G M, Chinoin GYKI-17230, hepsulfam, ifosfamide, iproplatin, lomustine, mafosfamide, mitolactolf Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN II, Ajinomoto AN3, Nippon Soda anisomycins, anthracycline, azino-mycinA, bisucaberin, Bristol-Myers BL-6859, Bristol-Myers BMY-25067, Bristol-Myers BNY-25551, Bristol-Myers BNY-26605 IBristolMyers BNY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko, DC89-Al, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-Al, esperamicin-Alb, Erbamont FCE21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SR1 International NSC-357704, oxalysine, oxaunomycin, peplomycin, pilatin, pirarubicin, porothramycin, pyrindanycin A, Tobishi RA-1, rapamycin, rhizoxin, rodorubicin, sibanomicin, siwenmycin, Sumitomo SM5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the invention consists of a miscellaneous family of antineoplastic agents, including tubulin interacting agents, topoisomerase II inhibitors, topoisomerase I inhibitors and hormonal agents, selected from but not limited to the group consisting of (xcarotene, (X-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1F Henkel APD, aphidicolin glycinate, asparaginase, Avarol, baccharin, batracylin, benfluoron, benzotript, Ipsen-Beaufour BIM-23015, bisantrene, BristoMyers BNY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, WarnerLambert CI-937, Warner-Lambert CI-941, Warner-Lambert CI958, clanfenur, claviridenone, ICN compound 1259, ICN compound 4711, Contracan, Yakult Honsha CPT-11, crisnatol, curaderm, cytochalasin B. cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704t gallium nitrate, genkwadaphnin, Chugai GLA-43, Glaxo GR-63178, grifolan NMF5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU 1121 Lilly LY-186641, NCI (US) MAP, marycin, Merrel Dow MDL-27048, Medco MEDR-340, merbarone, merocyanlne derivatives, methylanilinoacridine, Molecular Genetics MGI136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, WarnerLambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM Alternatively, the present compounds may also be used in co-therapies with other antineoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfaconl, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama, vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinidel filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM iodine 131 MAb (Techniclone), polymorphic epithelial mucin-yttrium 90 MAb (Antisoma), marimastat, menogaril, mitumomab, motexafin, gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN)y SU 6668 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Treatment Kits

In other embodiments, the invention relates to a kit for conveniently and effectively carrying out the methods in accordance with the invention. In general, the pharmaceutical pack or kit comprises one or more containers filled with one or more of the ingredients of the pharmaceutical compositions of the invention and instructions for administering the pharmaceutical composition (e.g., a label or package insert) as part of a method described herein. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Optionally associated with such container(s) can be a notice in the form prescribed by a governmental agency regulating the manufacture, use or sale of pharmaceutical products, which notice reflects approval by the agency of manufacture, use or sale for human administration.

The following representative examples contain important additional information, exemplification and guidance which can be adapted to the practice of the invention in its various embodiments and the equivalents thereof. These examples are intended to help illustrate the invention, and are not intended to, nor should they be construed to, limit its scope. Indeed, various modifications of the invention, and many further embodiments thereof, in addition to those shown and described herein, will become apparent to those skilled in the art upon review of this document, including the examples which follow and the references to the scientific and patent literature cited herein. The contents of those cited references are incorporated herein by reference to help illustrate the state of the art. In addition, for purposes of the invention, the chemical elements are identified in accordance with the Periodic Table of the Elements, CAS version, Handbook of Chemistry and Physics, 75$^{th}$ Ed., inside cover. Additionally, general principles of organic chemistry, as well as specific functional moieties and reactivity, are described in "Organic Chemistry", Thomas Sorrell, University Science Books, Sausalito: 1999, and "Organic Chemistry", Morrison & Boyd (3d Ed), the entire contents of both of which are incorporated herein by reference.

EXAMPLES

Example 1

N-[4-(dimethylphosphoryl)phenyl]-4-(4-methylpiperazin-1-yl)-5-(trifluoromethyl)pyrimidin-2-amine

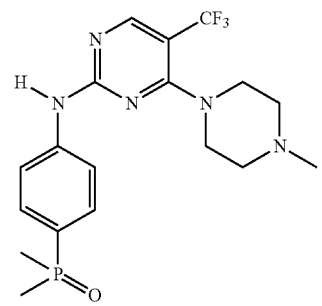 [SMILES: CN1CCN(c2nc(Nc3ccc(P(C)(C)=O)cc3)ncc2C(F)(F)F)CC1]

4-chloro-N-[4-(dimethylphosphoryl)phenyl]-5-(trifluoromethyl)pyrimidin-2-amine

A suspension of 4-amino-dimethylphenylphosphine oxide (3.7 g, 2.2 mmol) in 15 mL of N,N-Dimethylacetamide and 3.6 mL of Diisopropylethylamine, was allowed to stirred at room temperature for 15 minutes until a clear solution was obtained. 2,4-Dichloro-5-(trifluoromethyl)pyrimidine (5.7 g, 2.6 mmol) was added in four portions over 5 minutes. The reaction mixture was stirred at 60 degrees for 1 hour. The reaction mixture was cooled to room temperature and filtered to obtain a white solid. The white solid was washed with 50 mL of water three times and followed by 50 mL of Ethyl ether three times. The white solid was dried under vacuum to yield desired product (3.8 g, 49% yield). MS/ES+: m/z=350.

N-[4-(dimethylphosphoryl)phenyl]-4-(4-methylpiperazin-1-yl)-5-(trifluoromethyl)pyrimidin-2-amine To a solution of 4-chloro-N-[4-(dimethylphosphoryl)phenyl]-5-(trifluoromethyl)pyrimidin-2-amine (25 mg, 0.072 mmol) in 1.5 mL of ethanol was added 10 μL of triethylamine and 1-Methyl piperazine (7.2 mg, 0.072 mmol). The mixture was microwave at 120 degrees for 20 minutes. The reaction mixture was filtered through a syringe filter and purified by prep-HPLC (Waters Sunfire C18 column with ACN/water mobile phases) to yield a white solid as product (24 mg, 79% yield.) MS/ES+: m/z=414.

Example 2

$N^2$-[4-(dimethylphosphoryl)phenyl]-$N^4$-(tricyclo[3.3.1.1$^{3,7}$]dec-1-yl)-5-(trifluoromethyl)pyrimidine-2,4-diamine

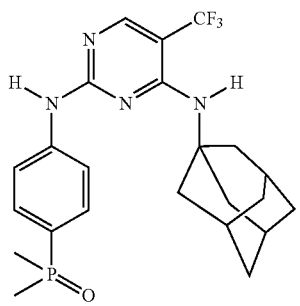 [SMILES: CP(C)(=O)c1ccc(Nc2ncc(C(F)(F)F)c(NC34CC5CC(CC(C5)C3)C4)n2)cc1]

To a solution of 4-chloro-N-[4-(dimethylphosphoryl)phenyl]-5-(trifluoromethyl)pyrimidin-2-amine (prepared as in Example 1: 27 mg, 0.078 mmol) in 1.5 mL of ethanol was added 10 μL of triethylamine and 1-Adamantanamine (12 mg, 0.078 mmol). The mixture was microwave at 120 degrees for 20 minutes. The reaction mixture was filtered through a syringe filter and purified by prep-HPLC (Waters Sunfire C18 column with ACN/water mobile phases) to yield a white solid as product (3 mg, 8% yield.) MS/ES+: m/z=465.

Example 4

$N^2$-[4-(dimethylphosphoryl)phenyl]-$N^4$-(morpholin-4-ylmethyl)-5(trifluoromethyl)pyrimidine-2,4-diamine

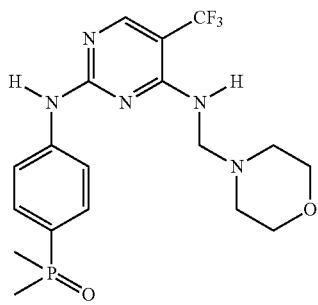 [SMILES: CP(C)(=O)c1ccc(Nc2ncc(C(F)(F)F)c(NCN3CCOCC3)n2)cc1]

To a solution of 4-chloro-N-[4-(dimethylphosphoryl)phenyl]-5-(trifluoromethyl)pyrimidin-2-amine (prepared as in Example 1: 40 mg, 0.12 mmol) in 2 mL of ethanol was added 50 μL of triethylamine and 4-(2-aminoethyl) morpholine (15 mg, 0.12 mmol). The mixture was microwave at 120 degrees for 20 minutes. The reaction mixture was filtered through a syringe filter and purified by prep-HPLC (Waters Sunfire C18 column with ACN/water mobile phases) to yield a white solid as product (42 mg, 81% yield.) MS/ES+: m/z=430.

Example 5

4-(2-{[2-{[4-(dimethylphosphoryl)phenyl]amino}-5-(trifluoromethyl)pyrimidin-4-yl]amino}ethyl)benzenesulfonamide

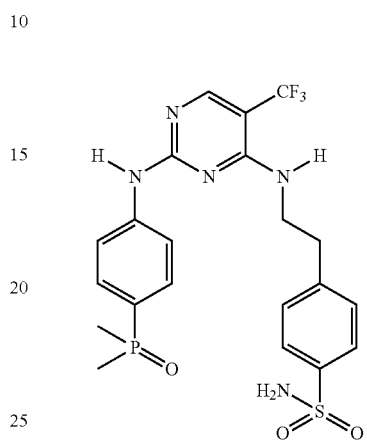

To a solution of 4-chloro-N-[4-(dimethylphosphoryl)phenyl]-5-(trifluoromethyl)pyrimidin-2-amine (prepared as in Example 1: 40 mg, 0.12 mmol) in 2 mL of ethanol was added 50 μL of triethylamine and 4-(2-aminoethyl)benzene-sulfonamide (23 mg, 0.12 mmol). The mixture was microwave at 120 degrees for 20 minutes. The reaction mixture was filtered through a syringe filter and purified by prep-HPLC (Waters Sunfire C18 column with ACN/water mobile phases) to yield a white solid as product (30 mg, 49% yield.) MS/ES+: m/z=514.

Example 6

$N^2$-[4-(dimethylphosphoryl)phenyl]-$N^4$-(tetrahydrofuran-2-yl)-5-(trifluoromethyl)pyrimidine-2,4-diamine

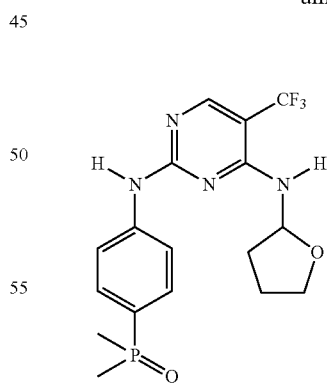

To a solution of 4-chloro-N-[4-(dimethylphosphoryl)phenyl]-5-(trifluoromethyl)pyrimidin-2-amine (prepared as in Example 1: 40 mg, 0.12 mmol) in 2 mL of ethanol was added 50 μL of triethylamine and (s)-3-aminotetrahydrofuran hydrochloride salt (14 mg, 0.12 mmol). The mixture was microwave at 120 degrees for 20 minutes. The reaction mixture was filtered through a syringe filter and purified by prep- HPLC (Waters Sunfire C18 column with ACN/water mobile phases) to yield a white solid as product (27 mg, 59% yield.) MS/ES+: m/z=401.

Example 7

$N^2$-[4-(dimethylphosphoryl)phenyl]-$N^4$-(hexahydro-cyclopenta[c]pyrrol-2(1H)-yl)-5-(trifluoromethyl)pyrimidine-2,4-diamine

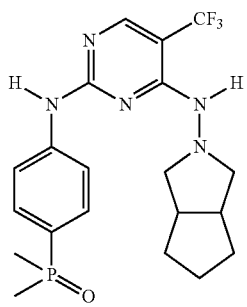 [SMILES: CP(C)(=O)c1ccc(Nc2ncc(C(F)(F)F)c(NN3CC4CCCC4C3)n2)cc1]

To a solution of 4-chloro-N-[4-(dimethylphosphoryl)phenyl]-5-(trifluoromethyl)pyrimidin-2-amine (prepared as in Example 1: 40 mg, 0.12 mmol) in 2 mL of ethanol was added 50 µL of triethylamine and 3-Amino-3-azabicyclo-[3,3,0]octane hydrochloride salt (19 mg, 0.12 mmol). The mixture was microwave at 120 degrees for 20 minutes. The reaction mixture was filtered through a syringe filter and purified by prep-HPLC (Waters Sunfire C18 column with ACN/water mobile phases) to yield a white solid as product (34 mg, 67% yield.) MS/ES+: m/z=440.

Example 8

$N^2$-[4-(dimethylphosphoryl)phenyl]-$N^4$-(morpholin-4-yl)-5-(trifluoromethyl)pyrimidine-2,4-diamine

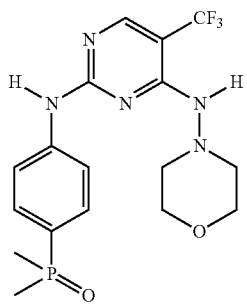 [SMILES: CP(C)(=O)c1ccc(Nc2ncc(C(F)(F)F)c(NN3CCOCC3)n2)cc1]

To a solution of 4-chloro-N-[4-(dimethylphosphoryl)phenyl]-5-(trifluoromethyl)pyrimidin-2-amine (prepared as in Example 1: 40 mg, 0.12 mmol) in 2 mL of ethanol was added 50 µL of triethylamine and 4-Aminomorpholine (12 mg, 0.12 mmol). The mixture was microwave at 120 degrees for 20 minutes. The reaction mixture was filtered through a syringe filter and purified by prep-HPLC (Waters Sunfire C18 column with ACN/water mobile phases) to yield a white solid as product (6 mg, 12% yield.) MS/ES+: m/z=416.

Example 9

N-[4-(dimethylphosphoryl)phenyl]-4-(4-phenylpiperazin-1-yl)-5-(trifluoromethyl)pyrimidin-2-amine

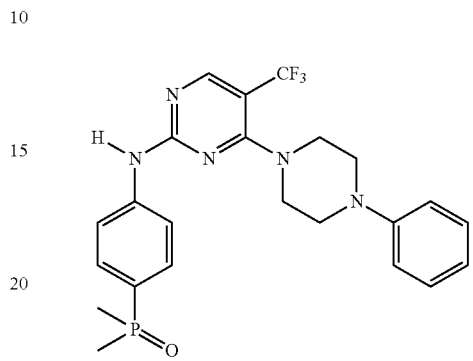

To a solution of 4-chloro-N-[4-(dimethylphosphoryl)phenyl]-5-(trifluoromethyl)pyrimidin-2-amine (prepared as in Example 1: 40 mg, 0.12 mmol) in 2 mL of ethanol was added 50 µL of triethylamine and 1-Phenylpiperazine (19 mg, 0.12 mmol). The mixture was microwave at 120 degrees for 20 minutes. The reaction mixture was filtered through a syringe filter and purified by prep-HPLC (Waters Sunfire C18 column with ACN/water mobile phases) to yield a white solid as product (40 mg, 73% yield.) MS/ES+: m/z=476.

Example 10

$N^2$-[4-(dimethylphosphoryl)phenyl]-$N^4$-[2-(1H-indol-3-yl)ethyl]-5-(trifluoromethyl)pyrimidine-2,4-diamine

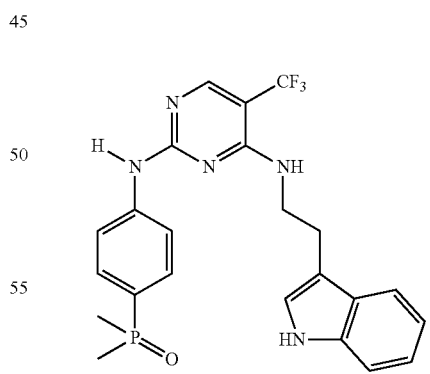

To a solution of 4-chloro-N-[4-(dimethylphosphoryl)phenyl]-5-(trifluoromethyl)pyrimidin-2-amine (prepared as in Example 1: 40 mg, 0.12 mmol) in 2 mL of ethanol was added 50 µL of triethylamine and Tryptamine (18 mg, 0.12 mmol). The mixture was microwave at 120 degrees for 20 minutes. The reaction mixture was filtered through a syringe filter and purified by prep-HPLC (Waters Sunfire C18 column with ACN/water mobile phases) to yield a white solid as product (44 mg, 81% yield.) MS/ES+: m/z=474.

Example 11

$N^2$-[4-(dimethylphosphoryl)phenyl]-$N^4$-(4-methylpiperazin-1-yl)-5-(trifluoromethyl)pyrimidine-2,4-diamine

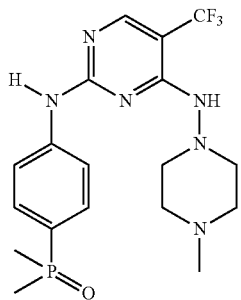

To a solution of 4-chloro-N-[4-(dimethylphosphoryl)phenyl]-5-(trifluoromethyl)pyrimidin-2-amine (prepared as in Example 1: 40 mg, 0.12 mmol) in 2 mL of ethanol was added 50 μL of triethylamine and 1-Amino-4-methyl-piperazine (13 mg, 0.12 mmol). The mixture was microwave at 120 degrees for 20 minutes. The reaction mixture was filtered through a syringe filter and purified by prep-HPLC (Waters Sunfire C18 column with ACN/water mobile phases) to yield a white solid as product (17 mg, 34% yield.) MS/ES+: m/z=429.

Example 12

$N^2$-[4-(dimethylphosphoryl)phenyl]-$N^4$-(tricyclo[3.3.1.1$^{3,7}$]dec-1-ylmethyl)-5-(trifluoromethyl)pyrimidine-2,4-diamine

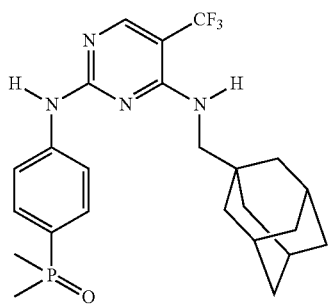 [SMILES: CP(C)(=O)c1ccc(Nc2ncc(C(F)(F)F)c(NCC34CC5CC(CC(C5)C3)C4)n2)cc1]

To a solution of 4-chloro-N-[4-(dimethylphosphoryl)phenyl]-5-(trifluoromethyl)pyrimidin-2-amine (prepared as in Example 1: 40 mg, 0.12 mmol) in 2 mL of ethanol was added 50 μL of triethylamine and 1-Adamantanemethylamine (19 mg, 0.12 mmol). The mixture was microwave at 120 degrees for 20 minutes. The reaction mixture was filtered through a syringe filter and purified by prep-HPLC (Waters Sunfire C18 column with ACN/water mobile phases) to yield a white solid as product (40 mg, 73% yield.) MS/ES+: m/z=479

Example 13

$N^2$-[4-(dimethylphosphoryl)phenyl]-$N^4$-[4-(4-methylpiperazin-1-yl)benzyl]-5-(trifluoromethyl)pyrimidine-2,4-diamine

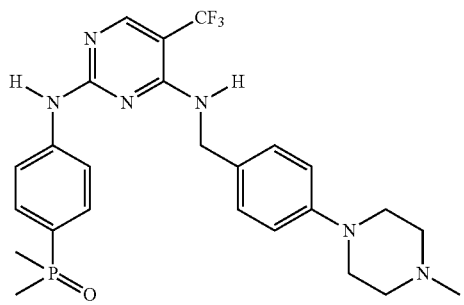 [SMILES: CN1CCN(c2ccc(CNc3nc(Nc4ccc(P(C)(C)=O)cc4)ncc3C(F)(F)F)cc2)CC1]

To a solution of 4-chloro-N-[4-(dimethylphosphoryl)phenyl]-5-(trifluoromethyl)pyrimidin-2-amine (prepared as in Example 1: 40 mg, 0.12 mmol) in 2 mL of ethanol was added 50 μL of triethylamine and 4-(4-methylpiperazine)-benzylamine (24 mg, 0.12 mmol). The mixture was microwave at 120 degrees for 20 minutes. The reaction mixture was filtered through a syringe filter and purified by prep-HPLC (Waters Sunfire C18 column with ACN/water mobile phases) to yield a white solid as product (21 mg, 73% yield.) MS/ES+: m/z=519

Example 14

$N^4$-(3,5-dimethylphenyl)-$N^2$-[4-(dimethylphosphoryl)phenyl]-5-(trifluoromethyl)pyrimidine-2,4-diamine

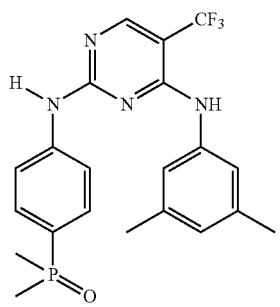 [SMILES: Cc1cc(C)cc(Nc2nc(Nc3ccc(P(C)(C)=O)cc3)ncc2C(F)(F)F)c1]

To a solution of 4-chloro-N-[4-(dimethylphosphoryl)phenyl]-5-(trifluoromethyl)pyrimidin-2-amine (prepared as in Example 1: 40 mg, 0.12 mmol) in 2 mL of ethanol was added 10 μL of Hydrochloric acid in Methanol (2M) and 3,5-Dimethyl aniline (14 mg, 0.12 mmol). The mixture was microwave at 120 degrees for 20 minutes. The reaction mixture was filtered through a syringe filter and purified by prep-HPLC (Waters Sunfire C18 column with ACN/water mobile phases) to yield a white solid as product (32 mg, 65% yield.) MS/ES+: m/z=435

Example 15

5-chloro-$N^2$-[4-(dimethylphosphoryl)-2-methoxyphenyl]-$N^4$-phenylpyrimidine-2,4-diamine

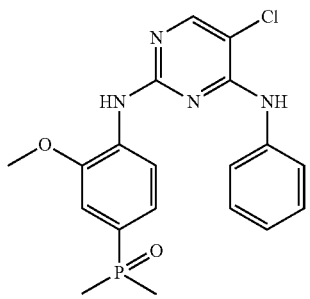 [SMILES: COc1cc(P(C)(C)=O)ccc1Nc1ncc(Cl)c(Nc2ccccc2)n1]

2,5-dichloro-N-phenylpyrimidin-4-amine

To a solution of Aniline (205 mg, 2.2 mmol) and 2,4,5-Trichloropyrimidine (500 mg, 2.7 mmol) in 5 mL of Ethanol, was added 500 mg of Potassium carbonate. The reaction mixture was stirred at room temperature for 2 hours. Solvent was removed under reduced pressure. The residue was purified by silica gel flash chromatography with 10% Ethyl Acetate in Heptane to yield the desired product as an oil (370 mg, 70% yield).

(3-methoxy-4-nitrophenyl)(dimethyl)phosphane oxide

To a solution of 5-Chloro-2-nitroanisole (0.5 g, 2.67 mmol) in 5 mL of DMF was added dimethylphosphine oxide (0.229 g, 2.93 mmol), palladium acetate (30 mg, 0.13 mmol), XANPHOS (0.092 g, 0.16 mmol) and potassium phosphate (0.623 g, 2.93 mmol). The mixture was purged with argon, and heated at 120° C. for 18 h. The reaction mixture was basified with saturated sodium bicarbonate solution, and extracted with ethyl acetate. The organic layer was concentrated and purified by prep-HPLC to give the final product (0.16 g, 30% yield). MS/ES+: m/z=229.

4-(dimethylphosphoryl)-2-methoxyaniline

To a solution of (3-methoxy-4-nitrophenyl)(dimethyl) phosphane oxide (0.1 g, 0.44 mmol) in 5 mL of EtOH was added 10% weight of palladium on carbon (0.2 g). The mixture was purged with argon, and hydrogenated under 30 psi for 2 h. The mixture was passed through Celite to a flask containing HCl in ethanol. Concentration of the filtrate gave the final product (0.088 g, 86% yield). MS/ES+: m/z=199.

5-chloro-$N^2$-[4-(dimethylphosphoryl)-2-methoxyphenyl]-$N^4$-phenylpyrimidine-2,4-diamine To a solution of 2,5-dichloro-N-phenylpyrimidin-4-amine (84 mg, 0.35 mmol) and 4-(dimethylphosphoryl)-2-methoxyaniline (60 mg, 0.30 mmol) in 1 mL of DMF, was added 0.36 mL of 2.5M HCl in Ethanol. The reaction mixture was heated in a sealed tube at 140 degrees over night. The reaction mixture was filtered through a syringe filter and purified by Prep-HPLC (Waters Sunfire C18 column with ACN/water mobile phases) to yield the desired product as a white solid. (23 mg, 16% yield). MS/ES+: m/z=403

Example 16

$N^2$-[4-(dimethylphosphoryl)-2-methoxyphenyl]-$N^4$-[2-(propan-2-ylsulfonyl)phenyl]-5-(trifluoromethyl) pyrimidine-2,4-diamine

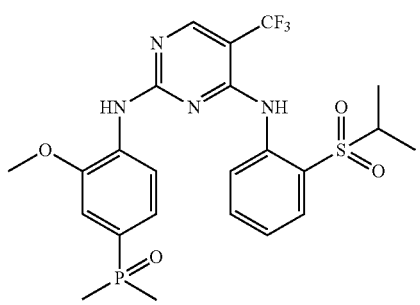 [SMILES: COc1cc(P(C)(C)=O)ccc1Nc1ncc(C(F)(F)F)c(Nc2ccccc2S(=O)(=O)C(C)C)n1]

2-chloro-N-[2-(propan-2-ylsulfonyl)phenyl]-5-(trifluoromethyl)pyrimidin-4-amine

To a solution of 1-Amino-2-(isopropylsulphonyl)benzene (350 mg, 1.6 mmol) in 4 mL of N,N-Dimethyl formamide at 0 degree, was added Sodium hydride (100 mg) and the reaction mixture was allowed to stirred at 0 degree for 20 minutes. 2,4-Dichloro-5-(trifluoromethyl)pyrimidine (350 mg, 1.6 mmol) was added in one portion and the reaction mixture was warmed to room temperature. The reaction mixture was stirred at room temperature overnight. The reaction mixture was quenched with water and extracted with Ethyl acetate. The combined Ethyl acetate layers were dried over Sodium Sulfate and solvent was removed under reduced pressure. The residue was purified by Prep-HPLC to yield the desired product as a white solid (10 mg, 2% yield).

$N^2$-[4-(dimethylphosphoryl)-2-methoxyphenyl]-$N^4$-[2-(propan-2-ylsulfonyl)phenyl]-5-(trifluoromethyl) pyrimidine-2,4-diamine To a solution of 2-chloro-N-[2-(propan-2-ylsulfonyl)phenyl]-5-(trifluoromethyl)pyrimidin-4-amine (7.5 mg, 0.02 mmol) and 4-(dimethylphosphoryl)-2-methoxyaniline (prepared as in Example 15: 15 mg, 0.7 mmol) in 1 mL of 2-Methoxy ethanol, was added 1 mL of 2.5M HCl in Ethanol. The reaction mixture was heated in a sealed tube at 140 degree over night. The reaction mixture was filtered through a syringe filter and purified by Prep-HPLC (Waters Sunfire C18 column with ACN/water mobile phases) to yield the desired product as a white solid. (0.9 mg, 8% yield). MS/ES+: m/z=543

Example 17

5-chloro-$N^2$-[4-(dimethylphosphoryl)-2-methoxyphenyl]-$N^4$-[2-(propan-2-ylsulfonyl)phenyl]pyrimidine-2,4-diamine

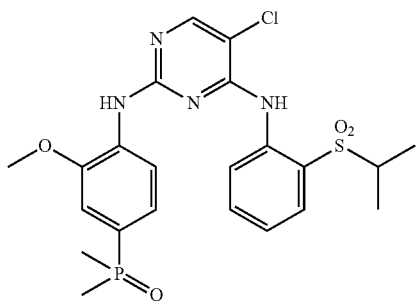 [SMILES: COc1cc(P(C)(C)=O)ccc1Nc1ncc(Cl)c(Nc2ccccc2S(=O)(=O)C(C)C)n1]

2,5-dichloro-N-[2-(propan-2-ylsulfonyl)phenyl]pyrimidin-4-amine

To a solution of 1-Amino-2-(isopropylsulphonyl)benzene (0.955 g, 4.80 mmol) in 2 mL of DMF at 0° C. was added NaH (60% in oil, 0.349 g, 8.72 mmol) in one portion. After stirring for 20 min, 2,4,5-trichloropyrimidine was added. The mixture was stirred at 0° C. for 30 minutes, and then at room temperature for 2 h. After quenching with saturated ammonium chloride solution, the mixture was poured in water and ethyl acetate mixture. Yellow suspension was filtered as final product (0.3 g, 20% yield). MS/ES+: m/z=346.

5-chloro-$N^2$-[4-(dimethylphosphoryl)-2-methoxyphenyl]-$N^4$-[2-(propan-2-ylsulfonyl)phenyl]pyrimidine-2,4-diamine To a solution of 2,5-dichloro-N-[2-(propan-2-ylsulfonyl)phenyl]pyrimidin-4-amine (0.050 g, 0.14 mmol) in 1 mL of 2-methoxyethanol was added 4-(dimethylphosphoryl)-2-methoxyaniline (prepared as in Example 15: 0.029 g, 0.14 mmol) and 0.12 ml of 2.5M HCl in EtOH. The mixture was heated in a sealed tube at 140° C. for 1 h. The mixture was basified with saturated sodium bicarbonate solution, and extracted with ethyl acetate. The organic layer was purified by prep-HPLC to give the final product (20 mg, 24% yield). MS/ES+: m/z=508.

Example 18

5-chloro-$N^2$-[4-(dimethylphosphoryl)phenyl]-$N^4$-[2-(propan-2-ylsulfonyl)phenyl]pyrimidine-2,4-diamine

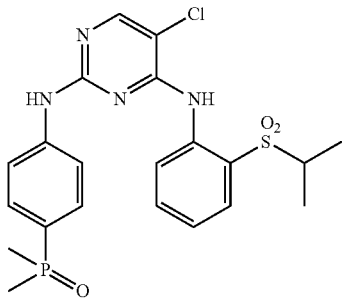 [SMILES: CC(C)S(=O)(=O)c1ccccc1Nc1nc(Nc2ccc(P(C)(C)=O)cc2)ncc1Cl]

To a solution of 2,5-dichloro-N-[2-(propan-2-ylsulfonyl)phenyl]pyrimidin-4-amine (prepared as in Example 17: 50 mg, 0.14 mmol) in 1 mL of 2-methoxyethanol was added 4-(dimethylphosphoryl)-2-methoxyaniline (prepared as in Example 15: 0.025 g, 0.14 mmol) and 0.12 ml of 2.5M HCl in EtOH. The mixture was heated in a sealed tube at 140° C. for 1 h. The mixture was basified with saturated sodium bicarbonate solution, and extracted with ethyl acetate. The organic layer was purified by prep-HPLC to give the final product (0.100 g, 15% yield). MS/ES+: m/z=478.

Example 19

5-chloro-$N^4$-[4-(dimethylphosphoryl)phenyl]-$N^2$-{2-methoxy-4-[4-(4-methylpiperazin-1-yl)piperidin-1-yl]phenyl}pyrimidine-2,4-diamine

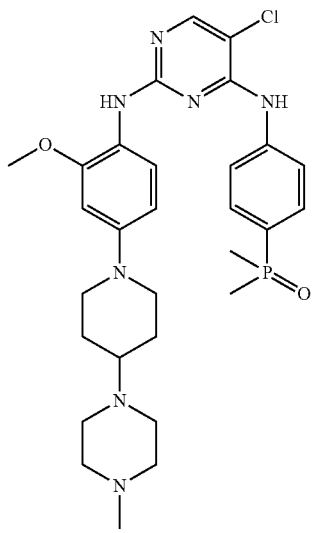 [SMILES: COc1cc(N2CCC(N3CCN(C)CC3)CC2)ccc1Nc1ncc(Cl)c(Nc2ccc(P(C)(C)=O)cc2)n1]

2,5-dichloro-N-[4-(dimethylphosphoryl)phenyl]pyrimidin-4-amine

To a solution of 2,4,5-trichloropyrimidine (0.15 ml, 1.31 mmol) in 1 mL of DMF was added 4-(dimethylphosphoryl)aniline (0.221 g, 1.31 mmol) and potassium carbonate (0.217 g, 1.57 mmol). The mixture was heated at 110° C. for 4 h. It was basified with saturated sodium bicarbonate solution. The suspension was filtered and washed with ethyl acetate to give the final product (0.15 g, 36% yield). MS/ES+: m/z=316.

1-[1-(3-methoxy-4-nitrophenyl)piperidin-4-yl]-4-methylpiperazine

To a solution of 5-fluoro-2-nitroanisoole (0.5 g, 2.92 mmol) in 3 mL of DMF was added 1-methyl-4-(piperidin)piperazine (0.536 g, 2.92 mmol) and potassium carbonate (0.808, 5.84 mmol). The mixture was heated at 120° C. for 18 h. The mixture was basified with saturated sodium bicarbonate solution and extracted with ethyl acetate. The organic layer was purified by chromatography to give final product as yellow solid (0.95 g, 95% yield). MS/ES+: m/z=334.

2-methoxy-4-[4-(4-methy/piperazin-1-yl)piperidin-1-yl]aniline

The a solution of 1-[1-(3-methoxy-4-nitrophenyl)piperidin-4-yl]-4-methylpiperazine (0.3 g, 0.90 mmol) in 10 mL of ethanol purged with argon was added 10% Palladium on carbon (0.060 g). The hydrogenation was finished under 30 psi after 4 h. The mixture was passed through Celite to a flask containing HCl in ethanol. Concentration of the filtrate gave the final product (0.15 g, 88% yield). MS/ES+: m/z=334.

5-chloro-N⁴-[4-(dimethylphosphoryl)phenyl]-N²-{2-methoxy-4-[4-(4-methylpiperazin-1-yl)piperidin-1-yl]phenyl}pyrimidine-2,4-diamine To the compound 2,5-dichloro-N-[4-(dimethylphosphoryl)phenyl]pyrimidin-4-amine (0.005 g, 0.16 mmol) in 1 mL of 2-methoxyethanol was added 2-methoxy-4-[4-(4-methylpiperazin-1-yl)piperidin-1-yl]aniline (0.71 g, 0.16 mmol). The mixture stirred at 110° C. for 18 h. The mixture was basified with saturated sodium bicarbonate solution and extracted with limited amount of ethyl acetate. The aqueous layer was purified by chromatography to give the final product (0.015 g, 20% yield). MS/ES+: m/z=583.

Example 20

N²-[4-(dimethylphosphoryl)-2-methoxyphenyl]-N⁴-[2-(propan-2-ylsulfonyl)phenyl]pyrimidine-2,4-diamine

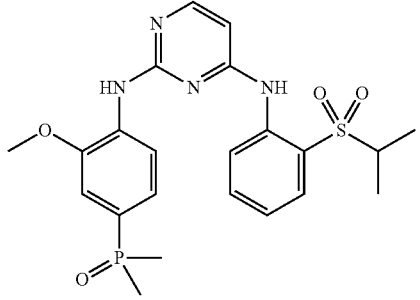 [SMILES: COc1cc(P(C)(C)=O)ccc1Nc1nccc(Nc2ccccc2S(=O)(=O)C(C)C)n1]

2-Chloro-N-[2-(propan-2-ylsulfonyl)phenyl]-pyrimidin-4-amine

To a suspension of NaH (60% dispersion in mineral oil, 40 mg, 1.0 mmol) in 2.0 mL of DMF at room temperature was added 1-amino-2-(isopropylsulphonyl)benzene (0.20 g, 1.0 mmol) as a solid in 3 portions. After 30 minutes of stirring at room temperature, 2,4-dichloropyrimidine (0.15 g, 1.0 mmol) was added as a solution in 1.0 mL DMF. The reaction mixture stirred for 3 h at room temperature. The reaction was quenched with saturated sodium bicarbonate solution and the solution extracted ethyl acetate. The organic layers were combined, washed with saturated sodium chloride solution, dried with sodium sulfate, filtered and concentrated. The crude residue was purified by silica gel chromatography (0-30% ethyl acetate:heptane) to afford the desired compound as an off-white solid (53 mg, 17% yield). MS/ES+: m/z=312.

N²-[4-(dimethylphosphoryl)-2-methoxyphenyl]-N⁴-[2-(propan-2-ylsulfonyl)phenyl]pyrimidine-2,4-diamine To a solution of 2-chloro-N-[2-(propan-2-ylsulfonyl)phenyl]-pyrimidin-4-amine (0.017 g, 0.054 mmol) in 0.5 mL of 2-methoxyethanol in a vial was added 4-(dimethylphosphoryl)-2-methyoxyaniline (0.010 g, 0.044 mmol) as the HCl salt. The vial was sealed and the reaction was heated at 90° C. for 16 h. The reaction was quenched with 1N NaOH solution and the solution extracted ethyl acetate. The organic layers were combined, washed with saturated sodium chloride solution, dried with sodium sulfate, filtered and concentrated. The crude residue was purified by silica gel chromatography (0-10% 7N ammonia in methanol:dichloromethane) to afford the desired compound (15 mg, 72% yield). MS/ES+: m/z=475.

Example 21

N²-[4-(Dimethylphosphoryl)-2-methoxyphenyl]-5-methyl-N⁴-[2-(propan-2-ylsulfonyl)phenyl]pyrimidine-2,4-diamine

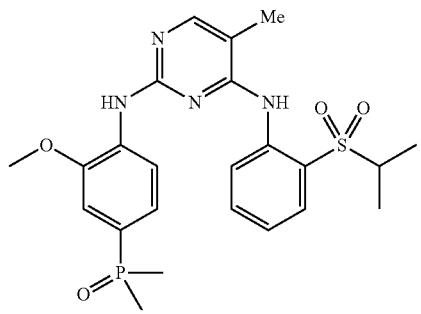

2-Chloro-5-methyl-N-[2-(propan-2-ylsulfonyl)phenyl]-pyrimidin-4-amine

To a suspension of NaH (60% dispersion in mineral oil, 40.0 mg, 1.00 mmol) in 2 mL of DMF at room temperature was added 1-amino-2-(isopropylsulphonyl)benzene (0.20 g, 1.0 mmol) as a solid in 3 portions. After 30 minutes of stirring at room temperature, 2,4-dichloro-5-methylpyrimidine (0.17 g, 1.0 mmol) was added as a solution in 1 mL DMF. The reaction mixture stirred for 3 h at room temperature. The reaction was quenched with saturated sodium bicarbonate solution and the solution extracted ethyl acetate. The organic layers were combined, washed with saturated sodium chloride solution, dried with sodium sulfate, filtered and concentrated. The crude residue was purified by silica gel chromatography (0-30% ethyl acetate:heptane) to afford the desired compound as an off-white solid (78 mg, 24% yield). MS/ES+: m/z=326.

N²-[4-(Dimethylphosphoryl)-2-methoxyphenyl]-5-methyl-N⁴-[2-(propan-2-ylsulfonyl)phenyl]pyrimidine-2,4-diamine To a solution of 2-chloro-5-methyl-N-[2-(propan-2-ylsulfonyl)phenyl]-pyrimidin-4-amine (0.035 g, 0.11 mmol) in 1 mL of 2-methoxyethanol in a vial was added 4-(dimethylphosphoryl)-2-methyoxyaniline (0.020 g, 0.085 mmol) as the HCl salt. The vial was sealed and the reaction was heated at 90° C. for 16 h. The reaction was quenched with 1N NaOH solution and the solution extracted ethyl acetate. The organic layers were combined, washed with saturated sodium chloride solution, dried with sodium sulfate, filtered and concentrated. The crude residue was purified by silica gel chromatography (0-10% 7N ammonia in methanol:dichloromethane) to afford the desired compound (12 mg, 29% yield). MS/ES+: m/z=489.

Example 22

5-Chloro-$N^2$-[5-(dimethylphosphoryl)-2-methoxyphenyl]-$N^4$-[2-(propan-2-ylsulfonyl)phenyl]pyrimidine-2,4-diamine

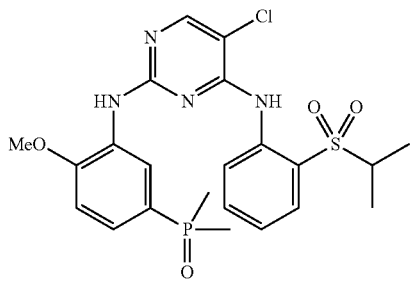 [SMILES: COc1ccc(P(C)(C)=O)cc1Nc1ncc(Cl)c(Nc2ccccc2S(=O)(=O)C(C)C)n1]

5-(Dimethylphosphoryl)-2-methoxyaniline

To a solution of 5-bromo-2-methoxyaniline (0.404 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (0.365 g, 85% yield).

5-Chloro-$N^2$-[5-(dimethylphosphoryl)-2-methoxyphenyl]-$N^4$-[2-(propan-2-ylsulfonyl)phenyl]pyrimidine-2,4-diamine To a solution of 2,5-dichloro-N-[2-(propan-2-ylsulfonyl)phenyl]pyrimidin-4-amine (as prepared in Example 17: 0.077 g, 0.22 mmol) in 1.5 mL of 2-methoxyethanol was added 5-(dimethylphosphoryl)-2-methoxyaniline (0.050 g, 0.21 mmol) as its hydrochloride salt. The mixture was heated in a sealed tube at 90° C. for 16 h. The mixture was basified with 1N NaOH solution, and extracted with ethyl acetate. The organic layers were combined, washed with saturated sodium chloride solution, dried with sodium sulfate, filtered and concentrated. The crude residue was purified by prep-HPLC to afford the final compound (52 mg, 48% yield). MS/ES+: m/z=509.

Example 23

5-Chloro-$N^2$-[4-(dimethylphosphoryl)-2-methylphenyl]-$N^4$-[2-(propan-2-ylsulfonyl)phenyl]pyrimidine-2,4-diamine

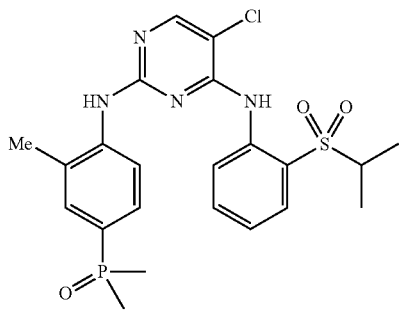 [SMILES: Cc1cc(P(C)(C)=O)ccc1Nc1ncc(Cl)c(Nc2ccccc2S(=O)(=O)C(C)C)n1]

4-(Dimethylphosphoryl)-2-methylaniline

To a solution of 4-bromo-2-methylaniline (0.372 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (0.313 g, 85% yield).

5-Chloro-$N^2$-[4-(dimethylphosphoryl)-2-methylphenyl]-$N^4$-[2-(propan-2-ylsulfonyl)phenyl]pyrimidine-2,4-diamine To a solution of 2,5-dichloro-N-[2-(propan-2-ylsulfonyl)phenyl]pyrimidin-4-amine (as prepared in Example 17: 0.083 g, 0.24 mmol) in 1.5 mL of 2-methoxyethanol was added 4-(dimethylphosphoryl)-2-methylaniline (0.050 g, 0.23 mmol) as its hydrochloride salt. The mixture was heated in a sealed tube at 90° C. for 16 h. The mixture was basified with 1N NaOH solution, and extracted with ethyl acetate. The organic layers were combined, washed with saturated sodium chloride solution, dried with sodium sulfate, filtered and concentrated. The crude residue was purified by prep-HPLC to afford the final compound (20 mg, 18% yield). MS/ES+: m/z=493.

Example 24

5-Chloro-$N^2$-[4-(dimethylphosphoryl)-2-ethylphenyl]-$N^4$-[2-(propan-2-ylsulfonyl)phenyl]pyrimidine-2,4-diamine

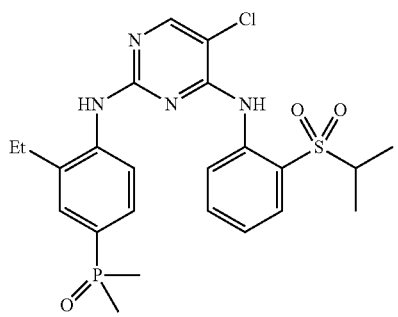 [SMILES: CCc1cc(P(C)(C)=O)ccc1Nc1ncc(Cl)c(Nc2ccccc2S(=O)(=O)C(C)C)n1]

4-(Dimethylphosphoryl)-2-ethylaniline

To a solution of 4-bromo-2-ethylaniline (0.400 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (0.308 g, 78% yield).

5-Chloro-$N^2$-[4-(dimethylphosphoryl)-2-ethylphenyl]-$N^4$-[2-(propan-2-ylsulfonyl)phenyl]pyrimidine-2,4-diamine To a solution of 2,5-dichloro-N-[2-(propan-2-ylsulfonyl)phenyl]pyrimidin-4-amine (as prepared in Example 17: 0.079 g, 0.22 mmol) in 1.5 mL of 2-methoxyethanol was added 4-(dimethylphosphoryl)-2-ethylaniline (0.050 g, 0.21 mmol) as its hydrochloride salt. The mixture was heated in a sealed tube at 90° C. for 16 h. The mixture was basified with 1N NaOH solution, and extracted with ethyl acetate. The organic layers were combined, washed with saturated sodium chloride solution, dried with sodium sulfate, filtered and concentrated. The crude residue was purified by prep-HPLC to afford the final compound (43 mg, 40% yield). MS/ES+: m/z=507.

Example 25

5-Chloro-$N^2$-[4-(dimethylphosphoryl)-2-(trifluoromethoxy)phenyl]-$N^4$-[2-(propan-2-ylsulfonyl)phenyl]pyrimidine-2,4-diamine

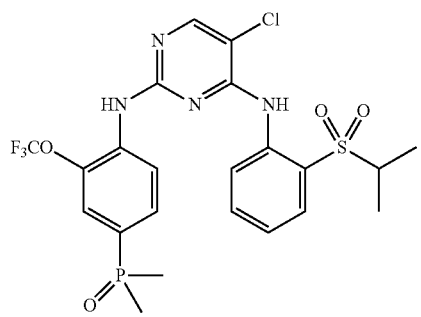 [SMILES: CC(C)S(=O)(=O)c1ccccc1Nc1nc(Nc2ccc(P(C)(C)=O)cc2OC(F)(F)F)ncc1Cl]

4-(Dimethylphosphoryl)-2-(trifluoromethoxy)aniline

To a solution of 4-iodo-2-(trifluoromethoxy)aniline (0.606 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) and acidified with HCl in methanol to afford the desired product as its hydrochloride salt (0.573 g, 98% yield).

5-Chloro-$N^2$-[4-(dimethylphosphoryl)-2-(trifluoromethoxy)phenyl]-$N^4$-[2-(propan-2-ylsulfonyl)phenyl]pyrimidine-2,4-diamine To a solution of 2,5-dichloro-N-[2-(propan-2-ylsulfonyl)phenyl]pyrimidin-4-amine (as prepared in Example 17: 0.040 g, 0.12 mmol) in 1 mL of 2-methoxyethanol was added 4-(dimethylphosphoryl)-2-(trifluoromethoxy)aniline (0.035 g, 0.12 mmol) as its hydrochloride salt. The mixture was heated in a sealed tube at 90° C. for 16 h. The mixture was basified with 1N NaOH solution, and extracted with ethyl acetate. The organic layers were combined, washed with saturated sodium chloride solution, dried with sodium sulfate, filtered and concentrated. The crude residue was purified by prep-HPLC to afford the final compound (5.8 mg, 9% yield). MS/ES+: m/z=563.

Example 26

5-Chloro-$N^2$-[2-chloro-4-(dimethylphosphoryl)phenyl]-$N^4$-[2-(propan-2-ylsulfonyl)phenyl]pyrimidine-2,4-diamine

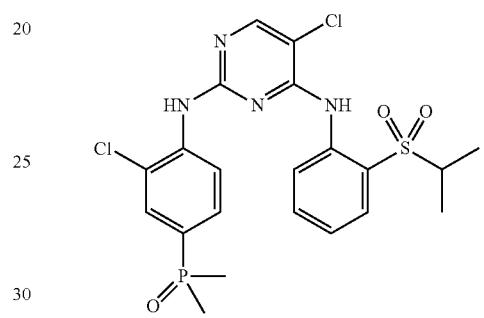

2-Chloro-4-(dimethylphosphoryl)aniline

To a solution of 2-chloro-4-iodoaniline (0.507 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (0.340 g, 83% yield).

5-Chloro-$N^2$-[2-chloro-4-(dimethylphosphoryl)phenyl]-$N^4$-[2-(propan-2-ylsulfonyl)phenyl]pyrimidine-2,4-diamine To a solution of 2,5-dichloro-N-[2-(propan-2-ylsulfonyl)phenyl]pyrimidin-4-amine (0.040 g, 0.12 mmol) in 1 mL of 2-methoxyethanol was added 2-chloro-4-(dimethylphosphoryl)aniline (as prepared in Example 17: 0.025 g, 0.12 mmol) and 49 µL of 2.5 M HCl in ethanol. The mixture was heated in a sealed tube at 90° C. for 16 h. The mixture was basified with 1N NaOH solution, and extracted with ethyl acetate. The organic layers were combined, washed with saturated sodium chloride solution, dried with sodium sulfate, filtered and concentrated. The crude residue was purified by prep-HPLC to afford the final compound (5.9 mg, 10% yield). MS/ES+: m/z=513.

Example 27

5-Chloro-$N^2$-[4-(dimethylphosphoryl)-2-fluorophenyl]-$N^4$-[2-(propan-2-ylsulfonyl)phenyl]pyrimidine-2,4-diamine

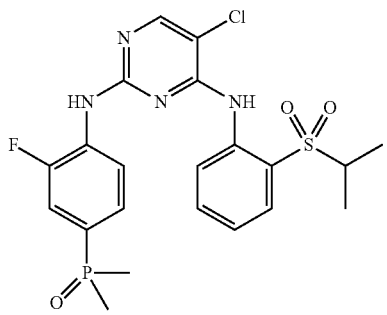 [SMILES: CC(C)S(=O)(=O)c1ccccc1Nc1nc(Nc2ccc(P(C)(C)=O)cc2F)ncc1Cl]

4-(Dimethylphosphoryl)-2-fluoroaniline

To a solution of 4-bromo-2-fluoroaniline (0.380 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (73.5 mg, 20% yield).

5-Chloro-$N^2$-[4-(dimethylphosphoryl)-2-fluorophenyl]-$N^4$-[2-(propan-2-ylsulfonyl)phenyl]pyrimidine-2,4-diamine To a solution of 2,5-dichloro-N-[2-(propan-2-ylsulfonyl)phenyl]pyrimidin-4-amine (as prepared in Example 17: 0.040 g, 0.12 mmol) in 1 mL of 2-methoxyethanol was added 4-(dimethylphosphoryl)-2-fluoroaniline (0.023 g, 0.12 mmol) and 49 µL of 2.5 M HCl in ethanol. The mixture was heated in a sealed tube at 90° C. for 16 h. The mixture was basified with 1N NaOH solution, and extracted with ethyl acetate. The organic layers were combined, washed with saturated sodium chloride solution, dried with sodium sulfate, filtered and concentrated. The crude residue was purified by prep-HPLC to afford the final compound (9.0 mg, 22% yield). MS/ES+: m/z=497.

Example 28

$N^2$-[4-(dimethylphosphoryl)-2-methoxyphenyl]-$N^4$-[2-(propan-2-ylsulfonyl)phenyl]pyrimidine-2,4,5-triamine

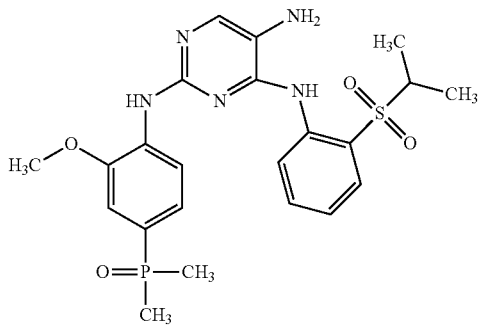 [SMILES: COc1cc(P(C)(C)=O)ccc1Nc1ncc(N)c(Nc2ccccc2S(=O)(=O)C(C)C)n1]

A suspension of $N^2$-[4-(dimethylphosphoryl)-2-methoxyphenyl]-5-nitro-$N^4$-[2-(propan-2-ylsulfonyl)phenyl]pyrimidine-2,4-diamine (461 mg, 0.89 mmol) in Ethanol was added 184 mg of 10% Pd on carbon. The reaction mixture was stirred at room temperature overnight and filtered through celite. The filtrate was concentrated under reduced pressure to yield the crude product. The crude product was purified by silica gel chromatography with 10% Methanol in DCM to yield $N^2$-[4-(dimethylphosphoryl)-2-methoxyphenyl]-$N^4$-[2-(propan-2-ylsulfonyl)phenyl]pyrimidine-2,4,5-triamine as a solid. MS ES+: m/z=490.

Example 29

2-{[4-(dimethylphosphoryl)-2-methoxyphenyl]amino}-9-[2-(propan-2-ylsulfonyl)phenyl]-7,9-dihydro-8H-purin-8-one

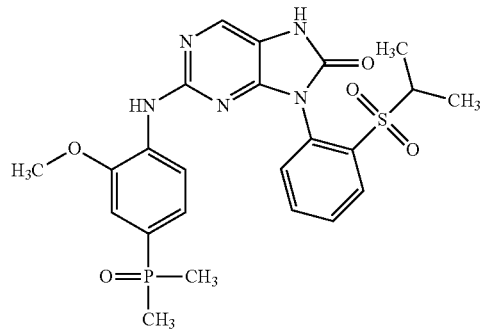 [SMILES: COc1cc(P(C)(C)=O)ccc1Nc1ncc2[nH]c(=O)n(-c3ccccc3S(=O)(=O)C(C)C)c2n1]

To a solution of $N^2$-[4-(dimethylphosphoryl)-2-methoxyphenyl]-$N^4$-[2-(propan-2-ylsulfonyl)phenyl]pyrimidine-2,4,5-triamine (as prepared in Example 28: 40 mg, 0.082 mmol) in THF was added N,N'-Carbonyldiimidazole (40 mg, 0.25 mmol). The solution was stirred at room temperature overnight. The solution was concentrated under reduced pressure and diluted with water and extracted with Ethyl Acetate. The combined organic layer was washed with brine and dried over Magnesium Sulfate. The organic layer was concentrated under reduced pressure and the residue was purified by RP Prep-HPLC to obtain the desired product as an off white solid. MS/ES+: m/z=516

Example 30

$N^2$-[2-methoxy-4-(4-oxido-1,4-azaphosphinan-4-yl)phenyl]-$N^4$-[2-(propan-2-ylsulfonyl)phenyl]pyrimidine-2,4-diamine

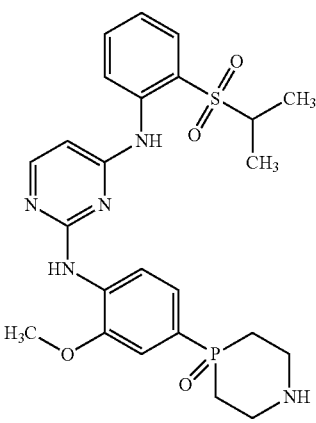 [SMILES: COc1cc(P2(=O)CCNCC2)ccc1Nc1nccc(Nc2ccccc2S(=O)(=O)C(C)C)n1]

(3-methoxy-4-nitrophenyl)(dimethyl)phosphane oxide

To a solution of 5-chloro-2-nitroanisole (1.00 g, 5.33 mmol) in 20 mL DMF was added diethyl phosphite (0.809 g, 5.86 mmol), palladium acetate (0.060 g, 0.27 mmol), XantPHOS (0.185 g, 0.320 mmol), and potassium phosphate (1.24 g, 5.86 mmol). The mixture was purged with nitrogen, and subjected to microwaves at 150° C. for 20 minutes. The reaction mixture was concentrated and purified by silica gel chromatography (0-45% ethyl acetate:heptane) to afford the desired product (0.504 g, 33% yield).

(3-methoxy-4-nitrophenyl)phosphonic dichloride

To a solution of (3-methoxy-4-nitrophenyl)(dimethyl) phosphane oxide (4.54 g, 15.7 mmol) in 1.2 mL DMF was added thionyl chloride (5.7 mL, 78.5 mmol). The reaction flask was equipped with a reflux condenser and the mixture was heated to reflux. After 2 h at reflux, the reaction was cooled to rt and concentrated in vacuo. The crude oil was redissolved in $CH_2Cl_2$ and heptane was added to precipitate the desired compound. The clear solution was decanted and the precipitate was collected and dried to afford the desired compound as a white solid (1.39 g, 33% yield).

Diethenyl(3-methoxy-4-nitrophenyl)phosphane oxide

To a solution of (3-methoxy-4-nitrophenyl)phosphonic dichloride (1.39 g, 5.15 mmol) in 15 mL THF at −78° C. under nitrogen was slowly added vinylmagnesium bromide (10.3 mL, 1.0 M in THF). After the addition was complete, the reaction stirred at −78° C. for an additional hour. The cold reaction mixture was quenched by the addition of saturated $NH_4Cl$ (20 mL) and the mixture was extracted with $CH_2Cl_2$. The combined organic layers were washed with 1 M NaOH, brine, and dried over $MgSO_4$. The organic extracts were filtered and concentrated to provide the desired compound (0.982 g, 75%).

1-benzyl-4-(3-methoxy-4-nitrophenyl)-1,4-azaphosphinane 4-oxide diethenyl(3-methoxy-4-nitrophenyl)phosphane oxide (0.480 g, 1.90 mmol) and benzylamine (0.23 mL, 2.08 mmol) were dissolved in 50% aqueous THF (6 mL) and heated to 105° C. under nitrogen. After one hour, another portion of benzylamine was added to the reaction mixture. The reaction mixture was refluxed for an additional 2 h, and then cooled to rt. The reaction mixture was partitioned between saturated aqueous $NaHCO_3$ and $CH_2Cl_2$. The aqueous phase was washed once with $CH_2Cl_2$ and the organic layers were combined. The organic extracts were washed with brine, dried over $MgSO_4$, filtered, and concentrated. The residue was purified by silica gel chromatography (0-5% 7N ammonia in methanol:dichloromethane) to afford the desired product (0.449 g, 66% yield).

4-(1-benzyl-4-oxido-1,4-azaphosphinan-4-yl)-2-methoxyaniline

To a solution of 1-benzyl-4-(3-methoxy-4-nitrophenyl)-1,4-azaphosphinane 4-oxide (0.224 g, 0.622 mmol) in 0.6 mL 4:1 ethanol:water was added iron powder (0.348 g, 6.22 mmol) and 0.30 mL ethanolic HCl (2.5 M). The reaction vessel was sealed and was heated to 95° C. for 1 h. The reaction mixture was cooled to rt, filtered, and concentrated. The crude residue was purified by silica gel chromatography (0-5% 7N ammonia in methanol:dichloromethane) to afford the desired product (86.1 mg, 42% yield).

$N^2$-[4-(1-benzyl-4-oxido-1,4-azaphosphinan-4-yl)-2-methoxyphenyl]-5-chloro-$N^4$-[2-(propan-2-ylsulfonyl)phenyl]pyrimidine-2,4-diamine To a solution of 2,5-dichloro-N-[2-(propan-2-ylsulfonyl) phenyl]pyrimidin-4-amine (47.3 mg, 0.137 mmol) in 1.5 mL of 2-methoxyethanol was added 4-(1-benzyl-4-oxido-1,4-azaphosphinan-4-yl)-2-methoxyaniline (43.0 mg, 0.13 mmol) and ethanolic HCl (0.10 mL, 2.5 M). The mixture was heated in a sealed vial at 90° C. for 16 h. The reaction was then heated at 100° C. for an additional 2 h. The mixture was basified with 1N NaOH solution, and extracted with ethyl acetate. The organic layers were combined, washed with saturated sodium chloride solution, dried with sodium sulfate, filtered and concentrated. The crude residue was purified by silica gel chromatography (0-12% 7N ammonia in methanol:dichloromethane) to afford the desired product (43.0 mg, 52% yield).

$N^2$-[4-methoxy-4-(4-oxido-1,4-azaphosphinan-4-yl) phenyl]-$N^4$-[2-(propan-2-ylsulfonyl)phenyl]pyrimidine-2,4-diamine A flask was charged with $N^2$-[4-(1-benzyl-4-oxido-1,4-azaphosphinan-4-yl)-2-methoxyphenyl]-5-chloro-$N^4$-[2-(propan-2-ylsulfonyl)phenyl]pyrimidine-2,4-diamine (40.0 mg, 0.0625 mmol) and 10% Pd—C (40.0 mg). The flask was evacuated and filled with nitrogen. Anhydrous methanol (2 mL) was added to the flask and the flask was equipped with a reflux condenser with a nitrogen inlet. Ammonium formate (31.5 mg, 0.500 mmol) was added in one portion at room temperature. The resulting mixture was stirred at reflux for 3 h. The reaction was filtered through a Celite pad and the Celite was washed with 2×5 mL methanol. The combined filtrate and washing was evaporated in vacuo. The crude residue was purified by prep-HPLC to afford the final compound (13.6 mg, 42% yield). MS/ES+: m/z=516.

Example 31

$N^2$-[4-(dimethylphosphoryl)-2-methoxyphenyl]-$N^4$-[2-(propan-2-ylsulfonyl)phenyl]-7H-pyrrolo[2,3-d] pyrimidine-2,4-diamine

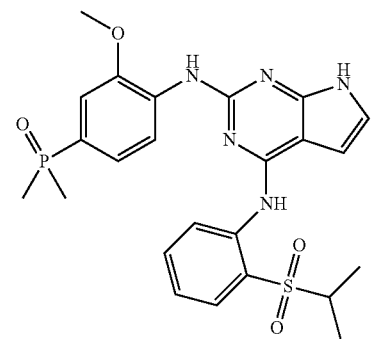 [SMILES: COc1cc(P(C)(C)=O)ccc1Nc1nc(Nc2ccccc2S(=O)(=O)C(C)C)c2cc[nH]c2n1]

2,4-dichloro-7-{[2-(trimethylsilyl)ethoxy]methyl}-7H-pyrrolo[2,3-d]pyrimidine To a suspension of NaH (119 mg, 60% in oil, 2.98 mmol) in DMF (5 mL) was added 2,4-dichloro-7H-pyrrolo[2,3-d]pyrimidine (400 mg, 2.13 mmol) at 0° C. The resulting mixture was stirred for 30 min before 2-(trimethylsilyl)ethoxymethyl chloride (0.42 mL, 1.1 eq) was added. The mixture was then warmed up to room temperature and stirred for 1 hr. Water was added to quench the reaction. Extraction with $CH_2Cl_2$ followed by drying combined organic layers, evaporation, and chromatography on silica gel (20% EtOAc in heptane as eluent) gave the desired product in 84% yield (570 mg).

2-chloro-N-[2-(propan-2-ylsulfonyl)phenyl]-7-{[2-(trimethylsilyl)ethoxy]methyl}-7H-pyrrolo[2,3-d]pyrimidin-4-amine To a solution of 1-amino-2-(isopropylsulphonyl)benzene (199 mg, 1 mmol) in 2 mL of DMF was added NaH (60% in oil, 44 mg, 1.1 mmol) in one portion at 0° C. After the reaction mixture was stirred for 20 min, 2,4-dichloro-7-{[2-(trimethylsilyl)ethoxy]methyl}-7H-pyrrolo[2,3-d]pyrimidine (317 mg, 1 mmol) was added at 0° C. The reaction mixture was then warmed up to room temperature and stirred for additional 2 h. The reaction was quenched with water. Extraction with EtOAc followed by silica gel column chromatography (20% EtOAc in heptane) gave the desired product (202 mg, 42% yield). MS/ES+: m/z=481.

$N^2$-[4-(dimethylphosphoryl)-2-methoxyphenyl]-$N^4$-[2-(propan-2-ylsulfonyl)phenyl]-7-{[2-(trimethylsilyl)ethoxy]methyl}-7H-pyrrolo[2,3-d]pyrimidine-2,4-diamine To a microwave reaction tube was charged with 2-chloro-N-[2-(propan-2-ylsulfonyl)phenyl]-7-{[2-(trimethylsilyl)ethoxy]methyl}-7H-pyrrolo[2,3-d]pyrimidin-4-amine (180 mg, 0.374 mmol), 4-(dimethylphosphoryl)-2-methoxyaniline hydrochloride (105 mg, 0.45 mmol), $Pd_2(dba)_3$ (34 mg, 0.0374 mmol), Xanthphos (26 mg, 0.045 mmol), and t-BuONa (129 mg, 1.346 mmol). This mixture was degassed via 3-cycle of vacuum and re-fill with N2. Anhydrous 1,4-dioxane (2 mL from sure-seal bottle) was added and the reaction was then run under microwave irradiation at 140° C. for 20 min. Water and EtOAc was added to facilitate extraction. Chromatography on silica gel (10% MeOH in $CH_2Cl_2$ as eluent) gave the desired product in 54% yield (130 mg). MS/ES+: m/z=644.

$N^2$-[4-(dimethylphosphoryl)-2-methoxyphenyl]-$N^4$-[2-propan-2-ylsulfonyl)phenyl]-7H-pyrrolo[2,3-d]pyrimidine-2,4-diamine To a solution of compound $N^2$-[4-(dimethylphosphoryl)-2-methoxyphenyl]-$N^4$-[2-(propan-2-ylsulfonyl)phenyl]-7-{[2-(trimethylsilyl)ethoxy]methyl}-7H-pyrrolo[2,3-d]pyrimidine-2,4-diamine in THF (1 mL) was added tetrabutylammonium fluoride (TBAF) in THF (1.0 M, 3 mL) and ethylenediamine (0.1 mL). The solution was heated at 60° C. for 24 hrs. About 40% conversion was observed by HPLC monitoring. Volatile components were removed on rotavap and the residue was subjected to prep-HPLC purification. The desired product was determined by NMR to be contaminated with TBAF, which was removed by water wash (4 times). Evaporation of EtOAc gave the pure compound (14 mg). MS/ES+: m/z=514.

Example 32

5-chloro-$N^2$-[6-(dimethylphosphoryl)-2-methoxypyridin-3-yl]-$N^4$-[2-(propan-2-ylsulfonyl)phenyl]pyrimidine-2,4-diamine

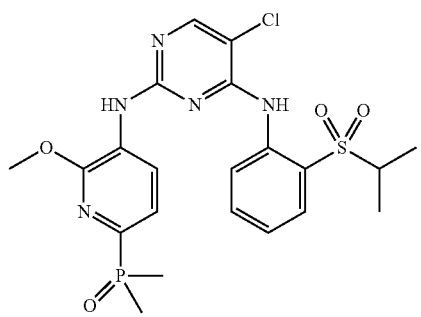 [SMILES: COc1nc(P(C)(C)=O)ccc1Nc1ncc(Cl)c(Nc2ccccc2S(=O)(=O)C(C)C)n1]

6-(Dimethylphosphoryl)-2-methoxypyridin-3-ylamine

To a solution of 6-bromo-2-methoxypyridin-3-ylamine (0.203 g, 1.00 mmol) in 4 mL DMF was added dimethylphosphine oxide (0.171 g, 1.10 mmol), palladium acetate (11.0 mg, 0.0490 mmol), XANTPHOS (35.0 mg, 0.0600 mmol), and potassium phosphate (0.233 g, 1.10 mmol). The mixture was purged with nitrogen, and subjected to microwaves at 150° C. for 20 minutes. The reaction mixture was concentrated and purified by silica gel chromatography (0-10% 7N ammonia in methanol:dichloromethane) to afford the desired product (77.2 mg, 39% yield).

2,5-dichloro-N-[2-(propan-2-ylsulfonyl)phenyl]pyrimidin-4-amine

To a solution of 1-Amino-2-(isopropylsulphonyl)benzene (0.955 g, 4.80 mmol) in 2 mL of DMF at 0° C. was added NaH (60% in oil, 0.349 g, 8.72 mmol) in one portion. After stirring for 20 min, 2,4,5-trichloropyrimidine was added. The mixture was stirred at 0° C. for 30 minutes, and then at room temperature for 2 h. After quenching with saturated ammonium chloride solution, the mixture was poured in water and ethyl acetate mixture. Yellow suspension was filtered as final product (0.3 g, 20% yield). MS/ES+: m/z=346.

5-chloro-$N^2$-[6-(dimethylphosphoryl)-2-methoxypyridin-3-yl]-$N^4$-[2-(propan-2-ylsulfonyl)phenyl]pyrimidine-2,4-diamine To a solution of 2,5-dichloro-N-[2-(propan-2-ylsulfonyl)phenyl]pyrimidin-4-amine (86.0 mg, 0.250 mmol) in 1 mL of 2-methoxyethanol was added 6-(dimethylphosphoryl)-2-methoxypyridin-3-ylamine (50.0 mg, 0.250 mmol) and 0.15 mL of 2.5 M HCl in ethanol. The mixture was heated in a sealed tube at 90° C. for 16 h. The mixture was basified with 1N NaOH solution, and extracted with ethyl acetate. The organic layers were combined, washed with saturated sodium chloride solution, dried with sodium sulfate, filtered and concentrated. The crude residue was purified by silica gel chromatography (0-10% 7N ammonia in methanol:dichloromethane) to afford the desired product (16.7 mg, 22% yield). MS/ES+: m/z=510.

Example 33

5-chloro-$N^2$-[5-(dimethylphosphoryl)-3-methoxypyrazin-2-yl]-$N^4$-[2-(propan-2-ylsulfonyl)phenyl]pyrimidine-2,4-diamine

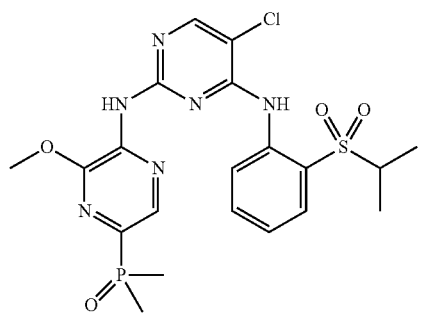 [SMILES: COc1nc(P(C)(C)=O)cnc1Nc1ncc(Cl)c(Nc2ccccc2S(=O)(=O)C(C)C)n1]

5-(dimethylphosphoryl)-3-methoxypyrazin-2-amine

To a solution of 5-bromo-3-methoxypyrazin-3-ylamine (0.204 g, 1.00 mmol) in 4 mL DMF was added dimethylphosphine oxide (0.171 g, 1.10 mmol), palladium acetate (11.0 mg, 0.0490 mmol), XANTPHOS (35.0 mg, 0.0600 mmol), and potassium phosphate (0.233 g, 1.10 mmol). The mixture was purged with nitrogen, and subjected to microwaves at 150° C. for 20 minutes. The reaction mixture was concentrated and purified by silica gel chromatography (0-10% 7N ammonia in methanol:dichloromethane) to afford the desired product (126 mg, 63% yield).

5-chloro-$N^2$-[5-(dimethylphosphoryl)-3-methoxypyrazin-2-yl]-$N^4$-[2-(propan-2-ylsulfonyl)phenyl]pyrimidine-2,4-diamine To a mixture of 2,5-dichloro-N-[2-(propan-2-ylsulfonyl)phenyl]pyrimidin-4-amine (prepared in Example 32: 0.120 g, 0.348 mmol) and 5-(dimethylphosphoryl)-3-methoxypyrazin-2-amine (70.0 mg, 0.348 mmol) was added tris(dibenzylideneacetone)dipalladium(0)-chloroform adduct (17.6 mg, 0.017 mmol), XANTPHOS (23.3 mg, 0.040 mmol), and cesium carbonate (0.228 g, 0.700 mmol), and dioxane (3.5 mL). The mixture was sealed and heated at 120° C. After 16 h, the reaction mixture was cooled to rt and concentrated. The crude residue was purified by silica gel chromatography (0-10% 7N ammonia in methanol:dichloromethane) to afford the desired product (11.4 mg, 6% yield). MS/ES+: m/z=511.

Example 34

5-chloro-$N^2$-[6-(dimethylphosphoryl)-2-methoxypyridin-3-yl]-$N^4$-phenylpyrimidine-2,4-diamine

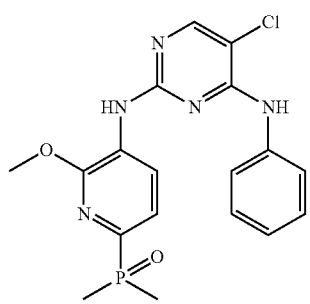

This compound can be prepared as in Example 32 by reacting 2,5-dichloro-N-phenylpyrimidin-4-amine with 6-(Dimethylphosphoryl)-2-methoxypyridin-3-ylamine (prepared in Example 32)

2,5-dichloro-N-phenylpyrimidin-4-amine

To a solution of Aniline (205 mg, 2.2 mmol) and 2,4,5-Trichloropyrimidine (500 mg, 2.7 mmol) in 5 mL of Ethanol, was added 500 mg of Potassium carbonate. The reaction mixture was stirred at room temperature for 2 hours. Solvent was removed under reduced pressure. The residue was purified by silica gel flash chromatography with 10% Ethyl Acetate in Heptane to yield the desired product as an oil (370 mg, 70% yield).

Example 35

$N^2$-[6-(dimethylphosphoryl)-2-methoxypyridin-3-yl]-$N^4$-[2-(propan-2-ylsulfonyl)phenyl]-5-(trifluoromethyl)pyrimidine-2,4-diamine

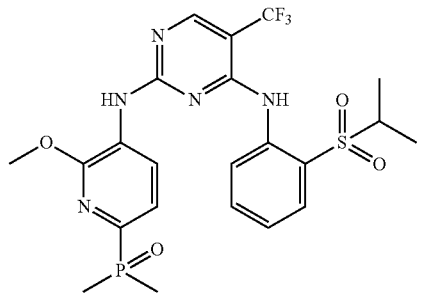

4-chloro-2-[6-(dimethylphosphoryl)-2-methoxypyridin-3-yl]-5-(trifluoromethyl) pyrimidine A suspension of 6-(dimethylphosphoryl)-2-methoxypyridin-3-ylamine (prepared in Example 32: 2.2 mmol) in 15 mL of N,N-Dimethylacetamide and 3.6 mL of Diisopropylethylamine, is allowed to stirred at room temperature for 15 minutes until a clear solution is obtained. 2,4-Dichloro-5-(trifluoromethyl)pyrimidine (5.7 g, 2.6 mmol) is added in four portions over 5 minutes. The reaction mixture is stirred at 60 degrees for 1 hour. The reaction mixture is cooled to room temperature and filtered to obtain a white solid. The white solid is washed with 50 mL of water three times and followed by 50 mL of Ethyl ether three times. The white solid is dried under vacuum to yield 4-chloro-2-[6-(dimethylphosphoryl)-2-methoxypyridin-3-yl]-5-(trifluoromethyl)pyrimidine.

$N^2$-[4-(dimethylphosphoryl)-2-methoxypyridin-3-yl]-$N^4$-[2-(propan-2-ylsulfonyl)phenyl]-5-(trifluoromethyl)pyrimidine-2,4-diamine To a solution of 4-chloro-2-[6-(dimethylphosphoryl)-2-methoxypyridin-3-yl]-5-(trifluoromethyl)pyrimidine (0.072 mmol) in 1.5 mL of ethanol is added 10 μL of triethylamine and 1-Amino-2-(isopropylsulphonyl)benzene (0.072 mmol). The mixture is microwave at 120 degrees for 20 minutes. The reaction mixture is filtered through a syringe filter and purified by prep-HPLC (Waters Sunfire C18 column with ACN/water mobile phases) to generate the desired compound.

Example 36

$N^2$-[5-(dimethylphosphoryl)-3-methoxypyrazin-2-yl]-$N^4$-[2-(propan-2-ylsulfonyl)phenyl]-5-(trifluoromethyl)pyrimidine-2,4-diamine

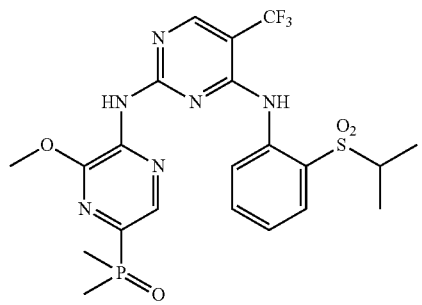 [SMILES: COc1nc(P(C)(C)=O)cnc1Nc1ncc(C(F)(F)F)c(Nc2ccccc2S(=O)(=O)C(C)C)n1]

4-chloro-2-[5-(dimethylphosphoryl)-3-methoxypyrazin-2-yl]-5-(trifluoromethyl)pyrimidine A suspension of 5-(dimethylphosphoryl)-3-methoxypyrazin-2-amine (prepared in Example 33: 2.2 mmol) in 15 mL of N,N-Dimethylacetamide and 3.6 mL of Diisopropylethylamine, is allowed to stirred at room temperature for 15 minutes until a clear solution is obtained. 2,4-Dichloro-5-(trifluoromethyl)pyrimidine (5.7 g, 2.6 mmol) is added in four portions over 5 minutes. The reaction mixture is stirred at 60 degrees for 1 hour. The reaction mixture is cooled to room temperature and filtered to obtain a white solid. The white solid is washed with 50 mL of water three times and followed by 50 mL of Ethyl ether three times. The white solid is dried under vacuum to yield 4-chloro-2-[5-(dimethylphosphoryl)-3-methoxypyrazin-2-yl]-5-(trifluoromethyl)pyrimidine.

$N^2$-[5-(dimethylphosphoryl)-3-methoxypyrazin-2-yl]-$N^4$-[2-(propan-2-ylsulfonyl)phenyl]-5-(trifluoromethyl)pyrimidine-2,4-diamine To a solution of 4-chloro-2-[5-(dimethylphosphoryl)-3-methoxypyrazin-2-yl]-5-(trifluoromethyl)pyrimidine (0.072 mmol) in 1.5 mL of ethanol is added 10 μL of triethylamine and 1-Amino-2-(isopropylsulphonyl)benzene (0.072 mmol). The mixture is microwave at 120 degrees for 20 minutes. The reaction mixture is filtered through a syringe filter and purified by prep-HPLC (Waters Sunfire C18 column with ACN/water mobile phases) to generate the desired compound.

Example 37

5-chloro-$N^2$-[6-(dimethylphosphoryl)-2-methoxypyridin-3-yl]-$N^4$-[4-(dimethylphosphoryl)phenyl]pyrimidine-2,4-diamine

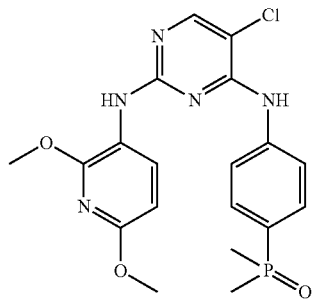 [SMILES: COc1ccc(Nc2ncc(Cl)c(Nc3ccc(P(C)(C)=O)cc3)n2)c(OC)n1]

This compound can be prepared as in Example 32 by reacting 2,5-dichloro-N-[4-(dimethylphosphoryl)phenyl]pyrimidin-4-amine with 2,6-Dimethoxypyridin-3-amine.

2,5-dichloro-N-[4-(dimethylphosphoryl)phenyl]pyrimidin-4-amine

To a solution of 2,4,5-trichloropyrimidine (0.15 ml, 1.31 mmol) in 1 mL of DMF was added 4-(dimethylphosphoryl)aniline (0.221 g, 1.31 mmol) and potassium carbonate (0.217 g, 1.57 mmol). The mixture was heated at 110° C. for 4 h. It was basified with saturated sodium bicarbonate solution. The suspension was filtered and washed with ethyl acetate to give the final product (0.15 g, 36% yield). MS/ES+: m/z=316.

Example 38

5-chloro-$N^2$-[5-(dimethylphosphoryl)-3-methoxypyrazin-2-yl]-$N^4$-{2-methoxy-4-[4-(4-methylpiperazin-1-yl)piperidin-1-yl]phenyl}pyrimidine-2,4-diamine

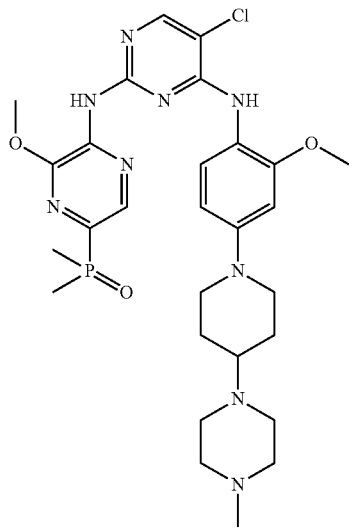 [SMILES: COc1cc(N2CCC(N3CCN(C)CC3)CC2)ccc1Nc1nc(Nc2ncc(P(C)(C)=O)nc2OC)ncc1Cl]

This compound can be prepared as in Example 32 by reacting 2-methoxy-4-[4-(4-methylpiperazin-1-yl)piperidin-1-yl]aniline with 2,4,5-trichloropyrimidine to generate 2,5-dichloro-N-{2-methoxy-4-[4-(4-methylpiperazin-1-yl)piperidin-1-yl]phenyl}pyrimidin-4-amine. 2,5-dichloro-N-{2-methoxy-4-[4-(4-methylpiperazin-1-yl)piperidin-1-yl]phenyl}pyrimidin-4-amine is then reacted with 5-(dimethylphosphoryl)-3-methoxypyrazin-2-amine (prepared in Example 33) according to the procedure described in Example 32.

1-[1-(3-methoxy-4-nitrophenyl)piperidin-4-yl]-4-methylpiperazine

To a solution of 5-fluoro-2-nitroanisoole (0.5 g, 2.92 mmol) in 3 mL of DMF was added 1-methyl-4-(piperidin)piperazine (0.536 g, 2.92 mmol) and potassium carbonate (0.808, 5.84 mmol). The mixture was heated at 120° C. for 18 h. The mixture was basified with saturated sodium bicarbonate solution and extracted with ethyl acetate. The organic layer was purified by chromatography to give final product as yellow solid (0.95 g, 95% yield). MS/ES+: m/z=334.

2-methoxy-4-[4-(4-methylpiperazin-1-yl)piperidin-1-yl]aniline

The a solution of 1-[1-(3-methoxy-4-nitrophenyl)piperidin-4-yl]-4-methylpiperazine (0.3 g, 0.90 mmol) in 10 mL of ethanol purged with argon was added 10% Palladium on carbon (0.060 g). The hydrogenation was finished under 30 psi after 4 h. The mixture was passed through Celite to a flask containing HCl in ethanol. Concentration of the filtrate gave the final product (0.15 g, 88% yield). MS/ES+: m/z=334.

Example 39

5-chloro-N-[6-(dimethylphosphoryl)-2-methoxypyridin-3-yl]-4-(4-methylpiperazin-1-yl)pyrimidin-2-amine

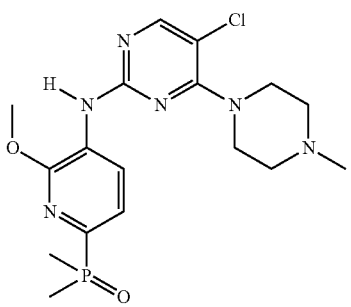 [SMILES: COc1nc(P(C)(C)=O)ccc1Nc1ncc(Cl)c(N2CCN(C)CC2)n1]

This compound can be prepared by reacting 2,4,5-trichloropyrimidine with 1-Methyl piperazine as described in Example 32 to generate 2,5-dichloro-4-(4-methylpiperazin-1-yl)pyrimidine. 2,5-dichloro-4-(4-methylpiperazin-1-yl)pyrimidine is then reacted with 6-(dimethylphosphoryl)-2-methoxypyridin-3-ylamine (prepared in Example 32) as described in Example 32.

Example 40

N²-[6-(dimethylphosphoryl)-2-methoxypyridin-3-yl]-N⁴-(morpholin-4-ylmethyl)-5-(trifluoromethyl)pyrimidine-2,4-diamine

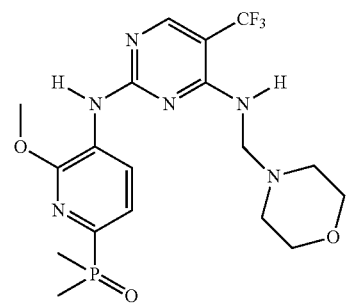 [SMILES: COc1nc(P(C)(C)=O)ccc1Nc1ncc(C(F)(F)F)c(NCN2CCOCC2)n1]

This compound can be prepared by reacting 1-(morpholin-4-yl)methaneamine with 4-chloro-2-[6-(dimethylphosphoryl)-2-methoxypyridin-3-yl]-5-(trifluoromethyl)pyrimidine as described in Example 35.

Example 41

4-(2-{[2-{[6-(dimethylphosphoryl)-2-methoxypyridin-3-yl]amino}-5-(trifluoromethyl)pyrimidin-4-yl]amino}ethyl)benzenesulfonamide

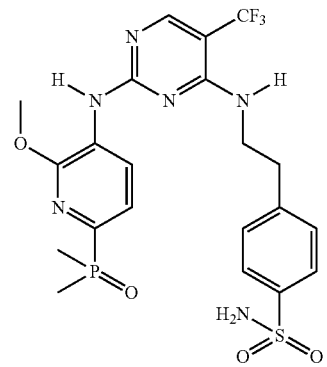 [SMILES: COc1nc(P(C)(C)=O)ccc1Nc1ncc(C(F)(F)F)c(NCCc2ccc(S(N)(=O)=O)cc2)n1]

This compound can be prepared by reacting 4-(2-aminoethyl)benzene-sulfonamide with 4-chloro-2-[6-(dimethylphosphoryl)-2-methoxypyridin-3-yl]-5-(trifluoromethyl)pyrimidine as described in Example 35.

Example 42

2-[5-(dimethylphosphoryl)-3-methoxypyrazin-2-yl]-4-(4-phenylpiperazin-1-yl)-5-(trifluoromethyl)pyrimidine

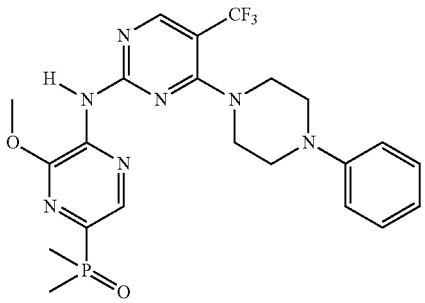 [SMILES: COc1nc(P(C)(C)=O)cnc1Nc1ncc(C(F)(F)F)c(N2CCN(c3ccccc3)CC2)n1]

This compound can be prepared by reacting 1-Phenylpiperazine with 4-chloro-2-[5-(dimethylphosphoryl)-3-methoxypyrazin-2-yl]-5-(trifluoromethyl)pyrimidine as described in Example 36.

Example 43

2-[5-(dimethylphosphoryl)-3-methoxypyrazin-2-yl]-N-[2-(1H-indol-3-yl)ethyl]-5-(trifluoromethyl)pyrimidin-4-amine

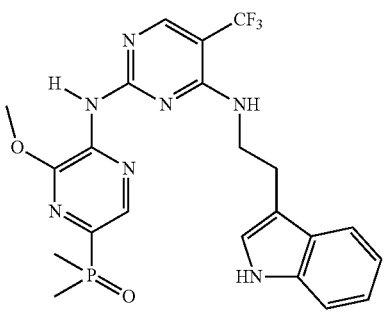 [SMILES: COc1nc(P(C)(C)=O)cnc1Nc1ncc(C(F)(F)F)c(NCCc2c[nH]c3ccccc23)n1]

This compound can be prepared by reacting tryptamine with 4-chloro-2-[5-(dimethylphosphoryl)-3-methoxypyrazin-2-yl]-5-(trifluoromethyl)pyrimidine as described in Example 36.

Example 44

$N^2$-[4-(dimethylphosphoryl)phenyl]-$N^4$-[4-(4-methylpiperazin-1-yl)benzyl]-5-(trifluoromethyl)pyrimidine-2,4-diamine

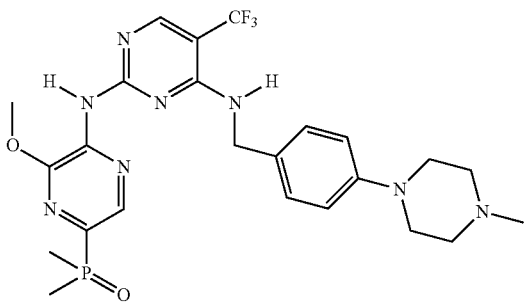 [SMILES: COc1nc(P(C)(C)=O)cnc1Nc1ncc(C(F)(F)F)c(NCc2ccc(N3CCN(C)CC3)cc2)n1]

This compound can be prepared by reacting 4-(4-methylpiperazine)-benzylamine with 4-chloro-2-[5-(dimethylphosphoryl)-3-methoxypyrazin-2-yl]-5-(trifluoromethyl) pyrimidine as described in Example 36.

Example 45

$N^2$-[6-(dimethylphosphoryl)-2-methoxypyridin-3-yl]-$N^4$-[2-(propan-2-ylsulfonyl)phenyl]pyrimidine-2,4-diamine

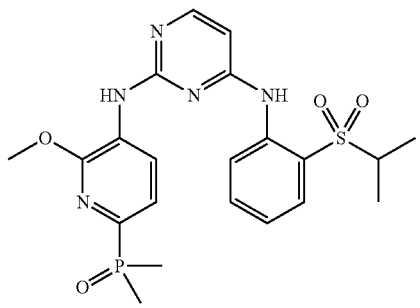

This compound can be prepared as in Example 32 by reacting 2-Chloro-N-[2-(propan-2-ylsulfonyl)phenyl]-pyrimidin-4-amine with 6-(dimethylphosphoryl)-2-methoxypyridin-3-ylamine (prepared in Example 32).

2-Chloro-N-[2-(propan-2-ylsulfonyl)phenyl]-pyrimidin-4-amine

To a suspension of NaH (60% dispersion in mineral oil, 40 mg, 1.0 mmol) in 2.0 mL of DMF at room temperature was added 1-amino-2-(isopropylsulphonyl)benzene (0.20 g, 1.0 mmol) as a solid in 3 portions. After 30 minutes of stirring at room temperature, 2,4-dichloropyrimidine (0.15 g, 1.0 mmol) was added as a solution in 1.0 mL DMF. The reaction mixture stirred for 3 h at room temperature. The reaction was quenched with saturated sodium bicarbonate solution and the solution extracted ethyl acetate. The organic layers were combined, washed with saturated sodium chloride solution, dried with sodium sulfate, filtered and concentrated. The crude residue was purified by silica gel chromatography (0-30% ethyl acetate:heptane) to afford the desired compound as an off-white solid (53 mg, 17% yield). MS/ES+: m/z=312.

Example 46

$N^2$-[6-(dimethylphosphoryl)-2-methoxypyridin-3-yl]-5-methyl-$N^4$-[2-(propan-2-ylsulfonyl)phenyl]pyrimidine-2,4-diamine

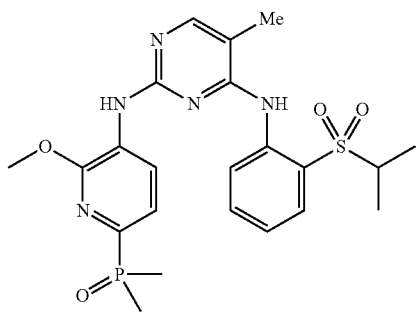

This compound can be prepared as in Example 32 by reacting 2-Chloro-5-methyl-N-[2-(propan-2-ylsulfonyl)phenyl]-pyrimidin-4-amine with 6-(dimethylphosphoryl)-2-methoxypyridin-3-ylamine (prepared in Example 32).

2-Chloro-5-methyl-N-[2-(propan-2-ylsulfonyl)phenyl]-pyrimidin-4-amine

To a suspension of NaH (60% dispersion in mineral oil, 40.0 mg, 1.00 mmol) in 2 mL of DMF at room temperature was added 1-amino-2-(isopropylsulphonyl)benzene (0.20 g, 1.0 mmol) as a solid in 3 portions. After 30 minutes of stirring at room temperature, 2,4-dichloro-5-methylpyrimidine (0.17 g, 1.0 mmol) was added as a solution in 1 mL DMF. The reaction mixture stirred for 3 h at room temperature. The reaction was quenched with saturated sodium bicarbonate solution and the solution extracted ethyl acetate. The organic layers were combined, washed with saturated sodium chloride solution, dried with sodium sulfate, filtered and concentrated. The crude residue was purified by silica gel chromatography (0-30% ethyl acetate:heptane) to afford the desired compound as an off-white solid (78 mg, 24% yield). MS/ES+: m/z=326.

Example 47

5-chloro-N⁴-[2-methoxy-4-(4-methyl-4-oxido-1,4-azaphosphinan-1-yl)phenyl]-N²-(thiophen-2-ylmethyl)pyrimidine-2,4-diamine

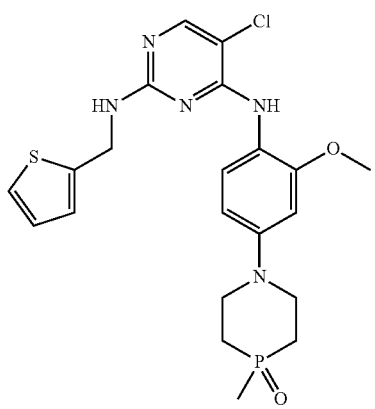 [SMILES: COc1cc(N2CCP(C)(=O)CC2)ccc1Nc1nc(NCc2cccs2)ncc1Cl]

The compound can be prepared as in Example 32 by reacting 2-methoxy-4-(4-methyl-4-oxido-1,4-azaphosphinan-1-yl)aniline with 2,4,5-trichloropyrimidine generating 2,5-dichloro-N-[2-methoxy-4-(4-methyl-4-oxido-1,4-azaphosphinan-1-yl)phenyl]pyrimidin-4-amine. 2,5-dichloro-N-[2-methoxy-4-(4-methyl-4-oxido-1,4-azaphosphinan-1-yl)phenyl]pyrimidin-4-amine is then reacted with 1-(thiophen-2-yl)methanamine as described in Example 32.

2-methoxy-4-(4-methyl-4-oxido-1,4-azaphosphinan-1-yl)aniline

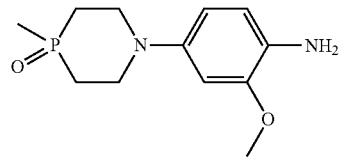 [SMILES: COc1cc(N2CCP(C)(=O)CC2)ccc1N]

1-benzyl-4-methyl-1,4-azaphosphinane 4-oxide

To a solution of methylphosphonic dischloride (10.0 g, 75.2 mmol) in CH₂Cl₂ at −78° C., was added vinylmagnesium bromide (175 mL, 1.0 M in THF) via addition funnel over 4 h. The solution was warmed to 0° C. and quenched with a minimum amount of saturated NH₄Cl. The mixture was filtered through a pad of silica gel and silica was extracted with 10% 7N ammonia in methanol:dichloromethane. The solution was concentrated under reduced pressure to afford methyl divinyl phosphine oxide as a viscous, yellow oil that was used without purification.

A solution of methyl divinyl phosphine oxide (1.16 g, 10.0 mmol) and benzylamine (1.20 mL, 11.0 mmol) in 1:1 THF/water (25 mL) was heated at reflux for 16 h. The reaction mixture was concentrated in vacuo and the residue was purified by silica gel chromatography (0-10% 7N ammonia in methanol:dichloromethane) to afford 1-benzyl-4-methyl-[1,4]azaphosphinane-4-oxide as a white solid (1.57 g, 70% yield).

4-methyl-[1,4]azaphosphinane-4-oxide

A flask was charged with 1-benzyl-4-methyl-[1,4]azaphosphinane-4-oxide (1.00 g, 4.47 mmol) and 10% Pd/C (100 mg). The flask was evacuated and filled with nitrogen. Anhydrous methanol (18 mL) was added to the flask and the flask was equipped with a reflux condenser with a nitrogen inlet. Ammonium formate (2.25 g, 35.8 mmol) was added in one portion at room temperature. The resulting mixture was stirred at reflux for 2 h. The reaction was filtered through a Celite pad and the Celite was washed with 2×5 mL methanol. The combined filtrate and washing was evaporated in vacuo. The crude residue was purified by silica gel chromatography (0-10% 7N ammonia in methanol:dichloromethane) to afford 4-methyl-[1,4]azaphosphinane-4-oxide as a yellow gel (0.589 g, 99% yield).

1-(3-methoxy-4-nitrophenyl)-4-methyl-1,4-azaphosphinane 4-oxide

A mixture of 4-methyl-[1,4]azaphosphinane-4-oxide (133 mg, 1.00 mmol), 5-fluoro-2-nitroanisole (340 mg, 2.00 mmol), K₂CO₃ (345 mg, 2.50 mmol), and DMF (5 mL) was heated to 50° C. After 2 h, the reaction mixture was concentrated and purified by silica gel chromatography (0-5% 7N ammonia in methanol:dichloromethane) to afford 1-(3-methoxy-4-nitrophenyl)-4-methyl-1,4-azaphosphinane 4-oxide as a bright yellow solid (272 mg, 96% yield).

2-methoxy-4-(4-methyl-4-oxido-1,4-azaphosphinan-1-yl)aniline

To a pressure vessel was added 1-(3-methoxy-4-nitrophenyl)-4-methyl-1,4-azaphosphinane 4-oxide (272 mg, 0.960 mmol), ethanol (5 mL), and 10% Pd/C (50 mg). The vessel was connected to a Parr apparatus, evacuated, and refilled with nitrogen. The vessel was then evacuated and filled with hydrogen gas to a pressure of 50 psi. The reaction mixture was shaken under 50 psi for 4 h. The mixture was filtered through Celite to a flask containing HCl in ethanol. Concentration of the filtrate afforded 2-methoxy-4-(4-methyl-4-oxido-1,4-azaphosphinan-1-yl)aniline as a gray solid (211 mg, 87% yield).

Example 48

5-chloro-$N^2$-[2-methoxy-4-(4-methyl-4-oxido-1,4-azaphosphinan-1-yl)phenyl]-$N^2$-[5-(propan-2-yl)-1,3-oxazol-2-yl]pyrimidine-2,4-diamine

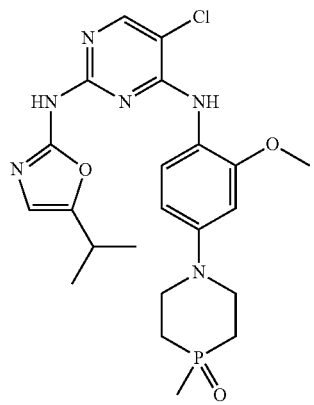 [SMILES: COc1cc(N2CCP(C)(=O)CC2)ccc1Nc1nc(Nc2ncc(C(C)C)o2)ncc1Cl]

The compound can be prepared as in Example 32 by reacting 2,5-dichloro-N-[2-methoxy-4-(4-methyl-4-oxido-1,4-azaphosphinan-1-yl)phenyl]pyrimidin-4-amine (as described in Example 47) with 5-(propan-2-yl)-1,3-oxazol-2-amine.

Example 49

5-chloro-$N^2$-[1-(4-fluorobenzyl)-1H-pyrrol-3-yl]-$N^4$-[2-methoxy-4-(4-methyl-4-oxido-1,4-azaphosphinan-1-yl)phenyl]pyrimidine-2,4-diamine

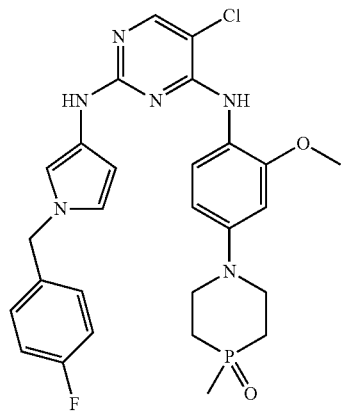 [SMILES: COc1cc(N2CCP(C)(=O)CC2)ccc1Nc1nc(Nc2ccn(Cc3ccc(F)cc3)c2)ncc1Cl]

The compound can be prepared as in Example 32 by reacting 2,5-dichloro-N-[2-methoxy-4-(4-methyl-4-oxido-1,4-azaphosphinan-1-yl)phenyl]pyrimidin-4-amine (as described in Example 47) with 1-(4-fluorobenzyl)-1H-pyrrol-3-amine.

Example 50

2-{[(5-chloro-4-{[2-methoxy-4-(4-methyl-4-oxido-1,4-azaphosphinan-1-yl)phenyl]amino}pyrimidin-2-yl)amino]methyl}-N,N-diethylthiophene-3-sulfonamide

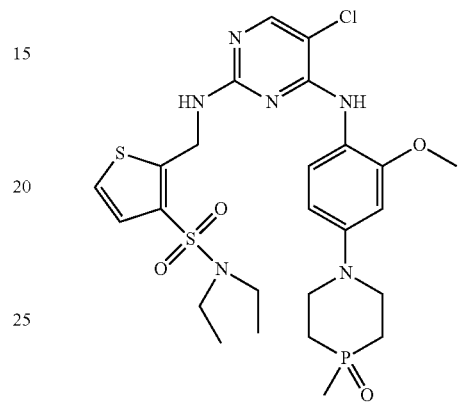

The compound can be prepared as in Example 32 by reacting 2,5-dichloro-N-[2-methoxy-4-(4-methyl-4-oxido-1,4-azaphosphinan-1-yl)phenyl]pyrimidin-4-amine (as described in Example 47) with 2-(aminomethyl)-N,N-diethylthiophene-3-sulfonamide.

Example 51

$N^2$-[5-(1,4'-bipiperidin-1'-yl)-1,3,4-thiadiazol-2-yl]-5-chloro-N-[5-(dimethylphosphoryl)-3-methoxypyrazin-2-yl]pyrimidine-2,4-diamine

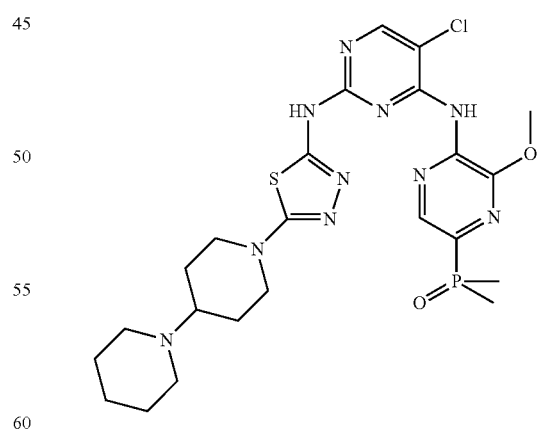

This compound can be prepared as in Example 32 by reacting 5-(dimethylphosphoryl)-3-methoxypyrazin-2-amine (prepared In example 33) with 2,4,5-trichloropyrimidine to generate 2,5-dichloro-N-[5-(dimethylphosphoryl)-3-methoxypyrazin-2-yl]pyrimidin-4-amine. 2,5-dichloro-N-[5-(dimethylphosphoryl)-3-methoxypyrazin-2-yl]

pyrimidin-4-amine is then reacted with 5-(1,4'-bipiperidin-1'-yl)-1,3,4-thiadiazol-2-amine according to the procedure described in Example 321.

Example 52

5-chloro-N⁴-[5-(dimethylphosphoryl)-3-methoxypyrazin-2-yl]-N²-{[5-(4-methylpiperazin-1-yl)-1,3,4-oxadiazol-2-yl]methyl}pyrimidine-2,4-diamine

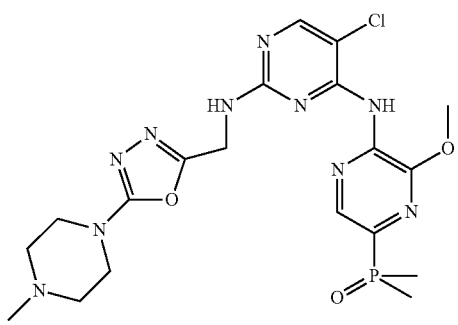

This compound can be prepared as in Example 32 by reacting 2,5-dichloro-N-[5-(dimethylphosphoryl)-3-methoxypyrazin-2-yl]pyrimidin-4-amine (as described in Example 51) with 1-[5-(4-methylpiperazin-1-yl)-1,3,4-oxadiazol-2-yl]methanamine.

Example 53

5-chloro-N⁴-[4-(dimethylphosphoryl)-2-(propan-2-ylsulfonyl)phenyl]-N²-{5-[4-(pyridin-2-yl)piperazin-1-yl]-1,3,4-oxadiazol-2-yl}pyrimidine-2,4-diamine

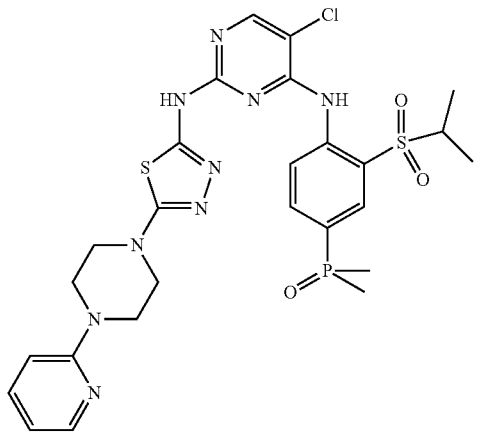 [SMILES: CC(C)S(=O)(=O)c1cc(P(C)(C)=O)ccc1Nc1nc(Nc2nnc(N3CCN(c4ccccn4)CC3)s2)ncc1Cl]

This compound can be prepared as in Example 32 by reacting 4-(dimethylphosphoryl)-2-(propan-2-ylsulfonyl)aniline with 2,4,5-trichloropyrimidine to generate 2,5-dichloro-N-[4-(dimethylphosphoryl)-2-(propan-2-ylsulfonyl)phenyl]pyrimidin-4-amine. 2,5-dichloro-N-[4-(dimethylphosphoryl)-2-(propan-2-ylsulfonyl)phenyl]pyrimidin-4-amine is then reacted with 5-[4-(pyridin-2-yl)piperazin-1-yl]-1,3,4-oxadiazol-2-amine according to the procedure described in Example 32.

4-(dimethylphosphoryl)-2-(propan-2-ylsulfonyl)aniline

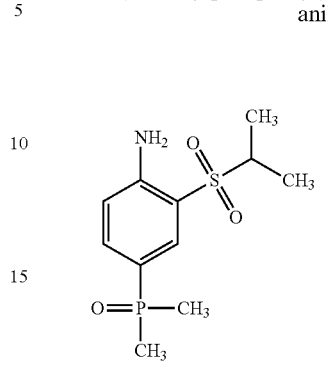

4-bromo-1-nitro-2-(propan-2-ylsulfanyl) benzene

At 0 degree, to a stirring solution of 4-Bromo-2-Floronitroaniline (2.0 g, 9.1 mmol) in DCM was added Sodium Isopropoxide (2.0 g, 20 mmol) in two portions. The reaction mixture was warmed to room temperature and stirred overnight. The reaction mixture was filtered through a syringe filter. The product was isolated by prep-HPLC (water/Acetonitrile) as a bright yellow solid (0.8 g, 2.9 mmol, 32% yield).

4-bromo-1-nitro-2-(propan-2-ylsulfonyl)benzene

To a stirring solution of 4-bromo-1-nitro-2-(propan-2-ylsulfanyl)benzene (0.8 g, 2.9 mmol) in Acetic Acid (10 ml) was added Hydrogen Peroxide (30% aqueous solution, 0.6 mL, 5.8 mmol). The reaction mixture was heated to 110 degrees C. for 2 hours in oil bath. The reaction mixture was treated with saturated Sodium Sulfide aqueous solution and basified with saturated sodium bicarbonate solution. The mixture was extracted with Ethyl Acetate and the combined organic layers were dried over sodium sulfate. The organic solvent was removed under reduced pressure and the residue was used for the next step reaction without further purification.

Dimethyl[4-nitro-3-(propan-2-ylsulfonyl)phenyl]phosphane oxide

To a stirring solution of 4-bromo-1-nitro-2-(propan-2-ylsulfonyl)benzene (0.44 g, 1.6 mmol) and Dimethyl Phosphine oxide (0.15 g, 1.9 mmol) in 1 mL of DMF, was added Potassium Phosphate (0.37 g, 1.8 mmol), Pd(OAc)₂ (18 mg, 0.08 mmol), Xanphos (55 mg, 0.10 mmol). The reaction mixture was stirred at 110 degrees C. overnight. The reaction mixture was cooled to room temperature and filtered through celite. The desired product was isolated through prep-HPLC to yield a brownish yellow solid (0.24 g, 55% yield)

4-(dimethylphosphoryl)-2-(propan-2-ylsulfonyl)aniline

To a solution of dimethyl[4-nitro-3-(propan-2-ylsulfonyl)phenyl]phosphane oxide (0.24 g, 0.88 mmol) in Ethanol was added Pd on carbon (10% w/w, 24 mg) and stirred under hydrogen overnight. The reaction mixture was filtered and the organic solvent was removed under reduced pressure. The residue was purified by prep-HPLC to yield 100 mg of desired product (50% yield).

Example 54

5-chloro-$N^4$-[4-(dimethylphosphoryl)-2-(propan-2-ylsulfonyl)phenyl]-$N^2$-{[2-(morpholin-4-yl)-1,3-thiazol-4-yl]methyl}pyrimidine-2,4-diamine

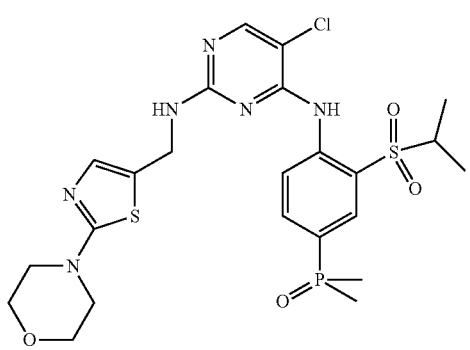 [SMILES: CC(C)S(=O)(=O)c1cc(P(C)(C)=O)ccc1Nc1nc(NCc2cnc(N3CCOCC3)s2)ncc1Cl]

This compound can be prepared as in Example 32 by reacting 2,5-dichloro-N-[4-(dimethylphosphoryl)-2-(propan-2-ylsulfonyl)phenyl]pyrimidin-4-amine (as described in Example 53) with 1-[2-(morpholin-4-yl)-1,3-thiazol-4-yl]methanamine.

Example 55

$N^2$-benzyl-5-chloro-$N^4$-[4-(dimethylphosphoryl)-2-(propan-2-ylsulfonyl)phenyl]pyrimidine-2,4-diamine

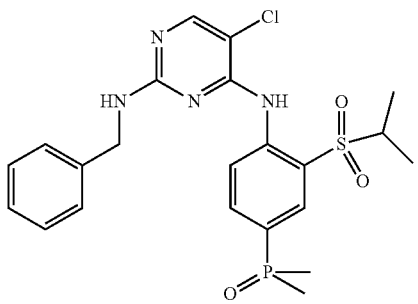 [SMILES: CC(C)S(=O)(=O)c1cc(P(C)(C)=O)ccc1Nc1nc(NCc2ccccc2)ncc1Cl]

This compound can be prepared as in Example 32 by reacting 2,5-dichloro-N-[4-(dimethylphosphoryl)-2-(propan-2-ylsulfonyl)phenyl]pyrimidin-4-amine (as described in Example 53) with benzylamine.

Example 56

5-chloro-$N^2$-(5-cyclopropyl-1,3-oxazol-2-yl)-$N^4$-{2-methoxy-4-[4-(4-methyl-4-oxido-1,4-azaphosphinan-1-yl)piperidin-1-yl]phenyl}pyrimidine-2,4-diamine

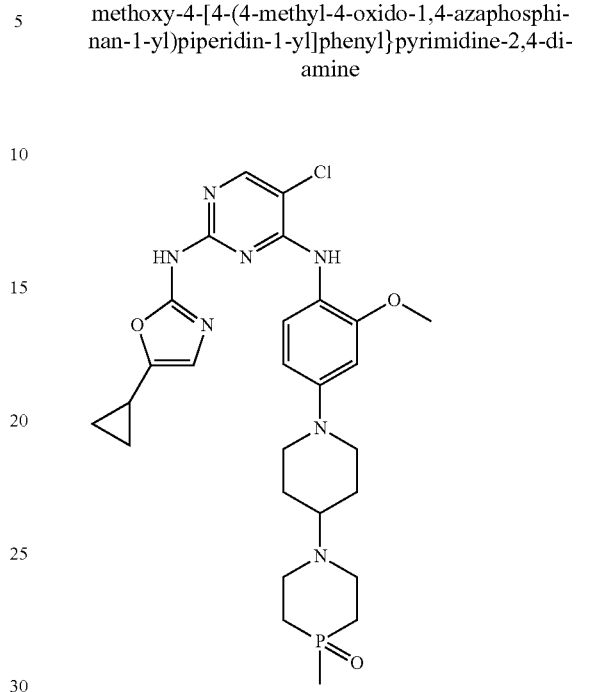

This compound can be prepared as in Example 32 by reacting 2-methoxy-4-[4-(4-methyl-4-oxido-1,4-azaphosphinan-1-yl)piperidin-1-yl]aniline with 2,4,5-trichloropyrimidine to generate 2,5-dichloro-N-{2-methoxy-4-[4-(4-methyl-4-oxido-1,4-azaphosphinan-1-yl)piperidin-1-yl]phenyl}pyrimidin-4-amine. 2,5-dichloro-N-{2-methoxy-4-[4-(4-methyl-4-oxido-1,4-azaphosphinan-1-yl)piperidin-1-yl]phenyl}pyrimidin-4-amine is then reacted with 5-cyclopropyl-1,3-oxazol-2-amine according to the procedure described in Example 32.

2-methoxy-4-[4-(4-methyl-4-oxido-1,4-azaphosphinan-1-yl)piperidin-1-yl]aniline

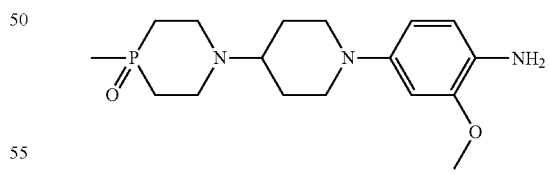

tert-butyl 4-(4-methyl-4-oxido-1,4-azaphosphinan-1-yl)piperidine-1-carboxylate

A solution of methyl divinyl phosphine oxide (140 mg, 1.21 mmol) and 1-Boc-4-aminopiperidine (265 mg, 1.33 mmol) in 1:1 THF/water (3 mL) was heated at reflux for 16 h. The reaction mixture was concentrated in vacuo and the residue was purified by silica gel chromatography (0-10% 7N ammonia in methanol:dichloromethane) to afford the desired compound as a white solid (178 mg, 38% yield).

1-[1-(3-methoxy-4-nitrophenyl)piperidin-4-yl]-4-methyl-1,4-azaphosphinane 4-oxide To a stirring solution of tert-butyl 4-(4-methyl-4-oxido-1,4-azaphosphinan-1-yl)piperidine-1-carboxylate (178 mg, 0.563 mmol) in $CH_2Cl_2$ (2 mL) was added trifluoroacetic acid (0.5 mL). After 20 min, the solution was concentrated and the resulting residue was redissolved in DMF (2 mL). Potassium carbonate (160 mg, 1.16 mmol) was added portionwise to the stirring solution followed by 5-fluoro-2-nitroanisole (158 mg, 0.930 mmol). The reaction mixture was heated to 50° C. After 2 h, the reaction mixture was concentrated and the residue was purified by silica gel chromatography (0-10% 7N ammonia in methanol:dichloromethane) to afford the compound as a bright yellow solid (176 mg, 86% yield).

2-methoxy-4-[4-(4-methyl-4-oxido-1,4-azaphosphinan-1-yl)piperidin-1-yl]aniline To a pressure vessel was added 1-[1-(3-methoxy-4-nitrophenyl)piperidin-4-yl]-4-methyl-1,4-azaphosphinane 4-oxide (176 mg, 0.485 mmol), ethanol (5 mL), and 10% Pd/C (50 mg). The vessel was connected to a Parr apparatus, evacuated, and refilled with nitrogen. The vessel was then evacuated and filled with hydrogen gas to a pressure of 50 psi. The reaction mixture was shaken under 50 psi for 4 h. The mixture was filtered through Celite to a flask containing HCl in ethanol. Concentration of the filtrate afforded the compound as a gray solid (178 mg, 98% yield).

Example 57

5-chloro-$N^2$-(5-cyclopropyl-1,3-oxazol-2-yl)-$N^4$-[4-(1-ethyl-4-oxido-1,4-azaphosphinan-4-yl)-2-methoxyphenyl]pyrimidine-2,4-diamine

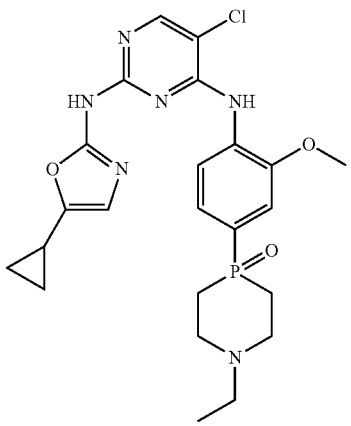 [SMILES: CCN1CCP(=O)(c2ccc(Nc3nc(Nc4ncc(C5CC5)o4)ncc3Cl)c(OC)c2)CC1]

This compound can be prepared as in Example 32 by reacting 4-(1-ethyl-4-oxido-1,4-azaphosphinan-4-yl)-2-methoxyaniline with 2,4,5-trichloropyrimidine to generate 2,5-dichloro-N-[4-(1-ethyl-4-oxido-1,4-azaphosphinan-4-yl)-2-methoxyphenyl]pyrimidin-4-amine. 2,5-dichloro-N-[4-(1-ethyl-4-oxido-1,4-azaphosphinan-4-yl)-2-methoxyphenyl]pyrimidin-4-amine is then reacted with 5-cyclopropyl-1,3-oxazol-2-amine according to the procedure described in Example 32.

4-(1-ethyl-4-oxido-1,4-azaphosphinan-4-yl)-2-methoxyaniline

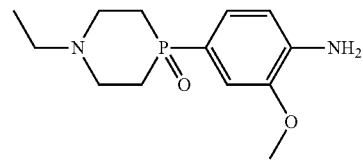 [SMILES: CCN1CCP(=O)(c2ccc(N)c(OC)c2)CC1]

Diethyl (3-methoxy-4-nitrophenyl)phosphonate

To a solution of 5-chloro-2-nitroanisole (1.00 g, 5.33 mmol) in 20 mL DMF was added diethyl phosphite (0.809 g, 5.86 mmol), palladium acetate (0.060 g, 0.27 mmol), XantPHOS (0.185 g, 0.320 mmol), and potassium phosphate (1.24 g, 5.86 mmol). The mixture was purged with nitrogen, and subjected to microwaves at 150° C. for 20 minutes. The reaction mixture was concentrated and purified by silica gel chromatography (0-45% ethyl acetate:heptane) to afford the desired product (0.504 g, 33% yield).

(3-methoxy-4-nitrophenyl)phosphonic dichloride

To a solution of diethyl (3-methoxy-4-nitrophenyl)phosphonate (4.54 g, 15.7 mmol) in 1.2 mL DMF was added thionyl chloride (5.7 mL, 78.5 mmol). The reaction flask was equipped with a reflux condenser and the mixture was heated to reflux. After 2 h at reflux, the reaction was cooled to rt and concentrated in vacuo. The crude oil was redissolved in $CH_2Cl_2$ and heptane was added to precipitate the desired compound. The clear solution was decanted and the precipitate was collected and dried to afford the desired compound as a white solid (1.39 g, 33% yield).

Diethenyl(3-methoxy-4-nitrophenyl)phosphane oxide

To a solution of (3-methoxy-4-nitrophenyl)phosphonic dichloride (1.39 g, 5.15 mmol) in 15 mL THF at −78° C. under nitrogen was slowly added vinylmagnesium bromide (10.3 mL, 1.0 M in THF). After the addition was complete, the reaction stirred at −78° C. for an additional hour. The cold reaction mixture was quenched by the addition of saturated $NH_4Cl$ (20 mL) and the mixture was extracted with $CH_2Cl_2$. The combined organic layers were washed with 1 M NaOH, brine, and dried over $MgSO_4$. The organic extracts were filtered and concentrated to provide Diethenyl(3-methoxy-4-nitrophenyl)phosphane oxide (0.982 g, 75%).

1-ethyl-4-(3-methoxy-4-nitrophenyl)-1,4-azaphosphinane 4-oxide

Diethenyl(3-methoxy-4-nitrophenyl)phosphane oxide (0.480 g, 1.94 mmol), ethylamine hydrochloride (0.174 g, 2.12 mmol), and 1 N NaOH (2 mL) were dissolved in 50% aqueous THF (5 mL) and heated to 105° C. under nitrogen. After one hour, another portion of benzylamine was added to the reaction mixture. The reaction mixture was refluxed for an additional 2 h, and then cooled to rt. The reaction mixture was partitioned between saturated aqueous $NaHCO_3$ and $CH_2Cl_2$.

The aqueous phase was washed once with CH₂Cl₂ and the organic layers were combined. The organic extracts were washed with brine, dried over MgSO₄, filtered, and concentrated. The residue was purified by silica gel chromatography (0-10% 7N ammonia in methanol:dichloromethane) to afford the compound (0.267 g, 46% yield).

4-(1-ethyl-4-oxido-1,4-azaphosphinan-4-yl)-2-methoxyaniline

To a solution of 1-ethyl-4-(3-methoxy-4-nitrophenyl)-1,4-azaphosphinane 4-oxide (0.267 g, 0.895 mmol) in 5 mL ethanol was added 10% Pd/C (27 mg) and 2.5 M HCl in ethanol (1.43 mL). The flask was equipped with a septum, evacuated, and refilled with hydrogen. The flask was equipped with a hydrogen balloon and the reaction stirred for 3 h. The flask was then evacuated and refilled with nitrogen. The reaction mixture was filtered through Celite and concentrated to provide the crude compound as the hydrochloride salt, which was used without purification.

Example 58

5-chloro-$N^2$-(2-cyclopropyl-1,3-oxazol-5-yl)-$N^4$-[4-(diethylphosphoryl)-2-methoxyphenyl]pyrimidine-2,4-diamine

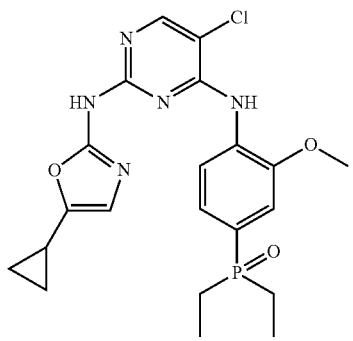 [SMILES: CCP(=O)(CC)c1ccc(Nc2nc(Nc3ncc(C4CC4)o3)ncc2Cl)c(OC)c1]

This compound can be prepared as in Example 32 by reacting 4-(diethylphosphoryl)-2-methoxyaniline with 2,4,5-trichloropyrimidine to 2,5-dichloro-N-[4-(diethylphosphoryl)-2-methoxyphenyl]pyrimidin-4-amine. 2,5-dichloro-N-[4-(diethylphosphoryl)-2-methoxyphenyl]pyrimidin-4-amine is then reacted with 5-cyclopropyl-1,3-oxazol-2-amine according to the procedure described in Example 32.

4-(Dipropylphosphoryl)-2-methoxyaniline

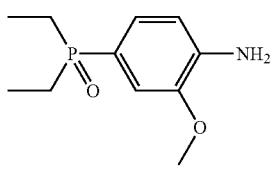

To a solution of 4-bromo-2-methoxyaniline (0.100 g, 0.495 mmol) in 2 mL DMF was added dipropylphosphine oxide (0.0730 g, 0.544 mmol), palladium acetate (5.6 mg, 0.025 mmol), XANTPHOS (17.2 mg, 0.030 mmol), and potassium phosphate (0.116 g, 0.544 mmol). The mixture was purged with nitrogen, and subjected to microwaves at 150° C. for 20 minutes. The reaction mixture was concentrated and purified by silica gel chromatography (0-12% 7N ammonia in methanol:dichloromethane) and the fractions were concentrated. The residue was acidified with 2.5 M HCl in ethanol and the solution was concentrated to provide 4-(dipropylphosphoryl)-2-methoxyaniline as the hydrochloride salt (0.132 g, 91% yield).

Example 59

N-[4-(dimethylphosphoryl)phenyl]-6-(4-methylpiperazin-1-yl)pyrimidin-4-amine

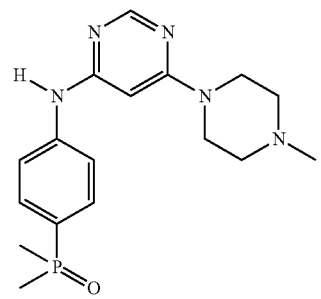

6-chloro-N-[4-(dimethylphosphoryl)phenyl]pyrimidin-4-amine

A suspension of 4-amino-dimethylphenylphosphine oxide (2.2 mmol) in 15 mL of N,N-Dimethylformamide and 3.6 mL of Diisopropylethylamine, is stirred at room temperature until a clear solution is obtained. 4,6-Dichloropyrimidine (2.6 mmol) is added in four portions over 5 minutes. The reaction mixture is stirred at high temperature until formation of the desired compound.

N-[4-(dimethylphosphoryl)phenyl]-6-(4-methylpiperazin-1-yl)pyrimidin-4-amine

To a solution of 6-chloro-N-[4-(dimethylphosphoryl)phenyl]pyrimidin-4-amine (0.072 mmol) in 1.5 mL of ethanol is added 10 μL of triethylamine and 1-Methyl piperazine (0.072 mmol). The mixture can be microwaved at 120 degrees. The reaction mixture can then be filtered through a syringe filter and can be purified by prep-HPLC.

Example 60

N-[4-(dimethylphosphoryl)phenyl]-N'-(tricyclo[3.3.1.1$^{3,7}$]dec-1-yl)pyrimidine-4,6-diamine

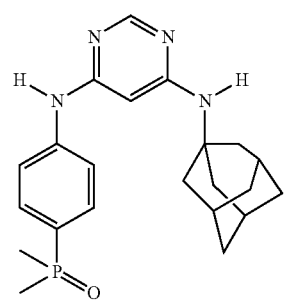 [SMILES: CP(C)(=O)c1ccc(Nc2cc(NC34CC5CC(CC(C5)C3)C4)ncn2)cc1]

To a solution of 6-chloro-N-[4-(dimethylphosphoryl)phenyl]pyrimidin-4-amine (prepared as in Example 59: 0.078 mmol) in 1.5 mL of ethanol is added 10 μL of triethylamine and 1-Adamantanamine (12 mg, 0.078 mmol). The mixture can be microwaved at 120 degrees until formation of the desired compound. The reaction mixture can then be filtered through a syringe filter and purified by prep-HPLC.

Example 61

N-[4-(dimethylphosphoryl)phenyl]-N'-(morpholin-4-ylmethyl)pyrimidine-4,6-diamine

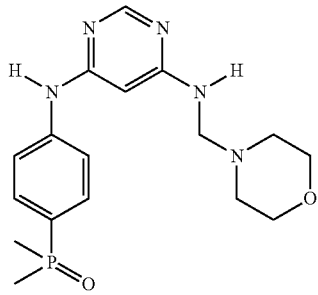 [SMILES: CP(C)(=O)c1ccc(Nc2cc(NCN3CCOCC3)ncn2)cc1]

To a solution of 6-chloro-N-[4-(dimethylphosphoryl)phenyl]pyrimidin-4-amine (prepared as in Example 59: 0.12 mmol) in 2 mL of ethanol is added 50 μL of triethylamine and 4-(2-aminoethyl)morpholine (15 mg, 0.12 mmol). The mixture can be microwaved at 120 degrees until formation of the desired compound. The reaction mixture can be filtered through a syringe filter and purified by prep-HPLC.

Example 62

4-{2-[(6-{[4-(dimethylphosphoryl)phenyl]amino}pyrimidin-4-yl)-amino]ethyl}benzene sulfonamide

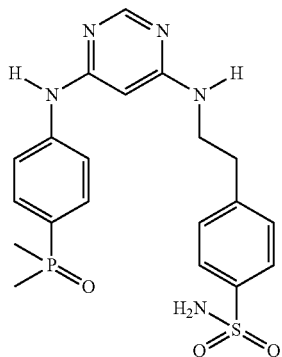 [SMILES: CP(C)(=O)c1ccc(Nc2cc(NCCc3ccc(S(N)(=O)=O)cc3)ncn2)cc1]

To a solution of 6-chloro-N-[4-(dimethylphosphoryl)phenyl]pyrimidin-4-amine (prepared as in Example 59: 0.12 mmol) in 2 mL of ethanol is added 50 μL of triethylamine and 4-(2-aminoethyl)benzene-sulfonamide (23 mg, 0.12 mmol). The mixture can be microwaved at 120 degrees until formation of the desired compound. The reaction mixture can be filtered through a syringe filter and purified by prep-HPLC.

Example 63

N-[4-(dimethylphosphoryl)phenyl]-N'-(tetrahydrofuran-2-yl)pyrimidine-4,6-diamine

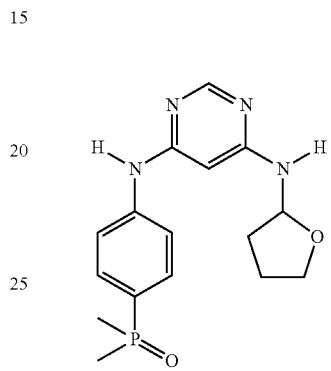

To a solution of 6-chloro-N-[4-(dimethylphosphoryl)phenyl]pyrimidin-4-amine (prepared as in Example 59: 0.12 mmol) in 2 mL of ethanol is added 50 μL of triethylamine and (s)-3-aminotetrahydrofuran hydrochloride salt (14 mg, 0.12 mmol). The mixture is microwaved at 120 degrees until formation of the desired compound. The reaction mixture can then be filtered through a syringe filter and purified by prep-HPLC.

Example 64

N-[4-(dimethylphosphoryl)phenyl]-N'-(hexahydro-cyclopenta[c]pyrrol-2(1H)-yl)pyrimidine-4,6-diamine

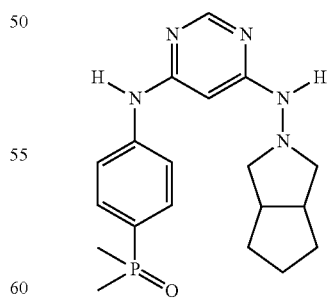

To a solution of 6-chloro-N-[4-(dimethylphosphoryl)phenyl]pyrimidin-4-amine (prepared as in Example 59: 0.12 mmol) in 2 mL of ethanol is added 50 μL of triethylamine and 3-Amino-3-azabicyclo-[3,3,0]octane hydrochloride salt (19 mg, 0.12 mmol). The mixture is microwaved at 120 degrees

Example 65

N-[4-(dimethylphosphoryl)phenyl]-N'-(morpholin-4-yl)pyrimidine-4,6-diamine

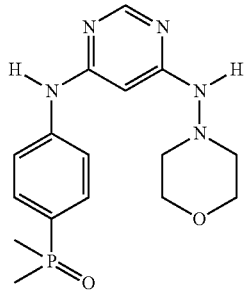

To a solution of 6-chloro-N-[4-(dimethylphosphoryl)phenyl]pyrimidin-4-amine (prepared as in Example 59: 0.12 mmol) in 2 mL of ethanol is added 50 μL of triethylamine and 4-Aminomorpholine (12 mg, 0.12 mmol). The mixture is microwaved at 120 degrees until formation of the desired compound. The reaction mixture can then be filtered through a syringe filter and purified by prep-HPLC.

Example 66

N-[4-(dimethylphosphoryl)phenyl]-6-(4-phenylpiperazin-1-yl)pyrimidin-4-amine

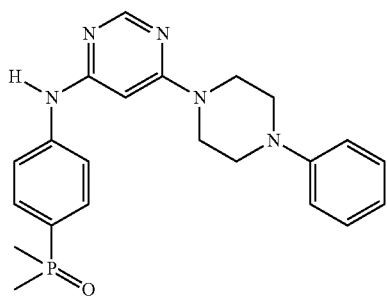

To a solution of 6-chloro-N-[4-(dimethylphosphoryl)phenyl]pyrimidin-4-amine (prepared as in Example 59: 0.12 mmol) in 2 mL of ethanol is added 50 μL of triethylamine and 1-Phenylpiperazine (19 mg, 0.12 mmol). The mixture is microwaved at 120 degrees until formation of the desired compound. The reaction mixture can then be filtered through a syringe filter and purified by prep-HPLC.

Example 67

N-[4-(dimethylphosphoryl)phenyl]-N'-[2-(1H-indol-3-yl)ethyl]pyrimidine-4,6-diamine

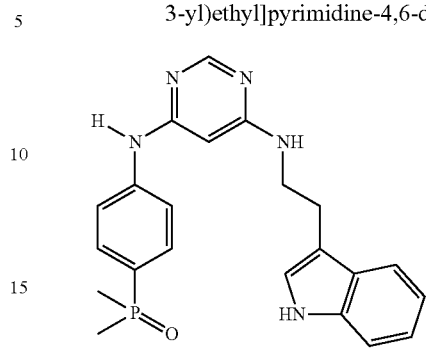

The compound is prepared as in Example 59 by reacting 6-chloro-N-[4-(dimethylphosphoryl)phenyl]pyrimidin-4-amine with Tryptamine.

Example 68

N-[4-(dimethylphosphoryl)phenyl]-N'-(4-methylpiperazin-1-yl)pyrimidine-4,6-diamine

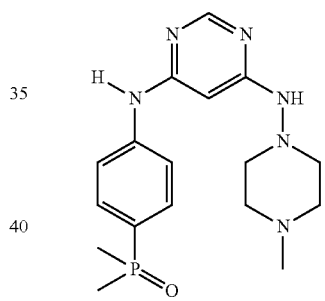

The compound is prepared as in Example 59 by reacting 6-chloro-N-[4-(dimethylphosphoryl)phenyl]pyrimidin-4-amine with 1-Amino-4-methyl-piperazine.

Example 69

N-[4-(dimethylphosphoryl)phenyl]-N'-(tricyclo[3.3.1.1$^{3,7}$]dec-1-ylmethyl)pyrimidine-4,6-diamine

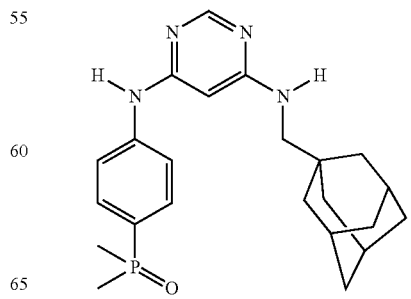

The compound is prepared as in Example 59 by reacting 6-chloro-N-[4-(dimethylphosphoryl)phenyl]pyrimidin-4-amine with 1-adamantanemethylamine.

Example 70

N-[4-(dimethylphosphoryl)phenyl]-N'-[4-(4-methylpiperazin-1-yl)benzyl]pyrimidine-4,6-diamine

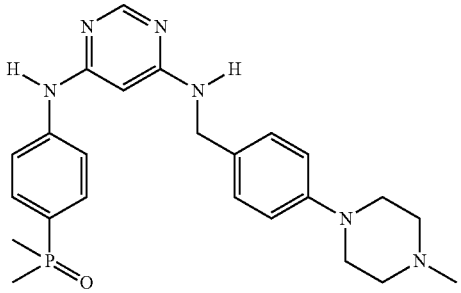 [SMILES: CN1CCN(c2ccc(CNc3cc(Nc4ccc(P(C)(C)=O)cc4)ncn3)cc2)CC1]

The compound is prepared as in Example 59 by reacting 6-chloro-N-[4-(dimethylphosphoryl)phenyl]pyrimidin-4-amine with 4-(4-methylpiperazine)-benzylamine.

Example 71

N-(3,5-dimethylphenyl)-N'-[4-(dimethylphosphoryl)phenyl]pyrimidine-4,6-diamine

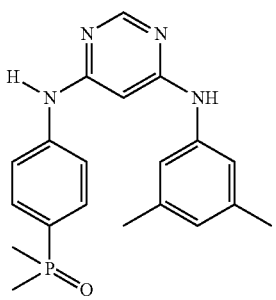 [SMILES: Cc1cc(C)cc(Nc2cc(Nc3ccc(P(C)(C)=O)cc3)ncn2)c1]

The compound is prepared as in Example 59 by reacting 6-chloro-N-[4-(dimethylphosphoryl)phenyl]pyrimidin-4-amine with 3,5-dimethylaniline.

Example 72

N-[4-(dimethylphosphoryl)-2-methoxyphenyl]-2-methyl-N'-phenylpyrimidine-4,6-diamine

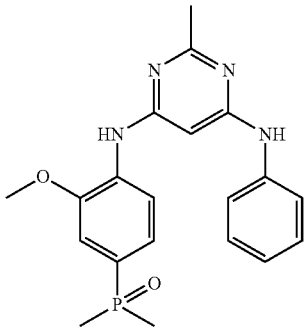 [SMILES: COc1cc(P(C)(C)=O)ccc1Nc1cc(Nc2ccccc2)nc(C)n1]

6-chloro-2-methyl-N-phenylpyrimidin-4-amine

To a solution of Aniline (205 mg, 2.2 mmol) and 4,6-dichloro-2-methylpyrimidine (2.7 mmol) in 5 mL of Ethanol, is added 500 mg of Potassium carbonate. The reaction mixture is stirred at room temperature until formation of the desired compound. Solvent is removed under reduced pressure. The residue can be purified by silica gel flash chromatography.

(3-methoxy-4-nitrophenyl)(dimethyl)phosphane oxide

To a solution of 5-Chloro-2-nitroanisole (0.5 g, 2.67 mmol) in 5 mL of DMF was added dimethylphosphine oxide (0.229 g, 2.93 mmol), palladium acetate (30 mg, 0.13 mmol), XANPHOS (0.092 g, 0.16 mmol) and potassium phosphate (0.623 g, 2.93 mmol). The mixture was purged with argon, and heated at 120° C. for 18 h. The reaction mixture was basified with saturated sodium bicarbonate solution, and extracted with ethyl acetate. The organic layer was concentrated and purified by prep-HPLC to give the final product (0.16 g, 30% yield). MS/ES+: m/z=229.

4-(dimethylphosphoryl)-2-methoxyaniline

To a solution of (3-methoxy-4-nitrophenyl)(dimethyl)phosphane oxide (0.1 g, 0.44 mmol) in 5 mL of EtOH was added 10% weight of palladium on carbon (0.2 g). The mixture was purged with argon, and hydrogenated under 30 psi for 2 h. The mixture was passed through Celite to a flask containing HCl in ethanol. Concentration of the filtrate gave the final product (0.088 g, 86% yield). MS/ES+: m/z=199.

N-[4-(dimethylphosphoryl)-2-methoxyphenyl]-2-methyl-N'-phenylpyrimidine-4,6-diamine To a solution of 6-chloro-2-methyl-N-phenylpyrimidin-4-amine (0.35 mmol) and 4-(dimethylphosphoryl)-2-methoxyaniline (60 mg, 0.30 mmol) in 1 mL of DMF, is added 0.36 mL of 2.5M HCl in Ethanol. The reaction mixture can be heated in a sealed tube at 140 degrees until formation of the desired compound. The reaction mixture is filtered through a syringe filter and can be purified by Prep-HPLC.

Example 73

$N^3$-[4-(dimethylphosphoryl)-2-methoxyphenyl]-$N^5$-[2-(propan-2-ylsulfonyl)phenyl]pyridazine-3,5-diamine

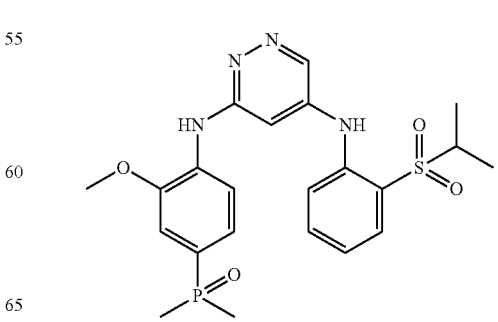

6-chloro-N-[2-(propan-2-ylsulfonyl)phenyl]pyridazin-4-amine

To a solution of 1-Amino-2-(isopropylsulphonyl)benzene (350 mg, 1.6 mmol) in 4 mL of N,N-Dimethyl formamide at 0 degree, is added Sodium hydride (100 mg) and the reaction mixture is allowed to stirred at 0 degree for 20 minutes. 3,5-dichloropyridazine (1.6 mmol) is added and the reaction mixture is warmed to room temperature. The reaction mixture is stirred at room temperature until formation of the desired compound. The reaction mixture is quenched with water and extracted with Ethyl acetate. The combined Ethyl acetate layers are dried over Sodium Sulfate and solvent is removed under reduced pressure. The residue can be purified by Prep-HPLC.

$N^3$-[4-(dimethylphosphoryl)-2-methoxyphenyl]-$N^5$-[2-(propan-2-ylsulfonyl)phenyl]pyridazine-3,5-diamine To a solution of 6-chloro-N-[2-(propan-2-ylsulfonyl)phenyl]pyridazin-4-amine (0.02 mmol) and 4-(dimethylphosphoryl)-2-methoxyaniline (prepared as in Example 72: 15 mg, 0.7 mmol) in 1 mL of 2-Methoxy ethanol, is added 1 mL of 2.5M HCl in Ethanol. The reaction mixture is heated in a sealed tube at 140 degree until formation of the desired compound. The reaction mixture is filtered through a syringe filter and can be purified by Prep-HPLC.

Example 74

N-[4-(dimethylphosphoryl)-2-methoxyphenyl]-5-[3-fluoro-5-(trifluoromethyl)phenoxy]pyridazin-3-amine

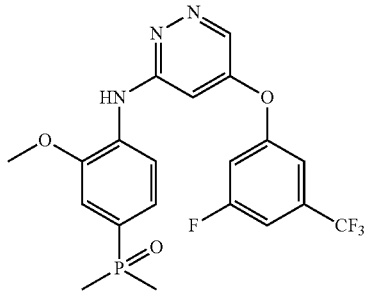 [SMILES: COc1cc(P(C)(C)=O)ccc1Nc1cc(Oc2cc(F)cc(C(F)(F)F)c2)cnn1]

3-chloro-5-[3-fluoro-5-(trifluoromethyl)phenoxy]pyridazine

To a solution of 3-fluoro-5-(trifluoromethyl)phenol (1.6 mmol) in 4 mL of N,N-Dimethyl formamide at 0 degree, is added Sodium hydride (100 mg) and the reaction mixture is allowed to stirred at 0 degree for 20 minutes. 3,5-dichloropyridazine (1.6 mmol) is added and the reaction mixture is warmed to room temperature. The reaction mixture is stirred at room temperature until formation of the desired compound. The reaction mixture is quenched with water and extracted with Ethyl acetate. The combined Ethyl acetate layers are dried over Sodium Sulfate and solvent is removed under reduced pressure. The residue can be purified by Prep-HPLC.

N-[4-(dimethylphosphoryl)-2-methoxyphenyl]-5-[3-fluoro-5-(trifluoromethyl)phenoxy]pyridazin-3-amine To a solution of 3-chloro-5-[3-fluoro-5-(trifluoromethyl)phenoxy]pyridazine (0.02 mmol) and 4-(dimethylphosphoryl)-2-methoxyaniline (prepared as in Example 72: 15 mg, 0.7 mmol) in 1 mL of 2-Methoxy ethanol, is added 1 mL of 2.5M HCl in Ethanol. The reaction mixture is heated in a sealed tube at 140 degree until formation of the desired compound. The reaction mixture is filtered through a syringe filter and can be purified by Prep-HPLC.

Example 75

N-{2-methoxy-4-[4-(4-methylpiperazin-1-yl)piperidin-1-yl]phenyl}-2-methyl-N'-[2-(propan-2-ylsulfonyl)phenyl]pyrimidine-4,6-diamine

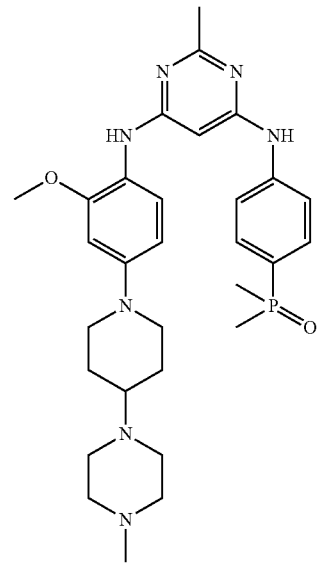 [SMILES: COc1cc(N2CCC(N3CCN(C)CC3)CC2)ccc1Nc1cc(Nc2ccc(P(C)(C)=O)cc2)nc(C)n1]

6-chloro-N-[4-(dimethylphosphoryl)phenyl]-2-methylpyrimidin-4-amine

To a solution of 4,6-dichloro-2-methylpyrimidine (1.31 mmol) in 1 mL of DMF is added 4-(dimethylphosphoryl)aniline (0.221 g, 1.31 mmol) and potassium carbonate (0.217 g, 1.57 mmol). The mixture is heated at 110° C. until formation of the desired compound. The reaction mixture is basified with saturated sodium bicarbonate solution. The suspension is filtered and washed with ethyl acetate.

1-[1-(3-methoxy-4-nitrophenyl)piperidin-4-yl]-4-methylpiperazine

To a solution of 5-fluoro-2-nitroanisoole (0.5 g, 2.92 mmol) in 3 mL of DMF was added 1-methyl-4-(piperidin)piperazine (0.536 g, 2.92 mmol) and potassium carbonate (0.808, 5.84 mmol). The mixture was heated at 120° C. for 18 h. The mixture was basified with saturated sodium bicarbonate solution and extracted with ethyl acetate. The organic layer was purified by chromatography to give final product as yellow solid (0.95 g, 95% yield). MS/ES+: m/z=334.

2-methoxy-4-[4-(4-methylpiperazin-1-yl)piperidin-1-yl]aniline

The a solution of 1-[1-(3-methoxy-4-nitrophenyl)piperidin-4-yl]-4-methylpiperazine (0.3 g, 0.90 mmol) in 10 mL of ethanol purged with argon was added 10% Palladium on carbon (0.060 g). The hydrogenation was finished under 30 psi after 4 h. The mixture was passed through Celite to a flask containing HCl in ethanol. Concentration of the filtrate gave the final product (0.15 g, 88% yield). MS/ES+: m/z=334.

N-{2-methoxy-4-[4-(4-methylpiperazin-1-yl)piperidin-1-yl]phenyl}-2-methyl-N'-[2-(propan-2-ylsulfonyl)phenyl]pyrimidine-4,6-diamine To the compound 6-chloro-2-methyl-N-[2-(propan-2-ylsulfonyl)phenyl]pyrimidin-4-amine (0.16 mmol) in 1 mL of 2-methoxyethanol is added 2-methoxy-4-[4-(4-methylpiperazin-1-yl)piperidin-1-yl]aniline (0.71 g, 0.16 mmol). The mixture is stirred at 110° C. until formation of the desired compound. The mixture is basified with saturated sodium bicarbonate solution and extracted with limited amount of ethyl acetate. The compound can be purified by chromatography.

Example 76

N-[6-(dimethylphosphoryl)-2-methoxypyridin-3-yl]-N'-[2-(propan-2-ylsulfonyl)phenyl]pyrimidine-4,6-diamine

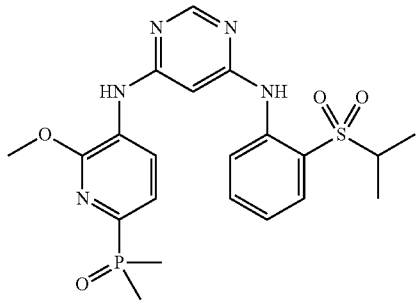 [SMILES: COc1nc(P(C)(C)=O)ccc1Nc1cc(Nc2ccccc2S(=O)(=O)C(C)C)ncn1]

6-(Dimethylphosphoryl)-2-methoxypyridin-3-ylamine

To a solution of 6-bromo-2-methoxypyridin-3-ylamine (0.203 g, 1.00 mmol) in 4 mL DMF was added dimethylphosphine oxide (0.171 g, 1.10 mmol), palladium acetate (11.0 mg, 0.0490 mmol), XANTPHOS (35.0 mg, 0.0600 mmol), and potassium phosphate (0.233 g, 1.10 mmol). The mixture was purged with nitrogen, and subjected to microwaves at 150° C. for 20 minutes. The reaction mixture was concentrated and purified by silica gel chromatography (0-10% 7N ammonia in methanol:dichloromethane) to afford the desired product (77.2 mg, 39% yield).

6-chloro-N-[2-(propan-2-ylsulfonyl)phenyl]pyrimidin-4-amine

To a solution of 1-Amino-2-(isopropylsulphonyl)benzene (0.955 g, 4.80 mmol) in 2 mL of DMF at 0° C. is added NaH (60% in oil, 0.349 g, 8.72 mmol) in one portion. After stirring for 20 min, 4,6-dichloropyrimidine can be added. The mixture is stirred at 0° C. for 30 minutes, and then at room temperature until formation of the desired compound. After quenching with saturated ammonium chloride solution, the mixture is poured in water and ethyl acetate mixture. The compound can be purified by HPLC.

N-[6-(dimethylphosphoryl)-2-methoxypyridin-3-yl]-N'-[2-(propan-2-ylsulfonyl)phenyl]pyrimidine-4,6-diamine To a solution of 6-chloro-N-[2-(propan-2-ylsulfonyl)phenyl]pyrimidin-4-amine (0.250 mmol) in 1 mL of 2-methoxyethanol is added 6-(dimethylphosphoryl)-2-methoxypyridin-3-ylamine (50.0 mg, 0.250 mmol) and 0.15 mL of 2.5 M HCl in ethanol. The mixture is heated in a sealed tube at 90° C. until formation of the desired compound. The mixture is basified with 1N NaOH solution, and extracted with ethyl acetate. The organic layers can be combined, washed with saturated sodium chloride solution, dried with sodium sulfate, filtered and concentrated. The crude residue can be purified by silica gel chromatography.

Example 77

N-[5-(dimethylphosphoryl)-3-methoxypyrazin-2-yl]-N'-[2-(propan-2-ylsulfonyl)phenyl]pyrimidine-4,6-diamine

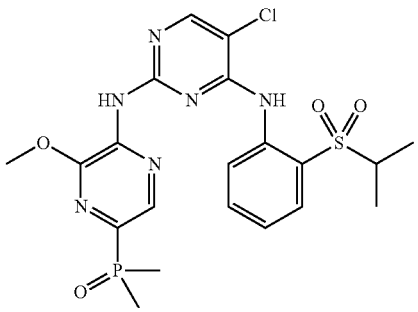 [SMILES: COc1nc(P(C)(C)=O)cnc1Nc1ncc(Cl)c(Nc2ccccc2S(=O)(=O)C(C)C)n1]

5-(dimethylphosphoryl)-3-methoxypyrazin-2-amine

To a solution of 5-bromo-3-methoxypyrazin-3-ylamine (0.204 g, 1.00 mmol) in 4 mL DMF was added dimethylphosphine oxide (0.171 g, 1.10 mmol), palladium acetate (11.0 mg, 0.0490 mmol), XANTPHOS (35.0 mg, 0.0600 mmol), and potassium phosphate (0.233 g, 1.10 mmol). The mixture was purged with nitrogen, and subjected to microwaves at 150° C. for 20 minutes. The reaction mixture was concentrated and purified by silica gel chromatography (0-10% 7N ammonia in methanol:dichloromethane) to afford the desired product (126 mg, 63% yield).

5-chloro-$N^2$-[5-(dimethylphosphoryl)-3-methoxypyrazin-2-yl]-$N^4$-[2-(propan-2-ylsulfonyl)phenyl]pyrimidine-2,4-diamine To a mixture of 6-chloro-N-[2-(propan-2-ylsulfonyl)phenyl]pyrimidin-4-amine (prepared in Example 76: 0.348 mmol) and 5-(dimethylphosphoryl)-3-methoxypyrazin-2-amine (70.0 mg, 0.348 mmol) is added tris(dibenzylideneacetone)dipalladium(0)-chloroform adduct (17.6 mg, 0.017 mmol), XANTPHOS (23.3 mg, 0.040 mmol), and cesium carbonate (0.228 g, 0.700 mmol), and dioxane (3.5 mL). The tube is sealed and heated at 120° C. until formation of the desired compound. The reaction mixture is then cooled to room temperature and concentrated. The crude residue can be purified by silica gel chromatography.

Example 77

N-[4-(dimethylphosphoryl)-2-methoxyphenyl]-N'-[2-(propan-2-ylsulfonyl)phenyl]pyrimidine-4,6-diamine

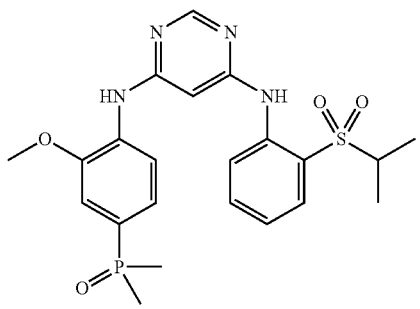 [SMILES: COc1cc(P(C)(C)=O)ccc1Nc1cc(Nc2ccccc2S(=O)(=O)C(C)C)ncn1]

$N^2$-[4-(dimethylphosphoryl)-2-methoxyphenyl]-$N^4$-[2-(propan-2-ylsulfonyl)phenyl]pyrimidine-2,4-diamine To a solution of 6-chloro-N-[2-(propan-2-ylsulfonyl)phenyl]pyrimidin-4-amine (prepared in Example 76: 0.054 mmol) in 0.5 mL of 2-methoxyethanol in a vial is added 4-(dimethylphosphoryl)-2-methoxyaniline (prepared in Example 73: 0.044 mmol) as the HCl salt. The vial is sealed and the reaction is heated at 90° C. until formation of the desired compound. The reaction is quenched with 1N NaOH solution and the solution extracted ethyl acetate. The organic layers are combined, washed with saturated sodium chloride solution, dried with sodium sulfate, filtered and concentrated. The crude residue can be purified by silica gel chromatography.

Example 79

$N^2$-[4-(dimethylphosphoryl)-2-methoxyphenyl]-$N^4$-[2-(propan-2-ylsulfonyl)phenyl]pyridine-2,4-diamine

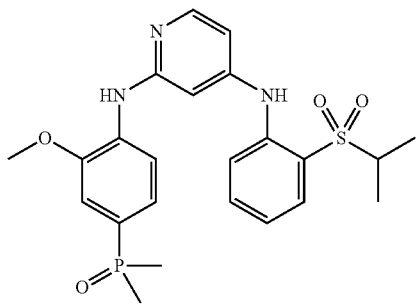 [SMILES: COc1cc(P(C)(C)=O)ccc1Nc1cc(Nc2ccccc2S(=O)(=O)C(C)C)ccn1]

2-chloro-N-[2-(propan-2-ylsulfonyl)phenyl]pyridin-4-amine

To a solution of 2-chloro-4-iodo-5-methylpyridine (2.00 mmol) in 8 mL toluene is added 1-amino-2-(isopropylsulphonyl)benzene (2.20 mmol), palladium acetate (22.4 mg, 0.0100 mmol), XANTPHOS (69.4 mg, 0.120 mmol), and cesium carbonate (2.20 mmol). The mixture is purged with nitrogen, and can be subjected to microwaves at 100° C. until formation of 2-chloro-5-methyl-N-[2-(propan-2-ylsulfonyl)phenyl]pyridin-4-amine. The reaction mixture can then be concentrated and purified by silica gel chromatography.

$N^2$-[4-(dimethylphosphoryl)-2-methoxyphenyl]-$N^4$-[2-(propan-2-ylsulfonyl)phenyl]pyridine-2,4-diamine To a solution of 2-chloro-N-[2-(propan-2-ylsulfonyl)phenyl]pyridin-4-amine (0.12 mmol) in 1 mL of 2-methoxyethanol is added 4-(dimethylphosphoryl)-2-methoxyaniline (prepared as in Example 72: 0.12 mmol) and 49 μL of 2.5 M HCl in ethanol. The mixture is heated in a sealed tube at 90° C. until formation of the desired compound. The mixture is then basified with 1N NaOH solution, and extracted with ethyl acetate. The organic layers can be combined, washed with saturated sodium chloride solution, dried with sodium sulfate, filtered and concentrated. The crude residue can be purified by prep-HPLC to afford the final compound.

Example 80

$N^2$-[4-(dimethylphosphoryl)-2-methoxyphenyl]-$N^4$-[2-(propan-2-ylsulfonyl)phenyl]-5-(trifluoromethyl)pyridine-2,4-diamine

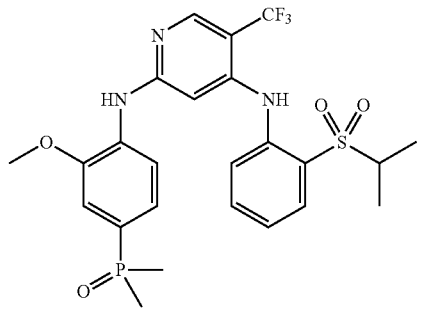 [SMILES: COc1cc(P(C)(C)=O)ccc1Nc1cc(Nc2ccccc2S(=O)(=O)C(C)C)c(C(F)(F)F)cn1]

2-chloro-N-[2-(propan-2-ylsulfonyl)phenyl]-5-(trifluoromethyl)pyridin-4-amine

To a solution of 2-chloro-4-iodo-5-(trifluoromethyl)pyridine (2.00 mmol) in 8 mL toluene is added 1-amino-2-(isopropylsulphonyl)benzene (2.20 mmol), palladium acetate (22.4 mg, 0.0100 mmol), XANTPHOS (69.4 mg, 0.120 mmol), and cesium carbonate (2.20 mmol). The mixture is purged with nitrogen, and can be subjected to microwaves at 100° C. until formation of 2-chloro-5-methyl-N-[2-(propan-2-ylsulfonyl)phenyl]pyridin-4-amine. The reaction mixture can then be concentrated and purified by silica gel chromatography.

$N^2$-[4-(dimethylphosphoryl)-2-methoxyphenyl]-5-methyl-$N^4$-[2-(propan-2-ylsulfonyl)phenyl]pyridine-2,4-diamine To a solution of 2-chloro-N-[2-(propan-2-ylsulfonyl)phenyl]-5-(trifluoromethyl)pyridin-4-amine (0.12 mmol) in 1 mL of 2-methoxyethanol is added 4-(dimethylphosphoryl)-2-methoxyaniline (prepared as in Example 72: 0.12 mmol) and 49 μL of 2.5 M HCl in ethanol. The mixture is heated in a sealed tube at 90° C. until formation of the desired compound. The mixture is then basified with 1N NaOH solution, and extracted with ethyl acetate. The organic layers can be combined, washed with saturated sodium chloride solution, dried with sodium sulfate, filtered and concentrated. The crude residue can be purified by prep-HPLC to afford the final compound.

Example 81

$N^2$-[5-(dimethylphosphoryl)-2-methoxyphenyl]-$N^4$-[2-(propan-2-ylsulfonyl)phenyl]-5-(trifluoromethyl)pyridine-2,4-diamine

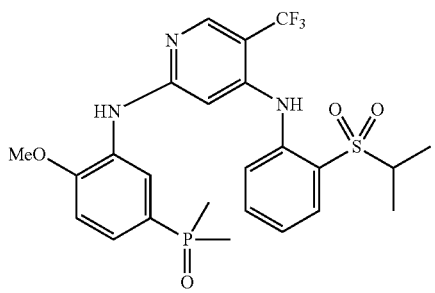 [SMILES: COc1ccc(P(C)(C)=O)cc1Nc1cc(Nc2ccccc2S(=O)(=O)C(C)C)c(C(F)(F)F)cn1]

This compound can be prepared as described in Example 80 by reacting 2-chloro-N-[2-(propan-2-ylsulfonyl)phenyl]-5-(trifluoromethyl)pyridin-4-amine with 5-(Dimethylphosphoryl)-2-methoxyaniline.

5-(Dimethylphosphoryl)-2-methoxyaniline

To a solution of 5-bromo-2-methoxyaniline (0.404 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (0.365 g, 85% yield).

Example 82

$N^2$-[4-dimethylphosphoryl)-2-methylphenyl]-$N^4$-[2-(propan-2-ylsulfonyl)phenyl]-5-(trifluoromethyl)pyridine-2,4-diamine

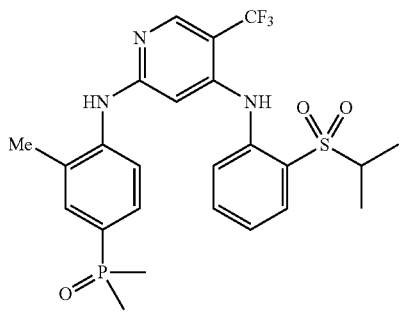 [SMILES: Cc1cc(P(C)(C)=O)ccc1Nc1cc(Nc2ccccc2S(=O)(=O)C(C)C)c(C(F)(F)F)cn1]

This compound can be prepared as described in Example 80 by reacting 2-chloro-N-[2-(propan-2-ylsulfonyl)phenyl]-5-(trifluoromethyl)pyridin-4-amine with 4-(Dimethylphosphoryl)-2-methylaniline.

4-(Dimethylphosphoryl)-2-methylaniline

To a solution of 4-bromo-2-methylaniline (0.372 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (0.313 g, 85% yield).

Example 83

$N^2$-[4-(dimethylphosphoryl)-2-ethylphenyl]-$N^4$-[2-(propan-2-ylsulfonyl)phenyl]-5-(trifluoromethyl)pyridine-2,4-diamine

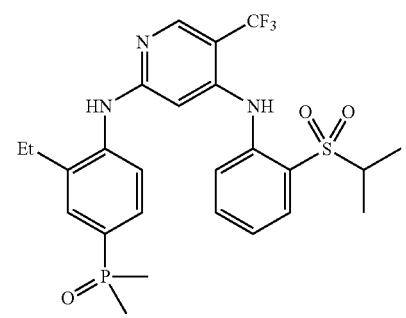 [SMILES: CCc1cc(P(C)(C)=O)ccc1Nc1cc(Nc2ccccc2S(=O)(=O)C(C)C)c(C(F)(F)F)cn1]

This compound can be prepared as described in Example 80 by reacting 2-chloro-N-[2-(propan-2-ylsulfonyl)phenyl]-5-(trifluoromethyl)pyridin-4-amine with 4-(Dimethylphosphoryl)-2-ethylaniline.

4-(Dimethylphosphoryl)-2-ethylaniline

To a solution of 4-bromo-2-ethylaniline (0.400 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (0.308 g, 78% yield).

Example 84

N²-[4-(dimethylphosphoryl)-2-(trifluoromethoxy)phenyl]-N⁴-[2-(propan-2-ylsulfonyl)phenyl]-5-(trifluoromethyl)pyridine-2,4-diamine

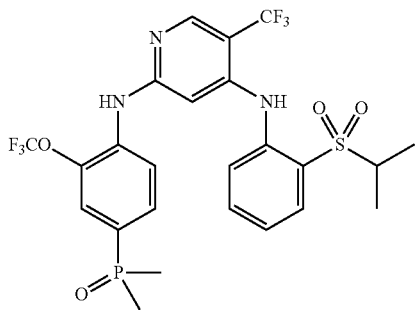 [SMILES: CC(C)S(=O)(=O)c1ccccc1Nc1cc(Nc2ccc(P(C)(C)=O)cc2OC(F)(F)F)ncc1C(F)(F)F]

This compound can be prepared as described in Example 80 by reacting 2-chloro-N-[2-(propan-2-ylsulfonyl)phenyl]-5-(trifluoromethyl)pyridin-4-amine with 4-(Dimethylphosphoryl)-2-(trifluoromethoxy)aniline.

4-(Dimethylphosphoryl)-2-(trifluoromethoxy)aniline

To a solution of 4-iodo-2-(trifluoromethoxy)aniline (0.606 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) and acidified with HCl in methanol to afford the desired product as its hydrochloride salt (0.573 g, 98% yield).

Example 85

N²-[2-chloro-4-(dimethylphosphoryl)phenyl]-N⁴-[2-(propan-2-ylsulfonyl)phenyl]-5-(trifluoromethyl)pyridine-2,4-diamine

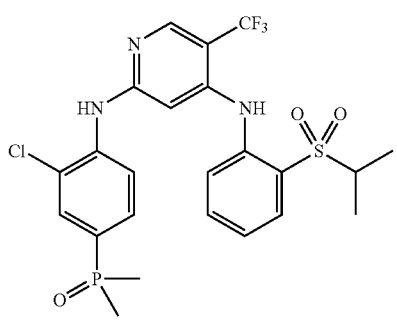 [SMILES: CC(C)S(=O)(=O)c1ccccc1Nc1cc(Nc2ccc(P(C)(C)=O)cc2Cl)ncc1C(F)(F)F]

This compound can be prepared as described in Example 80 by reacting 2-chloro-N-[2-(propan-2-ylsulfonyl)phenyl]-5-(trifluoromethyl)pyridin-4-amine with 2-chloro-4-(dimethylphosphoryl)-aniline.

2-Chloro-4-(dimethylphosphoryl)aniline

To a solution of 2-chloro-4-iodoaniline (0.507 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (0.340 g, 83% yield).

Example 86

N²-[4-(dimethylphosphoryl)-2-fluorophenyl]-N⁴-[2-(propan-2-ylsulfonyl)phenyl]-5-(trifluoromethyl)pyridine-2,4-diamine

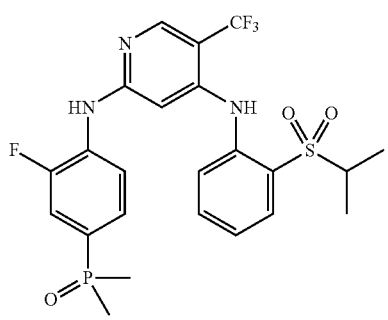 [SMILES: CC(C)S(=O)(=O)c1ccccc1Nc1cc(Nc2ccc(P(C)(C)=O)cc2F)ncc1C(F)(F)F]

This compound can be prepared as described in Example 80 by reacting 2-chloro-N-[2-(propan-2-ylsulfonyl)phenyl]-5-(trifluoromethyl)pyridin-4-amine with 4-(dimethylphosphoryl)-2-fluoroaniline.

4-(Dimethylphosphoryl)-2-fluoroaniline

To a solution of 4-bromo-2-fluoroaniline (0.380 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (73.5 mg, 20% yield).

Example 87

N-[4-(dimethylphosphoryl)-2-(propan-2-ylsulfonyl)
phenyl]-N'-{2-methoxy-4-[4-(4-methylpiperazin-1-
yl)piperidin-1-yl]phenyl}pyrimidine-4,6-diamine

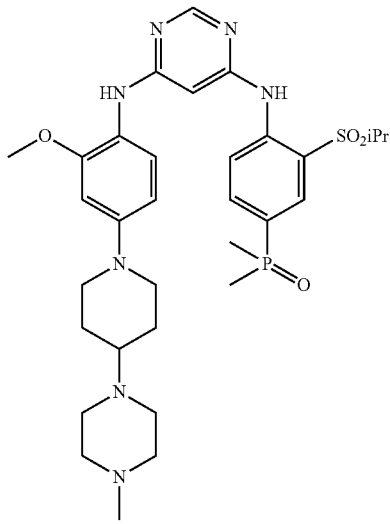

4-(dimethylphosphoryl)-2-(propan-2-ylsulfonyl)
aniline

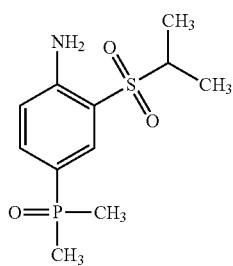 [SMILES: CC(C)S(=O)(=O)c1cc(P(C)(C)=O)ccc1N]

4-bromo-1-nitro-2-(propan-2-ylsulfanyl)benzene

At 0 degree, to a stirring solution of 4-Bromo-2-Floronitrobenzene (2.0 g, 9.1 mmol) in DCM was added Sodium 2-propane thiolate (2.0 g, 20 mmol) in two portions. The reaction mixture was warmed to room temperature and stirred overnight. The reaction mixture was filtered through a syringe filter. The product was isolated by prep-HPLC (water/Acetonitrile) as a bright yellow solid (0.8 g, 2.9 mmol, 32% yield).

4-bromo-1-nitro-2-(propan-2-ylsulfonyl)benzene

To a stirring solution of 4-bromo-1-nitro-2-(propan-2-ylsulfanyl)benzene (0.8 g, 2.9 mmol) in Acetic Acid (10 ml) was added Hydrogen Peroxide (30% aqueous solution, 0.6 mL, 5.8 mmol). The reaction mixture was heated to 110 degrees C. for 2 hours in oil bath. The reaction mixture was treated with saturated Sodium Sulfide aqueous solution and basified with saturated sodium bicarbonate solution. The mixture was extracted with Ethyl Acetate and the combined organic layers were dried over sodium sulfate. The organic solvent was removed under reduced pressure and the residue was used for the next step reaction without further purification.

Dimethyl[4-nitro-3-(propan-2-ylsulfonyl)phenyl]
phosphane oxide

To a stirring solution of 4-bromo-1-nitro-2-(propan-2-ylsulfonyl)benzene (0.44 g, 1.6 mmol) and Dimethyl Phosphine oxide (0.15 g, 1.9 mmol) in 1 mL of DMF, was added Potassium Phosphate (0.37 g, 1.8 mmol), Pd(OAc)$_2$ (18 mg, 0.08 mmol), Xanphos (55 mg, 0.10 mmol). The reaction mixture was stirred at 110 degrees C. overnight. The reaction mixture was cooled to room temperature and filtered through celite. The desired product was isolated through prep-HPLC to yield a brownish yellow solid (0.24 g, 55% yield)

4-(dimethylphosphoryl)-2-(propan-2-ylsulfonyl)
aniline

To a solution of dimethyl[4-nitro-3-(propan-2-ylsulfonyl)phenyl]phosphane oxide (0.24 g, 0.88 mmol) in Ethanol was added Pd on carbon (10% w/w, 24 mg) and stirred under hydrogen overnight. The reaction mixture was filtered and the organic solvent was removed under reduced pressure. The residue was purified by prep-HPLC to yield 100 mg of desired product (50% yield).

6-chloro-N-[4-(dimethylphosphoryl)-2-(propan-2-
ylsulfonyl)phenyl]pyrimidin-4-amine To a solution of 4,6-dichloropyrimidine (1.31 mmol) in 1 mL of DMF is added 4-(dimethylphosphoryl)-2-(propan-2-ylsulfonyl)aniline: (1.31 mmol) and potassium carbonate (0.217 g, 1.57 mmol). The mixture is heated at 110° C. until formation of the desired compound. The reaction mixture is basified with saturated sodium bicarbonate solution. The suspension is filtered and washed with ethyl acetate.

N-[4-(dimethylphosphoryl)-2-(propan-2-ylsulfonyl)
phenyl]-N'-{2-methoxy-4-[4-(4-methylpiperazin-1-
yl)piperidin-1-yl]phenyl}pyrimidine-4,6-diamine To the compound 6-chloro-N-[4-(dimethylphosphoryl)-2-(propan-2-ylsulfonyl)phenyl]pyrimidin-4-amine (0.16 mmol) in 1 mL of 2-methoxyethanol is added 2-methoxy-4-[4-(4-methylpiperazin-1-yl)piperidin-1-yl]aniline (prepared in Example 75: 0.71 g, 0.16 mmol). The mixture is stirred at 110° C. until formation of the desired compound. The mixture is basified with saturated sodium bicarbonate solution and extracted with limited amount of ethyl acetate. The compound can be purified by chromatography.

Example 88

N³-[4-(1-ethyl-4-oxido-1,4-azaphosphinan-4-yl)-2-methoxyphenyl]N⁵-[2-(propan-2-ylsulfonyl)phenyl]pyridazine-3,5-diamine

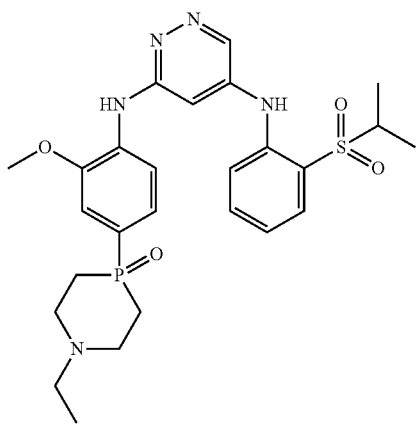 [SMILES: CCN1CCP(=O)(c2ccc(Nc3cc(Nc4ccccc4S(=O)(=O)C(C)C)cnn3)c(OC)c2)CC1]

4-(1-ethyl-4-oxido-1,4-azaphosphinan-4-yl)-2-methoxyaniline

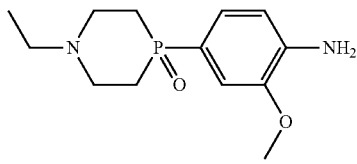 [SMILES: CCN1CCP(=O)(c2ccc(N)c(OC)c2)CC1]

Diethyl (3-methoxy-4-nitrophenyl)phosphonate

To a solution of 5-chloro-2-nitroanisole (1.00 g, 5.33 mmol) in 20 mL DMF was added diethyl phosphite (0.809 g, 5.86 mmol), palladium acetate (0.060 g, 0.27 mmol), XANTPHOS (0.185 g, 0.320 mmol), and potassium phosphate (1.24 g, 5.86 mmol). The mixture was purged with nitrogen, and subjected to microwaves at 150° C. for 20 minutes. The reaction mixture was concentrated and purified by silica gel chromatography (0-45% ethyl acetate:heptane) to afford the desired product (0.504 g, 33% yield).

(3-methoxy-4-nitrophenyl)phosphonic dichloride

To a solution of diethyl (3-methoxy-4-nitrophenyl)phosphonate (4.54 g, 15.7 mmol) in 1.2 mL DMF was added thionyl chloride (5.7 mL, 78.5 mmol). The reaction flask was equipped with a reflux condenser and the mixture was heated to reflux. After 2 h at reflux, the reaction was cooled to rt and concentrated in vacuo. The crude oil was redissolved in CH₂Cl₂ and heptane was added to precipitate the desired compound. The clear solution was decanted and the precipitate was collected and dried to afford the desired compound as a white solid (1.39 g, 33% yield).

Diethenyl(3-methoxy-4-nitrophenyl)phosphane oxide

To a solution of (3-methoxy-4-nitrophenyl)phosphonic dichloride (1.39 g, 5.15 mmol) in 15 mL THF at −78° C. under nitrogen was slowly added vinylmagnesium bromide (10.3 mL, 1.0 M in THF). After the addition was complete, the reaction stirred at −78° C. for an additional hour. The cold reaction mixture was quenched by the addition of saturated NH₄Cl (20 mL) and the mixture was extracted with CH₂Cl₂. The combined organic layers were washed with 1 M NaOH, brine, and dried over MgSO₄. The organic extracts were filtered and concentrated to provide Diethenyl(3-methoxy-4-nitrophenyl)phosphane oxide (0.982 g, 75%).

1-ethyl-4-(3-methoxy-4-nitrophenyl)-1,4-azaphosphinane 4-oxide

Diethenyl(3-methoxy-4-nitrophenyl)phosphane oxide (0.480 g, 1.94 mmol), ethylamine hydrochloride (0.174 g, 2.12 mmol), and 1 N NaOH (2 mL) were dissolved in 50% aqueous THF (5 mL) and heated to 105° C. under nitrogen. After one hour, another portion of benzylamine was added to the reaction mixture. The reaction mixture was refluxed for an additional 2 h, and then cooled to rt. The reaction mixture was partitioned between saturated aqueous NaHCO₃ and CH₂Cl₂. The aqueous phase was washed once with CH₂Cl₂ and the organic layers were combined. The organic extracts were washed with brine, dried over MgSO₄, filtered, and concentrated. The residue was purified by silica gel chromatography (0-10% 7N ammonia in methanol:dichloromethane) to afford the compound (0.267 g, 46% yield).

4-(1-ethyl-4-oxido-1,4-azaphosphinan-4-yl)-2-methoxyaniline

To a solution of 1-ethyl-4-(3-methoxy-4-nitrophenyl)-1,4-azaphosphinane 4-oxide (0.267 g, 0.895 mmol) in 5 mL ethanol was added 10% Pd/C (27 mg) and 2.5 M HCl in ethanol (1.43 mL). The flask was equipped with a septum, evacuated, and refilled with hydrogen. The flask was equipped with a hydrogen balloon and the reaction stirred for 3 h. The flask was then evacuated and refilled with nitrogen. The reaction mixture was filtered through Celite and concentrated to provide the crude compound as the hydrochloride salt, which was used without purification.

N³-[4-(1-ethyl-4-oxido-1,4-azaphosphinan-4-yl)-2-methoxyphenyl]-N⁵-[2-(propan-2-ylsulfonyl)phenyl]pyridazine-3,5-diamine To a solution of 6-chloro-N-[2-(propan-2-ylsulfonyl)phenyl]pyridazin-4-amine (prepared in Example 73: 0.02 mmol) and 4-(1-ethyl-4-oxido-1,4-azaphosphinan-4-yl)-2-methoxyaniline (0.7 mmol) in 1 mL of 2-Methoxy ethanol, is added 1 mL of 2.5M HCl in Ethanol. The reaction mixture is heated in a sealed tube at 140 degree until formation of the desired compound. The reaction mixture is filtered through a syringe filter and can be purified by Prep-HPLC.

Example 89

N³-[2-methoxy-4-(4-methyl-4-oxido-1,4-azaphosphinan-1-yl)phenyl]-N⁵-[2-(propan-2-ylsulfonyl)phenyl]pyridazine-3,5-diamine

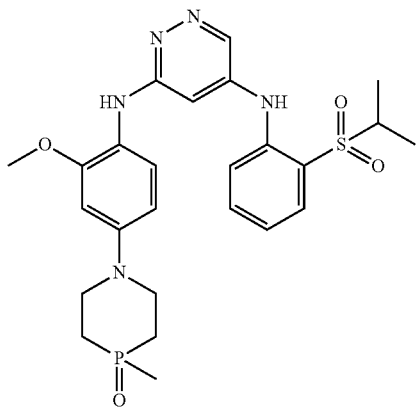 [SMILES: COc1cc(N2CCP(C)(=O)CC2)ccc1Nc1cc(Nc2ccccc2S(=O)(=O)C(C)C)cnn1]

2-methoxy-4-(4-methyl-4-oxido-1,4-azaphosphinan-1-yl)aniline

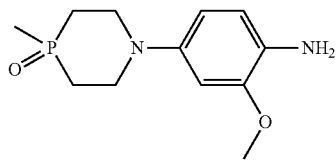 [SMILES: COc1cc(N2CCP(C)(=O)CC2)ccc1N]

1-benzyl-4-methyl-1,4-azaphosphinane 4-oxide

To a solution of methylphosphonic dischloride (10.0 g, 75.2 mmol) in CH₂Cl₂ at −78° C., was added vinylmagnesium bromide (175 mL, 1.0 M in THF) via addition funnel over 4 h. The solution was warmed to 0° C. and quenched with a minimum amount of saturated NH₄Cl. The mixture was filtered through a pad of silica gel and silica was extracted with 10% 7N ammonia in methanol:dichloromethane. The solution was concentrated under reduced pressure to afford methyl divinyl phosphine oxide as a viscous, yellow oil that was used without purification.

A solution of methyl divinyl phosphine oxide (1.16 g, 10.0 mmol) and benzylamine (1.20 mL, 11.0 mmol) in 1:1 THF/water (25 mL) was heated at reflux for 16 h. The reaction mixture was concentrated in vacuo and the residue was purified by silica gel chromatography (0-10% 7N ammonia in methanol: dichloromethane) to afford 1-benzyl-4-methyl-[1,4]azaphosphinane-4-oxide as a white solid (1.57 g, 70% yield).

4-methyl-[1,4]azaphosphinane-4-oxide

A flask was charged with 1-benzyl-4-methyl-[1,4]azaphosphinane-4-oxide (1.00 g, 4.47 mmol) and 10% Pd/C (100 mg). The flask was evacuated and filled with nitrogen. Anhydrous methanol (18 mL) was added to the flask and the flask was equipped with a reflux condenser with a nitrogen inlet. Ammonium formate (2.25 g, 35.8 mmol) was added in one portion at room temperature. The resulting mixture was stirred at reflux for 2 h. The reaction was filtered through a Celite pad and the Celite was washed with 2×5 mL methanol. The combined filtrate and washing was evaporated in vacuo. The crude residue was purified by silica gel chromatography (0-10% 7N ammonia in methanol:dichloromethane) to afford 4-methyl-[1,4]azaphosphinane-4-oxide as a yellow gel (0.589 g, 99% yield).

1-(3-methoxy-4-nitrophenyl)-4-methyl-1,4-azaphosphinane 4-oxide

A mixture of 4-methyl-[1,4]azaphosphinane-4-oxide (133 mg, 1.00 mmol), 5-fluoro-2-nitroanisole (340 mg, 2.00 mmol), K₂CO₃ (345 mg, 2.50 mmol), and DMF (5 mL) was heated to 50° C. After 2 h, the reaction mixture was concentrated and purified by silica gel chromatography (0-5% 7N ammonia in methanol:dichloromethane) to afford 1-(3-methoxy-4-nitrophenyl)-4-methyl-1,4-azaphosphinane 4-oxide as a bright yellow solid (272 mg, 96% yield).

2-methoxy-4-(4-methyl-4-oxido-1,4-azaphosphinan-1-yl)aniline

To a pressure vessel was added 1-(3-methoxy-4-nitrophenyl)-4-methyl-1,4-azaphosphinane 4-oxide (272 mg, 0.960 mmol), ethanol (5 mL), and 10% Pd/C (50 mg). The vessel was connected to a Parr apparatus, evacuated, and refilled with nitrogen. The vessel was then evacuated and filled with hydrogen gas to a pressure of 50 psi. The reaction mixture was shaken under 50 psi for 4 h. The mixture was filtered through Celite to a flask containing HCl in ethanol. Concentration of the filtrate afforded 2-methoxy-4-(4-methyl-4-oxido-1,4-azaphosphinan-1-yl)aniline as a gray solid (211 mg, 87% yield).

N³-[2-methoxy-4-(4-methyl-4-oxido-1,4-azaphosphinan-1-yl)phenyl]-N⁵-[2-(propan-2-ylsulfonyl)phenyl]pyridazine-3,5-diamine To a solution of 6-chloro-N-[2-(propan-2-ylsulfonyl)phenyl]pyridazin-4-amine (prepared in Example 73: 0.02 mmol) and 2-methoxy-4-(4-methyl-4-oxido-1,4-azaphosphinan-1-yl)aniline (0.7 mmol) in 1 mL of 2-Methoxy ethanol, is added 1 mL of 2.5M HCl in Ethanol. The reaction mixture is heated in a sealed tube at 140 degree until formation of the desired compound. The reaction mixture is filtered through a syringe filter and can be purified by Prep-HPLC.

Example 90

N³-{2-methoxy-4-[4-(4-methyl-4-oxido-1,4-aza-phosphinan-1-yl)piperidin-1-yl]phenyl}-N⁵-[2-(pro-pan-2-ylsulfonyl)phenyl]pyridazine-3,5-diamine

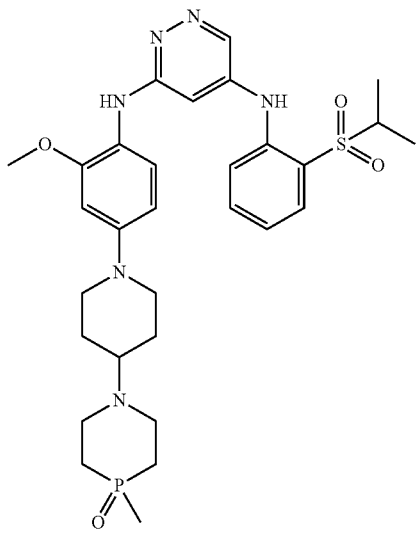 [SMILES: COc1cc(N2CCC(N3CCP(C)(=O)CC3)CC2)ccc1Nc1cc(Nc2ccccc2S(=O)(=O)C(C)C)cnn1]

2-methoxy-4-[4-(4-methyl-4-oxido-1,4-azaphosphi-nan-1-yl)piperidin-1-yl]aniline

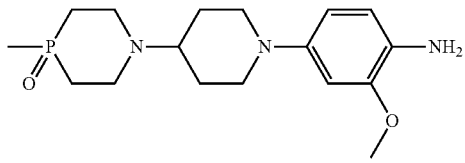 [SMILES: COc1cc(N2CCC(N3CCP(C)(=O)CC3)CC2)ccc1N]

tert-butyl 4-(4-methyl-4-oxido-1,4-azaphosphinan-1-yl)piperidine-1-carboxylate

A solution of methyl divinyl phosphine oxide (140 mg, 1.21 mmol) and 1-Boc-4-aminopiperidine (265 mg, 1.33 mmol) in 1:1 THF/water (3 mL) was heated at reflux for 16 h. The reaction mixture was concentrated in vacuo and the residue was purified by silica gel chromatography (0-10% 7N ammonia in methanol:dichloromethane) to afford the desired compound as a white solid (178 mg, 38% yield).

1-[1-(3-methoxy-4-nitrophenyl)piperidin-4-yl]-4-methyl-1,4-azaphosphinane 4-oxide To a stirring solution of tert-butyl 4-(4-methyl-4-oxido-1, 4-azaphosphinan-1-yl)piperidine-1-carboxylate (178 mg, 0.563 mmol) in CH₂Cl₂ (2 mL) was added trifluoroacetic acid (0.5 mL). After 20 min, the solution was concentrated and the resulting residue was redissolved in DMF (2 mL). Potassium carbonate (160 mg, 1.16 mmol) was added portionwise to the stirring solution followed by 5-fluoro-2-nitroanisole (158 mg, 0.930 mmol). The reaction mixture was heated to 50° C. After 2 h, the reaction mixture was concentrated and the residue was purified by silica gel chromatography (0-10% 7N ammonia in methanol:dichloromethane) to afford the compound as a bright yellow solid (176 mg, 86% yield).

2-methoxy-4-[4-(4-methyl-4-oxido-1,4-azaphosphi-nan-1-yl)piperidin-1-yl]aniline

To a pressure vessel was added 1-[1-(3-methoxy-4-nitro-phenyl)piperidin-4-yl]-4-methyl-1,4-azaphosphinane 4-ox-ide (176 mg, 0.485 mmol), ethanol (5 mL), and 10% Pd/C (50 mg). The vessel was connected to a Parr apparatus, evacuated, and refilled with nitrogen. The vessel was then evacuated and filled with hydrogen gas to a pressure of 50 psi. The reaction mixture was shaken under 50 psi for 4 h. The mixture was filtered through Celite to a flask containing HCl in ethanol. Concentration of the filtrate afforded the compound as a gray solid (178 mg, 98% yield).

N³-{2-methoxy-4-[4-(4-methyl-4-oxido-1,4-aza-phosphinan-1-yl)piperidin-1-yl]phenyl}-N⁵-[2-(pro-pan-2-ylsulfonyl)phenyl]pyridazine-3,5-diamine To a solution of 6-chloro-N-[2-(propan-2-ylsulfonyl)phe-nyl]pyridazin-4-amine (prepared in Example 73: 0.02 mmol) and 2-methoxy-4-[4-(4-methyl-4-oxido-1,4-azaphosphinan-1-yl)piperidin-1-yl]aniline (0.7 mmol) in 1 mL of 2-Methoxy ethanol, is added 1 mL of 2.5M HCl in Ethanol. The reaction mixture is heated in a sealed tube at 140 degree until forma-tion of the desired compound. The reaction mixture is filtered through a syringe filter and can be purified by Prep-HPLC.

Example 91

N³-[4-(diethylphosphoryl)-2-methoxyphenyl]-N⁵-[2-(propan-2-ylsulfonyl)phenyl]pyridazine-3,5-diamine

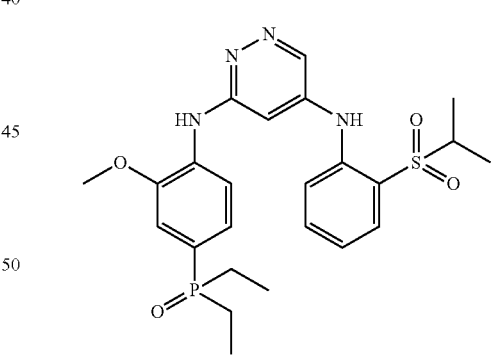

4-(Dipropylphosphoryl)-2-methoxyaniline

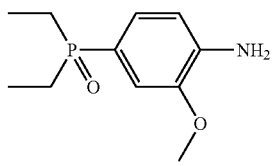

To a solution of 4-bromo-2-methoxyaniline (0.100 g, 0.495 mmol) in 2 mL DMF was added dipropylphosphine oxide (0.0730 g, 0.544 mmol), palladium acetate (5.6 mg, 0.025 mmol), XANTPHOS (17.2 mg, 0.030 mmol), and potassium phosphate (0.116 g, 0.544 mmol). The mixture was purged with nitrogen, and subjected to microwaves at 150° C. for 20 minutes. The reaction mixture was concentrated and purified by silica gel chromatography (0-12% 7N ammonia in methanol:dichloromethane) and the fractions were concentrated. The residue was acidified with 2.5 M HCl in ethanol and the solution was concentrated to provide 4-(dipropylphosphoryl)-2-methoxyaniline as the hydrochloride salt (0.132 g, 91% yield).

$N^3$-[4-(diethylphosphoryl)-2-methoxyphenyl]-$N^5$-[2-(propan-2-ylsulfonyl)phenyl]pyridazine-3,5-diamine To a solution of 6-chloro-N-[2-(propan-2-ylsulfonyl)phenyl]pyridazin-4-amine (prepared in Example 73: 0.02 mmol) and 4-(Dipropylphosphoryl)-2-methoxyaniline (0.7 mmol) in 1 mL of 2-Methoxy ethanol, is added 1 mL of 2.5M HCl in Ethanol. The reaction mixture is heated in a sealed tube at 140 degree until formation of the desired compound. The reaction mixture is filtered through a syringe filter and can be purified by Prep-HPLC.

Example 92

N-[4-(dimethylphosphoryl)phenyl]-4-(4-methylpiperazin-1-yl)-1,3,5-triazin-2-amine

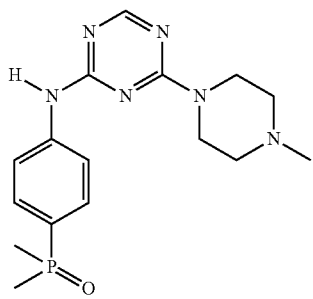

4-chloro-N-[4-(dimethylphosphoryl)phenyl]-1,3,5-triazin-2-amine

A suspension of 4-amino-dimethylphenylphosphine oxide (3.7 g, 2.2 mmol) in 15 mL of N,N-Dimethylacetamide and 3.6 mL of Diisopropylethylamine, can be stirred at room temperature for 15 minutes until a clear solution is obtained. 2,4-Dichloro-1,3,5-triazine (2.6 mmol) is added in four portions over 5 minutes. The reaction mixture is stirred at 60 degrees for 1 hour. The reaction mixture is cooled to room temperature, filtered and purified by prep-HPLC.

N-[4-(dimethylphosphoryl)phenyl]-4-(4-methylpiperazin-1-yl)-1,3,5-triazin-2-amine To a solution of 4-chloro-N-[4-(dimethylphosphoryl)phenyl]-1,3,5-triazin-2-amine (0.072 mmol) in 1.5 mL of ethanol is added 10 µL of triethylamine and 1-Methyl piperazine (7.2 mg, 0.072 mmol). The mixture can be microwaved at 120 degrees until formation of the desired compound. The reaction mixture is filtered through a syringe filter and purified by prep-HPLC.

Example 93

N-[4-(dimethylphosphoryl)phenyl]-N'-(tricyclo[3.3.1.1$^{3,7}$]dec-1-yl)-1,3,5-triazine-2,4-diamine

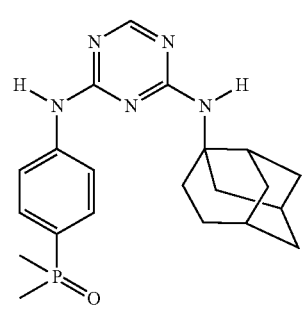 [SMILES: CP(C)(=O)c1ccc(Nc2ncnc(NC34CCC5CC(CC3C5)C4)n2)cc1]

To a solution of 4-chloro-N-[4-(dimethylphosphoryl)phenyl]-1,3,5-triazin-2-amine (prepared as in Example 92: 0.078 mmol) in 1.5 mL of ethanol is added 10 µL of triethylamine and 1-Adamantanamine (12 mg, 0.078 mmol). The mixture can be microwaved at 120 degrees until formation of the desired compound. The reaction mixture is filtered through a syringe filter and purified by prep-HPLC.

Example 94

N-[4-(dimethylphosphoryl)phenyl]-N'-(morpholin-4-ylmethyl)-1,3,5-triazine-2,4-diamine

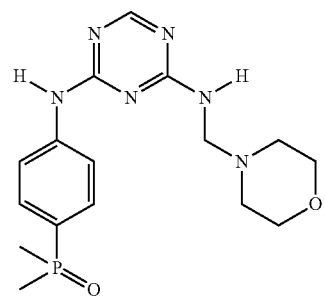 [SMILES: CP(C)(=O)c1ccc(Nc2ncnc(NCN3CCOCC3)n2)cc1]

To a solution of 4-chloro-N-[4-(dimethylphosphoryl)phenyl]-1,3,5-triazin-2-amine (prepared as in Example 92: 0.12 mmol) in 2 mL of ethanol is added 50 µL of triethylamine and 4-(2-aminoethyl)morpholine (15 mg, 0.12 mmol). The mixture can be microwaved at 120 degrees until formation of the desired compound. The reaction mixture is filtered through a syringe filter and purified by prep-HPLC.

Example 95

4-{2-[(4-{[4-(dimethylphosphoryl)phenyl]amino}-1,3,5-triazin-2-yl)amino]ethyl}benzene sulfonamide

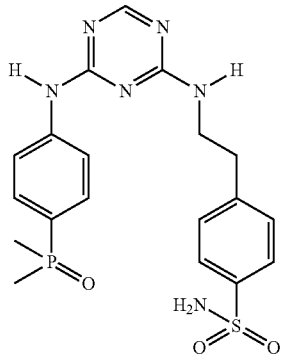 [SMILES: CP(C)(=O)c1ccc(Nc2ncnc(NCCc3ccc(S(N)(=O)=O)cc3)n2)cc1]

To a solution of 4-chloro-N-[4-(dimethylphosphoryl)phenyl]-1,3,5-triazin-2-amine (prepared as in Example 92: 0.12 mmol) in 2 mL of ethanol is added 50 μL of triethylamine and 4-(2-aminoethyl)benzene-sulfonamide (23 mg, 0.12 mmol). The mixture can be microwaved at 120 degrees until formation of the desired compound. The reaction mixture is filtered through a syringe filter and purified by prep-HPLC.

Example 96

N-[4-(dimethylphosphoryl)phenyl]-N'-(tetrahydrofuran-2-yl)-1,3,5-triazine-2,4-diamine

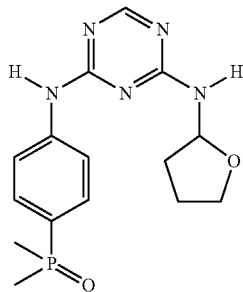 [SMILES: CP(C)(=O)c1ccc(Nc2ncnc(NC3CCCO3)n2)cc1]

To a solution of 4-chloro-N-[4-(dimethylphosphoryl)phenyl]-1,3,5-triazin-2-amine (prepared as in Example 92: 0.12 mmol) in 2 mL of ethanol is added 50 μL of triethylamine and (s)-3-aminotetrahydrofuran hydrochloride salt (14 mg, 0.12 mmol). The mixture can be microwaved at 120 degrees until formation of the desired compound. The reaction mixture is filtered through a syringe filter and purified by prep-HPLC.

Example 97

N-[4-(dimethylphosphoryl)phenyl]-N'-(hexahydro-cyclopenta[c]pyrrol-2(1H)-yl)-1,3,5-triazine-2,4-diamine

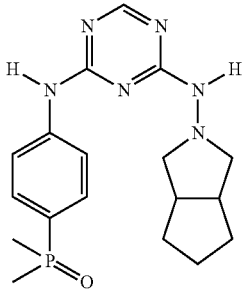 [SMILES: CP(C)(=O)c1ccc(Nc2ncnc(NN3CC4CCCC4C3)n2)cc1]

To a solution of 4-chloro-N-[4-(dimethylphosphoryl)phenyl]-1,3,5-triazin-2-amine (prepared as in Example 92: 0.12 mmol) in 2 mL of ethanol is added 50 μL of triethylamine and 3-Amino-3-azabicyclo-[3,3,0]octane hydrochloride salt (19 mg, 0.12 mmol). The mixture is microwaved at 120 degrees until formation of the desired compound. The reaction mixture is filtered through a syringe filter and purified by prep-HPLC.

Example 98

N-[4-(dimethylphosphoryl)phenyl]-N'-(morpholin-4-yl)-1,3,5-triazine-2,4-diamine

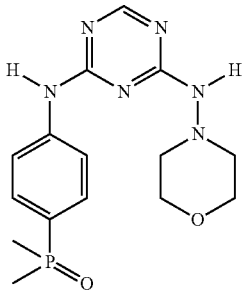 [SMILES: CP(C)(=O)c1ccc(Nc2ncnc(NN3CCOCC3)n2)cc1]

To a solution of 4-chloro-N-[4-(dimethylphosphoryl)phenyl]-1,3,5-triazin-2-amine (prepared as in Example 92: 0.12 mmol) in 2 mL of ethanol is added 50 μL of triethylamine and 4-Aminomorpholine (12 mg, 0.12 mmol). The mixture is microwave at 120 degrees until formation of the desired compound. The reaction mixture is filtered through a syringe filter and purified by prep-HPLC.

Example 99

N-[4-(dimethylphosphoryl)phenyl]-4-(4-phenylpiperazin-1-yl)-1,3,5-triazin-2-amine

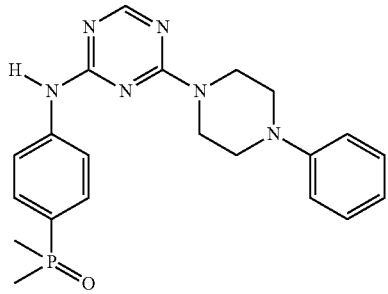 [SMILES: CP(C)(=O)c1ccc(Nc2ncnc(N3CCN(c4ccccc4)CC3)n2)cc1]

To a solution of 4-chloro-N-[4-(dimethylphosphoryl)phenyl]-1,3,5-triazin-2-amine (prepared as in Example 92: 0.12 mmol) in 2 mL of ethanol is added 50 µL of triethylamine and 1-Phenylpiperazine (19 mg, 0.12 mmol). The mixture is microwaved at 120 degrees until formation of the desired compound. The reaction mixture is filtered through a syringe filter and purified by prep-HPLC.

Example 100

N-[4-(dimethylphosphoryl)phenyl]-N %[2-(1H-indol-3-yl)ethyl]-1,3,5-triazine-2,4-diamine

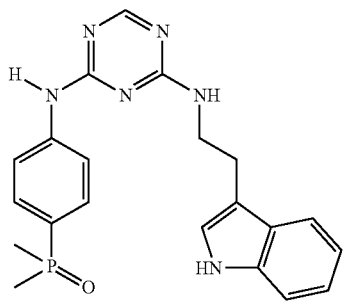 [SMILES: CP(C)(=O)c1ccc(Nc2ncnc(NCCc3c[nH]c4ccccc34)n2)cc1]

To a solution of 4-chloro-N-[4-(dimethylphosphoryl)phenyl]-1,3,5-triazin-2-amine (prepared as in Example 92: 0.12 mmol) in 2 mL of ethanol is added 50 µL of triethylamine and Tryptamine (18 mg, 0.12 mmol). The mixture is microwaved at 120 degrees until formation of the desired compound. The reaction mixture is filtered through a syringe filter and purified by prep-HPLC.

Example 101

N-[4-(dimethylphosphoryl)phenyl]-N'-(4-methylpiperazin-1-yl)-1,3,5-triazine-2,4-diamine

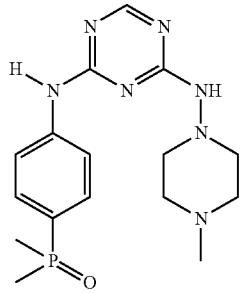 [SMILES: CN1CCN(Nc2ncnc(Nc3ccc(P(C)(C)=O)cc3)n2)CC1]

To a solution of 4-chloro-N-[4-(dimethylphosphoryl)phenyl]-1,3,5-triazin-2-amine (prepared as in Example 92: 0.12 mmol) in 2 mL of ethanol is added 50 µL of triethylamine and 1-Amino-4-methyl-piperazine (13 mg, 0.12 mmol). The mixture is microwaved at 120 degrees until formation of the desired compound. The reaction mixture is filtered through a syringe filter and purified by prep-HPLC.

Example 102

6-chloro-N-[4-(dimethylphosphoryl)phenyl]-N'-(tricyclo[3.3.1.1$^{3,7}$]dec-1-ylmethyl)-1,3,5-triazine-2,4-diamine

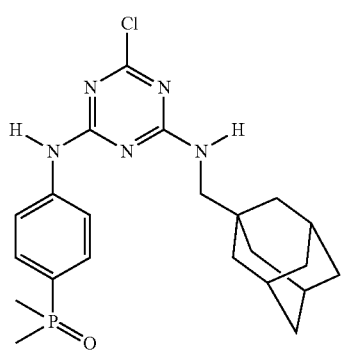 [SMILES: CP(C)(=O)c1ccc(Nc2nc(Cl)nc(NCC34CC5CC(CC(C5)C3)C4)n2)cc1]

4,6-dichloro-N-[4-(dimethylphosphoryl)phenyl]-1,3,5-triazin-2-amine

A suspension of 4-amino-dimethylphenylphosphine oxide (3.7 g, 2.2 mmol) in 15 mL of N,N-Dimethylformamide and 3.6 mL of Diisopropylethylamine is cooled to 0° C. 2,4,6-trichloro-1,3,5-triazine (2.6 mmol) is added in four portions over 5 minutes. The reaction mixture is warmed up to room temperature and stirred until formation of the desired compound. The reaction mixture is filtered and purified by prep-HPLC.

6-chloro-N-[4-(dimethylphosphoryl)phenyl]-N'-(tricyclo[3.3.1.1³,⁷]dec-1-ylmethyl)-1,3,5-triazine-2,4-diamine To a solution of 4,6-dichloro-N-[4-(dimethylphosphoryl)phenyl]-1,3,5-triazin-2-amine (0.072 mmol) in 1.5 mL of ethanol is added 10 μL of triethylamine and 1-(1-adamantyl)-methanamine (7.2 mg, 0.072 mmol). The mixture can be microwaved at 120 degrees for 20 minutes. The reaction mixture is filtered through a syringe filter and purified by prep-HPLC.

Example 103

6-chloro-N-[4-(dimethylphosphoryl)phenyl]-N'-[4-(4-methylpiperazin-1-yl)benzyl]-1,3,5-triazine-2,4-diamine

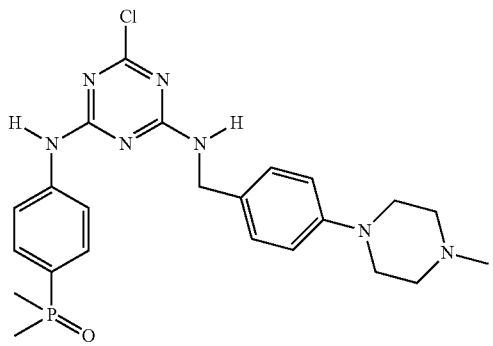 [SMILES: CN1CCN(c2ccc(CNc3nc(Cl)nc(Nc4ccc(P(C)(C)=O)cc4)n3)cc2)CC1]

To a solution of 4,6-dichloro-N-[4-(dimethylphosphoryl)phenyl]-1,3,5-triazin-2-amine (prepared as in Example 102: 0.12 mmol) in 2 mL of ethanol is added 50 μL of triethylamine and 4-(4-methylpiperazine)-benzylamine (24 mg, 0.12 mmol). The mixture is microwaved at 120 degrees until formation of the desired compound. The reaction mixture is filtered through a syringe filter and purified by prep-HPLC.

Example 104

6-chloro-N-(3,5-dimethylphenyl)-N'-[4-(dimethylphosphoryl)phenyl]-1,3,5-triazine-2,4-diamine

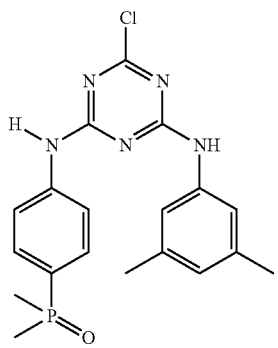 [SMILES: Cc1cc(C)cc(Nc2nc(Cl)nc(Nc3ccc(P(C)(C)=O)cc3)n2)c1]

To a solution of 4,6-dichloro-N-[4-(dimethylphosphoryl)phenyl]-1,3,5-triazin-2-amine (prepared as in Example 102: 0.12 mmol) in 2 mL of ethanol is added 50 μL of triethylamine and 3,5-dimethylaniline (24 mg, 0.12 mmol). The mixture is microwaved at 120 degrees until formation of the desired compound. The reaction mixture is filtered through a syringe filter and purified by prep-HPLC.

Example 105

6-chloro-N³-[4-(dimethylphosphoryl)-2-methoxyphenyl]-N⁵-phenyl-1,2,4-triazine-3,5-diamine

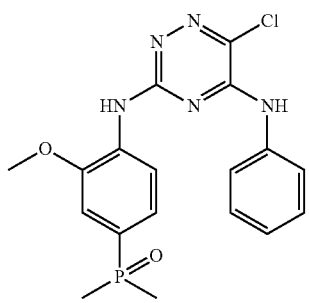 [SMILES: COc1cc(P(C)(C)=O)ccc1Nc1nnc(Cl)c(Nc2ccccc2)n1]

3,6-dichloro-N-phenyl-1,2,4-triazin-5-amine

To a solution of Aniline (205 mg, 2.2 mmol) and 3,5,6-trichloro-1,2,4-triazine (2.7 mmol) in $CH_2Cl_2$, is added triethylamine (3 mmol). The reaction mixture is stirred at room temperature until formation of the desired product. Solvent is removed under reduced pressure. The residue can be purified by silica gel flash chromatography.

(3-methoxy-4-nitrophenyl)(dimethyl)phosphane oxide

To a solution of 5-Chloro-2-nitroanisole (0.5 g, 2.67 mmol) in 5 mL of DMF was added dimethylphosphine oxide (0.229 g, 2.93 mmol), palladium acetate (30 mg, 0.13 mmol), XANTPHOS (0.092 g, 0.16 mmol) and potassium phosphate (0.623 g, 2.93 mmol). The mixture was purged with argon, and heated at 120° C. for 18 h. The reaction mixture was basified with saturated sodium bicarbonate solution, and extracted with ethyl acetate. The organic layer was concentrated and purified by prep-HPLC to give the final product (0.16 g, 30% yield). MS/ES+: m/z=229.

4-(dimethylphosphoryl)-2-methoxyaniline

To a solution of (3-methoxy-4-nitrophenyl)(dimethyl)phosphane oxide (0.1 g, 0.44 mmol) in 5 mL of EtOH was added 10% weight of palladium on carbon (0.2 g). The mixture was purged with argon, and hydrogenated under 30 psi for 2 h. The mixture was passed through Celite to a flask containing HCl in ethanol. Concentration of the filtrate gave the final product (0.088 g, 86% yield). MS/ES+: m/z=199.

6-chloro-N³-[4-(dimethylphosphoryl)-2-methoxyphenyl]-N⁵-phenyl-1,2,4-triazine-3,5-diamine A mixture of 3,6-dichloro-N-phenyl-1,2,4-triazin-5-amine (1 mmol), 4-(dimethylphosphoryl)-2-methoxyaniline (1 mmol) and camphorsulfonic acid (0.7 equiv.), is refluxed for 20-48 h in 2-propanol. The reaction mixture is allowed to cool to room temperature, dissolved in dichloromethane and washed with an aqueous solution of $Na_2CO_3$. The dichloromethane extract is dried over MgSO₄ and evaporated. The crude product is purified by Prep-HPLC.

Example 106

6-chloro-N³-[4-(dimethylphosphoryl)-2-methoxyphenyl]-N⁵-[2-(propan-2-ylsulfonyl)phenyl]-1,2,4-triazine-3,5-diamine

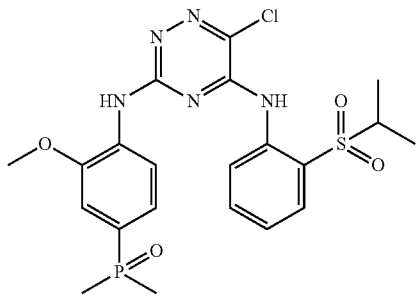 [SMILES: COc1cc(P(C)(C)=O)ccc1Nc1nnc(Cl)c(Nc2ccccc2S(=O)(=O)C(C)C)n1]

3,6-dichloro-N-[2-(propan-2-ylsulfonyl)phenyl]-1,2,4-triazin-5-amine

To a solution of 1-Amino-2-(isopropylsulphonyl)benzene (350 mg, 1.6 mmol) and 3,5,6-trichloro-1,2,4-triazine (1.6 mmol) in CH₂Cl₂, is added triethylamine (2 mmol). The reaction mixture is allowed to cool to room temperature, dissolved in dichloromethane and washed with an aqueous solution of Na₂CO₃. The dichloromethane extract is dried over MgSO₄ and evaporated. The crude product is purified by Prep-HPLC.

6-chloro-N⁴-[4-(dimethylphosphoryl)-2-methoxyphenyl]-N⁵-[2-(propan-2-ylsulfonyl)phenyl]-1,2,4-triazine-3,5-diamine A mixture of 3,6-dichloro-N-[2-(propan-2-ylsulfonyl)phenyl]-1,2,4-triazin-5-amine (1 mmol), 4-(dimethylphosphoryl)-2-methoxyaniline (prepared as in Example 105: 1 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of Na₂CO₃. The dichloromethane extract is dried over MgSO₄ and evaporated. The crude product is purified by Prep-HPLC.

Example 107

6-chloro-N-[4-(dimethylphosphoryl)-2-methoxyphenyl]-5-{[3-fluoro-5-(trifluoromethyl)phenyl]sulfanyl}-1,2,4-triazin-3-amine

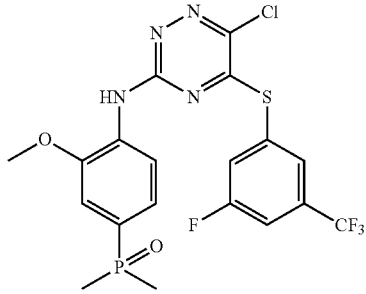 [SMILES: COc1cc(P(C)(C)=O)ccc1Nc1nnc(Cl)c(Sc2cc(F)cc(C(F)(F)F)c2)n1]

3,6-dichloro-5-{[3-fluoro-5-(trifluoromethyl)phenyl]sulfanyl}-1,2,4-triazine

To a solution of 3,5,6-trichloro-1,2,4-triazine (3 mmol) in dry THF (30 mL) at −78° C. under nitrogen atmosphere is added 3-fluoro-5-(trifluoromethyl)benzenethiol (3 mmol) and sodium carbonate (3 mmol). The reaction is allowed to reach room temperature and is stirred at room temperature until formation of the desired compound. The solvent is evaporated. The residue is suspended in water and extracted with CH₂Cl₂. The dichloromethane solution is dried over MgSO₄ and evaporated. The residue is chromatographed on a silica gel column.

6-chloro-N-[4-(dimethylphosphoryl)-2-methoxyphenyl]-5-{[3-fluoro-5-(trifluoromethyl)phenyl]sulfanyl}-1,2,4-triazin-3-amine A mixture of 3,6-dichloro-5-{[3-fluoro-5-(trifluoromethyl)phenyl]sulfanyl}-1,2,4-triazine (0.7 mmol), 4-(dimethylphosphoryl)-2-methoxyaniline (prepared as in Example 105: 15 mg, 0.7 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of Na₂CO₃. The dichloromethane extract is dried over MgSO₄ and evaporated. The crude product is purified by Prep-HPLC.

Example 108

6-chloro-N⁵-[4-(dimethylphosphoryl)phenyl]-N³-{2-methoxy-4-[4-(4-methylpiperazin-1-yl)piperidin-1-yl]phenyl}-1,2,4-triazine-3,5-diamine

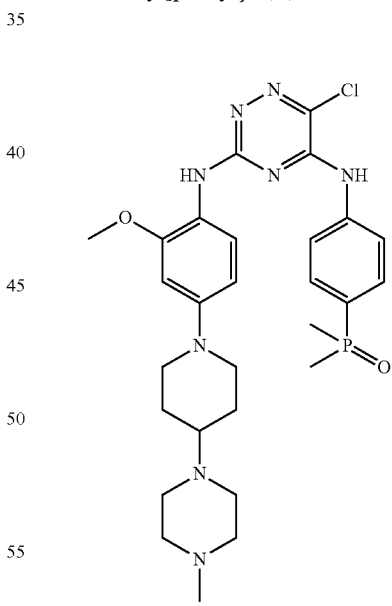

3,6-dichloro-N-[4-(dimethylphosphoryl)phenyl]-1,2,4-triazin-5-amine

To a solution of 4-amino-dimethylphenylphosphine oxide (1.6 mmol) and 3,5,6-trichloro-1,2,4-triazine (1.6 mmol) in CH₂Cl₂, is added triethylamine (2 mmol). The reaction mixture is allowed to cool to room temperature, dissolved in dichloromethane and washed with an aqueous solution of

1-[1-(3-methoxy-4-nitrophenyl)piperidin-4-yl]-4-methylpiperazine

To a solution of 5-fluoro-2-nitroanisole (0.5 g, 2.92 mmol) in 3 mL of DMF was added 1-methyl-4-(piperidin)piperazine (0.536 g, 2.92 mmol) and potassium carbonate (0.808, 5.84 mmol). The mixture was heated at 120° C. for 18 h. The mixture was basified with saturated sodium bicarbonate solution and extracted with ethyl acetate. The organic layer was purified by chromatography to give final product as yellow solid (0.95 g, 95% yield). MS/ES+: m/z=334.

2-methoxy-4-[4-(4-methylpiperazin-1-yl)piperidin-1-yl]aniline

The a solution of 1-[1(3-methoxy-4-nitrophenyl)piperidin-4-yl]-4-methylpiperazine (0.3 g, 0.90 mmol) in 10 mL of ethanol purged with argon was added 10% Palladium on carbon (0.060 g). The hydrogenation was finished under 30 psi after 4 h. The mixture was passed through Celite to a flask containing HCl in ethanol. Concentration of the filtrate gave the final product (0.15 g, 88% yield). MS/ES+: m/z=334.

6-chloro-$N^5$-[4-(dimethylphosphoryl)phenyl]-$N^3$-{2-methoxy-4-[4-(4-methylpiperazin-1-yl)piperidin-1-yl]phenyl}-1,2,4-triazine-3,5-diamine A mixture of 3,6-dichloro-N-[4-(dimethylphosphoryl)phenyl]-1,2,4-triazin-5-amine (0.7 mmol), 2-methoxy-4-[4-(4-methylpiperazin-1-yl)piperidin-1-yl]aniline (0.7 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of $Na_2CO_3$. The dichloromethane extract is dried over $MgSO_4$ and evaporated. The crude product is purified by Prep-HPLC.

Example 109

6-chloro-$N^3$-[6-(dimethylphosphoryl)-2-methoxypyridin-3-yl]-$N^5$-[2-(propan-2-ylsulfonyl)phenyl]-1,2,4-triazine-3,5-diamine

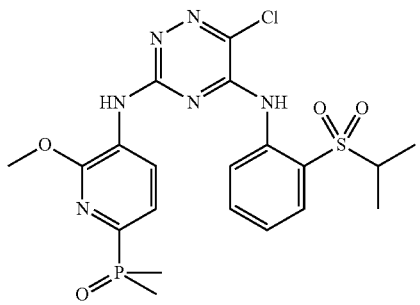

6-(Dimethylphosphoryl)-2-methoxypyridin-3-ylamine

To a solution of 6-bromo-2-methoxypyridin-3-ylamine (0.203 g, 1.00 mmol) in 4 mL DMF was added dimethylphosphine oxide (0.171 g, 1.10 mmol), palladium acetate (11.0 mg, 0.0490 mmol), XANTPHOS (35.0 mg, 0.0600 mmol), and potassium phosphate (0.233 g, 1.10 mmol). The mixture was purged with nitrogen, and subjected to microwaves at 150° C. for 20 minutes. The reaction mixture was concentrated and purified by silica gel chromatography (0-10% 7N ammonia in methanol:dichloromethane) to afford the desired product (77.2 mg, 39% yield).

6-chloro-$N^3$-[6-(dimethylphosphoryl)-2-methoxypyridin-3-yl]-$N^5$-[2-(propan-2-ylsulfonyl)phenyl]-1,2,4-triazine-3,5-diamine A mixture of 3,6-dichloro-N-[2-(propan-2-ylsulfonyl)phenyl]-1,2,4-triazin-5-amine (prepared as in Example 106: 0.7 mmol), 6-(Dimethylphosphoryl)-2-methoxypyridin-3-ylamine (0.7 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of $Na_2CO_3$. The dichloromethane extract is dried over $MgSO_4$ and evaporated. The crude product is purified by Prep-HPLC.

Example 110

6-chloro-$N^3$-[5-(dimethylphosphoryl)-3-methoxypyrazin-2-yl]-$N^5$-[2-(propan-2-ylsulfonyl)phenyl]-1,2,4-triazine-3,5-diamine

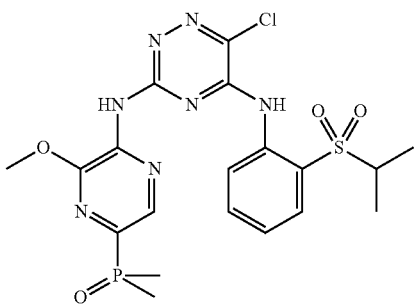 [SMILES: COc1nc(P(C)(C)=O)cnc1Nc1nnc(Cl)c(Nc2ccccc2S(=O)(=O)C(C)C)n1]

5-(dimethylphosphoryl)-3-methoxypyrazin-2-amine

To a solution of 5-bromo-3-methoxypyrazin-3-ylamine (0.204 g, 1.00 mmol) in 4 mL DMF was added dimethylphosphine oxide (0.171 g, 1.10 mmol), palladium acetate (11.0 mg, 0.0490 mmol), XANTPHOS (35.0 mg, 0.0600 mmol), and potassium phosphate (0.233 g, 1.10 mmol). The mixture was purged with nitrogen, and subjected to microwaves at 150° C. for 20 minutes. The reaction mixture was concentrated and purified by silica gel chromatography (0-10% 7N ammonia in methanol:dichloromethane) to afford the desired product (126 mg, 63% yield).

6-chloro-$N^3$-[5-(dimethylphosphoryl)-3-methoxypyrazin-2-yl]-$N^5$-[2-(propan-2-ylsulfonyl)phenyl]-1,2,4-triazine-3,5-diamine A mixture of 3,6-dichloro-N-[2-(propan-2-ylsulfonyl)phenyl]-1,2,4-triazin-5-amine (prepared as in Example 106: 0.7 mmol), 5-(dimethylphosphoryl)-3-methoxypyrazin-2-amine (0.7 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of Na₂CO₃. The dichloromethane extract is dried over MgSO₄ and evaporated. The crude product is purified by Prep-HPLC.

Example 111

N⁵-[4-(dimethylphosphoryl)-2-(propan-2-ylsulfonyl)phenyl]-N³-{2-methoxy-4-[(4-methylpiperazin-1-yl)sulfonyl]phenyl}-6-methyl-1,2,4-triazine-3,5-diamine

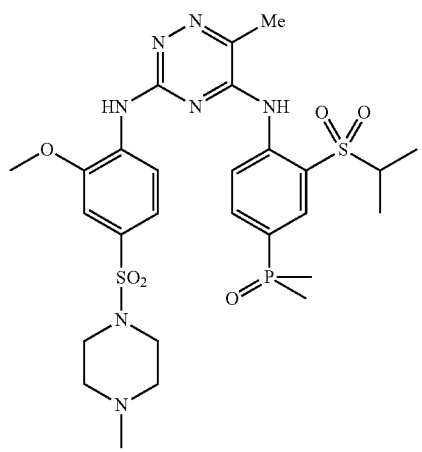 [SMILES: COc1cc(S(=O)(=O)N2CCN(C)CC2)ccc1Nc1nnc(C)c(Nc2ccc(P(C)(C)=O)cc2S(=O)(=O)C(C)C)n1]

4-(dimethylphosphoryl)-2-(propan-2-ylsulfonyl)aniline

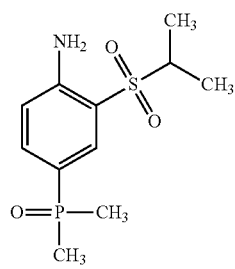 [SMILES: CC(C)S(=O)(=O)c1cc(P(C)(C)=O)ccc1N]

4-bromo-1-nitro-2-(propan-2-ylsulfanyl)benzene

At 0 degree, to a stirring solution of 4-Bromo-2-Floronitrobenzene (2.0 g, 9.1 mmol) in DCM was added Sodium propane-2-thiolate (2.0 g, 20 mmol) in two portions. The reaction mixture was warmed to room temperature and stirred overnight. The reaction mixture was filtered through a syringe filter. The product was isolated by prep-HPLC (water/Acetonitrile) as a bright yellow solid (0.8 g, 2.9 mmol, 32% yield).

4-bromo-1-nitro-2-(propan-2-ylsulfonyl)benzene

To a stirring solution of 4-bromo-1-nitro-2-(propan-2-ylsulfanyl)benzene (0.8 g, 2.9 mmol) in Acetic Acid (10 ml) was added Hydrogen Peroxide (30% aqueous solution, 0.6 mL, 5.8 mmol). The reaction mixture was heated to 110 degrees C. for 2 hours in oil bath. The reaction mixture was treated with saturated Sodium Sulfide aqueous solution and basified with saturated sodium bicarbonate solution. The mixture was extracted with Ethyl Acetate and the combined organic layers were dried over sodium sulfate. The organic solvent was removed under reduced pressure and the residue was used for the next step reaction without further purification.

Dimethyl[4-nitro-3-(propan-2-ylsulfonyl)phenyl]phosphane oxide

To a stirring solution of 4-bromo-1-nitro-2-(propan-2-ylsulfonyl)benzene (0.44 g, 1.6 mmol) and Dimethyl Phosphine oxide (0.15 g, 1.9 mmol) in 1 mL of DMF, was added Potassium Phosphate (0.37 g, 1.8 mmol), Pd(OAc)₂ (18 mg, 0.08 mmol), Xantphos (55 mg, 0.10 mmol). The reaction mixture was stirred at 110 degrees C overnight. The reaction mixture was cooled to room temperature and filtered through celite. The desired product was isolated through prep-HPLC to yield a brownish yellow solid (0.24 g, 55% yield).

4-(dimethylphosphoryl)-2-(propan-2-ylsulfonyl)aniline

To a solution of dimethyl[4-nitro-3-(propan-2-ylsulfonyl)phenyl]phosphane oxide (0.24 g, 0.88 mmol) in Ethanol was added Pd on carbon (10% w/w, 24 mg) and stirred under hydrogen overnight. The reaction mixture was filtered and the organic solvent was removed under reduced pressure. The residue was purified by prep-HPLC to yield 100 mg of desired product (50% yield).

5-chloro-N-{2-methoxy-4-[(4-methylpiperazin-1-yl)sulfonyl]phenyl}-6-methyl-1,2,4-triazin-3-amine To a solution of 5-chloro-6-methyl-1,2,4-triazin-3-amine (2.00 mmol) in 8 mL toluene is added 4-(dimethylphosphoryl)-2-(propan-2-ylsulfonyl)aniline (2.20 mmol), palladium acetate (22.4 mg, 0.0100 mmol), XANTPHOS (69.4 mg, 0.120 mmol), and cesium carbonate (2.20 mmol). The mixture is purged with nitrogen, and can be subjected to microwaves at 100° C. until formation of the desired product. The reaction mixture can then be concentrated and purified by silica gel chromatography.

N⁵-[4-(dimethylphosphoryl)-2-(propan-2-ylsulfonyl)phenyl]-N³-{2-methoxy-4-[(4-methylpiperazin-1-yl)sulfonyl]phenyl}-6-methyl-1,2,4-triazine-3,5-diamine To a solution of 5-chloro-N-{2-methoxy-4-[(4-methylpiperazin-1-yl)sulfonyl]phenyl}-6-methyl-1,2,4-triazin-3-amine (0.035 g, 0.11 mmol) in 1 mL of 2-methoxyethanol in a vial is added 2-methoxy-4-[(4-methylpiperazin-1-yl)sulfonyl]aniline (0.020 g, 0.085 mmol). The vial is sealed and the reaction is heated at 90° C. until formation of the desired compound. The reaction is then quenched with 1N NaOH solution and the solution extracted ethyl acetate. The organic layers are combined, washed with saturated sodium chloride solution, dried with sodium sulfate, filtered and concentrated. The crude residue is purified by silica gel chromatography.

Example 112

6-chloro-$N^3$-[5-(dimethylphosphoryl)-2-methoxyphenyl]-$N^5$-[2-(propan-2-ylsulfonyl)phenyl]-1,2,4-triazine-3,5-diamine

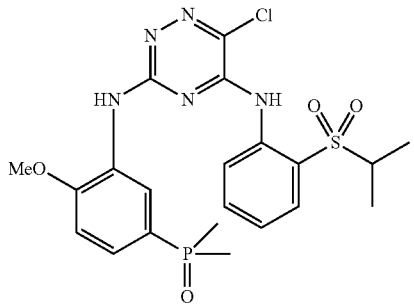 [SMILES: COc1ccc(P(C)(C)=O)cc1Nc1nnc(Cl)c(Nc2ccccc2S(=O)(=O)C(C)C)n1]

5-(Dimethylphosphoryl)-2-methoxyaniline

To a solution of 5-bromo-2-methoxyaniline (0.404 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (0.365 g, 85% yield).

6-chloro-$N^3$-[5-(dimethylphosphoryl)-2-methoxyphenyl]-$N^5$-[2-(propan-2-ylsulfonyl)phenyl]-1,2,4-triazine-3,5-diamine A mixture of 3,6-dichloro-N-[2-(propan-2-ylsulfonyl)phenyl]-1,2,4-triazin-5-amine (prepared as in Example 104: 0.7 mmol), 5-(Dimethylphosphoryl)-2-methoxyaniline (0.7 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of $Na_2CO_3$. The dichloromethane extract is dried over $MgSO_4$ and evaporated. The crude product is purified by Prep-HPLC.

Example 113

6-chloro-$N^3$-[4-(dimethylphosphoryl)-2-methylphenyl]-$N^5$-[2-(propan-2-ylsulfonyl)phenyl]-1,2,4-triazine-3,5-diamine

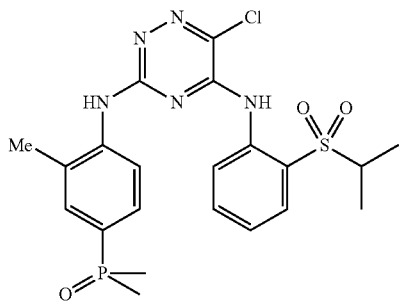 [SMILES: Cc1cc(P(C)(C)=O)ccc1Nc1nnc(Cl)c(Nc2ccccc2S(=O)(=O)C(C)C)n1]

4-(Dimethylphosphoryl)-2-methylaniline

To a solution of 4-bromo-2-methylaniline (0.372 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (0.313 g, 85% yield).

6-chloro-$N^3$-[4-(dimethylphosphoryl)-2-methylphenyl]-$N^5$-[2-(propan-2-ylsulfonyl)phenyl]-1,2,4-triazine-3,5-diamine A mixture of 3,6-dichloro-N-[2-(propan-2-ylsulfonyl)phenyl]-1,2,4-triazin-5-amine (prepared as in Example 106: 0.7 mmol), 4-(Dimethylphosphoryl)-2-methylaniline (0.7 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of $Na_2CO_3$.
The dichloromethane extract is dried over $MgSO_4$ and evaporated. The crude product is purified by Prep-HPLC.

Example 114

6-chloro-$N^3$-[4-(dimethylphosphoryl)-2-ethylphenyl]-$N^5$-[2-(propan-2-ylsulfonyl)phenyl]-1,2,4-triazine-3,5-diamine

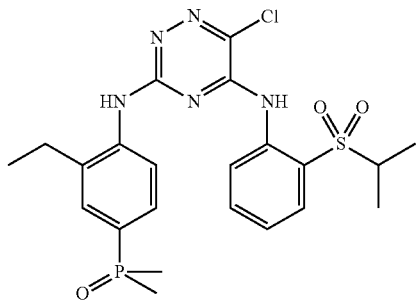 [SMILES: CCc1cc(P(C)(C)=O)ccc1Nc1nnc(Cl)c(Nc2ccccc2S(=O)(=O)C(C)C)n1]

4-(Dimethylphosphoryl)-2-ethylaniline

To a solution of 4-bromo-2-ethylaniline (0.400 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (0.308 g, 78% yield).

6-chloro-$N^3$-[4-(dimethylphosphoryl)-2-ethylphenyl]-$N^5$-[2-(propan-2-ylsulfonyl)phenyl]-1,2,4-triazine-3,5-diamine A mixture of 3,6-dichloro-N-[2-(propan-2-ylsulfonyl)phenyl]-1,2,4-triazin-5-amine (prepared as in Example 106:

0.7 mmol), 4-(Dimethylphosphoryl)-2-ethylaniline (0.7 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of $Na_2CO_3$. The dichloromethane extract is dried over $MgSO_4$ and evaporated. The crude product is purified by Prep-HPLC.

Example 115

6-chloro-$N^3$-[4-(dimethylphosphoryl)-2-(trifluoromethoxy)phenyl]-$N^5$-[2-(propan-2-ylsulfonyl)phenyl]-1,2,4-triazine-3,5-diamine

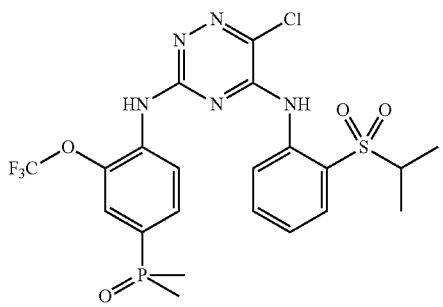 [SMILES: CC(C)S(=O)(=O)c1ccccc1Nc1nc(Nc2ccc(P(C)(C)=O)cc2OC(F)(F)F)nnc1Cl]

4-(Dimethylphosphoryl-2-(trifluoromethoxy)aniline

To a solution of 4-iodo-2-(trifluoromethoxy)aniline (0.606 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) and acidified with HCl in methanol to afford the desired product as its hydrochloride salt (0.573 g, 98% yield).

6-chloro-$N^3$-[4-(dimethylphosphoryl)-2-(trifluoromethoxy)phenyl]-$N^5$-[2-(propan-2-ylsulfonyl)phenyl]-1,2,4-triazine-3,5-diamine A mixture of 3,6-dichloro-N-[2-(propan-2-ylsulfonyl)phenyl]-1,2,4-triazin-5-amine (prepared as in Example 106: 0.7 mmol), 4-(Dimethylphosphoryl)-2-(trufluoroethoxy) aniline (0.7 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of $Na_2CO_3$. The dichloromethane extract is dried over $MgSO_4$ and evaporated. The crude product is purified by Prep-HPLC.

Example 116

6-chloro-$N^3$-[2-chloro-4-(dimethylphosphoryl)phenyl]-$N^5$-[2-(propan-2-ylsulfonyl)phenyl]-1,2,4-triazine-3,5-diamine

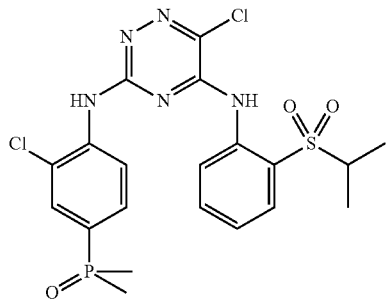 [SMILES: CC(C)S(=O)(=O)c1ccccc1Nc1nc(Nc2ccc(P(C)(C)=O)cc2Cl)nnc1Cl]

2-Chloro-4-(dimethylphosphoryl)aniline

To a solution of 2-chloro-4-iodoaniline (0.507 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (0.340 g, 83% yield).

6-chloro-$N^3$-[2-chloro-4-(dimethylphosphoryl)phenyl]-$N^5$-[2-(propan-2-ylsulfonyl)phenyl]-1,2,4-triazine-3,5-diamine A mixture of 3,6-dichloro-N-[2-(propan-2-ylsulfonyl)phenyl]-1,2,4-triazin-5-amine (prepared as in Example 106: 0.7 mmol), 2-Chloro-4-(dimethylphosphoryl)aniline (0.7 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of $Na_2CO_3$. The dichloromethane extract is dried over $MgSO_4$ and evaporated. The crude product is purified by Prep-HPLC.

Example 117

6-chloro-$N^3$-[4-(dimethylphosphoryl)-2-fluorophenyl]-$N^5$-[2-(propan-2-ylsulfonyl)phenyl]-1,2,4-triazine-3,5-diamine

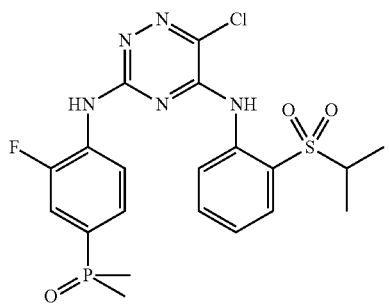 [SMILES: CC(C)S(=O)(=O)c1ccccc1Nc1nc(Nc2ccc(P(C)(C)=O)cc2F)nnc1Cl]

4-(Dimethylphosphoryl)-2-fluoroaniline

To a solution of 4-bromo-2-fluoroaniline (0.380 g, 2.00 mmol) in 8 mL DMF was added dimethylphosphine oxide (0.171 g, 2.20 mmol), palladium acetate (22.4 mg, 0.0100 mmol), XANTPHOS (69.4 mg, 0.120 mmol), and potassium phosphate (0.467 g, 2.20 mmol). The mixture was purged with nitrogen, and subjected to microwaves at 150° C. for 20 minutes. The reaction mixture was concentrated and purified by silica gel chromatography (0-20% 7N ammonia in methanol:dichloromethane) to afford the desired product (73.5 mg, 20% yield).

6-chloro-$N^3$-[4-(dimethylphosphoryl)-2-fluorophenyl]-$N^5$-[2-(propan-2-ylsulfonyl)phenyl]-1,2,4-triazine-3,5-diamine A mixture of 3,6-dichloro-N-[2-(propan-2-ylsulfonyl)phenyl]-1,2,4-triazin-5-amine (prepared as in Example 106: 0.7 mmol), 4-(Dimethylphosphoryl)-2-fluoroaniline (0.7 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of $Na_2CO_3$. The dichloromethane extract is dried over $MgSO_4$ and evaporated. The crude product is purified by Prep-HPLC.

Example 118

6-chloro-$N^3$-[4-(1-ethyl-4-oxido-1,4-azaphosphinan-4-yl)-2-methoxyphenyl]-$N^5$-[2-(propan-2-ylsulfonyl)phenyl]-1,2,4-triazine-3,5-diamine

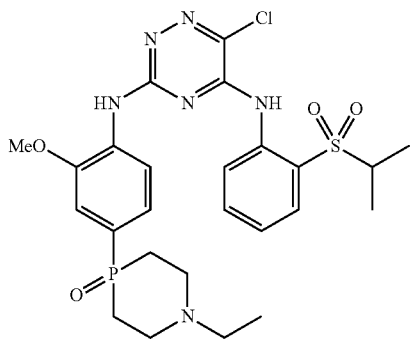 [SMILES: CCN1CCP(=O)(c2ccc(Nc3nnc(Cl)c(Nc4ccccc4S(=O)(=O)C(C)C)n3)c(OC)c2)CC1]

4-(1-ethyl-4-oxido-1,4-azaphosphinan-4-yl)-2-methoxyaniline

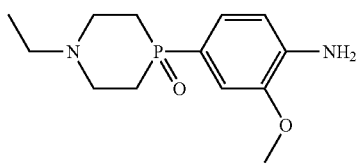

Diethyl (3-methoxy-4-nitrophenyl)phosphonate

To a solution of 5-chloro-2-nitroanisole (1.00 g, 5.33 mmol) in 20 mL DMF was added diethyl phosphite (0.809 g, 5.86 mmol), palladium acetate (0.060 g, 0.27 mmol), XANTPHOS (0.185 g, 0.320 mmol), and potassium phosphate (1.24 g, 5.86 mmol). The mixture was purged with nitrogen, and subjected to microwaves at 150° C. for 20 minutes. The reaction mixture was concentrated and purified by silica gel chromatography (0-45% ethyl acetate:heptane) to afford the desired product (0.504 g, 33% yield).

(3-methoxy-4-nitrophenyl)phosphonic dichloride

To a solution of diethyl (3-methoxy-4-nitrophenyl)phosphonate (4.54 g, 15.7 mmol) in 1.2 mL DMF was added thionyl chloride (5.7 mL, 78.5 mmol). The reaction flask was equipped with a reflux condenser and the mixture was heated to reflux. After 2 h at reflux, the reaction was cooled to room temperature and concentrated in vacuo. The crude oil was redissolved in $CH_2Cl_2$ and heptane was added to precipitate the desired compound. The clear solution was decanted and the precipitate was collected and dried to afford the desired compound as a white solid (1.39 g, 33% yield).

Diethenyl(3-methoxy-4-nitrophenyl)phosphane oxide

To a solution of (3-methoxy-4-nitrophenyl)phosphonic dichloride (1.39 g, 5.15 mmol) in 15 mL THF at −78° C. under nitrogen was slowly added vinylmagnesium bromide (10.3 mL, 1.0 M in THF). After the addition was complete, the reaction stirred at −78° C. for an additional hour. The cold reaction mixture was quenched by the addition of saturated $NH_4Cl$ (20 mL) and the mixture was extracted with $CH_2Cl_2$. The combined organic layers were washed with 1 M NaOH, brine, and dried over $MgSO_4$. The organic extracts were filtered and concentrated to provide Diethenyl(3-methoxy-4-nitrophenyl)phosphane oxide (0.982 g, 75%).

1-ethyl-4-(3-methoxy-4-nitrophenyl-1,4-azaphosphinane 4-oxide

Diethenyl(3-methoxy-4-nitrophenyl)phosphane oxide (0.480 g, 1.94 mmol), ethylamine hydrochloride (0.174 g, 2.12 mmol), and 1 N NaOH (2 mL) were dissolved in 50% aqueous THF (5 mL) and heated to 105° C. under nitrogen. After one hour, another portion of benzylamine was added to the reaction mixture. The reaction mixture was refluxed for an additional 2 h, and then cooled to room temperature. The reaction mixture was partitioned between saturated aqueous $NaHCO_3$ and $CH_2Cl_2$. The aqueous phase was washed once with $CH_2Cl_2$ and the organic layers were combined. The organic extracts were washed with brine, dried over $MgSO_4$, filtered, and concentrated. The residue was purified by silica gel chromatography (0-10% 7N ammonia in methanol:dichloromethane) to afford the compound (0.267 g, 46% yield).

4-(1-ethyl-4-oxido-1,4-azaphosphinan-4-yl)-2-methoxyaniline

To a solution of 1-ethyl-4-(3-methoxy-4-nitrophenyl)-1,4-azaphosphinane 4-oxide (0.267 g, 0.895 mmol) in 5 mL ethanol was added 10% Pd/C (27 mg) and 2.5 M HCl in ethanol (1.43 mL). The flask was equipped with a septum, evacuated, and refilled with hydrogen. The flask was equipped with a hydrogen balloon and the reaction stirred for 3 h. The flask was then evacuated and refilled with nitrogen. The reaction mixture was filtered through Celite and concentrated to provide the crude compound as the hydrochloride salt, which was used without purification.

6-chloro-$N^3$-[4-(1-ethyl-4-oxido-1,4-azaphosphinan-4-yl)-2-methoxyphenyl]-$N^5$-[2-(propan-2-ylsulfonyl)phenyl]-1,2,4-triazine-3,5-diamine A mixture of 3,6-dichloro-N-[2-(propan-2-ylsulfonyl)phenyl]-1,2,4-triazin-5-amine (prepared as in Example 106: 0.7 mmol), 4-(1-ethyl-4-oxido-1,4-azaphosphinan-4-yl)-2-methoxyaniline (0.7 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of $Na_2CO_3$. The dichloromethane extract is dried over $MgSO_4$ and evaporated. The crude product is purified by Prep-HPLC.

Example 119

6-chloro-$N^3$-[2-methoxy-4-(4-methyl-4-oxido-1,4-azaphosphinan-1-yl)phenyl]-$N^5$-[2-(propan-2-ylsulfonyl)phenyl]-1,2,4-triazine-3,5-diamine

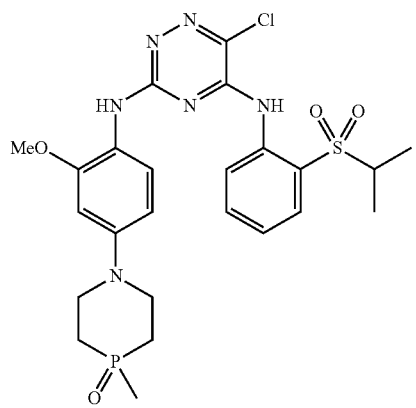 [SMILES: COc1cc(N2CCP(C)(=O)CC2)ccc1Nc1nnc(Cl)c(Nc2ccccc2S(=O)(=O)C(C)C)n1]

2-methoxy-4-(4-methyl-4-oxido-1,4-azaphosphinan-1-yl)aniline

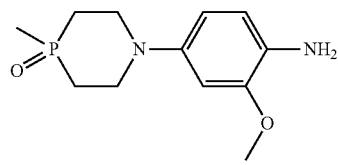 [SMILES: COc1cc(N2CCP(C)(=O)CC2)ccc1N]

1-benzyl-4-methyl-1,4-azaphosphinane 4-oxide

To a solution of methylphosphonic dischloride (10.0 g, 75.2 mmol) in $CH_2Cl_2$ at −78° C., was added vinylmagnesium bromide (175 mL, 1.0 M in THF) via addition funnel over 4 h. The solution was warmed to 0° C. and quenched with a minimum amount of saturated $NH_4Cl$. The mixture was filtered through a pad of silica gel and silica was extracted with 10% 7N ammonia in methanol:dichloromethane. The solution was concentrated under reduced pressure to afford methyl divinyl phosphine oxide as a viscous, yellow oil that was used without purification.

A solution of methyl divinyl phosphine oxide (1.16 g, 10.0 mmol) and benzylamine (1.20 mL, 11.0 mmol) in 1:1 THF/water (25 mL) was heated at reflux for 16 h. The reaction mixture was concentrated in vacuo and the residue was purified by silica gel chromatography (0-10% 7N ammonia in methanol:dichloromethane) to afford 1-benzyl-4-methyl-[1,4]azaphosphinane-4-oxide as a white solid (1.57 g, 70% yield).

4-methyl-[1,4]azaphosphinane-4-oxide

A flask was charged with 1-benzyl-4-methyl-[1,4]azaphosphinane-4-oxide (1.00 g, 4.47 mmol) and 10% Pd/C (100 mg). The flask was evacuated and filled with nitrogen. Anhydrous methanol (18 mL) was added to the flask and the flask was equipped with a reflux condenser with a nitrogen inlet. Ammonium formate (2.25 g, 35.8 mmol) was added in one portion at room temperature. The resulting mixture was stirred at reflux for 2 h. The reaction was filtered through a Celite pad and the Celite was washed with 2×5 mL methanol. The combined filtrate and washing was evaporated in vacuo. The crude residue was purified by silica gel chromatography (0-10% 7N ammonia in methanol:dichloromethane) to afford 4-methyl-[1,4]azaphosphinane-4-oxide as a yellow gel (0.589 g, 99% yield).

1-(3-methoxy-4-nitrophenyl)-4-methyl-1,4-azaphosphinane 4-oxide

A mixture of 4-methyl-[1,4]azaphosphinane-4-oxide (133 mg, 1.00 mmol), 5-fluoro-2-nitroanisole (340 mg, 2.00 mmol), $K_2CO_3$ (345 mg, 2.50 mmol), and DMF (5 mL) was heated to 50° C. After 2 h, the reaction mixture was concentrated and purified by silica gel chromatography (0-5% 7N ammonia in methanol:dichloromethane) to afford 1-(3-methoxy-4-nitrophenyl)-4-methyl-1,4-azaphosphinane 4-oxide as a bright yellow solid (272 mg, 96% yield).

2-methoxy-4-(4-methyl-4-oxido-1,4-azaphosphinan-1-yl)aniline

To a pressure vessel was added 1-(3-methoxy-4-nitrophenyl)-4-methyl-1,4-azaphosphinane 4-oxide (272 mg, 0.960 mmol), ethanol (5 mL), and 10% Pd/C (50 mg). The vessel was connected to a Parr apparatus, evacuated, and refilled with nitrogen. The vessel was then evacuated and filled with hydrogen gas to a pressure of 50 psi. The reaction mixture was shaken under 50 psi for 4 h. The mixture was filtered through Celite to a flask containing HCl in ethanol. Concentration of the filtrate afforded 2-methoxy-4-(4-methyl-4-oxido-1,4-azaphosphinan-1-yl)aniline as a gray solid (211 mg, 87% yield).

6-chloro-$N^3$-[2-methoxy-4-(4-methyl-4-oxido-1,4-azaphosphinan-1-yl)phenyl]-$N^5$-[2-(propan-2-ylsulfonyl)phenyl]-1,2,4-triazine-3,5-diamine A mixture of 3,6-dichloro-N-[2-(propan-2-ylsulfonyl)phenyl]-1,2,4-triazin-5-amine (prepared as in Example 106: 0.7 mmol), 2-methoxy-4-(4-methyl-4-oxido-1,4-azaphosphinan-1-yl)aniline (0.7 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of Na₂CO₃. The dichloromethane extract is dried over MgSO₄ and evaporated. The crude product is purified by Prep-HPLC.

Example 120

6-chloro-N³-{2-methoxy-4-[4-(4-methyl-4-oxido-1, 4-azaphosphinan-1-yl)piperidin-1-yl]phenyl}-N⁵-[2-(propan-2-ylsulfonyl)phenyl]-1,2,4-triazine-3,5-diamine

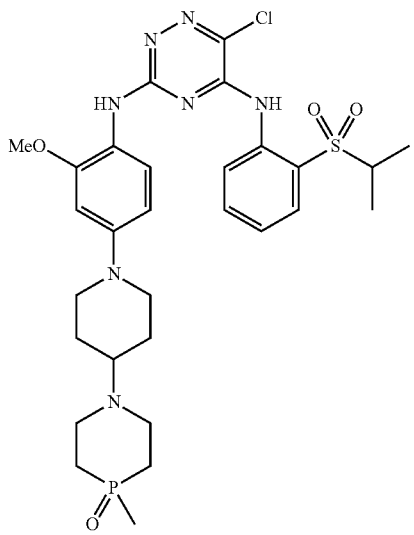 [SMILES: COc1cc(N2CCC(N3CCP(C)(=O)CC3)CC2)ccc1Nc1nnc(Cl)c(Nc2ccccc2S(=O)(=O)C(C)C)n1]

2-methoxy-4-[4-(4-methyl-4-oxido-1,4-azaphosphinan-1-yl)piperidin-1-yl]aniline

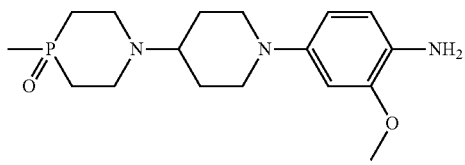 [SMILES: COc1cc(N2CCC(N3CCP(C)(=O)CC3)CC2)ccc1N]

tert-butyl 4-(4-methyl-4-oxido-1,4-azaphosphinan-1-yl)piperidine-1-carboxylate

A solution of methyl divinyl phosphine oxide (140 mg, 1.21 mmol) and 1-Boc-4-aminopiperidine (265 mg, 1.33 mmol) in 1:1 THF/water (3 mL) was heated at reflux for 16 h. The reaction mixture was concentrated in vacuo and the residue was purified by silica gel chromatography (0-10% 7N ammonia in methanol:dichloromethane) to afford the desired compound as a white solid (178 mg, 38% yield).

1-[1-(3-methoxy-4-nitrophenyl)piperidin-4-yl]-4-methyl-1,4-azaphosphinane 4-oxide To a stirring solution of tert-butyl 4-(4-methyl-4-oxido-1, 4-azaphosphinan-1-yl)piperidine-1-carboxylate (178 mg, 0.563 mmol) in CH₂Cl₂ (2 mL) was added trifluoroacetic acid (0.5 mL). After 20 min, the solution was concentrated and the resulting residue was redissolved in DMF (2 mL). Potassium carbonate (160 mg, 1.16 mmol) was added portionwise to the stirring solution followed by 5-fluoro-2-nitroanisole (158 mg, 0.930 mmol). The reaction mixture was heated to 50° C. After 2 h, the reaction mixture was concentrated and the residue was purified by silica gel chromatography (0-10% 7N ammonia in methanol:dichloromethane) to afford the compound as a bright yellow solid (176 mg, 86% yield).

2-methoxy-4-[4-(4-methyl-4-oxido-1,4-azaphosphinan-1-yl)piperidin-1-yl]aniline

To a pressure vessel was added 1-[1-(3-methoxy-4-nitrophenyl)piperidin-4-yl]-4-methyl-1,4-azaphosphinane 4-oxide (176 mg, 0.485 mmol), ethanol (5 mL), and 10% Pd/C (50 mg). The vessel was connected to a Parr apparatus, evacuated, and refilled with nitrogen. The vessel was then evacuated and filled with hydrogen gas to a pressure of 50 psi. The reaction mixture was shaken under 50 psi for 4 h. The mixture was filtered through Celite to a flask containing HCl in ethanol. Concentration of the filtrate afforded the compound as a gray solid (178 mg, 98% yield).

6-chloro-N³-{2-methoxy-4-[4-(4-methyl-4-oxido-1, 4-azaphosphinan-1-yl)piperidin-1-yl]phenyl}-N⁵-[2-(propan-2-ylsulfonyl)phenyl]-1,2,4-triazine-3,5-diamine A mixture of 3,6-dichloro-N-[2-(propan-2-ylsulfonyl)phenyl]-1,2,4-triazin-5-amine (prepared as in Example 106: 0.7 mmol), 2-methoxy-4-[4-(4-methyl-4-oxido-1,4-azaphosphinan-1-yl)piperidin-1-yl]aniline (0.7 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of Na₂CO₃. The dichloromethane extract is dried over MgSO₄ and evaporated. The crude product is purified by Prep-HPLC.

Example 121

6-chloro-N³-[4-(diethylphosphoryl)-2-methoxyphenyl]-N⁵-[2-(propan-2-ylsulfonyl)phenyl]-1,2,4-triazine-3,5-diamine

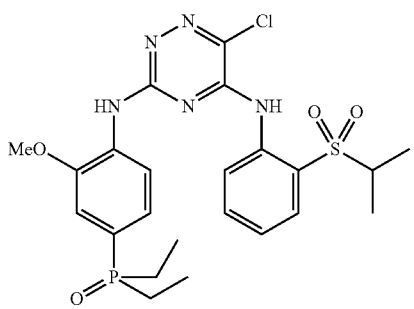 [SMILES: CCP(=O)(CC)c1ccc(Nc2nnc(Cl)c(Nc3ccccc3S(=O)(=O)C(C)C)n2)c(OC)c1]

255

4-(Diethylphosphoryl)-2-methoxyaniline

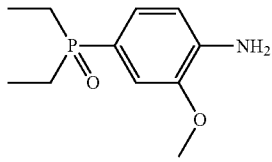

To a solution of 4-bromo-2-methoxyaniline (0.100 g, 0.495 mmol) in 2 mL DMF was added diethylphosphine oxide (0.0730 g, 0.544 mmol), palladium acetate (5.6 mg, 0.025 mmol), XANTPHOS (17.2 mg, 0.030 mmol), and potassium phosphate (0.116 g, 0.544 mmol). The mixture was purged with nitrogen, and subjected to microwaves at 150° C. for 20 minutes. The reaction mixture was concentrated and purified by silica gel chromatography (0-12% 7N ammonia in methanol:dichloromethane) and the fractions were concentrated. The residue was acidified with 2.5 M HCl in ethanol and the solution was concentrated to provide 4-(diethylphosphoryl)-2-methoxyaniline as the hydrochloride salt (0.132 g, 91% yield).

256

6-chloro-$N^3$-[4-(diethylphosphoryl)-2-methoxyphenyl]-$N^5$-[2-(propan-2-ylsulfonyl)phenyl]-1,2,4-triazine-3,5-diamine A mixture of 3,6-dichloro-N-[2-(propan-2-ylsulfonyl)phenyl]-1,2,4-triazin-5-amine (prepared as in Example 106: 0.7 mmol), 4-(Diethylphosphoryl)-2-methoxyaniline (0.7 mmol) and camphorsulfonic acid (0.7 equiv.), is refluxed for 20-48 hours in 2-propanol. The reaction mixture is allowed to cool to room temperature, dissolved in dichloromethane and washed with an aqueous solution of $Na_2CO_3$. The dichloromethane extract is dried over $MgSO_4$ and evaporated. The crude product is purified by Prep-HPLC.

Example 122

Synthesis of Compound 5

Compound 5 can be synthesized as outlined in Scheme 122 (below).

Scheme 122

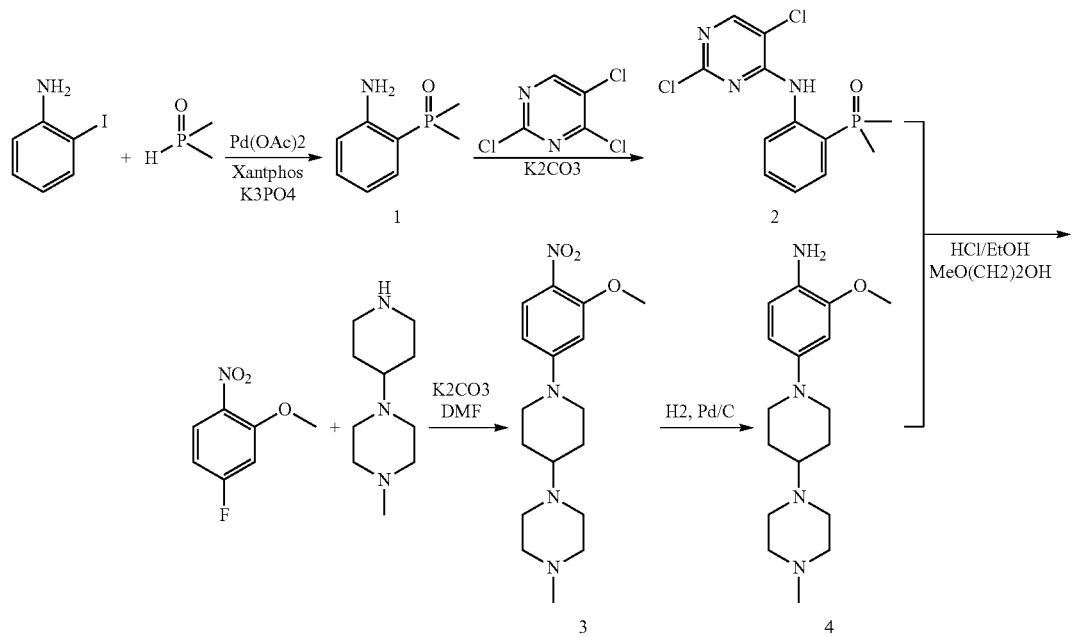

Synthesis of 1

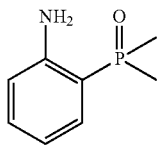
1

To a solution of 2-iodoaniline (1.0 eq) and dimethylphosphine oxide (1.1 eq) in DMF were added potassium phosphate (1.1 eq), palladium acetate/Xantphos (catalytic). The reaction was stirred at 150° C. for 3 hours and cooled to room temperature. The solvent was evaporated and the residue was worked up with DCM/water. The crude product was purified with a column (EtOAc/MeOH 10:1) to give 1 as a brown solid (80% yield).

Synthesis of 2

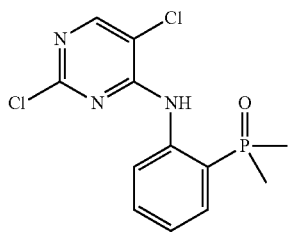
2

2,4,5-Trichloropyrimidine (1.57 eq), 1 (1.0 eq), and potassium carbonate (3.14 eq) in DMF were stirred at 60° C. for 5 hours and then cooled to r.t. The mixture was filtered and the filtrate was concentrated. The residue was purified with ISCO (DCM/MeOH 20:1) to give 2 as a yellow solid (61% yield).

Synthesis of 3

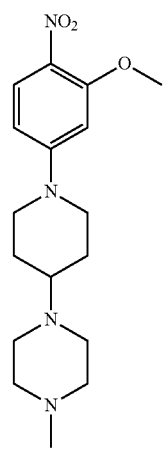
3

5-Fluoro-2-nitroanisole (1.0 eq), 1-methyl-4-(piperidin-4-yl)piperazine (1.0 eq), and potassium carbonate (2.0 eq) in DMF were stirred at 120° C. for 6 hours and then cooled to r.t. The mixture was filtered and evaporated. The crude product was crystallized from ethanol to give 3 as a yellow solid (72% yield).

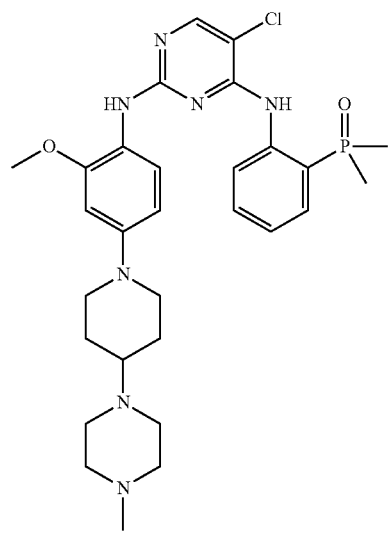
5

Synthesis of 4

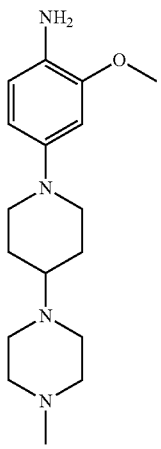
4

Palladium on activated carbon was added to a solution of 3 in ethanol under nitrogen. The suspension was then shaken under hydrogen (50 psi) for 3 hours. The mixture was filtered and the filtration was evaporated to give 4 as a purple solid in a quantitative yield.

Synthesis of 5

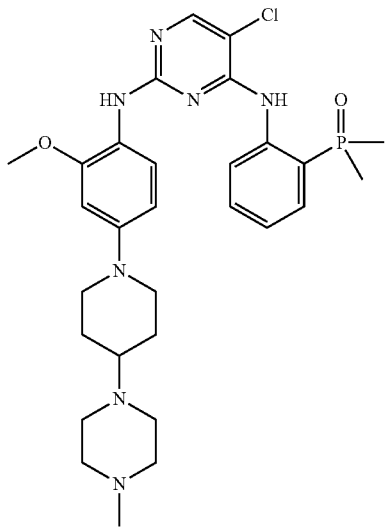
5

A solution of 2 (1.0 eq), 4 (1.4 eq), and 2.5 M HCl in ethanol (excess) in 2-methoxyethanol was sealed and heated at 120° C. with stirring for 5.5 hours and then cooled to r.t. The reaction was repeated 5 times and combined. The mixture was filtered and evaporated. Saturated $Na_2CO_3$ was added, followed by DCM with stirring strongly. The layers were separated and the aqueous layer was extracted with DCM. The organics were dried, evaporated and chromatographed [EtOAc/MeOH (7M ammonia) 20:1] to give a yellow solid. EtOAc was added and the suspension was refluxed for 30 minutes. After cooled to r.t., filtration gave a solid, which was dissolved in DCM, filtered, and evaporated to afford 5 as an off-white solid (66% yield).

Example 123

Biological Evaluation of Compounds

Compounds of the invention are evaluated in a variety of assays to determine their biological activities. For example, compounds of the invention can be tested for their ability to inhibit various protein kinases of interest. Some of the compounds tested displayed potent nanomolar activity against the following kinases: ALK and c-Met. Furthermore, some of these compounds were screened for antiproliferative activity in the human Karpas-299 and in the human SU-DHL-1 lymphoma cell lines and demonstrated activity on the range of 1-100 nM. The compounds can also be evaluated for their cytotoxic or growth inhibitory effects on tumor cells of interest, e.g., as described in more detail below and as shown above for some representative compounds. See e.g., WO 03/000188, pages 115-136, the full contents of which are incorporated herein by reference.

Some representative compounds of the invention are depicted below:

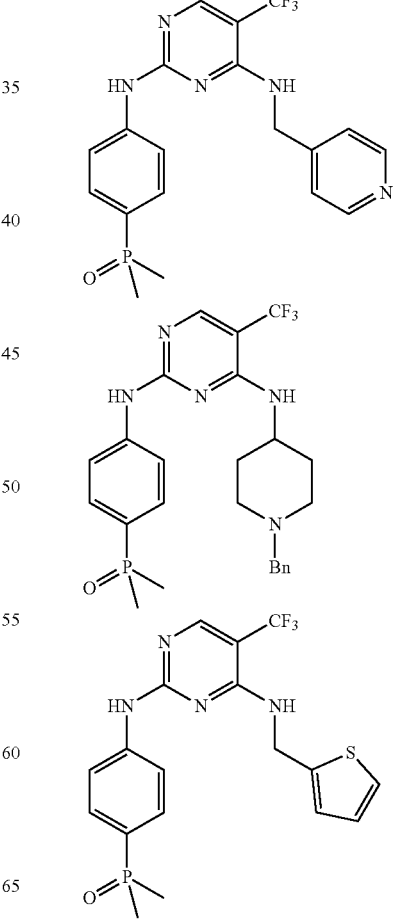

-continued
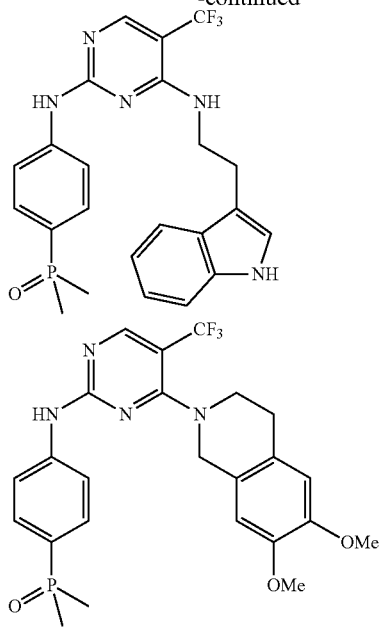
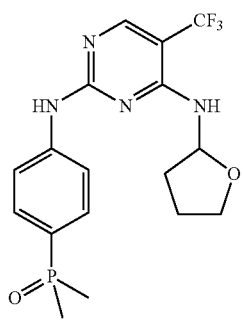
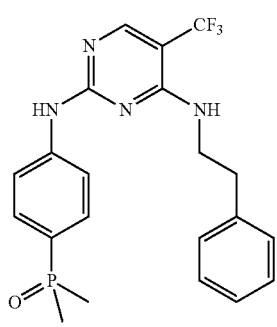
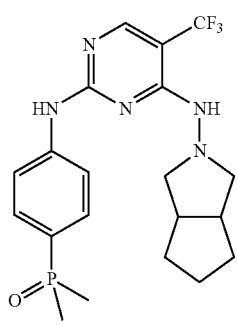
-continued
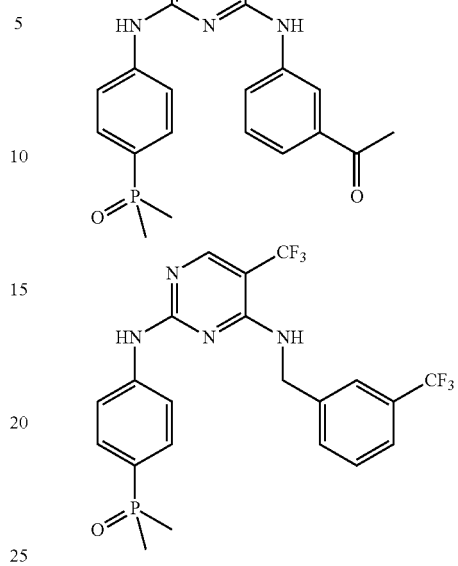
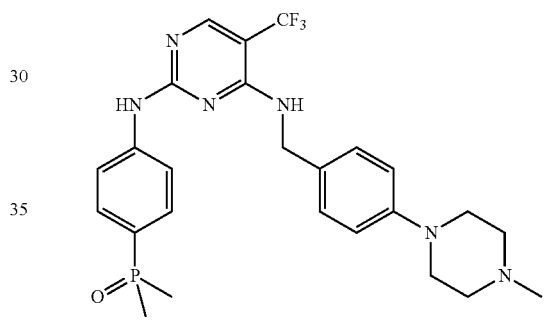
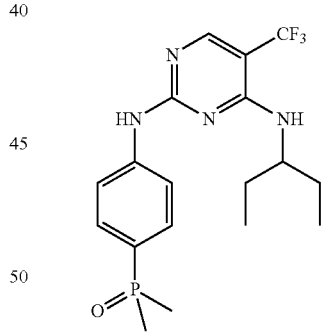
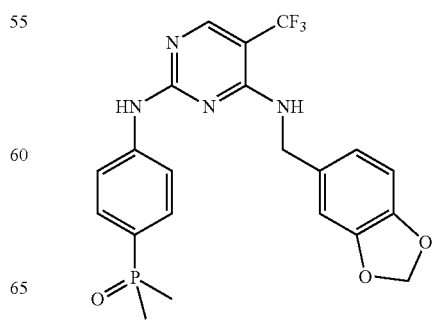

263 264
-continued -continued
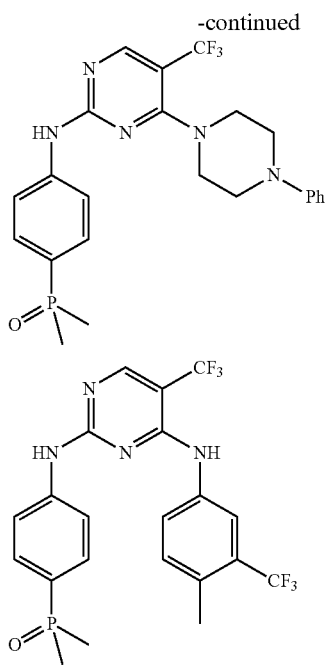
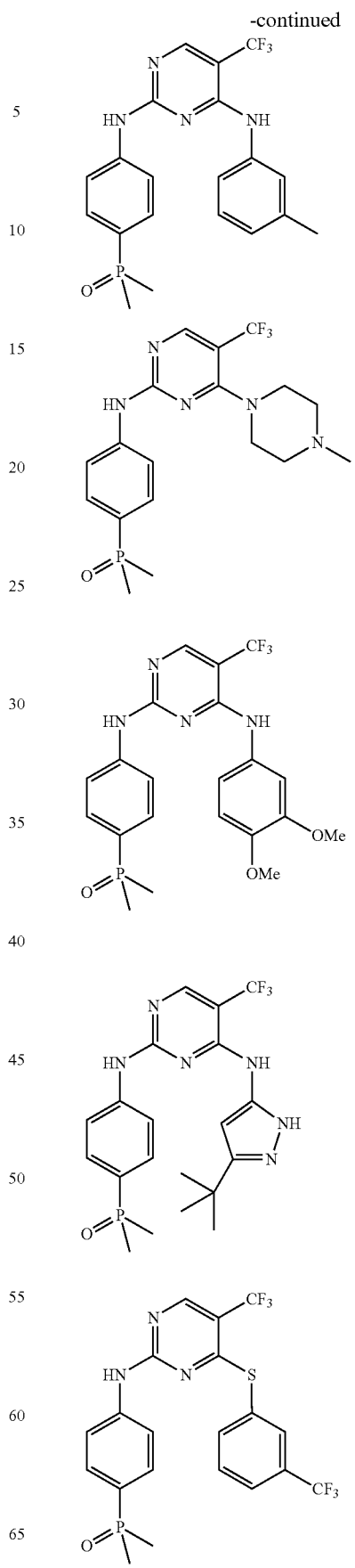

-continued
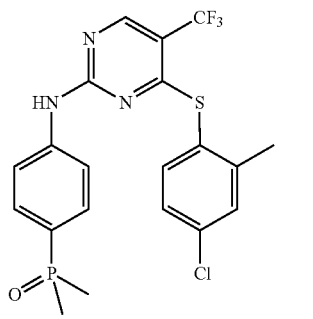
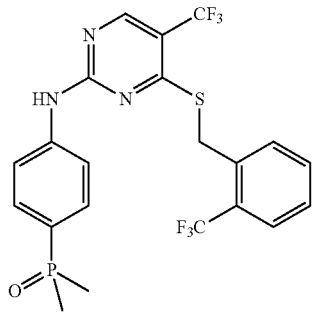
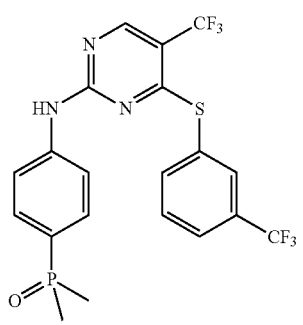
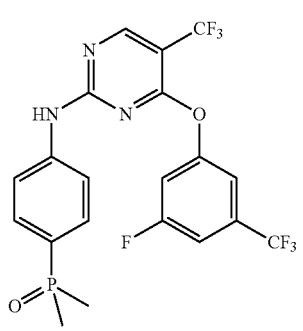
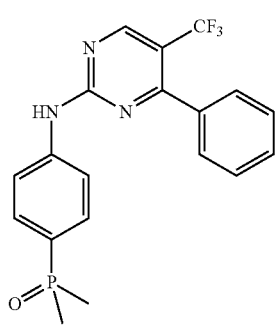
-continued
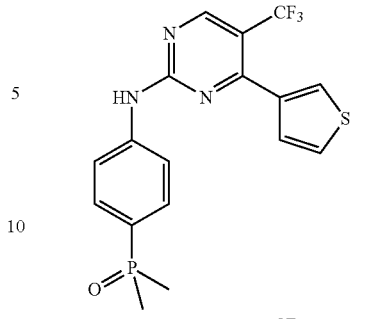
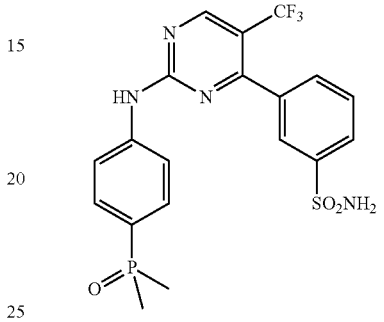
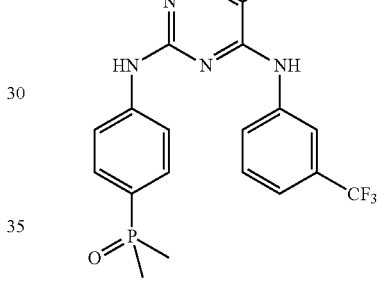
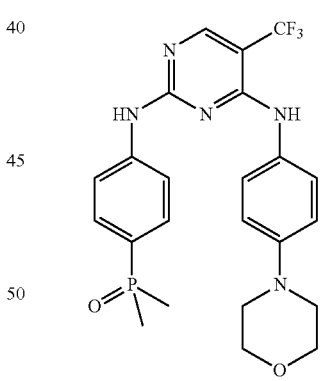
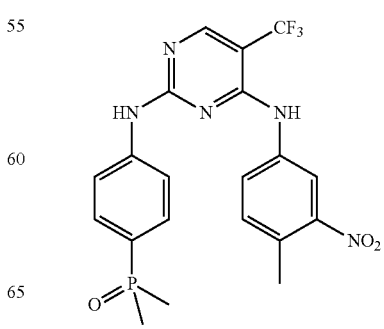

267
-continued
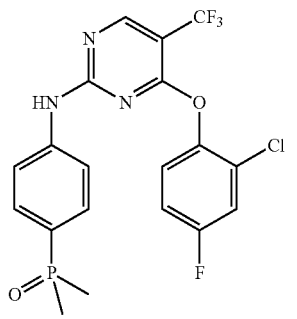
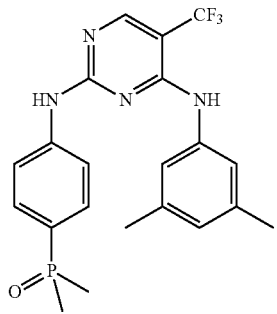
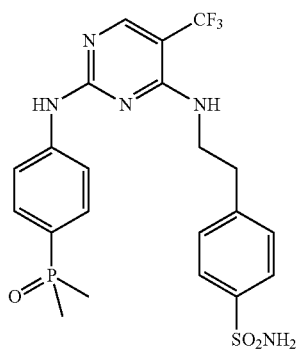
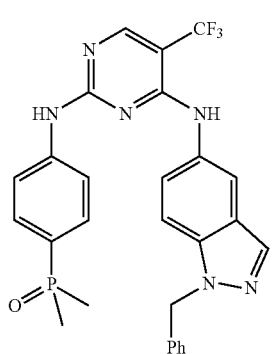
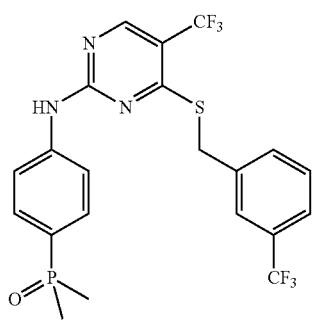
268
-continued
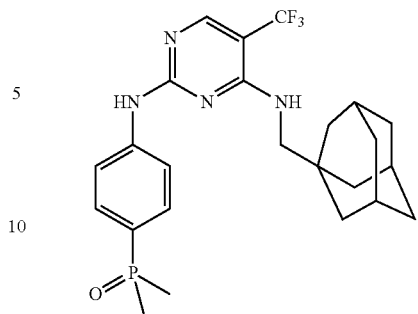
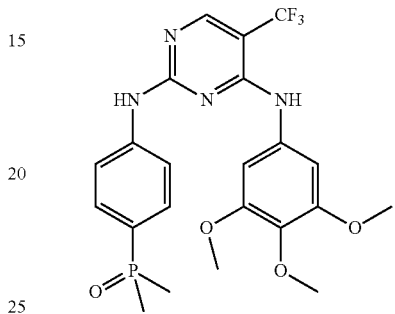
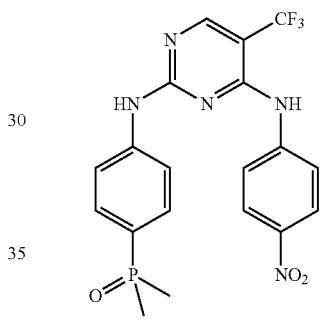
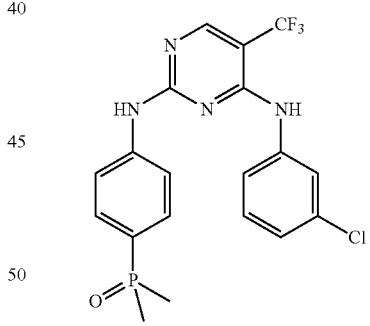
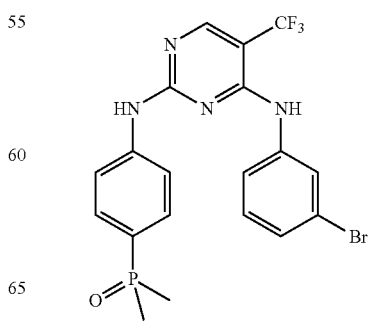

269
-continued
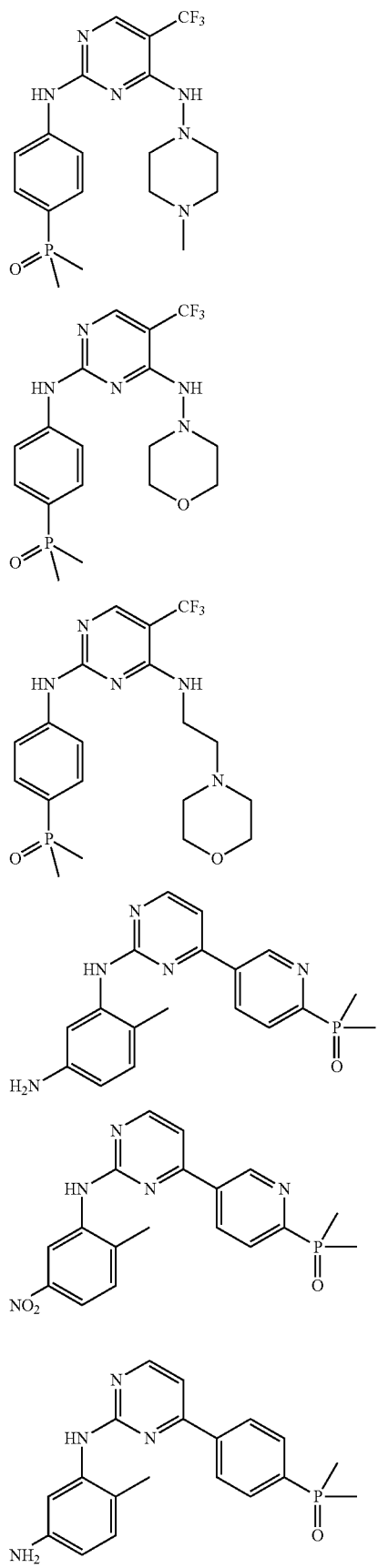
270
-continued
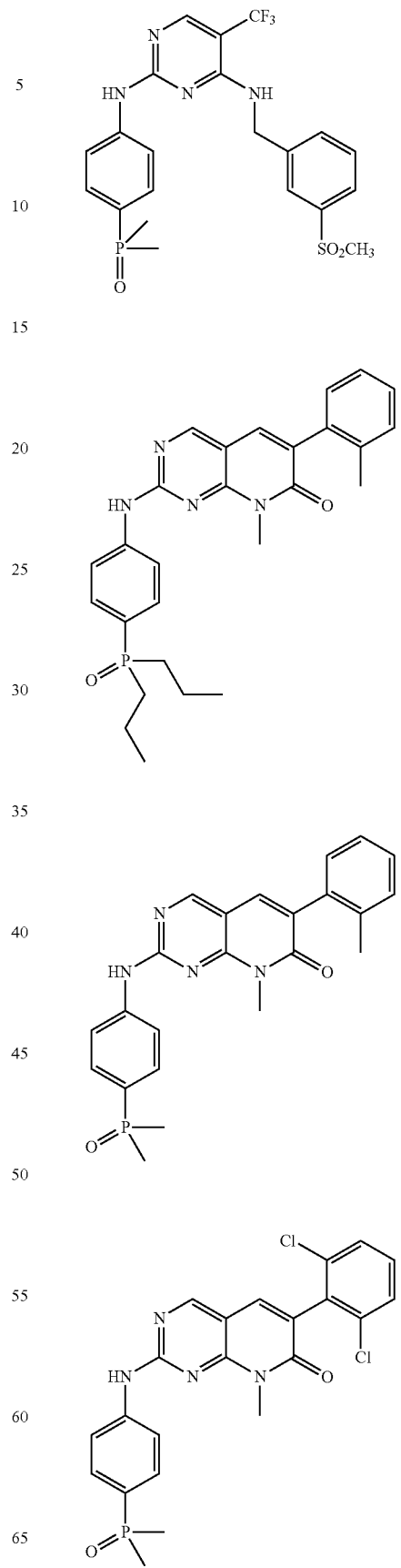

271
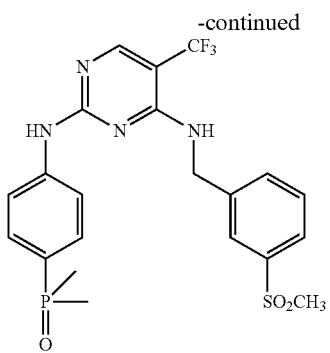
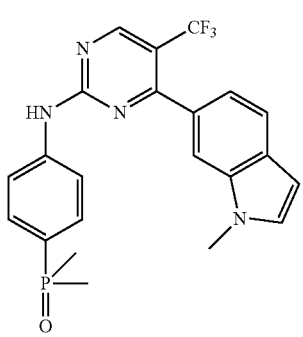
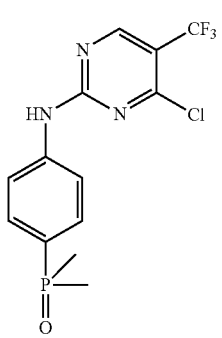
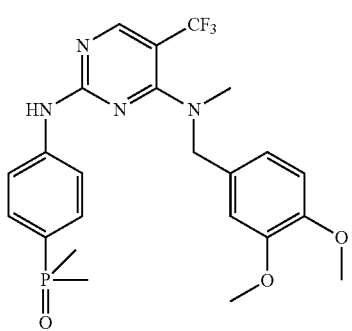
272
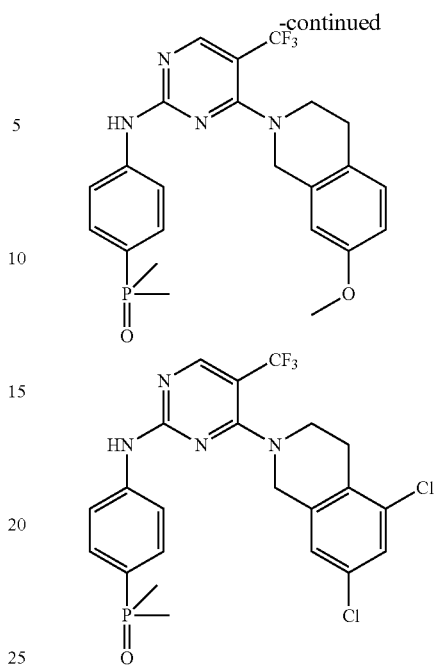
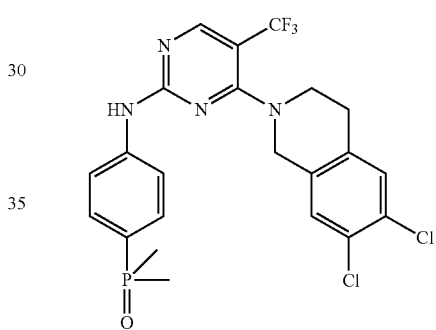
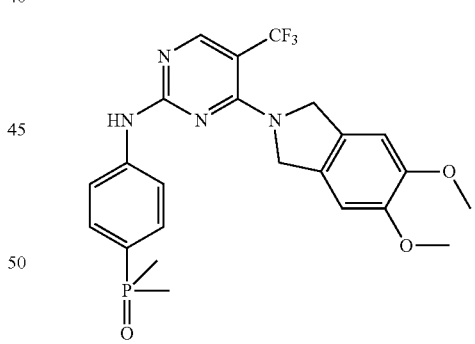
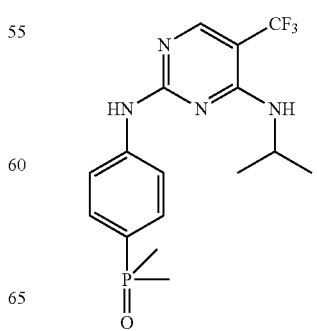

273
-continued
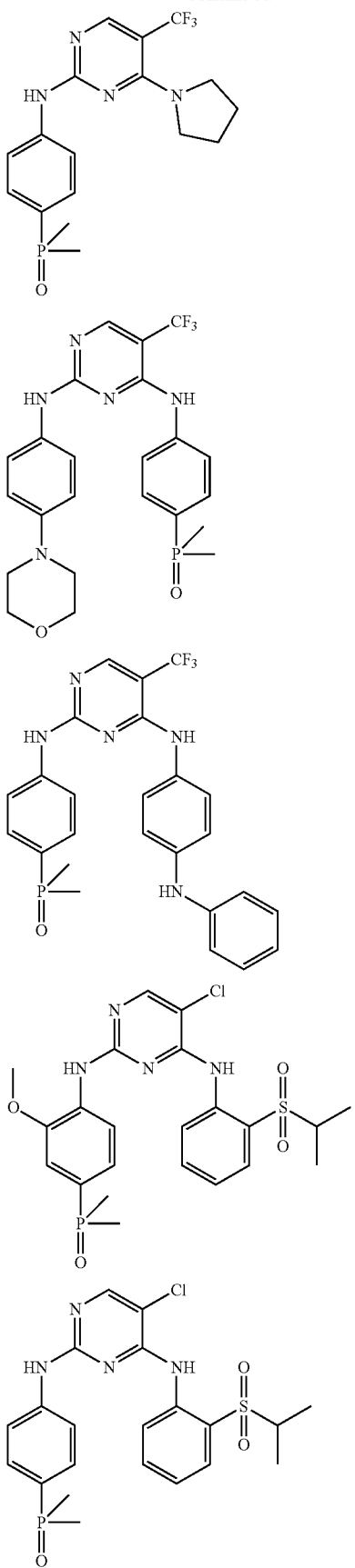
274
-continued
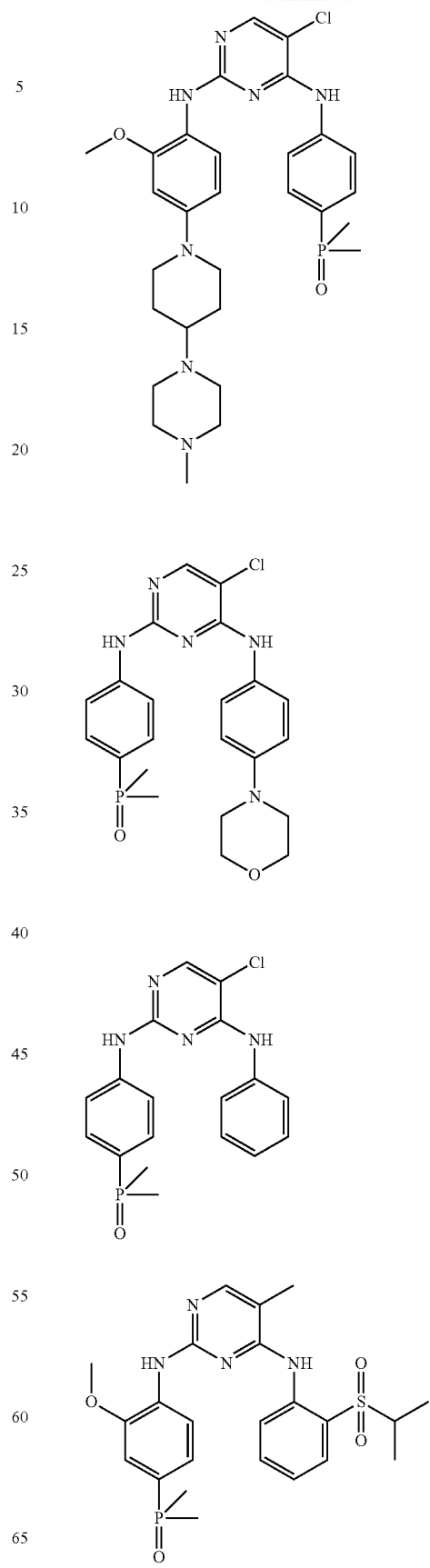

275
-continued
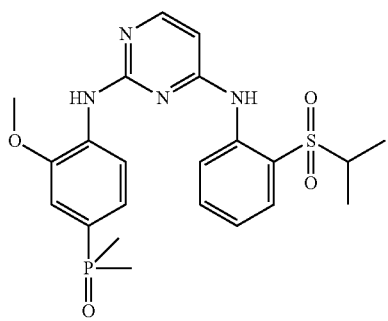
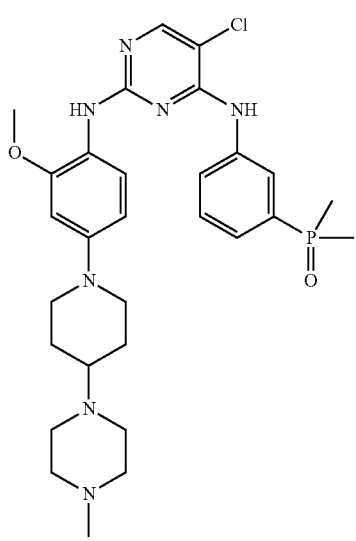
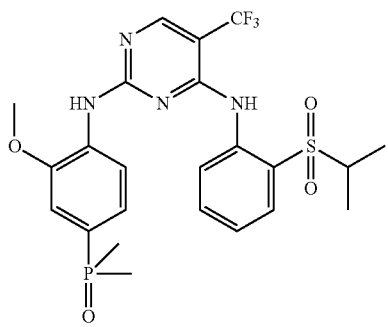
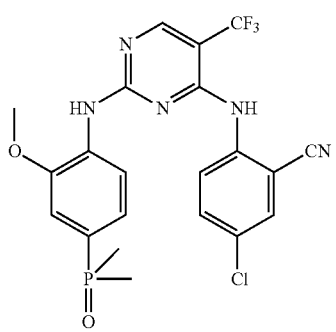
276
-continued
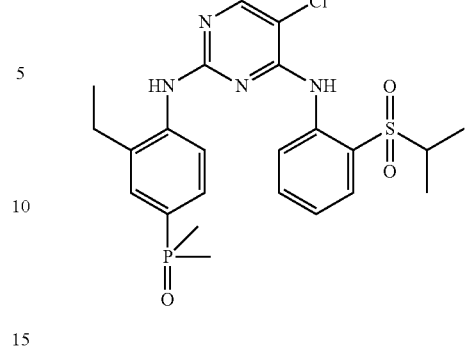
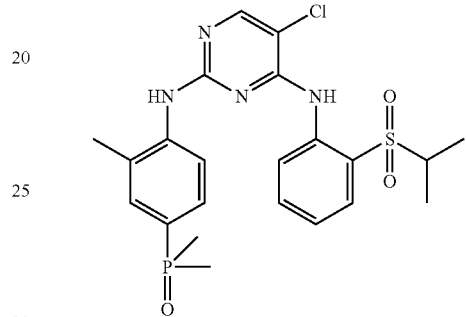
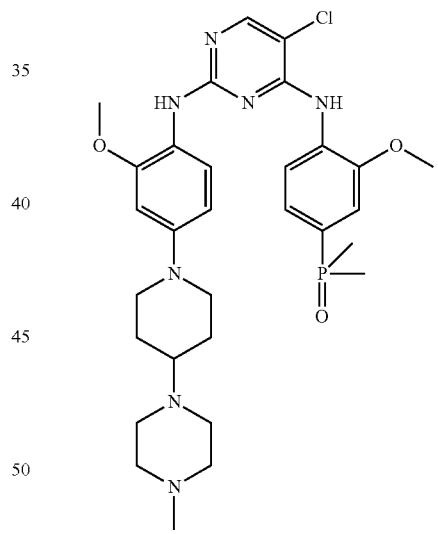
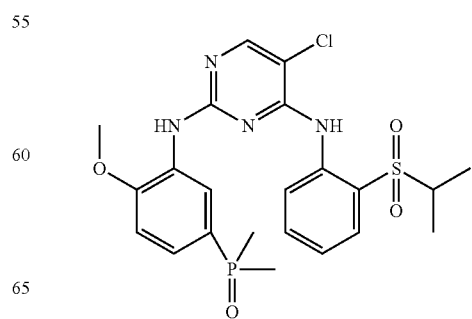

277
-continued
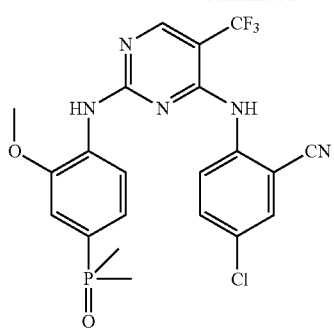
The following representative compounds were synthesized and tested for kinase inhibition against a panel of kinases and some also tested in various cell lines. Many of the compounds were found to be active in in vitro assays.
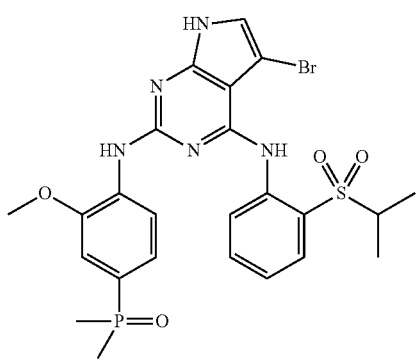
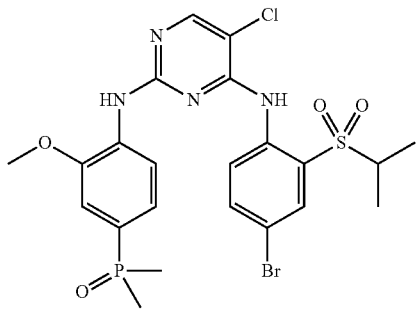
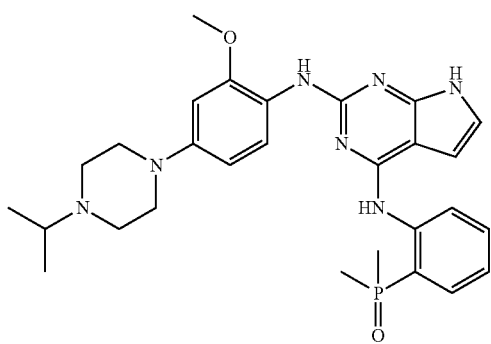
278
-continued
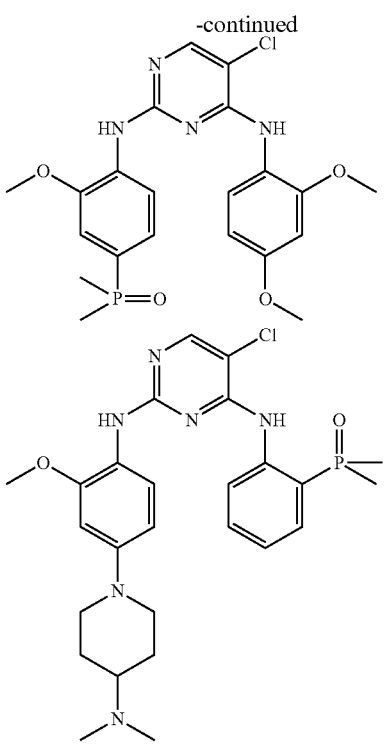
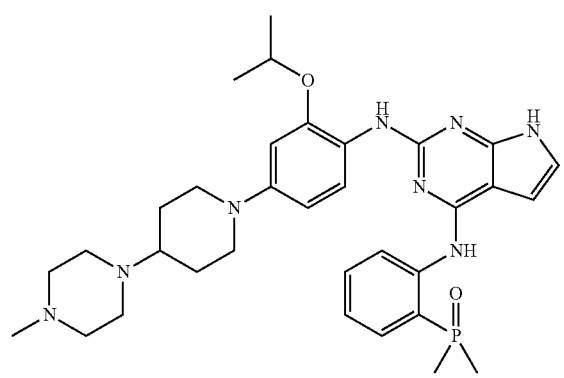
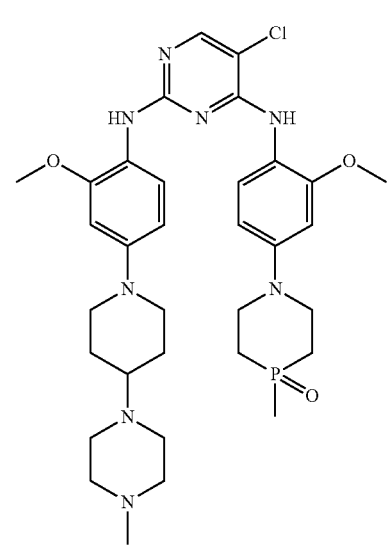

279
-continued
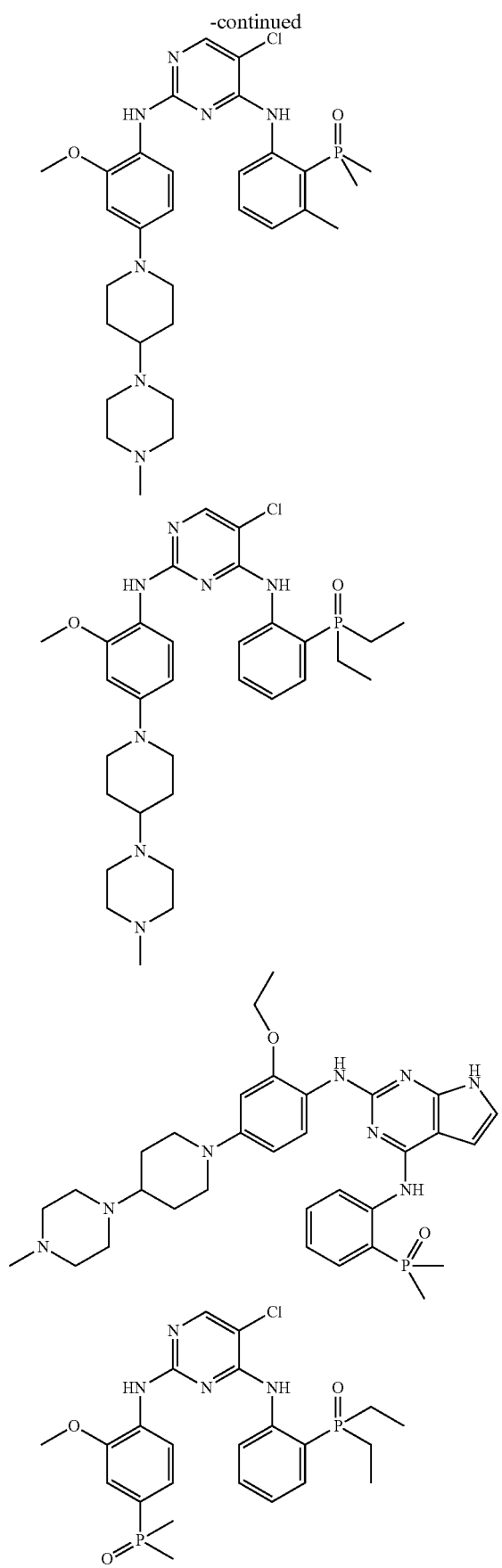
280
-continued
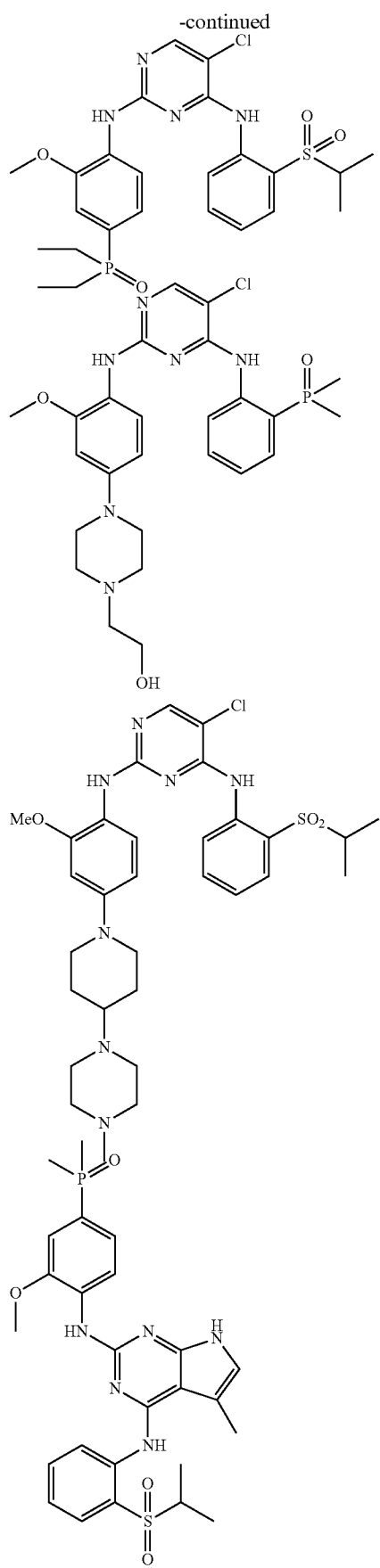

281
-continued
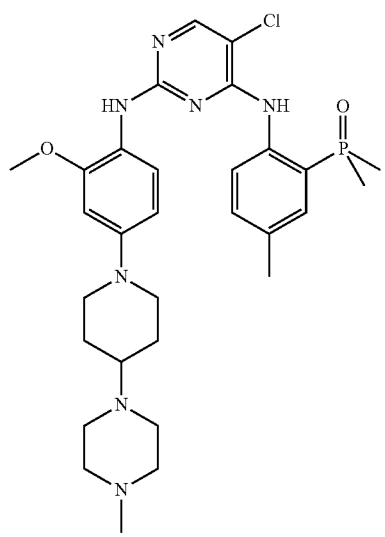
282
-continued
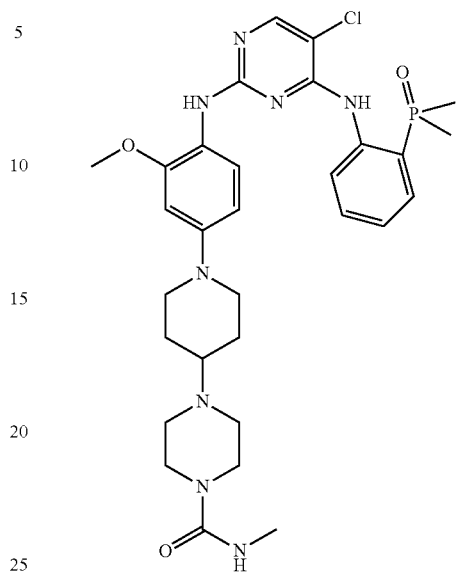
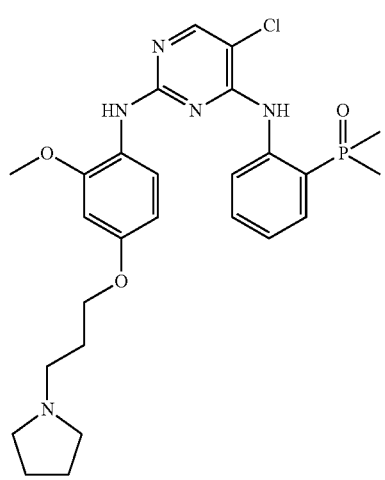
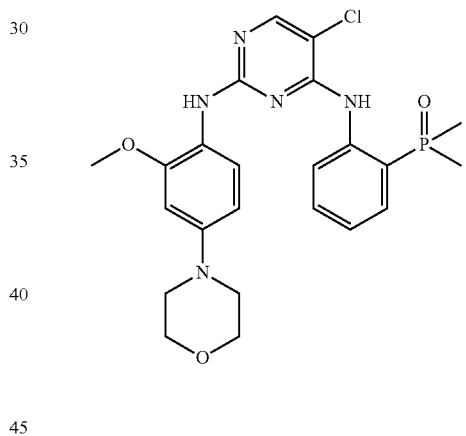
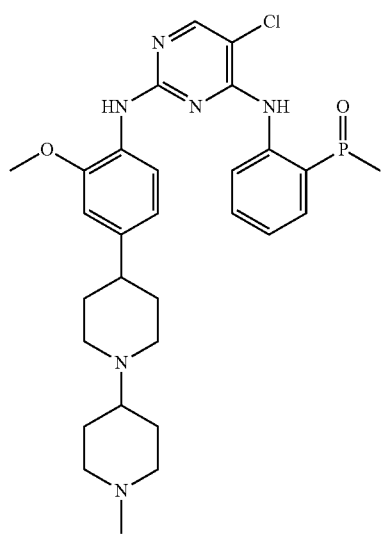
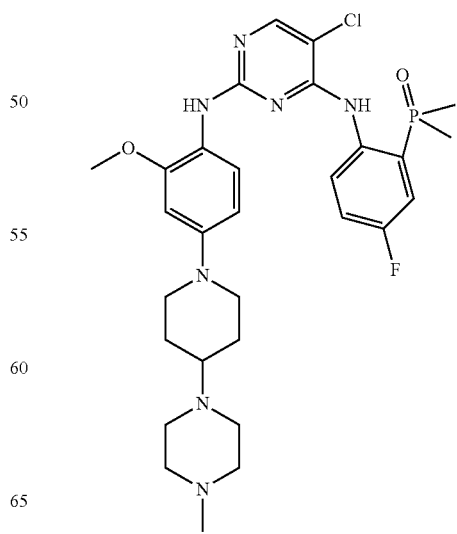

283
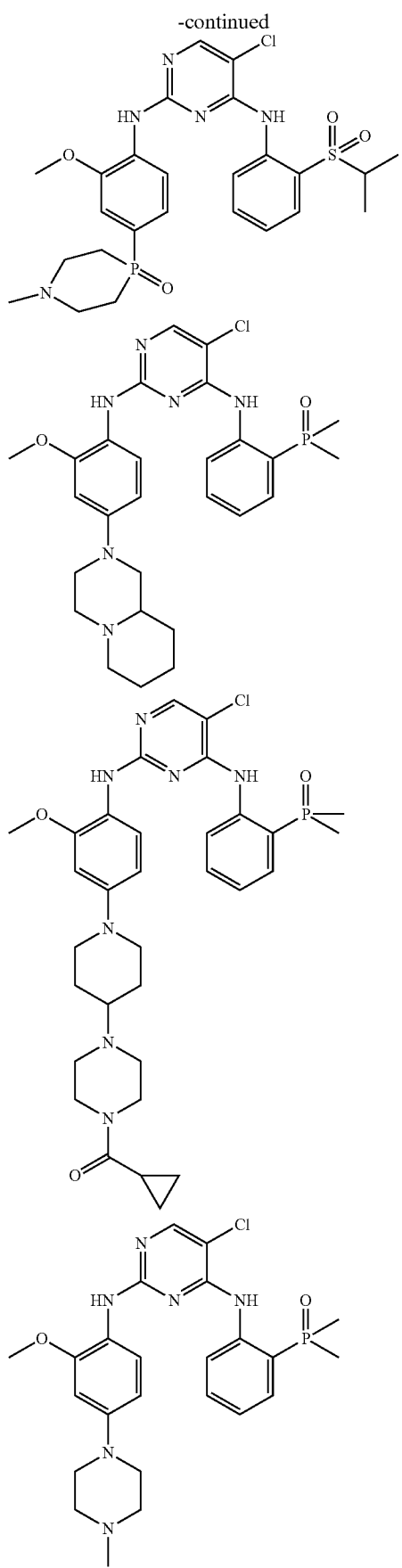
284
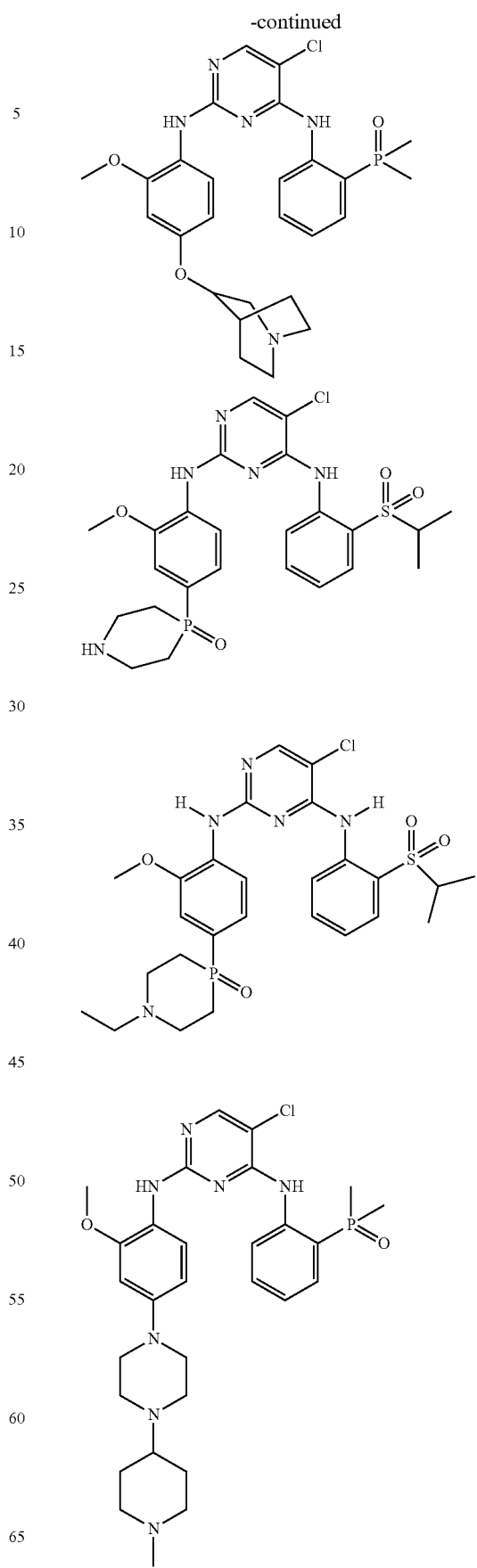

285 -continued
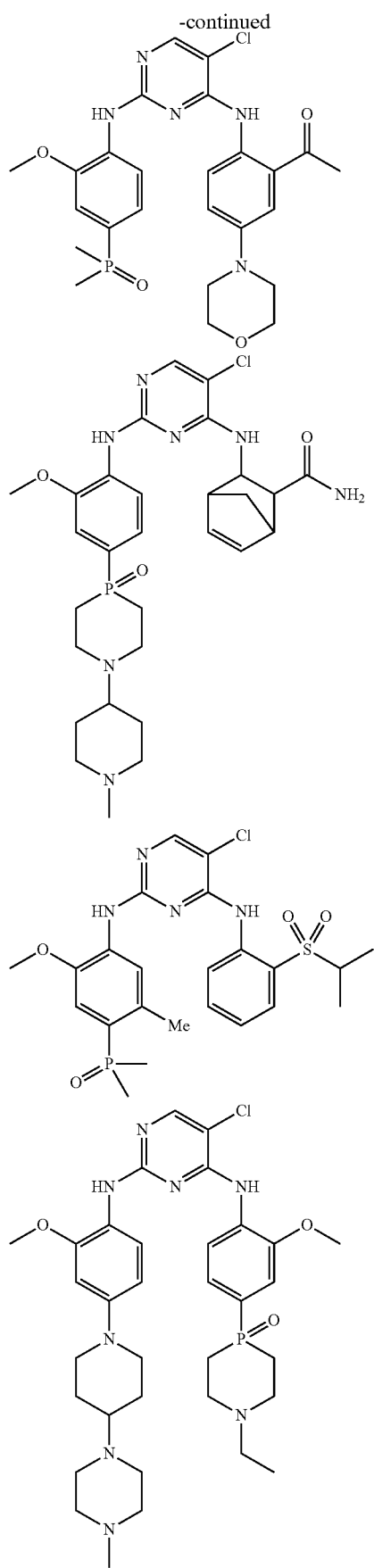
286 -continued
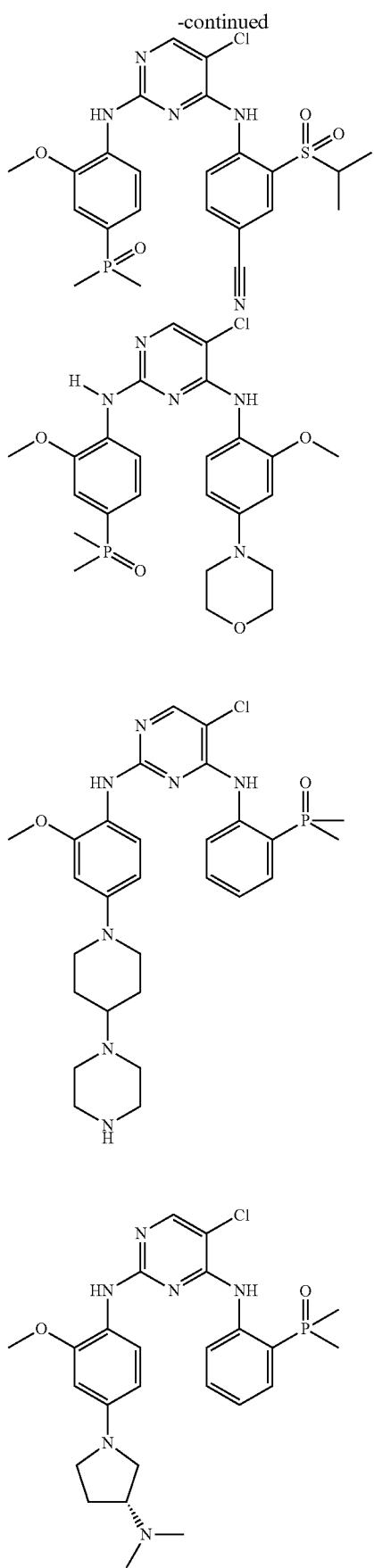

287
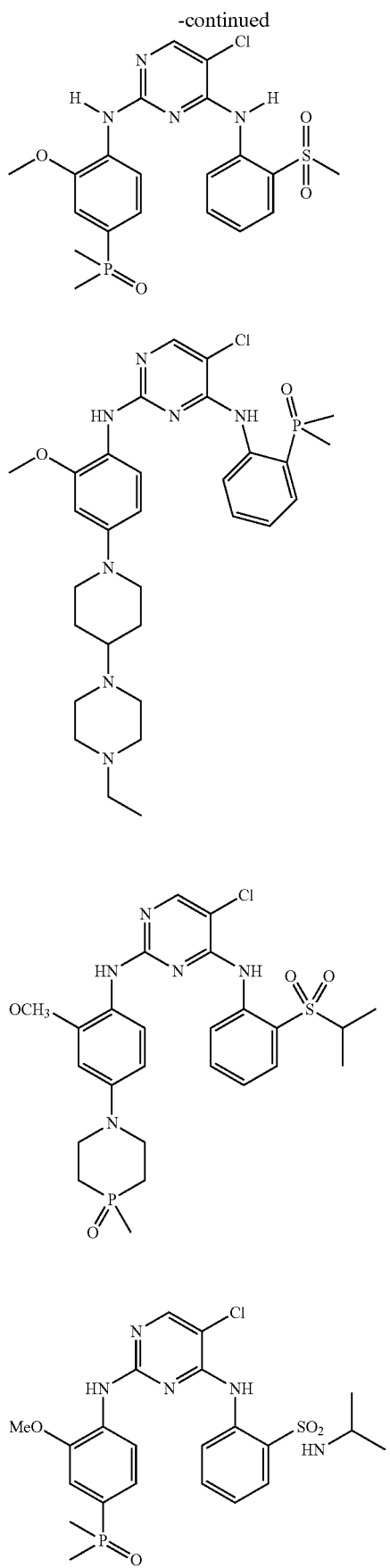
288
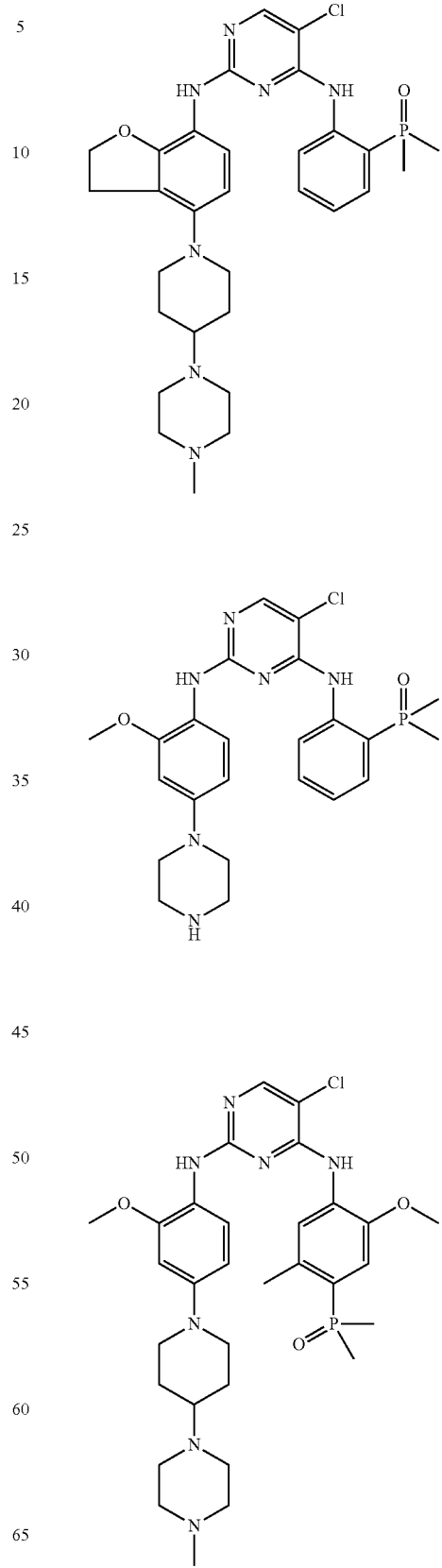

289
-continued
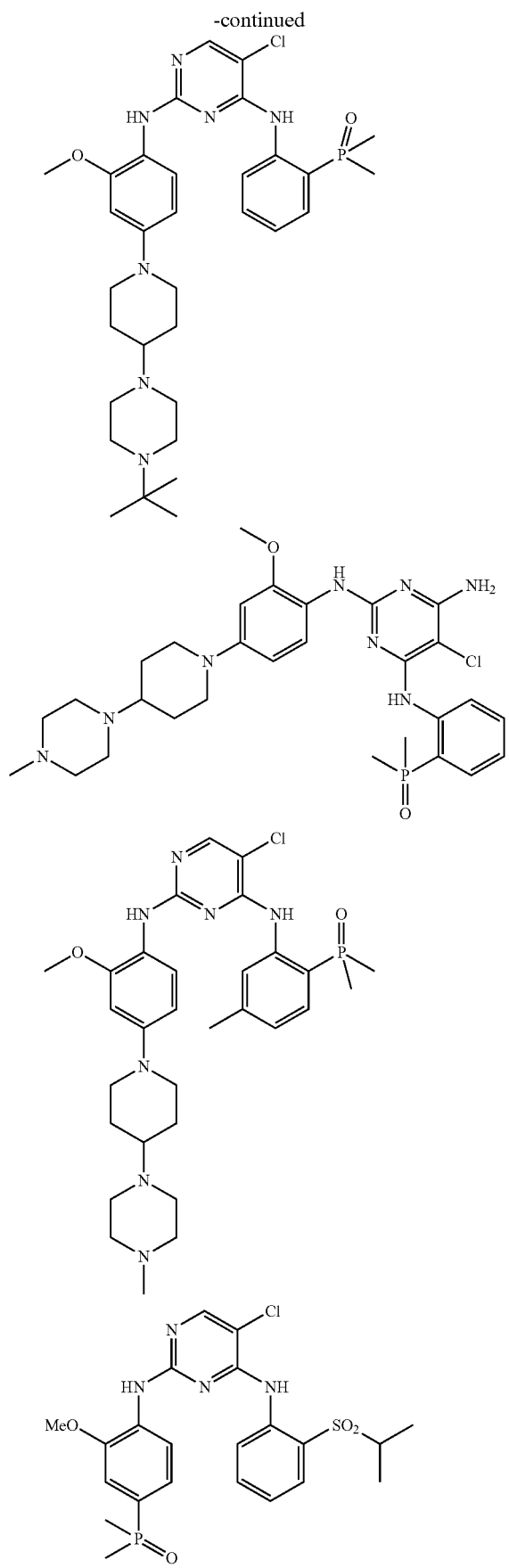
290
-continued
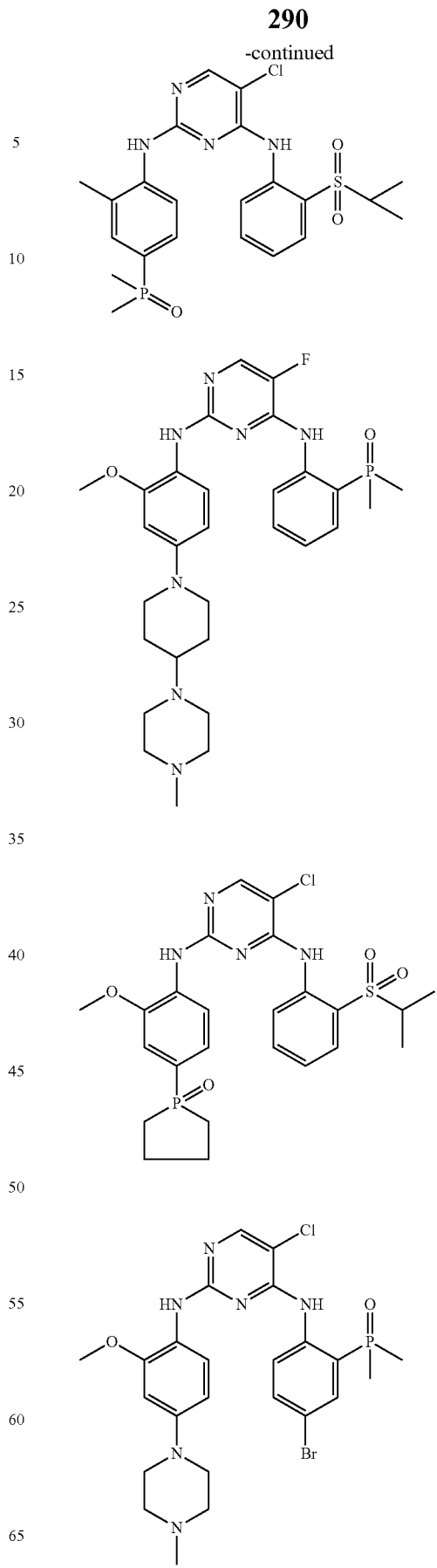

291                                    292
-continued                             -continued
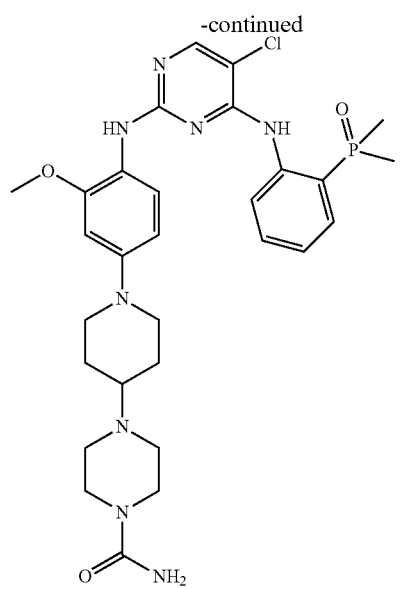
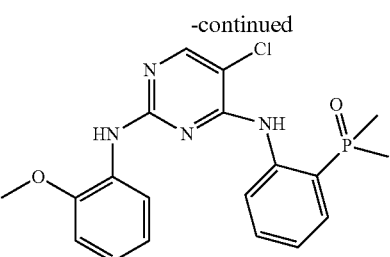
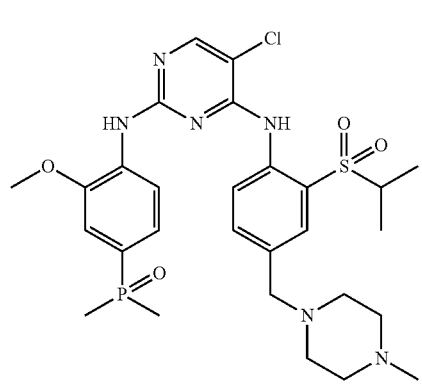
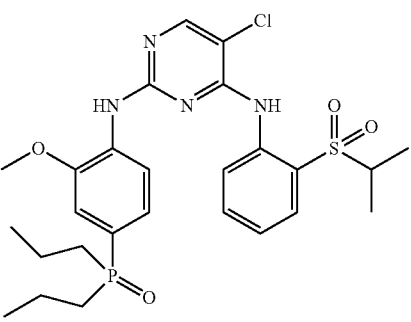
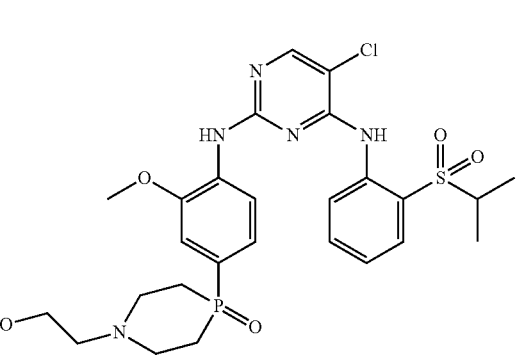
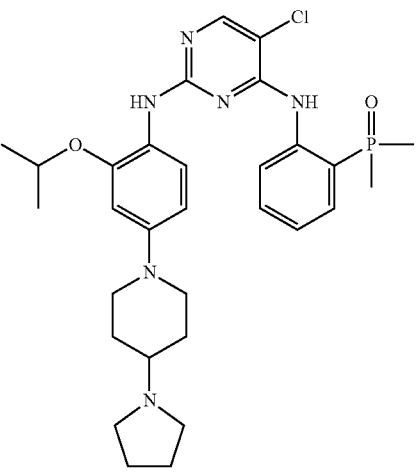
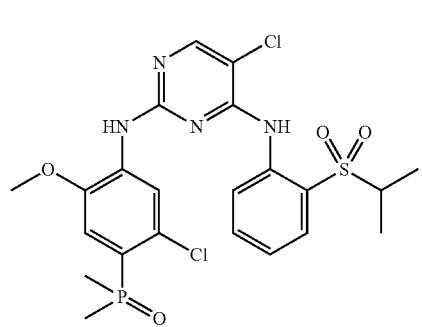
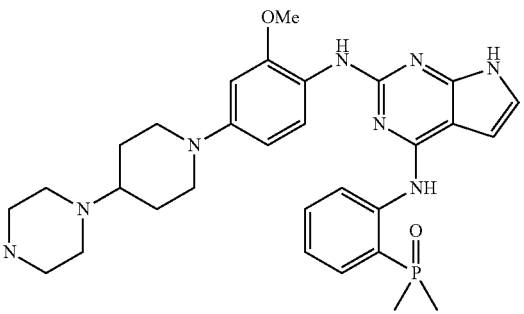

293
-continued
294
-continued
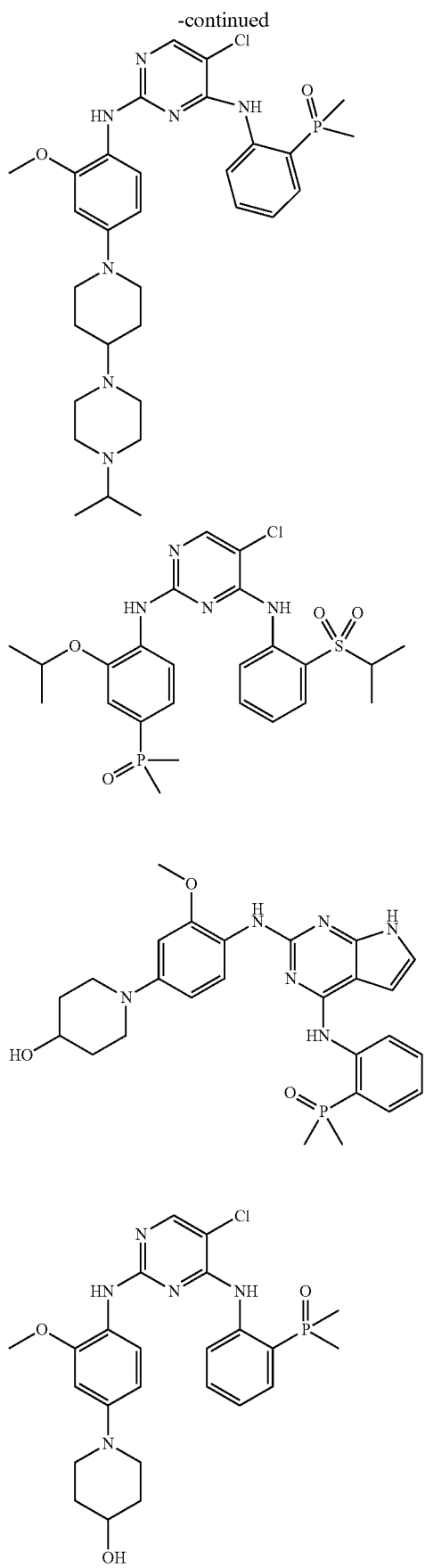
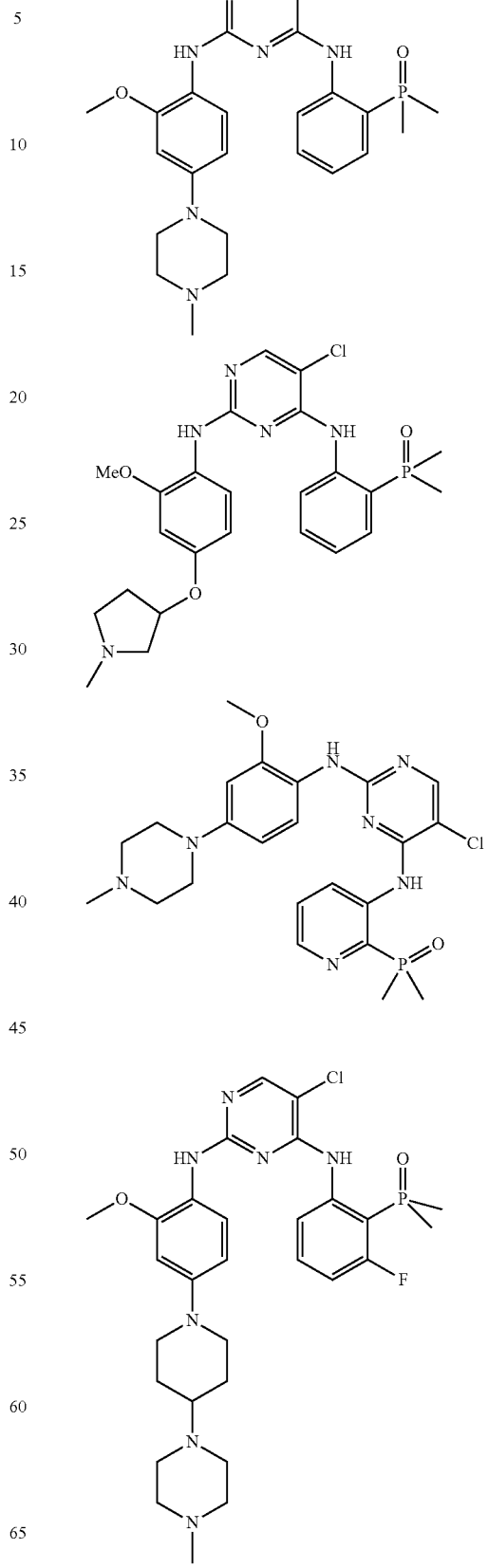

295
-continued
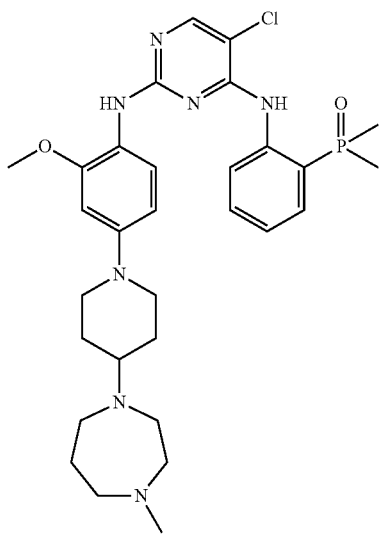
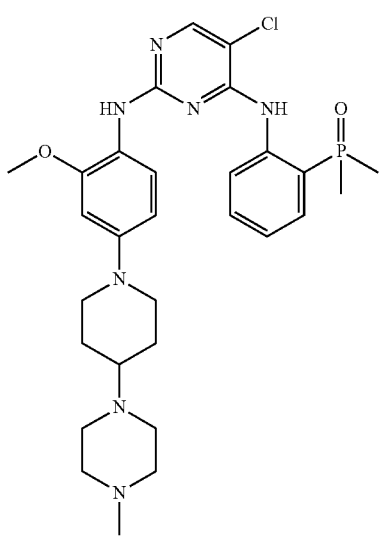
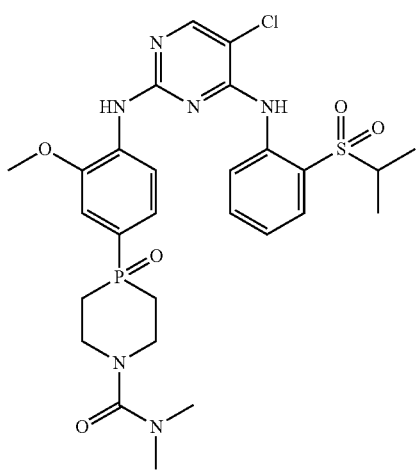
296
-continued
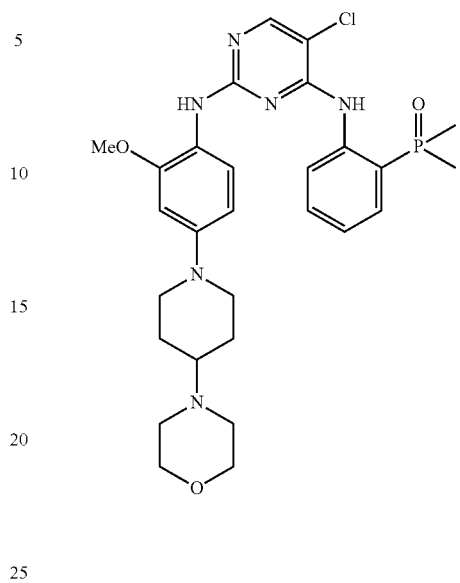
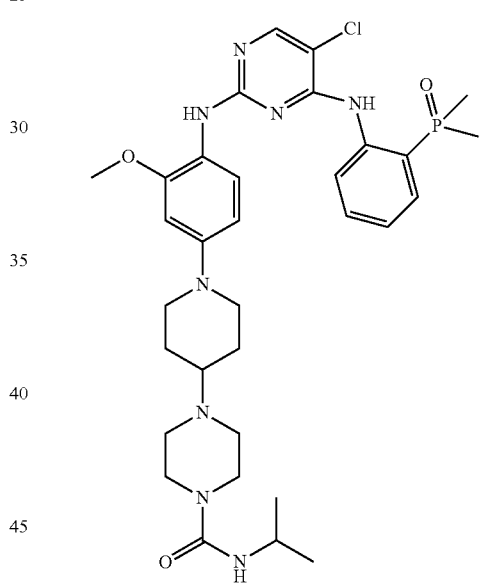
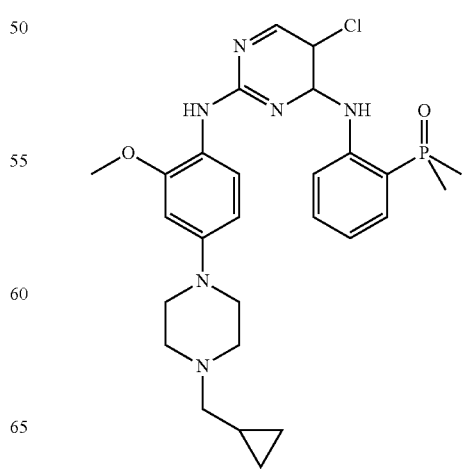

297
-continued
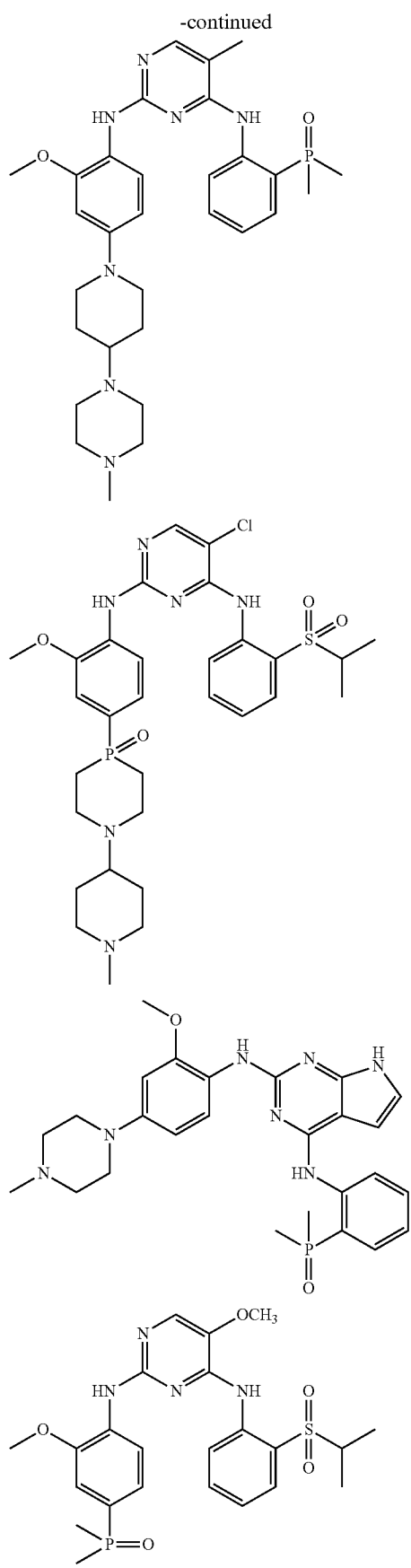
298
-continued
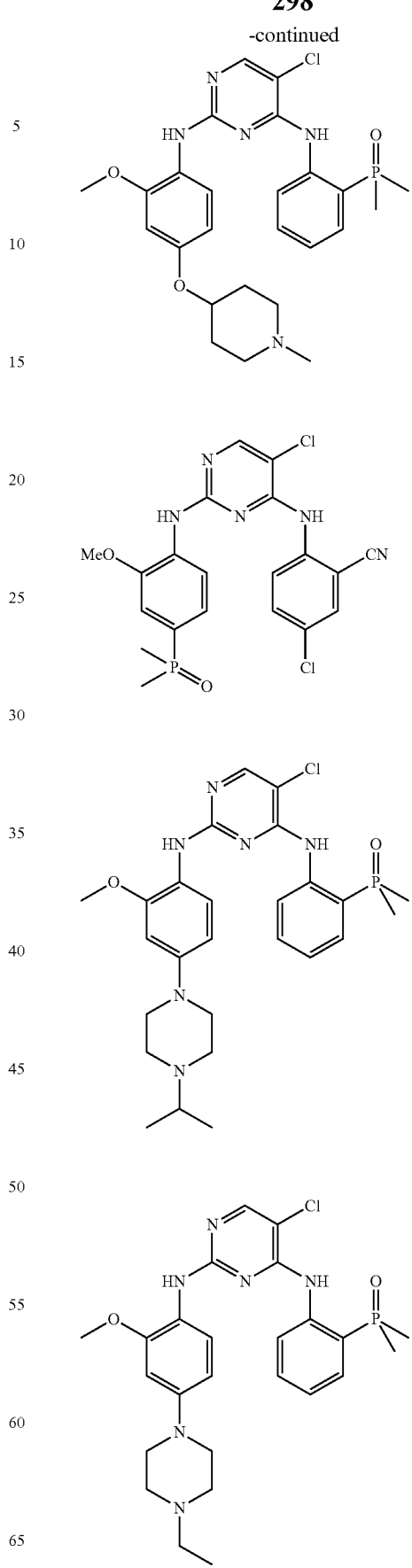

299
-continued
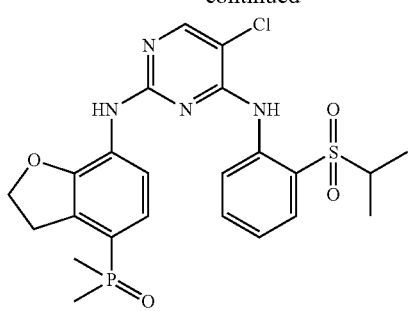
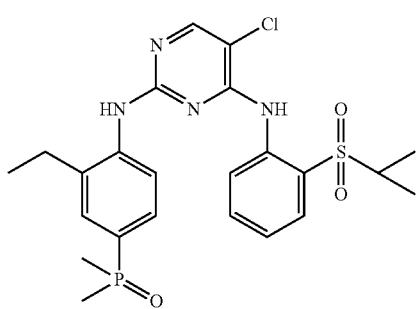
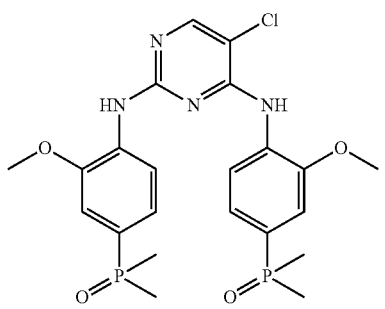
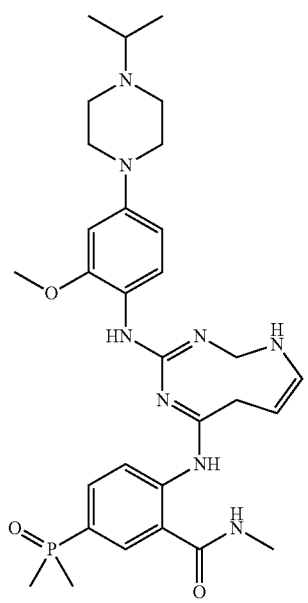
300
-continued
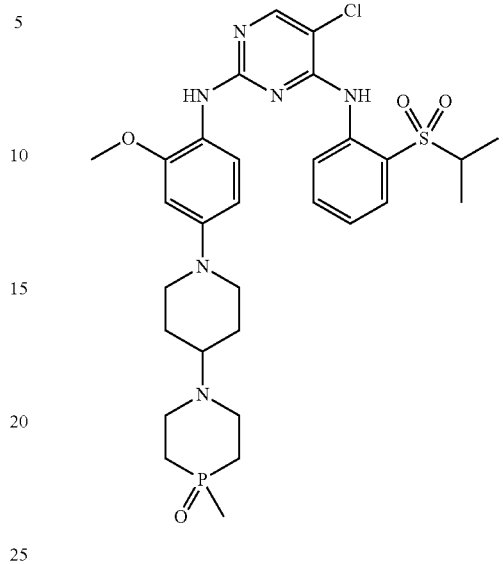
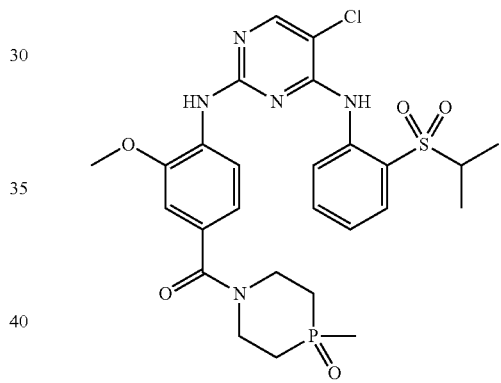
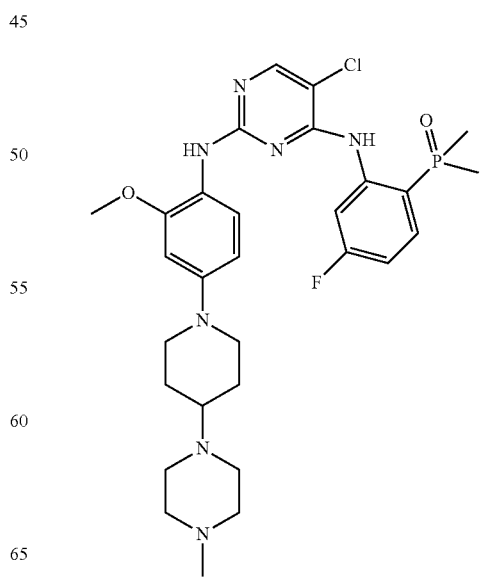

-continued
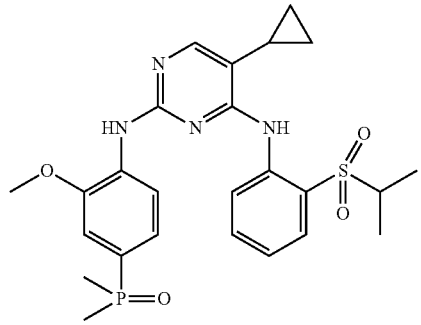
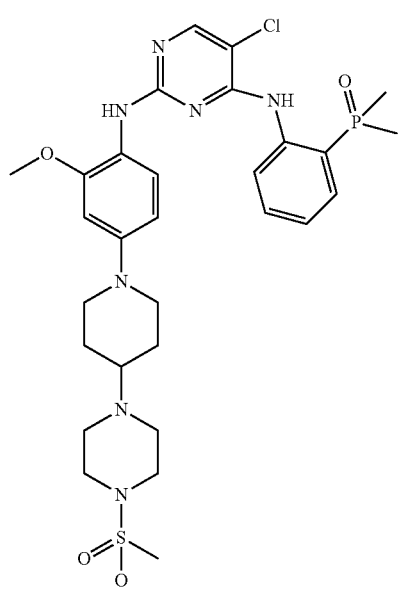
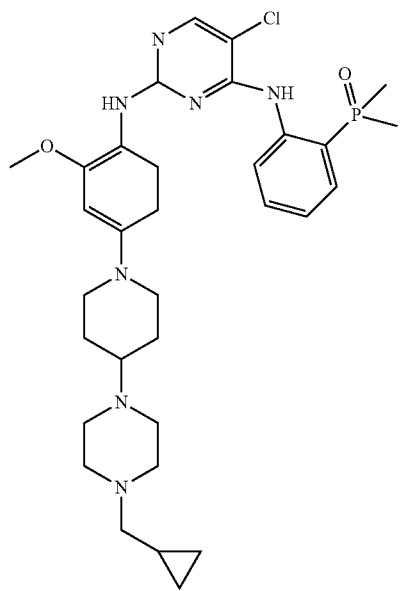
-continued
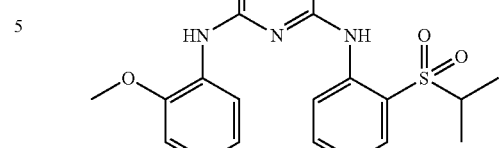
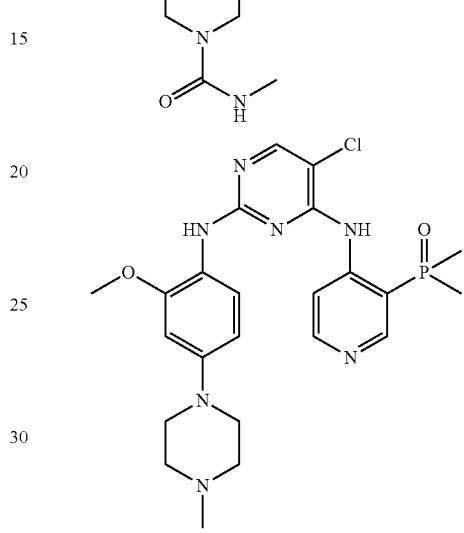
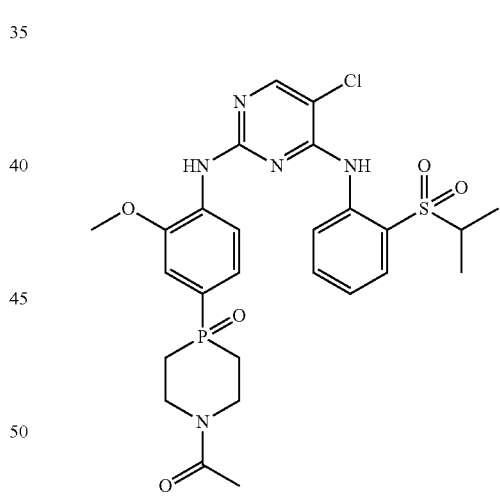
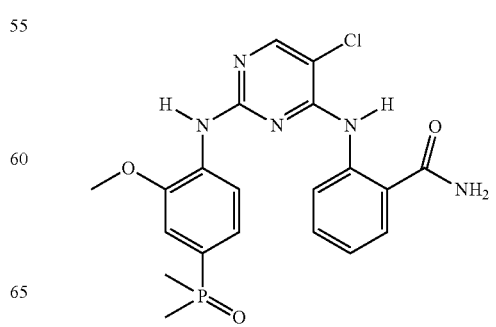

303
-continued
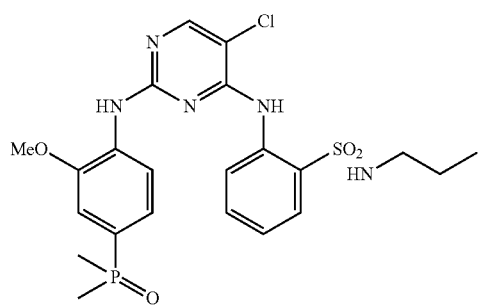
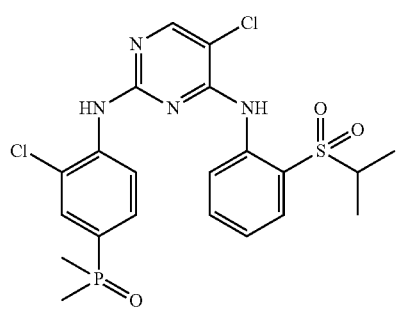
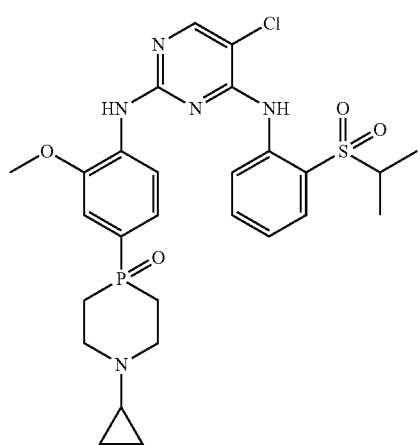
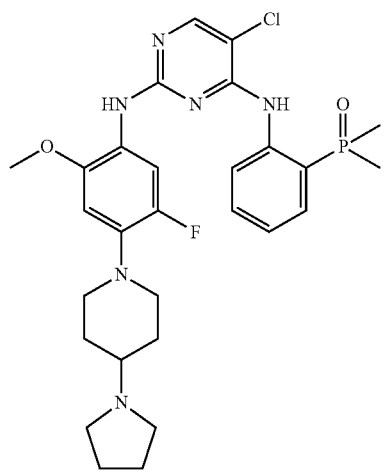
304
-continued
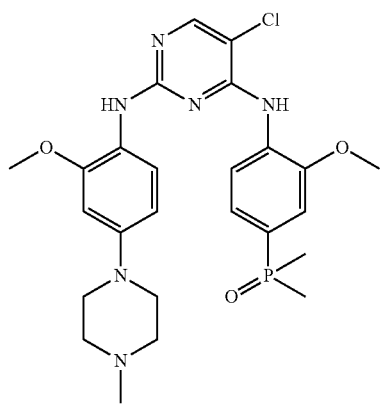
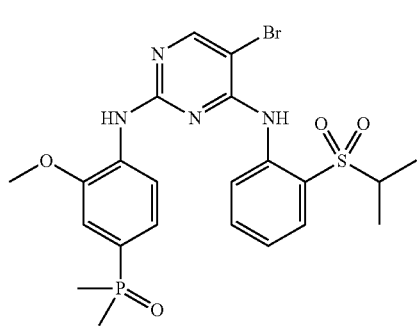
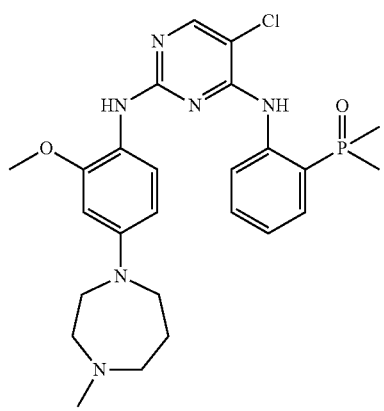
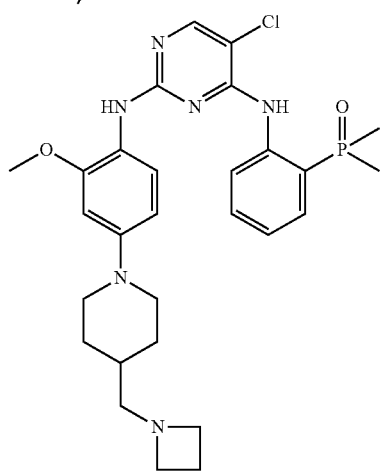

305
-continued
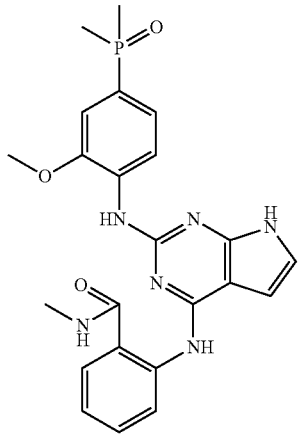
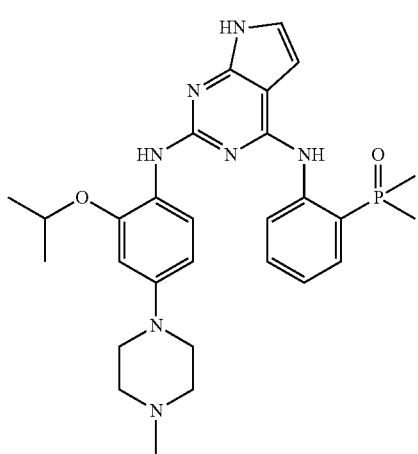
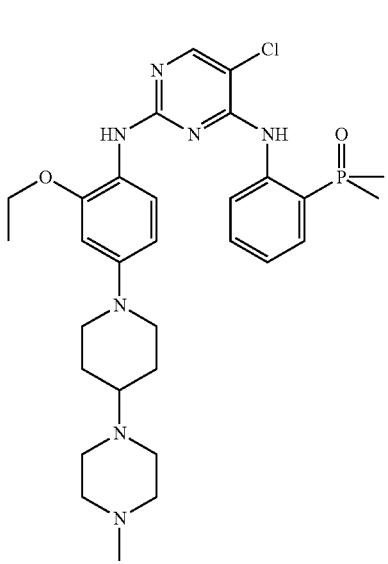
306
-continued
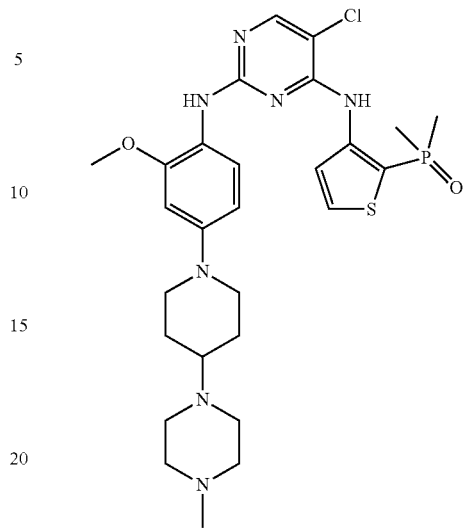
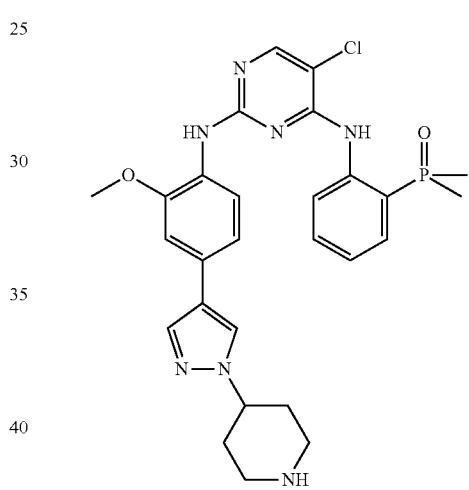
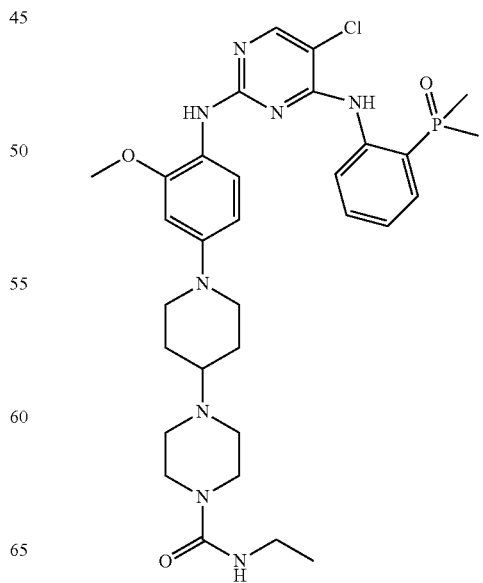

307
-continued
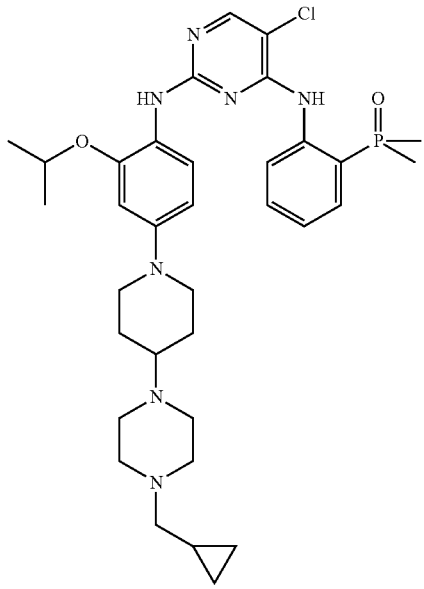
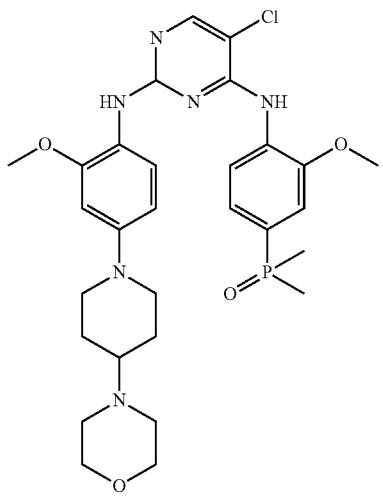
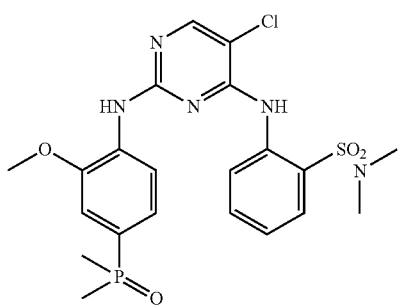
308
-continued
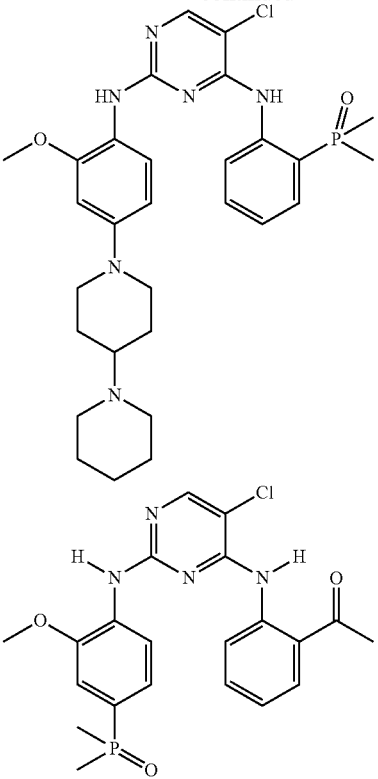
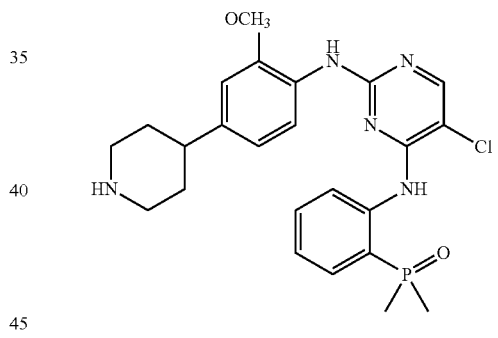
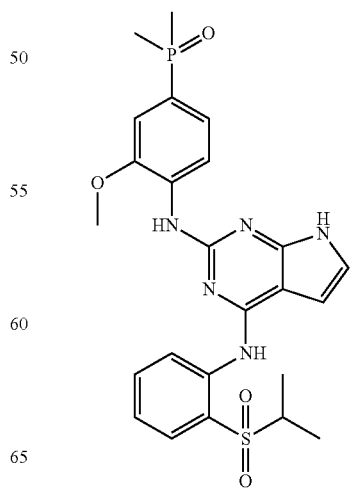

309
-continued
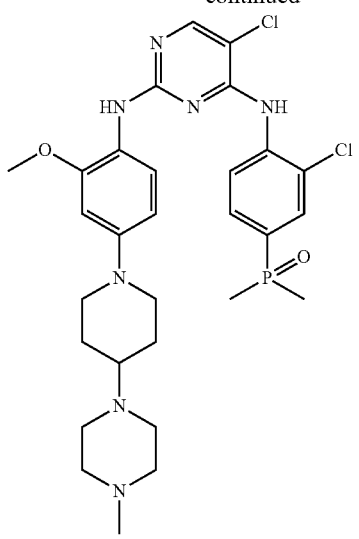
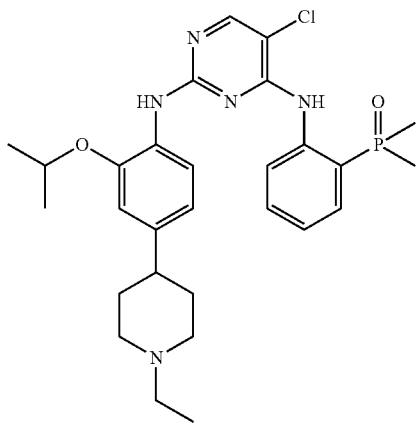
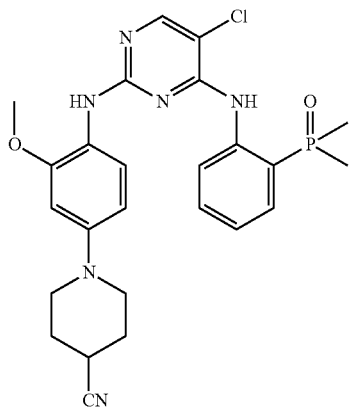
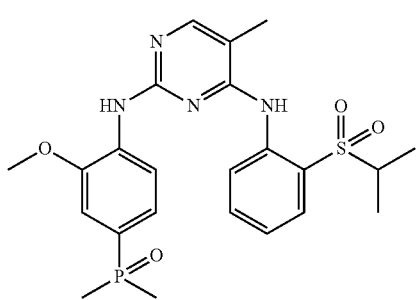
310
-continued
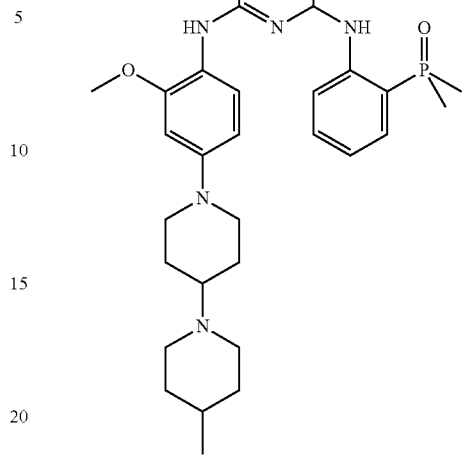
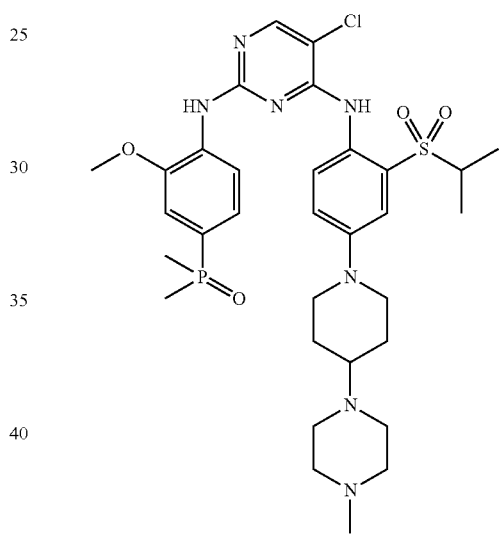
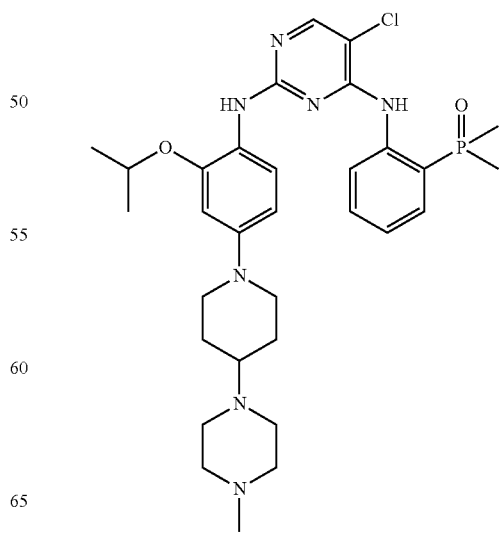

311
-continued
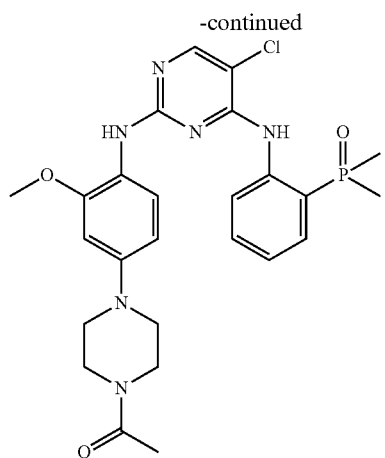
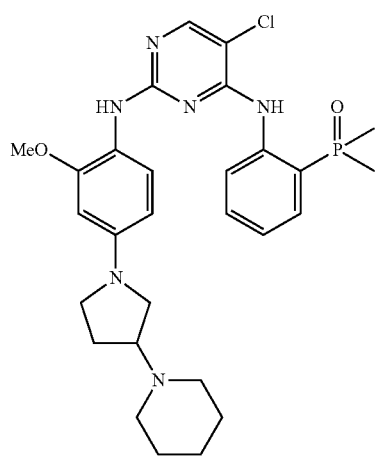
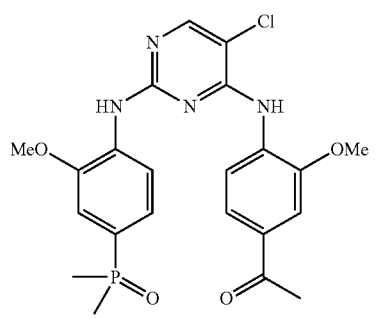
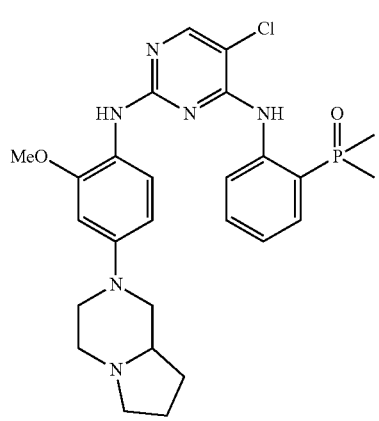
312
-continued
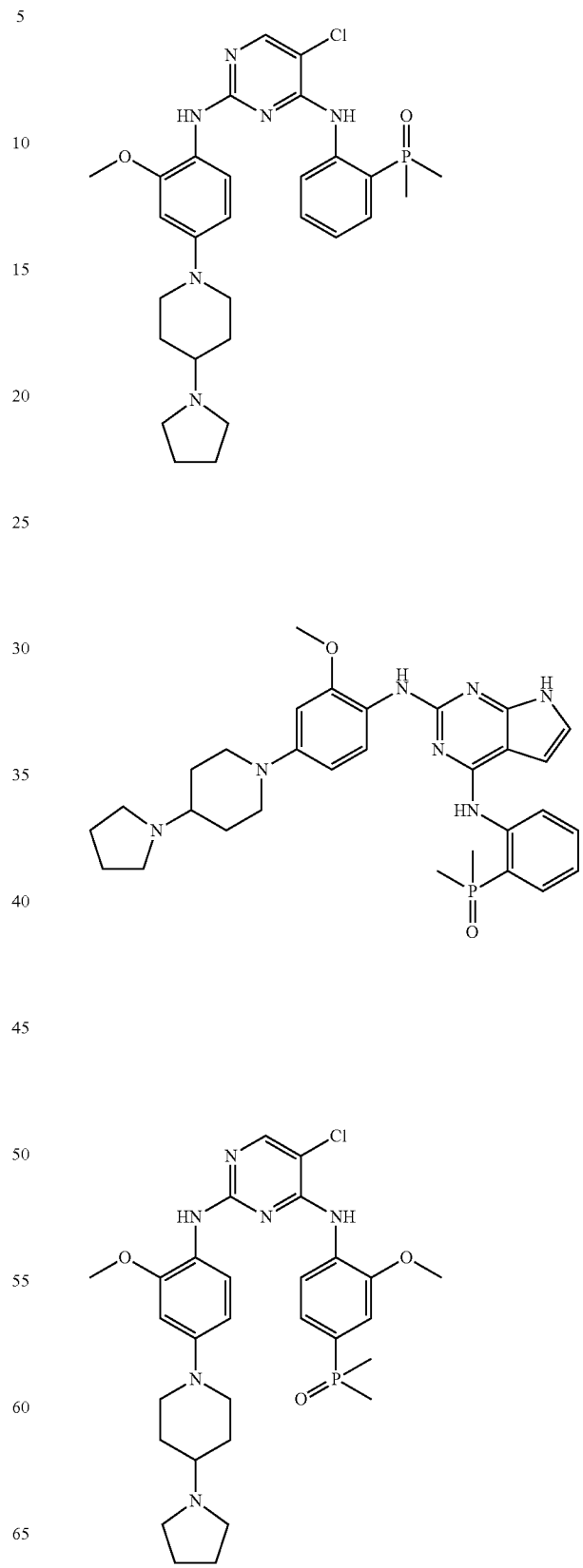

313
-continued
314
-continued
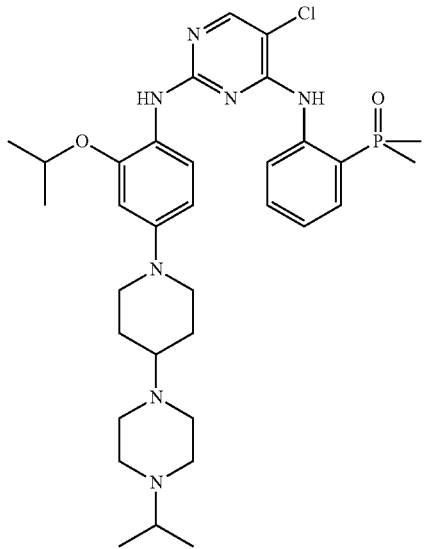
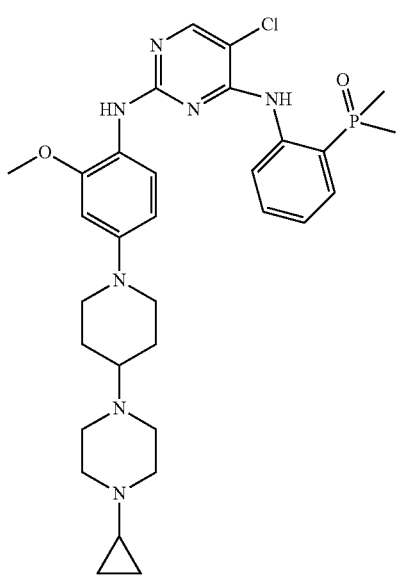
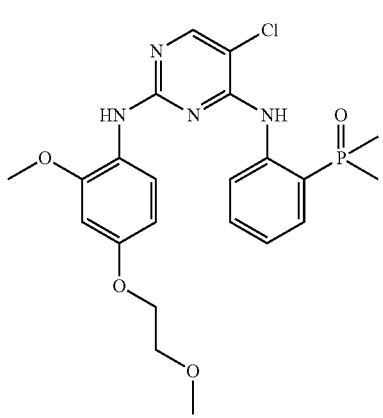
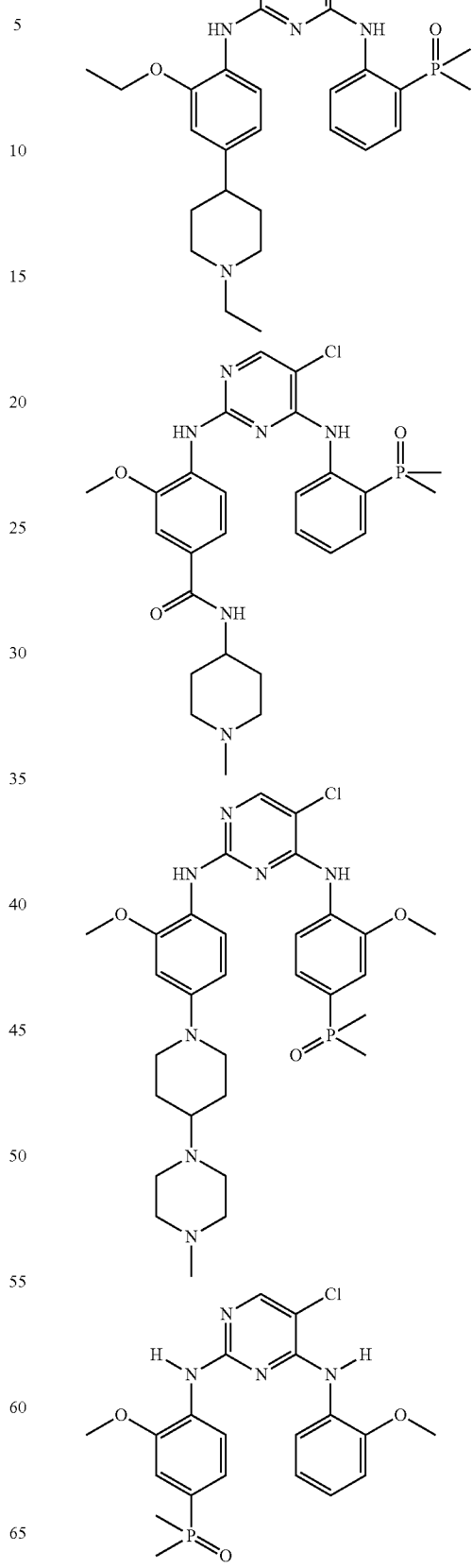

315
-continued
316
-continued
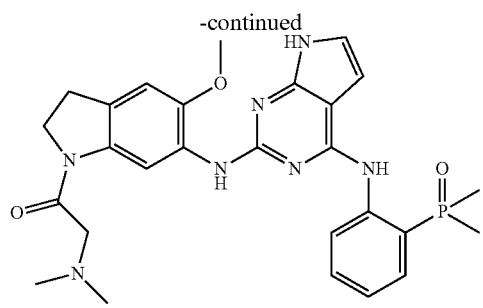
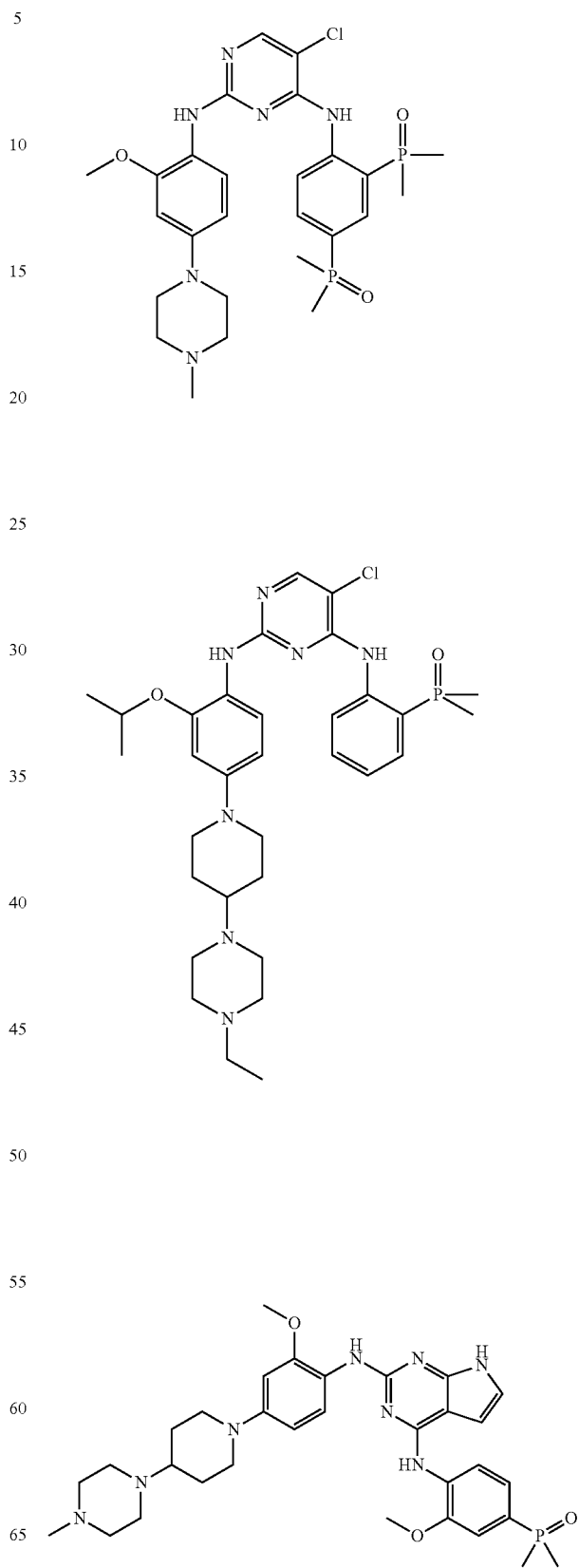

317
-continued
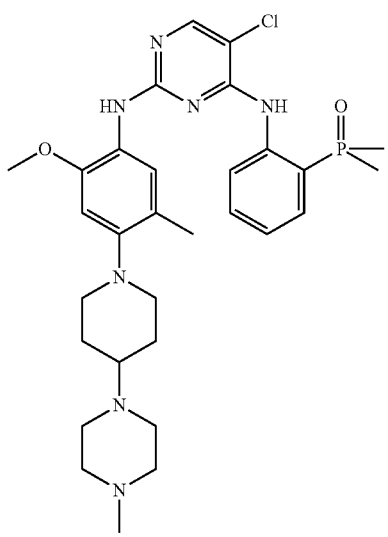
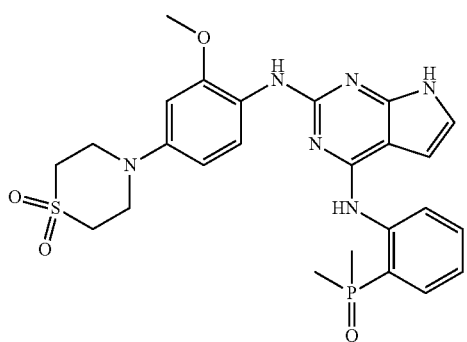
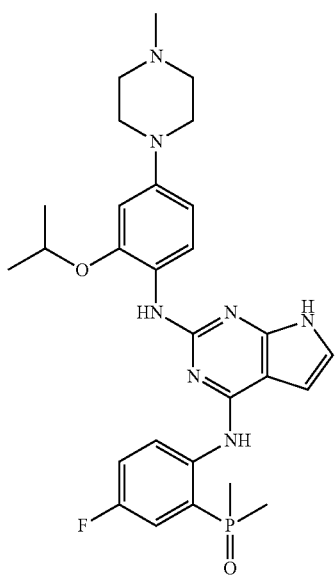
318
-continued
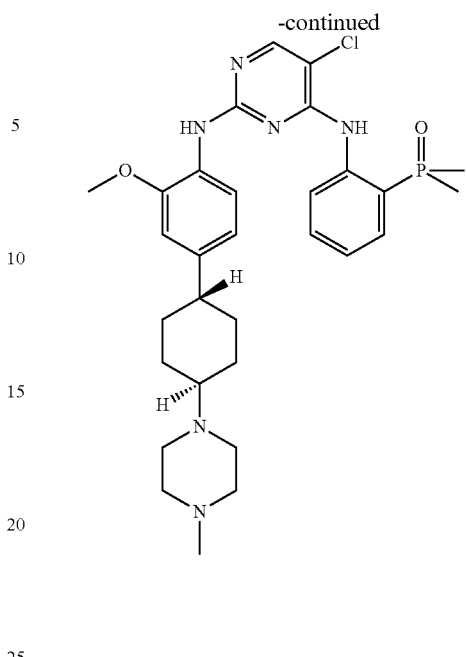
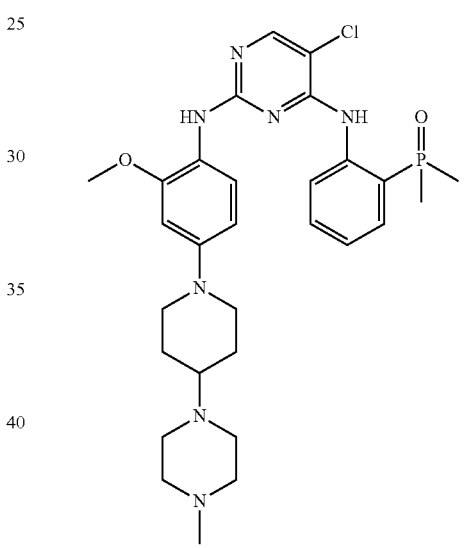
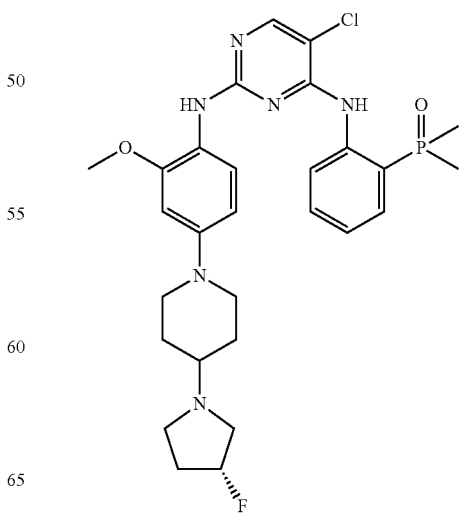

319
-continued
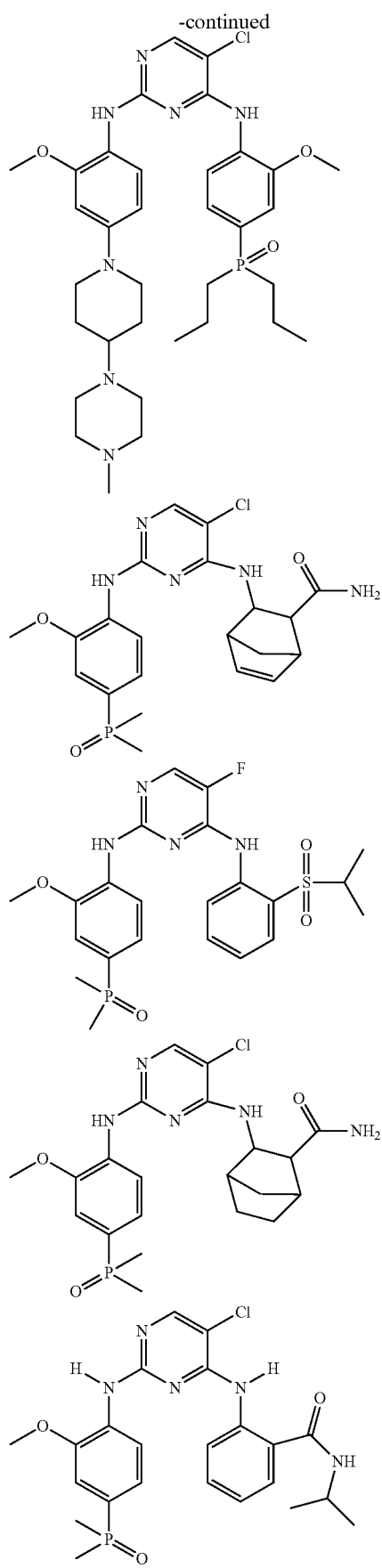
320
-continued
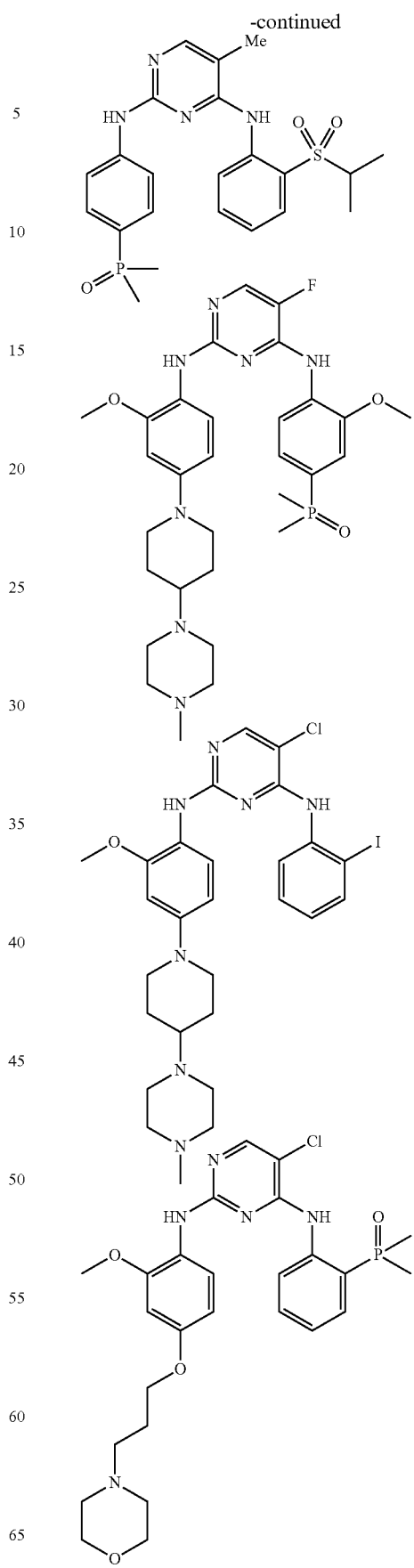

321
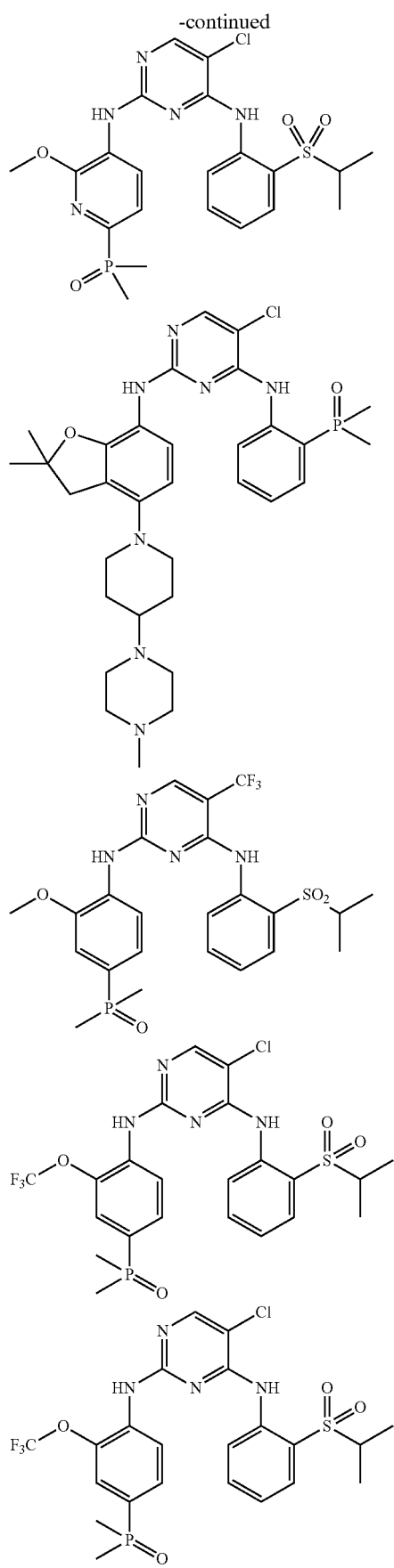
322
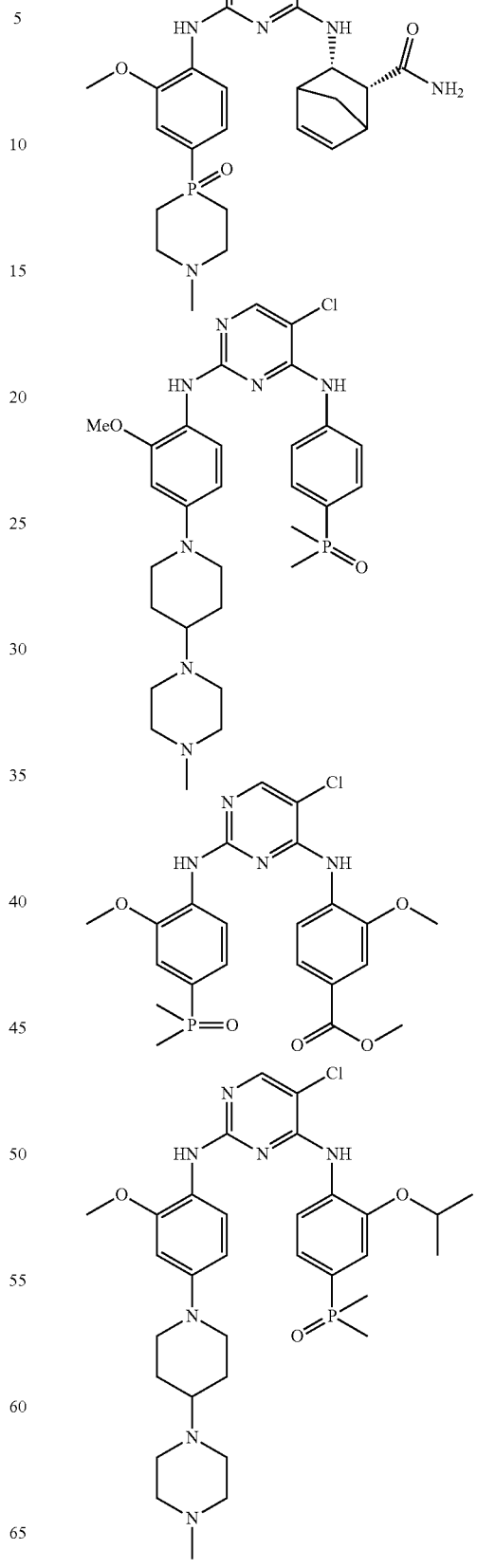

323
-continued
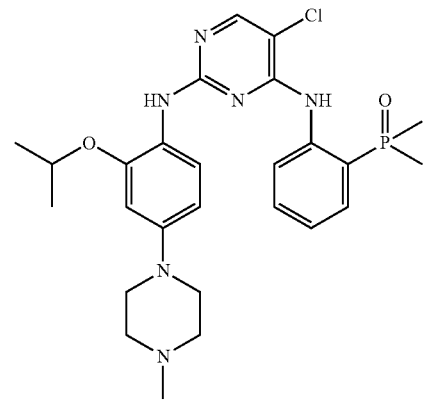
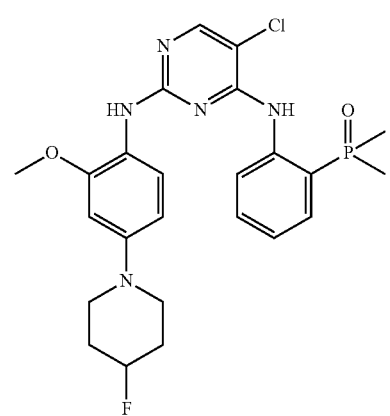
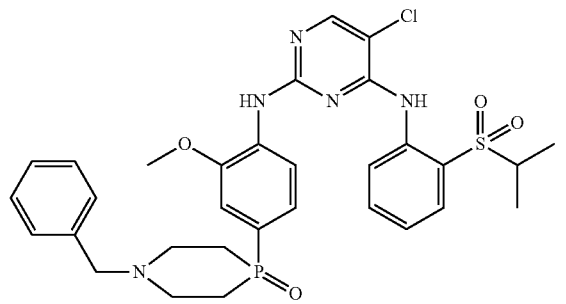
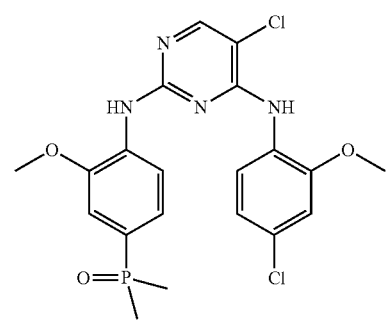
324
-continued
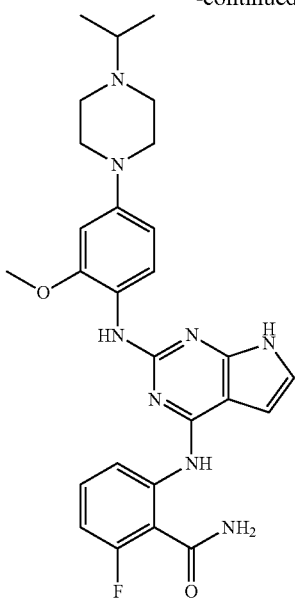
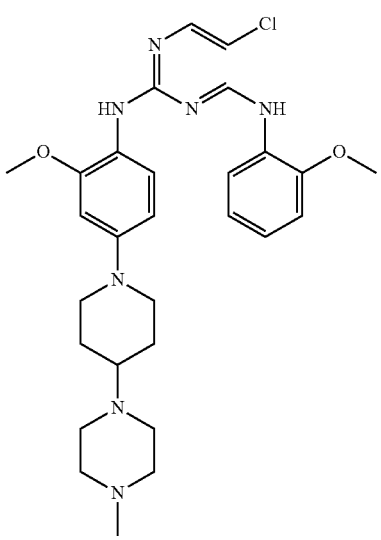
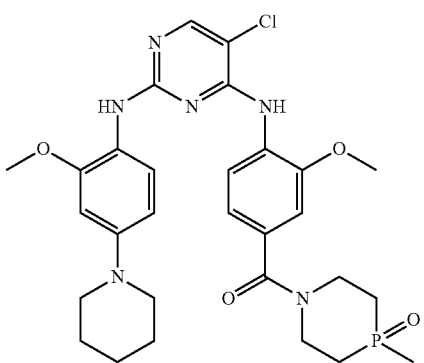

325
-continued
326
-continued
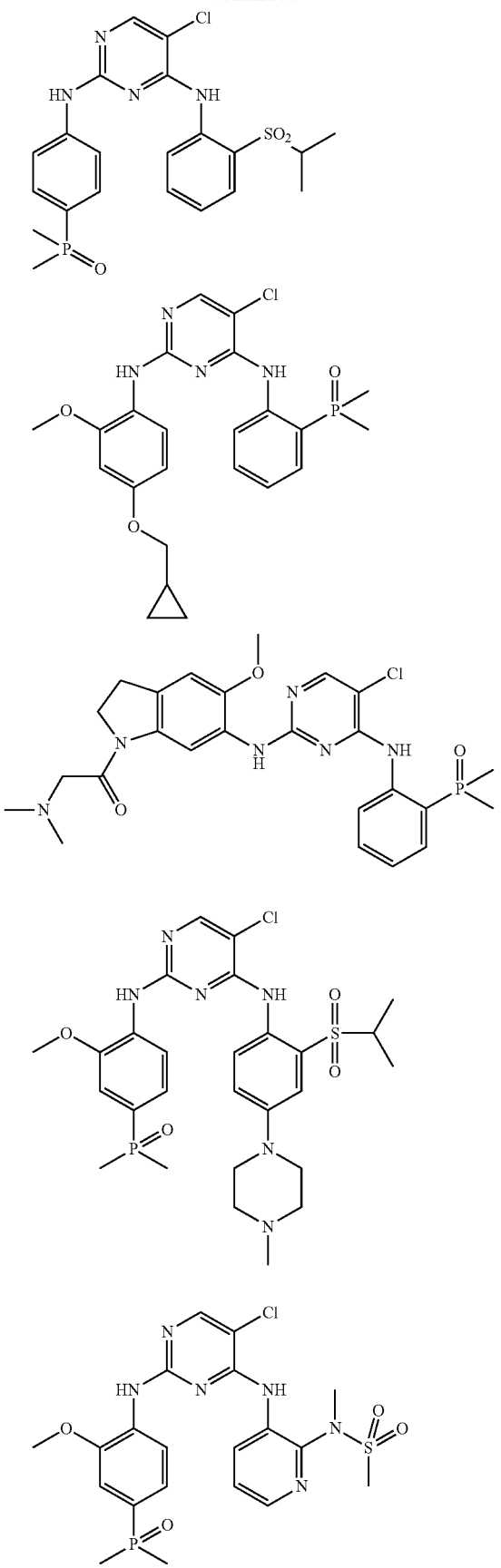
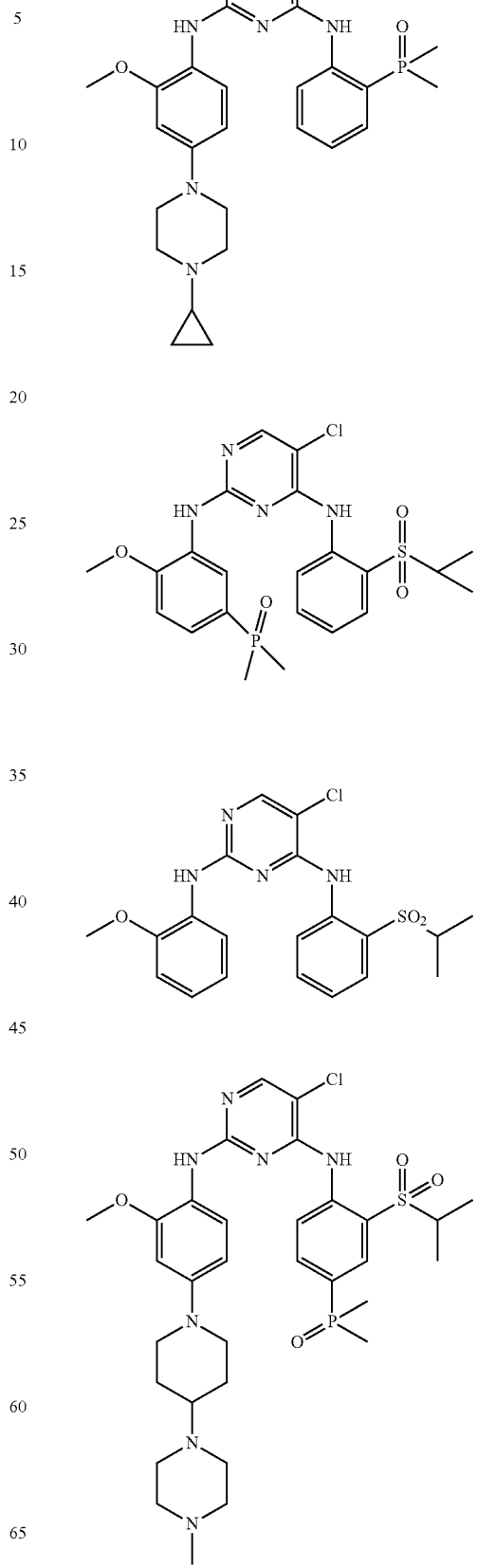

327
-continued
328
-continued
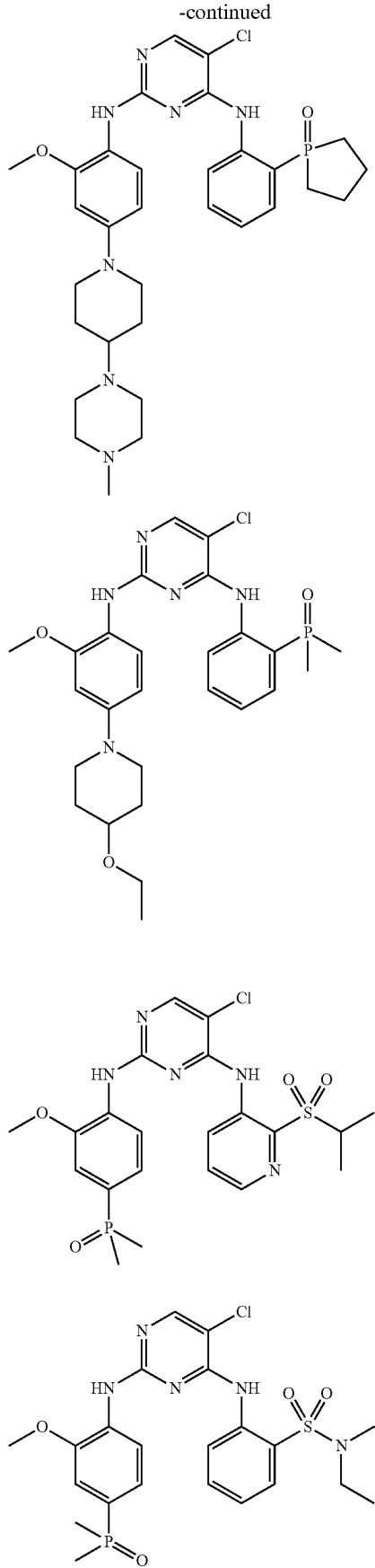
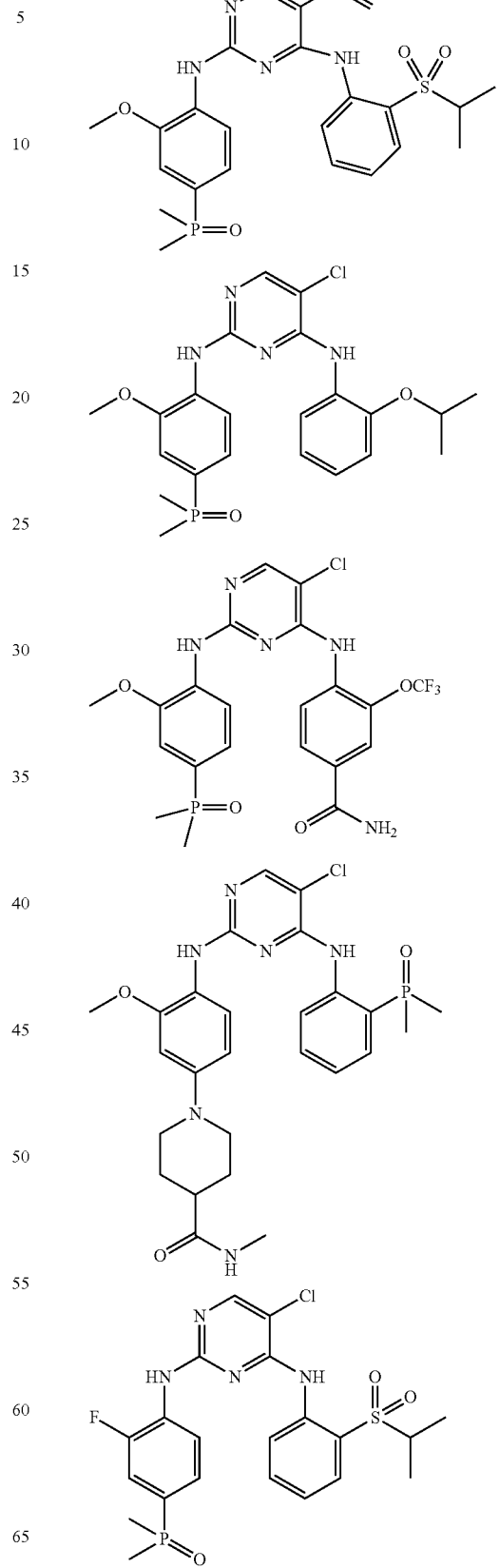

329
-continued
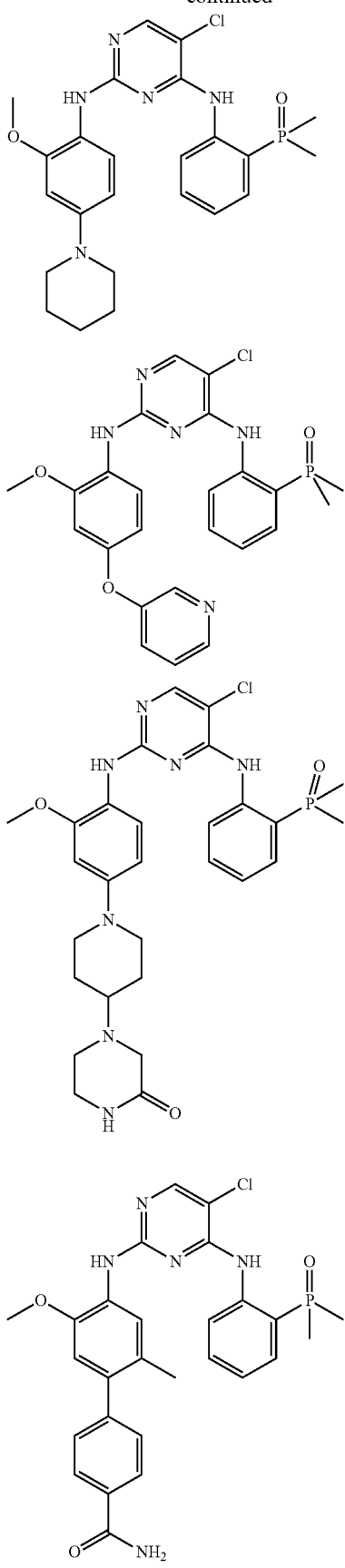
330
-continued
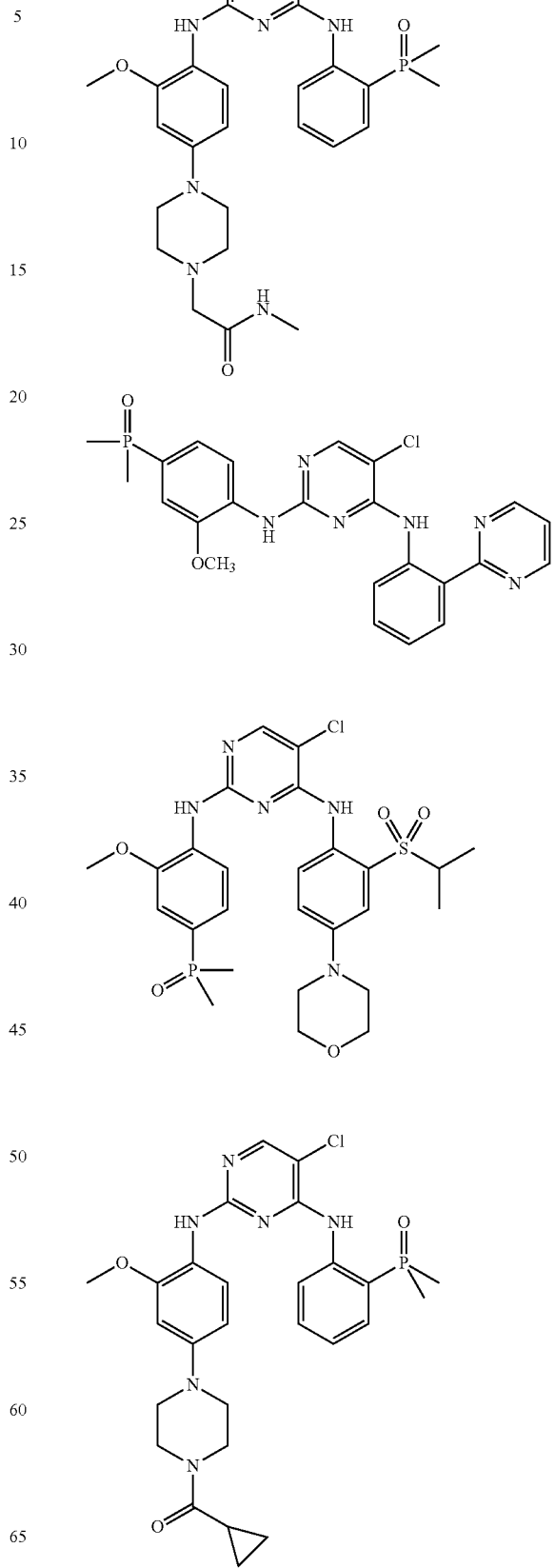

-continued
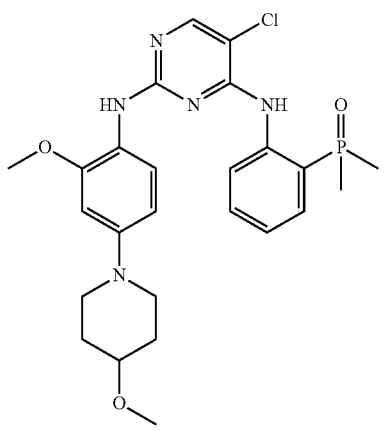
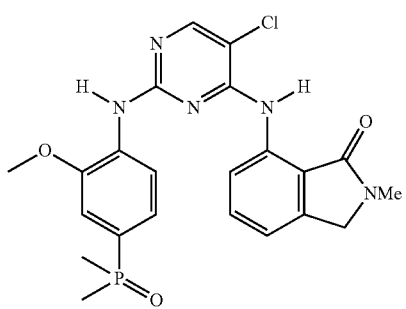
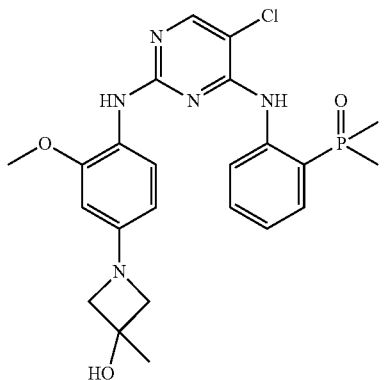
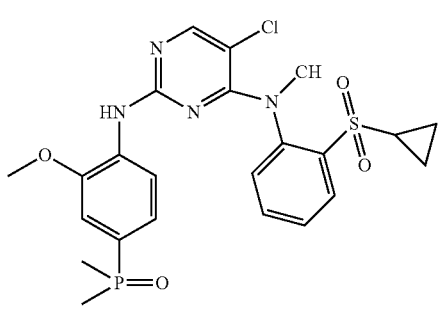
-continued
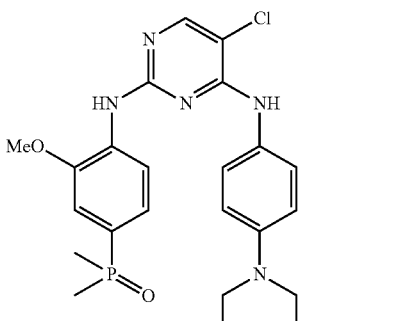
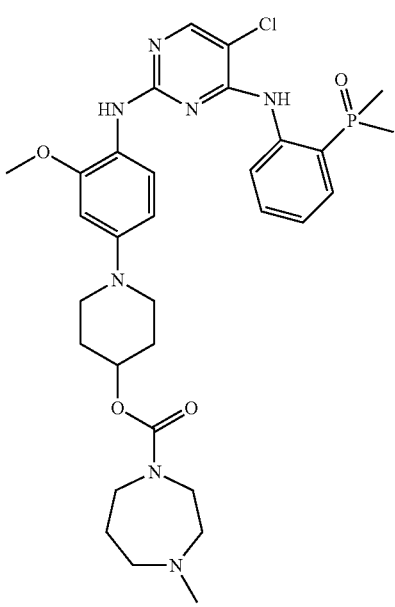
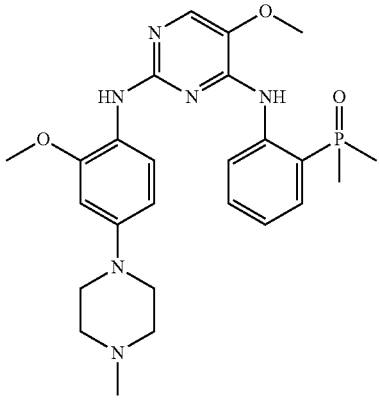
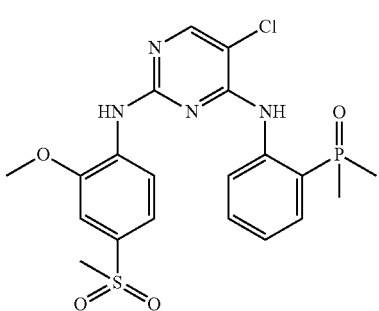

333
-continued
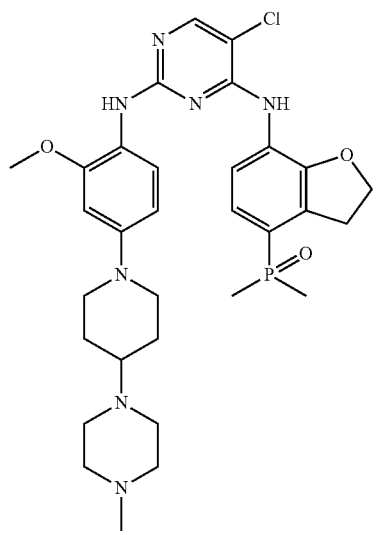
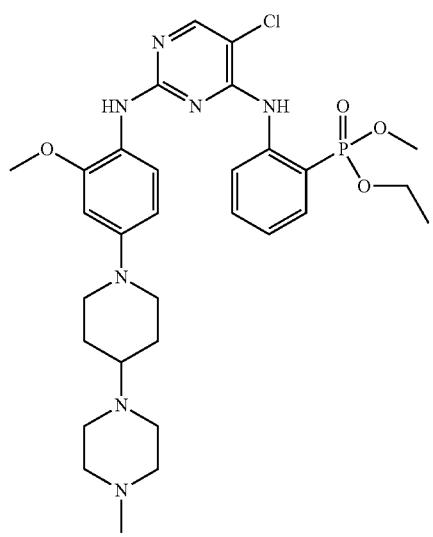
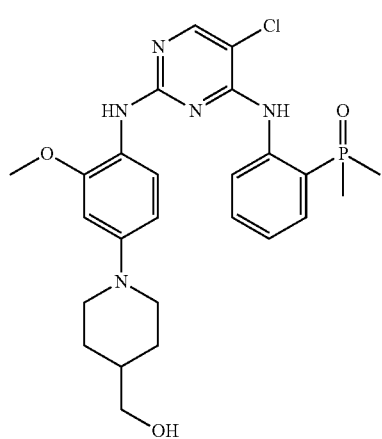
334
-continued
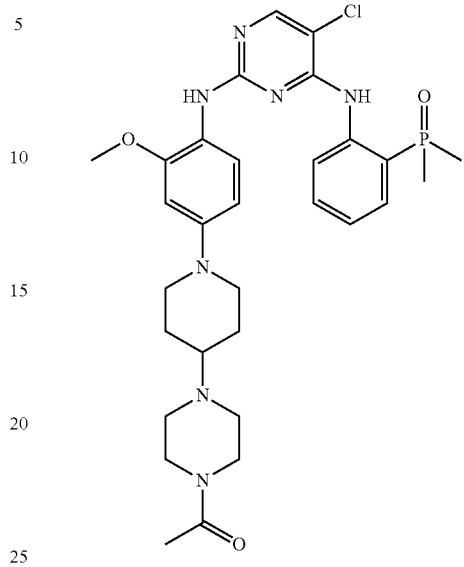
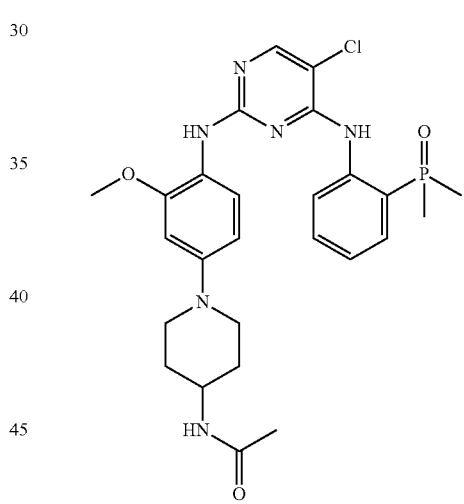
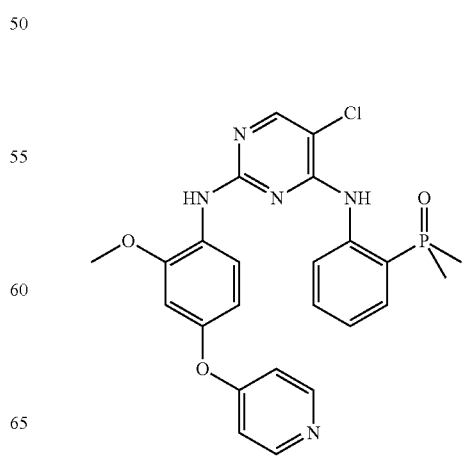

-continued
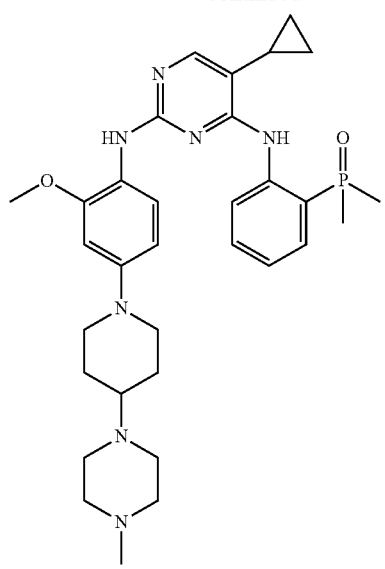
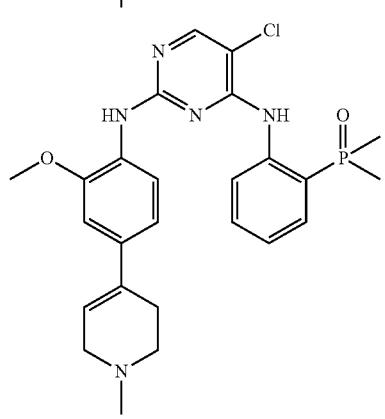
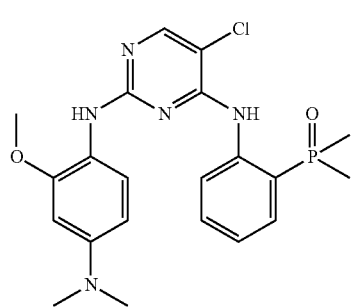
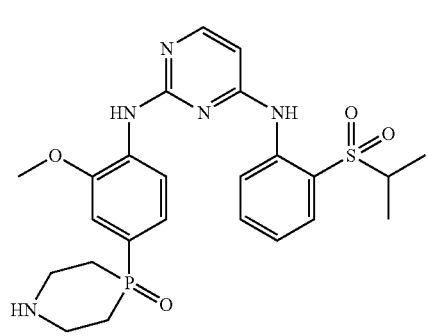
-continued
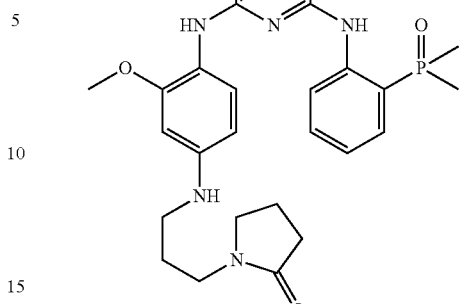
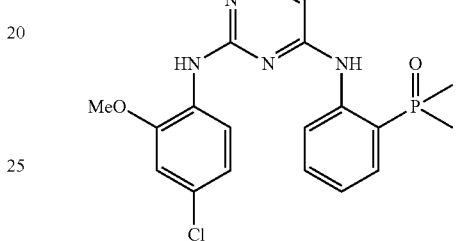
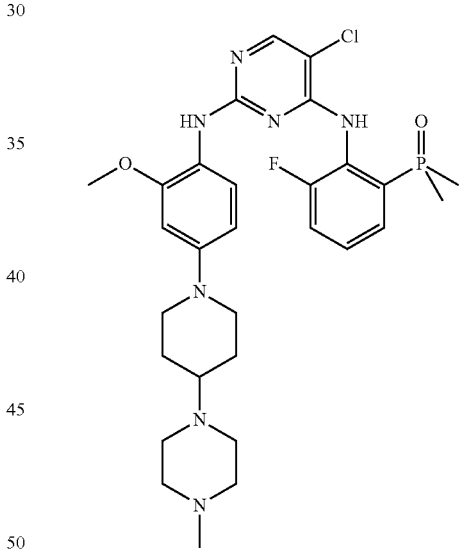
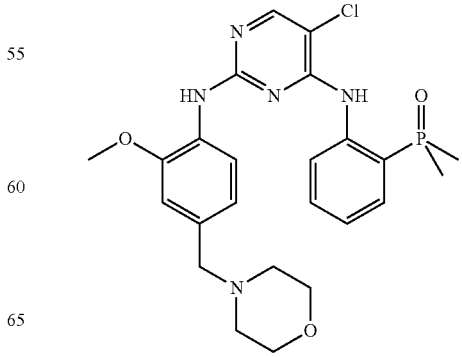

337
-continued
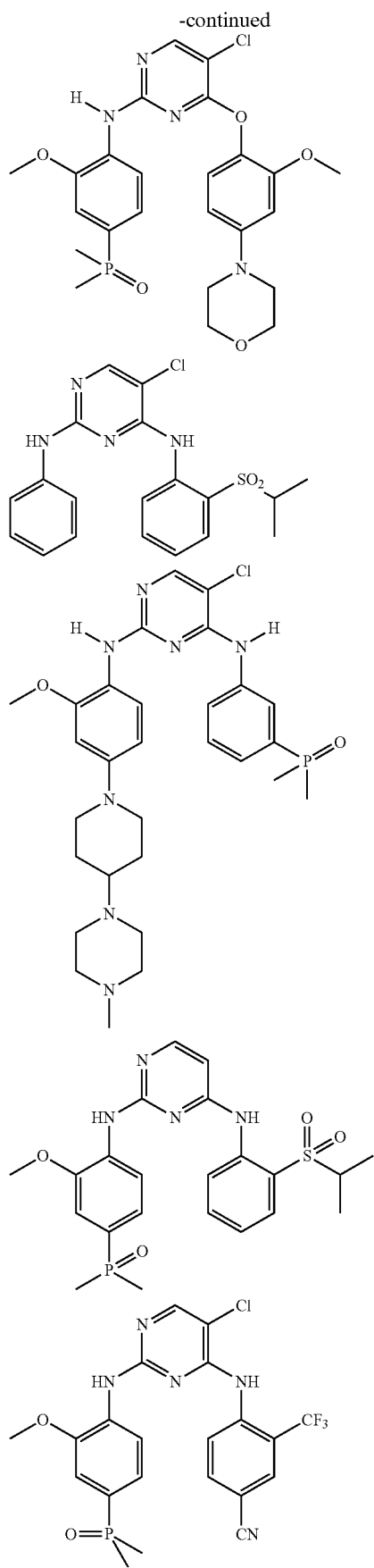
338
-continued
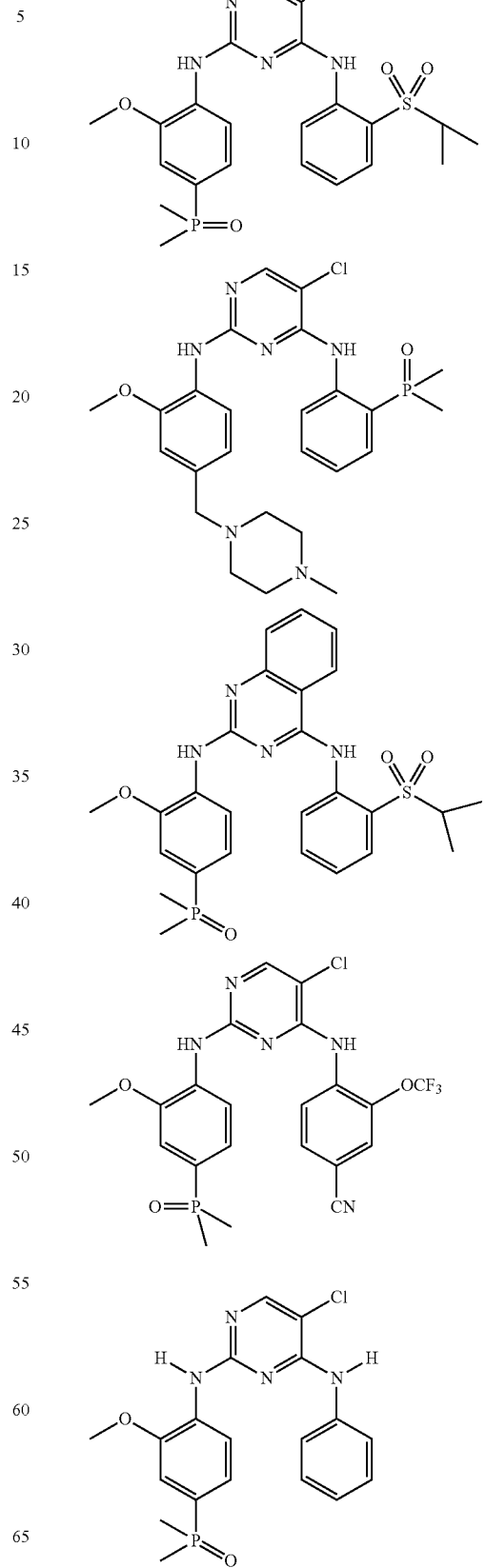

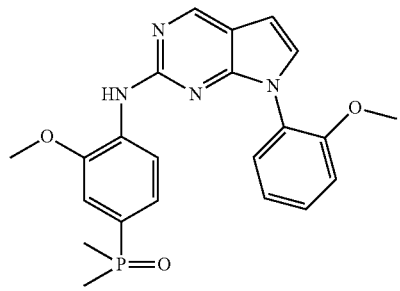
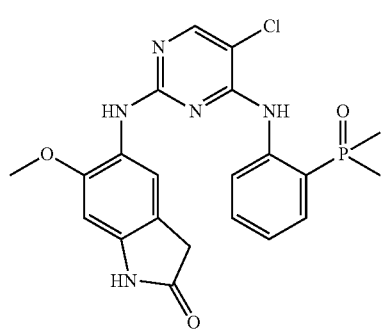
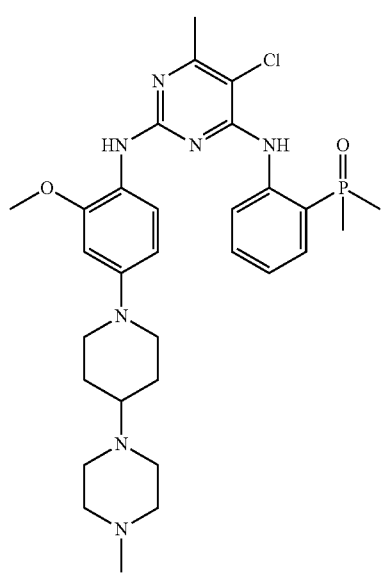
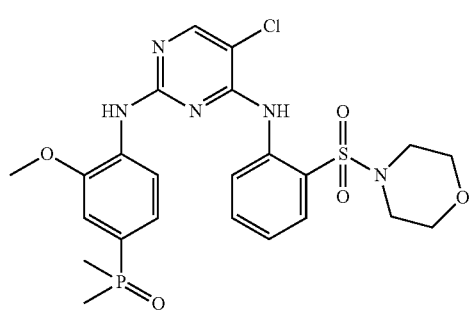
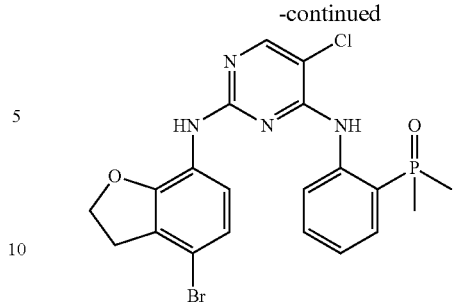
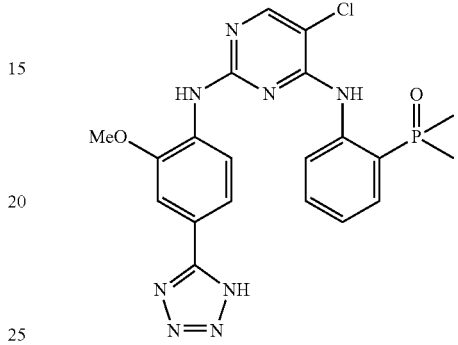
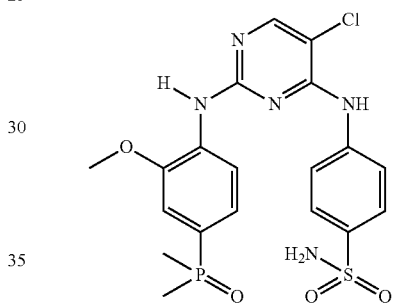
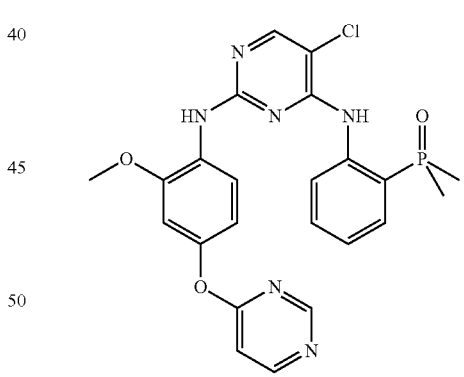
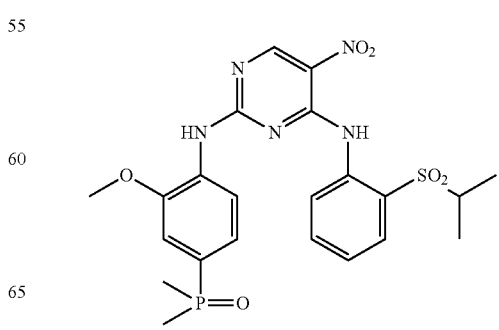

341
-continued
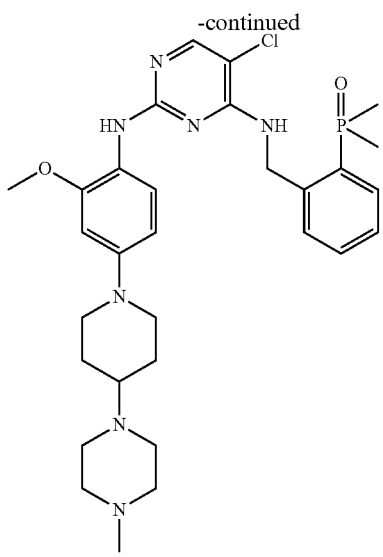
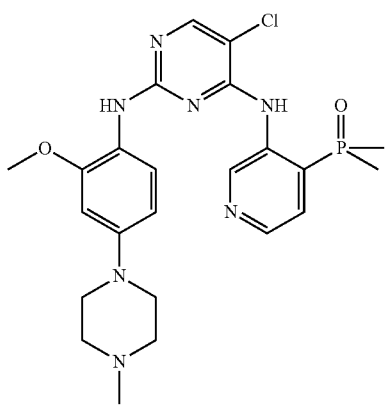
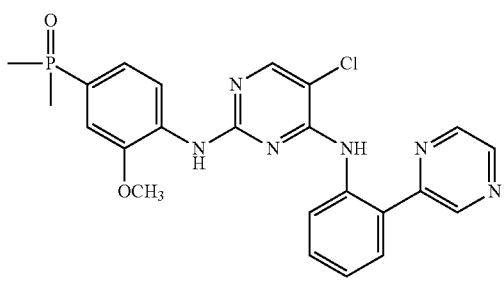
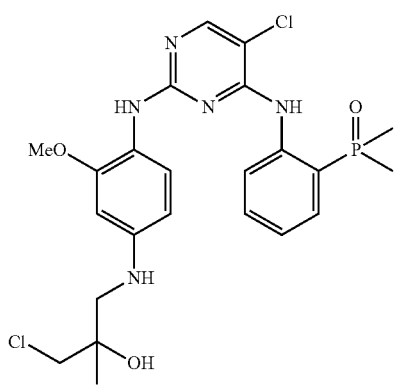
342
-continued
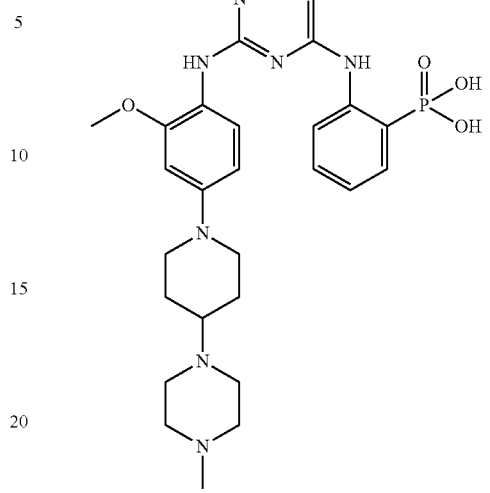
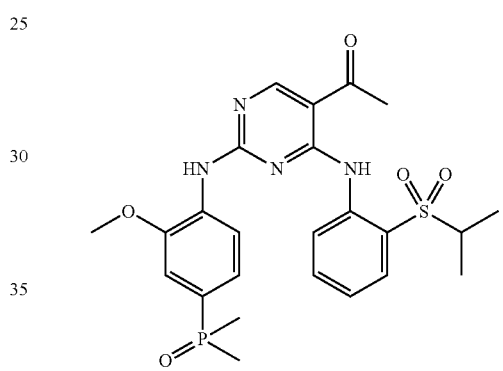
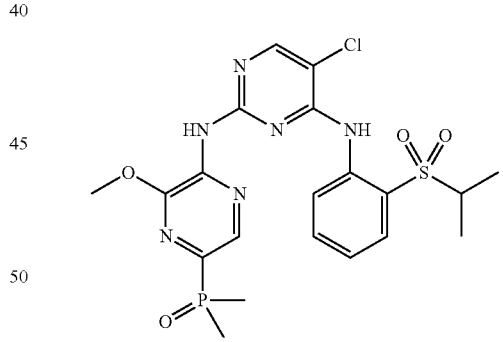
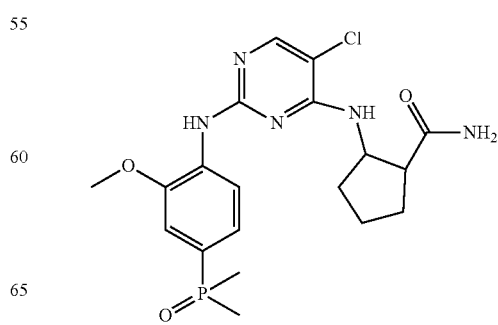

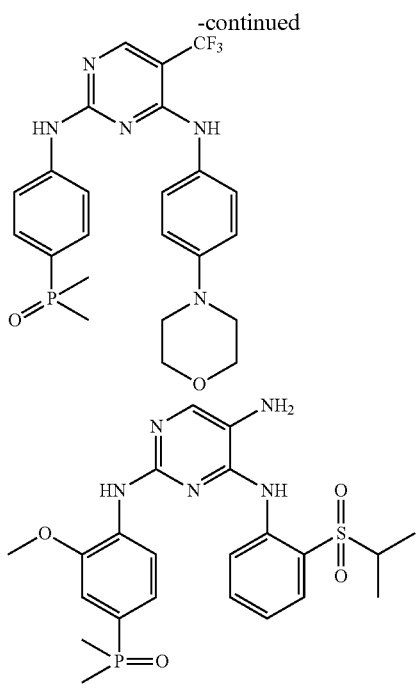
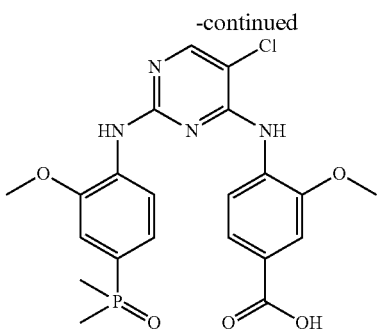
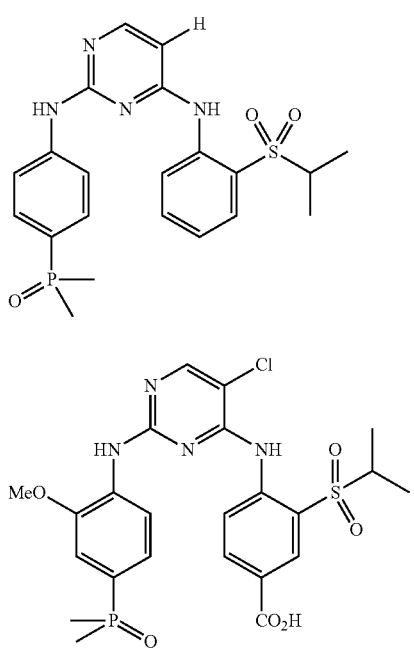
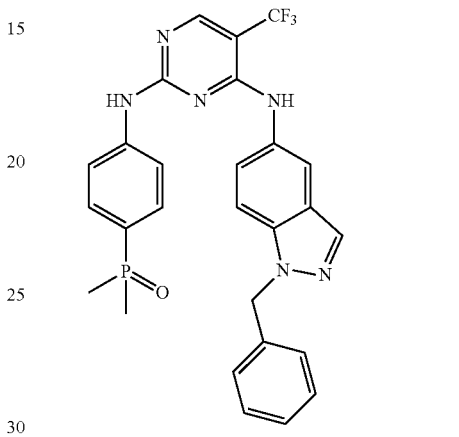
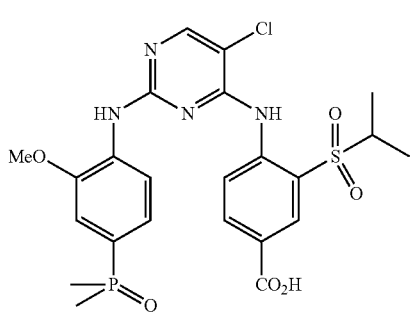
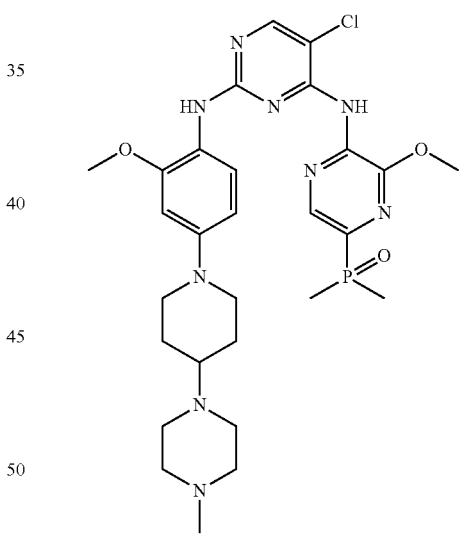
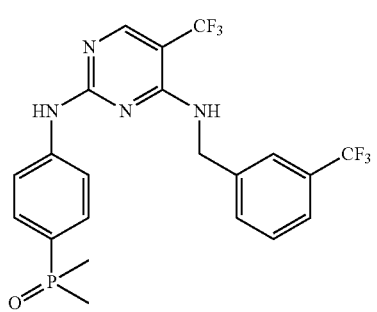
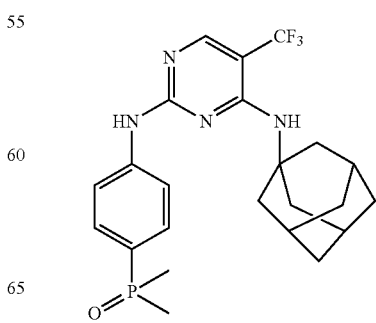

-continued
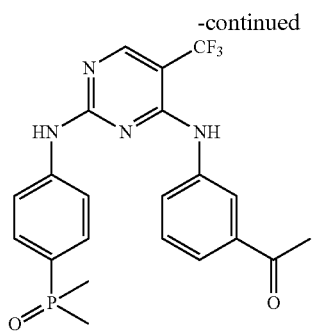
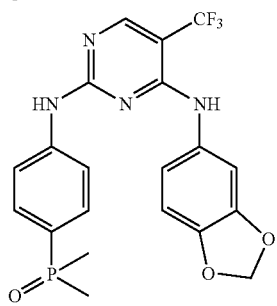
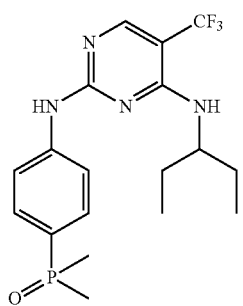
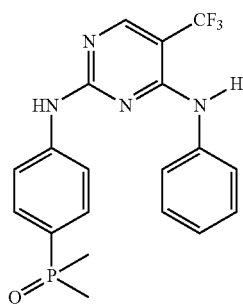
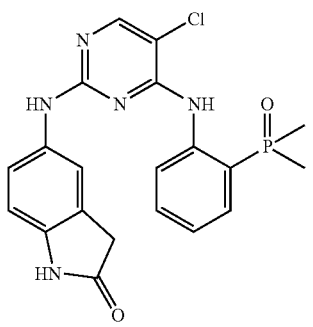
-continued
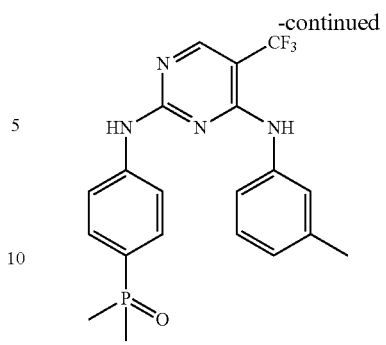
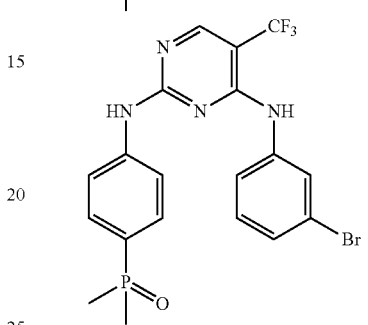
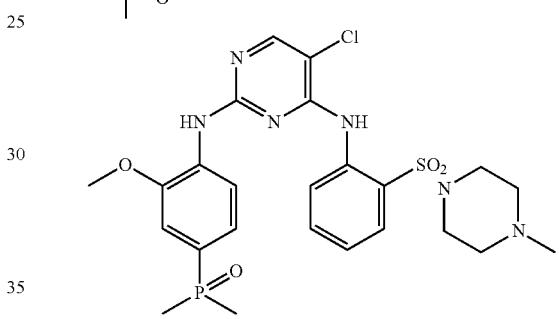
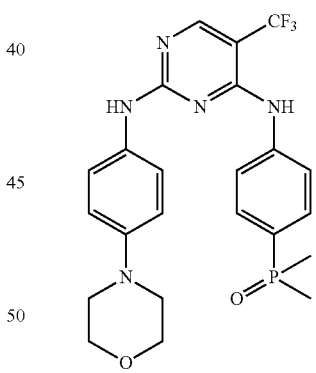
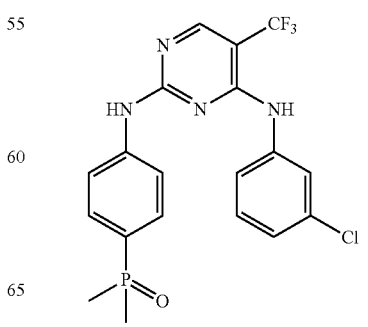

347
-continued
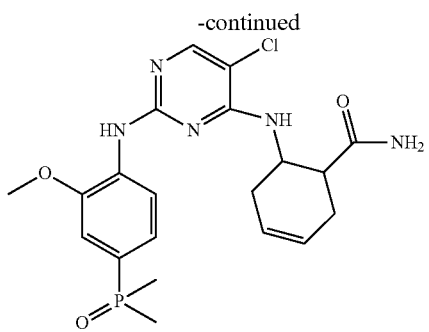
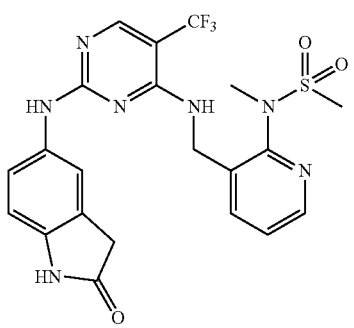
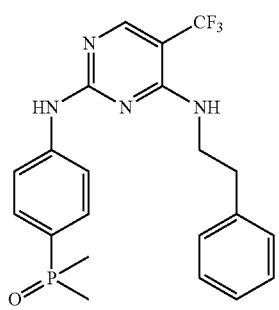
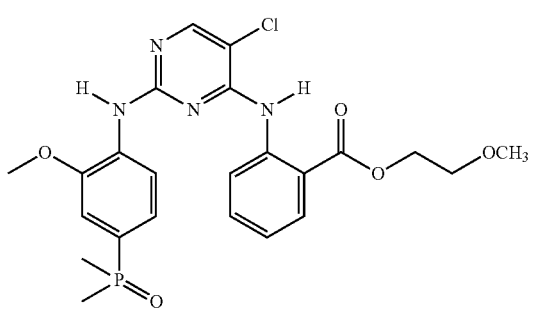
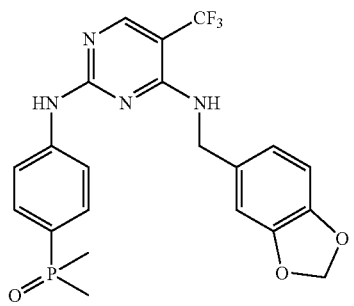
348
-continued
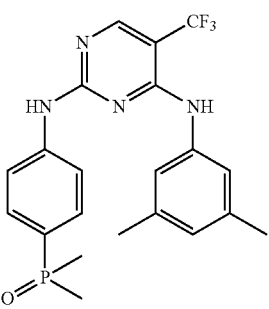
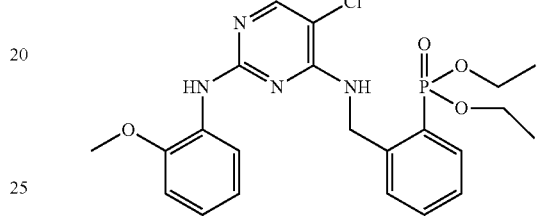
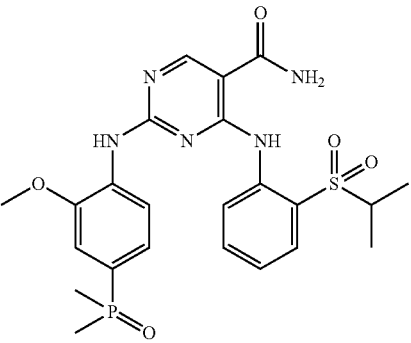
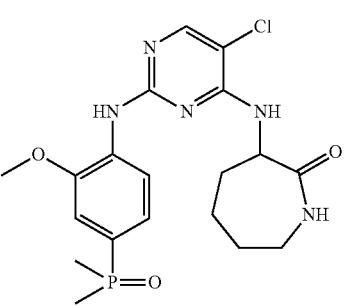

-continued
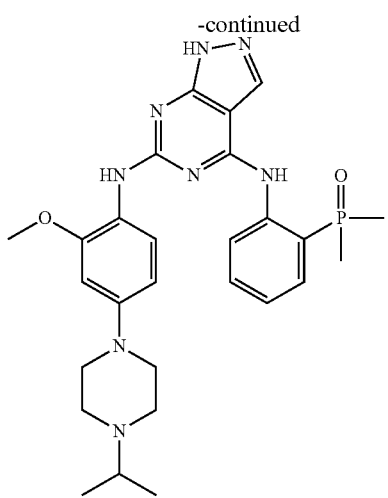
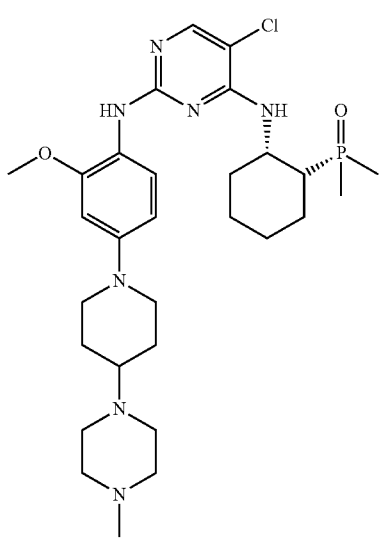
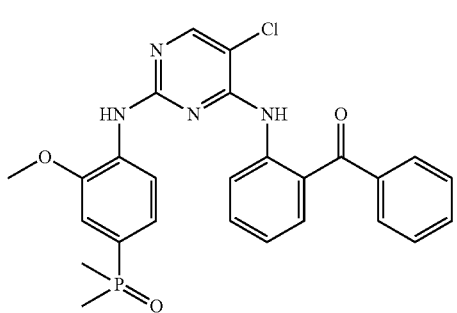
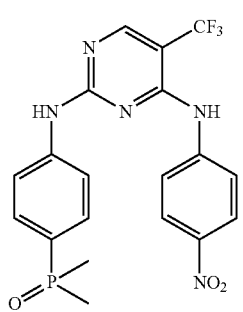
-continued
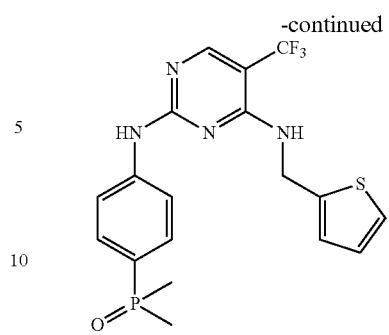
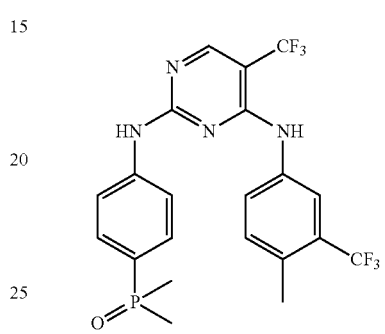
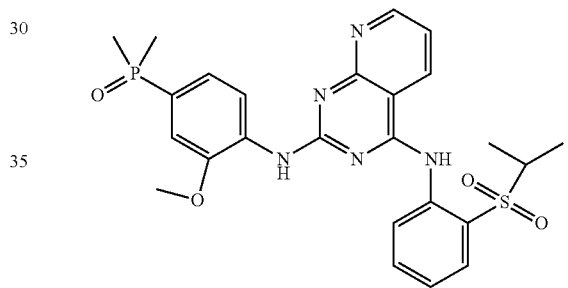
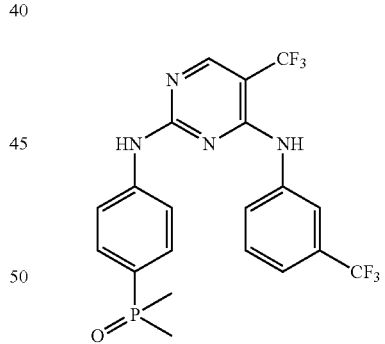
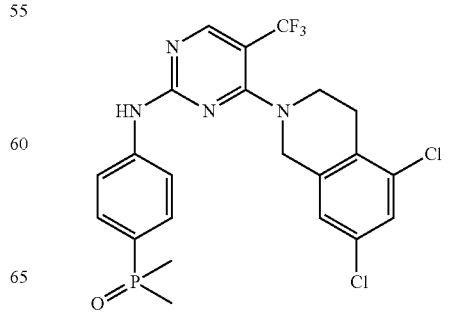

351
-continued
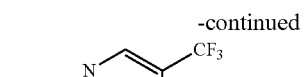
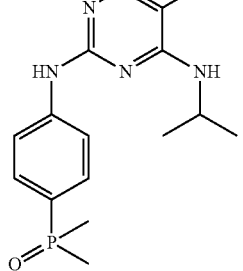
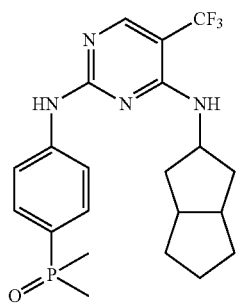
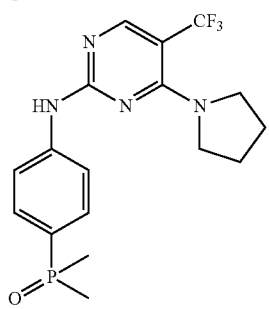
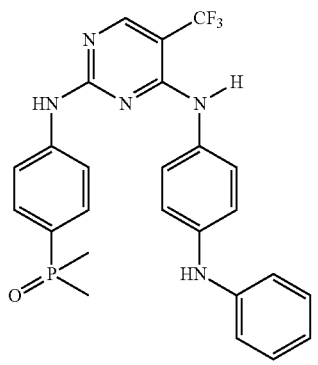
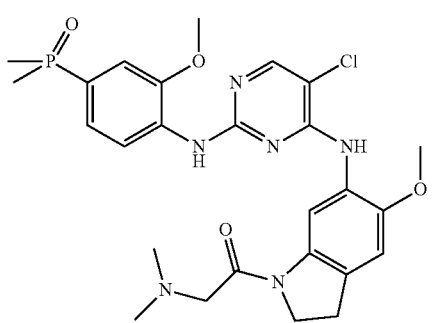
352
-continued
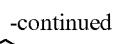
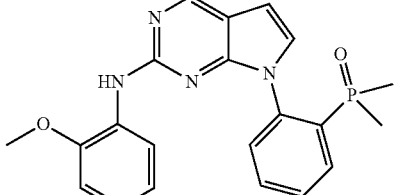
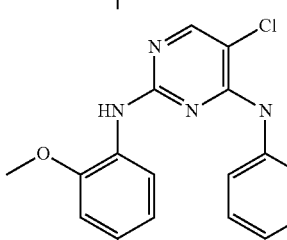
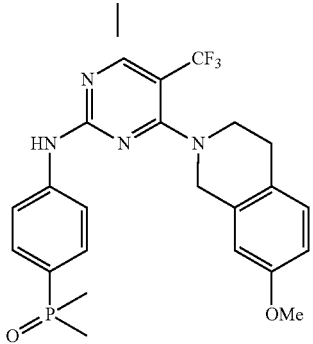
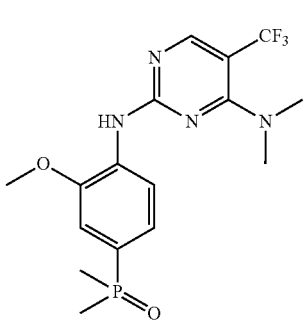

353
-continued
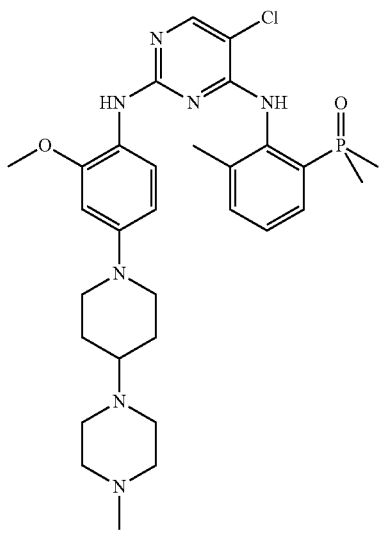
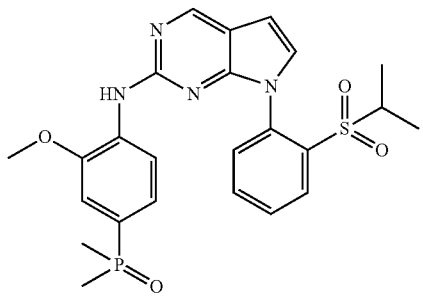
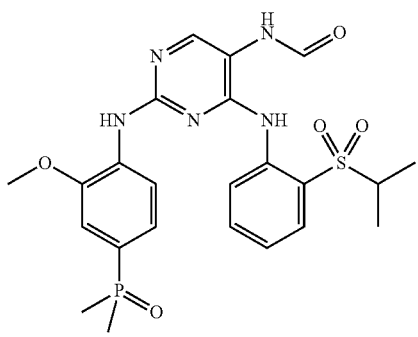
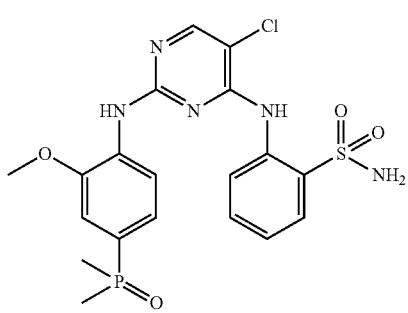
354
-continued
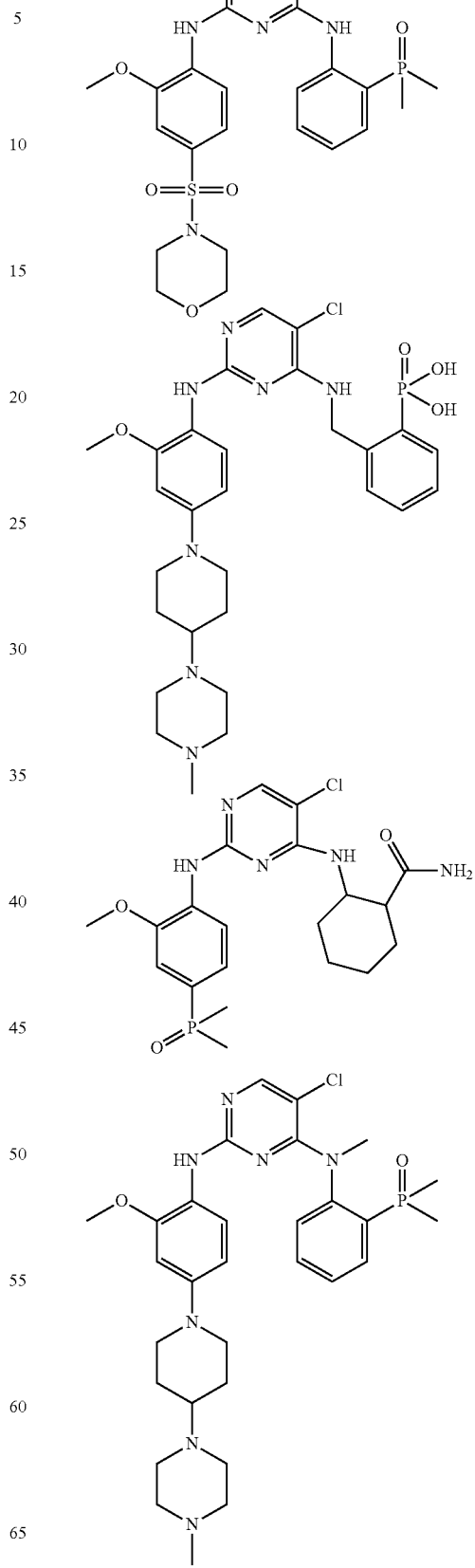

355
-continued
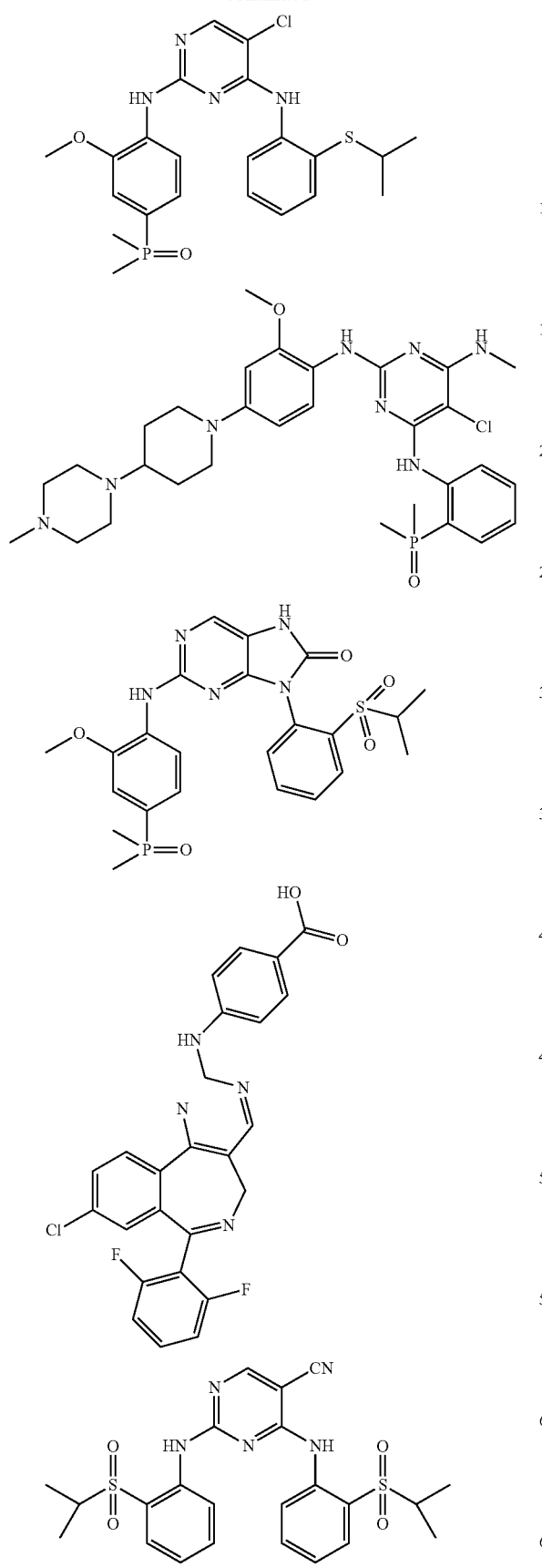
356
-continued
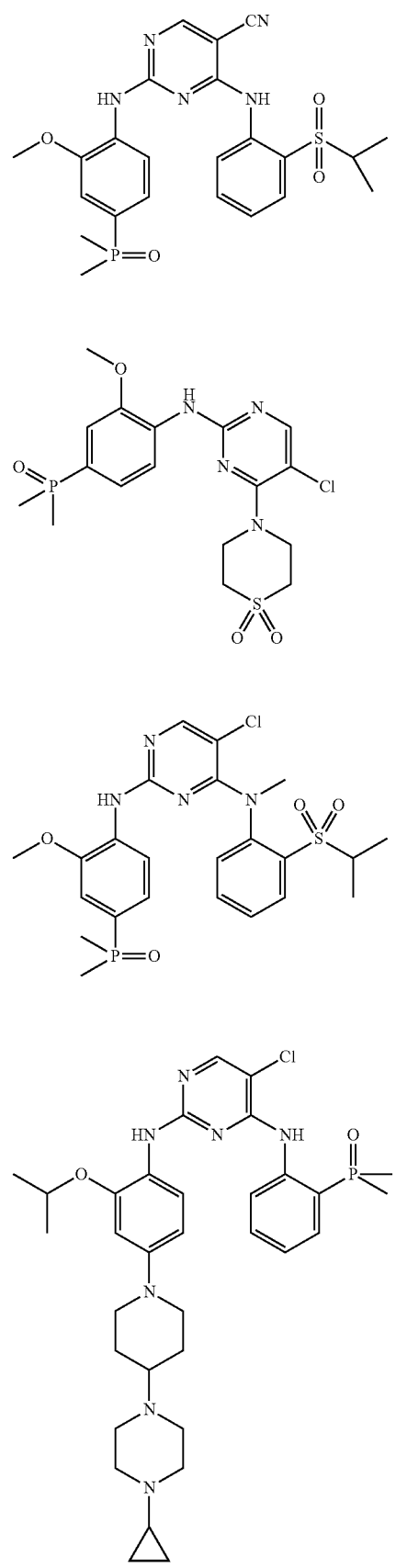

-continued

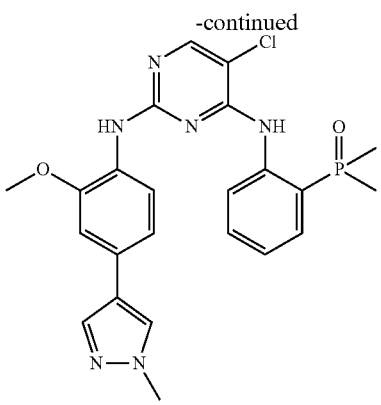

Kinase Inhibition

More specifically, the compounds described herein are screened for kinase inhibition activity as follows. Kinases suitable for use in the following protocol include, but are not limited to: ALK, Jak2, b-Raf, c-Met, Tie-2, FLT3, Abl, Lek, Lyn, Src, Fyn, Syk, Zap-70, Itk, Tec, Btk, EGFR, ErbB2, Kdr, FLT1, Tek, InsR, and AKT.

Kinases are expressed as either kinase domains or full length constructs fused to glutathione S-transferase (GST) or polyHistidine tagged fusion proteins in either E. coli or Baculovirus-High Five expression systems. They are purified to near homogeneity by affinity chromatography as previously described (Lehr et al., 1996; Gish et al., 1995). In some instances, kinases are co-expressed or mixed with purified or partially purified regulatory polypeptides prior to measurement of activity.

Kinase activity and inhibition can be measured by established protocols (see e.g., Braunwalder et al., 1996). In such cases, the transfer of $^{33}PO_4$ from ATP to the synthetic substrates poly(Glu, Tyr) 4:1 or poly(Arg, Ser) 3:1 attached to the bioactive surface of microtiter plates is taken as a measure of enzyme activity. After an incubation period, the amount of phosphate transferred is measured by first washing the plate with 0.5% phosphoric acid, adding liquid scintillant, and then counting in a liquid scintillation detector. The $IC_{50}$ is determined by the concentration of compound that causes a 50% reduction in the amount of $^{33}P$ incorporated onto the substrate bound to the plate.

Other methods relying upon the transfer of phosphate to peptide or polypeptide substrate containing tyrosine, serine, threonine or histidine, alone, in combination with each other, or in combination with other amino acids, in solution or immobilized (i.e., solid phase) are also useful.

For example, transfer of phosphate to a peptide or polypeptide can also be detected using scintillation proximity, Fluorescence Polarization and homogeneous time-resolved fluorescence.

Alternatively, kinase activity can be measured using antibody-based methods in which an antibody or polypeptide is used as a reagent to detect phosphorylated target polypeptide.

For additional background information on such assay methodologies, see e, g., Braunwalder et al., 1996, Anal. Biochem. 234(1):23; Cleaveland et al., 1990, Anal Biochem. 190(2):249 Gish et al. (1995). Protein Eng. 8(6):609 Kolb et al. (1998). Drug Discov. Toda V. 3:333 Lehr et al. (1996). Gene 169(2):27527-87 Seethala et al. (1998). Anal Biochem. 255(2):257 Wu et al. (2000).

The inhibition of ALK tyrosine kinase activity can be demonstrated using known methods. For example, in one method, compounds can be tested for their ability to inhibit kinase activity of baculovirus-expressed ALK using a modification of the ELISA protocol reported for trkA in Angeles, T. S. et al., Anal. Biochem. 1996, 236, 49-55, which is incorporated herein by reference. Phosphorylation of the substrate, phopholipase C-gamma (PLC-γ) generated as a fusion protein with glutathione-S-transferase (GST) as reported in rotin, D. et al., EMBO J. 1992, 11, 559-567, which is incorporated by reference, can be detected with europium-labeled anti-phosphotyrosine antibody and measured by time-resolved fluorescence (TRF). In this assay, 96-well plate is coated with 100 μL/well of 10 μg/mL substrate (phospholipase C-γ in tris-buffered saline (TBS). The assay mixture (total volume=1004/well) consisting of 20 nM HEPES (pH 7.2, 1 μMATP ($K_m$ level), 5 nM $MnCl_2$, 0.1% BSA, 2.5% DMSO, and various concentrations of test compound is then added to the assay plate. The reaction is initiated by adding the enzyme (30 ng/mL ALK) and is allowed to proceed at 37 degrees C. for 15 minutes. Detection of the phosphorylated product can be performed by adding 100 μL/well of Eu-N1 labeled PT66 antibody (Perkim Elmer #AD0041). Incubation at 37 degrees C. then proceeds for one hour, followed by addition of 100□L enhancement solution (for example Wallac #1244-105). The plate is gently agitated and after thirty minutes, the fluorescence of the resulting solution can be measured (for example using EnVision 2100 (or 2102) multilabel plate reader from Perkin Elmer).

Data analysis can then be performed. $IC_{50}$ values can be calculated by plotting percent inhibition versus $log_{10}$, of concentration of compound.

The inhibition of ALK tyrosine kinase activity can also be measured using the recombinant kinase domain of the ALK in analogy to VEDG-R kinase assay described in J. Wood et al., Cancer Res 2000, 60, 2178-2189. In vitro enzyme assays using GST-ALK protein tyrosine kinase can be performed in 96-well plate as a filter binding assay in 20 mMTris.HCl, pH 7.5, 3 mM $MgCl_2$, 10 mM $MnCl_2$, 1 nM DTT, 0.1 μCi/assay (=30 μL) [γ-$^{33}P$]-ATP, 2 μM ATP, 3 μg/mL poly (Glu, tyr 4:1) Poly-EY (sigma P-0275), 1% DMSO, 25 ng ALK enzyme. Assays can be incubated for 10 min, at ambient temperature. Reactions can be terminated by adding 50 μL of 125 mM EDTA, and the reaction mixture can be transferred onto a MAIP Multiscreen plate (Millipore, Bedford, Mass.) previously wet with methanol, and rehydrated for 5 minutes with water. Following washing (0.5% $H_3PO_4$), plates can be counted in a liquid scintillation counter. $IC_{50}$ values are calculated by linear regression analysis of the percentage inhibition.

Cell-Based Assays

Certain compounds of the invention have also been demonstrated cytotoxic or growth inhibitory effects on tumor and other cancer cell lines and thus may be useful in the treatment of cancer and other cell proliferative diseases. Compounds are assayed for anti-tumor activity using in vivo and in vitro assays which are well known to those skilled in the art. Generally, initial screens of compounds to identify candidate anti-cancer drugs are performed in cellular assays. Compounds identified as having anti-proliferative activity in such cell-based assays can then be subsequently assayed in whole organisms for anti-tumor activity and toxicity. Generally speaking, cell-based screens can be performed more rapidly and cost-effectively relative to assays that use whole organisms. For purposes of the invention, the terms "anti-tumor" and "anti-cancer" activity are used interchangeably.

Cell-based methods for measuring antiproliferative activity are well known and can be used for comparative characterization of compounds of the invention. In general, cell proliferation and cell viability assays are designed to provide a detectable signal when cells are metabolically active.

Compounds may be tested for antiproliferative activity by measuring any observed decrease in metabolic activity of the cells after exposure of the cells to compound. Commonly used methods include, for example, measurement of membrane integrity (as a measure of cell viability) (e.g. using trypan blue exclusion) or measurement of DNA synthesis (e.g. by measuring incorporation of BrdU or 3H-thymidine).

Some methods for assaying cell proliferation use a reagent that is converted into a detectable compound during cell proliferation. Particularly preferred compounds are tetrazolium salts and include without limitation MTT (3-(4,5-dimethylthiazol-2-yl)-2,5-diphenyltetrazolium bromide; Sigma-Aldrich, St. Louis, Mo.), MTS (3-(4,5-dimethylthiazol-2-yl)-5-(3-carboxymethoxyphenyl)-2-(4-sulfophenyl)-2H-tetrazolium), XTT (2,3-bis(2-Methoxy-4-nitro-5-sulfophenyl)-2H-tetrazolium-5-carboxanilide), INT, NBT, and NTV (Bernas et al. Biochim Biophys Acta 1451(1):73-81, 1999). More commonly used assays utilizing tetrazolium salts detect cell proliferation by detecting the product of the enzymatic conversion of the tetrazolium salts into blue formazan derivatives, which are readily detected by spectroscopic methods (Mosman. J. Immunol. Methods. 65:55-63, 1983).

Other methods for assaying cell proliferation involve incubating cells in a desired growth medium with and without the compounds to be tested. Growth conditions for various prokaryotic and eukaryotic cells are well-known to those of ordinary skill in the art (Ausubel et al. Current Protocols in Molecular Biology. Wiley and Sons. 1999; Bonifacino et al. Current Protocols in Cell Biology. Wiley and Sons. 1999 both incorporated herein by reference). To detect cell proliferation, the tetrazolium salts are added to the incubated cultured cells to allow enzymatic conversion to the detectable product by active cells. Cells are processed, and the optical density of the cells is determined to measure the amount of formazan derivatives. Furthermore, commercially available kits, including reagents and protocols, are available for examples, from Promega Corporation (Madison, Wis.), Sigma-Aldrich (St. Louis, Mo.), and Trevigen (Gaithersburg, Md.).

In addition, a wide variety of cell types may be used to screen compounds for antiproliferative activity, including the following cell lines, among others: COLO 205 (colon cancer), DLD-1 (colon cancer), HCT-15 (colon cancer), HT29 (colon cancer), HEP G2 (Hepatoma), K-562 (Leukemia), A549 (Lung), NCI-H249 (Lung), MCF7 (Mammary), MDA-MB-231 (Mammary), SAOS-2 (Osteosarcoma), OVCAR-3 (Ovarian), PANC-1 (Pancreas), DU-145 (Prostate), PC-3 (Prostate), ACHN (Renal), CAKI-1 (Renal), MG-63 (Sarcoma).

While the cell line is preferably mammalian, lower order eukaryotic cells such as yeast may also be used to screen compounds. Preferred mammalian cell lines are derived from humans, rats, mice, rabbits, monkeys, hamsters, and guinea pigs since cells lines from these organisms are well-studied and characterized. However, others may be used as well.

Suitable mammalian cell lines are often derived from tumors. For example, the following tumor cell-types may be sources of cells for culturing cells: melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and differentiation factors), osteoclasts, chondrocytes and other connective tissue cells, keratinocytes, melanocytes, liver cells, kidney cells, and adipocytes. Non-limiting examples of mammalian cells lines that have been widely used by researchers include HeLa, NIH/3T3, HT1080, CHO, COS-1, 293T, WI-38 and CV1/EBNA-1.

Other cellular assays may be used which rely upon a reporter gene to detect metabolically active cells. Non-limiting examples of reporter gene expression systems include green fluorescent protein (GFP), and luciferase. As an example of the use of GFP to screen for potential antitumor drugs, Sandman et al. (Chem. Biol. 6:541-51; incorporated herein by reference) used HeLa cells containing an inducible variant of GFP to detect compounds that inhibited expression of the GFP, and thus inhibited cell proliferation.

An example of cell-based assay is shown as below. The cell lines that can be used in the assay are Ba/F3, a murine pro-B cell line, which has been stably transfected with an expression vector pClneo™ (Promega Corp., Madison Wis.) coding for NPM-ALK and subsequent selection of G418 resistant cells. Non-transfected Ba/F3 cells depend on IL-3 for cell survival. In constrast NPM-ALK expressing Ba/F3 cells (named Ba/F3-NPM-ALK) can proliferate in the absence of IL-3 because they obtain proliferative signal through NMP-ALK kinase. Putative inhibitors of NPM-ALK kinase therefore abolish the growth signal and result in antiproliferative activity. The antiproliferative activity of inhibitors of the NPM-ALK kinase can however be overcome by addition of IL-3 which provides growth signals through an NPM-ALK independent mechanism. For an analogous cell system using FLT3 kinase see E. Weisberg et al. Cancer cell, 2002, 1, 433-443. The inhibitory activity of the compounds of formula I can be determined as follows: BaF3-NPM-ALK cells (15,000/microtitre plate well) can be transferred to a 96-well microtitre plates. The test compound (dissolved in DMSO) is then added in a series of concentrations (dilution series) in such a manner that the final concentration of DMSO is not greater than 1% (v/v). After the addition, the plates can be incubated for two days during which the control cultures without test compound are able to undergo two cell-division cycles. The growth of BaF3-NPM-ALK cells can be measured by means of Yopro™ staining (T Idziorek et al., J. Immunol. Methods 1995, 185, 249-258). 25 µL of lysis buffer consisting of 20 mM sodium citrate, pH 4.0, 26.8 nM sodium chloride, 0.4% NP40, 20 mM EDTA and 20 mM is added into each well. Cell lysis is completed within 60 minutes at room temperature and total amount of Yopro bound to DNA is determined by measurement using for example a CytoFluor II 96-well reader (PerSeptive Biosystems). The $IC_{50}$ can be determined by a computer aided system using the formula:

$$IC_{50}=[(ABS_{test}-ABS_{start})/(ABS_{control}-ABS_{start})]\times 100$$

in which ABS is absorption. The $IC_{50}$ value in such an experiment is given as that concentration of the test compound in question that results in a cell count that is 50% lower than that obtained using the control without inhibitor.

The antiproliferative action of compounds of the invention can also be determined in the human KARPAS-299 lymphoma cell line by means of an immunoblot as described in W G Dirks et al. Int. J. Cancer 2002, 100, 49-56., using the methodology described above for the BaF3-NPM-ALK cell line.

In another example, antiproliferative activity can be determined using KARPAS-299 lumphoma cell line in the following procedure: Compounds of the invention were incubated with the cells for 3 days, and the number of viable cells in each well was measured indirectly using an MTS tetrazolium assay (Promega). This assay is a colorimetric method for determining the number of viable cells through measurement of their metabolic activity. For example the detection of the product of the enzymatic conversion of tetrazolium salts into blue formazan derivatives is achieved by measuring absorbance at 490 nm using a plate reader. 40 µL of the MTS reagent was added to all wells except the edge wells and then the plates were returned to the incubator at 37° C. for 2 hours. The absorbance in each well was then measured at 490 nm using a Wallac Victor²V plate reader. The $IC_{50}$ was calculated by determining the concentration of compound required to decrease the MTS signal by 50% in best-fit curves using Microsoft XLfit software, by comparing with baseline, the DMSO control, as 0% inhibition.

Compounds identified by such cellular assays as having anti-cell proliferation activity are then tested for anti-tumor activity in whole organisms. Preferably, the organisms are mammalian. Well-characterized mammalians systems for studying cancer include rodents such as rats and mice. Typically, a tumor of interest is transplanted into a mouse having a reduced ability to mount an immune response to the tumor to reduce the likelihood of rejection. Such mice include for example, nude mice (athymic) and SCID (severe combined immunodeficiency) mice. Other transgenic mice such as oncogene containing mice may be used in the present assays (see for example U.S. Pat. No. 4,736,866 and U.S. Pat. No. 5,175,383). For a review and discussion on the use of rodent models for antitumor drug testing see Kerbel (Cancer Metastasis Rev. 17:301-304, 1998-99).

In general, the tumors of interest are implanted in a test organism preferably subcutaneously. The organism containing the tumor is treated with doses of candidate anti-tumor compounds. The size of the tumor is periodically measured to determine the effects of the test compound on the tumor. Some tumor types are implanted at sites other than subcutaneous sites (e.g. intraperitoneal sites) and survival is measured as the endpoint. Parameters to be assayed with routine screening include different tumor models, various tumor and drug routes, and dose amounts and schedule. For a review of the use of mice in detecting antitumor compounds see Corbett et al. (Invest New Drugs. 15:207-218, 1997; incorporated herein by reference).

Results

A wide variety of compounds of this invention were found to potently inhibit a number of important kinase targets. Many exhibited IC50's under 100 nM, and in many cases under 10 nM and in some cases under 1 nM when tested as inhibitors of the kinase, ALK, for instance. Those included compounds containing the phosphine oxide moiety as an $R^a$ or $R^e$ substituent as well as compounds in which positions $X^3$ and $X^4$ were the base of a substituted or unsubstituted fused ring which is present in a number of embodiments. Some compounds were single digit nanomolar inhibitors of a panel of kinases including kinases like ALK, FER, FLT3, FES/FPS, FAK/PTK2, BRK and others. Compounds of the invention of various structures were found to exhibit preferences for inhibiting some kinases over others as well as variations in pharmacokinetic profiles, confirming that this class of compounds is of great interest as a source of potential pharmaceutical agents.

To illustrate the foregoing, a varied group of compounds (shown below) were tested and found to have IC50 values under 1 nM when tested against the kinase ALK.

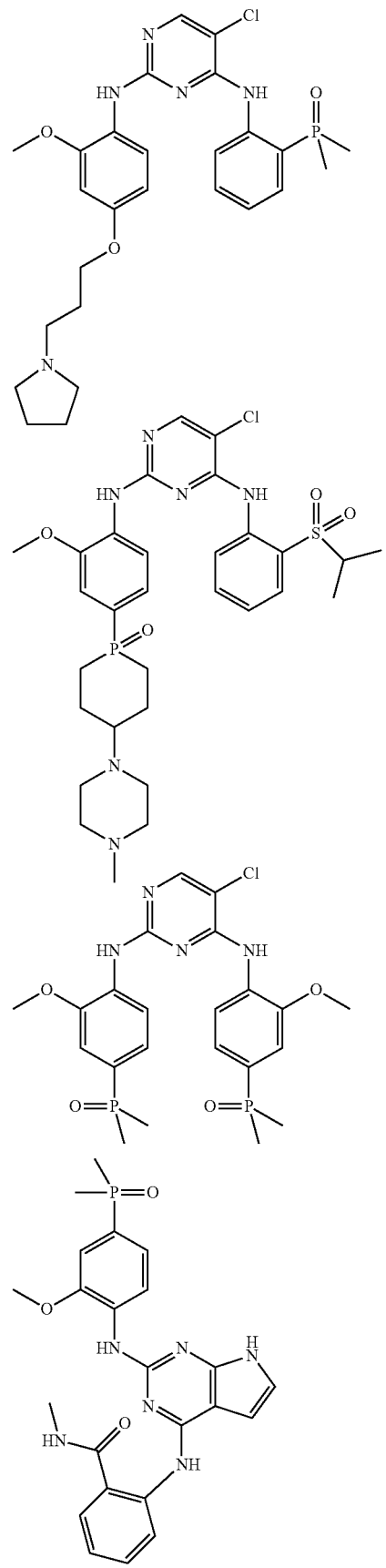

363
-continued
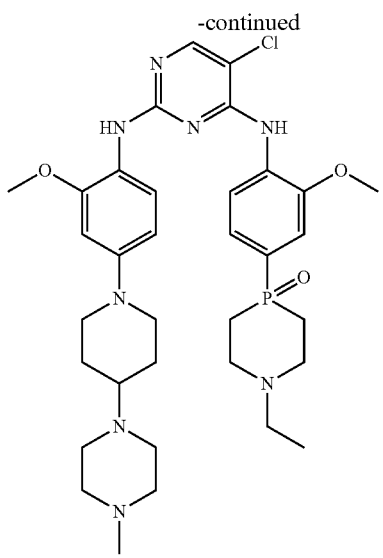
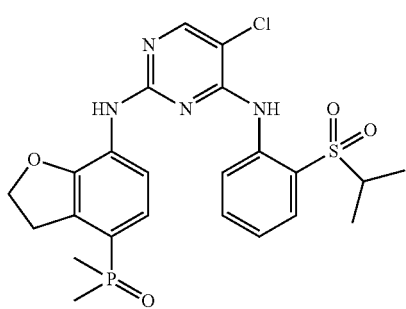
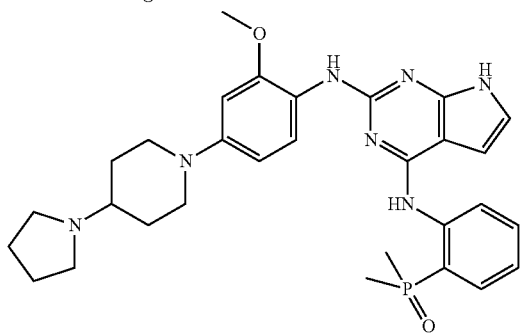
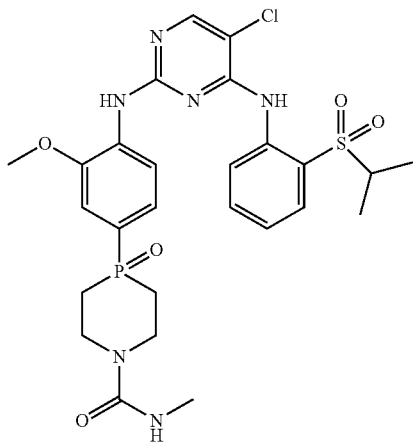
364
-continued
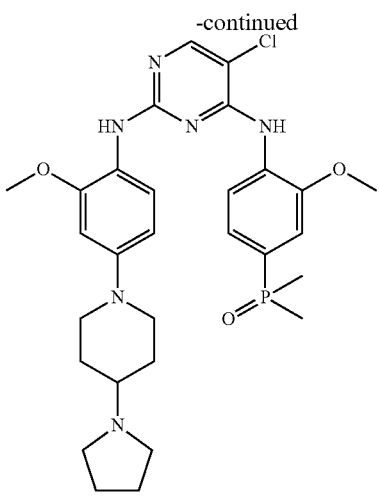
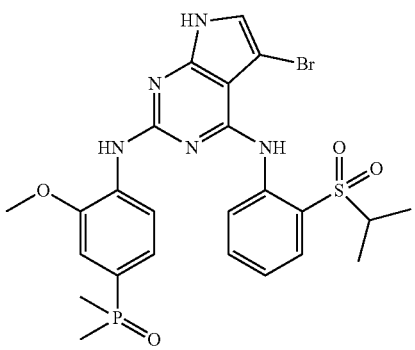
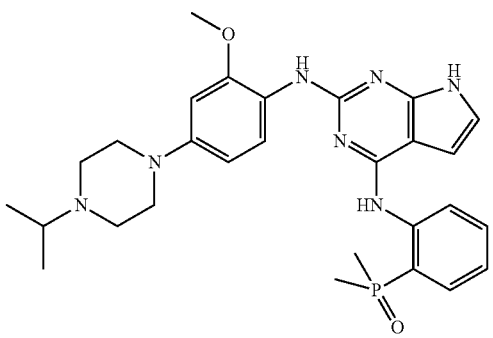
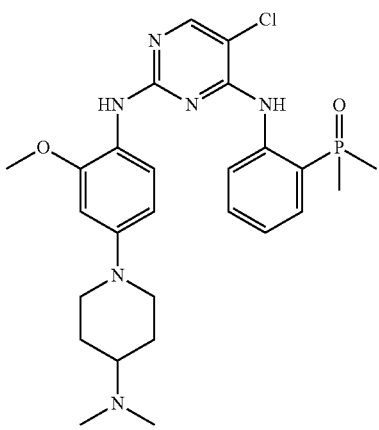

Example 21

Pharmaceutical Compositions

Representative pharmaceutical dosage forms of compounds of the invention (the active ingredient being referred to as "Compound"), are provided for therapeutic or prophylactic use in humans:

| (a) Tablet I | mg/tablet |
|---|---|
| Compound | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound | 1.0 |
| Lactose Ph. Eur | 93.25 |
| Croscarmellose sodium | 4.0 |
| Maize starch paste (5% w/v paste) | 0.75 |
| Magnesium stearate | 1.0-76 |

| (d) Capsule | mg/capsule |
|---|---|
| Compound | 10 |
| Lactose Ph. Eur | 488.5 |
| Magnesium | 1.5 |

| (e) Injection I | (50 mg/ml) |
|---|---|
| Compound | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound | 1.0% W/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH 6) |
|---|---|
| Compound | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound | 10.0 |
| Sorbitan trioleate | 13.5 |
| Trichlorofluoromethane | 910.0 |
| Dichlorodifluoromethane | 49.00 |

| (i) Aerosol II | mg/ml |
|---|---|
| Compound | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound | 2.5 |
| Sorbitan trioleate | 3.38 |
| Trichlorofluoromethane | 67.5 |
| Dichlorodifluoromethane | 1086.0 |
| Dichlorotetrafluoroethane | 19.16 |

| (k) Aerosol IV | mg/ml |
|---|---|
| Compound | 2.5 |
| Soya lecithin | 2.7 |
| Trichlorofluoromethane | 67.5 |
| Dichlorodifluoromethane | 108.60 |
| Dichlorotetrafluoroethane | 191.6 |

| (l) Ointment | /ml |
|---|---|
| Compound | 40 mg |
| Ethanol | 300 μl |
| Water | 300 μl |
| 1-Dodecylazacycloheptan one | 50 μl |
| Propylene glycol | to 1 ml |

These formulations may be prepared using conventional procedures well known in the pharmaceutical art. The tablets (a)-(c) may be enteric coated by conventional means, if desired to provide a coating of cellulose acetate phthalate, for example. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A compound of the formula:

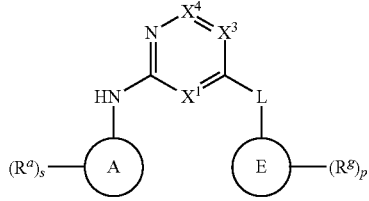

wherein
X$^1$ is NR$^{b1}$ or CR$^b$;
X$^3$ is NR$^{d1}$ or CR$^d$;
X$^4$ is NR$^{e1}$ or CR$^e$;
Ring A and Ring E are each an independently selected aryl or heteroaryl ring, the heteroaryl ring being a 5- or 6-membered ring containing 1 to 4 heteroatoms selected from N, O and S(O)$_r$;
each R$^a$, R$^b$, R$^d$, R$^e$, and R$^g$ is independently halo, —CN, —NO$_2$, —R$^1$, —OR$^2$, —O—NR$^1$R$^2$, —NR$^1$R$^2$, —NR$^1$—NR$^1$R$^2$, —NR$^1$—OR$^2$, —C(O)YR$^2$, —OC(O)YR$^2$, —NR$^1$C(O)YR$^2$, —SC(O)YR$^2$, —NR$^1$C(=S)YR$^2$, —OC(=S)YR$^2$, —C(=S)YR$^2$, —YC(=NR$^1$)YR$^2$, —YC(=N—OR$^1$)YR$^2$, —YC(=N—NR$^1$R$^2$)YR$^2$, —YP(=O)(YR$^3$)(YR$^3$), —Si(R$^{3a}$)$_3$, —NR$^1$SO$_2$R$^2$, —S(O)$_1$R$^2$, —SO$_2$NR$^1$R$^2$ or —NR$^1$SO$_2$NR$^1$R$^2$; provided that at least one of R$^a$ and R$^g$ is or includes —P(=O)(R$^3$)$_2$ or a ring system containing —P(=O)(R$^3$)— as a ring member;
and R$^{b1}$, R$^{d1}$ and R$^{e1}$ are absent;
or alternatively two adjacent substituents selected from R$^d$, R$^{d1}$, R$^e$, and R$^{e1}$, or two adjacent R$^a$ form, with the atoms to which they are attached, a fused, 5-, 6- or 7-membered saturated, partially saturated or unsaturated ring, which contains 0-4 heteroatoms selected from N, O and S(O)$_r$, and which may bear up to four substituents;
L is O or NH;
r is 0, 1 or 2;
s is 1, 2, 3, 4 or 5;
p is 1, 2, 3 or 4;
each Y is independently a bond, —O—, —S— or —NR$^1$—;
each R$^1$ and R$^2$ is independently H or an alkyl, alkenyl, alkynyl, cycloalkyl, cycloalkenyl, cycloalkynyl, aryl, heteroalkyl, heterocyclic or heteroaryl;
each R$^3$ is independently an alkyl, alkenyl, alkynyl, cycloalkyl, cycloalkenyl, cycloalkynyl, aryl, heteroalkyl, heterocyclic or heteroaryl, or two adjacent R$^3$ combine to form a ring system including a phosphorous atom;

each R$^{3a}$ is independently an alkyl, alkenyl, alkynyl, cycloalkyl, cycloalkenyl, cycloalkynyl, aryl, heteroalkyl, heterocyclic, or heteroaryl;
alternatively, each NR$^1$R$^2$ may be a 5-, 6- or 7-membered saturated, partially saturated or unsaturated ring, which can be optionally substituted and which contains 0-2 additional heteroatoms selected from N, O and S(O)$_r$; and
each of the foregoing alkyl, alkenyl, alkynyl, cycloalkyl, cycloalkenyl, cycloalkynyl, aryl, heteroaryl and heterocyclic is optionally substituted,
or a pharmaceutically acceptable salt thereof.

2. The compound of claim 1 in which:
(a) X$^1$ is N, X$^3$ is N and X$^4$ is CR$^e$;
(b) X$^1$ is N, X$^3$ is CR$^d$ and X$^4$ is CR$^e$;
(c) X$^1$ is CR$^b$, X$^3$ is N and X$^4$ is CR$^1$, or
(d) X$^1$ is CR$^b$, X$^3$ is CR$^d$ and X$^4$ is Cr.

3. The compound of claim 1 in which R$^d$ is selected from Cl, F, C1-C4 alkyl, trihaloalkyl, cycloalkyl, C2-C4 alkenyl, and alkynyl.

4. The compound of claim 1 in which X$^3$ is CR$^d$ and X$^4$ is CR$^e$ wherein R$^d$ and R$^e$, together with the atoms to which they are attached, form a fused, 5-, 6- or 7-membered saturated, partially saturated or unsaturated ring, which contains 0-4 heteroatoms selected from N, O and S(O)$_r$ and which may bear up to four substituents.

5. The compound of claim 1 in which s is 1, 2, 3 or 4, and each of the substituents R$^a$ is independently selected from halo, —R$^1$, —OR$^2$, —NR$^1$R$^2$ and —P(=O)(R$^3$)$_2$— wherein each R$^1$ and R$^2$ may be further substituted or unsubstituted.

6. The compound of claim 5 in which at least one substituent R$^a$ is —OR$^2$ and R$^2$ is selected from C1-C6 alkyl, C2-C6 alkenyl, and C2-C6 alkynyl.

7. The compound of claim 5 in which at least one substituent R$^a$ is a 5-, 6- or 7-membered heterocyclic or 5- or 6-membered heteroaryl, linked to Ring A either directly or by an ether bond, and which may be further substituted with 1, 2 or 3 substituents independently selected from halo, —CN, —NO$_2$, —R$^1$, —OR$^2$, —O—NR$^1$R$^2$, —NR$^1$R$^2$, —NR$^1$—NR$^1$R$^2$, —NR$^1$—OR$^2$, —C(O)YR$^2$, OC(O)YR$^2$, —NR$^1$C(O)YR$^2$, —SC(O)YR$^2$, —NR$^1$C(=S)YR$^2$, —OC(=S)YR$^2$, —C(=S)YR$^2$, —YC(=NR$^1$)YR$^2$, —YC(=N—OR$^1$)YR$^2$, —YC(=N—NR$^1$R$^2$)YR$^2$, —YP(=O)(YR$^3$)(YR$^3$), —Si(R$^{3a}$)$_3$, —NR$^1$SO$_2$R$^2$, —S(O)$_r$R$^2$, —SO$_2$NR$^1$R$^2$ and —NR$^1$SO$_2$NR$^1$R$^2$; wherein each Y is independently a bond, —O—, —S— or —NR$^1$—.

8. The compound of claim 5 in which at least one substituent R$^a$ is —P(=O)(R$^3$)$_2$ in which each R$^3$ is, independently, a C1-C4 alkyl.

9. The compound of claim 2 in which:
(a) X$^1$ is N, X$^3$ is CR$^d$ and X$^4$ is CR$^e$; or
(b) X$^1$ is CR$^b$, X$^3$ is CR$^d$ and X$^4$ is CR$^e$;
and R$^d$ is selected from Cl, F, C1-C4 alkyl, trihaloalkyl, cycloalkyl, C2-C4 alkenyl, and alkynyl.

10. The compound of claim 2 in which s is 1, 2, 3 or 4, and each of the substituents R$^a$ is independently selected from halo, —R$^1$, —OR$^2$, —NR$^1$R$^2$ and —P(=O)(R$^3$)$_2$, wherein each R$^1$ and R$^2$ may be further substituted or unsubstituted.

11. The compound of claim 3 in which s is 1, 2, 3 or 4, and each of the substituents R$^a$ is independently selected from halo, —R$^1$, —OR$^2$, —NR$^1$R$^2$ and —P(=O)(R$^3$)$_2$, wherein each R$^1$ and R$^2$ may be further substituted or unsubstituted.

12. The compound of claim 9 in which s is 1, 2, 3 or 4, and each of the substituents R$^a$ is independently selected from halo, —R$^1$, —OR$^2$, —NR$^1$R$^2$ and —P(=O)(R$^3$)$_2$, wherein each R$^1$ and R$^2$ may be further substituted or unsubstituted.

13. The compound of claim 4 in which s is 1, 2, 3 or 4, and each of the substituents $R^a$ is independently selected from halo, —$R^1$, —$OR^2$, —$NR^1R^2$ and —P(=O)$(R^3)_2$, wherein each $R^1$ and $R^2$ may be further substituted or unsubstituted.

14. The compound of claim 4 in which at least one substituent $R^a$ is —$OR^2$ and $R^2$ is selected from C1-C6 alkyl, C2-C6 alkenyl, and C2-C6 alkynyl.

15. The compound of claim 11 in which at least one substituent $R^a$ is —$OR^2$ and $R^2$ is selected from C1-C6 alkyl, C2-C6 alkenyl, and C2-C6 alkynyl.

16. The compound of claim 12 in which at least one substituent $R^a$ is —$OR^2$ and $R^2$ is selected from C1-C6 alkyl, C2-C6 alkenyl, and C2-C6 alkynyl.

17. The compound of claim 13 in which at least one substituent $R^a$ is —$OR^2$ and $R^2$ is selected from C1-C6 alkyl, C2-C6 alkenyl, and C2-C6 alkynyl.

18. The compound of claim 10 in which at least one substituent s a 5-, 6- or 7-membered heterocyclic or 5- or 6-membered heteroaryl, linked to Ring A either directly or by an ether bond, and which may be further substituted with 1, 2 or 3 substituents independently selected from halo, —CN, —$NO_2$, —$R^1$, —$OR^2$, —O—$NR^1R^2$, —$NR^1R^2$, —$NR^1$—$NR^1R^2$, —$NR^1$—$OR^2$, —OC(O)$YR^2$, —$NR^1$C(O)$YR^2$, —SC(O)$YR^2$, —$NR^1$C(=S)$YR^2$, —C(=S)$YR^2$, —YC(=$NR^1$)$YR^2$, —YC(=N—$OR^1$)$YR^2$, —YC(=N—$NR^1R^2$)$YR^2$, —YP(=O)$(YR^3)(YR^3)$, —Si$(R)_3$, —$NR^1SO_2R^2$, —S(O)$_rR^2$, —$SO_2NR^1R^2$ and —$NR^1SO_2NR^1R^2$; wherein each Y is independently a bond, —O—, —S— or —$NR^1$—.

19. The compound of claim 11 in which at least one substituent $R^a$ is a 5-, 6- or 7-membered heterocyclic or 5- or 6-membered heteroaryl, linked to Ring A either directly or by an ether bond, and which may be further substituted with 1, 2 or 3 substituents independently selected from halo, —CN, —$NO_2$, —$R^1$, —$OR^2$, —O—$NR^1R^2$, —$NR^1R^2$, —$NR^1$—$NR^1R^2$, —$NR^1$—$OR^2$, —C(O)$YR^2$, —OC(O)$YR^2$, —$NR^1$C(O)$YR^2$, —SC(O)$YR^2$, —$NR^1$C(=S)$YR^2$, —OC(=S)$YR^2$, —C(=S)$YR^2$, —YC(=$NR^1$)$YR^2$, —YC(=N—$OR^1$)$YR^2$, —YC(=N—$NR^1R^2$)$YR^2$, —YP(=O)$(YR^3)(YR^3)$, —Si$(R^{3a})_3$, —$NR^1SO_2R^2$, —S(O)$_rR^2$, —$SO_2NR^1R^2$ and —$NR^1SO_2NR^1R^2$; wherein each Y is independently a bond, —O—, —S— or —$NR^1$—.

20. The compound of claim 12 in which at least one substituent $R^a$ is a 5-, 6- or 7-membered heterocyclic or 5- or 6-membered heteroaryl, linked to Ring A either directly or by an ether bond, and which may be further substituted with 1, 2 or 3 substituents independently selected from halo, —CN, —$NO_2$, —$R^1$, —$OR^2$, —O—$NR^1R^2$, —$NR^1R^2$, —$NR^1$—$NR^1R^2$, —$NR^1$—$OR^2$, —C(O)$YR^3$, —OC(O)$YR^2$, —$NR^1$C(O)$YR^2$, —SC(O)$YR^2$, —$NR^1$C(=S)$YR^2$, —OC(=S)$YR^2$, —C(=S)$YR^2$, —YC(=$NR^1$)$YR^2$, —YC(=N—$OR^1$)$YR^2$, —YC(=N—$NR^1R^2$)$YR^2$, —YP(=O)$(YR^3)(YR^3)$, —Si$(R^{3a})_3$, —$NR^1SO_2R^2$, —S(O)$_rR^2$, —$SO_2NR^1R^2$ and —$NR^1SO_2NR^1R^2$; wherein each Y is independently a bond, —O—, —S— or —$NR^1$—.

21. The compound of claim 13 in which at least one substituent $R^a$ is a 5-, 6- or 7-membered heterocyclic or 5- or 6-membered heteroaryl, linked to Ring A either directly or by an ether bond, and which may be further substituted with 1, 2 or 3 substituents independently selected from halo, —CN, —$NO_2$, —$R^1$, —$OR^2$, —O—$NR^1R^2$, —$NR^1R^2$, —$NR^1$—$NR^1R^2$, —$NR^1$—$OR^2$, —C(O)$YR^2$, —OC(O)$YR^2$, —$NR^1$C(O)$YR^2$, —SC(O)$YR^2$, —$NR^1$C(=S)$YR^2$, —OC(=S)$YR^2$, —C(=S)$YR^2$, —YC(=$NR^1$)$YR^2$, —YC(=N—$OR^1$)$YR^2$, —YC(=N—$NR^1R^2$)$YR^2$, —YP(=O)$(YR^3)(YR^3)$, —Si$(R^{3a})_3$, —$NR^1SO_2R^2$, —S(O)$_rR^2$, —$SO_2NR^1R^2$ and —$NR^1SO_2NR^1R^2$; wherein each Y is independently a bond, —O—, —S— or —$NR^1$—.

22. The compound of claim 6 in which at least one substituent $R^a$ is —P(=O)$(R^3)_2$ in which each $R^3$ is, independently, a C1-C4 alkyl.

23. The compound of claim 7 in which at least one substituent $R^a$ is P(=O)$(R^3)_2$ in which each $R^3$ is, independently, a C1-C4 alkyl.

24. The compound of any of claim 7, 18, 19, 20, or 21, in which the heterocyclic or heteroaryl substituent $R^a$ is selected from the following:

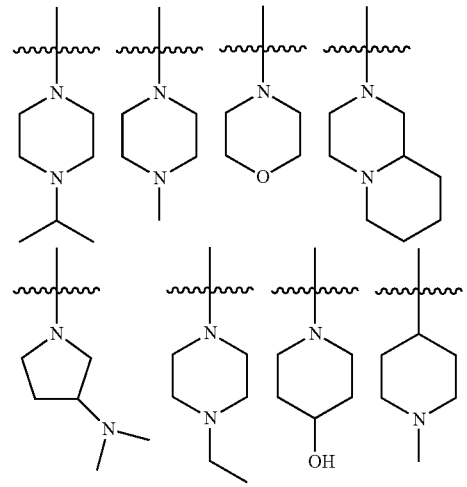

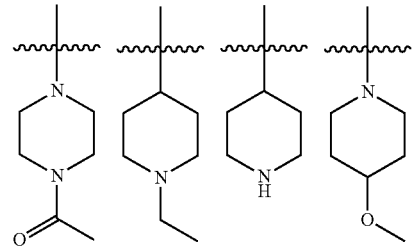

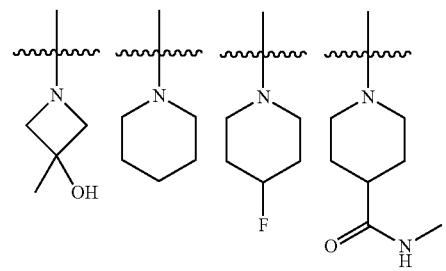

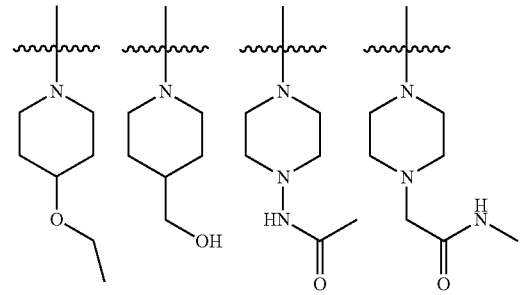

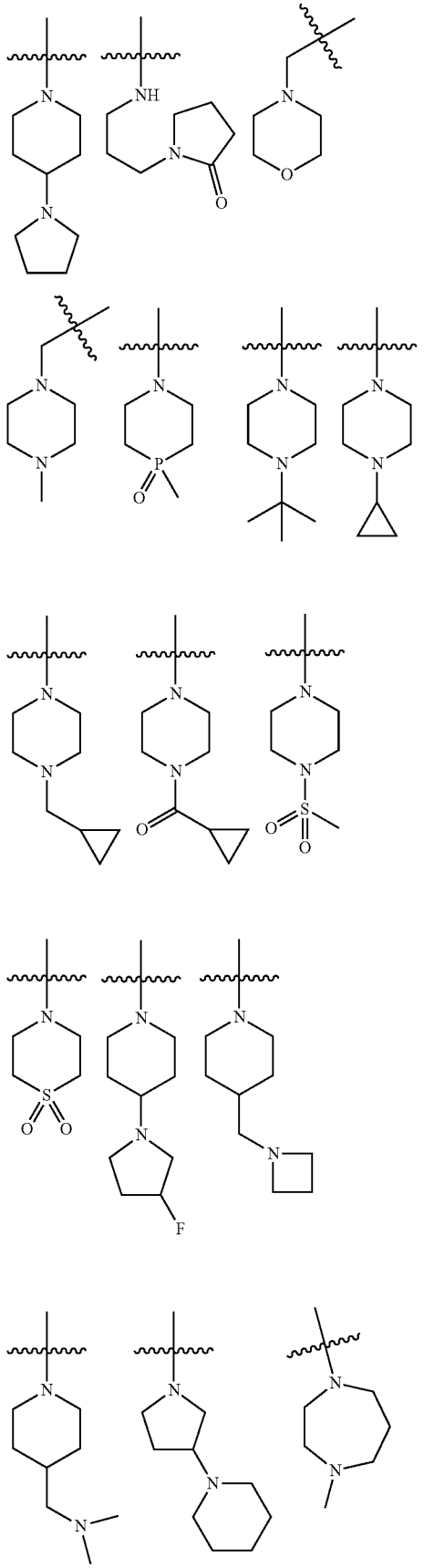
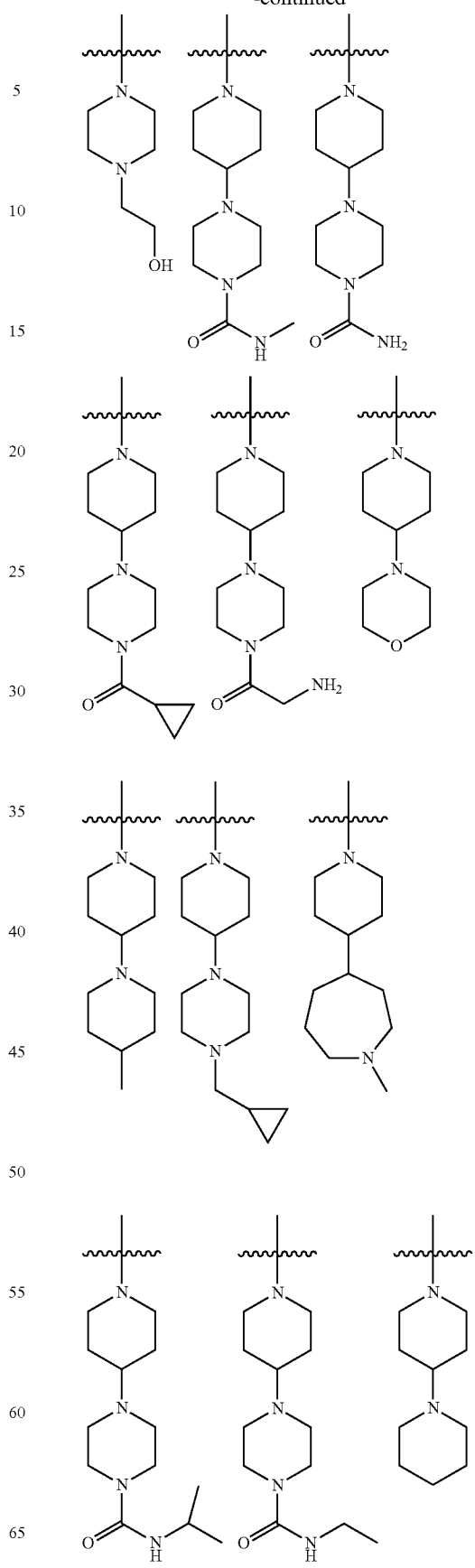

-continued

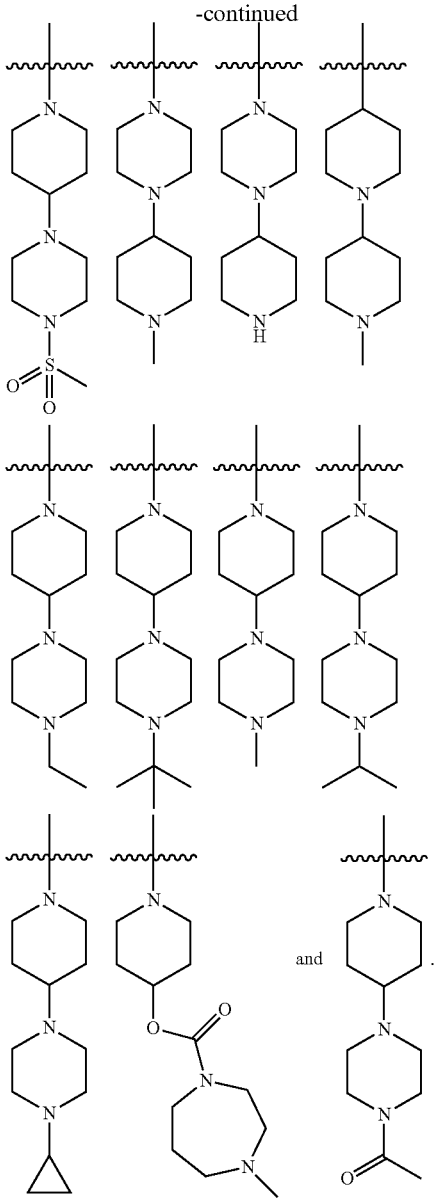

25. The compound of claim 24 in which at least one substituent $R^a$ is $P(=O)(R^3)_2$ in which each $R^3$ is, independently, a C1-C4 alkyl.

26. The compound of claim 24 in which L is NH, Ring E is aryl, and each $R^g$ is independently selected from halo, —$R^1$, —$OR^2$, —$S(O)_rR^2$ and —$P(=O)(R^3)_2$.

27. The compound of claim 25 in which L is NH, Ring E is aryl, and each $R^g$ is independently selected from halo, —$R^1$, —$OR^2$, —$S(O)_rR^2$ and —$P(=O)(R^3)_2$.

28. The compound of claim 26 in which Ring E contains at least one $R^g$ in the ortho position, relative to the ring atom attached to L.

29. The compound of claim 27 in which Ring E contains at least one $R^g$ in the ortho position, relative to the ring atom attached to L.

30. The compound of claim 26 in which Ring E contains at least one $R^g$ in the meta position, relative to the ring atom attached to L.

31. The compound of claim 27 in which Ring E contains at least one $R^g$ in the meta position, relative to the ring atom attached to L.

32. The compound of claim 26 in which Ring E contains at least one $R^g$ in the para position, relative to the ring atom attached to L.

33. The compound of claim 27 in which Ring E contains at least one $R^g$ in the para position, relative to the ring atom attached to L.

34. A pharmaceutical composition containing a compound of claim 24 or a pharmaceutically acceptable salt thereof, and a pharmaceutically acceptable vehicle.

35. A pharmaceutical composition containing a compound of claim 25 or a pharmaceutically acceptable salt thereof, and a pharmaceutically acceptable vehicle.

36. A pharmaceutical composition containing a compound of claim 26 or a pharmaceutically acceptable salt thereof, and a pharmaceutically acceptable vehicle.

37. A pharmaceutical composition containing a compound of claim 27 or a pharmaceutically acceptable salt thereof, and a pharmaceutically acceptable vehicle.

38. The compound of claim 1 selected from the following:

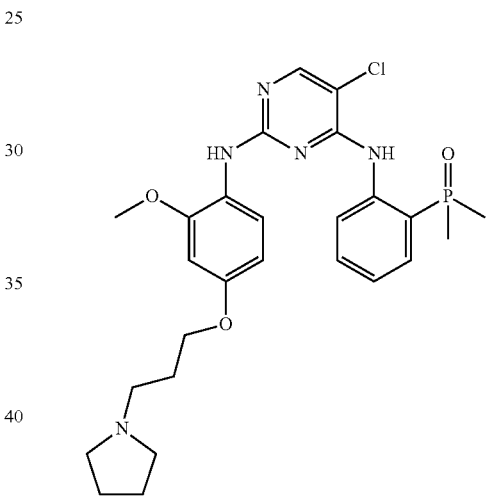

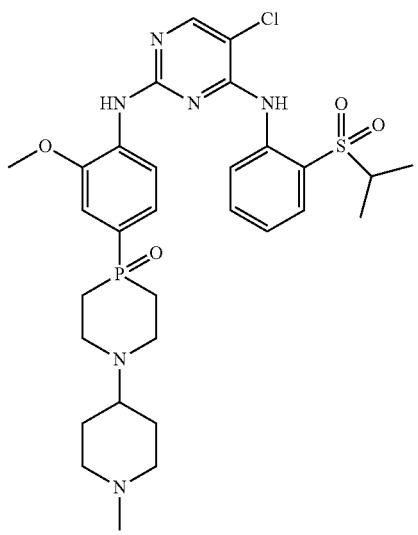

375
-continued
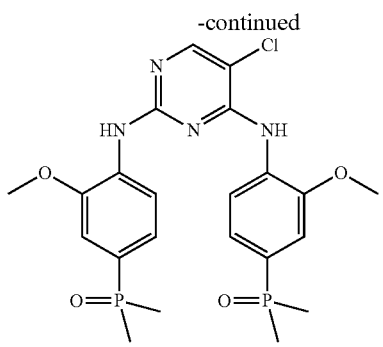
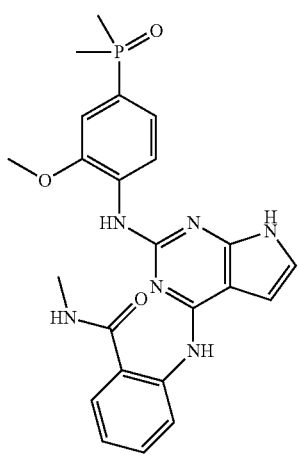
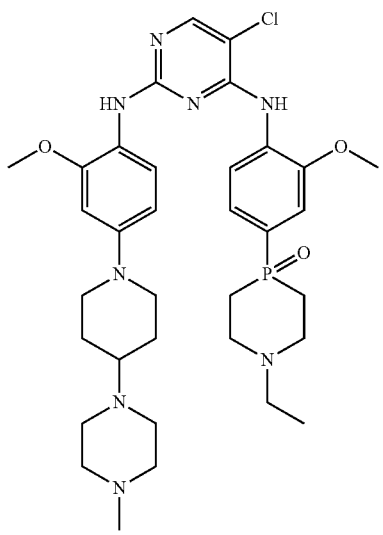
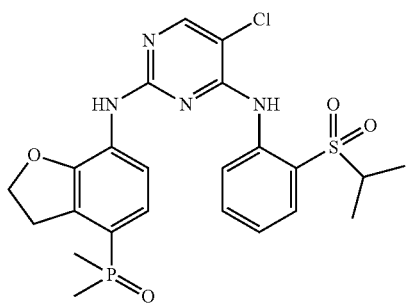
376
-continued
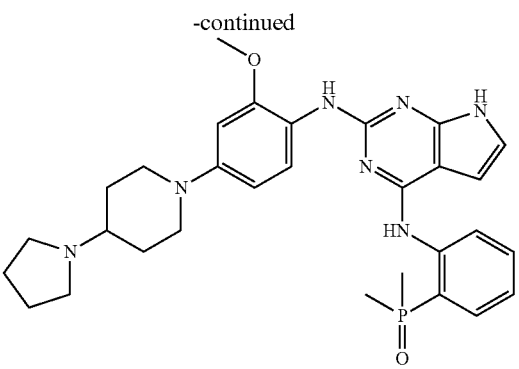
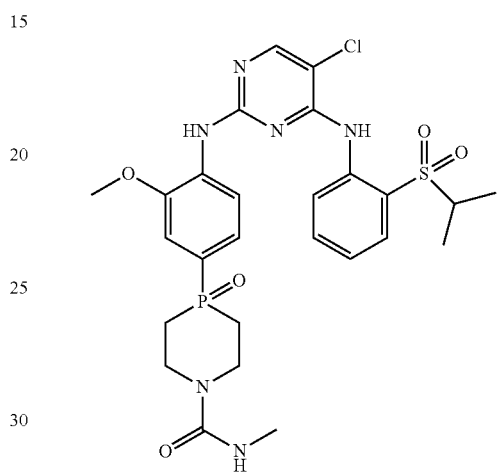
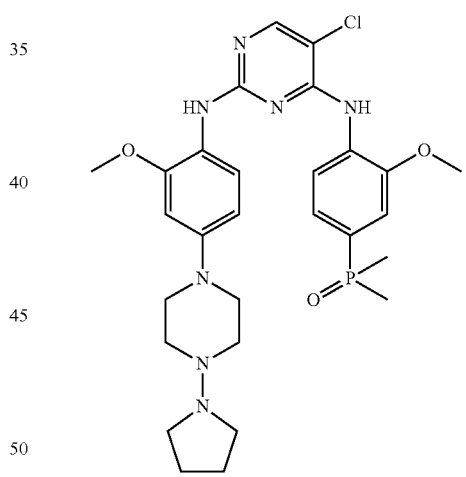
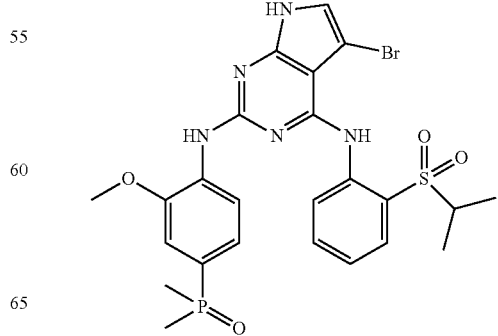

-continued

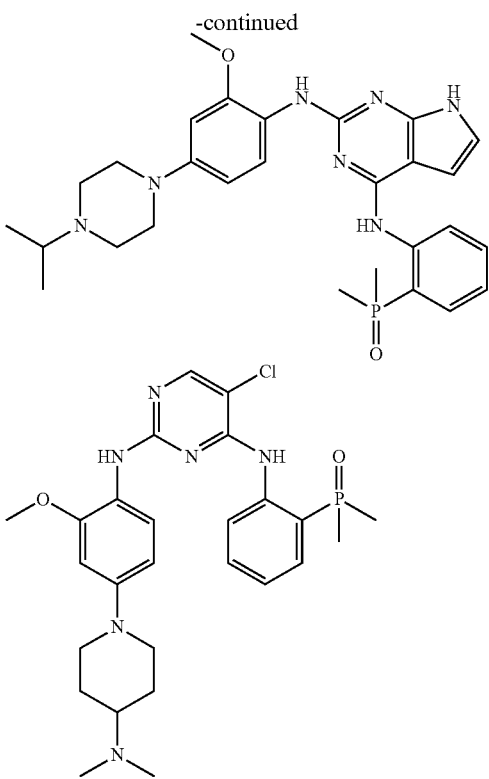

or a pharmaceutically acceptable salt thereof.

39. The compound of claim 1 selected from the following:
6-chloro-$N^3$-[4-(dimethylphosphoryl)-2-methoxyphenyl]-$N^5$-phenyl-1,2,4-triazine-3,5-diamine;
6-chloro-$N^3$-[4-(dimethylphosphoryl)-2-methoxyphenyl]-$N^5$-[2-(propan-2-ylsulfonyl)phenyl]-1,2,4-triazine-3,5-diamine;
6-chloro-$N^5$-[4-(dimethylphosphoryl)phenyl]-$N^3$-{2-methoxy-4-[4-(4-methylpiperazin-1-yl)piperidin-1-yl]phenyl}-1,2,4-triazine-3,5-diamine;
6-chloro-$N^3$-[6-(dimethylphosphoryl)-2-methoxypyridin-3-yl]-$N^5$-[2-(propan-2-ylsulfonyl)phenyl]-1,2,4-triazine-3,5-diamine;
6-chloro-$N^3$-[5-(dimethylphosphoryl)-3-methoxypyrazin-2-yl]-$N^5$-[2-(propan-2-ylsulfonyl)phenyl]-1,2,4-triazine-3,5-diamine;
$N^5$-[4-(dimethylphosphoryl)-2-(propan-2-ylsulfonyl)phenyl]-$N^3$-{2-methoxy-4-[(4-methylpiperazin-1-yl)sulfonyl]phenyl}-6-methyl-1,2,4-triazine-3,5-diamine;
6-chloro-$N^3$-[5-(dimethylphosphoryl)-2-methoxyphenyl]-$N^5$-[2-(propan-2-ylsulfonyl)phenyl]-1,2,4-triazine-3,5-diamine;
6-chloro-$N^3$-[4-(dimethylphosphoryl)-2-methylphenyl]-$N^5$-[2-(propan-2-ylsulfonyl)phenyl]-1,2,4-triazine-3,5-diamine;
6-chloro-$N^3$-[4-(dimethylphosphoryl)-2-ethylphenyl]-$N^5$-[2-(propan-2-ylsulfonyl)phenyl]-1,2,4-triazine-3,5-diamine;
6-chloro-$N^3$-[4-(dimethylphosphoryl)-2-(trifluoromethoxy)phenyl]-$N^5$-[2-(propan-2-ylsulfonyl)phenyl]-1,2,4-triazine-3,5-diamine;
6-chloro-$N^3$-[2-chloro-4-(dimethylphosphoryl)phenyl]-$N^5$-[2-(propan-2-ylsulfonyl)phenyl]-1,2,4-triazine-3,5-diamine;
6-chloro-$N^3$-[4-(dimethylphosphoryl)-2-fluorophenyl]-$N^5$-[2-(propan-2-ylsulfonyl)phenyl]-1,2,4-triazine-3,5-diamine;
6-chloro-$N^3$-[2-methoxy-4-(4-methyl-4-oxido-1,4-azaphosphinan-1-yl)phenyl]-$N^5$-[2-(propan-2-ylsulfonyl)phenyl]-1,2,4-triazine-3,5-diamine;
6-chloro-$N^3$-{2-methoxy-4-[4-(4-methyl-4-oxido-1,4-azaphosphinan-1-yl)piperidin-1-yl]phenyl}-$N^5$-[2-(propan-2-ylsulfonyl)phenyl]-1,2,4-triazine-3,5-diamine; and,
6-chloro-$N^3$-[4-(diethylphosphoryl)-2-methoxyphenyl]-$N^5$-[2-(propan-2-ylsulfonyl)phenyl]-1,2,4-triazine-3,5-diamine;
or a pharmaceutically acceptable salt thereof.

40. The compound of claim 1 selected from the following:
5-chloro-$N^4$-[4-(dimethylphosphoryl)phenyl]-$N^2$-{2-methoxy-4-[4-(4-methylpiperazin-1-yl)piperidin-1-yl]phenyl}pyrimidine-2,4-diamine;
5-chloro-$N^2$-[6-(dimethylphosphoryl)-2-methoxypyridin-3-yl]-$N^4$-[4-(dimethylphosphoryl)phenyl]pyrimidine-2,4-diamine;
5-chloro-$N^4$-[2-methoxy-4-(4-methyl-4-oxido-1,4-azaphosphinan-1-yl)phenyl]-$N^2$-[5-(propan-2-yl)-1,3-oxazol-2-yl]pyrimidine-2,4-diamine;
5-chloro-$N^2$-[1-(4-fluorobenzyl)-1H-pyrrol-3-yl]-$N^4$-[2-methoxy-4-(4-methyl-4-oxido-1,4-azaphosphinan-1-yl)phenyl]pyrimidine-2,4-diamine;
$N^2$-[5-(1,4'-bipiperidin-1'-yl)-1,3,4-thiadiazol-2-yl]-5-chloro-$N^4$-[5-(dimethylphosphoryl)-3-methoxypyrazin-2-yl]pyrimidine-2,4-diamine;
5-chloro-$N^4$-[4-(dimethylphosphoryl)-2-(propan-2-ylsulfonyl)phenyl]-$N^2$-{5-[4-(pyridin-2-yl)piperazin-1-yl]-1,3,4-oxadiazol-2-yl}pyrimidine-2,4-diamine;
5-chloro-$N^2$-(5-cyclopropyl-1,3-oxazol-2-yl)-$N^4$-{2-methoxy-4-[4-(4-methyl-4-oxido-1,4-azaphosphinan-1-yl)piperidin-1-yl]phenyl}pyrimidine-2,4-diamine;
5-chloro-$N^2$-(5-cyclopropyl-1,3-oxazol-2-yl)-$N^4$-[4-(1-ethyl-4-oxido-1,4-azaphosphinan-4-yl)-2-methoxyphenyl]pyrimidine-2,4-diamine;
5-chloro-$N^2$-(2-cyclopropyl-1,3-oxazol-5-yl)-$N^4$-[4-(diethylphosphoryl)-2-methoxyphenyl]pyrimidine-2,4-diamine;
N-[4-(dimethylphosphoryl)-2-(propan-2-ylsulfonyl)phenyl]-N'-{2-methoxy-4-[4-(4-methylpiperazin-1-yl)piperidin-1-yl]phenyl}pyrimidine-4,6-diamine;
6-chloro-$N^5$-[4-(dimethylphosphoryl)phenyl]-N'-{2-methoxy-4-[4-(4-methylpiperazin-1-yl)piperidin-1-yl]phenyl}-1,2,4-triazine-3,5-diamine;
$N^5$-[4-(dimethylphosphoryl)-2-(propan-2-ylsulfonyl)phenyl]-N'-{2-methoxy-[4(4-methylpiperazin-1-yl)sulfonyl]phenyl}-6-methyl-1,2,4-triazine-3,5-diamine; and,
5-chloro-$N^4$-[2-(dimethylphosphoryl)phenyl]-$N^2$-{2-methoxy-4-[4-(4-methylpiperazin-1-yl)piperidin-1-yl]phenyl}pyrimidine-2,4-diamine;
or a pharmaceutically acceptable salt thereof.

41. The compound of claim 1 selected from the following:
$N^4$-(3,5-dimethylphenyl)-$N^2$-[4-(dimethylphosphoryl)phenyl]-5-(trifluoromethyl)pyrimidine-2,4-diamine;
5-chloro-$N^2$-(4-(dimethylphosphoryl)-2-methoxyphenyl]-$N^4$-phenylpyrimidine-2,4-diamine;
$N^2$-[4-(dimethylphosphoryl)-2-methoxyphenyl]-$N^4$-[2-(propan-2-ylsulfonyl)phenyl]-5-(trifluoromethyl)pyrimidine-2,4-diamine;
5-chloro-$N^2$-[4-(dimethylphosphoryl)-2-methoxyphenyl]-$N^4$-[2-(propan-2-ylsulfonyl)phenyl]pyrimidine-2,4-diamine;
5-chloro-$N^2$-[4-(dimethylphosphoryl)phenyl]-$N^4$-[2-(propan-2-ylsulfonyl)phenyl]pyrimidine-2,4-diamine;

5-chloro-N$^4$-[4-(dimethylphosphoryl)phenyl]-N$^2$-{2-methoxy-4-[4-(4-methylpiperazin-1-yl)piperidin-1-yl]phenyl}pyrimidine-2,4-diamine;

N$^2$-[4-(dimethylphosphoryl)-2-methoxyphenyl]-N$^4$-[2-(propan-2-ylsulfonyl)phenyl]pyrimidine-2,4-diamine;

N$^2$-[4-(Dimethylphosphoryl)-2-methoxyphenyl]-5-methyl-N$^4$-[2-(propan-2-ylsulfonyl)phenyl]pyrimidine-2,4-diamine;

5-Chloro-N$^2$-[5-(dimethylphosphoryl)-2-methoxyphenyl]-N$^4$-[2-(propan-2-ylsulfonyl)phenyl]pyrimidine-2,4-diamine;

5-Chloro-N$^2$-[4-(dimethylphosphoryl)-2-methylphenyl]-N$^4$-[2-(propan-2-ylsulfonyl)phenyl]pyrimidine-2,4-diamine;

5-Chloro-N$^2$-[4-(dimethylphosphoryl)-2-ethylphenyl]-N$^4$-[2-(propan-2-ylsulfonyl)phenyl]pyrimidine-2,4-diamine;

5-Chloro-N$^2$-[4-(dimethylphosphoryl)-2-(trifluoromethoxy)phenyl]-N$^4$-[2-(propan-2-ylsulfonyl)phenyl]pyrimidine-2,4-diamine;

5-Chloro-N$^2$-[2-chloro-4-(dimethylphosphoryl)phenyl]-N$^4$-[2-(propan-2-ylsulfonyl)phenyl]pyrimidine-2,4-diamine;

5-Chloro-N$^2$-[4-(dimethylphosphoryl)-2-fluorophenyl]-N$^4$-[2-(propan-2-ylsulfonyl)phenyl]pyrimidine-2,4-diamine;

N$^2$-[4-(dimethylphosphoryl)-2-methoxyphenyl]-N$^4$-[2-(propan-2-ylsulfonyl)phenyl]pyrimidine-2,4,5-triamine;

N$^2$-[2-methoxy-4-(4-oxido-1,4-azaphosphinan-4-yl)phenyl]-N$^4$-[2-(propan-2-ylsulfonyl)phenyl]pyrimidine-2,4-diamine;

N$^2$-[4-(dimethylphosphoryl)-2-methoxyphenyl]-N$^4$-[2-(propan-2-ylsulfonyl)phenyl]-7H-pyrrolo[2,3-d]pyrimidine-2,4-diamine;

5-chloro-N$^2$-[6-(dimethylphosphoryl)-2-methoxypyridin-3-yl]-N$^4$-[2-(propan-2-ylsulfonyl)phenyl]pyrimidine-2,4-diamine;

5-chloro-N$^2$-[5-(dimethylphosphoryl)-3-methoxypyrazin-2-yl]-N$^4$-[2-(propan-2-ylsulfonyl)phenyl]pyrimidine-2,4-diamine;

5-chloro-N$^2$-[6-(dimethylphosphoryl)-2-methoxypyridin-3-yl]-N$^4$-phenylpyrimidine-2,4-diamine;

N$^2$-[6-(dimethylphosphoryl)-2-methoxypyridin-3-yl]-N$^4$-[2-(propan-2-ylsulfonyl)phenyl]-5-(trifluoromethyl)pyrimidine-2,4-diamine;

N$^2$-[5-(dimethylphosphoryl)-3-methoxypyrazin-2-yl]-N$^4$-[2-(propan-2-ylsulfonyl)phenyl]-5-(trifluoromethyl)pyrimidine-2,4-diamine;

5-chloro-N$^2$-[6-(dimethylphosphoryl)-2-methoxypyridin-3-yl]-N$^4$-[4-(dimethylphosphoryl)phenyl]pyrimidine-2,4-diamine;

5-chloro-N$^2$-[5-(dimethylphosphoryl)-3-methoxypyrazin-2-yl]-N$^4$-[2-ethoxy-4-[4-(4-methylpiperazin-1-yl)piperidin-1-yl]phenyl}pyrimidine-2,4-diamine;

N$^2$-[6-(dimethylphosphoryl)-2-methoxypyridin-3-yl]-N$^4$-[2-(propan-2-ylsulfonyl)phenyl]pyrimidine-2,4-diamine;

N$^2$-[6-(dimethylphosphoryl)-2-methoxypyridin-3-yl]-5-methyl-N$^4$-[2-(propan-2-ylsulfonyl)phenyl]pyrimidine-2,4-diamine;

5-chloro-N$^4$-[2-methoxy-4-(4-methyl-4-oxido-1,4-azaphosphinan-1-yl)phenyl]-N$^2$-[5-(propan-2-yl)-1,3-oxazol-2-yl]pyrimidine-2,4-diamine;

5-chloro-N$^2$-[1-(4-fluorobenzyl)-1H-pyrrol-3-yl]-N$^4$-[2-methoxy-4-(4-methyl-4-oxido-1,4-azaphosphinan-1-yl)phenyl]pyrimidine-2,4-diamine;

N$^2$-[5-(1,4'-bipiperidin-1'-yl)-1,3,4-thiadiazol-2-yl]-5-chloro-N$^4$-[5-(dimethylphosphoryl)-3-methoxypyrazin-2-yl]pyrimidine-2,4-diamine;

5-chloro-N$^4$-[4-(dimethylphosphoryl)-2-(propan-2-ylsulfonyl)phenyl]-N$^2$-{5-[4-(pyridin-2-yl)piperazin-1-yl]-1,3,4-oxadiazol-2-yl}pyrimidine-2,4-diamine-4;

5-chloro-N$^2$-(5-cyclopropyl-1,3-oxazol-2-yl)-N$^4$-{2-methoxy-4-[(4-methyl-4-oxido-1,4-azaphosphinan-1-yl)piperidin-1-yl]phenyl}pyrimidine-2,4-diamine;

5-chloro-N$^2$-(5-cyclopropyl-1,3-oxazol-2-yl)-N$^4$-[4-(1-ethyl-4-oxido-1,4-azaphosphinan-4-yl)-2-methoxyphenyl]pyrimidine-2,4-diamine;

5-chloro-N$^2$-(2-cyclopropyl-1,3-oxazol-5-yl)-N$^4$-[4-(diethylphosphoryl)-2-methoxyphenyl]pyrimidine-2,4-diamine;

N-(3,5-dimethylphenyl)-N$^4$-[4-(dimethylphosphoryl)phenyl]pyrimidine-4,6-diamine;

N-[4-(dimethylphosphoryl)-2-methoxyphenyl]-2-methyl-N'-phenylpyrimidine-4,6-diamine;

N$^3$-[4-(dimethylphosphoryl)-2-methoxyphenyl]-N$^5$-[2-(propan-2-ylsulfonyl)phenyl]pyridazine-3,5-diamine;

N-[4-(dimethylphosphoryl)-2-methoxyphenyl]-5-[3-fluoro-5-(trifluromethyl)phenoxy]pyridazin-3-amine;

N-[6-(dimethylphosphoryl)-2-methoxypyridin-3-yl]-N'-[2-(propan-2-ylsulfonyl)phenyl]pyrimidine-4,6-diamine;

N-[5-(dimethylphosphoryl)-3-methoxypyrazin-2-yl]-N'-[2-(propan-2-ylsulfonyl)phenyl]pyrimidine-4,6-diamine;

N-[4-(dimethylphosphoryl)-2-methoxyphenyl]-N'-[2-(propan-2-ylsulfonyl)phenyl]pyrimidine-4,6-diamine;

N$^2$-[4-(dimethylphosphoryl)-2-methoxyphenyl]-N$^4$-[2-(propan-2-ylsulfonyl)phenyl]pyridine-2,4-diamine;

N$^2$-[4-(dimethylphosphoryl)-2-methoxyphenyl]-N$^4$-[2-(propan-2-ylsulfonyl)phenyl]-5-(trifluoromethyl)pyridine-2,4-diamine;

N$^2$-[5-(dimethylphosphoryl)-2-methoxyphenyl]-N$^4$-[2-(propan-2-ylsulfonyl)phenyl]-5-(trifluoromethyl)pyridine-2,4-diamine;

N$^2$-[4-(dimethylphosphoryl)-2-methylphenyl]-N$^4$-[2-(propan-2-ylsulfonyl)phenyl]-5-(trifluoromethyl)pyridine-2,4-diamine;

N$^2$-[4-(dimethylphosphoryl)-2-ethylphenyl]-N$^4$-[2-(propan-2-ylsulfonyl)phenyl]-5-(trifluoromethyl)pyridine-2,4-diamine;

N$^2$-[4-(dimethylphosphoryl)-2-(trifluoromethoxy)phenyl]-N$^4$-[2-(propan-2-ylsulfonyl)phenyl]-5-(trifluoromethylpyridine-2,4-diamine;

N$^2$-[2-chloro-4-(dimethylphosphoryl)phenyl]-N$^4$-[2-(propan-2-ylsulfonyl)phenyl]-5-(trifluoromethyl)pyridine-2,4-diamine;

N$^2$-[4-(dimethylphosphoryl)-2-fluorophenyl]-N$^4$-[2-(propan-2-ylsulfonyl)phenyl]-5-(trifluoromethyl)pyridine-2,4-diamine;

N-[4-(dimethylphosphoryl)-2-(propan-2-ylsulfonyl)phenyl]-N'-{2-methoxy-4-[4-(4-methylpiperazin-1-yl)piperidin-1-yl]phenyl}pyrimidine-4,6-diamine;

N$^3$-[4-(1-ethyl-4-oxido-1,4-azaphosphinan-4-yl)-2-methoxyphenyl]-N$^5$-[2-(propan-2-ylsulfonyl)phenyl]pyridazine-3,5-diamine;

N$^3$-[2-methoxy-4-(4-methyl-4-oxido-1,4-azaphosphinan-1-yl)phenyl]-N$^5$-[2-(propan-2-ylsulfonyl)phenyl]pyridazine-3,5-diamine;

N³-{2-methoxy-4-[4-(4-methyl-4-oxido-1,4-azaphosphinan-1-yl)piperidin-1-yl]phenyl}-N⁵-[2-(propan-2-ylsulfonyl)phenyl]pyridazine-3,5-diamine;
N³-[4-(diethylphosphoryl)-2-methoxyphenyl]-N⁵-[2-(propan-2-ylsulfonyl)phenyl]pyridazine-3,5-diamine;
6-chloro-N³-[4-(dimethylphosphoryl)-2-methoxyphenyl]-N⁵-phenyl-1,2,4-triazine-3,5-diamine;
6-chloro-N³-[4-(dimethylphosphoryl)-2-methoxyphenyl]-N⁵-[2-(propan-2-ylsulfonyl) phenyl]-1,2,4-triazine-3,5-diamine;
6-chloro-N⁵-[4-(dimethylphosphoryl)phenyl]-N³-{2-methoxy-4-[4-(4-ethylpiperazin-1-yl)piperidin-1-yl]phenyl}-1,2,4-triazine-3,5-diamine;
6-chloro-N³-[6-(dimethylphosphoryl)-2-methoxypyridin-3-yl]-N⁵-[2-(propan-2-ylsulfonyl)phenyl]-1,2,4-triazine-3,5-diamine;
6-chloro-N³-[5-(dimethylphosphoryl)-3-methoxypyrazin-2-yl]-N⁵-[2-(propan-2-ylsulfonyl)phenyl]-1,2,4-triazine-3,5-diamine;
N⁵-[4-(dimethylphosphoryl)-2-(propan-2-ylsulfonyl)phenyl]-N³-{2-methoxy-4-[(4-methylpiperazin-1-yl)sulfonyl]phenyl}-6-methyl-1,2,4-triazine-3,5-diamine;
6-chloro-N³-[5-(dimethylphosphoryl)-2-methoxyphenyl]-N⁵-[2-(propan-2-ylsulfonyl)phenyl]-1,2,4-triazine-3,5 diamine;
6-chloro-N³-[4-(dimethylphosphoryl)-2-methylphenyl]-N⁵-[2-(propan-2-ylsulfonyl)phenyl]-1,2,4-triazine-3,5-diamine;
6-chloro-N³-[4-(dimethylphosphoryl)-2-ethylphenyl]-N⁵-[2-(propan-2-ylsulfonyl)phenyl]-1,2,4-triazine-3,5-diamine;
6-chloro-N³-[4-(dimethylphosphoryl)-2-(trifluoromethoxy)phenyl]-N⁵-[2-(propan-2-ylsulfonyl)phenyl]-1,2,4-triazine-3,5-diamine;
6-chloro-N³-[2-chloro-4-(dimethylphosphoryl)phenyl]-N⁵-[2-(propan-2-ylsulfonyl)phenyl]-1,2,4-triazine-3,5-diamine;
6-chloro-N³-[4-(dimethylphosphoryl)-2-fluorophenyl]-N⁵-[2-(propan-2-ylsulfonyl)phenyl]-1,2,4-triazine-3,5-diamine;
6-chloro-N³-[2-methoxy-4-(4-methyl-4-oxido-1,4-azaphosphinan-1-yl)phenyl]-N⁵-[2-(propan-2-ylsulfonyl) phenyl]-1,2,4-triazine-3,5-diamine;
6-chloro-N³-{2-methoxy-4-[4-(4-methyl-4-oxido-1,4-azaphosphinan-1-yl)piperidin-1-yl]phenyl}-N⁵-[2-(propan-2-ylsulfonyl)phenyl]-1,2,4-triazine-3,5-diamine;
6-chloro-N³-[4-(diethylphosphoryl)-2-methoxyphenyl]-N⁵-[2-(propan-2-ylsulfonyl)phenyl]-1,2,4-triazine-3,5-diamine; and,
5-chloro-N⁴-[2-(dimethylphosphoryl)phenyl]-N²-{2-methoxy-4-[4-(4-methylpiperazin-1-yl)piperidin-1-yl]phenyl}pyrimidine-2,4-diamine;
or a pharmaceutically acceptable salt thereof.

42. The compound of claim 1 of Formula VIA-i or Formula VIA-ii:

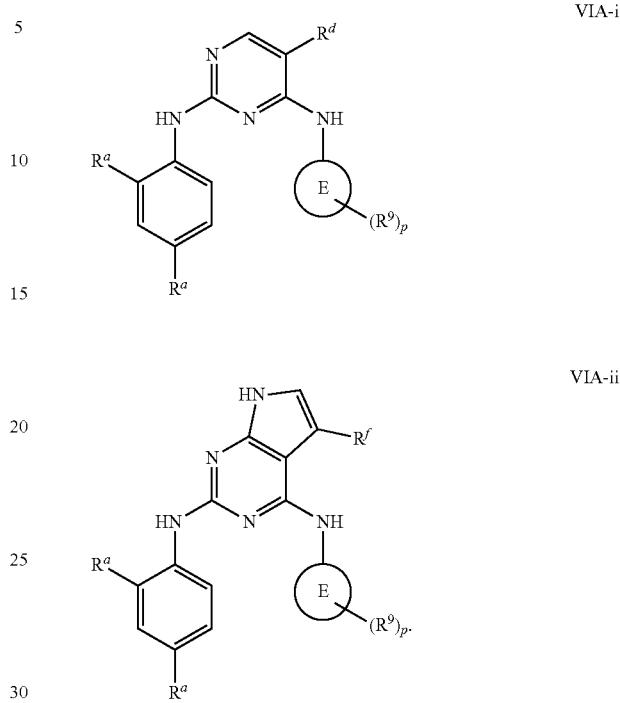

43. The compound of claim 42 in which the ortho R^a is H, halo, C1-C4 alkyl, C1-C4 haloalkyl, C1-C4 alkoxy, C1-C4 haloalkoxy or —P(O)(R³)₂.

44. The compound of claim 42 in which R^d is F, Cl, C1-C4 alkyl, cyclopropyl, CF₃, OMe, or OCF₃, or R^f is H, —CH₃ or halo.

45. The compound of claim 43 in which R^d is F, Cl, C1-C4 alkyl, cyclopropyl, CF₃, OMe, or OCF₃, or R^f is H, —CH₃ or halo.

46. The compound of claim 42 in which Ring E is aryl, and each R^g is independently —SO₂CH₃, —SO₂-iPr, —SO₂NH-iPr, —SONH-nPr, —SO₂NEt₂, —P(O)(CH₃)₂, —P(O)(Et)₂, —P(O)(Pr)₂, Me, OMe, —O-iPr, —OCF₃, CN, —C(O)CH₃, —C(O)NH₂, —C(O)NHCH₃, or, —C(O)NH-iPr.

47. The compound of claim 43 in which Ring E is aryl, and each R^g is independently —SO₂CH₃, —SO₂-iPr, —SO₂NH-iPr, —SONH-nPr, —SO₂NEt₂, —P(O)(CH₃)₂, —P(O)(Et)₂, —P(O)(Pr)₂, Me, OMe, —OCF₃, CN, —C(O)CH₃, —C(O)NH₂, —C(O)NHCH₃, or —C(O)NH-iPr.

48. The compound of claim 44 in which Ring E is aryl, and each R^g is independently —SO₂CH₃, —SO₂NH-iPr, —SONH-nPr, —SO₂NEt₂, —P(O)(CH₃)₂, —P(O)(Et)₂, —P(O)(Pr)₂, Me, OMe, —OCF₃, CN, —C(O)CH₃, —C(O)NH₂, —C(O)NHCH₃, or —C(O)NH-iPr.

49. The compound of claim 45 in which Ring E is aryl, and each R^g is independently —SO₂CH₃, —SO₂-iPr, —SO₂NH-iPr, —SONH-nPr, —SO₂NEt₂, —P(O)(CH₃)₂, —P(O)(Et)₂, —P(O)(Pr)₂, Me, OMe, —O-iPr, —OCF₃, CN, —C(O)CH₃, —C(O)NH₂, —C(O)NHCH₃, or —C(O)NH-iPr.

50. The compound of any of claim 42-45 or 47 in which the para R^a is or contains —P(O)(R³)₂ or is one of the following:

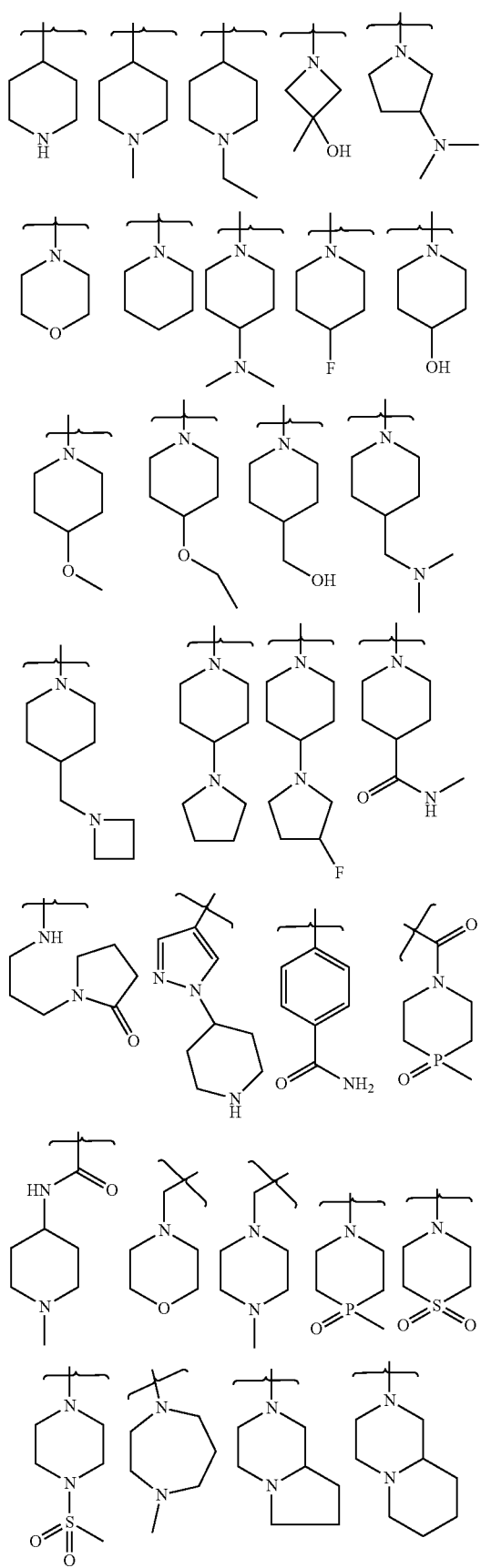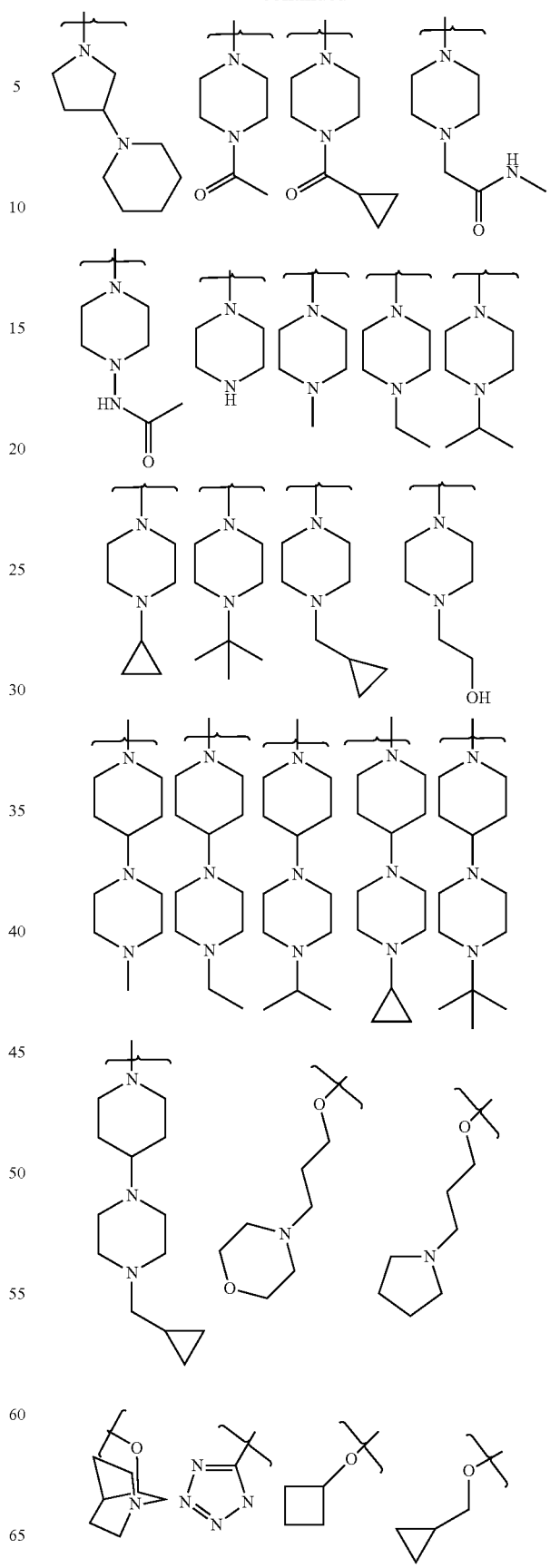

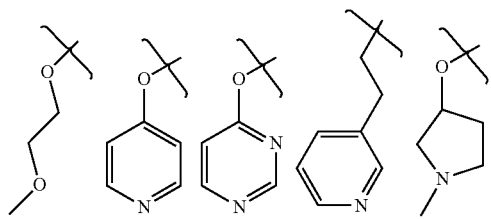
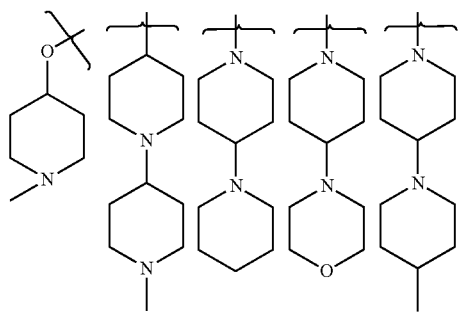
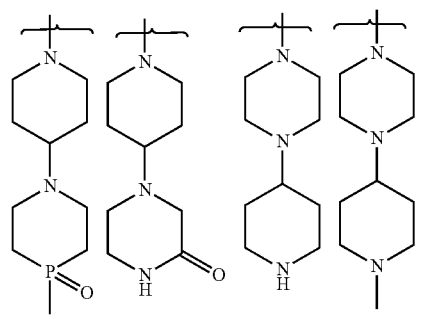
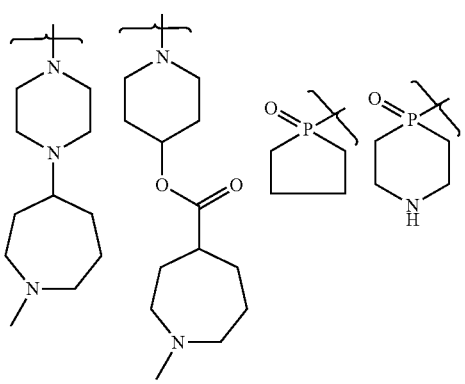
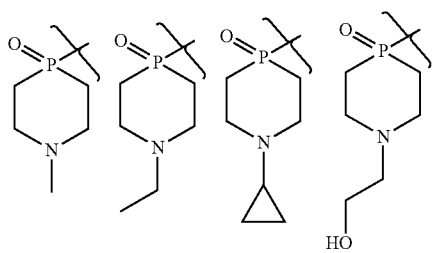
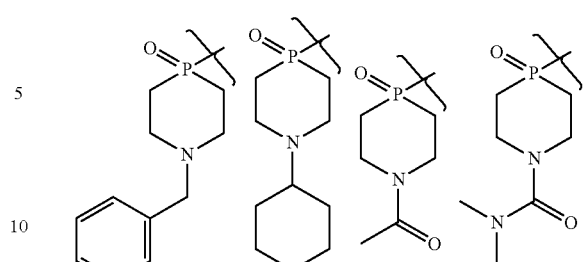
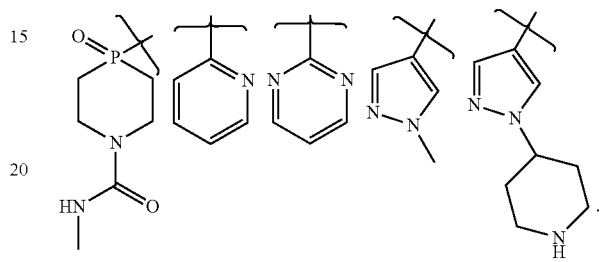
51. The compound of any of claim 42-45 or 47 in which at least one $R^g$ is or contains —P(O)($R^3$)$_2$ and the para $R^a$ one of the following:
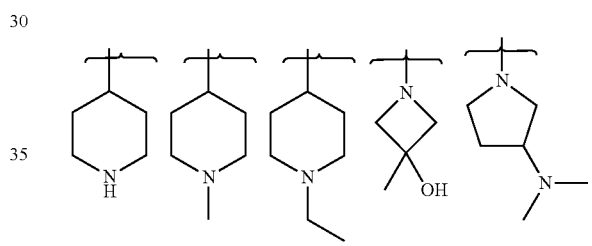
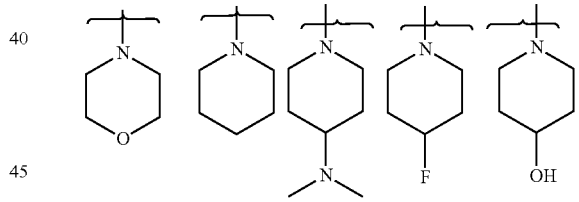
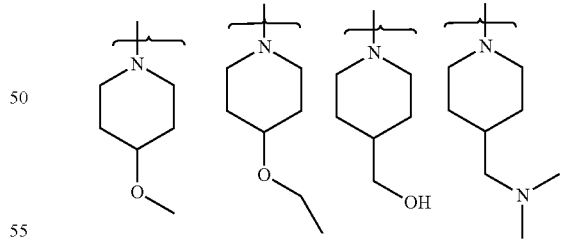
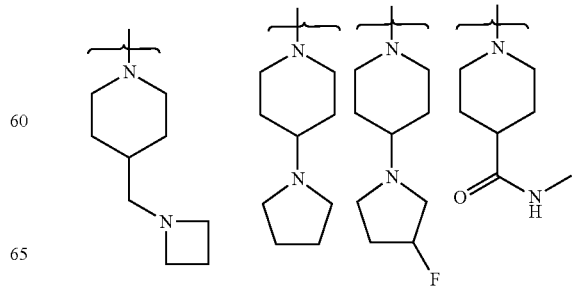

387
-continued
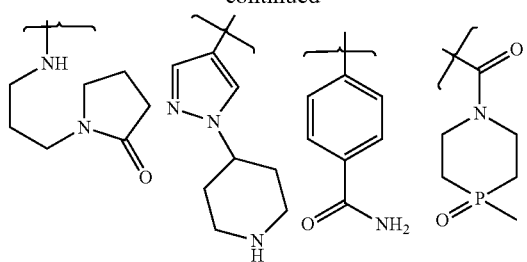
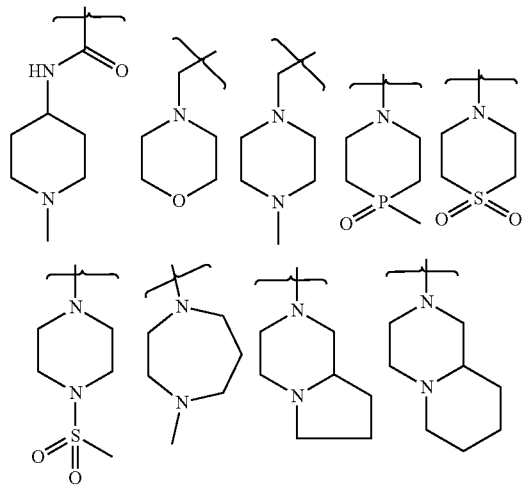
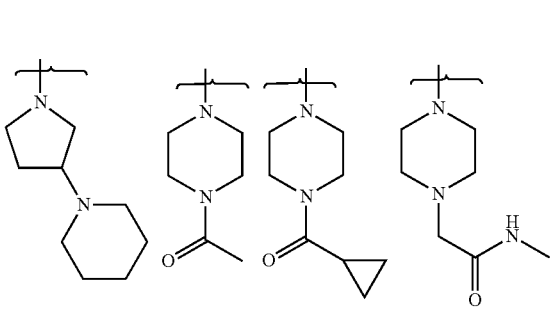
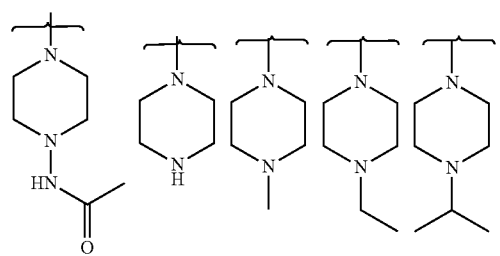
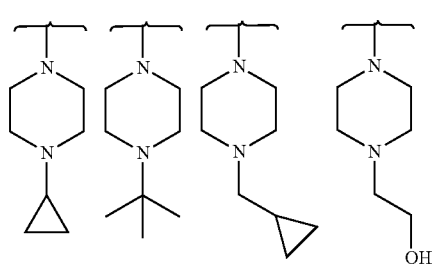
388
-continued
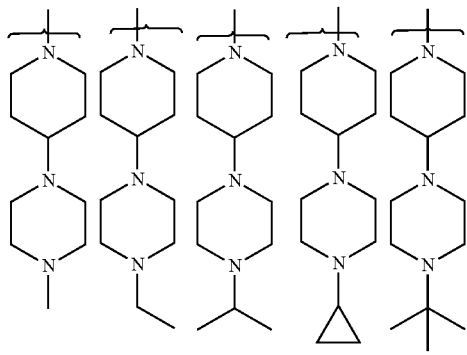
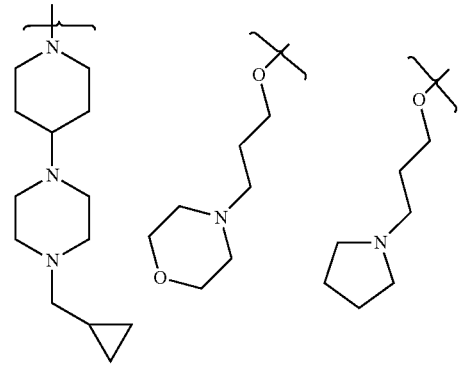
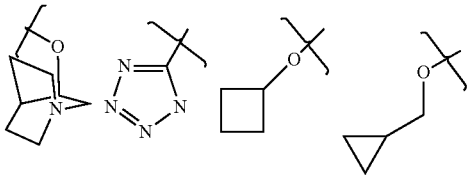
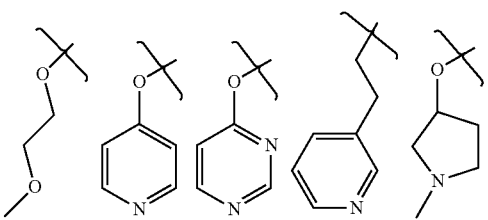
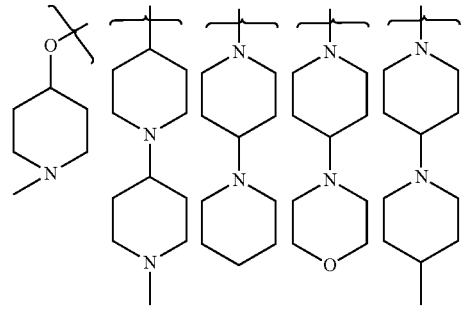

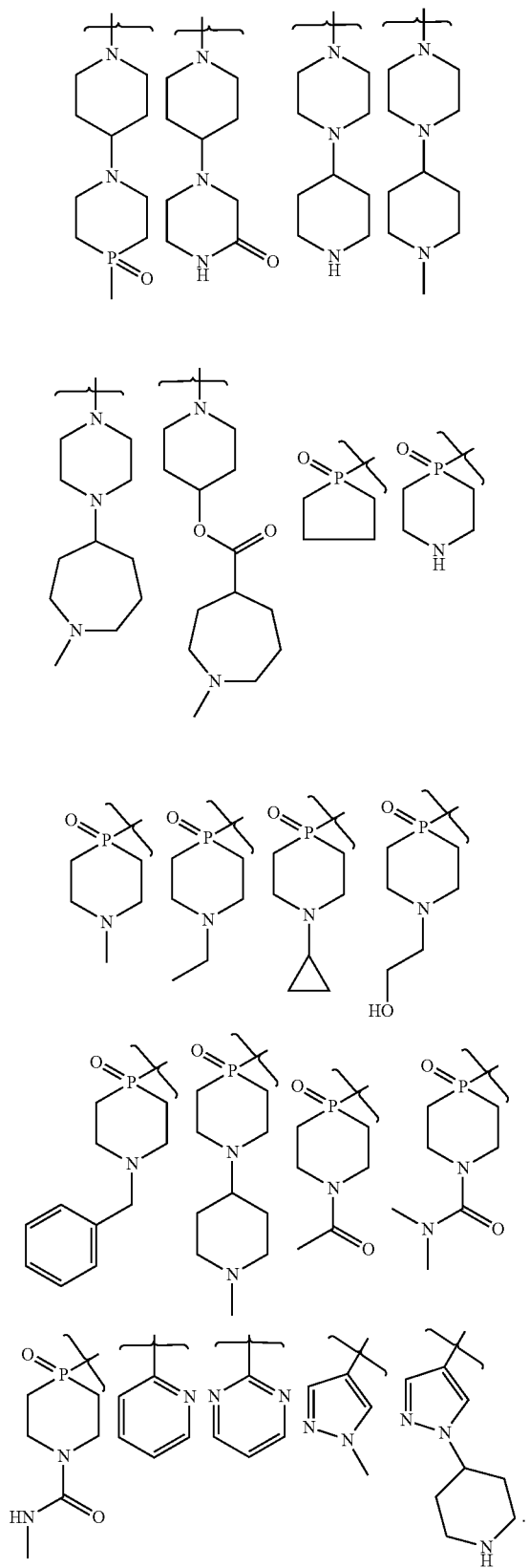

52. The compound of any of claims 1, 2, 3-7, 8 and 9-33 in which L is NH, Ring E is aryl, and each $R^g$ is independently selected from halo, —$R^1$, —$OR^2$, —$S(O)_rR^2$ and —$P(=O)(R^3)_2$.

53. The compound of claim 52 in which Ring E contains at least one $R^g$ in the ortho position, relative to the ring atom attached to L.

54. The compound of claim 52 in which Ring E contains at least one $R^g$ in the meta position, relative to the ring atom attached to L.

55. The compound of claim 52 in which Ring E contains at least one $R^g$ in the para position, relative to the ring atom attached to L.

56. The compound of claim 52 in which at least one $R^g$ is $P(=O)(R^3)_2$, and is —$P(=O)(CH_3)_2$ or —$P(=O)(CH_2CH_3)_2$.

57. The compound of claim 24 in which L is NH; $X^1$ is N; $X^3$ is $CR^d$; $X^4$ is $CR^e$; Ring A is aryl and optionally contains up to two additional $R^a$; and Ring E is aryl and contains 1-3$R^g$, one of which being an ortho, meta or para —$P(=O)(R^3)_2$.

58. The compound of claim 53 in which the at least one $R^g$ is —$P(=O)(R^3)_2$ and $R^3$ is —$CH_3$ or —$CH_2CH_3$.

59. The compound of claim 54 in which the at least one $R^g$ is —$P(=O)(R^3)_2$ and $R^3$ is —$CH_3$ or —$CH_2CH_3$.

60. The compound of claim 55 in which the at least one $R^g$ is —$P(=O)(R^3)_2$ and $R^3$ is —$CH_3$ or —$CH_2CH_3$.

61. A pharmaceutical composition containing a compound of claim 52 or a pharmaceutically acceptable salt thereof, and a pharmaceutically acceptable vehicle.

62. A pharmaceutical composition containing a compound of claim 56 or a pharmaceutically acceptable salt thereof, and a pharmaceutically acceptable vehicle.

63. A pharmaceutical composition containing a compound of claim 58 or a pharmaceutically acceptable salt thereof, and a pharmaceutically acceptable vehicle.

64. A pharmaceutical composition containing a compound of claim 59 or a pharmaceutically acceptable salt thereof, and a pharmaceutically acceptable vehicle.

65. A pharmaceutical composition containing a compound of claim 60 or a pharmaceutically acceptable salt thereof, and a pharmaceutically acceptable vehicle.

66. A pharmaceutical composition containing a compound of any of claim 1, 2, 3-7, 8, 9-23 or 38-41, or a pharmaceutically acceptable salt thereof, and a pharmaceutically acceptable vehicle.

67. The compound of claim 59, wherein the compound is

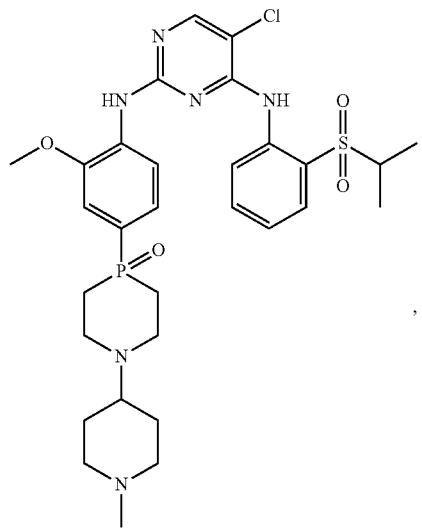 [SMILES: COc1cc(P2(=O)CCN(C3CCN(C)CC3)CC2)ccc1Nc1ncc(Cl)c(Nc2ccccc2S(=O)(=O)C(C)C)n1]

or a pharmaceutically acceptable salt thereof.

68. The compound of claim 38, wherein the compound is

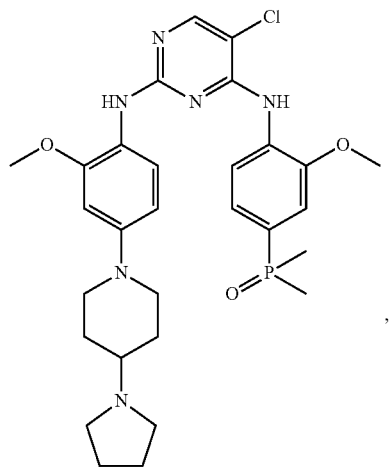

or a pharmaceutically acceptable salt thereof.

69. The compound of claim 38, wherein the compound is

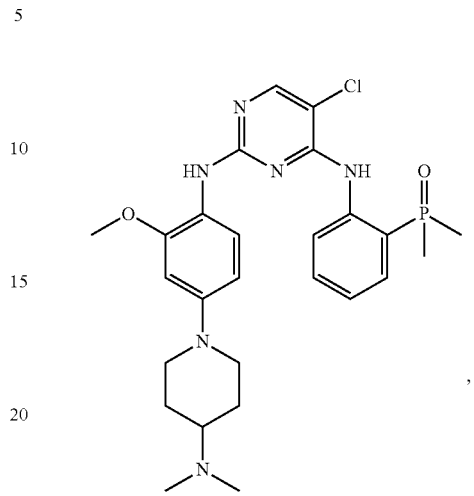

or a pharmaceutically acceptable salt thereof.

70. The compound of claim 40, wherein the compound is 5-chloro-$N^4$-[4-(dimethylphosphoryl)phenyl]-$N^2$-{2-methoxy-4-[4-(4-methylpiperazin-1-yl)piperidin-1-yl]phenyl}pyrimidine-2,4-diamine, or a pharmaceutically acceptable salt thereof.

71. The compound of claim 40, wherein the compound is 5-chloro-$N^2$-[6-(dimethylphosphoryl)-2-methoxypyridin-3-yl]-$N^4$-[4-(dimethylphosphoryl)phenyl]pyrimidine-2,4-diamine, or a pharmaceutically acceptable salt thereof.

72. The compound of claim 40, wherein the compound is 5-chloro-$N^4$-[2-(dimethylphosphoryl)phenyl]-$N^2$-{2-methoxy-4-[4-(4-methylpiperazin-1-yl)piperidin-1-yl]phenyl}pyrimidine-2,4-diamine, or a pharmaceutically acceptable salt thereof.

* * * * *